United States Patent
Deplazes-Lauber et al.

(10) Patent No.: US 10,538,587 B2
(45) Date of Patent: Jan. 21, 2020

(54) ANTIBODIES AGAINST NOTCH 3

(71) Applicants: Joelle Deplazes-Lauber, Planegg (DE);
Christy Fryer, Cambridge, MA (US);
Tiacen Hu, Cambridge, MA (US);
David Jenkins, Cambridge, MA (US);
Konstantin Petropoulos, Planegg (DE);
Philippe Thiel, Ludwigshafen (DE)

(72) Inventors: Joelle Deplazes-Lauber, Planegg (DE);
Christy Fryer, Cambridge, MA (US);
Tiacen Hu, Cambridge, MA (US);
David Jenkins, Cambridge, MA (US);
Konstantin Petropoulos, Planegg (DE);
Philippe Thiel, Ludwigshafen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/853,003

(22) Filed: Sep. 14, 2015

(65) Prior Publication Data
US 2018/0009889 A1    Jan. 11, 2018

Related U.S. Application Data

(63) Continuation-in-part of application No. PCT/US2014/022642, filed on Jun. 10, 2014.

(60) Provisional application No. 61/781,421, filed on Mar. 14, 2013.

(51) Int. Cl.
| | | |
|---|---|---|
| *C07K 16/28* | (2006.01) | |
| *A61K 39/395* | (2006.01) | |
| *G01N 33/574* | (2006.01) | |
| *C07K 14/705* | (2006.01) | |
| *C07K 14/71* | (2006.01) | |
| *A61K 39/00* | (2006.01) | |

(52) U.S. Cl.
CPC .......... *C07K 16/28* (2013.01); *A61K 39/3955* (2013.01); *G01N 33/57484* (2013.01); *A61K 2039/505* (2013.01); *C07K 2317/21* (2013.01); *C07K 2317/32* (2013.01); *C07K 2317/33* (2013.01); *C07K 2317/34* (2013.01); *C07K 2317/54* (2013.01); *C07K 2317/55* (2013.01); *C07K 2317/56* (2013.01); *C07K 2317/565* (2013.01); *C07K 2317/73* (2013.01); *C07K 2317/76* (2013.01); *C07K 2317/92* (2013.01); *G01N 2800/50* (2013.01); *G01N 2800/7028* (2013.01)

(58) Field of Classification Search
CPC ........ A61K 2039/505; A61K 39/39558; A61K 39/3955; A61K 39/395; A61K 39/39533; A61K 38/177; A61K 38/179; A61K 38/1793; C07K 16/28; C07K 2317/56; C07K 2317/76; C07K 14/705; C07K 16/2863; C07K 16/2866; C07K 2317/515; C07K 2317/51; C07K 2317/73; C07K 2317/62
See application file for complete search history.

(56) References Cited

U.S. PATENT DOCUMENTS

| | | | | |
|---|---|---|---|---|
| 7,915,390 B2* | 3/2011 | Li | ...................... | C07K 16/00 530/350 |
| 7,935,791 B2* | 5/2011 | Fung | .................... | C07K 14/705 530/387.1 |
| 7,994,285 B2* | 8/2011 | Li | ...................... | C07K 16/00 530/327 |
| 8,226,943 B2* | 7/2012 | Gurney | ................ | C07K 16/462 424/130.1 |
| 8,513,388 B2* | 8/2013 | Li | ...................... | C07K 16/28 530/327 |
| 8,921,106 B2* | 12/2014 | Gurney | ................ | A61K 31/337 435/326 |
| 9,200,071 B2* | 12/2015 | Siebel | .............. | A61K 39/39558 |
| 9,433,687 B2* | 9/2016 | Geles | ................ | A61K 47/6869 |
| 9,879,083 B2* | 1/2018 | Okamura | .............. | C07K 16/28 |

FOREIGN PATENT DOCUMENTS

| | | | |
|---|---|---|---|
| WO | WO-2008/051797 A2 * | 5/2008 | |
| WO | 2008/076960 A2 | 6/2008 | |
| WO | 2011/041336 A2 | 4/2011 | |
| WO | 2014/072897 A1 | 5/2014 | |

OTHER PUBLICATIONS

Li et al., "Modulation of Notch signaling by antibodies specific for the extracellular negative regulatory region of NOTCH3," J Biol Chem. Mar. 21, 2008;283(12):8046-54.
International Search Report for International Application No. PCT/US2014/022642, dated Dec. 18, 2014 (4 pages).

* cited by examiner

*Primary Examiner* — Bridget E Bunner

(57) ABSTRACT

The present disclosure relates to antibodies or fragments thereof that target at least one conformational epitope of a Notch 3 or mutant Notch 3 receptor; and compositions and methods of use thereof.

6 Claims, 49 Drawing Sheets
Specification includes a Sequence Listing.

| MOR | Protein domain | Human EC50 nM | Cyno EC50 nM | Mouse EC50 nM |
|---|---|---|---|---|
| 12215 | EGF32 NRR | 0.9 | 0.6 | 2.2 |
| 20337 | EGF32 NRR | 0.8 | 0.6 | 0.7 |
| 12225 | EGF32 NRR | 0.8 | 0.9 | 0.7 |
| 20345 | EGF32 NRR | 0.7 | 0.6 | 0.3 |
| 20350 | EGF32 NRR | 1.3 | 1.4 | 29.0 |
| 20351 | EGF32 NRR | 0.9 | 0.8 | 0.4 |
| 12981 | EGF32 NRR | 0.4 | 0.4 | no binding |
| 20358 | EGF32 NRR | 0.4 | 0.5 | s.n.r. |
| 12229 | LBD | 0.4 | 0.5 | 1.3 |
| 20364 | LBD | 1.0 | 1.5 | 1.6 |
| 20802 | LBD | 0.5 | 0.7 | 1.2 | s.n.r. saturation not reached

Figure 3a

| MOR | Protein domain | Human Kd nM | Cyno Kd nM | Mouse Kd nM |
|---|---|---|---|---|
| 12215 | EGF32 NRR | 0.9 | 2.7 | 1.0 |
| 20337 | EGF32 NRR | 0.5 | 0.4 | 4.4 |
| 12225 | EGF32 NRR | 2.3 | 2.7 | 6.8 |
| 20345 | EGF32 NRR | 1.0 | 0.7 | 4.1 |
| 20350 | EGF32 NRR | 0.1 | 0.3 | 2.9 |
| 20351 | EGF32 NRR | 0.2 | 1.2 | 2.7 |
| 12981 | EGF32 NRR | 43 | 19 | nsp |
| 20358 | EGF32 NRR | 1.6 | 2.7 | 70 |
| 12229 | LBD | 14 | 24 | 16 |
| 20364 | LBD | 0.2 | 0.1 | 0.1 | nsp: no statement possible (poor binding)

Figure 4

| MOR | FACS EC50 U2OS_N3 cells |
|---|---|
| 12215 | 0.65 |
| 20337 | 0.34 |
| 12225 | n.s.p. |
| 20345 | 0.38 |
| 20350 | 0.16 |
| 20351 | 0.34 |
| 12981 | s.n.r. |
| 20358 | 0.14 |
| 12229 | s.n.r. |
| 20364 | 0.09 |
| 20802 | 0.01 | s.n.r. saturation not reached
n.s.p. no statement possible (poor binding)

Figure 5a

| MOR | FACS EC50 U2OS_N3 cells |
|---|---|
| 12215 | 0.65 |
| 20337 | 0.34 |
| 12225 | n.s.p. |
| 20345 | 0.38 |
| 20350 | 0.16 |
| 20351 | 0.34 |
| 12981 | s.n.r. |
| 20358 | 0.14 |
| 12229 | s.n.r. |
| 20364 | 0.09 |
| 20802 | 0.01 | s.n.r: saturation not reached
nsp: no statement possible (poor binding)

Figure 6a

| MOR | Jagged1 % inhibition | Jagged1 IC50 (nM) | Delta 1 % inhibition | Delta 1 IC50 (nM) |
|---|---|---|---|---|
| 12215 | -5 | n.a. | -1 | n.a. |
| 20337 | 60 | 4.6 | 18 | 6.4 |
| 12225 | -165 | 5.8 | -8 | n.a. |
| 20345 | -88 | 0.4 | 19 | 0.3 |
| 20350 | -67 | 0.6 | 29 | 0.5 |
| 20351 | -50 | 0.8 | 30 | 1.4 |
| 12981 | 56 | 0.2 | 16 | 22 |
| 20358 | 80 | 0.1 | 29 | 0.4 |
| 12229 | 77 | 0.7 | 85 | 5.5 |
| 20364 | 72 | 2.0 | 91 | 1.8 |
| 20802 | 70 | 2.1 | 93 | 3.9 |

Figure 7a

| MOR | HCC1143 MMP7 10ug/ml | HCC1143 HES1 10ug/ml | MDA-MB468 DKK1 10ug/ml | MDA-MB468 HES1 10ug/ml |
|---|---|---|---|---|
| 20337 | 38 | 45 | 278 | 34 |
| 20345 | 44 | 38 | 215 | 63 |
| 20350 | 45 | 39 | 287 | 47 |
| 20351 | 49 | 39 | 292 | 42 |
| 20358 | 12 | 21 | 276 | 44 |
| 20364 | 63 | 34 | 167 | -14 |

Figure 8

| Cell Line_lineage | cDNA_Change | Codon_Change | Protein_Change |
|---|---|---|---|
| GMS10_CNS | c.4639C>G | c.(4639-4641)CTG>GTG | p.L1547V |
| HUH7_LIVER | c.4552C>A | c.(4552-4554)CTG>ATG | p.L1518M |
| ISHIKAWAHERAKLIO02ER_ENDOMETRIUM | c.4791T>A | c.(4789-4791)AAT>AAA | p.N1597K |
| KASUMI2_HAEMATOPOIETIC_AND_LYMPHOID | c.4552C>A | c.(4552-4554)CTG>ATG | p.L1518M |
| NCIH2B_PLEURA | c.4552C>A | c.(4552-4554)CTG>ATG | p.L1518M |
| OVKATE_OVARY | c.4870T>C | c.(4870-4872)TAC>CAC | p.Y1624H |
| SNU1040_LARGE_INTESTINE | c.4529G>A | c.(4528-4530)CGC>CAC | p.R1510H |
| SNU175_LARGE_INTESTINE | c.4552C>A | c.(4552-4554)CTG>ATG | p.L1518M |
| SNU201_CENTRAL_NERVOUS_SYSTEM | c.4739C>T | c.(4738-4740)TCG>TTG | p.S1580L |
| TALL1_HAEMATOPOIETIC_AND_LYMPHOID | | | |
| WM88_SKIN | c.4759G>A | c.(4759-4761)GAC>AAC | p.D1587N |

| Cell_Line_Lineage | cDNA_Change | Codon_Change | Protein_Change | Type |
|---|---|---|---|---|
| A704_KIDNEY | c.6335G>A | c.(6334-6336)GGT>GAT | p.G2112D | Missense |
| CW2_LARGE_INTESTINE | c.6634C>A | c.(6634-6636)CTG>ATG | p.L2212M | Missense |
| FTC133_THYROID | c.6361T>C | c.(6361-6363)TTC>CTC | p.F2121L | Missense |
| FTC238_THYROID-Tumor | c.6112G>A | c.(6112-6114)GGC>AGC | p.G2038S | Missense |
| GCT_SOFT_TISSUE | c.6175G>A | c.(6175-6177)GGG>AGG | p.G2059R | Missense |
| GMS10_CNS | c.6236G>A | c.(6238-6240)CGG>CAG | p.R2080Q | Missense |
| HEC108_ENDOMETRIUM | c.6065G>A | c.(6064-6066)CGC>CAC | p.R2022H | Missense |
| IGROV1_OVARY | c.6379T>C | c.(6379-6381)TAT>CAT | p.Y2127H | Missense |
| KG1_HAEM_LYMP | c.6632A>G | c.(6631-6633)TAC>TGC | p.Y2211C | Missense |
| KYM1_SOFT_TISSUE | c.6223C>T | c.(6223-6225)CAG>TAG | p.Q2075* | Nonsense |
| LS411N_LARGE_INTESTINE | c.6604G>A | c.(6604-6606)GTC>ATC | p.V2202I | Missense |
| LS513_LARGE_INTESTINE | c.6287C>T | c.(6286-6288)TCG>TTG | p.S2096L | Missense |
| NCIH2A7_LUNG | c.6515G>A | c.(6514-6516)TGG>TAG | p.W2172* | Nonsense |
| NCIH446_LUNG | c.6266C>T | c.(6265-6267)CCG>CTG | p.P2089L | Missense |
| NCIH716_LARGE_INTESTINE | c.6626C>T | c.(6625-6627)CCG>CTG | p.P2209L | Missense |
| NIHOVCAR3_OVARY | c.5941C>T | c.(5941-5943)CGC>TGC | p.R1981C | Missense |
| SF295_CNS | c.6434G>A | c.(6433-6435)CGG>CAG | p.R2145Q | Missense |
| SW1116_LARGE_INTESTINE | c.6632C>T | c.(6632-6634)CCT>TCT | p.P2178S | Missense |
| 2312397_STOMACH | c.6201_6202insC | c.(6199-6204)CCGGGfs | p.P2067fs | Frame shift |
| GP2D_LARGE_INTESTINE | c.6102delC | c.(6100-6102)CCCfs | p.P2034fs | Frame shift |
| HEC151_ENDOMETRIUM | c.6531_6531insC | c.(6529-6531)CCAfs | p.P2177fs | Frame shift |
| HEC59_ENDOMETRIUM | c.6530delC | c.(6529-6531)CCAfs | p.P2177fs | Frame shift |
| A549_LUNG-Tumor | c.6102_6103insC | c.(6100-6105)CCCGGfs | p.P2034fs | Frame shift |
| MDAMB468_BREAST | c.6102_6103insC | c.(6100-6105)CCCGGfs | p.P2034fs | Frame shift |
| SNUC2A_LARGE_INTESTINE | c.6201delC | c.(6199-6201)CCCfs | p.P2067fs | Frame shift |

Figure 9a

| Tumor_lineage | Protein_Change |
|---|---|
| X-1004 breast | G1487D |
| X-1407 breast | A1537T |
| X-1569 kidney | R1526C |

Figure 9b

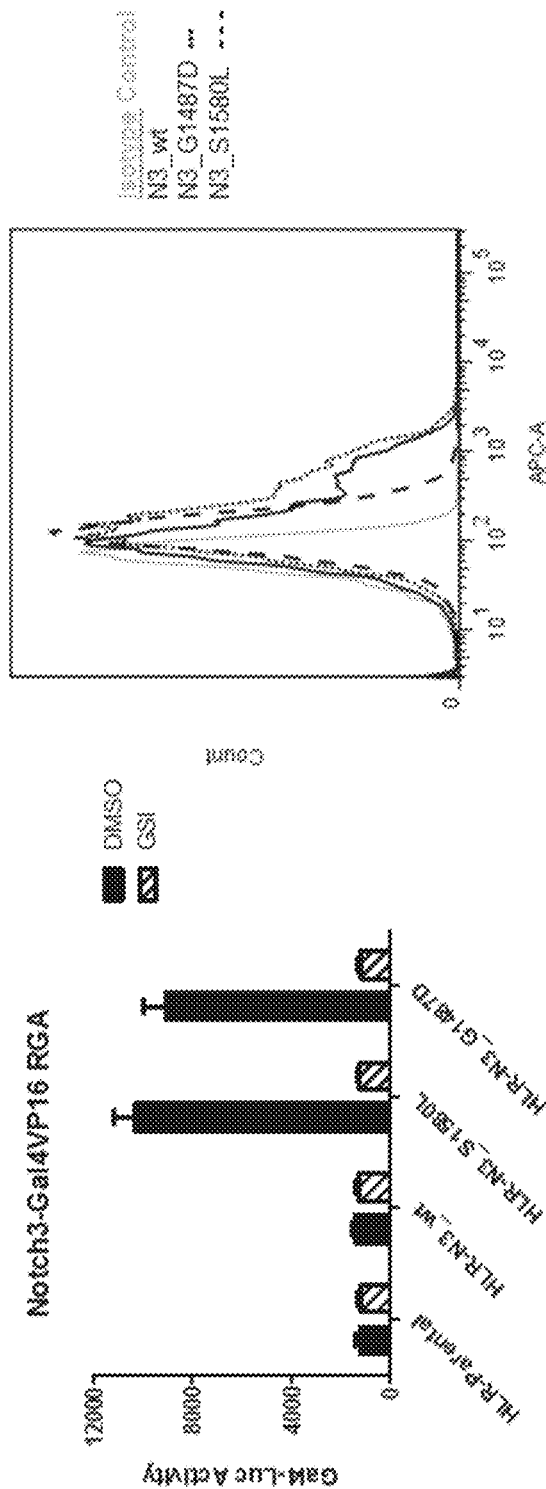

| parental | MOR | 20337 | 20345 | 20350 | 20351 | 20358 | A4 |
|---|---|---|---|---|---|---|---|
| 12215 | 20337 | -3.4 | 65.3 | 69.9 | 71.2 | 71 | 43.3 |
| 12225 | 20345 | 77.8 | 9.7 | 9 | 12.7 | 45.6 | 59.9 |
| 12225 | 20350 | 47.1 | 8.3 | 6.2 | 9.9 | 15 | 15.6 |
| 12225 | 20351 | 74 | 4.6 | 3.4 | 6.2 | 27 | 48.9 |
| 12981 | 20358 | 72.7 | 51.1 | 52.4 | 50.5 | 8.1 | 44.2 |
| Refmab | A4 | 81.6 | 78.9 | 78.9 | 78 | 60.4 | 0.2 |
|  | PBST | -1.1 | -1.5 | -1.5 | -2.3 | -9.5 | -19.7 |
| Epitope | Epitope | NRR_A | NRR_B | NRR_B | NRR_B | NRR_C | NRR_D |

IgG_sample 1 (columns) / IgG_sample 2 (rows)

Figure 20

Epitope Comparison among 20350, 20358, and A4

| 20350 epitope on Notch3 NRR | | |
|---|---|---|
| Domain | Residue | Number |
| LNR-A/B linker | GLN | 1427 |
| | CYS | 1428 |
| | GLU | 1429 |
| LNR-B | CYS | 1442 |
| | PRO | 1444 |
| | ALA | 1445 |
| | SER | 1447 |
| | SER | 1448 |
| | PRO | 1449 |
| | ALA | 1450 |
| | TYR | 1453 |
| | CYS | 1458 |
| LNR-B/C linker | GLY | 1461 |
| | GLU | 1462 |
| | GLU | 1464 |
| LNR-HD linker | LEU | 1507 |
| | LEU | 1508 |
| | ARG | 1510 |
| HD-C β4-α3 loop | LEU | 1592 |
| | SER | 1594 |
| | PRO | 1595 |
| | GLU | 1596 |
| | ASN | 1597 |
| | ASP | 1598 |
| | HIS | 1599 |
| | PRO | 1602 |
| HD-C α3 helix | SER | 1606 |

| 20358 epitope on Notch3 NRR | | |
|---|---|---|
| Domain | Residue | Number |
| LNR-B | SER | 1440 |
| LNR-B/C linker | ARG | 1463 |
| | ARG | 1465 |
| | THR | 1466 |
| | CYS | 1467 |
| | ASN | 1468 |
| | PRO | 1469 |
| | VAL | 1470 |
| LNR-C | TYR | 1471 |
| | GLU | 1472 |
| | TYR | 1474 |
| | GLN | 1486 |
| | GLY | 1487 |
| HD-N α2 helix | ARG | 1514 |
| HD-C α3-β5 loop | GLU* | 1618* |
| | ARG* | 1619* |
| | ASP* | 1621* |

| A4 epitope on Notch3 NRR | | |
|---|---|---|
| Domain | Residue | Number |
| LNR-A (LIN12 domain (L.1))ᵇ | ALA | 1394 | Cluster 1 |
| | LYS | 1395 | |
| | ARG | 1396 | Cluster 2 |
| | ASP | 1398 | |
| | GLN | 1399 | |
| | ARG | 1400 | Cluster 3 |
| | ASP | 1402 | |
| | ARG | 1403 | |
| | GLU | 1404 | Cluster 4 |
| | SER | 1420 | |
| | VAL | 1421 | |
| | GLY | 1422 | Cluster 5 |
| | GLU | 1576 | |
| | VAL | 1577 | |
| | ILE | 1578 | |
| HD-C (2ⁿᵈ dimerization domain (D2))ᵇ | SER | 1615 | |
| | ALA | 1616 | |
| | VAL | 1617 | |
| | GLU* | 1618* | Cluster 6 |
| | ARG* | 1619* | |
| | LEU | 1620 | |
| | ASP* | 1621* | |
| | PHE | 1622 | |
| | PRO | 1625 | Cluster 7 |
| | LEU | 1626 | |
| | ARG | 1627 | |

ᵃBold font indicates the three residues overlapped between 20358 epitope and the claimed A4 epitope.
ᵇCorresponding domain name from Patent US 7,935,791 B2

Figure 26

| 20K30 | | | 2053B | | |
|---|---|---|---|---|---|
| Buried Residues X-ray Crystal (5A) | Protected Regions HDx-MS | | Buried Residues X-ray Crystal (5A) | Protected Regions HDx-MS | |
| 1427-1439 | 1421-1429 | | 1443 | 1421-1429 | |
| 1442 | 1433-1457 | | 1463 | 1433-1457 | |
| 1444-1445 | 1490-1500 | | 1465-1474 | 1457-1477 | |
| 1447-1450 | 1532-1545 | | 1496-1497 | 1490-1500 | |
| 1453 | 1580-1583 | | 1493 | 1532-1545 | |
| 1458 | 1592-1616 | | 1534 | 1580-1583 | |
| 1461-1462 | 1617-1628 | | 1618-1619 | 1592-1616 | |
| 1464 | | | 1621 | 1617-1628 | |
| 1497-1498 | | | | | |
| 1510 | | | | | |
| 1592 | | | | | |
| 1594-1598 | | | | | |
| 1602 | | | | | |
| 1605 | | | | | |

Light Grey: buried amino acid only in X-Ray
Grey: buried or protected amino acids in X-ray or HDx-MS
Black: protection region observed in HDx-MS

Figure 30

ANTIBODIES AGAINST NOTCH 3

RELATED APPLICATIONS

This application is a continuation-in-part of PCT Patent Application No. PCT/US2014/022642, filed on Mar. 10, 2014, published as PCT Patent Publication No. WO 2014/159239 A2 on Oct. 2, 2014, which claims priority to U.S. Provisional Application No. 61/781,421 filed on Mar. 14, 2013. This application is also a continuation-in-part of PCT Patent Application No. PCT/US2014/022658, filed on Mar. 10, 2014, published as PCT Patent Publication No. WO 2014/159242 A1 on Oct. 2, 2014, which claims priority to U.S. Provisional Application No. 61/781,396 filed on Mar. 14, 2013.

FIELD OF THE INVENTION

This invention relates generally to antibodies or fragments thereof which interact with Notch 3. In particular, it relates to antibodies or fragments thereof that recognize at least one conformational epitope of Notch 3 or a mutant Notch 3 comprising continuous and discontinuous amino acid residues from the Lin Notch Repeat (LNR) region and the heterodimerization (HD) of the negative regulatory region (NRR) domain.

BACKGROUND OF THE INVENTION

Notch signaling is an evolutionarily conserved pathway that regulates a diverse set of biological functions including stem cell maintenance, cell differentiation and proliferation in both embryonic development and adult tissues (Kopan et al., (2009) Cell 137: 216-233, Guruharsha et al., (2012) Nat Rev Genet. 13: 654-66, and Andersson et al., (2001) Development 138: 3593-3612). In mammals, four Notch receptors have been described (Notch1-4), which have a conserved domain architecture. The extracellular domain (ECD) consists of a series of EGF-like repeats followed by a negative regulatory region (NRR) which contains 3 Lin Notch Repeat (LNR) repeats and a heterodimerization domain. Canonical Notch signaling is activated when a Notch receptor on one cell interacts with a ligand on a neighboring cell. In mammals there are five trans-membrane ligands, three Delta-like ligands (DLL1, DLL4, and DLL3) and two Jagged ligands (Jagged1, Jagged2). Ligand binding results in cleavage of Notch by ADAM proteases at the S2 site within the NRR domain. This initial cleavage generates the substrate for subsequent cleavage of the Notch receptor at the S3 site by the γ-secretase complex. Following γ-secretase cleavage, the intracellular domain of Notch (ICD) translocates to the nucleus where it interacts with a CSL transcription factor (CBF-1/RBP-Jk in mammals) and the co-activator mastermind (MAML1) to activate target gene transcription. The HES/HEY family of transcription factors are well-characterized Notch target genes, however a large number of transcriptional targets are cell-type specific.

To date, the evidence for Notch receptors in cancer has focused primarily on alterations in Notch1 signaling, but very little on other Notch receptors. Accordingly, a need exists to study and identify methods and compositions that alter other Notch receptor signaling, such as Notch 3 signaling.

SUMMARY OF THE INVENTION

The disclosure pertains to a number of distinct conformational epitopes in Notch 3 or mutant Notch 3. The disclosure also pertains to antibodies or fragments thereof that recognize at least one conformational epitope of Notch 3 or a mutant Notch 3 comprising continuous and discontinuous amino acid residues from the LNR region and the HD of the NRR domain.

Accordingly, in one aspect, the disclosure pertains to an isolated polypeptide comprising a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is selected from the group consisting of LNR-A, LNR-B, LNR-C and the corresponding linkers between these LNRs; wherein the HD domain is selected from the group consisting of the N-terminal HD and the C-terminal HD, and wherein the linker region is selected from the group consisting of LNR-A/B linker, LNR-B/C linker, LNR-HD linker.

In another aspect, the disclosure pertains an isolated polypeptide comprising a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-B, and the HD domain is the HD α3 helix, and wherein the linker region is selected from the group consisting of LNR-A/B linker, LNR-B/C linker, LNR-HD linker.

In another aspect, the disclosure pertains to an isolated polypeptide comprising a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and the linker region is selected from the group consisting of LNR-A/B linker, LNR-B/C linker, LNR-HD linker.

In another aspect, the disclosure pertains an isolated antibody or fragment thereof that recognizes a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is selected from the group consisting of LNR-A, LNR-B, LNR-C; wherein the HD domain is selected from the group consisting of the N-terminal HD and the C-terminal HD; and wherein the antibody or fragment thereof blocks ligand-dependent signal transduction.

In one embodiment, the antibody or fragment thereof stabilizes the Notch 3 receptor LNR region in the autoinhibited state. In one embodiment, the present disclosure provides a mutant Notch 3 receptor, where the LNR region or the HD domain has at least one amino acid residue mutation. In one embodiment, the Notch 3 mutant comprises a mutation selected from the group consisting of S1580L, and G1487D, or combinations thereof.

In another aspect, the disclosure pertains an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-B, and the HD domain is the HD α3 helix; and wherein the antibody or fragment thereof blocks ligand-dependent signal transduction.

In one embodiment, the conformational epitope further comprises amino acid residues in the LNR-A/B linker of the NRR region. In one embodiment, the conformational epitope further comprises amino acid residues in the LNR-B/C linker of the NRR region. In one embodiment, the conformational epitope further comprises amino acid residues in the LNR-HD linker of the NRR region. In one embodiment, the conformational epitope further comprises amino acid residues in a HD β4-α3 loop. In one embodiment, the conformational epitope further comprises amino acid residues in the LNR-A/B linker, the LNR-B/C linker, the LNR-HD linker, and the HD β4-α3 loop. In one embodiment, the antibody or fragment thereof stabilizes the Notch 3 receptor LNR region in the autoinhibited state. In one embodiment, the Notch 3 receptor is a mutant Notch 3 receptor, wherein the LNR region or the HD domain has at least one amino acid residue mutation. In one embodiment, the Notch 3 mutant comprises a mutation selected from the group consisting of S1580L D1587N, R1589Q, Y1624H, A1608T, L1518M, A1537T, N1597K, L1547V, R1526C (HD) and G1487D, A1476T (LNR-C), or combinations thereof. In one embodiment, the conformational epitope comprises amino acid residues: 1427-1429 (of the LNR-A/B linker), 1442, 1444-1445, 1447-1450, 1453, 1458 (of LNR-B), 1461-1462, 1464 (of the LNR-B/C linker), 1507-1508, 1510 (of the LNR-HD linker), 1592, 1594-1599, 1602 (of the HD β4-α3 loop), and 1606 (of the HD α3 helix), or a subset thereof. In one embodiment, the VH of the antibody or fragment thereof binds to at least one of the following Notch 3 residues: Cys1442, Pro1444, Ala1445, Ser1447, Ser1448, Pro1449, Tyr1453, Cys1458, Gly1461, Gly1462, Gly1464, Leu1592, Ser1594, Pro1595, Glu1596, Asn1597, Asp1598, and His1599. In one embodiment, the Notch 3 receptor is a mutant Notch 3 receptor, wherein the LNR region or the HD domain has at least one amino acid residue mutation. In one embodiment, the VL of the antibody or fragment thereof binds to at least one of the following Notch 3 residues: Gln1427, Cys1428, Glu1429, Pro1444, Ser1445, Ser1447, Ser1448, Pro1449, Tyr1453, Leu1507, Leu1508, Arg1510, Leu1592, Asp1598, Pro1602, and Ser1606. In one embodiment, the antibody is selected from the group consisting of a monoclonal antibody, a polyclonal antibody, a chimeric antibody, a humanized antibody, and a synthetic antibody.

In another aspect, the disclosure pertains an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker of a NRR domain of Notch 3 receptor; wherein the LNR region is LNR-C, and the HD domain is the HD α2 helix; and wherein the antibody or fragment thereof blocks ligand-dependent signal transduction.

In one embodiment, the conformational epitope further comprises amino acid residues in the LNR-B of the NRR region. In one embodiment, the conformational epitope further comprises amino acid residues in the LNR-B/C linker of the NRR region. In one embodiment, the conformational epitope further comprises amino acid residues in a HD α3-β5 loop. In one embodiment, the conformational epitope further comprises amino acid residues in LNR-B, the LNR-B/C linker, and the HD α3-β5 loop. In one embodiment, the antibody or fragment thereof stabilizes the Notch 3 receptor LNR region in the autoinhibited state. In one embodiment, the mutant Notch 3 receptor comprises a mutation selected from the group consisting of S1580L, R1510H, D1587N, R1589Q, Y1624H, L1518M, A1537T, N1597K, L1547V, R1526C (HD), and A1476T (LNR-C), or combinations thereof. In one embodiment, the conformational epitope comprises amino acid residues: 1440 (of LNR-B), 1463, 1465-1468 (of the LNR-B/C linker) 1469-1472, 1474, 1486-1487, (of LNR-C), 1534 (of HD α2 helix), and 1618, 1619, and 1621 (of the α3-β5 loop), or a subset thereof. In one embodiment, the VH of the antibody or fragment thereof binds to at least one of the following Notch 3 residues: Arg1463, Thr1466, Asn1468, Pro1469, Val1470, Tyr1471, Tyr1474, Gln1486, and Gly1487. In one embodiment, the VL of the antibody or fragment thereof binds to at least one of the following Notch 3 residues: Ser1440, Arg1465, Thr1466, Asn1468, Pro1469, Val1470, glu1472, Arg1434, Glu1618, Arg1619, and Asp1621. In one embodiment, the antibody is selected from the group consisting of a monoclonal antibody, a polyclonal antibody, a chimeric antibody, a humanized antibody, and a synthetic antibody. In one embodiment, the antibody or fragment thereof inhibits Notch 3 signalling as assessed by an assay selected from the group consisting of a Notch 3 ligand-driven reporter gene assay, FACS assay, Notch 3 target gene mRNA quantitation, in vitro proliferation of TALL-1 cells, and by detecting gamma secretase cleaved form of Notch 3 intracellular domain (ICD).

In another aspect, the disclosure pertains an isolated antibody or fragment thereof to a Notch 3 receptor, having a dissociation ($K_D$) of at least $1\times10^7$ M, $10^8$ M, $10^9$M, $10^{10}$ M, $10^{11}$ M, $10^{12}$ M, $10^{13}$M, wherein the antibody or fragment thereof inhibits Notch 3 signalling as assessed by an assay selected from the group consisting of a Notch 3 ligand-driven reporter gene assay, FACS assay, Notch 3 target gene mRNA quantitation, in vitro proliferation of TALL-1 cells, and by detecting gamma secretase cleaved form of Notch 3 intracellular domain (ICD).

In one embodiment, the antibody or fragment thereof binds to the same conformational epitope as an antibody described in Table 2. In one embodiment, the antibody or fragment thereof cross-competes with an antibody described in Table 2.

In another aspect, the disclosure pertains an isolated antibody or fragment thereof to Notch 3 receptor which antibody comprises a VH selected from the group consisting of SEQ ID NO: 9, SEQ ID NO: 29, SEQ ID NO: 49, SEQ ID NO: 69, SEQ ID NO: 89, SEQ ID NO: 109, SEQ ID NO: 129, SEQ ID NO: 149, SEQ ID NO: 169, SEQ ID NO: 189, SEQ ID NO: 209, and SEQ ID NO: 229; and a VL selected from the group consisting of SEQ ID NO: 19, SEQ ID NO: 39, SEQ ID NO: 59, SEQ ID NO: 79, SEQ ID NO: 99, SEQ ID NO: 119, SEQ ID NO: 139, SEQ ID NO: 159, SEQ ID NO: 179, SEQ ID NO: 199, SEQ ID NO: 219, and SEQ ID NO: 239 or an amino acid sequence with 97-99% identity thereof.

In another aspect, the disclosure pertains to a single chain antibody or fragment thereof comprising a variable heavy chain sequence and a variable light chain sequence selected from the group consisting of a variable heavy chain having SEQ ID NO: 9 and a variable light chain sequence having SEQ ID NO: 19; variable heavy chain sequence having SEQ ID NO: 29 and a variable light chain sequence having SEQ ID NO: 39; a variable heavy chain sequence having SEQ ID NO: 49 and a variable light chain sequence having SEQ ID NO: 59; a variable heavy chain sequence having SEQ ID NO: 69 and a variable light chain sequence having SEQ ID NO: 79; a variable heavy chain sequence having SEQ ID NO: 89 and a variable light chain sequence having SEQ ID NO: 99; a variable heavy chain sequence having SEQ ID NO: 109 and a variable light chain sequence having SEQ ID NO: 119; a variable heavy chain sequence having SEQ ID NO: 129 and a variable light chain sequence having SEQ ID NO: 139; a variable heavy chain sequence having SEQ ID NO: 149 and a variable light chain sequence having SEQ ID NO: 159; a variable heavy chain sequence having SEQ ID NO: 169 and a variable light chain sequence having SEQ ID NO: 179; a variable heavy chain sequence having SEQ ID NO: 189 and a variable light chain sequence having SEQ ID NO: 199; a variable heavy chain sequence having SEQ ID NO: 209 and a variable light chain sequence having SEQ ID NO: 219; and a variable heavy chain sequence having SEQ ID NO: 229 and a variable light chain sequence having SEQ ID NO: 239.

In another aspect, the disclosure pertains an isolated antibody or fragment thereof comprising a variable heavy chain sequence and a variable light chain sequence selected from the group consisting of a variable heavy chain having SEQ ID NO: 9 and a variable light chain sequence having SEQ ID NO: 19; variable heavy chain sequence having SEQ ID NO: 29 and a variable light chain sequence having SEQ ID NO: 39; a variable heavy chain sequence having SEQ ID NO: 49 and a variable light chain sequence having SEQ ID NO: 59; a variable heavy chain sequence having SEQ ID NO: 69 and a variable light chain sequence having SEQ ID NO: 79; a variable heavy chain sequence having SEQ ID NO: 89 and a variable light chain sequence having SEQ ID NO: 99; a variable heavy chain sequence having SEQ ID NO: 109 and a variable light chain sequence having SEQ ID NO: 119; a variable heavy chain sequence having SEQ ID NO: 129 and a variable light chain sequence having SEQ ID NO: 139; a variable heavy chain sequence having SEQ ID NO: 149 and a variable light chain sequence having SEQ ID NO: 159; a variable heavy chain sequence having SEQ ID NO: 169 and a variable light chain sequence having SEQ ID NO: 179; a variable heavy chain sequence having SEQ ID NO: 189 and a variable light chain sequence having SEQ ID NO: 199; a variable heavy chain sequence having SEQ ID NO: 209 and a variable light chain sequence having SEQ ID NO: 219; and a variable heavy chain sequence having SEQ ID NO: 229 and a variable light chain sequence having SEQ ID NO: 239.

In another aspect, the disclosure pertains an isolated antibody or fragment thereof to Notch 3 receptor comprising a heavy chain CDR3 selected from the group consisting of SEQ ID NO: 5, SEQ ID NO: 25, SEQ ID NO: 45, SEQ ID NO: 65, SEQ ID NO: 85, SEQ ID NO: 105, SEQ ID NO: 125, SEQ ID NO: 145, SEQ ID NO: 165, SEQ ID NO: 185, SEQ ID NO: 205, and SEQ ID NO: 225.

In another aspect, the disclosure pertains an isolated antibody or fragment thereof comprising heavy and light chain variable regions CDR1, CDR2 and CDR3 selected from the group consisting of a heavy chain variable region CDR1 of SEQ ID NO: 3; CDR2 of SEQ ID NO: 4; CDR3 of SEQ ID NO: 5; a light chain variable region CDR1 of SEQ ID NO:13; CDR2 of SEQ ID NO: 14; and CDR3 of SEQ ID NO: 15; a heavy chain variable region CDR1 of SEQ ID NO: 23; CDR2 of SEQ ID NO: 24; CDR3 of SEQ ID NO: 25; a light chain variable region CDR1 of SEQ ID NO: 33; CDR2 of SEQ ID NO: 34; and CDR3 of SEQ ID NO: 35; a heavy chain variable region CDR1 of SEQ ID NO: 43; CDR2 of SEQ ID NO: 44; CDR3 of SEQ ID NO: 45; a light chain variable region CDR1 of SEQ ID NO: 53; CDR2 of SEQ ID NO: 54; and CDR3 of SEQ ID NO: 55; a heavy chain variable region CDR1 of SEQ ID NO: 63; CDR2 of SEQ ID NO: 64; CDR3 of SEQ ID NO: 65; a light chain variable region CDR1 of SEQ ID NO: 73; CDR2 of SEQ ID NO: 74; and CDR3 of SEQ ID NO: 75; a heavy chain variable region CDR1 of SEQ ID NO: 83; CDR2 of SEQ ID NO: 84; CDR3 of SEQ ID NO: 85; a light chain variable region CDR1 of SEQ ID NO: 93; CDR2 of SEQ ID NO: 94; and CDR3 of SEQ ID NO: 95; a heavy chain variable region CDR1 of SEQ ID NO: 103; CDR2 of SEQ ID NO: 104; CDR3 of SEQ ID NO: 105; a light chain variable region CDR1 of SEQ ID NO: 113; CDR2 of SEQ ID NO: 114; and CDR3 of SEQ ID NO: 115; a heavy chain variable region CDR1 of SEQ ID NO: 123; CDR2 of SEQ ID NO: 124; CDR3 of SEQ ID NO: 125; a light chain variable region CDR1 of SEQ ID NO: 133; CDR2 of SEQ ID NO: 134; and CDR3 of SEQ ID NO: 135; a heavy chain variable region CDR1 of SEQ ID NO: 143; CDR2 of SEQ ID NO: 144; CDR3 of SEQ ID NO: 145; a light chain variable region CDR1 of SEQ ID NO: 153; CDR2 of SEQ ID NO: 154; and CDR3 of SEQ ID NO: 155; a heavy chain variable region CDR1 of SEQ ID NO: 163; CDR2 of SEQ ID NO: 164; CDR3 of SEQ ID NO: 165; a light chain variable region CDR1 of SEQ ID NO: 173; CDR2 of SEQ ID NO: 174; and CDR3 of SEQ ID NO: 175; a heavy chain variable region CDR1 of SEQ ID NO: 183; CDR2 of SEQ ID NO: 184; CDR3 of SEQ ID NO: 185; a light chain variable region CDR1 of SEQ ID NO: 193; CDR2 of SEQ ID NO: 194; and CDR3 of SEQ ID NO: 195; a heavy chain variable region CDR1 of SEQ ID NO: 203; CDR2 of SEQ ID NO: 204; CDR3 of SEQ ID NO: 205; a light chain variable region CDR1 of SEQ ID NO: 213; CDR2 of SEQ ID NO: 214; and CDR3 of SEQ ID NO: 215; a heavy chain variable region CDR1 of SEQ ID NO: 223; CDR2 of SEQ ID NO: 224; CDR3 of SEQ ID NO: 225; a light chain variable region CDR1 of SEQ ID NO: 233; CDR2 of SEQ ID NO: 234; and CDR3 of SEQ ID NO: 235.

In another aspect, the disclosure pertains to a pharmaceutical composition comprising an antibody or fragment thereof and a pharmaceutically acceptable carrier.

In another aspect, the disclosure pertains an antibody or fragment thereof for use in the treatment of a cancer mediated by Notch 3 signal transduction pathway selected from the group consisting of breast cancer, colorectal cancer, lung cancer, multiple myeloma, ovarian cancer, liver cancer, gastric cancer, pancreatic cancer, prostate cancer, acute myeloid leukemia, t-cell acute lymphoblastic leukemia, mantle cell lymphoma, chronic lymphocytic leukemia, Ewing's sarcoma, chronic myeloid leukemia, acute lymphoblastic leukemia, lymphoma, osteosarcoma, squamous cell carcinoma, peripheral nerve sheath tumors, schwannoma, head and neck cancer, bladder cancer, esophageal cancer, glioblastoma, clear cell sarcoma of soft tissue, malignant mesothelioma, neurofibromatosis, renal cancer, and melanoma.

In one embodiment, the antibody or fragment thereof is used for the treatment of a cancer mediated by Notch 3 signal transduction pathway wherein the cancer is T-cell acute lymphoblastic leukemia (TALL).

In another aspect, the disclosure pertains an antibody or fragment thereof for use as a medicament for treating a cancer mediated by Notch 3 signal transduction pathway selected from the group consisting of breast cancer, colorectal cancer, lung cancer, multiple myeloma, ovarian cancer, liver cancer, gastric cancer, pancreatic cancer, prostate cancer, acute myeloid leukemia, T-cell acute lymphoblastic leukemia, mantle cell lymphoma, chronic lymphocytic leukemia, Ewing's sarcoma, chronic myeloid leukemia, acute lymphoblastic leukemia, lymphoma, osteosarcoma, squamous cell carcinoma, peripheral nerve sheath tumors, schwannoma, head and neck cancer, bladder cancer, esophageal cancer, glioblastoma, clear cell sarcoma of soft tissue, malignant mesothelioma, neurofibromatosis, renal cancer, and melanoma. In one embodiment, the antibody or fragment thereof is used as a medicament for treating a cancer mediated by Notch 3 signal transduction pathway wherein the cancer is T-cell acute lymphoblastic leukemia (TALL).

In another aspect the disclosure pertains to a mutant Notch 3 receptor comprising at least one activating mutation set forth in Table 1, or combinations thereof, where the presence of the activating mutation is determined using an assay comprising a Notch 3 intracellular domain 3 (ICD3) antibody or fragment thereof that detects SEQ ID NO: 243 (VMVARRK).

In another aspect the disclosure pertains to a mutant Notch 3 receptor comprising at least one activating mutation located in the NRR of Notch 3, where the activating mutation activates Notch 3 signal transduction, and wherein the presence of the activating mutation is determined using an assay comprising a Notch 3 intracellular domain 3 (ICD3) antibody or fragment thereof that detects SEQ ID NO: 3. In one embodiment, the mutation in the NRR domain is selected from the group consisting of S1580L, D1587N, Y1624H, L1518M, A1537T, N1597K, L1547V, R1526C (HD) and G1487D (LNR-C)]. In one embodiment, the mutant Notch 3 receptor further comprises at least one mutation located in the PEST domain of Notch 3. In one embodiment, the mutation in the PEST domain is selected from the group consisting of P2034fs, P2067fs, p2177fs, Q2075*, W2172*, G2112D, L2212M, F2121L, G2038S, G2059R, R2022H, Y2127H, Y2211C, V2202I, S2096L, P2089L, P2209L, R1981C, R2145Q, and P2178S.

In another aspect the disclosure pertains to a mutant Notch 3 receptor comprising an amino acid sequence that is at least 90% identical to SEQ ID NO: 1, wherein the amino acid sequence of the mutant Notch 3 receptor differs from SEQ ID NO: 1 by virtue of containing a Leu at position 1580 rather than Ser in an NRR domain of Notch 3, and wherein the mutation in the Notch 3 polypeptide activates Notch 3 signal transduction.

In another aspect the disclosure pertains to a mutant Notch 3 receptor comprising an amino acid sequence that is at least 90% identical to SEQ ID NO: 1, wherein the amino acid sequence of the mutant Notch 3 receptor differs from SEQ ID NO: 1 by virtue of containing D at position 1487 rather than G in an NRR domain of Notch 3, and wherein the mutation in the Notch 3 polypeptide activates Notch 3 signal transduction.

In another aspect the disclosure pertains to a method of determining the increased likelihood of having or developing a cancer in a subject, comprising:
  assaying a biological sample obtained from a subject for the presence of a Notch 3 activating mutation using an assay comprising a Notch 3 intracellular domain 3 (ICD3) antibody or fragment thereof that detects SEQ ID NO: 3; and
  comparing the biological sample from subject with a non-cancerous or normal control cell, wherein the presence of the Notch 3 mutation indicates the likelihood of developing cancer.

In one embodiment, the biological sample is selected from the group consisting of blood, serum, urine, hair follicle, ascites, and tumor biopsy In one embodiment, the subject is a human and the cancer is selected from the group consisting of breast cancer, colorectal cancer, lung cancer, multiple myeloma, ovarian cancer, liver cancer, gastric cancer, pancreatic cancer, prostate cancer, acute myeloid leukemia, chronic myeloid leukemia, acute lymphoblastic leukemia, t-cell acute lymphoblastic leukemia, mantle cell lymphoma, chronic lymphocytic leukemia, Ewing's sarcoma, lymphoma, osteosarcoma, squamous cell carcinoma, peripheral nerve sheath tumors, schwannoma, head and neck cancer, bladder cancer, esophageal cancer, glioblastoma, clear cell sarcoma of soft tissue, malignant mesothelioma, neurofibromatosis, renal cancer, and melanoma. In one embodiment, the cancer is T-cell acute lymphoblastic leukemia (TALL).

In another aspect the disclosure pertains to a method for detecting the presence of an activated form of Notch 3 receptor in a biological sample, the method comprising:
  contacting the biological sample with a Notch 3 intracellular domain 3 (ICD3) antibody or fragment thereof that detects SEQ ID NO: 3;
  incubating the sample and the ICD3 antibody or fragment thereof under conditions to induce binding of the ICD3 antibody or fragment thereof to a Notch 3 receptor if present in the sample to form a complex; and
  detecting the ICD3 antibody, thereby detecting the presence of activated form of the Notch 3 receptor in a sample.

BRIEF DESCRIPTION OF FIGURES

FIG. 3A-C ELISA data of Notch 3 antibodies binding to human, cyno and mouse recombinant proteins;
FIG. 4 Biacore data of Notch 3 antibodies binding to human, cyno and mouse recombinant proteins
FIG. 5A-C FACS data of various Notch 3 antibodies;
FIG. 6A-F FACS data of Notch 3 antibodies in HCC1143 Notch amplified cells;
FIG. 7A-D: Percentage inhibition and $IC_{50}$ values of Notch3 antibodies in the presence of Notch ligands (Jagged 1 and Delta 1) in a Notch 3 reporter gene assay;
FIG. 8: Notch 3 target gene mRNA quantitation;
FIG. 9A-B: Notch 3 NRR (Top) and PEST (Bottom) mutations;
FIG. 10A-B: Graphs showing the characterization of Notch 3 NRR mutations.

FIG. 20: Shows epitope binning of the Notch 3 antibodies identifying 4 distinct epitopes in the NRR domain of Notch 3, designated as NRR-A, NRR-B, NRR-C and NRR-D;

FIG. 26: The amino acid residues in conformational epitopes of 20350, 20358, and A4;

FIG. 30: Comparison of buried X-ray amino acid residues to protected regions detected in HDx-MS;

DETAILED DESCRIPTION

Definitions

In order that the present invention may be more readily understood, certain terms are first defined. Additional definitions are set forth throughout the detailed description.

The phrase "Notch 3 activating mutation" or "activating mutation" as used herein refers to a mutation in a Notch 3 receptor that switches on Notch 3 signal transduction.

The terms "marker" or "biomarker" are used herein refers to a nucleic acid or polypeptide, of a mutation in a Notch 3 receptor. The presence or absence of the biomarker is used to determine the presence of a Notch 3 mutation. For example, Notch 3 is a biomarker when the presence of a mutation in a cancer cell when as compared to non-cancerous or normal control cell. Examples of mutations that represent a biomarker include, but are not limited to a mutation selected from the group consisting of S1580L, A1476T, G1487D, or combinations thereof.

The phrase "signal transduction" or "signaling activity" as used herein refers to a biochemical causal relationship generally initiated by a protein-protein interaction such as binding of a growth factor to a receptor, resulting in transmission of a signal from one portion of a cell to another portion of a cell. For Notch 3, ligand binding results in cleavage of Notch 3 by ADAM proteases at the S2 site within the NRR domain. This initial cleavage generates the substrate for subsequent cleavage of the Notch receptor at the S3 site by the γ-secretase complex. Following γ-secretase cleavage, the intracellular domain of Notch (ICD) translocates to the nucleus where it interacts with a CSL transcription factor (CBF-1/RBP-Jk in mammals) and the co-activator mastermind (MAML1) to activate target gene transcription.

Figure 1:
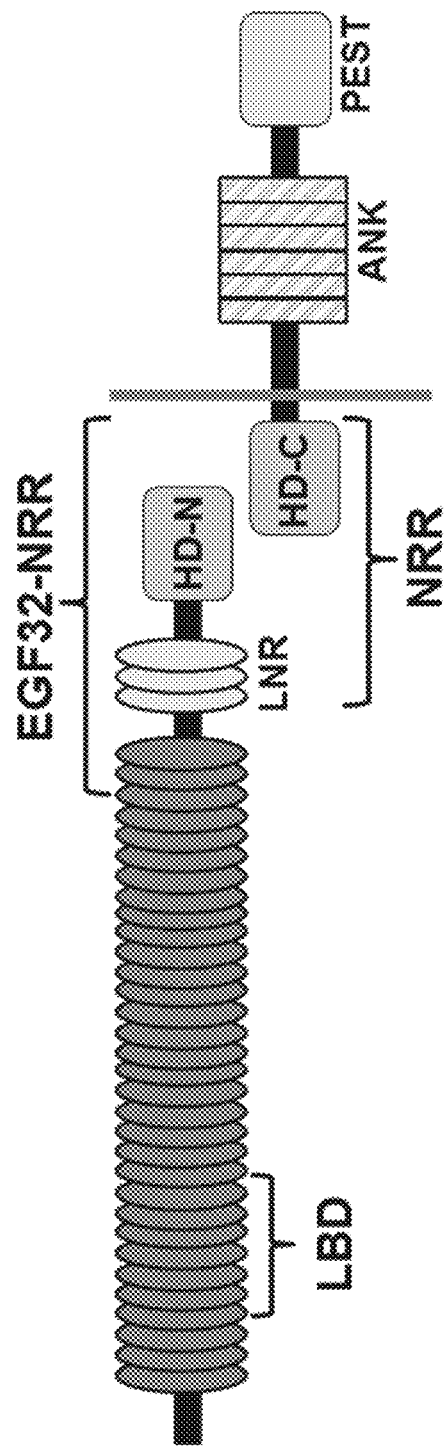
FIG. 1: Domain structure of Notch 3.
Figure 2:
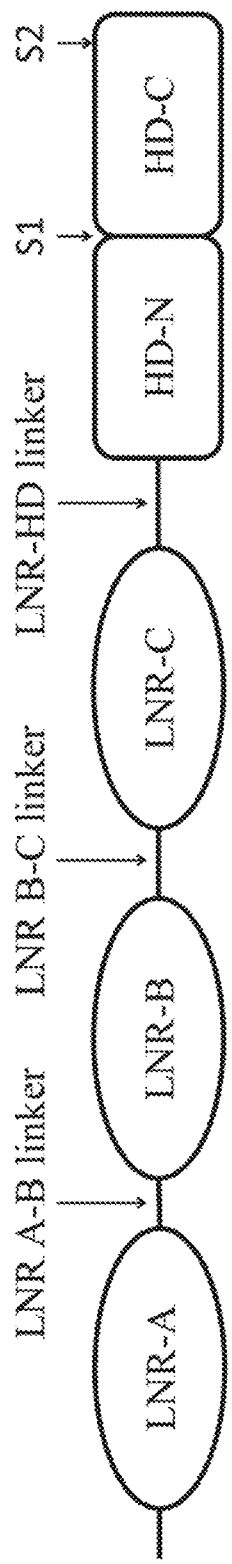
FIG. 2: Domain structure of Notch 3 NRR with amino acid positions of each region.
Figure 3B:
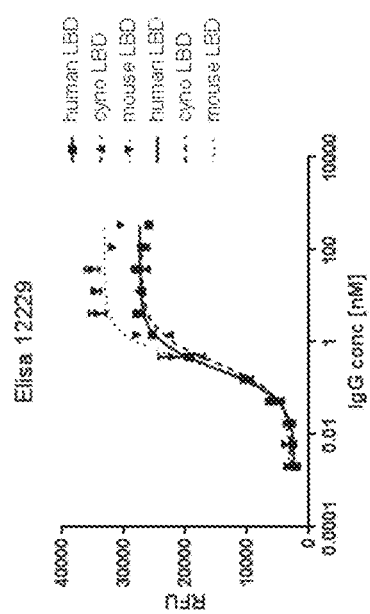
Figure 3C:
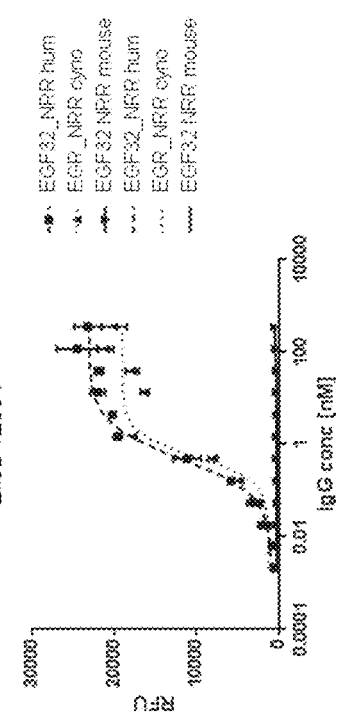
Figure 5B:
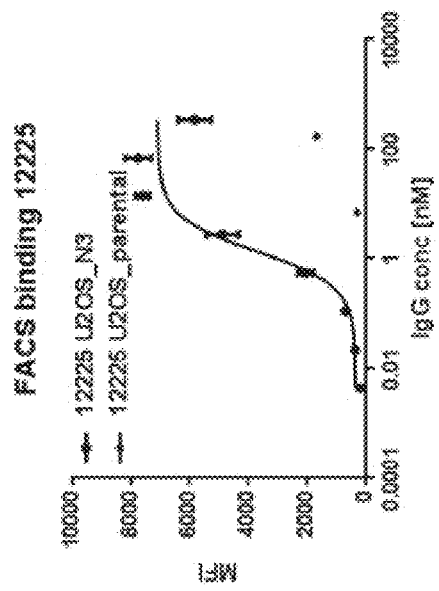
Figure 5C:
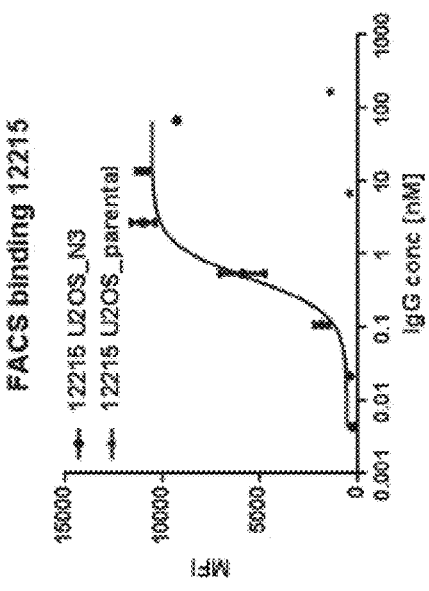
Figure 6B:
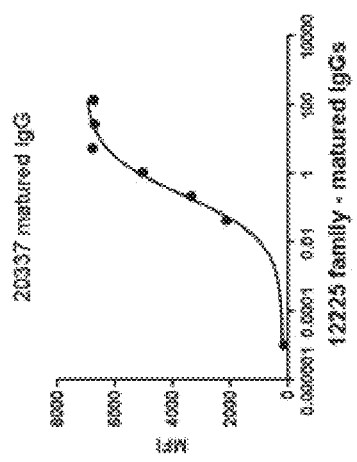
Figure 6C:
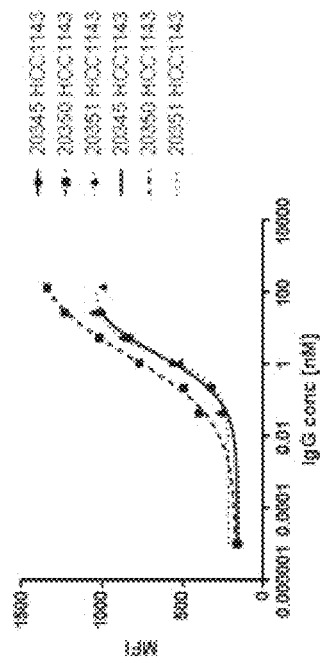
Figure 6D:
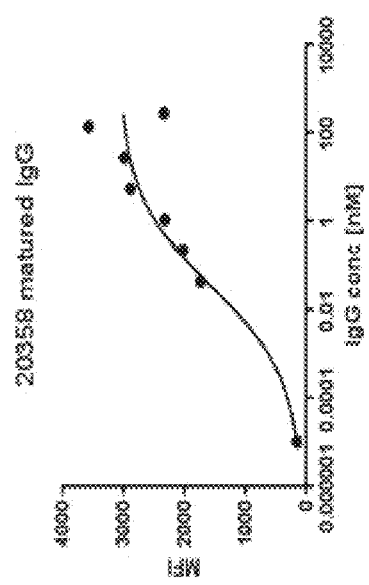
Figure 6E:
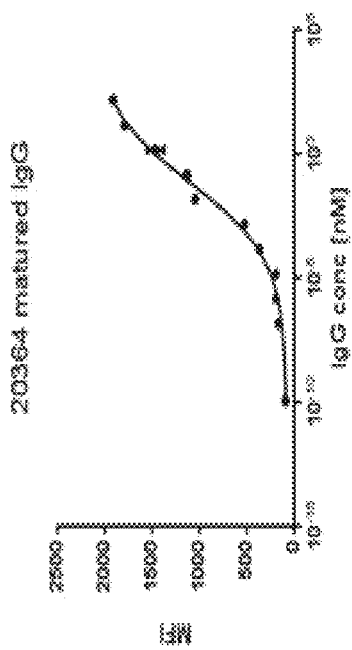
Figure 6F:
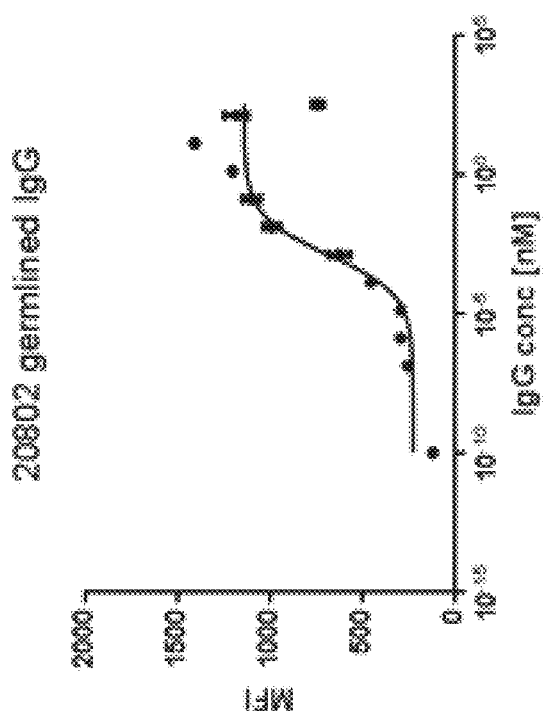
Figure 7B:
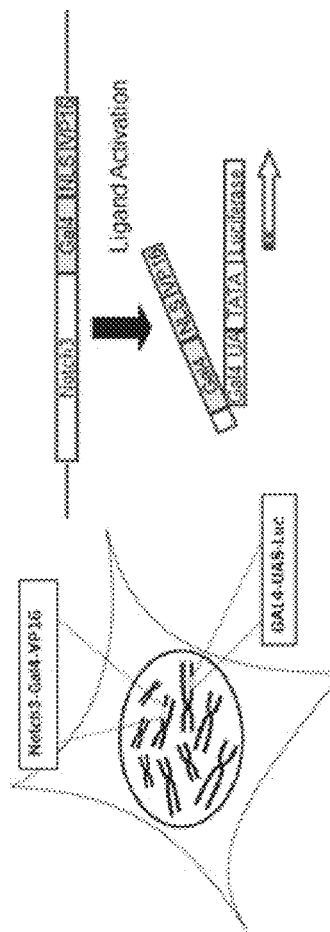
Figure 7C:
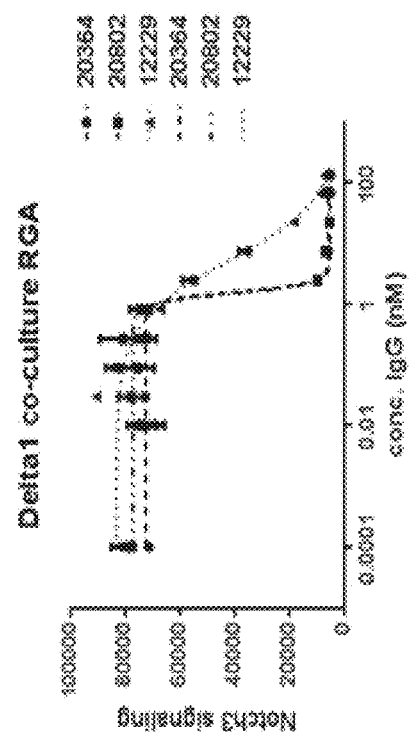
Figure 7D:
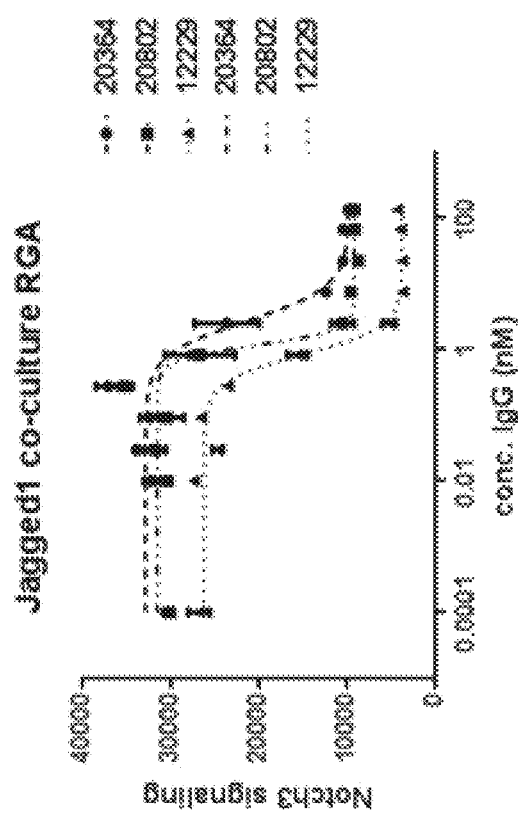

The term "Notch 3" or "Notch 3 receptor" as used herein refers to mammalian human Notch 3 protein. The domain structure of Notch 3 is depicted in FIG. 1, which shows the ligand binding domain (LBD), negative regulatory region (NRR) comprising the Lin Notch Repeats (LNR) and the N-, C-terminal heterodimerization domain (HD-N and HD-C, respectively), as well as the ankyrin domain (ANK) and PEST domains. FIG. 2 shows the overall structure of Notch 3 NRR and the corresponding amino acid residues: LNR-A has amino acid residues E1383-G1422; LNR-A-B linker has amino acid residues Asp1423-Leu-1431; LNR-B has amino acid residues Gln1432-Ala1460; LNR-BC linker has amino acid residues Gly1461-Asn1468; LNR-C has amino acid residues Pro1469-Ser1502; LNR-HD linker has amino acid residues Glu1503-Arg1510; HD-N has amino acid residues Gly1511-Arg1571; and HD-C has amino acid residues 1572-Ser1640.

Human Notch 3, as represented below as SEQ ID NO: 1.

```
(SEQ ID NO: 1)
MGPGARGRRRRRRPMSPPPPPPPVRALPLLLLLAGPGAAAPPCLDGSPCA

NGGRCTQLPSREAACLCPPGWVGERCQLEDPCHSGPCAGRGVCQSSVVAG

TARFSCRCPRGFRGPDCSLPDPCLSSPCAHGARCSVGPDGRFLCSCPPGY

QGRSCRSDVDECRVGEPCRHGGTCLNTPGSFRCQCPAGYTGPLCENPAVP

CAPSPCRNGGTCRQSGDLTYDCACLPGFEGQNCEVNVDDCPGHRCLNGGT

CVDGVNTYNCQCPPEWTGQFCTEDVDECQLQPNACHNGGTCFNTLGGHSC

VCVNGWTGESCSQNIDDCATAVCFHGATCHDRVASFYCACPMGKTGLLCH

LDDACVSNPCHEDAICDTNPVNGRAICTCPPGFTGGACDQDVDECSIGAN

PCEHLGRCVNTQGSFLCQCGRGYTGPRCETDVNECLSGPCRNQATCLDRI

GQFTCICMAGFTGTYCEVDIDECQSSPCVNGGVCKDRVNGFSCTCPSGFS

GSTCQLDVDECASTPCRNGAKCVDQPDGYECRCAEGFEGTLCDRNVDDCS

PDPCHHGRCVDGIASFSCACAPGYTGTRCESQVDECRSQPCRHGGKCLDL

VDKYLCRCPSGTTGVNCEVNIDDCASNPCTFGVCRDGINRYDCVCQPGFT

GPLCNVEINECASSPCGEGGSCVDGENGFRCLCPPGSLPPLCLPPSHPCA
```

-continued

HEPCSHGICYDAPGGFRCVCEPGWSGPRCSQSLARDACESQPCRAGGTCS
SDGMGFHCTCPPGVQGRQCELLSPCTPNPCEHGGRCESAPGQLPVCSCPQ
GWQGPRCQQDVDECAGPAPCGPHGICTNLAGSFSCTCHGGYTGPSCDQDI
NDCDPNPCLNGGSCQDGVGSFSCSCLPGFAGPRCARDVDECLSNPCGPGT
CTDHVASFTCTCPPGYGGFHCEQDLPDCSPSSCFNGGTCVDGVNSFSCLC
RPGYTGAHCQHEADPCLSRPCLHGGVCSAAHPGFRCTCLESFTGPQCQTL
VDWCSRQPCQNGGRCVQTGAYCLCPPGWSGRLCDIRSLPCREAAAQIGVR
LEQLCQAGGQCVDEDSSHYCVCPEGRTGSHCEQEVDPCLAQPCQHGGTCR
GYMGGYMCECLPGYNGDNCEDDVDECASQPCQHGGSCIDLVARYLCSCPP
GTLGVLCEINEDDCGPGPPLDSGPRCLHNGTCVDLVGGFRCTCPPGYTGL
RCEADINECRSGACHAAHTRDCLQDPGGGFRCLCHAGFSGPRCQTVLSPC
ESQPCQHGGQCRPSPGPGGGLTFTCHCAQPFWGPRCERVARSCRELQCPV
GVPCQQTPRGPRCACPPGLSGPSCRSFPGSPPGASNASCAAAPCLHGGSC
RPAPLAPFFRCACAQGWTGPRCEAPAAAPEVSEEPRCPRAACQAKRGDQR
CDRECNSPGCGWDGGDCSLSVGDPWRQCEALQCWRLFNNSRCDPACSSPA
CLYDNFDCHAGGRERTCNPVYEKYCADHFADGRCDQGCNTEECGWDGLDC
ASEVPALLARGVLVLTVLLPPEELLRSSADFLQRLSAILRTSLRFRLDAH
GQAMVFPYHRPSPGSEPRARRELAPEVIGSVVMLEIDNRLCLQSPENDHC
FPDAQSAADYLGALSAVERLDFPYPLRDVRGEPLEPPEPSVPLLPLLVAG
AVLLLVILVLGVMVARRKREHSTLWFPEGFSLHKDVASGHKGRREPVGQD
ALGMKNMAKGESLMGEVATDWMDTECPEAKRLKVEEPGMGAEEEAVDCRQW
TQHHLVAADIRVAPAMALTPPQGDADADGMDVNVRGPDGFTPLMLASFCG
GALEPMPTEEDEADDTSASIISDLICQGAQLGARTDRTGETALHLAARYA
RADAAKRLLDAGADTNAQDHSGRTPLHTAVTADAQGVFQILIRNRSTDLD
ARMADGSTALILAARLAVEGMVEELIASHADVNAVDELGKSALHWAAAVN
NVEATLALLKNGANKDMQDSKEETPLFLAAREGSYEAAKLLLDHFANREI
TDHLDRLPRDVAQERLHQDIVRLLDQPSGPRSPPGPHGLGPLLCPPGAFL
PGLKAAQSGSKKSRRPPGKAGLGPQGPRGRGKKLTLACPGPLADSSVTLS
PVDSLDSPRPFGGPPASPGGFPLEGPYAAATATAVSLAQLGGPGRAGLGR
QPPPGGCVLSLGLLNPVAVPLDWARLPPPAPPGPSFLLPLAPGPQLLNPGT
PVSPQERPPPYLAVPGHGEEYPAAGAHSSPPKARFLRVPSEHPYLTPSPE
SPEHWASPSPPSLSDWSESTPSPATATGAMATTTGALPAQPLPLSVPSSL
AQAQTQLGPQPEVTPKRQVLA

Cynomolgus monkey Notch 3 is represented below as SEQ ID NO: 2.

(SEQ ID NO: 2)
MGPGARGRRRRRRPMSPPPPPVRALPLLLLLAGPGAAVPPCLDGSPCANG
GRCTQLPSREAACLCPPGWVGERCQLEDPCHSGPCAGRGVCQSSVVAGTA
RFSCRCPRGFRGPDCSLPDPCLSSPCAHSARCSVGPDGRFLCSCPPGYQG
RSCRSDVDECRVGEPCRHGGTCLNTPGSFRCQCPAGYTGPLCENPAVPCA
PSPCRNGGTCRQSGDLTYDCACLPGFEGQNCEVNVDDCPGHRCLNGGTCV
DGVNTYNCQCPPEWTGQFCTEDVDECQLQPNACHNGGTCFNTLGGHSCVC
VNGWTGESCSQNIDDCATAVCFHGATCHDRVASFYCACPMGKTGLLCHLD
DACVSNPCHEDAICDTNPVNGRAICTCPPGFTGGACDQDVDECSIGANPC
EHLGRCVNTQGSFLCQCGRGYTGPRCETDVNECLSGPCRNQATCLDRIGQ
FTCICMAGFTGTYCEVDIDECQSSPCVNGGICKDRVNGFSCTCPSGFSGS
TCQLDVDECASTPCRNGAKCVDQPDGYECRCAEGFEGMLCERNVDDCSPD
PCHHGRCVDGIASFSCACAPGYTGTRCESQVDECRSQPCRHGGKCLDLVD
KYLCRCPSGTTGVNCEVNIDDCASNPCSFGVCRDGINRYDCVCQPGFTGP
LCNVEINECASSPCGEGGSCVDGENGFRCLCPPGSLPPLCLPPSHPCAHE
PCSHGICYDAPGGFRCVCEPGWSGPRCSQSLARDACESQPCRAGGTCSSD
GMGFHCTCPPGVQGRQCELLSPCTPNPCEHGGRCESAPGQLPVCSCPQGW
QGPRCQQDVDECAGPAPCGPHGICTNLAGSFSCTCHGGYTGPSCDQDIND
CDPNPCLNGGSCQDGVGSFSCSCLLGFAGPRCARDVDECLSNPCGPGTCT
DHVASFTCTCPPGYGGFHCEQDLPDCSPSSCFNGGTCVDGVNSFSCLCRP
GYTGAHCQHEADPCLSRPCLHGGVCSAAHPGFRCTCPQSFTGPQCQTLVD
WCSRQPCQNGGRCVQTGAYCLCPPGWSGRLCDIRSLPCREAAAQIGVRLE
QLCQAGGQCVDEDSSHYCVCPEGRTGSHCEQEVDPCLAQPCQHGGTCRGY
MGGYMCECLPGYNGENCEDDVDECASQPCQHGGSCIDLVARYLCSCPPGT
LGVLCEINEDDCGPGPPLDSGPRCLHNGTCVDLVGGFRCTCPPGYTGLRC
EADINECRSGACHAAHTRDCLQDPGGGFRCLCHAGFSGPRCQTVLSPCES
QPCQHGGQCRPSPGPGGGLTFTCHCAQPFWGPRCERVARSCRELQCPVGV
PCQQTPRGPRCACPPGLSGPSCRSFSGSPPGASNASCAAAPCLHGGSCRP
APLAPFFRCACAQGWTGPRCEAPAAAPEVSEEPRCPRAACQAKRGDQRCD
RECNSPGCGWDGGDCSLSVGDPWRQCEALQCWRLFNNSRCDPACSSPACL
YDNFDCHAGGRERTCNPVYEKYCADHFADGRCDQGCNTEECGWDGLDCAS
EVPALLARGVLVLTVLLPPEELLRSSADFLQRLSAILRTSLRFRLDAHGQ
AMVFPYHRPSPGSEPRARRELAPEVIGSVVMLEIDNRLCLQSPENDHCFP
DAQSAADYLGALSAVERLDFPYPLRDVRGEPLEPPEPSVPLLPLLVAGAV
LLLVILVLGVMVARRKREHSTLWFPEGFSLHKDVAAGHKGRREPVGQDAL
GMKNMAKGESLMGEVATDWMDTECPEAKRLKVEELGMGAEEEAVDCRQWTQ
HHLVAADIRVAPAMALTPPQGDADADGMDVNVRGPDGFTPLMLASFCGGA
LEPMPTEEDEADDTSASIISDLICQGAQLGARTDRTGETALHLAARYARA
DAAKRLLDAGADTNAQDHSGRTPLHTAVTADAQGVFQILIRNRSTDLDAR
MADGSTALILAARLAVEGMVEELIASHADVNAVDELGKSALHWAAAVNNV
EATLALLKNGANKDMQDSKEETPLFLAAREGSYEAAKLLLDHFANREITD
HLDRLPRDVAQERLHQDIVRLLDQPSGPRSPPGTHGLGPLLCPPGAFLPG
LKVTQSGSKKSRRPPGKAGLGPQGPRGRGKKLTLACPGPLADSSVTLSPV
DSLDSPRPFGGPPASPGGFPLEGPYAAATATAVSLAQLGGPGRAGLGRQP
PGGCVLSLGLLNPVAVPLDWARLPPPAPPGPSFLLPLAPGPQLLNPGTPV
SPQERPPPYLAVPGHGEEYPAAGAHSSPPKARFLRVPSEHPYLTPSPESP

-continued

EHWASPSPPSLSDWSESTPSPATATGAMATATGALPAQPLPLSVPSSLAQ

AQTQLGPQPEVTPKRQVLA

The term "Notch ligand" as used herein refers to polypeptides which bind and activate Notch 3 receptor. Examples of Notch 3 ligands include, but are not limited to Delta-like ligands (e.g., DLL1, DLL3, and DLL4) and Jagged ligands (e.g., Jagged 1, and Jagged 2).

The term "stabilization" or "stabilized" used in the context of Notch 3 refers to an antibody or fragment thereof that directly maintains (locks, tethers, holds, preferentially binds, favors) the autoinhibited conformation or state of Notch 3 receptor. Assays described in the Examples can be used to measure signal transduction of the stabilized Notch 3 receptor, e.g. in vitro screening using an ICD3 antibody disclosed herein.

The term "ligand-dependent signaling" as used herein refers to the activation of Notch 3 via ligand (e.g., Delta or Jagged ligand). Ligand binding results in Notch 3 proteolytic cleavage events that lead to Notch 3 signal transduction. The antibody or fragment thereof can inhibit Notch 3 signaling of a cell exposed to the antibody or fragment thereof relative to an untreated (control) cell, as measured using the assays described in the Examples. The cell which expresses Notch 3 can be a naturally occurring cell line or can be recombinantly produced by introducing nucleic acids encoding Notch 3 protein into a host cell.

The term "ligand-independent signaling" as used herein refers to cellular Notch 3 activity (e.g., Notch 3 cleaved at an S2 within the NRR domain and subsequently cleaved at S3 site in the absence of a requirement for ligand binding. For example, ligand-independent Notch 3 activation can be a result of Notch 3 overexpression/amplification or activating mutations in Notch 3. The antibody or fragment thereof can inhibit Notch 3 signaling of a cell exposed to antibody or fragment thereof relative to an unmutated (control) cell, as measured using the assays described in the Examples. The cell which overexpresses Notch 3 can be a naturally occurring cell line (e.g. HCC1143, TALL-1) or can be recombinantly produced by introducing nucleic acids encoding Notch 3 protein into a host cell. In another example, a cell may have both ligand-dependent and ligand-independent Notch 3 signaling.

The term "blocks" as used herein refers to stopping or preventing an interaction or a process, e.g., stopping ligand-dependent or ligand-independent signaling.

The term "recognize" as used herein refers to an antibody or fragment thereof that finds and interacts (e.g., binds) with its conformational epitope.

The term "antibody" as used herein refers to whole antibodies that interact with (e.g., by binding, steric hindrance, stabilizing spatial distribution) a Notch 3 epitope and inhibit signal transduction. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and $V_L$ regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes for example, monoclonal antibodies, human antibodies, humanized antibodies, camelized antibodies, chimeric antibodies, single-chain Fvs (scFv), disulfide-linked Fvs (sdFv), Fab fragments, F (ab') fragments, and anti-idiotypic (anti-Id) antibodies (including, e.g., anti-Id antibodies to antibodies of the disclosure), and epitope-binding fragments of any of the above. The antibodies can be of any isotype (e.g., IgG, IgE, IgM, IgD, IgA and IgY), class (e.g., IgG1, IgG2, IgG3, IgG4, IgA1 and IgA2) or subclass.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen-binding site or amino-terminus of the antibody. The N-terminus is a variable region and at the C-terminus is a constant region; the CH3 and CL domains actually comprise the carboxy-terminus of the heavy and light chain, respectively.

The phrase "antibody fragment", as used herein, refers to one or more portions of an antibody that retain the ability to specifically interact with (e.g., by binding, steric hindrance, stabilizing spatial distribution) a Notch 3 epitope and inhibit signal transduction. Examples of binding fragments include, but are not limited to, a Fab fragment, a monovalent fragment consisting of the VL, VH, CL and CH1 domains; a F(ab)$_2$ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR).

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883). Such single chain antibodies are also intended to be encompassed within the term "antibody fragment". These antibody fragments are obtained using conventional techniques known to those of skill in the art, and the fragments are screened for utility in the same manner, as are intact antibodies.

Antibody fragments can also be incorporated into single domain antibodies, maxibodies, minibodies, intrabodies, diabodies, triabodies, tetrabodies, v-NAR and bis-scFv (see, e.g., Hollinger and Hudson, (2005) Nature Biotechnology 23:1126-1136). Antibody fragments can be grafted into scaffolds based on polypeptides such as Fibronectin type III (Fn3) (see U.S. Pat. No. 6,703,199, which describes fibronectin polypeptide monobodies).

Antibody fragments can be incorporated into single chain molecules comprising a pair of tandem Fv segments (VH-CH1-VH-CH1) which, together with complementary light chain polypeptides, form a pair of antigen binding regions (Zapata et al., (1995) Protein Eng. 8:1057-1062; and U.S. Pat. No. 5,641,870).

The phrases "monoclonal antibody" or "monoclonal antibody composition" as used herein refers to polypeptides, including antibodies, antibody fragments, bispecific antibodies, etc. that have substantially identical to amino acid sequence or are derived from the same genetic source. This term also includes preparations of antibody molecules of single molecular composition. A monoclonal antibody composition displays a single binding specificity and affinity for a particular epitope.

The phrase "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., (2000) J Mol Biol 296:57-86). The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g., Sequences of Proteins of Immunological Interest, U.S. Department of Health and Human Services (1991), eds. Kabat et al.; Lazikani et al., (1997) J. Mol. Bio. 273:927-948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mol. Biol. 273:927-948.

The human antibodies disclosed herein may include amino acid residues not encoded by human sequences (e.g., mutations introduced by random or site-specific mutagenesis in vitro or by somatic mutation in vivo, or a conservative substitution to promote stability or manufacturing).

The phrase "human monoclonal antibody" as used herein refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The phrase "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Specific binding between two entities means a binding with an equilibrium constant ($K_A$) ($k_{on}/k_{off}$) of at least $10^2 M^{-1}$, at least $5 \times 10^2 M^{-1}$, at least $10^3 M^{-1}$, at least $5 \times 10^3 M^{-1}$, at least $10^4 M^{-1}$ at least $5 \times 10^4 M^{-1}$ at least $10^5 M^{-1}$ at least $5 \times 10^5 M^{-1}$ at least $10^6 M^{-1}$ at least $5 \times 10^6 M^{-1}$, at least $10^7 M^{-1}$, at least $5 \times 10^7 M^{-1}$, at least $10^8 M^{-1}$, at least $5 \times 10^8 M^{-1}$ at least $10^9 M^{-1}$, at least $5 \times 10^9 M^{-1}$ at least $10^{10} M^{-1}$, at least $5 \times 10^{10} M^{-1}$ at least $10^{11} M^{-1}$ at least $5 \times 10^{11} M^{-1}$, at least $10^{12} M^{-1}$, at least $5 \times 10^{12} M^{-1}$ at least $10^{13} M^{-1}$, at least $5 \times 10^{13} M^{-1}$, at least $10^{14} M^{-1}$, at least $5 \times 10^{14} M^{-1}$, at least $10^{15} M^{-1}$, or at least $5 \times 10^{15} M^{-1}$.

The phrase "specifically (or selectively) binds" to an antibody (e.g., a Notch 3 binding antibody) refers to a binding reaction that is determinative of the presence of a cognate antigen (e.g., a human Notch 3) in a heterogeneous population of proteins and other biologics. In addition to the equilibrium constant ($K_A$) noted above, a Notch 3 binding antibody disclosed herein typically also has a dissociation rate constant ($K_D$) ($k_{off}/k_{on}$) of less than $5 \times 10^{-2} M$, less than $10^{-2} M$, less than $5 \times 10^{-3} M$, less than $10^{-3} M$, less than $5 \times 10^{-4} M$, less than $10^{-4} M$, less than $5 \times 10^{-5} M$, less than $10^{-5} M$, less than $5 \times 10^{-6} M$, less than $10^{-6} M$, less than $5 \times 10^{-7} M$, less than $10^{-7} M$, less than $5 \times 10^{-8} M$, less than $10^{-8} M$, less than $5 \times 10^{-9} M$, less than $10^{-9} M$, less than $5 \times 10^{-10} M$, less than $10^{-10} M$, less than $5 \times 10^{-11} M$, less than $10^{-11} M$, less than $5 \times 10^{-12} M$, less than $10^{-12} M$, less than $5 \times 10^{-13} M$, less than $10^{-13} M$, less than $5 \times 10^{-14} M$, less than $10^{-14} M$, less than $5 \times 10^{-15} M$, or less than $10^{-15} M$ or lower, and binds to Notch 3 with an affinity that is at least two-fold greater than its affinity for binding to a non-specific antigen (e.g., HSA).

In one embodiment, the antibody or fragment thereof has dissociation constant ($K_d$) of less than 3000 pM, less than 2500 pM, less than 2000 pM, less than 1500 pM, less than 1000 pM, less than 750 pM, less than 500 pM, less than 250 pM, less than 200 pM, less than 150 pM, less than 100 pM, less than 75 pM, less than 10 pM, less than 1 pM as assessed using a method described herein or known to one of skill in the art (e.g., a BIAcore assay, ELISA, FACS, SET) (Biacore International AB, Uppsala, Sweden). The term "$K_{assoc}$," or "$K_a$," as used herein, refers to the association rate of a particular antibody-antigen interaction, whereas the term "$K_{dis}$" or "$K_d$," as used herein, refers to the dissociation rate of a particular antibody-antigen interaction. The term "$K_D$", as used herein, refers to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "avidity" as used herein refers to an informative measure of the overall stability or strength of the antibody-antigen complex. It is controlled by three major factors: antibody epitope affinity; the valence of both the antigen and antibody; and the structural arrangement of the interacting parts. Ultimately, these factors define the specificity of the antibody, that is, the likelihood that the particular antibody is binding to a precise antigen epitope.

The term "valency" as used herein refers to the number of potential target binding sites in a polypeptide. Each target-binding site specifically binds one target molecule or specific site (i.e. epitope) on a target molecule. When a polypeptide comprises more than one target-binding site, each target-binding site may specifically bind the same or different molecules (e.g., may bind to different molecules, e.g., different antigens, or different epitopes on the same molecule).

The phrase "antagonist antibody" as used herein refers to an antibody that binds with Notch 3 and inhibits Notch 3 signaling, as determined by the assays described herein, e.g., ICD3 assay. Accordingly, an antibody that "inhibits" one or more of the Notch 3 functional properties (e.g., biochemical, immunochemical, cellular, physiological or other biological activities, or the like) as determined according to the assays described herein, will be understood to relate to a statistically significant decrease in the particular activity relative to that seen in the absence of the antibody (e.g., or when a control antibody of irrelevant specificity is present). An antibody that inhibits Notch 3 activity effects such a statistically significant decrease by at least 10% of the measured parameter, by at least 50%, 80% or 90%, and in certain embodiments an antibody disclosed herein may inhibit greater than 95%, 98% or 99% of Notch 3 functional activity.

The phrase "isolated antibody" refers to an antibody that is substantially free of other antibodies having different antigenic specificities (e.g., an isolated antibody that specifically binds Notch 3 is substantially free of antibodies that specifically bind antigens other than Notch 3). An isolated antibody that specifically binds Notch 3 may, however, have cross-reactivity to other antigens. Moreover, an isolated antibody may be substantially free of other cellular material and/or chemicals.

The term "epitope" includes any protein determinant capable of specific binding to an immunoglobulin or otherwise interacting with a molecule. Epitopic determinants generally consist of chemically active surface groupings of molecules such as amino acids or carbohydrate or sugar side chains and can have specific three-dimensional structural characteristics, as well as specific charge characteristics. An epitope may be "linear" or "conformational."

The term "linear epitope" refers to an epitope with all of the points of interaction between the protein and the interacting molecule (such as an antibody or fragment thereof) occur linearly along the primary amino acid sequence of the protein (continuous). Once a desired epitope on an antigen is determined, it is possible to generate antibodies to that epitope, e.g., using the techniques described herein. Alternatively, during the discovery process, the generation and characterization of antibodies or fragments thereof may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughput process for "binning" antibodies based upon their cross-competition is described in International Patent Application No. WO2003/4873.

The term "conformational epitope" refers to an epitope in which discontinuous amino acid residues come together in a three dimensional shape. In a conformational epitope, the points of interaction occur across amino acid residues that are separated from one another by at least one amino acid residue (discontinuous), i.e., the points of contact occur on distinct and separate regions of the NRR such as the LNR region, the HD, as well as a linker region. For illustrative purposes only, the conformational epitope may also comprise continuous contacts on separate and distinct regions of NRR, for example continuous contacts with at least two amino acids in the LNR region, at least two amino acids in the HD region, and at least one amino acid residue in a linker region (e.g., LNR-A/B linker, LNR-B/C linker, LNR-HD linker). In one embodiment, the conformational epitope is that described in Examples herein. In one embodiment, the conformational epitope comprising discontinuous points of interaction between amino acid residues within the LNR region (LNR-A, LNR-B, LNR-C) and the HD (e.g., α3 helix). In one embodiment, the conformational epitope comprising discontinuous points of interaction between amino acid residues within the LNR region (LNR-A, LNR-B, LNR-C) and the HD and at least one linker between the LNR region (e.g., α3 helix) and the HD (e.g., LNR-HD linker). In one embodiment, the conformational epitope comprising discontinuous points of interaction between amino acid residues within the LNR region (LNR-A, LNR-B, LNR-C) and the HD (e.g., α3 helix), and at least one linker within the HD (e.g., β4-α3 loop). In one embodiment, the conformational epitope comprising discontinuous points of interaction between amino acid residues within the LNR region (LNR-A, LNR-B, LNR-C) and the HD (e.g., α2 helix), and at least one linker within the HD (e.g., α3-β5 loop). In one embodiment, the conformational epitope is defined by Notch 3 amino acid residues: 1427-1429 (of the LNR-A/B linker), 1442, 1444-1445, 1447-1450, 1453, 1458 (of LNR-B), 1461-1462, 1464 (of the LNR-B/C linker), 1507-1508, 1510 (of the LNR-HD linker), 1592, 1594-1599, 1602 (of the HD β4-α3 loop), and 1606 (of the HD α3 helix) or SEQ ID NO:1, or a subset thereof. In one embodiment, the conformational epitope is defined by Notch 3 amino acid residues: 1440 (of LNR-B), 1463, 1465-1468 (of the LNR-B/C linker) 1469-1472, 1474, 1486-1487 (of LNR-C), 1534 (of HD α2 helix), and 1618, 1619, and 1621 (of the α3-β5 loop) of SEQ ID NO: 1, or a subset thereof. In one embodiment, the conformational epitope is defined by Notch 3 amino acid residues: 1489-1498 (LNR-C), 1500-1506 (LNR-HD linker), 1538-1568 (HD) and 1571-1591 (HD). As will be appreciated by one of skill in the art, the space that is occupied by a residue or side chain that creates the shape of a molecule helps to determine what an epitope is.

Generally, antibodies specific for a particular target antigen will preferentially recognize an epitope on the target antigen in a complex mixture of proteins and/or macromolecules.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids such as by, e.g., hydrogen/deuterium exchange, X-ray crystallography and two-dimensional nuclear magnetic resonance. See, e.g. Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. Mol. Biol. 157:105-132; for hydropathy plots.

The term "paratope" as used herein refers to the general structure of a binding region that determines binding to an epitope. This structure influences whether or not and in what manner the binding region might bind to an epitope. The term "pratope" can refer to an antigenic site of an antibody or fragment thereof that is responsible for an antibody or fragment thereof binding to an antigenic determinant. Paratope also refers to the idiotype of the antibody, and the complementary determining region (CDR) region that binds to the epitope.

In one embodiment, the conformational epitope is defined by Notch 3 amino acid residues: 1427-1429 (of the LNR-A/B linker), 1442, 1444-1445, 1447-1450, 1453, 1458 (of LNR-B), 1461-1462, 1464 (of the LNR-B/C linker), 1507-1508, 1510 (of the LNR-HD linker), 1592, 1594-1599, 1602 (of the HD β4-α3 loop), and 1606 (of the HD α3 helix) of SEQ ID NO:1, or a subset thereof. In one embodiment, the paratope is the region of the antibody that comprises the CDR sequences. In one embodiment, the paratope comprises the sequences listed in Table 2. In one embodiment, the paratope comprises at least one amino acid residue that binds with Notch 3 residues: Cys1442, Pro1444, Ala1445, Ser1447, Ser1448, Pro1449, Tyr1453, Cys1458, Gly1461, Gly1462, Gly1464, Leu1592, Ser1594, Pro1595, Glu1596, Asn1597, Asp1598, and His1599. In one embodiment, the paratope comprises at least one amino acid residue that binds with Notch 3 residues: Gln1427, Cys1428, Glu1429, Pro1444, Ser1445, Ser1447, Ser1448, Pro1449, Tyr1453, Leu1507, Leu1508, Arg1510, Leu1592, Asp1598, Pro1602, and Ser1606.

In one embodiment, the conformational epitope is defined by Notch 3 amino acid residues: 1440 (of LNR-B), 1463, 1465-1468 (of the LNR-B/C linker) 1469-1472, 1474, 1486-1487 (of LNR-C), 1534 (of HD α2 helix), and 1618, 1619, and 1621 (of the α3-β5 loop) of SEQ ID NO: 1, or a subset thereof. In one embodiment, the paratope comprises at least one amino acid residue that binds with Notch 3 residues: Arg1463, Thr1466, Asn1468, Pro1469, Val1470, Tyr1471, Tyr1474, Gln1486, and Gly1487. In one embodiment, the paratope comprises at least one amino acid residue that binds with Notch 3 residues: Ser1440, Arg1465, Thr1466, Asn1468, Pro1469, Val1470, Glu1472, Arg1434, Glu1618, Arg1619, and Asp1621.

As will be appreciated by one of skill in the art, the paratope of any antibody, or variant thereof, can be determined in the manner set forth by the present application.

The terms "cross-compete" and "cross-competing" are used interchangeably herein to mean the ability of an antibody or fragment thereof to interfere with the binding of other antibodies or fragments to Notch 3 in a standard competitive binding assay. In one embodiment, the term "cross-competes" refers to an antibody or fragment thereof that interferes with the binding of other antibodies or fragments thereof to at least one conformational epitope of Notch 3.

The ability or extent to which an antibody or other binding agent is able to interfere with the binding of another antibody or fragment thereof to Notch 3, and therefore whether it can be said to cross-compete according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competing uses an ELISA-based approach.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The phrase "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles disclosed herein. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "optimized" as used herein refers to a nucleotide sequence has been altered to encode an amino acid sequence using codons that are preferred in the production cell or organism, generally a eukaryotic cell, for example, a cell of *Pichia*, a cell of *Trichoderma*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

Standard assays to evaluate the binding ability of the antibodies toward Notch 3 of various species are known in the art, including for example, ELISAs, western blots and RIAs. Suitable assays are described in detail in the Examples. The binding kinetics (e.g., binding affinity) of the antibodies also can be assessed by standard assays known in the art, such as by Biacore analysis, or FACS relative affinity (Scatchard). Assays to evaluate the effects of the antibodies on functional properties of Notch 3 (e.g., receptor binding assays, modulating the Notch 3 signaling pathway) are described in further detail in the Examples.

The phrases "percent identical" or "percent identity," in the context of two or more nucleic acids or polypeptide sequences, refers to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman (1988) Proc. Natl. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The phrase "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The phrase "differentially expressed" as used herein refers to the differential production of the mRNA transcribed and/or translated from the gene or the protein product encoded by the gene. A differentially expressed gene may be overexpressed or underexpressed as compared to the expression level of a normal or control cell. However, as used herein, overexpression is an increase in gene expression and generally is at least 1.25 fold or, alternatively, at least 1.5 fold or, alternatively, at least 2 fold, or alternatively, at least 3 fold or alternatively, at least 4 fold expression over that detected in a normal or control counterpart cell or tissue. As used herein, underexpression is a reduction of gene expression and generally is at least 1.25 fold, or alternatively, at least 1.5 fold, or alternatively, at least 2 fold or alternatively, at least 3 fold or alternatively, at least 4 fold expression under that detected in a normal or control counterpart cell or tissue. The term "differentially expressed" also refers to where expression in a cancer cell or cancerous tissue is detected but expression in a control cell or normal tissue (e.g. non-cancerous cell or tissue) is undetectable.

A high expression level of the gene can occur because of over expression of the gene or an increase in gene copy number. The gene can also be translated into increased protein levels because of deregulation or absence of a negative regulator. Lastly, high expression of the gene can occur due to increased stabilization or reduced degradation of the protein, resulting in accumulation of the protein.

A "gene expression profile" or "gene signature" refers to a pattern of expression of at least one biomarker that recurs in multiple samples and reflects a property shared by those samples, such as mutation, response to a particular treatment, or activation of a particular biological process or pathway in the cells. A gene expression profile differentiates between samples that share that common property and those that do not with better accuracy than would likely be achieved by assigning the samples to the two groups at random. A gene expression profile may be used to predict whether samples of unknown status share that common property or not. Some variation between the biomarker(s) and the typical profile is to be expected, but the overall similarity of biomarker(s) to the typical profile is such that it is statistically unlikely that the similarity would be observed by chance in samples not sharing the common property that the biomarker(s) reflects.

Various aspects of the disclosure are described in further detail in the following sections and subsections Notch 3 Receptor Notch signaling is an evolutionarily conserved pathway that regulates a diverse set of biological functions including stem cell maintenance, cell differentiation and proliferation in both embryonic development and adult tissues (Kopan et al., (2009) Cell 137: 216-233, Guruharsha et al., (2012) Nat Rev Genet. 13: 654-66, and Andersson et al., (2001) Development 138: 3593-3612). In mammals, four Notch receptors have been described (Notch1-4), which have a conserved domain architecture. The extracellular domain (ECD) consists of a series of EGF-like repeats followed by a negative regulatory region (NRR) which contains 3 LNR repeats and a heterodimerization domain as shown in FIG. 1.

In solid tumors, the role of Notch signaling in tumor initiation and progression is not well understood (Ranganathan et al., (2011) Nat Rev Cancer 11:338-51). Early evidence for Notch receptors in transformation of epithelial cells came from mouse mammary tumor virus (MMTV)

insertional mutagenesis studies. For example, activation of Notch4 (initially known as Int3) by MMTV, resulted in mammary tumorigenesis (Gallahan et al., (1987) J Virol 61:218-220, Gallahan et al., (1997) Oncogene 14: 1883-1890). In 2011, rearrangements of Notch1 or Notch2 in estrogen receptor (ER) negative breast cancer were identified (Robinson et al., (2011) Nat Med 17:1646-51). These rearrangements of the Notch receptor result in production of a membrane tethered form of the receptor lacking an intact NRR domain or an ICD-like protein.

Notch3 NRR has a similar overall folding as that of Notch1 (Gordan et al., (2009) Blood 113:4381-4390; Gordon et al., (2009) 4:e6613; Wu et al., (2010) Nature 464: 1052-1057) and Notch2 (Gordon et al., (2007) Nat Struct Mol Biol 14:295-300). It is composed of three Lin12/Notch repeats (LNR), namely LNR-A, LNR-B and LNR-C; and a heterodimerization (HD) domain divided into N-terminal part (HD-N) and C-terminal part (HD-C) by furin cleavage at S1 site (between R1571 and E1572) (see FIG. 2).

NRR domains regulate the activation of Notch receptors, which involves three proteolysis steps. Furin-like convertase cleaves at S1 site within NRR during maturation of Notch precursor, to prime the activation. ADAM proteases cleave at S2 site, also within NRR, to create the substrate for intramembrane proteolysis at S3 site by gamma secretase. Following S3 cleavage, the intracellular part of Notch then enters nucleus to activate transcription. S2 cleavage is the key step of this activation series and is negatively regulated by NRR domains. The mechanism of this so called autoinhibition can be explained by NRR structures below.

Although not bound to provide a theory, one possible model for the mechanism of action is that Notch 3 NRR typically exists in an autoinhibited conformation in which the three LNRs, each coordinating a $Ca^{2+}$ ion, wrap around HD to protect S2 site from access by ADAM proteases. The stability of the interactions between LNRs and HD, as well as those within these regions, is critical to maintain the autoinhibited conformation of NRR. Mutations in the Notch 3 NRR alter the autoinhibited conformation, thereby exposing the HD domain, such that the S2, and subsequently the S3 site is available for cleavage by proteases, thereby activating downstream Notch 3 signal transduction. Therefore, mutations destabilizing NRR, like those found in relevant cancers (disclosed herein), could enhance activation of Notch 3. On the other hand, reagents like antibodies or fragments thereof that can stabilize LNR-HD interaction can potentially inhibit Notch 3 signaling. Antibodies or fragments thereof such as 20350, and 20358 bind the autoinhibited conformation of Notch 3 and stabilizes (directly maintains, holds, locks,) the autoinhibited conformation thereby preventing exposure of the S2 site to protease cleavage, and subsequent downstream Notch 3 signaling.

In some embodiments, the antibody or fragment thereof binds to the conformational epitope such that it restricts the mobility of the LNR regions (LNR-A, LNR-B, LNR-C as well as corresponding linkers between LNR domains) relative to HD, stabilizing Notch 3 NRR in an autoinhibited conformation. The failure to form the active (uninhibited, open) conformation results in failure to activate signal transduction. In some embodiments, the antibody or fragment thereof binds to the conformational epitope such that it prevents the HD within the NRR from becoming exposed, thereby rendering it unavailable for cleavage at the S2, and/or S3 sites by proteases. The failure to cleave the S2 site results in failure to activate signal transduction.

Notch 3 Mutants

In one aspect, the disclosure pertains to mutations in the Notch 3 receptor. Activating mutations in Notch1 were identified in >50% of T-ALL patients in two general regions of the receptor (Weng et al., (2004) Science 306:269-71). One class of mutations was found to be clustered in the hydrophobic core of the HD domain of the NRR. Rare mutations have also been identified in the LNR domain (Gordon et al., (2009) Blood 113:4381-4390). The NRR mutations likely act by partially, or completely unfolding the HD domain, altering the pocket that protects the S2 site and disrupting interactions with the LNR. This hypothesis is supported by biochemical data that HD domains with leukemia-associated mutations are less stable (Malecki et al., (2006) Mol. Cell Biol. 26:4642-4651).

Mutations were also identified in the PEST (proline-glutamate-serine-threonine-rich) domain at the C-terminus of the protein. The levels of the ICD are tightly regulated and phosphorylation of the PEST domain and subsequent ubiquitination, target the ICD for degradation by E3 ligases such as Fbw7. Mutations are either nonsense mutations or frameshift mutations that result in deletion of the PEST domain and result in an ICD with increased stability and longer protein half-life.

To date, the evidence for Notch receptors in cancer has focused primarily on alterations in Notch1 signaling. However, Notch 3 has been shown in several studies, including the TCGA analysis of serous ovarian cancer to be amplified in 11-25% of patient samples (Nakayama et al., (2007) Int J Cancer 120:2613-17, Etemadmoghadam et al., (2009) Clin Can Res 15: 1417-27, Bell et al., (2011) Nature 474:609-615). Although mutations in Notch 3 have been reported in Cerebral Autosomal Dominant Arteriopathy with Subcortical Infarcts and Leukoencephalopathy (CADASIL) syndrome, these mutations are generally missense in nature and the link to alterations in Notch 3 function and disease pathology is not clear (see Ayata, (2010), Stroke 41:S129-S134). Comprehensive analysis of gene mutations in various cancer types has been performed by TCGA and other organizations. The standard technique used is exon-capture. As part of these studies, Notch 3 mutations have been reported in around 1% of head and neck squamous carcinomas, ovarian cancers and lung adenocarcinoma. However, the lack of sufficient exon coverage for Notch 3 exon 25, and 33 make it difficult for the skilled artisan to look for mutations in the Notch 3 gene. Further, the high GC content in the Notch 3 gene has discouraged the skilled artisan from looking at mutations. In addition, the mutations identified in squamous cell lung cancer have been suggested to be loss of function mutations (see Egloff & Grandis (2012) Clin Can Res 18:5188-519). In contrast, and contrary to previous studies, the disclosure herein shows a number of mutations that activate Notch 3 signal transduction ("activating mutations") and lead to increased cancer.

To identify Notch 3 mutations, 947 human cancer cell lines were characterized and mutation information was obtained for >1600 genes by massively parallel sequencing using a solution phase hybrid capture technology, as described in Example 5. In addition primary tumor samples were sequenced with RNAseq (Wang et al. (2009) Nature Reviews Genetics 10:57-63. Mutations were identified in both the NRR and PEST domain in multiple cell lines and tumor samples as shown in Table 1.

Activating mutations which interfere with the function of Notch 3 are involved in the pathogenesis of cancer. As the presence of an altered Notch 3 having a loss of function, gain of function or altered function, directly increases the risk of cancer, detection of such mutations lends itself to diagnostic and prognostic methods. The identification of such activating mutations may then be treated by antibodies or fragments thereof that bind to the mutant Notch 3.

TABLE 1

Notch 3 activating mutations

| Mutation | Cellular data | Structure-based interpretation |
|---|---|---|
| Group 1 | | |
| S1580L | Activating | Lose intra-domain hydrogen bonds and thus destabilize HD domain |
| R1510H | | |
| D1587N | | |
| R1589Q | | |
| Y1624H | | |
| Group 2 | | |
| G1487D | Activating | Affect structural integrity, cause clash |
| A1476T | | |
| A1609T | | |
| L1518M | | |
| A1537T | | |
| Group 3 | | |
| N1597K | Activating | On the surface of NRR, no obvious interpretation, but might interfere with protein-protein interaction |
| L1547V | | |
| R1526C | | |

Two mutations from the NRR domain from different cell-lines were selected for characterization: (i) TALL-1 cells, which are a T-cell acute lymphoblastic cell line with a S1580L mutation; and (ii) breast tumor (X-1004) with a G1487D mutation. The Examples show that introduction of either a S1580L mutation or a G1487D mutation into a Notch 3 receptor resulted in an approximately 10 fold increase in the basal signaling from the receptor relative to a wild-type control. In this system, the wild-type and mutant receptors were expressed at approximately equivalent levels as determined by FACS assay. This data shows that these mutations activate Notch3 signaling in cell lines and tumors expressing these and other similar mutations. This activation of Notch 3 signaling is inhibited by Notch 3 antibodies or fragments thereof.

In order to detect a Notch 3 mutant, a biological sample is prepared and analyzed for a difference between the sequence of the test sample thought to contain the mutant Notch 3 with the sequence of the wild-type Notch 3. Mutant Notch 3 can be identified by any of the techniques described herein. The mutant Notch 3 can be sequenced to identify the specific mutation (activating mutations that increase Notch 3 signal transduction). The mutations, especially those which lead to an altered function of the protein, are then used for the diagnostic and prognostic methods of the present invention.

For further analysis, cancer mutations of the Notch 3 mutants were mapped onto Notch 3 NRR X-ray crystal structure. Structural analysis shows that some of these mutations can disrupt intra- and inter-domain interactions, destabilize the autoinhibitory conformation of Notch 3 NRR and cause Notch 3 activation and signal transduction.

A comparison of these mutations with 20350 and 20358 epitopes (described below) shows that most of them are not within the epitopes, indicating that the 20350 and 20358 antibody fragments can bind both wild type and mutant Notch3 NRRs in its autoinhibited conformation and inhibit Notch 3 signal transduction.

In some embodiments, mutants can be introduced into wild-type Notch 3 (SEQ ID NO: 1) to investigate the effect on Notch 3 binding agents such as small molecule drugs or biologics, e.g., antibodies or fragments thereof. Mutagenesis using known techniques such as alanine-scanning can help define functionally relevant epitopes. Mutagenesis utilizing an arginine/glutamic acid scanning protocol can also be employed (see, e.g., Nanevicz et al., (1995), J. Biol. Chem. 270(37):21619-21625 and Zupnick et al., (2006), J. Biol. Chem. 281(29):20464-20473). In general, arginine and glutamic acids are substituted (typically individually) for an amino acid in the wild-type polypeptide because these amino acids are charged and bulky and thus have the potential to disrupt binding between an antigen binding protein and an antigen in the region of the antigen where the mutation is introduced. Arginines that exist in the wild-type antigen are replaced with glutamic acid. A variety of such individual mutants can be obtained and the collected binding results analyzed to determine what residues affect binding. A series of mutant Notch 3 can be created, with each mutant Notch 3 having a single mutation. Binding of each mutant Notch 3 with various Notch 3 Notch 3 binding agents such as small molecule drugs or biologics, e.g., antibodies or fragments thereof, and can be measured and compared to the ability of the selected Notch binding agents to bind wild-type Notch 3 (SEQ ID NO: 1).

An alteration (for example a reduction or increase) in binding between a Notch 3 binding agents such as antibodies or fragments thereof f and a mutant or variant Notch 3 means that there is a change in binding affinity (e.g., as measured by known methods such as Biacore testing or the bead based assay described below in the examples), $EC_{50}$, and/or a change (for example a reduction) in the total binding capacity of the antigen binding protein (for example, as evidenced by a decrease in $B_{max}$ in a plot of antigen binding protein concentration versus antigen concentration). A significant alteration in binding indicates that the mutated residue is involved in binding to the antibody or fragment thereof.

In some embodiments, a significant reduction in binding means that the binding affinity, $EC_{50}$, and/or capacity between an antibody or fragments thereof and a mutant Notch 3 antigen is reduced by greater than 10%, greater than 20%, greater than 40%, greater than 50%, greater than 55%, greater than 60%, greater than 65%, greater than 70%, greater than 75%, greater than 80%, greater than 85%, greater than 90% or greater than 95% relative to binding between the an antibody or fragment thereof and a wild type Notch 3 (e.g., SEQ ID NO: 1).

In some embodiments, binding of an antibody or fragments thereof is significantly reduced or increased for a mutant Notch 3 having one or more (e.g., 1, 2, 3, 4, 5, 6, 7, 8, 9, 10, or more) mutations as compared to a wild-type Notch3 protein (e.g., SEQ ID NO: 1).

Although the variant forms are referenced with respect to the wild-type sequence shown in SEQ ID NO: 1, it will be appreciated that in an allelic or splice variants of Notch 3 the amino acids could differ. Antibodies or fragments thereof showing significantly altered binding (e.g., lower or higher binding) for such allelic forms of Notch 3 are also contemplated. The skilled artisan will appreciate that any one of the mutants described in Table 1 can be combined with any other 1, 2, 3, 4, 5, 6, 7, 8, 9, 10, 11, or 12 of the other mutants in Table 1 to produce an "expression pattern" or "expression signature" that can be used to identify, diagnose, or monitor a subject.

In some embodiments, the expression signature comprises one or more group 1 mutations, for example a combination of S1580L, R1510H, D1587N, R1580Q, and Y1624H. In some embodiments, the expression signature comprises one or more group 2 mutations, for example a combination of G1487D, A1476T, A1609T, L1518M, and A1537T. In some embodiments, the expression signature comprises one or more group 3 mutations, for example a combination of N1597K, L1547V, and R1526C.

In some embodiments, the expression signature comprises one or more group 1 mutations, for example a combination of S1580L, R1510H, D1587N, R1580Q, and Y1624H; and one or more group 2 mutations, for example a combination of G1487D, A1476T, A1609T, L1518M, and A1537T. In some embodiments, the expression signature comprises one or more group 1 mutations, for example a combination of S1580L, R1510H, D1587N, R1580Q, and Y1624H; and one or more group 3 mutations, for example a combination of N1597K, L1547V, and R1526C. In some embodiments, the expression signature comprises one or more group 2 mutations, for example a combination of G1487D, A1476T, A1609T, L1518M, and A1537T; and one or more group 3 mutations, for example a combination of N1597K, L1547V, and R1526C.

Notch 3 Inhibitors

In one aspect, the disclosure pertains to Notch 3 inhibitors that inhibit Notch 3 activation.

Antibodies

In one embodiment, the Notch 3 inhibitor is an antibody or fragment thereof. Examples of antibodies include but are not limited to an antibody that binds a Notch protein or a Notch ligand protein and inhibits Notch ligand induced stimulation of Notch signaling. Such antibodies include, but are not limited to, polyclonal, monoclonal, chimeric, single chain, Fab fragments and fragments produced by a Fab expression library, bifunctional/bispecific antibodies, humanized antibodies, CDR grafted antibodies, human antibodies and antibodies which include portions of CDR sequences specific for a Notch protein or a Notch ligand protein.

Means for preparing and characterizing antibodies are well known in the art (see, e.g., Harlow and Lane, (1988). Antibodies: A Laboratory manual. Cold Spring Harbor Laboratory, Cold Spring Harbor, N.Y.). Briefly, a polyclonal antibody is prepared by immunizing an animal with an immunogen comprising a polypeptide of the present invention and collecting antisera from that immunized animal. A wide range of animal species can be used for the production of antisera. Typically, an animal used for production of anti-antisera is a non-human animal including rabbits, mice, rats, hamsters, goat, sheep, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. As used herein, the term "specific for" is intended to mean that the variable regions of the antibodies recognize and bind a Notch protein or a Notch ligand protein and are capable of distinguishing a Notch protein or a Notch ligand protein from other antigens. A composition containing antigenic epitopes of a Notch protein or a Notch ligand protein can be used to immunize one or more experimental animals, such as a rabbit or mouse, which will then proceed to produce specific antibodies against the Notch protein or a Notch ligand protein. Polyclonal antisera may be obtained, after allowing time for antibody generation, simply by bleeding the animal and preparing serum samples from the whole blood.

Monoclonal antibodies to a Notch protein or a Notch ligand protein may be prepared using any technique which provides for the production of antibody molecules by continuous cell lines in culture. These include but are not limited to the hybridoma technique originally described by Koehler and Milstein (1975) Nature, 256(5517), 495-497; the human B-cell hybridoma technique (Kosbor et al., (1983) Immunol. Today, 4, 72-79; Cote et al., (1983) Proc. Natl. Acad. Sci. USA., 80(7), 2026-2030; and the EBV-hybridoma technique (Cole et al., (1985 Monoclonal Antibodies and Cancer Therapy. (eds. R. A. Reisfeld and S. Sell), Alan R Liss Inc, New York N.Y., pp 77-96).

Methods of making antibody fusion proteins are well known in the art. See, e.g., U.S. Pat. No. 6,306,393, the disclosure of which is incorporated herein by reference in its entirety. In certain embodiments of the invention, fusion proteins are produced which may include a flexible linker, which connects the chimeric scFv antibody to the heterologous protein moiety. Appropriate linker sequences are those that do not affect the ability of the resulting fusion protein to be recognized and bind the epitope specifically bound by the V domain of the protein (see, e.g., WO 98/25965, the disclosure of which is incorporated herein by reference in its entirety).

In addition to the production of monoclonal antibodies, techniques developed for the production of "chimeric antibodies", the splicing of mouse antibody genes to human antibody genes to obtain a molecule with appropriate antigen specificity and biological activity can be used (Morrison et al., (1984), Nature, 368(6474), 812-813; Neuberger et al., (1984) Nature 312(5995), 604-608; Takeda et al., (1985) Nature, 314(6010), 452-454. Alternatively, techniques described for the production of single chain antibodies (U.S. Pat. No. 4,946,778) can be adapted to produce a Notch protein or a Notch ligand protein-specific single chain antibodies.

Antibodies may also be produced by inducing in vivo production in the lymphocyte population or by screening recombinant immunoglobulin libraries or panels of highly specific binding reagents as disclosed in Orlandi et al. (1989) Proc Natl Acad Sci 86: 3833-3837; and Winter and Milstein (1991) Nature 349: 293-299, 1991.

Figure 14A:
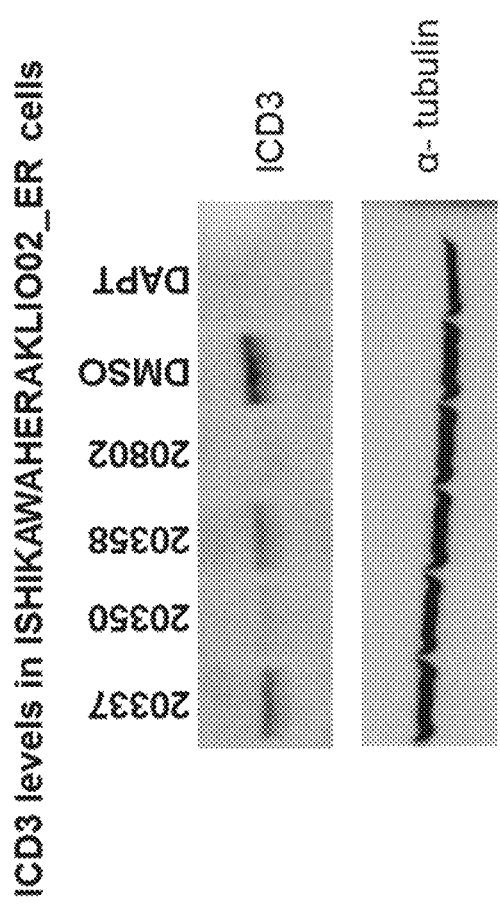
FIG. 14A-C: Photographs of Western blots showing decreased Notch 3 signaling with Notch 3 antibody treatment in Ishikawaheraklio02_ER cells, TE-11 cells, and A549 cells.

Fully human antibodies relate to antibody molecules in which essentially the entire sequences of both the light chain and the heavy chain, including the CDRs, arise from human genes. Such antibodies are termed "human antibodies" or "fully human antibodies" herein. Antibodies against human Notch3 proteins were generated by selection of clones having high affinity binding affinities, using as the source of antibody variant proteins a commercially available phage display library—HuCAL PLATINUM® library (Prassler et al., (2011) J Mol Biol 413:261-278). Using the HuCAL PLATINUM® library, anti-Notch 3 antibodies, Ab-A, Ab-C, Ab-D, and others were identified. The three dimensional structure of the NRR domain (residues 1379-1640) of Notch 3 complexed with an antibody or fragment thereof is presented. The Notch 3 NRR/Ab-B Fab complex and the Notch 3 NRR/Ab-C Fab have been determined at 3.2 angstrom (A) and 2.1 Å resolution, respectively, and shown in FIGS. 14 A and B.

Other methods for generating human monoclonal antibodies include, but are not limited to, trioma technique; the human B cell hybridoma technique (see Kozbor et al., (1983) Immunol. Today, 4, 72-79); and the EBV hybridoma technique to produce human monoclonal antibodies (see Cole et al., (1985)) In, Monoclonal Antibodies and Cancer Therapy. (eds. R. A. Reisfeld and S. Sell), Alan R Liss Inc, New York N.Y., pp 77-96. Human monoclonal antibodies may be utilized in the practice of the present invention and may be produced by using human hybridomas (see Cote et al., (1983) Proc. Natl. Acad. Sci. USA., 80, 2026-2030) or by transforming human B cells with Epstein Barr Virus in vitro (see Cole et al., 1985, supra).

In addition, human antibodies can also be produced using additional techniques, including phage display libraries (Hoogenboom and Winter (1992) J. Mol. Biol., 227(2), 381-388; Marks et al., (1991) J. Mol. Biol., 222(3), 581-597). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (1992) BioTechnology, 10, 779-783; Lonberg et al. (1994) Nature, 368(6474), 856-859; Morrison (1994) Nature, 368(6474), 812-813; Fishwild et al., (1996); Neuberger (1996) Nature Biotechnology, 14, 845-851; and Lonberg and Huszar (1995) Rev. Immunol., 13(1), 65-93.

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

Antisense

In another embodiment, the Notch 3 inhibitor is an siRNAs, shRNAs or targeted synthetic oligonucleotides that hybridize with Notch3 mRNA (i.e. by RNA interference, RNAi), thus inhibiting the synthesis of Notch3 receptors (see e.g., US20100189775). Short hairpin RNA (shRNA) is an RNA molecule in the form of a stable hairpin which silences gene expression via RNA interference in vivo. The shRNA hairpin structure is cleaved by cellular processing machinery to produce the mature siRNA, whose anti-sense strand is specifically taken up by the RNA-induced silencing complex (RISC). The latter complex binds to and cleaves mRNAs which match the siRNA sequence contained in the RISC, thus guiding the targeted RNA to degradation. Hence, the said inhibition will result in a certain time, in the depletion of Notch3 receptors from the target cells as the pre-existing receptors will eventually turn over but will not be replenished aced by newly synthesized Notch 3 receptors.

A skilled person could design RNAs suitable for Notch 3 inhibition using protocols and services for designing siRNAs or shRNAs are available online from genelink, ambion, or psilencer. siRNAs that specifically target Notch3 would decrease Notch3 wild type and mutant Notch 3 receptors. In some embodiments, siRNA could be designed to only inhibit mutant Notch 3.

The shRNAs can be inserted in any vector suitable for gene therapy. shRNA expression vectors have been engineered using both viral (including retroviral, adenoviral and lentiviral vectors), and plasmid systems. These vectors utilize promoters from a small class of pol. III promoters to drive the expression of shRNA. All vectors have to include a promoter for human Pol III. The Human U6 promoter is the best studied type III pol promoter frequently used in RNAi.

shRNAs are exported from the nucleus by Exportin 5, which recognizes short RNA loop. Once in the cytoplasm, both pre-miRNAs and shRNAs are processed into siRNA duplexes by cleavage with a second RNase III enzyme termed Dicer. Importantly, Dicer binds the base of the shRNA and cleaves 21 or 22 nt up the stem, leaving a second 2 nt 3' overhang and forming an siRNA duplex structure. RNA duplex is taken up by the RNAi-Induced Silencing Complex (RISC). RISC unwinds the double-strand RNA and the activated complex with the associated antisense.

The genetic material in retroviruses is in the form of RNA molecules, while the genetic material of their hosts is in the form of DNA. When a retrovirus infects a host cell, it will introduce its RNA together with some enzymes into the cell. This RNA molecule from the retrovirus must produce a DNA copy from its RNA molecule before it can be considered as part of the genetic material of the host cell. The process of producing a DNA copy from an RNA molecule is termed reverse transcription. It is carried out by one of the enzymes carried in the virus, called reverse transcriptase. After this DNA copy is produced and is free in the nucleus of the host cell, it must be incorporated into the genome of the host cell by using another enzyme carried in the virus called integrase. One of the problems of gene therapy using retroviruses is that the integrase enzyme can insert the genetic material of the virus in any arbitrary position in the host's genome. If genetic material happens to be inserted in the middle of one of the original genes of the host cell, this gene will be disrupted (insertional mutagenesis). If the gene happens to be one regulating cell division, uncontrolled cell division (i.e., cancer) can occur. The state of the art in this field has disclosed the use of retroviral vectors utilizing zinc finger nucleases or including certain sequences such as the beta-globin locus control region to direct the site of integration to specific chromosomal sites The skilled person would know, however, where to find indications in the state of the art for the construction of a vector suitable for the pharmaceutical composition of the invention. Vectors, kit construction vectors and services for the construction of vectors for the expression and the targeting of said RNAs are known in the art, such as, by way of example, the INGENEX GeneSuppressorRetro Construction Kit, or are available online, or are described in the art in: Arts, et al. ((2003) Genome Res. 13: 2325-2332), that demonstrates adenovirus-based shRNA expression in a variety of cell types, including primary cells; Matta, et al. ((2003) Cancer Biol. Ther. 2: 206-210) where the authors use Invitrogen's pLenti6 backbone to express an shRNA cassette; Tiscornia, et al. ((2003) Proc. Natl. Acad. Sci. USA 100: 1844-1848) demonstrates the utility of lentiviral vectors for delivery of shRNA to cells and mice.

The vector could comprise a tumor specific promoter driving shRNA or siRNA expression in cells only in the tumor. The oligonucleotides can be covered with lipids in an organized structure like a micelle or a liposome. When the organized structure is complexed with the nucleic acid, it is called a lipoplex. There are three types of lipids, anionic (negatively charged), neutral, or cationic (positively charged). Initially, anionic and neutral lipids were used for the construction of lipoplexes for synthetic vectors. Cationic lipids, due to their positive charge, naturally complex with the negatively charged nucleic acids and they are also less time consuming to produce than anionic of neutral lipids. Moreover, due to their positive charge they also interact with the cell membrane facilitating their endocytosis and subsequent release of the nucleic acid into the cytoplasm. The cationic lipids also protect against degradation of the nucleic acid by the cell.

Low Molecular Weight Compounds

Known inhibitors of Notch signaling include low molecular weight compounds that inhibit the gamma secretase enzyme (gamma secretase inhibitors) or the ADAM metalloprotease enzymes (metalloprotease inhibitors).

Inhibitors of Notch 3 that inhibit by cleavage by γ-secretase include but are not limited to, γ-secretase inhibitor I (GSI I) Z-Leu-Leu-Norleucine; γ-secretase inhibitor II (GSI II); γ-secretase inhibitor III (GSI III), N-Benzyloxycarbonyl-Leu-leucinal, N-(2-Naphthoyl)-Val-phenylalaninal; γ-secretase inhibitor III (GSI IV); γ-secretase inhibitor III (GSI V), N-Benzyloxycarbonyl-Leu-phenylalaninal; γ-secretase inhibitor III (GSI VI), 1-(S)-endo-N-(1,3,3)-Trimethylbicyclo[2.2.1]hept-2-yl)-4-fluorophenyl Sulfonamide; γ-secretase inhibitor III (GSI VII), Menthyloxycarbonyl-LL-CHO; γ-secretase inhibitor III (GSI IX), (DAPT), N—[N-(3,5-Difluorophenacetyl-L-alanyl)]-S-phenylglycine t-Butyl Ester; γ-secretase inhibitor X (GSI X), {1S-Benzyl-4R-[1-(1S-carbamoyl-2-phenethylcarbamoyl)-1S-3-methylbutylcarb-amoyl]-2R-hydroxy-5-phenylpentyl}carbamic Acid tert-butyl Ester; γ-secretase inhibitor XI (GSI XI), 7-Amino-4-chloro-3-methoxyisocoumarin; γ-secretase inhibitor XII (GSI XII), Z-Ile-Leu-CHO; γ-secretase inhibitor XIII (GSI XIII), Z-Tyr-Ile-Leu-CHO; γ-secretase inhibitor XIV (GSI XIV), Z-Cys(t-Bu)-Ile-Leu-CHO; γ-secretase inhibitor XVI (GSI XVI), N—[N-3,5-Difluorophenacetyl]-L-alanyl-S-phenylglycine Methyl Ester; γ-secretase inhibitor XVII (GSI XVII); γ-secretase inhibitor XIX (GSI XIX), benzo[e][1,4]diazepin-3-yl)-butyramide; γ-secretase inhibitor XX (GSI XX), (S,S)-2-[2-(3,5-Difluorophenyl)acetylamino]-N-(5-methyl-6-oxo-6,7-dihydro-5H-dibenzo[b,d]azepin-7-yl)propionamide; γ-secretase inhibitor XXI (GSI XXI), (S,S)-2-[2-(3,5-Difluorophenyl)-acetylamino]-N-(1-methyl-2-oxo-5-phenyl-2,-3-dihydro-1H-benzo[e][1,4]diazepin-3-yl)-propionamide; Gamma40 secretase inhibitor I, N-trans-3,5-Dimethoxycinnamoyl-Ile-leucinal; Gamma40 secretase inhibitor II, N-tert-Butyloxycarbonyl-Gly-Val-Valinal Isovaleryl-V V-Sta-A-Sta-OCH$_3$, MK-0752 (Merck); LY450139 (Eli Lilly); RO4929097; PF-03084,014; BMS-708163; MPC-7869 (γ-secretase modifier), and semagacestat.

Inhibition of Notch 3 by inhibition by interference with Notch nuclear co-activator include, but are not limited to MAML1, MAML-CSL-Notch, Antennapedia/dominant-MAML. Inhibition of notch 3 inhibition by interference with D114 ligand-receptor interaction include, but are not limited to OMP-21M18 (DLL4 antibody).

The γ-secretase inhibitors, γ-secretase inhibitor MK-0752 (Merck) has been administered to human subjects in single doses of 110 to 1000 mg (Rosen et al., 2006). MK-0752 is in Phase I clinical trials for patients with breast cancer tumors (ClinicalTrials.gov Identifier NCT00106145). The γ-secretase inhibitor LY450139 (Eli Lilly) has been administered to human subjects at doses ranging from 5 mg/day to 50 mg/day for 14 days (Seimers et al., (2005) Clin Neuropharmacol., 28(3), 126-132). A longer term study with LY450139 has been conducted at a dose of 60 mg/day for 2 weeks, followed by 100 mg/day for 6 weeks, followed by either 100 mg/day or 140 mg/day for another 6 weeks (Beals, (2007) Reporting on press briefing by Dr. Siemers at Alzheimer's Association International Conference on Prevention of Dementia: Abstract HT-005. Presented Jun. 11, 2007-Medscape Medical News.

Notch 3 Structure and Conformational Epitopes

Figure 24:
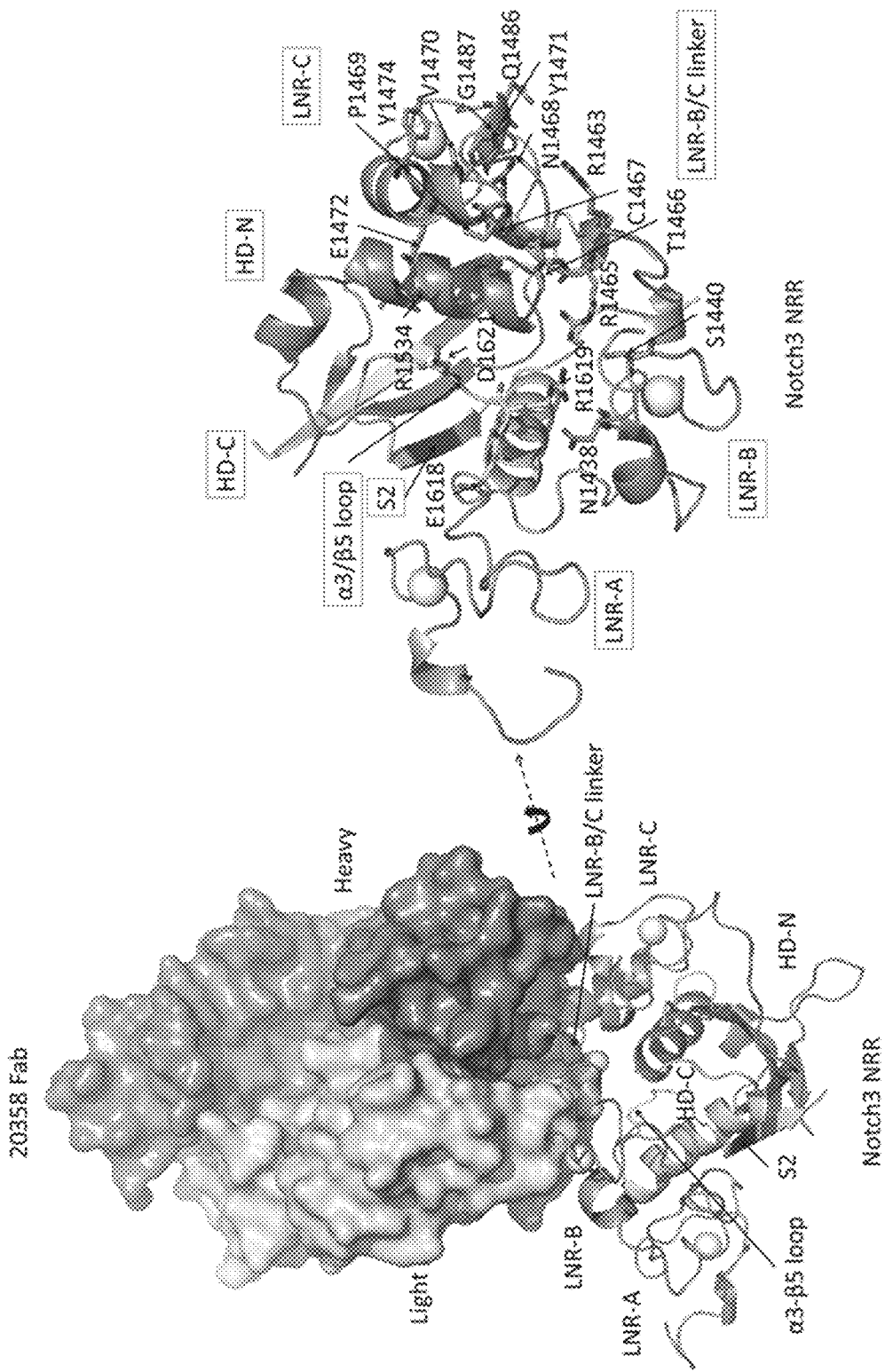
FIG. 24: X-ray crystal structure of the Notch3/20358 Fab complex determined at 2.1 Å, with the overall structure of 20358 Fab binding to Notch3 NRR (left panel) and detailed interactions on Notch3 NRR with epitope residues labelled (right panel)
Figure 25:
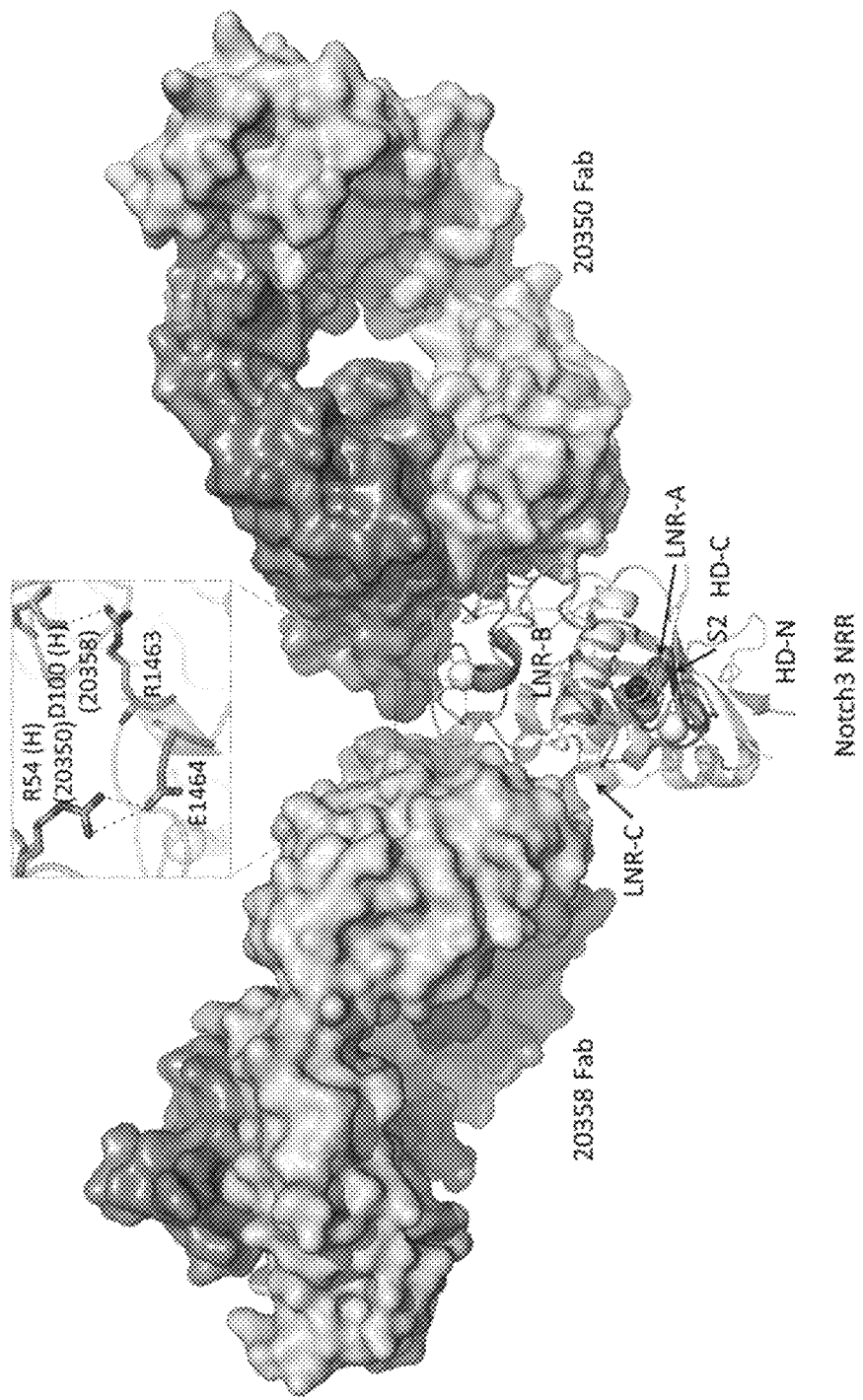
FIG. 25: Comparison of 20350 and 20358 epitopes on Notch3 NRR. X-ray crystal structure of the Notch3/20350 Fab complex and Notch 3/20358 Fab complex superimposed on Notch 3 NRR showing that the two antibodies bind to distinct epitopes on Notch 3 NR.

In one aspect, the disclosure pertains to the identification of a number of distinct conformational epitopes in Notch 3. For the first time, the three dimensional structure of the NRR domain (residues 1379-1640) of Notch 3 complexed with an antibody or fragment thereof of a number of antibodies has been shown. The Notch 3 NRR/20350 Fab complex and the Notch 3 NRR/20358 Fab have been determined at 3.2 angstrom (Å) and 2.1 Å resolution, respectively, and shown in FIGS. 23 and 24. The disclosure also shows for the first time that there are multiple conformational epitopes within the NRR and that antibody fragment binds to a unique conformational epitope that are separated from each other, as shown in FIG. 25. The antibodies or fragments thereof bind to the autoinhibited state of Notch 3 and stabilizes Notch 3 in this autoinhibited state.

The disclosure herein shows that there are number of distinct conformational epitopes in the NRR to which different classes of Notch 3 antibodies or fragments thereof bind. In one embodiment, a first class of antibodies (e.g., 20350) binds to a first conformational epitope in the NRR domain; a second class of antibodies (e.g., 20358) binds to a second conformational epitope in the NRR domain; and a third class of antibodies binds to a third conformational epitope in the NRR domain. In one embodiment, the first, second and third conformational epitopes of the NRR do not overlap; and the first, second and third class of antibodies bind to distinct regions of the NRR. In one embodiment, the first and second conformational epitopes of the NRR do not overlap; and the first and second class of antibodies bind to distinct regions of the NRR. In one embodiment, the first and third conformational epitopes of the NRR do not overlap, and the first and third class of antibodies bind to distinct regions of the NRR. In one embodiment, the second and conformational epitopes of the NRR do not overlap, and the second and third class of antibodies bind to distinct regions of the NRR.

In one embodiment, the first, second and third conformational epitopes of the NRR overlap with each other by at least one, two, three, four, five, six, seven, eight, nine, or ten amino acid residues; and the first, second, and third class of antibodies bind to at least one, two, three, four, five, six, seven, eight, nine, or ten overlapping amino acid residues. In one embodiment, the first and second conformational epitopes of the NRR overlap with each other by at least one, two, three, four, five, six, seven, eight, nine, or ten amino acid residues; and the first and second class of antibodies bind to at least one, two, three, four, five, six, seven, eight, nine, or ten overlapping amino acid residues. In one embodiment, the first and third conformational epitopes of the NRR overlap with each other by at least one, two, three, four, five, six, seven, eight, nine, or ten amino acid residues; and the first and third class of antibodies bind to at least one, two, three, four, five, six, seven, eight, nine, or ten overlapping amino acid residues. In one embodiment, the second and third conformational epitopes of the NRR overlap with each other by at least one, two, three, four, or five, six, seven, eight, nine, or ten amino acid residues; and the second and third class of antibodies bind to at least one, two, three, four, five, six, seven, eight, nine, or ten overlapping amino acid residues.

To analyze the different conformational epitopes within the NRR, X-ray crystallography and hydrogen-deuterium exchange experiments were conducted as described in detail in the experiments section. The crystals of Notch 3 can be prepared by expressing a nucleotide sequence encoding Notch 3 or a variant thereof in a suitable host cell, and then crystallizing the purified protein(s) in the presence of the relevant Notch 3 targeted Fab.

Notch 3 polypeptides may also be produced as fusion proteins, for example to aid in extraction and purification. Examples of fusion protein partners include glutathione-S-transferase (GST), histidine (HIS), hexahistidine (6HIS), GAL4 (DNA binding and/or transcriptional activation domains) and beta-galactosidase. It may also be convenient to include a proteolytic cleavage site between the fusion protein partner and the protein sequence of interest to allow removal of fusion protein sequences.

After expression, the proteins may be purified and/or concentrated, for example by immobilized metal affinity chromatography, ion-exchange chromatography, and/or gel filtration.

The protein(s) may be crystallized using techniques described herein. Commonly, in a crystallization process, a drop containing the protein solution is mixed with the crystallization buffer and allowed to equilibrate in a sealed container. Equilibration may be achieved by known techniques such as the "hanging drop" or the "sitting drop" method. In these methods, the drop is hung above or sitting beside a much larger reservoir of crystallization buffer and equilibration is reached through vapor diffusion. Alternatively, equilibration may occur by other methods, for example under oil, through a semi-permeable membrane, or by free-interface diffusion (See e.g., Chayen et al., (2008) Nature Methods 5, 147-153).

Once the crystals have been obtained, the structure may be solved by known X-ray diffraction techniques. Many techniques use chemically modified crystals, such as those modified by heavy atom derivatization to approximate phases. In practice, a crystal is soaked in a solution containing heavy metal atom salts, or organometallic compounds, e.g., lead chloride, gold thiomalate, thimerosal or uranyl acetate, which can diffuse through the crystal and bind to the surface of the protein. The location(s) of the bound heavy metal atom(s) can then be determined by X-ray diffraction analysis of the soaked crystal. The patterns obtained on diffraction of a monochromatic beam of X-rays by the atoms (scattering centers) of the crystal can be solved by mathematical equations to give mathematical coordinates. The diffraction data are used to calculate an electron density map of the repeating unit of the crystal. Another method of obtaining phase information is using a technique known as molecular replacement. In this method, rotational and translational algorithms are applied to a search model derived from a related structure, resulting in an approximate orientation for the protein of interest (See Rossmann, (1990) Acta Crystals A 46, 73-82). The electron density maps are used to establish the positions of the individual atoms within the unit cell of the crystal (Blundel et al., (1976) Protein Crystallography, Academic Press).

The present disclosure describes for the first time, multiple three-dimensional structures of Notch 3 and a Fab of a Notch 3 antibody, and show there are multiple conformational epitopes within the NRR. The extracellular NRR domain of Notch 3 is shown in FIG. 2. The approximate domain boundaries are as follows: LNR-A has amino acid residues E1383-G1422; LNR-A-B linker has amino acid residues Asp1423-Leu1431; LNR-B has amino acid residues Gln1432-Ala1460; LNR-B—C linker has amino acid residues Gly1461-Asn1468; LNR-C has amino acid residues Pro1469-Ser1502; LNR-HD liner has amino acid residues Glu1503-Arg1510; HD-N has amino acid residues Gly1511-Arg1571; and HD-C has amino acid residues 1572-Ser1640. Human Notch 3 has Accession No. (NP_000426) (human), and represented below as SEQ ID NO: 1.

The three-dimensional structure of Notch 3 and the antibody or fragment thereof allows the identification of target binding sites for potential Notch 3 receptor modulators. Preferred target binding sites are those involved in the activation of Notch 3. In one embodiment, the target binding site is located within the LNR and HD domains of Notch 3. Thus an antibody or fragment thereof which binds to either LNR or HD, and preferably to both LNR and HD domains can modulate Notch 3 activation by preventing the domains from dissociating from each other and exposing the HD domain such that the S2, and subsequently the S3 cleavage sites are exposed. Thus, an antibody or fragment thereof that bind to amino acid residues within these domains causes Notch 3 to maintain an autoinhibited conformation that prevents activation and downstream signal transduction.

In one embodiment, the conformational epitope is defined by Notch 3 amino acid residues: 1427-1429 (of the LNR-A/B linker), 1442, 1444-1445, 1447-1450, 1453, 1458 (of LNR-B), 1461-1462, 1464 (of the LNR-B/C linker), 1507-1508, 1510 (of the LNR-HD linker), 1592, 1594-1599, 1602 (of the HD β4-α3 loop), and 1606 (of the HD α3 helix) of SEQ ID NO:1, or a subset thereof. In one embodiment, the paratope is the region of the antibody that comprises the CDR sequences. In one embodiment, the paratope comprises the sequences listed in Table 1. In one embodiment, the paratope comprises at least one amino acid residue that binds with Notch 3 residues: Cys1442, Pro1444, Ala1445, Ser1447, Ser1448, Pro1449, Tyr1453, Cys1458, Gly1461, Gly1462, Gly1464, Leu1592, Ser1594, Pro1595, Glu1596, Asn1597, Asp1598, and His1599. In one embodiment, the paratope comprises at least one amino acid residue that binds with Notch 3 residues: Gln1427, Cys1428, Glu1429, Pro1444, Ser1445, Ser1447, Ser1448, Pro1449, Tyr1453, Leu1507, Leu1508, Arg1510, Leu1592, Asp1598, Pro1602, and Ser1606.

In some embodiments, the antibody or fragment thereof binds to human Notch 3 protein having a conformational epitope comprising amino acid residues: 1427-1429 (of the LNR-A/B linker), 1442, 1444-1445, 1447-1450, 1453, 1458 (of LNR-B), 1461-1462, 1464 (of the LNR-B/C linker), 1507-1508, 1510 (of the LNR-HD linker), 1592, 1594-1599, 1602 (of the HD β4-α3 loop), and 1606 (of the HD α3 helix) of SEQ ID NO:1, or a subset thereof. In some embodiments, the antibody or fragment thereof binds to amino acids within or overlapping amino acid residues amino acid residues: 1427-1429 (of the LNR-A/B linker), 1442, 1444-1445, 1447-1450, 1453, 1458 (of LNR-B), 1461-1462, 1464 (of the LNR-B/C linker), 1507-1508, 1510 (of the LNR-HD linker), 1592, 1594-1599, 1602 (of the HD β4-α3 loop), and 1606 (of the HD α3 helix) of SEQ ID NO:1, or a subset thereof. In some embodiments, the antibody or fragment thereof binds to amino acids within (and/or amino acid sequences consisting of) amino acid residues: 1427-1429 (of the LNR-A/B linker), 1442, 1444-1445, 1447-1450, 1453, 1458 (of LNR-B), 1461-1462, 1464 (of the LNR-B/C linker), 1507-1508, 1510 (of the LNR-HD linker), 1592, 1594-1599, 1602 (of the HD β4-α3 loop), and 1606 (of the HD α3 helix) of SEQ ID NO:1, or a subset thereof.

In one embodiment, the conformational epitope is defined by Notch 3 amino acid residues: 1440 (of LNR-B), 1463, 1465-1468 (of the LNR-B/C linker) 1469-1472, 1474, 1486-1487 (of LNR-C), 1534 (of HD α2 helix), and 1618, 1619, and 1621 (of the α3-β5 loop) of SEQ ID NO: 1, or a subset thereof. In one embodiment, the paratope comprises at least one amino acid residue that binds with Notch 3 residues: Arg1463, Thr1466, Asn1468, Pro1469, Val1470, Tyr1471, Tyr1474, Gln1486, and Gly1487. In one embodiment, the paratope comprises at least one amino acid residue that binds with Notch 3 residues: Ser1440, Arg1465, Thr1466, Asn1468, Pro1469, Val1470, glu1472, Arg1434, Glu1618, Arg1619, and Asp1621.

In some embodiments, the antibody or fragment thereof binds to human Notch 3 protein having a conformational epitope comprising amino acid residues: 1440 (of LNR-B), 1463, 1465-1468 (of the LNR-B/C linker) 1469-1472, 1474, 1486-1487 (of LNR-C), 1534 (of HD α2 helix), and 1618, 1619, and 1621 (of the α3-β5 loop) of SEQ ID NO: 1, or a subset thereof. In some embodiments, the antibody or fragment thereof binds to amino acids within or overlapping amino acid residues amino acid residues: 1440 (of LNR-B), 1463, 1465-1468 (of the LNR-B/C linker) 1469-1472, 1474, 1486-1487 (of LNR-C), 1534 (of HD α2 helix), and 1618, 1619, and 1621 (of the α3-β5 loop) of SEQ ID NO:1, or a subset thereof. In some embodiments, the antibody or fragment thereof binds to amino acids within (and/or amino acid sequences consisting of) amino acid residues: 1440 (of LNR-B), 1463, 1465-1468 (of the LNR-B/C linker) 1469-1472, 1474, 1486-1487 (of LNR-C), 1534 (of HD α2 helix), and 1618, 1619, and 1621 (of the α3-β5 loop) of SEQ ID NO:1, or a subset thereof. In some embodiments, the antibody or fragment thereof binds to the conformational epitope such that it restricts the mobility of the LNR regions (LNR-A, LNR-B, LNR-C), stabilizing it in an autoinhibited conformation. The failure to form the active (uninhibited, open) conformation results in failure to activate signal transduction. In some embodiments, the antibody or fragment thereof binds to the conformational epitope such that it prevents the HD within the NRR from becoming exposed, thereby rendering it unavailable for cleavage at the S2, and/or S3 sites by proteases. The failure to cleave the HD results in failure to activate signal transduction.

The depicted structures also allows one to identify specific core Notch 3 amino acid residues for the interaction interface of an antibody or fragment thereof (e.g., 20350 and 20358) with Notch 3. For 20350, these were defined as residues that are within 5 Å of the 20350 VH chain. The core residues are as follows: Cys1442, Pro1444, Ala1445, Ser1447, Ser1448, Pro1449, Tyr1453, Cys1458, Gly1461, Gly1462, Gly1464, Leu1592, Ser1594, Pro1595, Glu1596, Asn1597, Asp1598, and His1599. For the VL chain, the core residues are as follows: Gln1427, Cys1428, Glu1429, Pro1444, Ser1445, Ser1447, Ser1448, Pro1449, Tyr1453, Leu1507, Leu1508, Arg1510, Leu1592, Asp1598, Pro1602, and Ser1606.

For 20358, these residues were defined as residues that are within 5 Å of the 20358 VH chain. The core residues are as follows: Arg1463, Thr1466, Asn1468, Pro1469, Val1470, Tyr1471, Tyr1474, Gln1486, and Gly1487. For the VL chain, the core residues are as follows: Ser1440, Arg1465, Thr1466, Asn1468, Pro1469, Val1470, glu1472, Arg1434, Glu1618, Arg1619, and Asp1621.

The Experimental section shows that the conformational epitopes of 20350 and 20358 do not overlap as determined by superimposing the crystal structures of Notch 3 NRR/20350 complex and Notch3 NRR/20358 complex on Notch3 NRR, as shown in FIG. 25. 20350 and 20358 bind to distinct separate conformational epitopes that do not overlap. Even the closest region (E1464-R54 hydrogen bond with 20350 and R1463-D100 salt bridge with 20358) is completely separated. This indicates that the two antibodies can bind Notch 3 NRR at the same time and do not cross-compete. This observation is in alignment with the binning experiment showing that these antibodies are in different bins and do not compete with each other in binding Notch 3.

Using the teachings disclosed herein, the skilled artisan can predict which residues and areas of the antigen binding proteins can be varied without unduly interfering with the antigen binding protein's ability to bind to Notch 3.

Interaction interface amino acids were determined as all amino acid residues with at least one atom less than or equal to 5 Å from the Notch 3 partner protein. 5 Å was chosen as the cutoff distance to allow for atoms within a van der Waals radius plus a possible water-mediated hydrogen bond.

In some embodiments, any antigen binding protein that binds to, covers, or prevents 20350 from interacting with any of the above residues can be employed to bind to or inhibit Notch 3. In some embodiments, the antibodies or fragments thereof bind to or interact with at least one of the following Notch 3 residues: Cys1442, Pro1444, Ala1445, Ser1447, Ser1448, Pro1449, Tyr1453, Cys1458, Gly1461, Gly1462, Gly1464, Leu1592, Ser1594, Pro1595, Glu1596, Asn1597, Asp1598, and His1599. In some embodiments, the antibodies and fragments thereof bind to or interact with at least one of the following Notch 3 residues: Gln1427, Cys1428, Glu1429, Pro1444, Ser1445, Ser1447, Ser1448, Pro1449, Tyr1453, Leu1507, Leu1508, Arg1510, Leu1592, Asp1598, Pro1602, and Ser1606. In some embodiments, the antibodies or fragments thereof bind to or interact with at least one of the following Notch 3 residues: Cys1442, Pro1444, Ala1445, Ser1447, Ser1448, Pro1449, Tyr1453, Cys1458, Gly1461, Gly1462, Gly1464, Leu1592, Ser1594, Pro1595, Glu1596, Asn1597, Asp1598, His1599, Gln1427, Cys1428, Glu1429, Pro1444, Ser1445, Ser1447, Ser1448, Pro1449, Tyr1453, Leu1507, Leu1508, Arg1510, Leu1592, Asp1598, Pro1602, and Ser1606. In some embodiments, the antibodies or fragments thereof bind to or interact with a combination of the following Notch 3 residues: Cys1442, Pro1444, Ala1445, Ser1447, Ser1448, Pro1449, Tyr1453, Cys1458, Gly1461, Gly1462, Gly1464, Leu1592, Ser1594, Pro1595, Glu1596, Asn1597, Asp1598, His1599, Gln1427, Cys1428, Glu1429, Pro1444, Ser1445, Ser1447, Ser1448, Pro1449, Tyr1453, Leu1507, Leu1508, Arg1510, Leu1592, Asp1598, Pro1602, and Ser1606. In some embodiments, the antibodies or fragments thereof bind to or interact with all of the following Notch 3 residues: Cys1442, Pro1444, Ala1445, Ser1447, Ser1448, Pro1449, Tyr1453, Cys1458, Gly1461, Gly1462, Gly1464, Leu1592, Ser1594, Pro1595, Glu1596, Asn1597, Asp1598, His1599, Gln1427, Cys1428, Glu1429, Pro1444, Ser1445, Ser1447, Ser1448, Pro1449, Tyr1453, Leu1507, Leu1508, Arg1510, Leu1592, Asp1598, Pro1602, and Ser1606.

In some embodiments, any antigen binding protein that binds to, covers, or prevents 20358 from interacting with any of the above residues can be employed to bind to or inhibit Notch 3. In some embodiments, the antibodies or fragments thereof bind to or interact with at least one of the following Notch 3 residues: Arg1463, Thr1466, Asn1468, Pro1469, Val1470, Tyr1471, Tyr1474, Gln1486, and Gly1487. In some embodiments, the antibodies or fragments thereof bind to or interact with at least one of the following Notch 3 residues: Ser1440, Arg1465, Thr1466, Asn1468, Pro1469, Val1470, Glu1472, Arg1434, Glu1618, Arg1619, and Asp1621. In some embodiments, the antibodies or fragments thereof bind to or interact with at least one of the following Notch 3 residues: Arg1463, Thr1466, Asn1468, Pro1469, Val1470, Tyr1471, Tyr1474, Gln1486, Gly1487, Ser1440, Arg1465, Thr1466, Asn1468, Pro1469, Val1470, glu1472, Arg1434, Glu1618, Arg1619, and Asp1621. In some embodiments, the antibodies or fragments thereof bind to or interact with a combination of the following Notch 3 residues: Arg1463, Thr1466, Asn1468, Pro1469, Val1470, Tyr1471, Tyr1474, Gln1486, Gly1487, Ser1440, Arg1465, Thr1466, Asn1468, Pro1469, Val1470, Glu1472, Arg1434, Glu1618, Arg1619, and Asp1621. In some embodiments, the antibodies or fragments thereof bind to or interact with all of the following Notch 3 residues: Arg1463, Thr1466, Asn1468, Pro1469, Val1470, Tyr1471, Tyr1474, Gln1486, Gly1487, Ser1440, Arg1465, Thr1466, Asn1468, Pro1469, Val1470, Glu1472, Arg1434, Glu1618, Arg1619, and Asp1621.

In one embodiment, the antibodies disclosed herein bind to the same conformational epitope as 20350. In one embodiment, the antibodies disclosed herein bind to the same conformational epitope as 20358. In some embodiments, the conformational epitope bound by any of the antibodies listed in Table 1 is especially useful. In certain embodiments, a Notch 3 conformational epitope can be utilized to isolate antibodies of fragments thereof that bind to Notch 3. In certain embodiments, a Notch 3 conformational epitope can be utilized to generate antibodies or fragments thereof which bind to Notch 3. In certain embodiments, a Notch 3 conformational epitope can be utilized as an immunogen to generate antibodies of fragments thereof that bind to the Notch 3 conformational epitope. In certain embodiments, a Notch 3 conformational epitope can be administered to an animal, and antibodies that bind to Notch 3 can subsequently be obtained from the animal.

In addition to the conformational epitopes identified for 20337, 20350, and 20358, further conformational epitopes on Notch 3 NRR can also be found using the methods disclosed herein and as disclosed in the Examples. In particular, conformational epitopes that bridge LNR and HD; and conformational epitopes in which the S2 plug (L1419) is part of an epitope.

In addition to the conformational epitopes identified for 20337, 20350, and 20358, further conformational epitopes on Notch 3 NRR can also be found using the methods disclosed herein and as disclosed in the Examples. In particular, conformational epitopes that bridge LNR and HD; and conformational epitopes in which the S2 plug (L1419) is part of an epitope.

The availability of 3D structures for the Notch 3 NRR and the complex of Notch 3 NRR/20350 and Notch 3 NRR/20358 provides the framework to explore other Notch 3 antibodies in more detail. The 3D structure of Notch 3 allows the epitopes for monoclonal antibodies to be mapped and their mode of action inferred, since some inhibit, some stimulate and others have no effect on cell growth. The conformational epitope for Notch 3 comprises discontinuous amino acid residues from the LNR region and the HDs of the NRR. The availability of the 3D structures of Notch 3 will facilitate the determination of the precise mechanism of action of these inhibitory agents and the design of new approaches for interfering with Notch 3 function.

In addition to the general structural aspects of antibodies, the more specific interaction between the paratope and the epitope may be examined through structural approaches. In one embodiment, the structure of the CDRs contributes to a paratope, through which an antibody is able to bind to an epitope. The shape of such a paratope may be determined in a number of ways. Traditional structural examination approaches can be used, such as NMR or x-ray crystallography. These approaches can examine the shape of the paratope alone, or while it is bound to the epitope.

In one embodiment, the paratope is the region of the antibody that comprises the CDR sequences. In one embodiment, the paratope comprises the sequences listed in Table 1. In one embodiment, the paratope comprises at least one amino acid residue that binds with Notch 3 residues: Cys1442, Pro1444, Ala1445, Ser1447, Ser1448, Pro1449, Tyr1453, Cys1458, Gly1461, Gly1462, Gly1464, Leu1592, Ser1594, Pro1595, Glu1596, Asn1597, Asp1598, and His1599. In one embodiment, the paratope comprises at least one amino acid residue that binds with Notch 3 residues: Gln1427, Cys1428, Glu1429, Pro1444, Ser1445, Ser1447, Ser1448, Pro1449, Tyr1453, Leu1507, Leu1508, Arg1510, Leu1592, Asp1598, Pro1602, and Ser1606.

In one embodiment, the paratope comprises at least one amino acid residue that binds with Notch 3 residues: Arg1463, Thr1466, Asn1468, Pro1469, Val1470, Tyr1471, Tyr1474, Gln1486, and Gly1487. In one embodiment, the paratope comprises at least one amino acid residue that binds with Notch 3 residues: Ser1440, Arg1465, Thr1466, Asn1468, Pro1469, Val1470, Glu1472, Arg1434, Glu1618, Arg1619, and Asp1621.

Alternatively, molecular models may be generated in silico. A structure can be generated through homology modeling, aided with a commercial package, such as InsightII modeling package from Accelrys (San Diego, Calif.). Briefly, one can use the sequence of the antibody to be examined to search against a database of proteins of known structures, such as the Protein Data Bank. After one identifies homologous proteins with known structures, these homologous proteins are used as modeling templates. Each of the possible templates can be aligned, thus producing structure based sequence alignments among the templates. The sequence of the antibody with the unknown structure can then be aligned with these templates to generate a molecular model for the antibody with the unknown structure. As will be appreciated by one of skill in the art, there are many alternative methods for generating such structures in silico, any of which may be used. For instance, a process similar to the one described in Hardman et al., issued U.S. Pat. No. 5,958,708 employing QUANTA (Polygen Corp., Waltham, Mass.) and CHARM (Brooks et al., (1983), J. Comp. Chem. 4:187) may be used (hereby incorporated in its entirety by reference).

Not only is the shape of the paratope important in determining whether and how well a possible paratope will bind to an epitope, but the interaction itself, between the epitope and the paratope is a source of great information in the design of variant antibodies. As appreciated by one of skill in the art, there are a variety of ways in which this interaction can be studied. One way is to use the structural model generated, perhaps as described above, and then to use a program such as InsightII (Accelrys, San Diego, Calif.), which has a docking module, which, among other things, is capable of performing a Monte Carlo search on the conformational and orientational spaces between the paratope and its epitope. The result is that one is able to estimate where and how the epitope interacts with the paratope. In one embodiment, only a fragment, or variant, of the epitope is used to assist in determining the relevant interactions. In one embodiment, the entire epitope is used in the modeling of the interaction between the paratope and the epitope.

Through the use of these modelled structures, one is able to predict which residues are the most important in the interaction between the epitope and the paratope. Thus, in one embodiment, one is able to readily select which residues to change in order to alter the binding characteristics of the antibody. For instance, it may be apparent from the docking models that the side chains of certain residues in the paratope may sterically hinder the binding of the epitope, thus altering these residues to residues with smaller side chains may be beneficial. One can determine this in many ways. For example, one may simply look at the two models and estimate interactions based on functional groups and proximity. Alternatively, one may perform repeated pairings of epitope and paratope, as described above, in order to obtain more favorable energy interactions. One can also determine these interactions for a variety of variants of the antibody to determine alternative ways in which the antibody may bind to the epitope. One can also combine the various models to determine how one should alter the structure of the antibodies in order to obtain an antibody with the particular characteristics that are desired.

The models determined above can be tested through various techniques. For example, the interaction energy can be determined with the programs discussed above in order to determine which of the variants to further examine. Also, coulombic and van der Waals interactions are used to determine the interaction energies of the epitope and the variant paratopes. Also site directed mutagenesis is used to see if predicted changes in antibody structure actually result in the desired changes in binding characteristics. Alternatively, changes may be made to the epitope to verify that the models are correct or to determine general binding themes that may be occurring between the paratope and the epitope.

As will be appreciated by one of skill in the art, while these models will provide the guidance necessary to make the antibodies and variants thereof of the present embodiments, it may still be desirable to perform routine testing of the in silico models, perhaps through in vitro studies. In addition, as will be apparent to one of skill in the art, any modification may also have additional side effects on the activity of the antibody. For instance, while any alteration predicted to result in greater binding, may induce greater binding, it may also cause other structural changes which might reduce or alter the activity of the antibody. The determination of whether or not this is the case is routine in the art and can be achieved in many ways. For example, the activity can be tested through an ELISA test. Alternatively, the samples can be tested through the use of a surface plasmon resonance device.

Notch 3 Antibodies

The present disclosure provides antibodies that recognize at least one conformational epitope of Notch 3. The disclosure is based on the finding that a class of antibodies against Notch 3 bind to the particular conformation epitope of Notch 3 is disclosed in Table 2.

TABLE 2

Examples of Notch 3 Antibodies

20350

| | | | |
|---|---|---|---|
| SEQ ID NO: 3 (Kabat) | HCDR1 | SYTIS | |
| SEQ ID NO: 4 (Kabat) | HCDR2 | WIKPRWGAAHYAQKFQG | |
| SEQ ID NO: 5 (Kabat) | HCDR3 | GSFWFGY | |
| SEQ ID NO: 6 (Chothia) | HCDR1 | GGTFSSY | |
| SEQ ID NO: 7 (Chothia) | HCDR2 | KPRWGA | |
| SEQ ID NO: 8 (Chothia) | HCDR3 | GSFWFGY | |
| SEQ ID NO: 9 | VH | QVQLVQSGAEVKKPGSSVKVSCKASGGTFSSYTISWVRQAPGQGLEWMGWIKPRWGAAH YAQKFQGRVTITADESTSTAYMELSSLRSEDTAVYYCARGSFWFGYWGQGTLVTVSS | |
| SEQ ID NO: 10 | DNA VH | CAGGTGCAGCTGGTGCAGTCAGGCGCCGAAGTGAAGAAACCCGGCTCTAGCGTGAAAG TCAGCTGTAAAGCTAGTGGCGGAACCTTCTCTAGCTACACTATTAGCTGGGTCAGACAGG CCCCAGGTCAAGGCCTGGAGTGGATGGGCTGGATTAAGCCTCGCTGGGGCGCTGCTCAC TACGCTCAGAAATTTCAGGGTAGAGTGACTATCACCGCCGACGAGTCTACTAGCACCGCC TATATGGAACTGAGTTCCCTGAGGTCAGAGGACACCGCCGTCTACTACTGCGCTAGAGG CTCCTTTTGGTTCGGCTACTGGGGTCAGGGCACCCTGGTCACCGTGTCTAGC | |
| SEQ ID NO: 11 | Heavy Chain | QVQLVQSGAEVKKPGSSVKVSCKASGGTFSSYTISWVRQAPGQGLEWMGWIKPRWGAAH YAQKFQGRVTITADESTSTAYMELSSLRSEDTAVYYCARGSFWFGYWGQGTLVTVSSASTKG PSVFPLAPSSKSTSGGTAALGCLVKDYFPEPVTVSWNSGALTSGVHTFPAVLQSSGLYSLSSVV TVPSSSLGTQTYICNVNHKPSNTKVDKRVEPKSCDKTHTCPPCPAPELLGGPSVFLFPPKPKDT LMISRTPEVTCVVVDVSHEDPEVKFNWYVDGVEVHNAKTKPREEQYNSTYRVVSVLTVLHQ DWLNGKEYKCKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVMHEALHN HYTQKSLSLSPGK | |
| SEQ ID NO: 12 | DNA Heavy Chain | CAGGTGCAGCTGGTGCAGTCAGGCGCCGAAGTGAAGAAACCCGGCTCTAGCGTGAAAG TCAGCTGTAAAGCTAGTGGCGGAACCTTCTCTAGCTACACTATTAGCTGGGTCAGACAGG CCCCAGGTCAAGGCCTGGAGTGGATGGGCTGGATTAAGCCTCGCTGGGGCGCTGCTCAC | |

TABLE 2-continued

Examples of Notch 3 Antibodies

| | | |
|---|---|---|
| | | TACGCTCAGAAATTTCAGGGTAGAGTGACTATCACCGCCGACGAGTCTACTAGCACCGCC
TATATGGAACTGAGTTCCCTGAGGTCAGAGGACACCGCCGTCTACTACTGCGCTAGAGG
CTCCTTTTGGTTCGGCTACTGGGGTCAGGGCACCCTGGTCACCGTGTCTAGCGCTAGCAC
TAAGGGCCCAAGTGTGTTTCCCCTGGCCCCCAGCAGCAAGTCTACTTCCGGCGGAACTGC
TGCCCTGGGTTGCCTGGTGAAGGACTACTTCCCCGAGCCCGTGACAGTGTCCTGGAACTC
TGGGGCTCTGACTTCCGGCGTGCACACCTTCCCCGCCGTGCTGCAGAGCAGCGGCCTGT
ACAGCCTGAGCAGCGTGGTGACAGTGCCCTCCAGCTCTCTGGGAACCCAGACCTATATCT
GCAACGTGAACCACAAGCCCAGCAACACCAAGGTGGACAAGAGAGTGGAGCCCAAGAG
CTGCGACAAGACCCACACCTGCCCCCCCTGCCCAGCTCCAGAACTGCTGGGAGGGCCTTC
CGTGTTCCTGTTCCCCCCAAGCCCAAGGACACCCTGATGATCAGCAGGACCCCCGAGGT
GACCTGCGTGGTGGTGGACGTGTCCACGAGGACCCAGAGGTGAAGTTCAACTGGTAC
GTGGACGGCGTGGAGGTGCACAACGCCAAGACCAAGCCCAGAGAGGAGCAGTACAACA
GCACCTACAGGGTGGTGTCCGTGCTGACCGTGCTGCACCAGGACTGGCTGAACGGCAAA
GAATACAAGTGCAAAGTCTCCAACAAGGCCCTGCCAGCCCCAATCGAAAAGACAATCAG
CAAGGCCAAGGGCCAGCCACGGGAGCCCCAGGTGTACACCCTGCCCCCCAGCCGGGAG
GAGATGACCAAGAACCAGGTGTCCCTGACCTGTCTGGTGAAGGGCTTCTACCCCAGCGA
TATCGCCGTGGAGTGGGAGAGCAACGGCCAGCCCGAGAACAACTACAAGACCACCCCC
CAGTGCTGGACAGCGACGGCAGCTTCTTCCTGTACAGCAAGCTGACCGTGGACAAGTCC
AGGTGGCAGCAGGGCAACGTGTTCAGCTGCAGCGTGATGCACGAGGCCCTGCACAACC
ACTACACCCAGAAGTCCCTGAGCCTGAGCCCCGGCAAG |
| SEQ ID NO: 13 (Kabat) | LCDR1 | RASQGINNYLN |
| SEQ ID NO: 14 (Kabat) | LCDR2 | DASKLQS |
| SEQ ID NO: 15 (Kabat) | LCDR3 | QQYLQYPMT |
| SEQ ID NO: 16 (Chothia) | LCDR1 | SQGINNY |
| SEQ ID NO: 17 (Chothia) | LCDR2 | DAS |
| SEQ ID NO: 18 (Chothia) | LCDR3 | YLQYPM |
| SEQ ID NO: 19 | VL | DIQMTQSPSSLSASVGDRVTITCRASQGINNYLNWYQQKPGKAPKLLIYDASKLQSGVPSRFS
GSGSGTDFTLTISSLQPEDFATYYCQQYLQYPMTFGQGTKVEIK |
| SEQ ID NO: 20 | DNA VL | GATATTCAGATGACTCAGTCACCTAGTAGCCTGAGCGCTAGTGTGGGCGATAGAGTGAC
TATCACCTGTAGAGCCTCTCAGGGGATTAACAACTACCTGAACTGGTATCAGCAGAAGCC
CGGTAAAGCCCCTAAGCTGCTGATCTACGACGCCTCTAAGCTGCAGTCAGGCGTGCCCTC
TAGGTTTAGCGGTAGCGGTAGTGGCACCGACTTCACCCTGACTATCTCTAGCCTGCAGCC
CGAGGACTTCGCTACCTACTACTGTCAGCAGTACCTGCAGTACCCTATGACCTTCGGTCA
AGGCACTAAGGTCGAGATTAAG |
| SEQ ID NO: 21 | Light Chain | DIQMTQSPSSLSASVGDRVTITCRASQGINNYLNWYQQKPGKAPKLLIYDASKLQSGVPSRFS
GSGSGTDFTLTISSLQPEDFATYYCQQYLQYPMTFGQGTKVEIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC |
| SEQ ID NO: 22 | DNA Light Chain | GATATTCAGATGACTCAGTCACCTAGTAGCCTGAGCGCTAGTGTGGGCGATAGAGTGAC
TATCACCTGTAGAGCCTCTCAGGGGATTAACAACTACCTGAACTGGTATCAGCAGAAGCC
CGGTAAAGCCCCTAAGCTGCTGATCTACGACGCCTCTAAGCTGCAGTCAGGCGTGCCCTC
TAGGTTTAGCGGTAGCGGTAGTGGCACCGACTTCACCCTGACTATCTCTAGCCTGCAGCC
CGAGGACTTCGCTACCTACTACTGTCAGCAGTACCTGCAGTACCCTATGACCTTCGGTCA
AGGCACTAAGGTCGAGATTAAGCGTACGGTGGCCGCTCCCAGCGTGTTCATCTTCCCCCC
CAGCGACGAGCAGCTGAAGAGCGGCACCGCCAGCGTGGTGTGCCTGCTGAACAACTTCT
ACCCCCGGGAGGCCAAGGTGCAGTGGAAGGTGGACAACGCCCTGCAGAGCGGCAACAG
CCAGGAGAGCGTCACCGAGCAGGACAGCAAGGACTCCACCTACAGCCTGAGCAGCACC
CTGACCCTGAGCAAGGCCGACTACGAGAAGCATAAGGTGTACGCCTGCGAGGTGACCCA
CCAGGGCCTGTCCAGCCCCGTGACCAAGAGCTTCAACAGGGGCGAGTGC |
| 20358 | | |
| SEQ ID NO: 23 (Kabat) | HCDR1 | TYAMH |
| SEQ ID NO: 24 (Kabat) | HCDR2 | GIVPYHGITDYAQKFQG |
| SEQ ID NO: 25 (Kabat) | HCDR3 | DDYSTYAFAY |
| SEQ ID NO: 26 (Chothia) | HCDR1 | GGTFRTY |
| SEQ ID NO: 27 (Chothia) | HCDR2 | VPYHGI |
| SEQ ID NO: 28 (Chothia) | HCDR3 | DDYSTYAFAY |
| SEQ ID NO: 29 | VH | QVQLVQSGAEVKKPGSSVKVSCKASGGTFRTYAMHWVRQAPGQGLEWMGGIVPYHGITD
YAQKFQGRVTITADESTSTAYMELSSLRSEDTAVYYCARDDYSTYAFAYWGQGTLVTVSS |

TABLE 2-continued

Examples of Notch 3 Antibodies

| SEQ ID NO: 30 | DNA VH | CAGGTGCAGCTGGTGCAGTCAGGCGCCGAAGTGAAGAAACCCGGCTCTAGCGTGAAAG<br>TCAGCTGTGTAAAGCTAGTGGCGGAACCTTTAGAACCTACGCTATGCACTGGGTCAGACAG<br>GCCCCAGGTCAAGGCCTGGAGTGGATGGGCGGAATCGTGCCCTATCACGGAATCACCG<br>ACTACGCTCAGAAATTTCAGGGTAGAGTGACTATCACCGCCGACGAGTCTACTAGCACCG<br>CCTATATGGAACTGAGTTCCCTGAGGTCAGAGGACACCGCCGTCTACTACTGCGCTAGG<br>GACGACTACTCTACCTACGCCTTCGCCTACTGGGGTCAAGGCACCCTGGTCACCGTGTCT<br>AGC |
| --- | --- | --- |
| SEQ ID NO: 31 | Heavy Chain | QVQLVQSGAEVKKPGSSVKVSCKASGGTFRTYAMHWVRQAPGQGLEWMGGIVPYHGITD<br>YAQKFQGRVTITADESTSTAYMELSSLRSEDTAVYYCARDDYSTYAFAYWGQGTLVTVSSAST<br>KGPSVFPLAPSSKSTSGGTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPAPELLGGPSVFLFPPKPK<br>DTLMISRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEAL<br>HNHYTQKSLSLSPGK |
| SEQ ID NO: 32 | DNA Heavy Chain | CAGGTGCAGCTGGTGCAGTCAGGCGCCGAAGTGAAGAAACCCGGCTCTAGCGTGAAAG<br>TCAGCTGTGTAAAGCTAGTGGCGGAACCTTTAGAACCTACGCTATGCACTGGGTCAGACAG<br>GCCCCAGGTCAAGGCCTGGAGTGGATGGGCGGAATCGTGCCCTATCACGGAATCACCG<br>ACTACGCTCAGAAATTTCAGGGTAGAGTGACTATCACCGCCGACGAGTCTACTAGCACCG<br>CCTATATGGAACTGAGTTCCCTGAGGTCAGAGGACACCGCCGTCTACTACTGCGCTAGG<br>GACGACTACTCTACCTACGCCTTCGCCTACTGGGGTCAAGGCACCCTGGTCACCGTGTCT<br>AGCGCTAGCACTAAGGGCCCAAGTGTGTTTCCCCTGGCCCCCAGCAGCAAGTCTACTTCC<br>GGCGGAACTGCTGCCCTGGGTTGCCTGGTGAAGGACTACTTCCCCGAGCCCGTGACAGT<br>GTCCTGGAACTCTGGGGCTCTGACTTCCGGCGTGCACACCTTCCCCGCCGTGCTGCAGAG<br>CAGCGGCCTGTACAGCCTGAGCAGCGTGGTGACAGTGCCCTCCAGCTCTCTGGGAACCC<br>AGACCTATATCTGCAACGTGAACCACAAGCCCAGCAACACCAAGGTGGACAAGAGAGTG<br>GAGCCCAAGAGCTGCGACAAGACCCACACCTGCCCCCCTGCCCAGCTCCAGAACTGCT<br>GGGAGGGCTTCCGTGTTCCTGTTCCCCCCCAAGCCCAAGGACACCCTGATGATCAGCAG<br>GACCCCCGAGGTGACCTGCGTGGTGGTGGACGTGTGTCCCACGAGGACCCAGAGGTGAAG<br>TTCAACTGGTACGTGGACGGCGTGGAGGTGCACAACGCCAAGACCAAGCCCAGAGAGG<br>AGCAGTACAACAGCACCTACAGGGTGGTGTCCGTGCTGACCGTGCTGCACCAGGACTGG<br>CTGAACGGCAAAGAATACAAGTGCAAAGTCTCCAACAAGGCCCTGCCAGCCCCAATCGA<br>AAAGACAATCAGCAAGGCCAAGGGCCAGCCACGGGAGCCCCAGGTGTACACCCTGCCC<br>CCCAGCCGGGAGGAGATGACCAAGAACCAGGTGTCCCTGACCTGTCTGGTGAAGGGCTT<br>CTACCCCAGCGATATCGCCGTGGAGTGGGAGAGCAACGGCCAGCCCGAGAACAACTAC<br>AAGACCACCCCCCCAGTGCTGGACAGCGACGGCAGCTTCTTCCTGTACAGCAAGCTGACC<br>GTGGACAAGTCCAGGTGGCAGCAGGGCAACGTGTTCAGCTGCAGCGTGATGCACGAGG<br>CCCTGCACAACCACTACACCCAGAAGTCCCTGAGCCTGAGCCCCGGCAAG |
| SEQ ID NO: 33 (Kabat) | LCDR1 | RASQSIASYLA |
| SEQ ID NO: 34 (Kabat) | LCDR2 | DASNLQS |
| SEQ ID NO: 35 (Kabat) | LCDR3 | QQAYKTPYT |
| SEQ ID NO: 36 (Chothia) | LCDR1 | SQSIASY |
| SEQ ID NO: 37 (Chothia) | LCDR2 | DAS |
| SEQ ID NO: 38 (Chothia) | LCDR3 | AYKTPY |
| SEQ ID NO: 39 | VL | DIQMTQSPSSLSASVGDRVTITCRASQSIASYLAWYQQKPGKAPKLLIYDASNLQSGVPSRFS<br>GSGSGTDFTLTISSLQPEDFATYYCQQAYKTPYTFGQGTKVEIK |
| SEQ ID NO: 40 | DNA VL | GATATTCAGATGACTCAGTCACCTAGTAGCCTGAGCGCTAGTGTGGGCGATAGAGTGAC<br>TATCACCTGTAGAGCCTCTCAGTCTATCGCTAGTTACCTGGCCTGGTATCAGCAGAAGCC<br>CGGTAAAGCCCCTAAGCTGCTGATCTACGACGCCTCTAACCTGCAGTCAGGCGTGCCCTC<br>TAGGTTTAGCGGTAGCGGTAGTGGCACCGACTTCACCCTGACTATCTCTAGCCTGCAGCC<br>CGAGGACTTCGCTACCTACTACTGTCAGCAGGCCTATAAGACCCCCTACACCTTCGGTCA<br>AGGCACTAAGGTCGAGATTAAG |
| SEQ ID NO: 41 | Light Chain | DIQMTQSPSSLSASVGDRVTITCRASQSIASYLAWYQQKPGKAPKLLIYDASNLQSGVPSRFS<br>GSGSGTDFTLTISSLQPEDFATYYCQQAYKTPYTFGQGTKVEIKRTVAAPSVFIFPPSDEQLKS<br>GTASVVCLLNNFYPREAKVQWKVDNALQSGNSQESVTEQDSKDSTYSLSSTLTLSKADYEKH<br>KVYACEVTHQGLSSPVTKSFNRGEC |
| SEQ ID NO: 42 | DNA Light Chain | GATATTCAGATGACTCAGTCACCTAGTAGCCTGAGCGCTAGTGTGGGCGATAGAGTGAC<br>TATCACCTGTAGAGCCTCTCAGTCTATCGCTAGTTACCTGGCCTGGTATCAGCAGAAGCC<br>CGGTAAAGCCCCTAAGCTGCTGATCTACGACGCCTCTAACCTGCAGTCAGGCGTGCCCTC<br>TAGGTTTAGCGGTAGCGGTAGTGGCACCGACTTCACCCTGACTATCTCTAGCCTGCAGCC<br>CGAGGACTTCGCTACCTACTACTGTCAGCAGGCCTATAAGACCCCCTACACCTTCGGTCA<br>AGGCACTAAGGTCGAGATTAAGCGTACGGTGGCCGCTCCCAGCGTGTTCATCTTCCCCCC<br>CAGCGACGAGCAGCTGAAGAGCGGCACCGCCAGCGTGGTGTGCCTGCTGAACAACTTCT<br>ACCCCCGGGAGGCCAAGGTGCAGTGGAAGGTGGACAACGCCCTGCAGAGCGGCAACAG<br>CCAGGAGAGCGTCACCGAGCAGGACAGCAAGGACTCCACCTACAGCCTGAGCAGCACC |

TABLE 2-continued

Examples of Notch 3 Antibodies

| | | | |
|---|---|---|---|
| | | | CTGACCCTGAGCAAGGCCGACTACGAGAAGCATAAGGTGTACGCCTGCGAGGTGACCCA<br>CCAGGGCCTGTCCAGCCCCGTGACCAAGAGCTTCAACAGGGGCGAGTGC |
| 20802 | | | |
| SEQ ID NO: 43 (Kabat) | | HCDR1 | SYTMN |
| SEQ ID NO: 44 (Kabat) | | HCDR2 | RVKGEQFGGSIHYAASVKG |
| SEQ ID NO: 45 (Kabat) | | HCDR3 | ERSRAGSIFDP |
| SEQ ID NO: 46 (Chothia) | | HCDR1 | GFTFSSY |
| SEQ ID NO: 47 (Chothia) | | HCDR2 | KGEQFGGS |
| SEQ ID NO: 48 (Chothia) | | HCDR3 | ERSRAGSIFDP |
| SEQ ID NO: 49 | | VH | QVQLVESGGGLVKPGGSLRLSCAASGFTFSSYTMNWVRQAPGKGLEWVGRVKGEQFGGSI<br>HYAASVKGRFTISRDDSKNTLYLQMNSLKTEDTAVYYCARERSRAGSIFDPWGQGTLVTVSS |
| SEQ ID NO: 50 | | DNA VH | CAGGTGCAGCTGGTGGAATCAGGCGGCGGACTGGTCAAGCCTGGCGGTAGCCTGAGAC<br>TGAGCTGCGCTGCTAGTGGCTTCACCTTCTCTAGCTACACTATGAACTGGGTCAGACAGG<br>CCCCTGGTAAAGGCCTGGAGTGGGTCGGAAGAGTGAAGGGCGAGCAGTTCGGCGGCTC<br>TATTCACTACGCCGCTAGTGTGAAGGGCCGGTTCACTATCTCTAGGGACGACTCTAAGAA<br>CACCCTGTACCTGCAGATGAATAGCCTGAAAACCGAGGACACCGCCGTCTACTACTGCGC<br>TAGAGAGCGGTCTAGGGCCGGCTCTATCTTCGACCCTTGGGGTCAAGGCACCCTGGTCA<br>CCGTGTCTAGC |
| SEQ ID NO: 51 | | Heavy Chain | QVQLVESGGGLVKPGGSLRLSCAASGFTFSSYTMNWVRQAPGKGLEWVGRVKGEQFGGSI<br>HYAASVKGRFTISRDDSKNTLYLQMNSLKTEDTAVYYCARERSRAGSIFDPWGQGTLVTVSS<br>ASTKGPSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKRVEPKSCDKTHTCPPCPAPELLGGPSVFLFP<br>PKPKDTLMISRTPEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSREEMTKNQVSLTCL<br>VKGFYPSDIAVEWESNGQPENNYKTTPPVLDSDGSFFLYSKLTVDKSRWQQGNVFSCSVMH<br>EALHNHYTQKSLSLSPGK |
| SEQ ID NO: 52 | | DNA Heavy Chain | CAGGTGCAGCTGGTGGAATCAGGCGGCGGACTGGTCAAGCCTGGCGGTAGCCTGAGAC<br>TGAGCTGCGCTGCTAGTGGCTTCACCTTCTCTAGCTACACTATGAACTGGGTCAGACAGG<br>CCCCTGGTAAAGGCCTGGAGTGGGTCGGAAGAGTGAAGGGCGAGCAGTTCGGCGGCTC<br>TATTCACTACGCCGCTAGTGTGAAGGGCCGGTTCACTATCTCTAGGGACGACTCTAAGAA<br>CACCCTGTACCTGCAGATGAATAGCCTGAAAACCGAGGACACCGCCGTCTACTACTGCGC<br>TAGAGAGCGGTCTAGGGCCGGCTCTATCTTCGACCCTTGGGGTCAAGGCACCCTGGTCA<br>CCGTGTCTAGCGCTAGCACTAAGGGCCCAAGTGTGTTTCCCCTGGCCCCCAGCAGCAAGT<br>CTACTTCCGGCGGAACTGCTGCCCTGGGTTGCCTGGTGAAGGACTACTTCCCCGAGCCCG<br>TGACAGTGTCCTGGAACTCTGGGGCTCTGACTTCCGGCGTGCACACCTTCCCCGCCGTGC<br>TGCAGAGCAGCGGCCTGTACAGCCTGAGCAGCGTGGTGACAGTGCCCTCCAGCTCTCTG<br>GGAACCCAGACCTATATCTGCAACGTGAACCACAAGCCCAGCAACACCAAGGTGGACAA<br>GAGAGTGGAGCCCAAGAGCTGCGACAAGACCCACACCTGCCCCCCCTGCCCAGCTCCAG<br>AACTGCTGGGAGGGCCTTCCGTGTTCCTGTTCCCCCCAAGCCCAAGGACACCCTGATGA<br>TCAGCAGGACCCCCGAGGTGACCTGCGTGGTGGTGGACGTGTCCCACGAGGACCCAGA<br>GGTGAAGTTCAACTGGTACGTGGACGGCGTGGAGGTGCACAACGCCAAGACCAAGCCC<br>AGAGAGGAGCAGTACAACAGCACCTACAGGGTGGTGTCCGTGCTGACCGTGCTGCACCA<br>GGACTGGCTGAACGGCAAAGAATACAAGTGCAAAGTCTCCAACAAGGCCCTGCCAGCCC<br>CAATCGAAAAGACAATCAGCAAGGCCAAGGGCCAGCCACGGGAGCCCCAGGTGTACAC<br>CCTGCCCCCCAGCCGGGAGGAGATGACCAAGAACCAGGTGTCCCTGACCTGTCTGGTGA<br>AGGGCTTCTACCCCAGCGATATCGCCGTGGAGTGGGAGAGCAACGGCCAGCCCGAGAA<br>CAACTACAAGACCACCCCCCCAGTGCTGGACAGCGACGGCAGCTTCTTCCTGTACAGCAA<br>GCTGACCGTGGACAAGTCCAGGTGGCAGCAGGGCAACGTGTTCAGCTGCAGCGTGATG<br>CACGAGGCCCTGCACAACCACTACACCCAGAAGTCCCTGAGCCTGAGCCCCGGCAAG |
| SEQ ID NO: 53 (Kabat) | | LCDR1 | SGSSSNIGFNYVS |
| SEQ ID NO: 54 (Kabat) | | LCDR2 | YNNQRPS |
| SEQ ID NO: 55 (Kabat) | | LCDR3 | STWTGTSESHV |
| SEQ ID NO: 56 (Chothia) | | LCDR1 | SSSNIGFNY |
| SEQ ID NO: 57 (Chothia) | | LCDR2 | YNN |
| SEQ ID NO: 58 (Chothia) | | LCDR3 | WTGTSESH |
| SEQ ID NO: 59 | | VL | QSVLTQPPSVSGAPGQRVTISCSGSSSNIGFNYVSWYQQLPGTAPKLLIYYNNQRPSGVPDRF<br>SGSKSGTSASLAITGLQAEDEADYYCSTWTGTSESHVFGGGTKLTVL |
| SEQ ID NO: 60 | | DNA VL | CAGTCAGTCCTGACTCAGCCCCCTAGCGTCAGCGGCGCTCCCGGTCAAAGAGTGACTATT<br>AGCTGTAGCGGCTCTAGCTCTAATATCGGCTTTAACTACGTCAGCTGGTATCAGCAGCTG |

TABLE 2-continued

Examples of Notch 3 Antibodies

| | | |
|---|---|---|
| | | CCCGGCACCGCCCCTAAGCTGCTGATCTACTATAACAATCAGCGGCCTAGCGGCGTGCCC<br>GATAGGTTTAGCGGATCTAAGTCAGGCACTTCTGCTAGTCTGGCTATCACCGGACTGCAG<br>GCTGAGGACGAGGCCGACTACTACTGCTCTACCTGGACCGGAACTAGCGAGTCTCACGT<br>GTTCGGCGGAGGCACTAAGCTGACCGTGCTG |
| SEQ ID NO: 61 | Light Chain | QSVLTQPPSVSGAPGQRVTISCSGSSSNIGFNYVSWYQQLPGTAPKLLIYYNNQRPSGVPDRF<br>SGSKSGTSASLAITGLQAEDEADYYCSTWTGTSESHVFGGGTKLTVLGQPKAAPSVTLFPPSS<br>EELQANKATLVCLISDFYPGAVTVAWKADSSPVKAGVETTTPSKQSNNKYAASSYLSLTPEQ<br>WKSHRSYSCQVTHEGSTVEKTVAPTECS |
| SEQ ID NO: 62 | DNA Light<br>Chain | CAGTCAGTCCTGACTCAGCCCCCTAGCGTCAGCGGCGCTCCCGGTCAAAGAGTGACTATT<br>AGCTGTAGCGGCTCTAGCTCTAATATCGGCTTTAACTACGTCAGCTGGTATCAGCAGCTG<br>CCCGGCACCGCCCCTAAGCTGCTGATCTACTATAACAATCAGCGGCCTAGCGGCGTGCCC<br>GATAGGTTTAGCGGATCTAAGTCAGGCACTTCTGCTAGTCTGGCTATCACCGGACTGCAG<br>GCTGAGGACGAGGCCGACTACTACTGCTCTACCTGGACCGGAACTAGCGAGTCTCACGT<br>GTTCGGCGGAGGCACTAAGCTGACCGTGCTGGGTCAACCTAAGGCTGCCCCCAGCGTGA<br>CCCTGTTCCCCCCCAGCAGCGAGGAGCTGCAGGCCAACAAGGCCACCCTGGTGTGCCTG<br>ATCAGCGACTTCTACCCAGGCGCCGTGACCGTGGCCTGGAAGGCCGACAGCAGCCCCGT<br>GAAGGCCGGCGTGGAGACCACCACCCCCAGCAAGCAGAGCAACAACAAGTACGCCGCC<br>AGCAGCTACCTGAGCCTGACCCCCGAGCAGTGGAAGAGCCACAGGTCCTACAGCTGCCA<br>GGTGACCCACGAGGGCAGCACCGTGGAAAAGACCGTGGCCCCAACCGAGTGCAGC |

20337

| | | |
|---|---|---|
| SEQ ID NO: 63 (Kabat) | HCDR1 | TYVMH |
| SEQ ID NO: 64 (Kabat) | HCDR2 | RIRANAYGGAADYAAPVKG |
| SEQ ID NO: 65 (Kabat) | HCDR3 | AEARYRDV |
| SEQ ID NO: 66 (Chothia) | HCDR1 | GFTFSTY |
| SEQ ID NO: 67 (Chothia) | HCDR2 | RANAYGGA |
| SEQ ID NO: 68 (Chothia) | HCDR3 | AEARYRDV |
| SEQ ID NO: 69 | VH | QVQLVESGGGLVKPGGSLRLSCAASGFTFSTYVMHWVRQAPGKGLEWVGRIRANAYGGA<br>ADYAAPVKGRFTISRDDSKNTLYLQMNSLKTEDTAVYYCARAEARYRDVWGQGTLVTVSS |
| SEQ ID NO: 70 | DNA VH | CAGGTGCAGCTGGTGGAATCAGGCGGCGGACTGGTCAAGCCTGGCGGCTCCCTGAGGC<br>TGAGCTGCGCTGCTAGTGGCTTCACCTTTAGCACCTACGTGATGCACTGGGTCCGCCAGG<br>CCCCTGGTAAAGGCCTGGAGTGGGTCGGACGGATTAGAGCTAACGCCTACGGCGGAGC<br>CGCCGACTACGCTGCCCCTGTGAAGGGCCGGTTCACTATCTCTAGGGACGACTCTAAGA<br>ACACCCTGTACCTGCAGATGAATAGCCTGAAAACCGAGGACACCGCCGTCTACTACTGCG<br>CTAGAGCCGAGGCTAGATATAGGGACGTGTGGGGTCAAGGCACCCTGGTCACCGTGTCT<br>AGC |
| SEQ ID NO: 71 | Heavy Chain | QVQLVESGGGLVKPGGSLRLSCAASGFTFSTYVMHWVRQAPGKGLEWVGRIRANAYGGA<br>ADYAAPVKGRFTISRDDSKNTLYLQMNSLKTEDTAVYYCARAEARYRDVWGQGTLVTVSSA<br>STKGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKRVEPKSCDKTHTCPPCPAPELLGGPSVFLFPPK<br>PKDTLMISRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNVFSCSVMHE<br>ALHNHYTQKSLSLSPGK |
| SEQ ID NO: 72 | DNA Heavy<br>Chain | CAGGTGCAGCTGGTGGAATCAGGCGGCGGACTGGTCAAGCCTGGCGGCTCCCTGAGGC<br>TGAGCTGCGCTGCTAGTGGCTTCACCTTTAGCACCTACGTGATGCACTGGGTCCGCCAGG<br>CCCCTGGTAAAGGCCTGGAGTGGGTCGGACGGATTAGAGCTAACGCCTACGGCGGAGC<br>CGCCGACTACGCTGCCCCTGTGAAGGGCCGGTTCACTATCTCTAGGGACGACTCTAAGA<br>ACACCCTGTACCTGCAGATGAATAGCCTGAAAACCGAGGACACCGCCGTCTACTACTGCG<br>CTAGAGCCGAGGCTAGATATAGGGACGTGTGGGGTCAAGGCACCCTGGTCACCGTGTCT<br>AGCGCTAGCACTAAGGGCCCAAGTGTGTTTCCCCTGGCCCCAGCAGCAAGTCTACTTCC<br>GGCGGAACTGCTGCCCTGGGTTGCCTGGTGAAGGACTACTTCCCCGAGCCCGTGACAGT<br>GTCCTGGAACTCTGGGGCTCTGACTTCCGGCGTGCACACCTTCCCCGCCGTGCTGCAGAG<br>CAGCGGCCTGTACAGCCTGAGCAGCGTGGTGACAGTGCCCTCCAGCTCTCTGGGAACCC<br>AGACCTATATCTGCAACGTGAACCACAAGCCCAGCAACACCAAGGTGGACAAGAGAGTG<br>GAGCCCAAGAGCTGCGACAAGACCCACACCTGCCCCCCTGCCCAGCTCCAGAACTGCT<br>GGGAGGGCCTTCCGTGTTCCTGTTCCCCCCCAAGCCCAAGGACACCCTGATGATCAGCAG<br>GACCCCCGAGGTGACCTGCGTGGTGGTGGACGTGTCCCACGAGGACCCAGAGGTGAAG<br>TTCAACTGGTACGTGGACGGCGTGGAGGTGCACAACGCCAAGACCAAGCCCAGAGAGG<br>AGCAGTACAACAGCACCTACAGGGTGGTGTCCGTGCTGACCGTGCTGCACCAGGACTGG<br>CTGAACGGCAAGGAATACAAGTGCAAGTCTCCAACAAGGCCCTGCCAGCCCCAATCGA<br>AAAGACAATCAGCAAGGCCAAGGGCCAGCCACGGGAGCCCCAGGTGTACACCCTGCCC<br>CCCAGCCGGGAGGAGATGACCAAGAACCAGGTGTCCCTGACCTGTCTGGTGAAGGGCTT<br>CTACCCCAGCGATATCGCCGTGGAGTGGGAGAGCAACGGCCAGCCCGAGAACAACTAC<br>AAGACCACCCCCCCAGTGCTGGACAGCGACGGCAGCTTCTTCCTGTACAGCAAGCTGACC |

TABLE 2-continued

Examples of Notch 3 Antibodies

|   |   |   |
|---|---|---|
|   |   | GTGGACAAGTCCAGGTGGCAGCAGGGCAACGTGTTCAGCTGCAGCGTGATGCACGAGG<br>CCCTGCACAACCACTACACCCAGAAGTCCCTGAGCCTGAGCCCCGGCAAG |
| SEQ ID NO: 73 (Kabat) | LCDR1 | RASQSISSHLN |
| SEQ ID NO: 74 (Kabat) | LCDR2 | AASNLQS |
| SEQ ID NO: 75 (Kabat) | LCDR3 | QQDYHTPFT |
| SEQ ID NO: 76 (Chothia) | LCDR1 | SQSISSH |
| SEQ ID NO: 77 (Chothia) | LCDR2 | AAS |
| SEQ ID NO: 78 (Chothia) | LCDR3 | DYHTPF |
| SEQ ID NO: 79 | VL | DIQMTQSPSSLSASVGDRVTITCRASQSISSHLNWYQQKPGKAPKLLIYAASNLQSGVPSRFS<br>GSGSGTDFTLTISSLQPEDFATYYCQQDYHTPFTFGQGTKVEIK |
| SEQ ID NO: 80 | DNA VL | GATATTCAGATGACTCAGTCACCTAGTAGCCTGAGCGCTAGTGTGGGCGATAGAGTGAC<br>TATCACCTGTAGAGCCTCTCAGTCTATTAGCTCTCACCTGAACTGGTATCAGCAGAAGCCC<br>GGTAAAGCCCCTAAGCTGCTGATCTACGCCGCCTCTAACCTGCAGTCAGGCGTGCCCTCT<br>AGGTTTAGCGGTAGCGGTAGTGGCACCGACTTCACCCTGACTATCTCTAGCCTGCAGCCC<br>GAGGACTTCGCTACCTACTACTGTCAGCAGGACTATCACACCCCCTTCACCTTCGGTCAA<br>GGCACTAAGGTCGAGATTAAG |
| SEQ ID NO: 81 | Light Chain | DIQMTQSPSSLSASVGDRVTITCRASQSISSHLNWYQQKPGKAPKLLIYAASNLQSGVPSRFS<br>GSGSGTDFTLTISSLQPEDFATYYCQQDYHTPFTFGQGTKVEIKRTVAAPSVFIFPPSDEQLKS<br>GTASVVCLLNNFYPREAKVQWKVDNALQSGNSQESVTEQDSKDSTYSLSSTLTLSKADYEKH<br>KVYACEVTHQGLSSPVTKSFNRGEC |
| SEQ ID NO: 82 | DNA Light<br>Chain | GATATTCAGATGACTCAGTCACCTAGTAGCCTGAGCGCTAGTGTGGGCGATAGAGTGAC<br>TATCACCTGTAGAGCCTCTCAGTCTATTAGCTCTCACCTGAACTGGTATCAGCAGAAGCCC<br>GGTAAAGCCCCTAAGCTGCTGATCTACGCCGCCTCTAACCTGCAGTCAGGCGTGCCCTCT<br>AGGTTTAGCGGTAGCGGTAGTGGCACCGACTTCACCCTGACTATCTCTAGCCTGCAGCCC<br>GAGGACTTCGCTACCTACTACTGTCAGCAGGACTATCACACCCCCTTCACCTTCGGTCAA<br>GGCACTAAGGTCGAGATTAAGCGTACGGTGGCTGCTCCCAGCGTGTTCATCTTCCCCCCC<br>AGCGACGAGCAGCTGAAGAGCGGCACCGCCAGCGTGGTGTGCCTGCTGAACAACTTCTA<br>CCCCCGGGAGGCCAAGGTGCAGTGGAAGGTGGACAACGCCCTGCAGAGCGGCAACAGC<br>CAGGAGAGCGTCACCGAGCAGGACAGCAAGGACTCCACCTACAGCCTGAGCAGCACCCT<br>GACCCTGAGCAAGGCCGACTACGAGAAGCATAAGGTGTACGCCTGCGAGGTGACCCAC<br>CAGGGCCTGTCCAGCCCCGTGACCAAGAGCTTCAACAGGGGCGAGTGC |
| 20345 | | |
| SEQ ID NO: 83 (Kabat) | HCDR1 | SYTIS |
| SEQ ID NO: 84 (Kabat) | HCDR2 | WIKPKLGMAHYAQKFQG |
| SEQ ID NO: 85 (Kabat) | HCDR3 | GSFWFGY |
| SEQ ID NO: 86 (Chothia) | HCDR1 | GGTFSSY |
| SEQ ID NO: 87 (Chothia) | HCDR2 | KPKLGM |
| SEQ ID NO: 88 (Chothia) | HCDR3 | GSFWFGY |
| SEQ ID NO: 89 | VH | QVQLVQSGAEVKKPGSSVKVSCKASGGTFSSYTISWVRQAPGQGLEWMGWIKPKLGMAH<br>YAQKFQGRVTITADESTSTAYMELSSLRSEDTAVYYCARGSFWFGYWGQGTLVTVSS |
| SEQ ID NO: 90 | DNA VH | CAGGTGCAATTGGTGCAGAGCGGTGCCGAAGTGAAAAAACCGGGCAGCAGCGTGAAAG<br>TTAGCTGCAAAGCATCCGGAGGGACGTTTTCTTCTTACACTATCTCTTGGGTGCGCCAGG<br>CCCCGGGCCAGGGCCTCGAGTGGATGGGCTGGATCAAACCGAAACTGGGCATGGCTCA<br>TTACGCCCAGAAATTTCAGGGCCGGGTGACCATTACCGCCGATGAAAGCACCAGCACCG<br>CCTATATGGAACTGAGCAGCCTGCGCAGCGAAGATACGGCCGTGTATTATTGCGCGCGT<br>GGTTCTTTCTGGTTCGGTTACTGGGGCCAAGGCACCCTGGTGACTGTTAGCTCA |
| SEQ ID NO: 91 | Heavy Chain | QVQLVQSGAEVKKPGSSVKVSCKASGGTFSSYTISWVRQAPGQGLEWMGWIKPKLGMAH<br>YAQKFQGRVTITADESTSTAYMELSSLRSEDTAVYYCARGSFWFGYWGQGTLVTVSSASTKG<br>PSVFPLAPSSKSTSGGTAALGCLVKDYFPEPVTVSWNSGALTSGVHTFPAVLQSSGLYSLSSVV<br>TVPSSSLGTQTYICNVNHKPSNTKVDKRVEPKSCDKTHTCPPCPAPELLGGPSVFLFPPKPKDT<br>LMISRTPEVTCVVVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVMHEALHN<br>HYTQKSLSLSPGK |
| SEQ ID NO: 92 | DNA Heavy<br>Chain | CAGGTGCAATTGGTGCAGAGCGGTGCCGAAGTGAAAAAACCGGGCAGCAGCGTGAAAG<br>TTAGCTGCAAAGCATCCGGAGGGACGTTTTCTTCTTACACTATCTCTTGGGTGCGCCAGG<br>CCCCGGGCCAGGGCCTCGAGTGGATGGGCTGGATCAAACCGAAACTGGGCATGGCTCA<br>TTACGCCCAGAAATTTCAGGGCCGGGTGACCATTACCGCCGATGAAAGCACCAGCACCG |

TABLE 2-continued

Examples of Notch 3 Antibodies

| | | |
|---|---|---|
| | | CCTATATGGAACTGAGCAGCCTGCGCAGCGAAGATACGGCCGTGTATTATTGCGCGCGT<br>GGTTCTTTTCTGGTTCGGTTACTGGGGCCAAGGCACCCTGGTGACTGTTAGCTCAGCCTCC<br>ACCAAGGGTCCATCGGTCTTCCCCCTGGCACCCTCCTCCAAGAGCACCTCTGGGGGCACA<br>GCGGCCCTGGGCTGCCTGGTCAAGGACTACTTCCCCGAACCGGTGACGGTGTCGTGGAA<br>CTCAGGCGCCCTGACCAGCGGCGTGCACACCTTCCCGGCTGTCCTACAGTCCTCAGGACT<br>CTACTCCCTCAGCAGCGTGGTGACCGTGCCCTCCAGCAGCTTGGGCACCCAGACCTACAT<br>CTGCAACGTGAATCACAAGCCCAGCAACACCAAGGTGGACAAGAGAGTTGAGCCCAAAT<br>CTTGTGACAAAACTCACACATGCCCACCGTGCCCAGCACCTGAACTCCTGGGGGGACCGT<br>CAGTCTTCCTCTTCCCCCCAAAACCCAAGGACACCCTCATGATCTCCCGGACCCCTGAGGT<br>CACATGCGTGGTGGTGGACGTGAGCCACGAAGACCCTGAGGTCAAGTTCAACTGGTACG<br>TGGACGGCGTGGAGGTGCATAATGCCAAGACAAAGCCGCGGGAGGAGCAGTACAACA<br>GCACGTACCGGGTGGTCAGCGTCCTCACCGTCCTGCACCAGGACTGGCTGAATGGCAAG<br>GAGTACAAGTGCAAGGTCTCCAACAAAGCCCTCCCAGCCCCCATCGAGAAAACCATCTCC<br>AAAGCCAAAGGGCAGCCCCGAGAACCACAGGTGTACACCCTGCCCCCATCCCGGGAGG<br>AGATGACCAAGAACCAGGTCAGCCTGACCTGCCTGGTCAAAGGCTTCTATCCCAGCGAC<br>ATCGCCGTGGAGTGGGAGAGCAATGGGCAGCCGGAGAACAACTACAAGACCACGCCTC<br>CCGTGCTGGACTCCGACGGCTCCTTCTTCCTCTACAGCAAGCTCACCGTGGACAAGAGCA<br>GGTGGCAGCAGGGGAACGTCTTCTCATGCTCCGTGATGCATGAGGCTCTGCACAACCAC<br>TACACGCAGAAGAGCCTCTCCCTGTCTCCGGGTAAA |
| SEQ ID NO: 93 (Kabat) | LCDR1 | RASQGINNYLN |
| SEQ ID NO: 94 (Kabat) | LCDR2 | DASKLQS |
| SEQ ID NO: 95 (Kabat) | LCDR3 | QQYLQYPMT |
| SEQ ID NO: 96 (Chothia) | LCDR1 | SQGINNY |
| SEQ ID NO: 97 (Chothia) | LCDR2 | DAS |
| SEQ ID NO: 98 (Chothia) | LCDR3 | YLQYPM |
| SEQ ID NO: 99 | VL | DIQMTQSPSSLSASVGDRVTITCRASQGINNYLNWYQQKPGKAPKLLIYDASKLQSGVPSRFS<br>GSGSGTDFTLTISSLQPEDFATYYCQQYLQYPMTFGQGTKVEIK |
| SEQ ID NO: 100 | DNA VL | GATATCCAGATGACCCAGAGCCCGAGCAGCCTGAGCGCCAGCGTGGGCGATCGCGTGA<br>CCATTACCTGCAGAGCCAGCCAGGGTATTAACAACTACCTGAACTGGTACCAGCAGAAA<br>CCGGGCAAAGCGCCGAAACTATTAATCTACGACGCTTCTAAACTGCAAAGCGGCGTGCC<br>GAGCCGCTTTAGCGGCAGCGGATCCGGCACCGATTTCACCCTGACCATTAGCTCTCTGCA<br>ACCGGAAGACTTTGCGACCTATTATTGCCAGCAGTACCTGCAGTACCCGATGACCTTTGG<br>CCAGGGCACGAAAGTTGAAATTAAA |
| SEQ ID NO: 101 | Light Chain | DIQMTQSPSSLSASVGDRVTITCRASQGINNYLNWYQQKPGKAPKLLIYDASKLQSGVPSRFS<br>GSGSGTDFTLTISSLQPEDFATYYCQQYLQYPMTFGQGTKVEIKRTVAAPSVFIFPPSDEQLKS<br>GTASVVCLLNNFYPREAKVQWKVDNALQSGNSQESVTEQDSKDSTYSLSSTLTLSKADYEKH<br>KVYACEVTHQGLSSPVTKSFNRGEC |
| SEQ ID NO: 102 | DNA Light<br>Chain | GATATCCAGATGACCCAGAGCCCGAGCAGCCTGAGCGCCAGCGTGGGCGATCGCGTGA<br>CCATTACCTGCAGAGCCAGCCAGGGTATTAACAACTACCTGAACTGGTACCAGCAGAAA<br>CCGGGCAAAGCGCCGAAACTATTAATCTACGACGCTTCTAAACTGCAAAGCGGCGTGCC<br>GAGCCGCTTTAGCGGCAGCGGATCCGGCACCGATTTCACCCTGACCATTAGCTCTCTGCA<br>ACCGGAAGACTTTGCGACCTATTATTGCCAGCAGTACCTGCAGTACCCGATGACCTTTGG<br>CCAGGGCACGAAAGTTGAAATTAAACGTACGGTGGCCGCTCCCAGCGTGTTCATCTTCCC<br>CCCCAGCGACGAGCAGCTGAAGAGCGGCACCGCCAGCGTGGTGTGCCTGCTGAACAACT<br>TCTACCCCGGAGGCCAAGGTGCAGTGGAAGGTGGACAACGCCCTGCAGAGCGGCAA<br>CAGCCAGGAAAGCGTCACCGAGCAGGACAGCAAGGACTCCACCTACAGCCTGAGCAGC<br>ACCCTGACCCTGAGCAAGGCCGACTACGAGAAGCACAAGGTGTACGCCTGCGAGGTGA<br>CCCACCAGGGCCTGTCCAGCCCCGTGACCAAGAGCTTCAACCGGGGCGAGTGT |
| 20351 | | |
| SEQ ID NO: 103 (Kabat) | HCDR1 | SYTIS |
| SEQ ID NO: 104 (Kabat) | HCDR2 | WIKPRYGAAMYAQKFQG |
| SEQ ID NO: 105 (Kabat) | HCDR3 | GSFWFGY |
| SEQ ID NO: 106 (Chothia) | HCDR1 | GGTFSSY |
| SEQ ID NO: 107 (Chothia) | HCDR2 | KPRYGA |
| SEQ ID NO: 108 (Chothia) | HCDR3 | GSFWFGY |
| SEQ ID NO: 109 | VH | QVQLVQSGAEVKKPGSSVKVSCKASGGTFSSYTISWVRQAPGQGLEWMGWIKPRYGAAM<br>YAQKFQGRVTITADESTSTAYMELSSLRSEDTAVYYCARGSFWFGYWGQGTLVTVSS |
| SEQ ID NO: 110 | DNA VH | CAGGTGCAATTGGTGCAGAGCGGTGCCGAAGTGAAAAAACCGGGCAGCAGCGTGAAAG<br>TTAGCTGCAAAGCATCCGGAGGGACGTTTTCTTCTTACACTATCTCTTGGGTGCGCCAGG |

TABLE 2-continued

Examples of Notch 3 Antibodies

| | | |
|---|---|---|
| | | CCCCGGGCCAGGGCCTCGAGTGGATGGGCTGGATCAAACCGCGTTACGGCGCTGCTATG<br>TACGCCCAGAAATTTCAGGGCCGGGTGACCATTACCGCCGATGAAAGCACCAGCACCGC<br>CTATATGGAACTGAGCAGCCTGCGCAGCGAAGATACGGCCGTGTATTATTGCGCGCGTG<br>GTTCTTTCTGGTTCGGTTACTGGGGCCAAGGCACCCTGGTGACTGTTAGCTCA |
| SEQ ID NO: 111 | Heavy Chain | QVQLVQSGAEVKKPGSSVKVSCKASGGTFSSYTISWVRQAPGQGLEWMGWIKPRYGAAM<br>YAQKFQGRVTITADESTSTAYMELSSLRSEDTAVYYCARGSFWFGYWGQGTLVTVSSASTKG<br>PSVFPLAPSSKSTSGGTAALGCLVKDYFPEPVTVSWNSGALTSGVHTFPAVLQSSGLYSLSSVV<br>TVPSSSLGTQTYICNVNHKPSNTKVDKRVEPKSCDKTHTCPPCPAPELLGGPSVFLFPPKPKDT<br>LMISRTPEVTCVVVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVMHEALHN<br>HYTQKSLSLSPGK |
| SEQ ID NO: 112 | DNA Heavy<br>Chain | CAGGTGCAATTGGTGCAGAGCGGTGCCGAAGTGAAAAAACCGGGCAGCAGCGTGAAAG<br>TTAGCTGCAAAGCATCCGGAGGGACGTTTTCTTCTTACACTATCTCTTGGGTGCGCCAGG<br>CCCCGGGCCAGGGCCTCGAGTGGATGGGCTGGATCAAACCGCGTTACGGCGCTGCTATG<br>TACGCCCAGAAATTTCAGGGCCGGGTGACCATTACCGCCGATGAAAGCACCAGCACCGC<br>CTATATGGAACTGAGCAGCCTGCGCAGCGAAGATACGGCCGTGTATTATTGCGCGCGTG<br>GTTCTTTCTGGTTCGGTTACTGGGGCCAAGGCACCCTGGTGACTGTTAGCTCAGCCTCCA<br>CCAAGGGTCCATCGGTCTTCCCCCTGGCACCCTCCTCCAAGAGCACCTCTGGGGGCACAG<br>CGGCCCTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCAGGACTC<br>TACTCCCTCAGCAGCGTGGTGACCGTGCCCTCCAGCAGCTTGGGCACCCAGACCTACATC<br>TGCAACGTGAATCACAAGCCCAGCAACACCAAGGTGGACAAGAGAGTTGAGCCCAAATC<br>TTGTGACAAAACTCACACATGCCCACCGTGCCCAGCACCTGAACTCCTGGGGGGACCGTC<br>AGTCTTCCTCTTCCCCCCAAAGACCAAGGACACCCTCATGATCTCCCGGACCCCTGAGGTC<br>ACATGCGTGGTGGTGGACGTGAGCCACGAAGACCCTGAGGTCAAGTTCAACTGGTACGT<br>GGACGGCGTGGAGGTGCATAATGCCAAGACAAAGCCGCGGGAGGAGCAGTACAACAG<br>CACGTACCGGGTGGTCAGCGTCCTCACCGTCCTGCACCAGGACTGGCTGAATGGCAAGG<br>AGTACAAGTGCAAGGTCTCCAACAAAGCCCTCCCAGCCCCCATCGAGAAAACCATCTCCA<br>AAGCCAAAGGGCAGCCCCGAGAACCACAGGTGTACACCCTGCCCCCATCCCGGGAGGA<br>GATGACCAAGAACCAGGTCAGCCTGACCTGCCTGGTCAAAGGCTTCTATCCCAGCGACAT<br>CGCCGTGGAGTGGGAGAGCAATGGGCAGCCGGAGAACAACTACAAGACCACGCCTCCC<br>GTGCTGGACTCCGACGGCTCCTTCTTCCTCTACAGCAAGCTCACCGTGGACAAGAGCAGG<br>TGGCAGCAGGGGAACGTCTTCTCATGCTCCGTGATGCATGAGGCTCTGCACAACCACTAC<br>ACGCAGAAGAGCCTCTCCCTGTCTCCGGGTAAA |
| SEQ ID NO: 113 (Kabat) | LCDR1 | RASQGINNYLN |
| SEQ ID NO: 114 (Kabat) | LCDR2 | DASKLQS |
| SEQ ID NO: 115 (Kabat) | LCDR3 | QQYLQYPMT |
| SEQ ID NO: 116 (Chothia) | LCDR1 | SQGINNY |
| SEQ ID NO: 117 (Chothia) | LCDR2 | DAS |
| SEQ ID NO: 118 (Chothia) | LCDR3 | YLQYPM |
| SEQ ID NO: 119 | VL | DIQMTQSPSSLSASVGDRVTITCRASQGINNYLNWYQQKPGKAPKLLIYDASKLQSGVPSRFS<br>GSGSGTDFTLTISSLQPEDFATYYCQQYLQYPMTFGQGTKVEIK |
| SEQ ID NO: 120 | DNA VL | GATATCCAGATGACCCAGAGCCCGAGCAGCCTGAGCGCCAGCGTGGGCGATCGCGTGA<br>CCATTACCTGCAGAGCCAGCCAGGGTATTAACAACTACCTGAACTGGTACCAGCAGAAA<br>CCGGGCAAAGCGCCGAAACTATTAATCTACGACGCTTCTAAACTGCAAAGCGGCGTGCC<br>GAGCCGCTTTAGCGGCAGCGGATCCGGCACCGATTTCACCCTGACCATTAGCTCTCTGCA<br>ACCGGAAGACTTTGCGACCTATTATTGCCAGCAGTACCTGCAGTACCCGATGACCTTTGG<br>CCAGGGCACGAAAGTTGAAATTAAA |
| SEQ ID NO: 121 | Light Chain | DIQMTQSPSSLSASVGDRVTITCRASQGINNYLNWYQQKPGKAPKLLIYDASKLQSGVPSRFS<br>GSGSGTDFTLTISSLQPEDFATYYCQQYLQYPMTFGQGTKVEIKRTVAAPSVFIFPPSDEQLKS<br>GTASVVCLLNNFYPREAKVQWKVDNALQSGNSQESVTEQDSKDSTYSLSSTLTLSKADYEKH<br>KVYACEVTHQGLSSPVTKSFNRGEC |
| SEQ ID NO: 122 | DNA Light<br>Chain | GATATCCAGATGACCCAGAGCCCGAGCAGCCTGAGCGCCAGCGTGGGCGATCGCGTGA<br>CCATTACCTGCAGAGCCAGCCAGGGTATTAACAACTACCTGAACTGGTACCAGCAGAAA<br>CCGGGCAAAGCGCCGAAACTATTAATCTACGACGCTTCTAAACTGCAAAGCGGCGTGCC<br>GAGCCGCTTTAGCGGCAGCGGATCCGGCACCGATTTCACCCTGACCATTAGCTCTCTGCA<br>ACCGGAAGACTTTGCGACCTATTATTGCCAGCAGTACCTGCAGTACCCGATGACCTTTGG<br>CCAGGGCACGAAAGTTGAAATTAAACGTACGGTGGCCGCTCCCAGCGTGTTCATCTTCCC<br>CCCCAGCGACGAGCAGCTGAAGAGCGGCACCGCCAGCGTGGTGTGCCTGCTGAACAACT<br>TCTACCCCGGGAGGCCAAGGTGCAGTGGAAGGTGGACAACGCCCTGCAGAGCGGCAA<br>CAGCCAGGAAAGCGTCACCGAGCAGGACAGCAAGGACTCCACCTACAGCCTGAGCAGC<br>ACCCTGACCCTGAGCAAGGCCGACTACGAGAAGCACAAGGTGTACGCCTGCGAGGTGA<br>CCCACCAGGGCCTGTCAGCCCCGTGACCAAGAGCTTCAACCGGGGCGAGTGT |

TABLE 2-continued

Examples of Notch 3 Antibodies

12215

| | | |
|---|---|---|
| SEQ ID NO: 123 (Kabat) | HCDR1 | TYVMH |
| SEQ ID NO: 124 (Kabat) | HCDR2 | RIRSNTYGGITDYAAPVKG |
| SEQ ID NO: 125 (Kabat) | HCDR3 | AEARYRDV |
| SEQ ID NO: 126 (Chothia) | HCDR1 | GFTFSTY |
| SEQ ID NO: 127 (Chothia) | HCDR2 | RSNTYGGI |
| SEQ ID NO: 128 (Chothia) | HCDR3 | AEARYRDV |
| SEQ ID NO: 129 | VH | QVQLVESGGGLVKPGGSLRLSCAASGFTFSTYVMHWVRQAPGKGLEWVGRIRSNTYGGITD YAAPVKGRFTISRDDSKNTLYLQMNSLKTEDTAVYYCARAEARYRDVWGQGTLVTVSS |
| SEQ ID NO: 130 | DNA VH | CAGGTGCAATTGGTGGAAAGCGGCGGTGGCCTGGTGAAACCAGGCGGCAGCCTGCGCC TGAGCTGCGCCGCCTCCGGATTCACCTTTTCTACTTACGTTATGCATTGGGTGCGCCAGG CCCCGGGCAAAGGTCTCGAGTGGGTGGGCCGTATCCGTTCTAACACTTACGGTGGTATC ACTGACTATGCCGCCCCAGTGAAAGGCCGCTTTACCATTAGCCGCGATGATTCGAAAAAC ACCCTGTATCTGCAAATGAACAGCCTGAAAACCGAAGATACGGCCGTGTATTATTGCGCG CGTGCTGAAGCTCGTTACCGTGATGTTTGGGGCCAAGGCACCCTGGTGACTGTTAGCTCA |
| SEQ ID NO: 131 | Heavy Chain | QVQLVESGGGLVKPGGSLRLSCAASGFTFSTYVMHWVRQAPGKGLEWVGRIRSNTYGGITD YAAPVKGRFTISRDDSKNTLYLQMNSLKTEDTAVYYCARAEARYRDVWGQGTLVTVSSASTK GPSVFPLAPSSKSTSGGTAALGCLVKDYFPEPVTVSWNSGALTSGVHTFPAVLQSSGLYSLSS VVTVPSSSLGTQTYICNVNHKPSNTKVDKRVEPKSCDKTHTCPPCPAPELLGGPSVFLFPPKPK DTLMISRTPEVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSREEMTKNQVSLTCLVKG FYPSDIAVEWESNGQPENNYKTTPPVLDSDGSFFLYSKLTVDKSRWQQGNVFSCSVMHEAL HNHYTQKSLSLSPGK |
| SEQ ID NO: 132 | DNA Heavy Chain | CAGGTGCAATTGGTGGAAAGCGGCGGTGGCCTGGTGAAACCAGGCGGCAGCCTGCGCC TGAGCTGCGCCGCCTCCGGATTCACCTTTTCTACTTACGTTATGCATTGGGTGCGCCAGG CCCCGGGCAAAGGTCTCGAGTGGGTGGGCCGTATCCGTTCTAACACTTACGGTGGTATC ACTGACTATGCCGCCCCAGTGAAAGGCCGCTTTACCATTAGCCGCGATGATTCGAAAAAC ACCCTGTATCTGCAAATGAACAGCCTGAAAACCGAAGATACGGCCGTGTATTATTGCGCG CGTGCTGAAGCTCGTTACCGTGATGTTTGGGGCCAAGGCACCCTGGTGACTGTTAGCTCA GCCTCCACCAAGGGTCCATCGGTCTTCCCCCTGGCACCCTCCTCCAAGAGCACCTCTGGG GGCACAGCGGCCCTGGGCTGCCTGGTCAAGGACTACTTCCCCGAACCGGTGACGGTGTC GTGGAACTCAGGCGCCCTGACCAGCGGCGTGCACACCTTCCCGGCTGTCCTACAGTCCTC AGGACTCTACTCCCTCAGCAGCGTGGTGACCGTGCCCTCCAGCAGCTTGGGCACCCAGA CCTACATCTGCAACGTGAATCACAAGCCCAGCAACACCAAGGTGGACAAGAGAGTTGAG CCCAAATCTTGTGACAAAACTCACACATGCCCACCGTGCCCAGCACCTGAACTCCTGGGG GGACCGTCAGTCTTCCTCTTCCCCCCAAAACCCAAGGACACCCTCATGATCTCCCGGACCC CTGAGGTCACATGCGTGGTGGTGGACGTGAGCCACGAAGACCCTGAGGTCAAGTTCAAC TGGTACGTGGACGGCGTGGAGGTGCATAATGCCAAGACAAAGCCGCGGGAGGAGCAGT ACAACAGCACGTACCGGGTGGTCAGCGTCCTCACCGTCCTGCACCAGGACTGGCTGAAT GGCAAGGAGTACAAGTGCAAGGTCTCCAACAAAGCCCTCCCAGCCCCCATCGAGAAAAC CATCTCCAAAGCCAAAGGGCAGCCCCGAGAACCACAGGTGTACACCCTGCCCCCATCCC GGGAGGAGATGACCAAGAACCAGGTCAGCCTGACCTGCCTGGTCAAAGGCTTCTATCCC AGCGACATCGCCGTGGAGTGGGAGAGCAATGGGCAGCCGGAGAACAACTACAAGACCA CGCCTCCCGTGCTGGACTCCGACGGCTCCTTCTTCCTCTACAGCAAGCTCACCGTGGACA AGAGCAGGTGGCAGCAGGGGAACGTCTTCTCATGCTCCGTGATGCATGAGGCTCTGCAC AACCACTACACGCAGAAGAGCCTCTCCCTGTCTCCGGGTAAA |
| SEQ ID NO: 133 (Kabat) | LCDR1 | RASQSISSHLN |
| SEQ ID NO: 134 (Kabat) | LCDR2 | AASNLQS |
| SEQ ID NO: 135 (Kabat) | LCDR3 | QQDYHTPFT |
| SEQ ID NO: 136 (Chothia) | LCDR1 | SQSISSH |
| SEQ ID NO: 137 (Chothia) | LCDR2 | AAS |
| SEQ ID NO: 138 (Chothia) | LCDR3 | DYHTPF |
| SEQ ID NO: 139 | VL | DIQMTQSPSSLSASVGDRVTITCRASQSISSHLNWYQQKPGKAPKLLIYAASNLQSGVPSRFS GSGSGTDFTLTISSLQPEDFATYYCQQDYHTPFTFGQGTKVEIK |
| SEQ ID NO: 140 | DNA VL | GATATCCAGATGACCCAGAGCCCGAGCAGCCTGAGCGCCAGCGTGGGCGATCGCGTGA CCATTACCTGCAGAGCCAGCCAGTCTATTTCTTCTCATCTGAACTGGTACCAGCAGAAACC GGGCAAAGCGCCGAAATTATTAATCTACGCTGCTTCTAACCTGCAAAGCGGCGTGCCGA GCCGCTTTAGCGGCAGCGGATCCGGCACCGATTTCACCCTGACCATTAGCTCTCTGCAAC CGGAAGACTTTGCGACCTATTATTGCCAGCAGGACTACCATACTCCGTTCACCTTTGGCC AGGGCACGAAAGTTGAAATTAAA |

TABLE 2-continued

Examples of Notch 3 Antibodies

| SEQ ID NO: 141 | Light Chain | DIQMTQSPSSLSASVGDRVTITCRASQSISSHLNWYQQKPGKAPKLLIYAASNLQSGVPSRFS
GSGSGTDFTLTISSLQPEDFATYYCQQDYHTPFTFGQGTKVEIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC |
|---|---|---|
| SEQ ID NO: 142 | DNA Light Chain | GATATCCAGATGACCCAGAGCCCGAGCAGCCTGAGCGCCAGCGTGGGCGATCGCGTGA
CCATTACCTGCAGAGCCAGCCAGTCTATTTCTTCTCATCTGAACTGGTACCAGCAGAAACC
GGGCAAAGCGCCGAAACTATTAATCTACGCTGCTTCTAACCTGCAAAGCGGCGTGCCGA
GCCGCTTTAGCGGCAGCGGATCCGGCACCGATTTCACCCTGACCATTAGCTCTCTGCAAC
CGGAAGACTTTGCGACCTATTATTGCCAGCAGGACTACCATACTCCGTTCACCTTTGGCC
AGGGCACGAAAGTTGAAATTAAACGTACGGTGGCCGCTCCCAGCGTGTTCATCTTCCCCC
CCAGCGACGAGCAGCTGAAGAGCGGCACCGCCAGCGTGGTGTGCCTGCTGAACAACTTC
TACCCCCGGGAGGCCAAGGTGCAGTGGAAGGTGGACAACGCCCTGCAGAGCGGCAACA
GCCAGGAAAGCGTCACCGAGCAGGACAGCAAGGACTCCACCTACAGCCTGAGCAGCAC
CCTGACCCTGAGCAAGGCCGACTACGAGAAGCACAAGGTGTACGCCTGCGAGGTGACCC
ACCAGGGCCTGTCCAGCCCCGTGACCAAGAGCTTCAACGGGGGCGAGTGT |

12225

| SEQ ID NO: 143 (Kabat) | HCDR1 | SYTIS |
|---|---|---|
| SEQ ID NO: 144 (Kabat) | HCDR2 | WIKPAFGTANYAQKFQG |
| SEQ ID NO: 145 (Kabat) | HCDR3 | GSFWFGY |
| SEQ ID NO: 146 (Chothia) | HCDR1 | GGTFSSY |
| SEQ ID NO: 147 (Chothia) | HCDR2 | KPAFGT |
| SEQ ID NO: 148 (Chothia) | HCDR3 | GSFWFGY |
| SEQ ID NO: 149 | VH | QVQLVQSGAEVKKPGSSVKVSCKASGGTFSSYTISWVRQAPGQGLEWMGWIKPAFGTANY
AQKFQGRVTITADESTSTAYMELSSLRSEDTAVYYCARGSFWFGYWGQGTLVTVSS |
| SEQ ID NO: 150 | DNA VH | CAGGTGCAATTGGTGCAGAGCGGTGCCGAAGTGAAAAAACCGGGCAGCAGCGTGAAAG
TTAGCTGCAAAGCATCCGGAGGGACGTTTTCTTCTTACACTATCTCTTGGGTGCGCCAGG
CCCCGGGCCAGGGCCTCGAGTGGATGGGCTGGATCAAACCGGCTTTCGGCACTGCGAAC
TACGCCCAGAAATTTCAGGGCCGGGTGACCATTACCGCCGATGAAAGCACCAGCACCGC
CTATATGGAACTGAGCAGCCTGCGCAGCGAAGATACGGCCGTGTATTATTGCGCGCGTG
GTTCTTTCTGGTTCGGTTACTGGGGCCAAGGCACCCTGGTGACTGTTAGCTCA |
| SEQ ID NO: 151 | Heavy Chain | QVQLVQSGAEVKKPGSSVKVSCKASGGTFSSYTISWVRQAPGQGLEWMGWIKPAFGTANY
AQKFQGRVTITADESTSTAYMELSSLRSEDTAVYYCARGSFWFGYWGQGTLVTVSSASTKGP
SVFPLAPSSKSTSGGTAALGCLVKDYFPEPVTVSWNSGALTSGVHTFPAVLQSSGLYSLSSVVT
VPSSSLGTQTYICNVNHKPSNTKVDKRVEPKSCDKTHTCPPCPAPELLGGPSVFLFPPKPKDTL
MISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEALHNH
YTQKSLSLSPGK |
| SEQ ID NO: 152 | DNA Heavy Chain | CAGGTGCAATTGGTGCAGAGCGGTGCCGAAGTGAAAAAACCGGGCAGCAGCGTGAAAG
TTAGCTGCAAAGCATCCGGAGGGACGTTTTCTTCTTACACTATCTCTTGGGTGCGCCAGG
CCCCGGGCCAGGGCCTCGAGTGGATGGGCTGGATCAAACCGGCTTTCGGCACTGCGAAC
TACGCCCAGAAATTTCAGGGCCGGGTGACCATTACCGCCGATGAAAGCACCAGCACCGC
CTATATGGAACTGAGCAGCCTGCGCAGCGAAGATACGGCCGTGTATTATTGCGCGCGTG
GTTCTTTCTGGTTCGGTTACTGGGGCCAAGGCACCCTGGTGACTGTTAGCTCAGCCTCCA
CCAAGGGTCCATCGGTCTTCCCCCTGGCACCCTCCTCCAAGAGCACCTCTGGGGGCACAG
CGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATC
TTGTGACAAAACTCACACATGCCCACCGTGCCCAGCACCTGAACTCCTGGGGGGACCGTC
AGTCTTCCTCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACTGGTACGT
GGACGGCGTGGAGGTGCATAATGCCAAGACAAAGCCGCGGGAGGAGCAGTACAACAG
CACGTACCGGGTGGTCAGCGTCCTCACCGTCCTGCACCAGGACTGGCTGAATGGCAAGG
AGTACAAGTGCAAGGTCTCCAACAAAGCCCTCCCAGCCCCCATCGAGAAAACCATCTCCA
AAGCCAAAGGGCAGCCCCGAGAACCACAGGTGTACACCCTGCCCCCATCCCGGGAGGA
GATGACCAAGAACCAGGTCAGCCTGACCTGCCTGGTCAAAGGCTTCTATCCCAGCGACAT
CGCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTAC
ACGCAGAAGAGCCTCTCCCTGTCTCCGGGTAAA |
| SEQ ID NO: 153 (Kabat) | LCDR1 | RASQGINNYLN |
| SEQ ID NO: 154 (Kabat) | LCDR2 | DASKLQS |

TABLE 2-continued

Examples of Notch 3 Antibodies

| SEQ ID NO: 155 (Kabat) | LCDR3 | QQYLQYPMT |
| --- | --- | --- |
| SEQ ID NO: 156 (Chothia) | LCDR1 | SQGINNY |
| SEQ ID NO: 157 (Chothia) | LCDR2 | DAS |
| SEQ ID NO: 158 (Chothia) | LCDR3 | YLQYPM |
| SEQ ID NO: 159 | VL | DIQMTQSPSSLSASVGDRVTITCRASQGINNYLNWYQQKPGKAPKLLIYDASKLQSGVPSRFS<br>GSGSGTDFTLTISSLQPEDFATYYCQQYLQYPMTFGQGTKVEIK |
| SEQ ID NO: 160 | DNA VL | GATATCCAGATGACCCAGAGCCCGAGCAGCCTGAGCGCCAGCGTGGGCGATCGCGTGA<br>CCATTACCTGCAGAGCCAGCCAGGGTATTAACAACTACCTGAACTGGTACCAGCAGAAA<br>CCGGGCAAAGCGCCGAAACATTATTAATCTACGACGCTTCTAAACTGCAAAGCGGCGTGCC<br>GAGCCGCTTTAGCGGCAGCGGATCCGGCACCGATTTCACCCTGACCATTAGCTCTCTGCA<br>ACCGGAAGACTTTGCGACCTATTATTGCCAGCAGTACCTGCAGTACCCGATGACCTTTGG<br>CCAGGGCACGAAAGTTGAAATTAAA |
| SEQ ID NO: 161 | Light Chain | DIQMTQSPSSLSASVGDRVTITCRASQGINNYLNWYQQKPGKAPKLLIYDASKLQSGVPSRFS<br>GSGSGTDFTLTISSLQPEDFATYYCQQYLQYPMTFGQGTKVEIKRTVAAPSVFIFPPSDEQLKS<br>GTASVVCLLNNFYPREAKVQWKVDNALQSGNSQESVTEQDSKDSTYSLSSTLTLSKADYEKH<br>KVYACEVTHQGLSSPVTKSFNRGEC |
| SEQ ID NO: 162 | DNA Light<br>Chain | GATATCCAGATGACCCAGAGCCCGAGCAGCCTGAGCGCCAGCGTGGGCGATCGCGTGA<br>CCATTACCTGCAGAGCCAGCCAGGGTATTAACAACTACCTGAACTGGTACCAGCAGAAA<br>CCGGGCAAAGCGCCGAAACATTATTAATCTACGACGCTTCTAAACTGCAAAGCGGCGTGCC<br>GAGCCGCTTTAGCGGCAGCGGATCCGGCACCGATTTCACCCTGACCATTAGCTCTCTGCA<br>ACCGGAAGACTTTGCGACCTATTATTGCCAGCAGTACCTGCAGTACCCGATGACCTTTGG<br>CCAGGGCACGAAAGTTGAAATTAAACGTACGGTGGCCGCTCCCAGCGTGTTCATCTTCCC<br>CCCCAGCGACGAGCAGCTGAAGAGCGGCACCGCCAGCGTGGTGTGCCTGCTGAACAACT<br>TCTACCCCCGGGAGGCCAAGGTGCAGTGGAAGGTGGACAACGCCCTGCAGAGCGGCAA<br>CAGCCAGGAAAGCGTCACCGAGCAGGACAGCAAGGACTCCACCTACAGCCTGAGCAGC<br>ACCCTGACCCTGAGCAAGGCCGACTACGAGAAGCACAAGGTGTACGCCTGCGAGGTGA<br>CCCACCAGGGCCTGTCCAGCCCCGTGACCAAGAGCTTCAACCGGGGCGAGTGT |

12981

| SEQ ID NO: 163 (Kabat) | HCDR1 | TYAMH |
| --- | --- | --- |
| SEQ ID NO: 164 (Kabat) | HCDR2 | GIIPIFGIANYAQKFQG |
| SEQ ID NO: 165 (Kabat) | HCDR3 | DDYSTYAFAY |
| SEQ ID NO: 166 (Chothia) | HCDR1 | GGTFRTY |
| SEQ ID NO: 167 (Chothia) | HCDR2 | IPIFGI |
| SEQ ID NO: 168 (Chothia) | HCDR3 | DDYSTYAFAY |
| SEQ ID NO: 169 | VH | QVQLVQSGAEVKKPGSSVKVSCKASGGTFRTYAMHWVRQAPGQGLEWMGGIIPIFGIANY<br>AQKFQGRVTITADESTSTAYMELSSLRSEDTAVYYCARDDYSTYAFAYWGQGTLVTVSS |
| SEQ ID NO: 170 | DNA VH | CAGGTGCAATTGGTGCAGAGCGGTGCCGAAGTGAAAAAACCGGGCAGCAGCGTGAAAG<br>TTAGCTGCAAAGCATCCGGAGGGACGTTTCGTACTTACGCTATGCATTGGGTGCGCCAG<br>GCCCCCGGGCCAGGGCCTCGAGTGGATGGGCGGTATCATCCCGATCTTCGGCATCGCGAA<br>CTACGCCCAGAAATTTCAGGGCCGGGTGACCATTACCGCCGATGAAAGCACCAGCACCG<br>CCTATATGGAACTGAGCAGCCTGCGCAGCGAAGATACGGCCGTGTATTATTGCGCGCGT<br>GACGACTACTCTACTTACGCTTTCGCTTACTGGGGCCAAGGCACCCTGGTGACTGTTAGC<br>TCA |
| SEQ ID NO: 171 | Heavy Chain | QVQLVQSGAEVKKPGSSVKVSCKASGGTFRTYAMHWVRQAPGQGLEWMGGIIPIFGIANY<br>AQKFQGRVTITADESTSTAYMELSSLRSEDTAVYYCARDDYSTYAFAYWGQGTLVTVSSASTK<br>GPSVFPLAPSSKSTSGGTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPAPELLGGPSVFLFPPKPK<br>DTLMISRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEAL<br>HNHYTQKSLSLSPGK |
| SEQ ID NO: 172 | DNA Heavy<br>Chain | CAGGTGCAATTGGTGCAGAGCGGTGCCGAAGTGAAAAAACCGGGCAGCAGCGTGAAAG<br>TTAGCTGCAAAGCATCCGGAGGGACGTTTCGTACTTACGCTATGCATTGGGTGCGCCAG<br>GCCCCCGGGCCAGGGCCTCGAGTGGATGGGCGGTATCATCCCGATCTTCGGCATCGCGAA<br>CTACGCCCAGAAATTTCAGGGCCGGGTGACCATTACCGCCGATGAAAGCACCAGCACCG<br>CCTATATGGAACTGAGCAGCCTGCGCAGCGAAGATACGGCCGTGTATTATTGCGCGCGT<br>GACGACTACTCTACTTACGCTTTCGCTTACTGGGGCCAAGGCACCCTGGTGACTGTTAGC<br>TCAGCCTCCACCAAGGGTCCATCGGTCTTCCCCCTGGCACCCTCCTCCAAGAGCACCTCTG<br>GGGGCACAGCGGCCCTGGGCTGCCTGGTCAAGGACTACTTCCCCGAACCGGTGACGGT<br>GTCGTGGAACTCAGGCGCCCTGACCAGCGGCGTGCACACCTTCCCGGCTGTCCTACAGTC |

TABLE 2-continued

Examples of Notch 3 Antibodies

|  |  |  |
|---|---|---|
|  |  | CTCAGGACTCTACTCCCTCAGCAGCGTGGTGACCGTGCCCTCCAGCAGCTTGGGCACCCA<br>GACCTACATCTGCAACGTGAATCACAAGCCCAGCAACACCAAGGTGGACAAGAGAGTTG<br>AGCCCAAATCTTGTGACAAAACTCACACATGCCCACCGTGCCCAGCACCTGAACTCCTGG<br>GGGGACCGTCAGTCTTCCTCTTCCCCCCAAAACCCAAGGACACCCTCATGATCTCCCGGA<br>CCCCTGAGGTCACATGCGTGGTGGTGGACGTGAGCCACGAAGACCCTGAGGTCAAGTTC<br>AACTGGTACGTGGACGGCGTGGAGGTGCATAATGCCAAGACAAAGCCGCGGGAGGAGC<br>AGTACAACAGCACGTACCGGGTGGTCAGCGTCCTCACCGTCCTGCACCAGGACTGGCTG<br>AATGGCAAGGAGTACAAGTGCAAGGTCTCCAACAAAGCCCTCCCAGCCCCCATCGAGAA<br>AACCATCTCCAAAGCCAAAGGGCAGCCCCGAGAACCACAGGTGTACACCCTGCCCCCAT<br>CCCGGGAGGAGATGACCAAGAACCAGGTCAGCCTGACCTGCCTGGTCAAAGGCTTCTAT<br>CCCAGCGACATCGCCGTGGAGTGGGAGAGCAATGGGCAGCCGGAGAACAACTACAAGA<br>CCACGCCTCCCGTGCTGGACTCCGACGGCTCCTTCTTCCTCTACAGCAAGCTCACCGTGG<br>ACAAGAGCAGGTGGCAGCAGGGGAACGTCTTCTCATGCTCCGTGATGCATGAGGCTCTG<br>CACAACCACTACACGCAGAAGAGCCTCTCCCTGTCTCCGGGTAAA |
| SEQ ID NO: 173 (Kabat) | LCDR1 | RASQSIASYLA |
| SEQ ID NO: 174 (Kabat) | LCDR2 | DASNLQS |
| SEQ ID NO: 175 (Kabat) | LCDR3 | QQAYKTPYT |
| SEQ ID NO: 176 (Chothia) | LCDR1 | SQSIASY |
| SEQ ID NO: 177 (Chothia) | LCDR2 | DAS |
| SEQ ID NO: 178 (Chothia) | LCDR3 | AYKTPY |
| SEQ ID NO: 179 | VL | DIQMTQSPSSLSASVGDRVTITCRASQSIASYLAWYQQKPGKAPKLLIYDASNLQSGVPSRFS<br>GSGSGTDFTLTISSLQPEDFATYYCQQAYKTPYTFGQGTKVEIK |
| SEQ ID NO: 180 | DNA VL | GATATCCAGATGACCCAGAGCCCGAGCAGCCTGAGCGCCAGCGTGGGCGATCGCGTGA<br>CCATTACCTGCAGAGCCAGCCAGTCTATTGCTTCTTACCTGGCTTGGTACCAGCAGAAAC<br>CGGGCAAAGCGCCGAAACTATTAATCTACGACGCTTCTAACCTGCAAAGCGGCGTGCCG<br>AGCCGCTTTAGCGGCAGCGGATCCGGCACCGATTTCACCCTGACCATTAGCTCTCTGCAA<br>CCGGAAGACTTTGCGACCTATTATTGCCAGCAGGCTTACAAAACTCCGTACACCTTTGGC<br>CAGGGCACGAAAGTTGAAATTAAA |
| SEQ ID NO: 181 | Light Chain | DIQMTQSPSSLSASVGDRVTITCRASQSIASYLAWYQQKPGKAPKLLIYDASNLQSGVPSRFS<br>GSGSGTDFTLTISSLQPEDFATYYCQQAYKTPYTFGQGTKVEIKRTVAAPSVFIFPPSDEQLKS<br>GTASVVCLLNNFYPREAKVQWKVDNALQSGNSQESVTEQDSKDSTYSLSSTLTLSKADYEKH<br>KVYACEVTHQGLSSPVTKSFNRGEC |
| SEQ ID NO: 182 | DNA Light Chain | GATATCCAGATGACCCAGAGCCCGAGCAGCCTGAGCGCCAGCGTGGGCGATCGCGTGA<br>CCATTACCTGCAGAGCCAGCCAGTCTATTGCTTCTTACCTGGCTTGGTACCAGCAGAAAC<br>CGGGCAAAGCGCCGAAACTATTAATCTACGACGCTTCTAACCTGCAAAGCGGCGTGCCG<br>AGCCGCTTTAGCGGCAGCGGATCCGGCACCGATTTCACCCTGACCATTAGCTCTCTGCAA<br>CCGGAAGACTTTGCGACCTATTATTGCCAGCAGGCTTACAAAACTCCGTACACCTTTGGC<br>CAGGGCACGAAAGTTGAAATTAAACGTACGGTGGCCGCTCCCAGCGTCTTCATCTTCCCC<br>CCAGCGACGAGCAGCTGAAGAGCGGCACCGCCAGCGTGGTGTGCCTGCTGAACAACTT<br>CTACCCCCGGGAGGCCAAGGTGCAGTGGAAGGTGGACAACGCCCTGCAGAGCGGCAAC<br>AGCCAGGAAAGCGTCACCGAGCAGGACAGCAAGGACTCCACCTACAGCCTGAGCAGCA<br>CCCTGACCCTGAGCAAGGCCGACTACGAGAAGCACAAGGTGTACGCCTGCGAGGTGACC<br>CACCAGGGCCTGTCCAGCCCCGTGACCAAGAGCTTCAACCGGGGCGAGTGT |
| 20364 |  |  |
| SEQ ID NO: 183 (Kabat) | HCDR1 | SYTMN |
| SEQ ID NO: 184 (Kabat) | HCDR2 | RVKGEQFGGSIHYAASVKG |
| SEQ ID NO: 185 (Kabat) | HCDR3 | ERSRAGSIFDP |
| SEQ ID NO: 186 (Chothia) | HCDR1 | GFTFSSY |
| SEQ ID NO: 187 (Chothia) | HCDR2 | KGEQFGGS |
| SEQ ID NO: 188 (Chothia) | HCDR3 | ERSRAGSIFDP |
| SEQ ID NO: 189 | VH | QVQLVESGGGLVKPGGSLRLSCAASGFTFSSYTMNWVRQAPGKGLEWVGRVKGEQFGGSI<br>HYAASVKGRFTISRDDSKNTLYLQMNSLKTEDTAVYYCARERSRAGSIFDPWGQGTLVTVSS |
| SEQ ID NO: 190 | DNA VH | CAGGTGCAATTGGTGGAAAGCGGCGGTGGCCTGGTGAAACCAGGCGGCAGCCTGCGCC<br>TGAGCTGCGCCGCCTCCGGATTCACCTTTTCTTCTTACACTATGAACTGGGTGCGCCAGG<br>CCCCGGGCAAAGGTCTCGAGTGGGTGGGCCGTGTTAAAGGTGAACAGTTCGGCGGTTCT<br>ATCCATTATGCCGCCTCTGTGAAAGGCCGCTTTACCATTAGCCGCGATGATTCGAAAAAC<br>ACCCTGTATCTGCAAATGAACAGCCTGAAAACCGAAGATACGGCCGTGTATTATTGCGCG<br>CGTGAACGTTCTCGTGCTGGTTCTATCTTCGATCCGTGGGGCCAAGGCACCCTGGTGACT<br>GTTAGCTCA |

TABLE 2-continued

Examples of Notch 3 Antibodies

| | | |
|---|---|---|
| SEQ ID NO: 191 | Heavy Chain | QVQLVESGGGLVKPGGSLRLSCAASGFTFSSYTMNWVRQAPGKGLEWVGRVKGEQFGGSI<br>HYAASVKGRFTISRDDSKNTLYLQMNSLKTEDTAVYYCARERSRAGSIFDPWGQGTLVTVSS<br>ASTKGPSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKRVEPKSCDKTHTCPPCPAPELLGGPSVFLFP<br>PKPKDTLMISRTPEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSREEMTKNQVSLTCL<br>VKGFYPSDIAVEWESNGQPENNYKTTPPVLDSDGSFFLYSKLTVDKSRWQQGNVFSCSVMH<br>EALHNHYTQKSLSLSPGK |
| SEQ ID NO: 192 | DNA Heavy<br>Chain | CAGGTGCAATTGGTGGAAAGCGGCGGTGGCCTGGTGAAACCAGGCGGCAGCCTGCGCC<br>TGAGCTGCGCCGCCTCCGGATTCACCTTTTCTTCTTACACTATGAACTGGGTGCGCCAGG<br>CCCCGGGCAAAGGTCTCGAGTGGGTGGGCCGTGTTAAAGGTGAACAGTTCGGCGGTTCT<br>ATCCATTATGCCGCCTCTGTGAAAGGCCGCTTTACCATTAGCCGCGATGATTCGAAAAAC<br>ACCCTGTATCTGCAAATGAACAGCCTGAAAACCGAAGATACGGCCGTGTATTATTGCGCG<br>CGTGAACGTTCTCGTGCTGGTTCTATCTTCGATCCGTGGGGCCAAGGCACCCTGGTGACT<br>GTTAGCTCAGCCTCCACCAAGGGTCCATCGGTCTTCCCCCTGGCACCCTCCTCCAAGAGC<br>ACCTCTGGGGGCACAGCGGCCCTGGGCTGCCTGGTCAAGGACTACTTCCCCGAACCGGT<br>GACGGTGTCGTGGAACTCAGGCGCCCTGACCAGCGGCGTGCACACCTTCCCGGCTGTCC<br>TACAGTCCTCAGGACTCTACTCCCTCAGCAGCGTGGTGACCGTGCCCTCCAGCAGCTTGG<br>GCACCCAGACCTACATCTGCAACGTGAATCACAAGCCCAGCAACACCAAGGTGGACAAG<br>AGAGTTGAGCCCAAATCTTGTGACAAAACTCACACATGCCCACCGTGCCCAGCACCTGAA<br>CTCCTGGGGGGACCGTCAGTCTTCCTCTTCCCCCCAAAACCCAAGGACACCCTCATGATCT<br>CCCGGACCCCTGAGGTCACATGCGTGGTGGTGGACGTGAGCCACGAAGACCCTGAGGT<br>CAAGTTCAACTGGTACGTGGACGGCGTGGAGGTGCATAATGCCAAGACAAAGCCGCGG<br>GAGGAGCAGTACAACAGCACGTACCGGGTGGTCAGCGTCCTCACCGTCCTGCACCAGGA<br>CTGGCTGAATGGCAAGGAGTACAAGTGCAAGGTCTCCAACAAAGCCCTCCCAGCCCCCA<br>TCGAGAAAACCATCTCCAAAGCCAAAGGGCAGCCCCGAGAACCACAGGTGTACACCCTG<br>CCCCCATCCCGGGAGGAGATGACCAAGAACCAGGTCAGCCTGACCTGCCTGGTCAAAGG<br>CTTCTATCCCAGCGACATCGCCGTGGAGTGGGAGAGCAATGGGCAGCCGGAGAACAACT<br>ACAAGACCACGCCTCCCGTGCTGGACTCCGACGGCTCCTTCTTCCTCTACAGCAAGCTCA<br>CCGTGGACAAGAGCAGGTGGCAGCAGGGGAACGTCTTCTCATGCTCCGTGATGCATGA<br>GGCTCTGCACAACCACTACACGCAGAAGAGCCTCTCCCTGTCTCCGGGTAAA |
| SEQ ID NO: 193 (Kabat) | LCDR1 | SGSSSNIGFNYVS |
| SEQ ID NO: 194 (Kabat) | LCDR2 | YNNQRPS |
| SEQ ID NO: 195 (Kabat) | LCDR3 | STWTGTSESHV |
| SEQ ID NO: 196 (Chothia) | LCDR1 | SSSNIGFNY |
| SEQ ID NO: 197 (Chothia) | LCDR2 | YNN |
| SEQ ID NO: 198 (Chothia) | LCDR3 | WTGTSESH |
| SEQ ID NO: 199 | VL | DIVLTQPPSVSGAPGQRVTISCSGSSSNIGFNYVSWYQQLPGTAPKLLIYYNNQRPSGVPDRF<br>SGSKSGTSASLAITGLQAEDEADYYCSTWTGTSESHVFGGGTKLTVL |
| SEQ ID NO: 200 | DNA VL | GATATCGTGCTGACCCAGCCGCCGAGCGTGAGCGGTGCACCGGGCCAGCGCGTGACCA<br>TTAGCTGTAGCGGCAGCAGCAGCAACATTGGTTTCAACTACGTGTCTTGGTACCAGCAGC<br>TGCCGGGCACGGCGCCGAAACTGCTGATCTACTACAACAACCAGCGCCCGAGCGGCGTG<br>CCGGATCGCTTTAGCGGATCCAAAAGCGGCACCAGCGCCAGCCTGGCGATTACCGGCCT<br>GCAAGCAGAAGACGAAGCGGATTATTACTGCTCTACTTGGACTGGTACTTCTGAATCTCA<br>TGTGTTTGGCGGCGGCACGAAGTTAACCGTCCTA |
| SEQ ID NO: 201 | Light Chain | DIVLTQPPSVSGAPGQRVTISCSGSSSNIGFNYVSWYQQLPGTAPKLLIYYNNQRPSGVPDRF<br>SGSKSGTSASLAITGLQAEDEADYYCSTWTGTSESHVFGGGTKLTVLGQPKAAPSVTLFPPSS<br>EELQANKATLVCLISDFYPGAVTVAWKADSSPVKAGVETTTPSKQSNNKYAASSYLSLTPEQ<br>WKSHRSYSCQVTHEGSTVEKTVAPTECS |
| SEQ ID NO: 202 | DNA Light<br>Chain | GATATCGTGCTGACCCAGCCGCCGAGCGTGAGCGGTGCACCGGGCCAGCGCGTGACCA<br>TTAGCTGTAGCGGCAGCAGCAGCAACATTGGTTTCAACTACGTGTCTTGGTACCAGCAGC<br>TGCCGGGCACGGCGCCGAAACTGCTGATCTACTACAACAACCAGCGCCCGAGCGGCGTG<br>CCGGATCGCTTTAGCGGATCCAAAAGCGGCACCAGCGCCAGCCTGGCGATTACCGGCCT<br>GCAAGCAGAAGACGAAGCGGATTATTACTGCTCTACTTGGACTGGTACTTCTGAATCTCA<br>TGTGTTTGGCGGCGGCACGAAGTTAACCGTCCTAGGTCAGCCCAAGGCTGCCCCCTCGG<br>TCACTCTGTTCCCGCCCTCCTCTGAGGAGCTTCAAGCCAACAAGGCCACACTGGTGTGTC<br>TCATAAGTGACTTCTACCCGGGAGCCGTGACAGTGGCCTGGAAGGCAGATAGCAGCCCC<br>GTCAAGGCGGGAGTGGAGACCACCACACCCTCCAAACAAAGCAACAACAAGTACGCGG<br>CCAGCAGCTATCTGAGCCTGACGCCTGAGCAGTGGAAGTCCACAGAAGCTACAGCTGC<br>AGGTCACGCATGAAGGGAGCACCGTGGAGAAGACAGTGGCCCCTACAGAATGTTCA |
| 12229 | | |
| SEQ ID NO: 203 (Kabat) | HCDR1 | SYTMN |
| SEQ ID NO: 204 (Kabat) | HCDR2 | RIKTKTNGGTTDYAAPVKG |

TABLE 2-continued

Examples of Notch 3 Antibodies

| SEQ ID NO: 205 (Kabat) | HCDR3 | ERSRAGSIFDP |
|---|---|---|
| SEQ ID NO: 206 (Chothia) | HCDR1 | GFTFSSY |
| SEQ ID NO: 207 (Chothia) | HCDR2 | KTKTNGGT |
| SEQ ID NO: 208 (Chothia) | HCDR3 | ERSRAGSIFDP |
| SEQ ID NO: 209 | VH | QVQLVESGGGLVKPGGSLRLSCAASGFTFSSYTMNWVRQAPGKGLEWVGRIKTKTNGGTT DYAAPVKGRFTISRDDSKNTLYLQMNSLKTEDTAVYYCARERSRAGSIFDPWGQGTLVTVSS |
| SEQ ID NO: 210 | DNA VH | CAGGTGCAATTGGTGGAAAGCGGCGGTGGCCTGGTGAAACCAGGCGGCAGCCTGCGCC TGAGCTGCGCCGCCTCCGGATTCACCTTTTCTTCTTACACTATGAACTGGGTGCGCCAGG CCCCCGGGCAAAGGTCTCGAGTGGGTGGGCCGTATCAAAACTAAAACTAACGGTGGTACT ACTGACTATGCCGCCCCAGTGAAAGGCCGCTTTACCATTAGCCGCGATGATTCGAAAAAC ACCCTGTATCTGCAAATGAACAGCCTGAAAACCGAAGATACGGCCGTGTATTATTGCGCG CGTGAACGTTCTCGTGCTGGTTCTATCTTCGATCCGTGGGGCCAAGGCACCCTGGTGACT GTTAGCTCA |
| SEQ ID NO: 211 | Heavy Chain | QVQLVESGGGLVKPGGSLRLSCAASGFTFSSYTMNWVRQAPGKGLEWVGRIKTKTNGGTT DYAAPVKGRFTISRDDSKNTLYLQMNSLKTEDTAVYYCARERSRAGSIFDPWGQGTLVTVSS ASTKGPSVFPLAPSSKSTSGGTAALGCLVKDYFPEPVTVSWNSGALTSGVHTFPAVLQSSGLY SLSSVVTVPSSSLGTQTYICNVNHKPSNTKVDKRVEPKSCDKTHTCPPCPAPELLGGPSVFLFP PKPKDTLMISRTPEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQGNVFSCSVMH EALHNHYTQKSLSLSPGK |
| SEQ ID NO: 212 | DNA Heavy Chain | CAGGTGCAATTGGTGGAAAGCGGCGGTGGCCTGGTGAAACCAGGCGGCAGCCTGCGCC TGAGCTGCGCCGCCTCCGGATTCACCTTTTCTTCTTACACTATGAACTGGGTGCGCCAGG CCCCCGGGCAAAGGTCTCGAGTGGGTGGGCCGTATCAAAACTAAAACTAACGGTGGTACT ACTGACTATGCCGCCCCAGTGAAAGGCCGCTTTACCATTAGCCGCGATGATTCGAAAAAC ACCCTGTATCTGCAAATGAACAGCCTGAAAACCGAAGATACGGCCGTGTATTATTGCGCG CGTGAACGTTCTCGTGCTGGTTCTATCTTCGATCCGTGGGGCCAAGGCACCCTGGTGACT GTTAGCTCAGCCTCCACCAAGGGTCCATCGGTCTTCCCCCTGGCACCCTCCTCCAAGAGC ACCTCTGGGGGCACAGCGGCCCTGGGCTGCCTGGTCAAGGACTACTTCCCCGAACCGGT GACGGTGTCGTGGAACTCAGGCGCCCTGACCAGCGGCGTGCACACCTTCCCGGCTGTCC TACAGTCCTCAGGACTCTACTCCCTCAGCAGCGTGGTGACCGTGCCCTCCAGCAGCTTGG GCACCCAGACCTACATCTGCAACGTGAATCACAAGCCCAGCAACACCAAGGTGGACAAG AGAGTTGAGCCCAAATCTTGTGACAAAACTCACACATGCCCACCGTGCCCAGCACCTGAA CTCCTGGGGGGACCGTCAGTCTTCCTCTTCCCCCCAAAACCCAAGGACACCCTCATGATCT CCCGGACCCCTGAGGTCACATGCGTGGTGGTGGACGTGAGCCACGAAGACCCTGAGGT CAAGTTCAACTGGTACGTGGACGGCGTGGAGGTGCATAATGCCAAGACAAAGCCGCGG GAGGAGCAGTACAACAGCACGTACCGGGTGGTCAGCGTCCTCACCGTCCTGCACCAGGA CTGGCTGAATGGCAAGGAGTACAAGTGCAAGGTCTCCAACAAAGCCCTCCCAGCCCCCA TCGAGAAAACCATCTCCAAAGCCAAAGGGCAGCCCCGAGAACCACAGGTGTACACCCTG CCCCCATCCCGGGAGGAGATGACCAAGAACCAGGTCAGCCTGACCTGCCTGGTCAAAGG CTTCTATCCCAGCGACATCGCCGTGGAGTGGGAGAGCAATGGGCAGCCGGAGAACAACT ACAAGACCACGCCTCCCGTGCTGGACTCCGACGGCTCCTTCTTCCTCTACAGCAAGCTCA CCGTGGACAAGAGCAGGTGGCAGCAGGGGAACGTCTTCTCATGCTCCGTGATGCATGA GGCTCTGCACAACCACTACACGCAGAAGAGCCTCTCCCTGTCTCCGGGTAAA |
| SEQ ID NO: 213 (Kabat) | LCDR1 | SGSSSNIGFNYVS |
| SEQ ID NO: 214 (Kabat) | LCDR2 | YNNQRPS |
| SEQ ID NO: 215 (Kabat) | LCDR3 | STWTGTSESHV |
| SEQ ID NO: 216 (Chothia) | LCDR1 | SSSNIGFNY |
| SEQ ID NO: 217 (Chothia) | LCDR2 | YNN |
| SEQ ID NO: 218 (Chothia) | LCDR3 | WTGTSESH |
| SEQ ID NO: 219 | VL | DIVLTQPPSVSGAPGQRVTISCSGSSSNIGFNYVSWYQQLPGTAPKLLIYYNNQRPSGVPDRF SGSKSGTSASLAITGLQAEDEADYYCSTWTGTSESHVFGGGTKLTVL |
| SEQ ID NO: 220 | DNA VL | GATATCGTGCTGACCCAGCCGCCGAGCGTGAGCGGTGCACCGGGCCAGCGCGTGACCA TTAGCTGTAGCGGCAGCAGCAGCAACATTGGTTTCAACTACGTGTCTTGGTACCAGCAGC TGCCGGGCACGGCGCCGAAACTGCTGATCTACTACAACAACCAGCGCCCGAGCGGCGTG CCGGATCGCTTTAGCGGATCCAAAAGCGGCACCAGCGCCAGCCTGGCGATTACCGGCCT GCAAGCAGAAGACGAAGCGGATTATTACTGCTCTACTTGGACTGGTACTTCTGAATCTCA TGTGTTTGGCGGCGGCACGAAGTTAACCGTCCTA |
| SEQ ID NO: 221 | Light Chain | DIVLTQPPSVSGAPGQRVTISCSGSSSNIGFNYVSWYQQLPGTAPKLLIYYNNQRPSGVPDRF SGSKSGTSASLAITGLQAEDEADYYCSTWTGTSESHVFGGGTKLTVLGQPKAAPSVTLFPPSS EELQANKATLVCLISDFYPGAVTVAWKADSSPVKAGVETTTPSKQSNNKYAASSYLSLTPEQ WKSHRSYSCQVTHEGSTVEKTVAPTECS |

TABLE 2-continued

Examples of Notch 3 Antibodies

| SEQ ID NO: 222 | DNA Light Chain | GATATCGTGCTGACCCAGCCGCCGAGCGTGAGCGGTGCACCGGGCCAGCGCGTGACCA TTAGCTGTAGCGGCAGCAGCAGCAACATTGGTTTCAACTACGTGTCTTGGTACCAGCAGC TGCCGGGCACGGCGCCGAAACTGCTGATCTACTACAACAACCAGCGCCCGAGCGGCGTG CCGGATCGCTTTAGCGGATCCAAAAGCGGCACCAGCGCCAGCCTGGCGATTACCGGCCT GCAAGCAGAAGACGAAGCGGATTATTACTGCTCTACTTGGACTGGTACTTCTGAATCTCA TGTGTTTGGCGGCGGCACGAAGTTAACCGTCCTAGGTCAGCCCAAGGCTGCCCCCTCGG TCACTCTGTTCCCGCCCTCCTCTGAGGAGCTTCAAGCCAACAAGGCCACACTGGTGTGTC TCATAAGTGACTTCTACCCGGGAGCCGTGACAGTGGCCTGGAAGGCAGATAGCAGCCCC GTCAAGGCGGGAGTGGAGACCACCACACCCTCCAAACAAAGCAACAACAAGTACGCGG CCAGCAGTATCTGAGCCTGACGCCTGAGCAGTGGAAGTCCCACAGAAGCTACAGCTGC CAGGTCACGCATGAAGGGAGCACCGTGGAGAAGACAGTGGCCCCTACAGAATGTTCA |
|---|---|---|

ICD3 Ab

| SEQ ID NO: 223 (Kabat) | HCDR1 | KNAYMC |
|---|---|---|
| SEQ ID NO: 224 (Kabat) | HCDR2 | CIETGDGTTYYASWAKG |
| SEQ ID NO: 225 (Kabat) | HCDR3 | ELYDDYGDYFNL |
| SEQ ID NO: 226 (Chothia) | HCDR1 | GFSFTKNA |
| SEQ ID NO: 227 (Chothia) | HCDR2 | ETGDGT |
| SEQ ID NO: 228 (Chothia) | HCDR3 | ELYDDYGDYFNL |
| SEQ ID NO: 229 | VH | QSLEESGGDLVKPGASLTLTCTASGFSFTKNAYMCWDRQAPGKRPEWIACIETGDGTTYYAS WAKGRFTVSKTSSTTVTLQMTSLTAADTATYFCARELYDDYGDYFNLWGPGTLVTVSS |
| SEQ ID NO: 230 | DNA VH | CAGTCGTTGGAGGAGTCTGGGGGAGACCTGGTCAAGCCTGGGGCATCCCTGACACTCAC CTGCACAGCCTCTGGATTCTCCTTCACTAAGAACGCCTACATGTGCTGGGACCGCCAGGC TCCAGGGAAGAGGCCTGAGTGGATCGCATGCATTGAGACTGGTGACGGCACCACATATT ATGCGAGCTGGGCGAAAGGCCGATTCACCGTCTCCAAAACCTCGTCGACCACGGTGACT CTGCAAATGACCAGTCTGACAGCCGCGGACACGGCCACCTATTTCTGTGCGAGGGAATT ATACGATGACTATGGTGATTACTTCAATTTGTGGGGCCCAGGCACCCTGGTCACCGTCTC CTCA |
| SEQ ID NO: 231 | Heavy Chain | QSLEESGGDLVKPGASLTLTCTASGFSFTKNAYMCWDRQAPGKRPEWIACIETGDGTTYYAS WAKGRFTVSKTSSTTVTLQMTSLTAADTATYFCARELYDDYGDYFNLWGPGTLVTVSSGQP KAPSVFPLAPCCGDTPSSTVTLGCLVKGYLPEPVTVTWNSGTLTNGVRTFPSVRQSSGLYSLSS VVSVTSSSQPVTCNVAHPATNTKVDKTVAPSTCSKPTCPPPELLGGPSVFIFPPKPKDTLMISR TPEVTCVVVDVSQDDPEVQFTWYINNEQVRTARPPLREQQFNSTIRVVSTLPIAHQDWLRG KEFKCKVHNKALPAPIEKTISKARGQPLEPKVYTMGPPREELSSRSVSLTCMINGFYPSDISVE WEKNGKAEDNYKTTPAVLDSDGSYFLYSKLSVPTSEWQRGDVFTCSVMHEALHNHYTQKSI SRSPGK |
| SEQ ID NO: 232 | DNA Heavy Chain | CAGTCGTTGGAGGAGTCTGGGGGAGACCTGGTCAAGCCTGGGGCATCCCTGACACTCAC CTGCACAGCCTCTGGATTCTCCTTCACTAAGAACGCCTACATGTGCTGGGACCGCCAGGC TCCAGGGAAGAGGCCTGAGTGGATCGCATGCATTGAGACTGGTGACGGCACCACATATT ATGCGAGCTGGGCGAAAGGCCGATTCACCGTCTCCAAAACCTCGTCGACCACGGTGACT CTGCAAATGACCAGTCTGACAGCCGCGGACACGGCCACCTATTTCTGTGCGAGGGAATT ATACGATGACTATGGTGATTACTTCAATTTGTGGGGCCCAGGCACCCTGGTCACCGTCTC CTCAGGGCAACCTAAGGCTCCATCAGTCTTCCCACTGGCCCCCTGCTGCGGGGACACACC CAGCTCCACGGTGACCCTGGGCTGCCTGGTCAAAGGGTACCTCCCGGAGCCAGTGACCG TGACCTGGAACTCGGGCACCCTCACCAATGGGGTACGCACCTTCCCGTCCGTCGGCAGT CCTCAGGCCTCTACTCGCTGAGCAGCGTGGTGAGCGTGACCTCAAGCAGCCAGCCCGTC ACCTGCAACGTGGCCCACCCAGCCACCAACACCAAAGTGGACAAGACCGTTGCGCCCTC GACATGCAGCAAGCCCACGTGCCCACCCCCTGAACTCCTGGGGGGACCGTCTGTCTTCAT CTTCCCCCCAAAACCCAAGGACACCCTCATGATCTCACGCACCCCCGAGGTCACATGCGT GGTGGTGGACGTGAGCCAGGATGACCCCGAGGTGCAGTTCACATGGTACATAAACAAC GAGCAGGTGCGCACCGCCCGGCCGCCGCTACGGGAGCAGCAGTTCAACAGCACGATCC GCGTGGTCAGCACCCTCCCCATCGCGCACCAGGACTGGCTGAGGGGCAAGGAGTTCAA GTGCAAAGTCCACAACAAGGCACTCCCGGCCCCCATCGAGAAAACCATCTCCAAAGCCA GAGGGCAGCCCCTGGAGCCGAAGGTCTACACCATGGGCCCTCCCCGGGAGGAGCTGAG CAGCAGGTCGGTCAGCCTGACCTGCATGATCAACGGCTTCTACCCTTCCGACATCTCGGT GGAGTGGGAAGAACGGGAAGGCAGAGGACAACTACAAGACCACGCCGGCCGTGCT GGACAGCGACGGCTCCTACTTCCTCTACAGCAAGCTCTCAGTGCCCACGAGTGAGTGG AGCGGGGCGACGTCTTCACCTGCTCCGTGATGCACGAGGCCTTGCACAACCACTACACG CAGAAGTCCATCTCCCGCTCTCCGGGTAAA |
| SEQ ID NO: 233 (Kabat) | LCDR1 | QTSENFYSNDILS |
| SEQ ID NO: 234 (Kabat) | LCDR2 | EASTLAS |
| SEQ ID NO: 235 (Kabat) | LCDR3 | QGSVLDSGWYDIS |
| SEQ ID NO: 236 (Chothia) | LCDR1 | SENFYSNDI |

TABLE 2-continued

Examples of Notch 3 Antibodies

| SEQ ID NO: 237 (Chothia) | LCDR2 | EAS |
|---|---|---|
| SEQ ID NO: 238 (Chothia) | LCDR3 | SVLDSGWYDI |
| SEQ ID NO: 239 | VL | ALVMTQTPSSVSAAVGGTVTINCQTSENFYSNDILSWYQQKPGQPPKLLIYEASTLASGVPSR FKGSGSGTQFTLTISDVQCDDAATYYCQGSVLDSGWYDISFGGGTEVVVK |
| SEQ ID NO: 240 | DNA VL | GCCCTTGTGATGACCCAGACTCCATCGTCCGTGTCTGCAGCTGTGGGAGGCACAGTCACC ATCAATTGCCAGACCAGTGAGAATTTTTATAGTAACGACATCTTATCCTGGTATCAGCAG AAGCCAGGGCAGCCTCCCAAGCTCCTGATCTATGAAGCATCCACTCTGGCATCTGGGGTC CCCTCGCGATTCAAAGGCAGTGGATCTGGGACACAGTTCACTCTCACCATCAGCGACGTG CAGTGTGACGATGCTGCCACTTACTATTGTCAAGGCAGTGTTCTTGATAGTGGTTGGTAC GATATTTCTTTCGGCGGAGGGACCGAGGTGGTGGTCAAA |
| SEQ ID NO: 241 | Light Chain | ALVMTQTPSSVSAAVGGTVTINCQTSENFYSNDILSWYQQKPGQPPKLLIYEASTLASGVPSR FKGSGSGTQFTLTISDVQCDDAATYYCQGSVLDSGWYDISFGGGTEVVVKGDPVAPTVLIFP PAADQVATGTVTIVCVANKYFPDVTVTWEVDGTTQTTGIENSKTPQNSADCTYNLSSTLTLT STQYNSHKEYTCKVTQGTTSVVQSFNRGDC |
| SEQ ID NO: 242 | DNA Light Chain | GCCCTTGTGATGACCCAGACTCCATCGTCCGTGTCTGCAGCTGTGGGAGGCACAGTCACC ATCAATTGCCAGACCAGTGAGAATTTTTATAGTAACGACATCTTATCCTGGTATCAGCAG AAGCCAGGGCAGCCTCCCAAGCTCCTGATCTATGAAGCATCCACTCTGGCATCTGGGGTC CCCTCGCGATTCAAAGGCAGTGGATCTGGGACACAGTTCACTCTCACCATCAGCGACGTG CAGTGTGACGATGCTGCCACTTACTATTGTCAAGGCAGTGTTCTTGATAGTGGTTGGTAC GATATTTCTTTCGGCGGAGGGACCGAGGTGGTGGTCAAAGGTGATCCAGTTGCACCTAC TGTCCTCATCTTCCCACCAGCTGCTGATCAGGTGGCAACTGGAACAGTCACCATCGTGTG TGTGGCGAATAAATACTTTCCCGATGTCACTGTCACCTGGGAGGTGGATGGCACCACCCA AACAACTGGCATCGAGAACAGTAAAACACCGCAGAATTCTGCAGATTGTACCTACAACCT CAGCAGCACTCTGACACTGACCAGCACACAGTACAACAGCCACAAAGAGTACACCTGCA AGGTGACCCAGGGCACGACCTCAGTCGTCCAGAGCTTCAATAGGGGTGACTGT |

The present disclosure provides antibodies or fragments thereof that specifically bind a Notch 3 protein (e.g., human and/or cynomolgus Notch 3), the antibodies comprising a VH domain having an amino acid sequence of SEQ ID NO: 9, 29, 49, 69, 89, 109, 129, 149, 169, 189, and 209. The present disclosure provides antibodies or fragments thereof that specifically bind a Notch 3 protein (e.g., human and/or cynomolgus Notch 3), said antibodies comprising a VL domain having an amino acid sequence of SEQ ID NO: 19, 39, 59, 79, 99, 119, 139, 159, 179, 199, and 219. The present disclosure also provides antibodies or fragments thereof that specifically bind to a Notch 3 (e.g., human and/or cynomolgus Notch 3), said antibodies comprising a CDR having an amino acid sequence of any one of the CDRs listed in Table 1, infra. In particular, the disclosure provides antibodies that specifically bind to a Notch 3 protein (e.g., human and/or cynomolgus Notch 3), said antibodies comprising (or alternatively, consisting of) one, two, three, four, five or more CDRs having an amino acid sequence of any of the CDRs listed in Table 2.

Other antibodies or fragments thereof include those where the amino acids or nucleic acids encoding the amino acids have been mutated, yet have at least 60, 70, 80, 90, 95, 96, 97, 98, and 99 percent identity to the sequences described in Table 2. In some embodiments, it include mutant amino acid sequences wherein no more than 1, 2, 3, 4 or 5 amino acids have been mutated in the variable regions when compared with the variable regions depicted in the sequence described in Table 2, while retaining substantially the same therapeutic activity.

Since each of these antibodies or fragments thereof can bind to Notch 3, the VH, VL, full length light chain, and full length heavy chain sequences (amino acid sequences and the nucleotide sequences encoding the amino acid sequences) can be "mixed and matched" to create other Notch 3-binding antibodies. Such "mixed and matched" Notch 3-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

Accordingly, in one aspect, the disclosure provides an isolated monoclonal antibody or fragment thereof having: a heavy chain variable region comprising an amino acid sequence selected from the group consisting of SEQ ID NO: 9, 29, 49, 69, 89, 109, 129, 149, 169, 189, and 209; and a light chain variable region comprising an amino acid sequence selected from the group consisting of SEQ ID NOs: 19, 39, 59, 79, 99, 119, 139, 159, 179, 199, and 219, wherein the antibody specifically binds to Notch 3 (e.g., human and/or cynomolgus).

In another aspect, the present disclosure provides Notch 3 antibodies that comprise the heavy chain and light chain CDR1s, CDR2s and CDR3s as described in Table 2, or combinations thereof. The amino acid sequences of the heavy chain variable region CDR1s of the antibodies are shown in SEQ ID NOs: 3, 23, 43, 63, 83, 103, 123, 143, 163, 183, and 203. The amino acid sequences of the heavy chain variable region CDR2s of the antibodies and are shown in SEQ ID NOs: 4, 24, 44, 64, 84, 104, 124, 144, 164, 184, and 204. The amino acid sequences of the heavy chain variable region CDR3s of the antibodies are shown in SEQ ID NOs: 5, 25, 45, 65, 85, 105, 125, 145, 165, 185, and 205. The amino acid sequences of the light chain variable region CDR1s of the antibodies are shown in SEQ ID NOs: 13, 33, 53, 73, 93, 113, 133, 153, 173, 193, and 213. The amino acid sequences of the light chain variable region CDR2s of the antibodies are shown in SEQ ID NOs: 14, 34, 54, 74, 94, 114, 134, 154, 174, 194, and 214. The amino acid sequences of the light chain variable region CDR3s of the antibodies are shown in SEQ ID NOs: 15, 35, 55, 75, 95, 115, 135, 155, 175, 195, and 215. The CDR regions are delineated using the Kabat system (Kabat et al., (1991) Sequences of Proteins of Immunological Interest, Fifth Edition, U.S. Department of Health and Human Services, NIH Publication No. 91-3242; Chothia et al., (1987) J. Mol. Biol. 196:901-917; Chothia et al., (1989) Nature 342: 877-883; and Al-Lazikani et al., (1997) J. Mol. Biol. 273, 927-948).

In a specific embodiment, an antibody that binds to Notch 3 comprises a heavy chain variable region CDR1 of SEQ ID NO: 3; a CDR2 of SEQ ID NO: 4; a CDR3 of SEQ ID NO: 5; a light chain variable region CDR1 of SEQ ID NO: 13; a CDR2 of SEQ ID NO: 14; and a CDR3 of SEQ ID NO: 15.

In a specific embodiment, an antibody that binds to Notch 3 comprises a VH of SEQ ID NO: 9 and VL of SEQ ID NO: 19.

In a specific embodiment, an antibody that binds to Notch 3 comprises a heavy chain variable region CDR1 of SEQ ID NO: 23; a CDR2 of SEQ ID NO: 24; a CDR3 of SEQ ID NO: 25; a light chain variable region CDR1 of SEQ ID NO: 33; a CDR2 of SEQ ID NO: 34; and a CDR3 of SEQ ID NO: 35.

In a specific embodiment, an antibody that binds to Notch 3 comprises a VH of SEQ ID NO: 29 and VL of SEQ ID NO: 39.

In a specific embodiment, an antibody that binds to Notch 3 comprises a heavy chain variable region CDR1 of SEQ ID NO: 43; a CDR2 of SEQ ID NO: 44; a CDR3 of SEQ ID NO: 45; a light chain variable region CDR1 of SEQ ID NO: 53; a CDR2 of SEQ ID NO: 54; and a CDR3 of SEQ ID NO: 55.

In a specific embodiment, an antibody that binds to Notch 3 comprises a VH of SEQ ID NO: 49 and VL of SEQ ID NO: 59.

In a specific embodiment, an antibody that binds to Notch 3 comprises a heavy chain variable region CDR1 of SEQ ID NO: 63; a CDR2 of SEQ ID NO: 64; a CDR3 of SEQ ID NO: 65; a light chain variable region CDR1 of SEQ ID NO: 73; a CDR2 of SEQ ID NO: 74; and a CDR3 of SEQ ID NO: 75.

In a specific embodiment, an antibody that binds to Notch 3 comprises a VH of SEQ ID NO: 69 and VL of SEQ ID NO: 79.

In a specific embodiment, an antibody that binds to Notch 3 comprises a heavy chain variable region CDR1 of SEQ ID NO: 83; a CDR2 of SEQ ID NO: 84; a CDR3 of SEQ ID NO: 85; a light chain variable region CDR1 of SEQ ID NO: 93; a CDR2 of SEQ ID NO: 94; and a CDR3 of SEQ ID NO: 95.

In a specific embodiment, an antibody that binds to Notch 3 comprises a VH of SEQ ID NO: 89 and VL of SEQ ID NO: 99.

In a specific embodiment, an antibody that binds to Notch 3 comprises a heavy chain variable region CDR1 of SEQ ID NO: 103; a CDR2 of SEQ ID NO: 104; a CDR3 of SEQ ID NO: 105; a light chain variable region CDR1 of SEQ ID NO: 113; a CDR2 of SEQ ID NO: 114; and a CDR3 of SEQ ID NO: 115.

In a specific embodiment, an antibody that binds to Notch 3 comprises a VH of SEQ ID NO: 109 and VL of SEQ ID NO: 119.

In a specific embodiment, an antibody that binds to Notch 3 comprises a heavy chain variable region CDR1 of SEQ ID NO: 123; a CDR2 of SEQ ID NO: 124; a CDR3 of SEQ ID NO: 125; a light chain variable region CDR1 of SEQ ID NO: 133; a CDR2 of SEQ ID NO: 134; and a CDR3 of SEQ ID NO: 135.

In a specific embodiment, an antibody that binds to Notch 3 comprises a VH of SEQ ID NO: 129 and VL of SEQ ID NO: 139.

In a specific embodiment, an antibody that binds to Notch 3 comprises a heavy chain variable region CDR1 of SEQ ID NO: 143; a CDR2 of SEQ ID NO: 144; a CDR3 of SEQ ID NO: 145; a light chain variable region CDR1 of SEQ ID NO: 153; a CDR2 of SEQ ID NO: 154; and a CDR3 of SEQ ID NO: 155.

In a specific embodiment, an antibody that binds to Notch 3 comprises a VH of SEQ ID NO: 149 and VL of SEQ ID NO: 159.

In a specific embodiment, an antibody that binds to Notch 3 comprises a heavy chain variable region CDR1 of SEQ ID NO: 163; a CDR2 of SEQ ID NO: 164; a CDR3 of SEQ ID NO: 165; a light chain variable region CDR1 of SEQ ID NO: 173; a CDR2 of SEQ ID NO: 174; and a CDR3 of SEQ ID NO: 175.

In a specific embodiment, an antibody that binds to Notch 3 comprises a VH of SEQ ID NO: 169 and VL of SEQ ID NO: 179.

In a specific embodiment, an antibody that binds to Notch 3 comprises a heavy chain variable region CDR1 of SEQ ID NO: 183; a CDR2 of SEQ ID NO: 184; a CDR3 of SEQ ID NO: 185; a light chain variable region CDR1 of SEQ ID NO: 193; a CDR2 of SEQ ID NO: 194; and a CDR3 of SEQ ID NO: 195.

In a specific embodiment, an antibody that binds to Notch 3 comprises a VH of SEQ ID NO: 189 and VL of SEQ ID NO: 199.

In a specific embodiment, an antibody that binds to Notch 3 comprises a heavy chain variable region CDR1 of SEQ ID NO: 203; a CDR2 of SEQ ID NO: 204; a CDR3 of SEQ ID NO: 205; a light chain variable region CDR1 of SEQ ID NO: 213; a CDR2 of SEQ ID NO: 214; and a CDR3 of SEQ ID NO: 215.

In a specific embodiment, an antibody that binds to Notch 3 comprises a VH of SEQ ID NO: 209 and VL of SEQ ID NO: 219.

In a specific embodiment, an antibody that binds to Notch 3 comprises a heavy chain variable region CDR1 of SEQ ID NO: 223; a CDR2 of SEQ ID NO: 224; a CDR3 of SEQ ID NO: 225; a light chain variable region CDR1 of SEQ ID NO: 233; a CDR2 of SEQ ID NO: 234; and a CDR3 of SEQ ID NO: 235.

In a specific embodiment, an antibody that binds to Notch 3 comprises a VH of SEQ ID NO: 229 and VL of SEQ ID NO: 239.

In one embodiment, the Notch 3 antibodies are antagonist antibodies. In certain embodiments, an antibody that binds to Notch 3 is an antibody that is described in Table 2.

In one embodiment, the invention pertains to an isolated antibody or fragment thereof that recognizes a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is selected from the group consisting of LNR-A, LNR-B, LNR-C; wherein the HD domain is selected from the group consisting of the N-terminal HD and the C-terminal HD; wherein the antibody or fragment thereof blocks ligand-dependent signal transduction; and wherein the antibody or fragment thereof stabilizes the Notch 3 receptor LNR region in the autoinhibited state.

In one embodiment, the invention pertains to an isolated antibody or fragment thereof that recognizes a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is selected from the group consisting of LNR-A, LNR-B, LNR-C; wherein the HD domain is selected from the group consisting of the N-terminal HD and the C-terminal HD; wherein the antibody or fragment thereof blocks ligand-dependent signal transduction; and wherein the antibody or fragment thereof stabilizes the Notch 3 receptor LNR region in the autoinhibited state, and wherein the LNR region or the HD domain has at least one amino acid residue mutation.

In one embodiment, the invention pertains to an isolated antibody or fragment thereof that recognizes a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is selected from the group consisting of LNR-A, LNR-B, LNR-C; wherein the HD domain is selected from the group consisting of the N-terminal HD and the C-terminal HD; wherein the antibody or fragment thereof blocks ligand-dependent signal transduction; and wherein the antibody or fragment thereof stabilizes the Notch 3 receptor LNR region in the autoinhibited state; and wherein the LNR region or the HD domain has at least one amino acid residue mutation.

In one embodiment, the invention pertains to an isolated antibody or fragment thereof that recognizes a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is selected from the group consisting of LNR-A, LNR-B, LNR-C; wherein the HD domain is selected from the group consisting of the N-terminal HD and the C-terminal HD; wherein the antibody or fragment thereof blocks ligand-dependent signal transduction; and wherein the antibody or fragment thereof stabilizes the Notch 3 receptor LNR region in the autoinhibited state; and wherein the LNR region or the HD domain has at least one amino acid residue mutation; wherein the mutation is selected from the group consisting of S1580L, and G1487D.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, the heterodimerization (HD) domain, and a linker region of the NRR domain of Notch 3 receptor; wherein the LNR region is LNR-B, and the HD domain is the HD α3 helix; and wherein the antibody or fragment thereof blocks ligand-dependent signal transduction.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, the heterodimerization (HD) domain, and a linker region of the NRR domain of Notch 3 receptor; wherein the LNR region is LNR-B, and the HD domain is the HD α3 helix; and wherein the antibody or fragment thereof blocks ligand-dependent signal transduction, wherein the conformational epitope further comprises amino acid residues in the LNR-A/B linker of the NRR region.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, the heterodimerization (HD) domain, and a linker region of the NRR domain of Notch 3 receptor; wherein the LNR region is LNR-B, and the HD domain is the HD α3 helix; and wherein the antibody or fragment thereof blocks ligand-dependent signal transduction, wherein the conformational epitope further comprises amino acid residues in the LNR-A/B linker of the NRR region and amino acid residues in the LNR-HD linker of the NRR region.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, the heterodimerization (HD) domain, and a linker region of the NRR domain of Notch 3 receptor; wherein the LNR region is LNR-B, and the HD domain is the HD α3 helix; and wherein the conformational epitope further comprises amino acid residues in the LNR-HD linker of the NRR region.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-B, and the HD domain is the HD α3 helix; and wherein the conformational epitope further comprises amino acid residues in the LNR-HD linker of the NRR region and amino acid residues in the HD β4-α3 loop.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-B, and the HD domain is the HD α3 helix; and wherein the conformational epitope further comprises amino acid residues in the HD β4-α3 loop.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-B, and the HD domain is the HD α3 helix; and wherein the conformational epitope further comprises amino acid residues amino acid residues in the LNR-A/B linker, the LNR-B/C linker, the LNR-HD linker, and the HD β4-α3 loop.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-B, and the HD domain is the HD α3 helix; and wherein the conformational epitope further comprises amino acid residues amino acid residues in the LNR-A/B linker, the LNR-B/C linker, the LNR-HD linker, and the HD β4-α3 loop, and wherein the antibody or fragment thereof stabilizes the Notch 3 receptor LNR region in the autoinhibited state.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, the heterodimerization (HD) domain, and a linker region of the NRR domain of Notch 3 receptor; wherein the LNR region is LNR-B, and the HD domain is the HD α3 helix; and wherein the antibody or fragment thereof stabilizes the Notch 3 receptor LNR region in the autoinhibited state.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, the heterodimerization (HD) domain, and a linker region of the NRR domain of Notch 3 receptor; wherein the LNR region is LNR-B, and the HD domain is the HD α3 helix; and wherein the antibody or fragment thereof stabilizes the Notch 3 receptor LNR region in the autoinhibited state, and wherein the LNR region or the HD domain has at least one amino acid residue mutation.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, the heterodimerization (HD) domain, and a linker region of the NRR domain of Notch 3 receptor; wherein the LNR region is LNR-B, and the HD domain is the HD α3 helix, wherein the LNR region or the HD domain has at least one amino acid residue mutation.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, the heterodimerization (HD) domain, and a linker region of the NRR domain of Notch 3 receptor; wherein the LNR region is LNR-B, and the HD domain is the HD α3 helix, wherein the LNR region or the HD domain has at least one amino acid residue mutation selected from the group consisting of S1580L, D1587N, Y1624H, L1518M, A1537T, N1597K, L1547V, R1526C (HD) and G1487D, (LNR-C), P2034fs, P2067fs ("fs" refers to frame shift), p2177fs, Q2075* ("*" refers to stop codon), W2172*, G2112D, L2212M, F2121L, G2038S, G2059R, R2022H, Y2127H, Y2211C, V2202I, S2096L, P2089L, P2209L, R1981C, R2145Q, P2178S, or combinations thereof.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-B, and the HD domain is the HD α3 helix, wherein the conformational epitope comprises amino acid residues: 1427-1429 (of the LNR-A/B linker), 1442, 1444-1445, 1447-1450, 1453, 1458 (of LNR-B), 1461-1462, 1464 (of the LNR-B/C linker), 1507-1508, 1510 (of the LNR-HD linker), 1592, 1594-1599, 1602 (of the HD β4-α3 loop), and 1606 (of the HD α3 helix), or a subset thereof.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-B, and the HD domain is the HD α3 helix, and wherein the VH of the antibody or fragment thereof binds to at least one of the following Notch 3 residues: Cys1442, Pro1444, Ala1445, Ser1447, Ser1448, Pro1449, Tyr1453, Cys1458, Gly1461, Gly1462, Gly1464, Leu1592, Ser1594, Pro1595, Glu1596, Asn1597, Asp1598, and His1599.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-B, and the HD domain is the HD α3 helix, and wherein the VL of the antibody or fragment thereof binds to at least one of the following Notch 3 residues: Gln1427, Cys1428, Glu1429, Pro1444, Ser1445, Ser1447, Ser1448, Pro1449, Tyr1453, Leu1507, Leu1508, Arg1510, Leu1592, Asp1598, Pro1602, and Ser1606.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the conformational epitope further comprises amino acid residues in the LNR-B of the NRR region.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the conformational epitope further comprises amino acid residues in the LNR-B of the NRR region and further comprises amino acid residues in the LNR-B/C linker of the NRR region.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the conformational epitope further comprises amino acid residues in the LNR-B/C linker of the NRR region.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the conformational epitope further comprises amino acid residues in the LNR-B/C linker of the NRR region, and further comprises amino acid residues in a HD α3-β5 loop.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the conformational epitope further comprises amino acid residues in a HD α3-β5 loop.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the conformational epitope further comprises amino acid residues in LNR-B, the LNR-B/C linker, and the HD α3-β5 loop.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the antibody or fragment thereof stabilizes the Notch 3 receptor LNR region in the autoinhibited state.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the Notch 3 receptor is a mutant Notch 3 receptor, wherein the LNR region or the HD domain has at least one amino acid residue mutation.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the Notch 3 receptor is a mutant Notch 3 receptor, wherein the LNR region or the HD domain has at least one amino acid residue mutation selected from the group consisting of S1580L, D1587N, Y1624H, L1518M, A1537T, N1597K, L1547V, R1526C (HD) and G1487D, (LNR-C), P2034fs, P2067fs, p2177fs, Q2075*, W2172*, G2112D, L2212M, F2121L, G2038S, G2059R, R2022H, Y2127H, Y2211C, V2202I, S2096L, P2089L, P2209L, R1981C, R2145Q, P2178S, or combinations thereof.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the Notch 3 receptor is a mutant Notch 3 receptor, wherein the LNR region or the HD domain has at least one amino acid residue mutation, wherein the conformational epitope comprises amino acid residues: 1440 (of LNR-B), 1463, 1465-1468 (of the LNR-B/C linker) 1469-1472, 1474, 1486-1487, (of LNR-C), 1534 (of HD α2 helix), and 1618, 1619, and 1621 (of the α3-β5 loop), or a subset thereof.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the Notch 3 receptor is a mutant Notch 3 receptor, wherein the LNR region or the HD domain has at least one amino acid residue mutation, wherein the VH of the antibody or fragment thereof binds to at least one of the following Notch 3 residues: Arg1463, Thr1466, Asn1468, Pro1469, Val1470, Tyr1471, Tyr1474, Gln1486, and Gly1487.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the Notch 3 receptor is a mutant Notch 3 receptor, wherein the LNR region or the HD domain has at least one amino acid residue mutation, wherein the VL of the antibody or fragment thereof binds to at least one of the following Notch 3 residues: Ser1440, Arg1465, Thr1466, Asn1468, Pro1469, Val1470, Glu1472, Arg1434, Glu1618, Arg1619, and Asp1621.

In one embodiment, the invention pertains to an isolated antibody or fragment thereof that specifically binds a conformational epitope of a Notch 3 receptor, wherein the conformational epitope comprises continuous and discontinuous amino acid sequences within a Lin Notch Repeat (LNR) region, a heterodimerization (HD) domain, and a linker region of a NRR domain of Notch 3 receptor; wherein the LNR region is LNR-C, and the HD domain is the HD α2 helix; and wherein the antibody or fragment thereof blocks ligand-dependent signal transduction, wherein the Notch 3 receptor is a mutant Notch 3 receptor, wherein the LNR region or the HD domain has at least one amino acid residue mutation.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene.

The antibodies disclosed herein can be derivatives of single chain antibodies, diabodies, domain antibodies, nanobodies, and unibodies. A "single-chain antibody" (scFv) consists of a single polypeptide chain comprising a VL domain linked to a VH domain, wherein VL domain and VH domain are paired to form a monovalent molecule. Single chain antibody can be prepared according to method known in the art (see, for example, Bird et al., (1988) Science 242:423-426 and Huston et al., (1988) Proc. Natl. Acad. Sci. USA 85:5879-5883). A "disbud" consists of two chains, each chain comprising a heavy chain variable region connected to a light chain variable region on the same polypeptide chain connected by a short peptide linker, wherein the two regions on the same chain do not pair with each other but with complementary domains on the other chain to form a bispecific molecule. Methods of preparing diabodies are known in the art (See, e.g., Holliger et al., (1993) Proc. Natl. Acad. Sci. USA 90:6444-6448, and Poljak et al., (1994) Structure 2:1121-1123). Domain antibodies (dAbs) are small functional binding units of antibodies, corresponding to the variable regions of either the heavy or light chains of antibodies. Domain antibodies are well expressed in bacterial, yeast, and mammalian cell systems. Further details of domain antibodies and methods of production thereof are known in the art (see, for example, U.S. Pat. Nos. 6,291,158; 6,582,915; 6,593,081; 6,172,197; 6,696,245; European Patents 0368684 & 0616640; WO05/035572, WO04/101790, WO04/081026, WO04/058821, WO04/003019 and WO03/002609. Nanobodies are derived from the heavy chains of an antibody. A nanobody typically comprises a single variable domain and two constant domains (CH2 and CH3) and retains antigen-binding capacity of the original antibody. Nanobodies can be prepared by methods known in the art (See e.g., U.S. Pat. Nos. 6,765,087; 6,838,254, WO 06/079372). Unibodies consist of one light chain and one heavy chain of a IgG4 antibody. Unibodies may be made by the removal of the hinge region of IgG4 antibodies. Further details of unibodies and methods of preparing them may be found in WO2007/059782.

Homologous Antibodies

In yet another embodiment, the present disclosure provides an antibody or fragment thereof comprising amino acid sequences that are homologous to the sequences described in Table 2, and said antibody binds to a Notch 3 protein (e.g., human and/or cynomolgus Notch 3), and retains the desired functional properties of those antibodies described in Table 2.

For example, the disclosure provides an isolated monoclonal antibody (or a functional fragment thereof) comprising a heavy chain variable region and a light chain variable region, wherein the heavy chain variable region comprises an amino acid sequence that is at least 80%, at least 90%, or at least 95% identical to an amino acid sequence selected from the group consisting of SEQ ID NOs: 9, 29, 49, 69, 89, 109, 129, 149, 169, 189, 209, and 229; the light chain variable region comprises an amino acid sequence that is at least 80%, at least 90%, or at least 95% identical to an amino acid sequence selected from the group consisting of SEQ ID NOs: 19, 39, 59, 79, 99, 119, 139, 159, 179, 199, and 219; the antibody binds to Notch 3 (e.g., human and/or cynomolgus Notch 3) and inhibits the signaling activity of Notch 3, which can be measured for example, by the ICD3 assay as described in the Examples). Also includes within the scope are variable heavy and light chain parental nucleotide sequences; and full length heavy and light chain sequences optimized for expression in a mammalian cell. Other antibodies include amino acids or nucleic acids that have been mutated, yet have at least 60, 70, 80, 90, 95, or 98% percent identity to the sequences described above. In some embodiments, it include mutant amino acid sequences wherein no more than 1, 2, 3, 4 or 5 amino acids have been mutated by amino acid deletion, insertion or substitution in the variable regions when compared with the variable regions depicted in the sequence described above.

In other embodiments, the VH and/or VL amino acid sequences may be 50%, 60%, 70%, 80%, 90%, 95%, 96%, 97%, 98% or 99% identical to the sequences set forth in Table 2. In other embodiments, the VH and/or VL amino acid sequences may be identical except an amino acid substitution in no more than 1, 2, 3, 4 or 5 amino acid position. An antibody having VH and VL regions having high (i.e., 80% or greater) identity to the VH and VL regions of the antibodies described in Table 2 can be obtained by mutagenesis (e.g., site-directed or PCR-mediated mutagenesis), followed by testing of the encoded altered antibody for retained function using the functional assays described herein.

In other embodiments, the variable regions of heavy chain and/or light chain nucleotide sequences may be 60%, 70%, 80%, 90%, 95%, 96%, 97%, 98% or 99% identical to the sequences set forth above.

As used herein, "percent identity" between the two sequences is a function of the number of identical positions shared by the sequences (i.e., % identity equals number of identical positions/total number of positions×100), taking into account the number of gaps, and the length of each gap, which needs to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present disclosure can further be used as a "query sequence" to perform a search against public databases to, for example, identifies related sequences. For example, such searches can be performed using the BLAST program (version 2.0) of Altschul et al., (1990) J. Mol. Biol. 215:403-10.

Antibodies with Conservative Modifications

Other antibodies or fragments thereof include amino acids that have been mutated, yet have at least 60, 70, 80, 90, 95, or 98 percent identity in the CDR regions with the CDR regions depicted in the sequences described in Table 2. In some embodiments, it includes mutant amino acid sequences wherein no more than 1, 2, 3, 4 or 5 amino acids have been mutated in the CDR regions when compared with the CDR regions depicted in the sequence described Table 2, while still maintaining their specificity for the original antibody's epitope Other antibodies or fragments thereof include amino acids that have been mutated, yet have at least 60, 70, 80, 90, 95, or 98 percent identity in the framework regions with the framework regions depicted in the sequences described in Table 2. In some embodiments, it includes mutant amino acid sequences wherein no more than 1, 2, 3, 4, 5, 6, or 7 amino acids have been mutated in the framework regions when compared with the framework regions depicted in the sequence described Table 2, while still maintaining their specificity for the original antibody's epitope. The present disclosure also provides nucleic acid sequences that encode VH, VL, the full length heavy chain, and the full length light chain of the antibodies that specifically bind to a Notch 3 protein (e.g., human and/or cynomolgus Notch 3).

In certain embodiments, an antibody has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the Notch 3-binding antibodies of the disclosure.

Accordingly, the disclosure provides an isolated Notch 3 monoclonal antibody, or a fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 3, 23, 43, 63, 83, 103, 123, 143, 163, 183, and 203, and conservative modifications thereof; the heavy chain variable region CDR2 amino acid sequences are selected from the group consisting of SEQ ID NOs: 4, 24, 44, 64, 84, 104, 124, 144, 164, 184, and 204, and conservative modifications thereof; the heavy chain variable region CDR3 amino acid sequences are selected from the group consisting of SEQ ID NOs: 5, 25, 45, 65, 85, 105, 125, 145, 165, 185, and 205, and conservative modifications thereof; the light chain variable regions CDR1 amino acid sequences are selected from the group consisting of SEQ ID NOs: 13, 33, 53, 73, 93, 113, 133, 153, 173, 193, and 213, and conservative modifications thereof; the light chain variable regions CDR2 amino acid sequences are selected from the group consisting of SEQ ID NOs: 14, 34, 54, 74, 94, 114, 134, 154, 174, 194, and 214, and conservative modifications thereof; the light chain variable regions of CDR3 amino acid sequences are selected from the group consisting of SEQ ID NOs: 15, 35, 55, 75, 95, 115, 135, 155, 175, 195, and 215, and conservative modifications thereof; the antibody or fragment thereof specifically binds to Notch 3, and inhibits Notch 3 activity by inhibiting a Notch 3 signaling pathway, which can be measured a Notch 3 assay (e.g., ICD3 assay) described in the Examples.

Antibodies that Bind to the Same Conformational Epitope

The present disclosure provides antibodies that interacts with (e.g., by binding, steric hindrance, stabilizing spatial distribution) the same conformational epitope as do the Notch 3-binding antibodies described in Table 2. Additional antibodies can therefore be identified based on their ability to cross-compete (e.g., to competitively inhibit the binding of, in a statistically significant manner) with other antibodies in Notch 3 binding assays. The ability of a test antibody to inhibit the binding of antibodies of the present disclosure to a Notch 3 protein (e.g., human and/or cynomolgus Notch 3) demonstrates that the test antibody can compete with that antibody for binding to Notch 3; such an antibody may, according to non-limiting theory, bind to the same or a related (e.g., a structurally similar or spatially proximal) conformational epitope on the Notch 3 protein as the antibody with which it competes. In a certain embodiment, the antibody that binds to the same conformational epitope on Notch 3 is a human monoclonal antibody. Such human monoclonal antibodies can be prepared and isolated as described herein.

In one embodiment, the antibody or fragments thereof binds to a conformational epitope comprising discontinuous amino acid residues in both an LNR region and a HD of Notch 3 to hold the Notch 3 in an autoinhibited conformation which prevents exposure of the S2 sites within the HD to proteases and subsequent cleavage of S3 sites by proteases. The lack of cleavage at these sites prevents downstream Notch 3 signal transduction.

Although not bound to provide a theory, one possible model for the mechanism of action is that Notch 3 NRR typically exists in an autoinhibited conformation in which the three LNRs, each coordinating a $Ca^{2+}$ ion, wrap around HD to protect S2 site from access by ADAM proteases (e.g., the conserved L1419 from LNR-A/B linker directly plugs into S2 site and sterically occludes it from protease access). The stability of the interactions between LNRs and HD, as well as those within these regions, is critical to maintain the autoinhibited conformation of NRR. Mutations in the Notch 3 NRR open the autoinhibited conformation, thereby exposing the HD domain, such that the S2 sites and subsequently S3 sites are available for cleavage by proteases, thereby activating downstream Notch 3 signal transduction. Therefore, mutations destabilizing NRR, like those found in relevant cancers (disclosed herein), could enhance activation of Notch3. On the other hand, reagents like antibodies that can stabilize LNR-HD interaction can potentially inhibit Notch3 signaling. Antibodies or fragments thereof such as 20350, and 20358 bind the autoinhibited conformation of Notch 3 and stabilizes (directly maintains, holds, locks,) the autoinhibited conformation thereby preventing exposure of the HD to protease cleavage, and subsequent downstream Notch 3 signaling.

The antibodies or fragments thereof inhibit ligand activation of Notch 3; ligand independent activation of Notch 3; and both ligand dependent and independent activation of Notch 3 without preventing ligand binding. This is considered advantageous as the therapeutic antibody would have clinical utility in a broad spectrum of tumors than an antibody which targeted a single mechanism of Notch 3 activation (i.e. ligand dependent or ligand independent) since distinct tumor types are driven by each mechanism.

Consequently, the antibodies may be used to treat conditions where existing therapeutic antibodies are clinically ineffective.

Engineered and Modified Antibodies

An antibody further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i. e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Reichmann et al., (1998) Nature 332:323-327; Jones et al., (1986) Nature 321:522-525; Queen et al., (1989) Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.).

Accordingly, another embodiment pertains to an isolated Notch 3 antibody, or fragment thereof, comprising a heavy chain variable region comprising CDR1 sequences having an amino acid sequence selected from the group consisting of SEQ ID NOs: 3, 23, 43, 63, 83, 103, 123, 143, 163, 183, and 203; CDR2 sequences having an amino acid sequence selected from the group consisting of SEQ ID NOs:4, 24, 44, 64, 84, 104, 124, 144, 164, 184, and 204; CDR3 sequences having an amino acid sequence selected from the group consisting of SEQ ID NOs: 4, 10, 22, 28, 40, 46, 58, 64, 76, 82, 94, 100, 112, 118, 130, 136, 148, 154, 166, 172, 184, 190, 202, 208, 220, 226, 238, 244, 256, 262, 274, 280, 292, 298, 310, 316, 328, 334, 346, 352, 364, and 370, respectively; and a light chain variable region having CDR1 sequences having an amino acid sequence selected from the group consisting of SEQ ID NOs: 13, 33, 53, 73, 93, 113, 133, 153, 173, 193, and 213; CDR2 sequences having an amino acid sequence selected from the group consisting of SEQ ID NOs: 14, 34, 54, 74, 94, 114, 134, 154, 174, 194, and 214; and CDR3 sequences consisting of an amino acid sequence selected from the group consisting of SEQ ID NOs: 15, 35, 55, 75, 95, 115, 135, 155, 175, 195, and 215, respectively.

Thus, such antibodies contain the VH and VL CDR sequences of antibodies, yet may contain different framework sequences from these antibodies. Such framework sequences can be obtained from public DNA databases or published references that include germline antibody gene sequences. For example, germline DNA sequences for human heavy and light chain variable region genes can be found in the "Vase" human germline sequence database (available on the Internet at www.mrc-cpe.cam.ac.uk/vbase), as well as in Kabat et al., (1991) Sequences of Proteins of Immunological Interest, Fifth Edition, U.S. Department of Health and Human Services, NIH Publication No. 91-3242; Chothia et al., (1987) J. Mol. Biol. 196:901-917; Chothia et al., (1989) Nature 342:877-883; and Al-Lazikani et al., (1997) J. Mol. Biol. 273:927-948; Tomlinson et al., (1992) J. fol. Biol. 227:776-798; and Cox et al., (1994) Eur. J Immunol. 24:827-836; the contents of each of which are expressly incorporated herein by reference.

An example of framework sequences for use in the antibodies are those that are structurally similar to the framework sequences used by selected antibodies of the disclosure, e.g., consensus sequences and/or framework sequences used by monoclonal antibodies of the disclosure. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180, 370 to Queen et al).

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the disclosure provides isolated Notch 3 antibodies, or fragment thereof, consisting of a heavy chain variable region having: a VH CDR1 region consisting of an amino acid sequence selected from the group having SEQ ID NOs: 3, 23, 43, 63, 83, 103, 123, 143, 163, 183, and 203, or an amino acid sequence having one, two, three, four or five amino acid substitutions, deletions or additions as compared to SEQ ID NOs: 3, 23, 43, 63, 83, 103, 123, 143, 163, 183, and 203; a VH CDR2 region having an amino acid sequence selected from the group consisting of SEQ ID NOs: 4, 24, 44, 64, 84, 104, 124, 144, 164, 184, and 204, or an amino acid sequence having one, two, three, four or five amino acid substitutions, deletions or additions as compared to SEQ ID NOs: 4, 24, 44, 64, 84, 104, 124, 144, 164, 184, and 204; a VH CDR3 region having an amino acid sequence selected from the group consisting of SEQ ID NOs: 5, 25, 45, 65, 85, 105, 125, 145, 165, 185, and 205, or an amino acid sequence having one, two, three, four or five amino acid substitutions, deletions or additions as compared to SEQ ID NOs: 5, 25, 45, 65, 85, 105, 125, 145, 165, 185, and 205; a VL CDR1 region having an amino acid sequence selected from the group consisting of SEQ ID NOs:13, 33, 53, 73, 93, 113, 133, 153, 173, 193, and 213, or an amino acid sequence having one, two, three, four or five amino acid substitutions, deletions or additions as compared to SEQ ID NOs: 13, 33, 53, 73, 93, 113, 133, 153, 173, 193, and 213; a VL CDR2 region having an amino acid sequence selected from the group consisting of SEQ ID NOs: 14, 34, 54, 74, 94, 114, 134, 154, 174, 194, and 214, or an amino acid sequence having one, two, three, four or five amino acid substitutions, deletions or additions as compared to SEQ ID NOs: 14, 34, 54, 74, 94, 114, 134, 154, 174, 194, and 214; and a VL CDR3 region having an amino acid sequence selected from the group consisting of SEQ ID NOs: 15, 35, 55, 75, 95, 115, 135, 155, 175, 195, and 215, or an amino acid sequence having one, two, three, four or five amino acid substitutions, deletions or additions as compared to SEQ ID NOs: 15, 35, 55, 75, 95, 115, 135, 155, 175, 195, and 215.

Grafting Antibody Fragments into Alternative Frameworks or Scaffolds

A wide variety of antibody/immunoglobulin frameworks or scaffolds can be employed so long as the resulting polypeptide includes at least one binding region which specifically binds to Notch 3. Such frameworks or scaffolds include the 5 main idiotypes of human immunoglobulins, or fragments thereof, and include immunoglobulins of other animal species, preferably having humanized aspects. Novel frameworks, scaffolds and fragments continue to be discovered and developed by those skilled in the art.

In one aspect, the disclosure pertains to generating non-immunoglobulin based antibodies using non-immunoglobulin scaffolds onto which CDRs can be grafted. Known or future non-immunoglobulin frameworks and scaffolds may be employed, as long as they comprise a binding region specific for the target Notch 3 protein (e.g., human and/or cynomolgus Notch 3). Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx Nev., Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III ($^{10}$Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as Notch 3. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company *Pieris* ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

In some embodiments, the Fabs are converted to silent IgG1 format by changing the Fc region. For example, antibodies in Table 2 can be converted to IgG format.

Human or Humanized Antibodies

The present disclosure provides fully human antibodies that specifically bind to a Notch 3 protein (e.g., human and/or cynomolgus/mouse/mouse Notch 3). Compared to the chimeric or humanized antibodies, the human Notch 3-binding antibodies have further reduced antigenicity when administered to human subjects.

The human Notch 3-binding antibodies can be generated using methods that are known in the art. For example, the humaneering technology used to converting non-human antibodies into engineered human antibodies. U.S. Patent Publication No. 20050008625 describes an in vivo method for replacing a nonhuman antibody variable region with a human variable region in an antibody while maintaining the same or providing better binding characteristics relative to that of the nonhuman antibody. The method relies on epitope guided replacement of variable regions of a non-human reference antibody with a fully human antibody. The resulting human antibody is generally unrelated structurally to the reference nonhuman antibody, but binds to the same epitope on the same antigen as the reference antibody. Briefly, the serial epitope-guided complementarity replacement approach is enabled by setting up a competition in cells between a "competitor" and a library of diverse hybrids of the reference antibody ("test antibodies") for binding to limiting amounts of antigen in the presence of a reporter system which responds to the binding of test antibody to antigen. The competitor can be the reference antibody or derivative thereof such as a single-chain Fv fragment. The competitor can also be a natural or artificial ligand of the antigen which binds to the same epitope as the reference antibody. The only requirements of the competitor are that it binds to the same epitope as the reference antibody, and that it competes with the reference antibody for antigen binding. The test antibodies have one antigen-binding V-region in common from the nonhuman reference antibody, and the other V-region selected at random from a diverse source such as a repertoire library of human antibodies. The common V-region from the reference antibody serves as a guide, positioning the test antibodies on the same epitope on the antigen, and in the same orientation, so that selection is biased toward the highest antigen-binding fidelity to the reference antibody.

Many types of reporter system can be used to detect desired interactions between test antibodies and antigen. For example, complementing reporter fragments may be linked to antigen and test antibody, respectively, so that reporter activation by fragment complementation only occurs when the test antibody binds to the antigen. When the test antibody- and antigen-reporter fragment fusions are co-expressed with a competitor, reporter activation becomes dependent on the ability of the test antibody to compete with the competitor, which is proportional to the affinity of the test antibody for the antigen. Other reporter systems that can be used include the reactivator of an auto-inhibited reporter reactivation system (RAIR) as disclosed in U.S. patent application Ser. No. 10/208,730 (Publication No. 20030198971), or competitive activation system disclosed in U.S. patent application Ser. No. 10/076,845 (Publication No. 20030157579).

With the serial epitope-guided complementarity replacement system, selection is made to identify cells expresses a single test antibody along with the competitor, antigen, and reporter components. In these cells, each test antibody competes one-on-one with the competitor for binding to a limiting amount of antigen. Activity of the reporter is proportional to the amount of antigen bound to the test antibody, which in turn is proportional to the affinity of the test antibody for the antigen and the stability of the test antibody. Test antibodies are initially selected on the basis of their activity relative to that of the reference antibody when expressed as the test antibody. The result of the first round of selection is a set of "hybrid" antibodies, each of which is comprised of the same non-human V-region from the reference antibody and a human V-region from the library, and each of which binds to the same epitope on the antigen as the reference antibody. One of more of the hybrid antibodies selected in the first round will have an affinity for the antigen comparable to or higher than that of the reference antibody.

In the second V-region replacement step, the human V-regions selected in the first step are used as guide for the selection of human replacements for the remaining nonhuman reference antibody V-region with a diverse library of cognate human V-regions. The hybrid antibodies selected in the first round may also be used as competitors for the second round of selection. The result of the second round of selection is a set of fully human antibodies which differ structurally from the reference antibody, but which compete with the reference antibody for binding to the same antigen. Some of the selected human antibodies bind to the same epitope on the same antigen as the reference antibody.

Among these selected human antibodies, one or more binds to the same epitope with an affinity which is comparable to or higher than that of the reference antibody.

Using one of the mouse or chimeric Notch 3-binding antibodies described above as the reference antibody, this method can be readily employed to generate human antibodies that bind to human Notch 3 with the same binding specificity and the same or better binding affinity. In addition, such human Notch 3-binding antibodies can also be commercially obtained from companies which customarily produce human antibodies, e.g., KaloBios, Inc. (Mountain View, Calif.).

Camelid Antibodies

Antibody proteins obtained from members of the camel and dromedary (Camelus bactrianus and Calelus dromaderius) family including new world members such as llama species (Lama paccos, Lama glama and Lama vicugna) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans et al., (2004) J Biol Chem 279:1256-1261; Dumoulin et al., (2003) Nature 424:783-788; Pleschberger et al., (2003) Bioconjugate Chem 14:440-448; Cortez-Retamozo et al., (2002) Int J Cancer 89:456-62; and Lauwereys et al., (1998) EMBO J 17:3512-3520. Engineered libraries of camelid antibodies and antibody fragments are commercially available, for example, from Ablynx, Ghent, Belgium (e.g., US20060115470; Domantis (US20070065440, US20090148434). As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as E. coli and are expressed as fusion proteins with bacteriophage and are functional.

Accordingly, a feature of the present disclosure is a camelid antibody or nanobody having high affinity for Notch 3. In certain embodiments herein, the camelid antibody or nanobody is naturally produced in the camelid animal, i.e., is produced by the camelid following immunization with Notch 3 or a peptide fragment thereof, using techniques described herein for other antibodies. Alternatively, the Notch 3-binding camelid nanobody is engineered, i.e., produced by selection for example from a library of phage displaying appropriately mutagenized camelid nanobody proteins using panning procedures with Notch 3 as a target as described in the examples herein. Engineered nanobodies can further be customized by genetic engineering to have a half-life in a recipient subject of from 45 minutes to two weeks. In a specific embodiment, the camelid antibody or nanobody is obtained by grafting the CDRs sequences of the heavy or light chain of the human antibodies into nanobody or single domain antibody framework sequences, as described for example in PCT/EP93/02214

In one embodiment, the camelid antibody or nanobody binds to at least one of the following Notch 3 residues: Cys1442, Pro1444, Ala1445, Ser1447, Ser1448, Pro1449, Tyr1453, Cys1458, Gly1461, Gly1462, Gly1464, Leu1592, Ser1594, Pro1595, Glu1596, Asn1597, Asp1598, and His1599. In one embodiment, the camelid antibody or nanobody binds to at least one of the following Notch 3 residues: Gln1427, Cys1428, Glu1429, Pro1444, Ser1445, Ser1447, Ser1448, Pro1449, Tyr1453, Leu1507, Leu1508, Arg1510, Leu1592, Asp1598, Pro1602, and Ser1606.

In one embodiment, the camelid antibody or nanobody binds to at least one of the following Notch 3 residues: Arg1463, Thr1466, Asn1468, Pro1469, Val1470, Tyr1471, Tyr1474, Gln1486, and Gly1487. In one embodiment, the camelid antibody or nanobody binds to at least one of the following Notch 3 residues: Ser1440, Arg1465, Thr1466, Asn1468, Pro1469, Val1470, Glu1472, Arg1434, Glu1618, Arg1619, and Asp1621.

Bispecific Molecules and Multivalent Antibodies

In another aspect, the present disclosure features biparatopic, bispecific or multispecific molecules comprising a Notch 3 antibody, or a fragment thereof, of the disclosure. An antibody of the disclosure, or fragments thereof, can be derivatized or linked to another functional molecule, e.g., another peptide or protein (e.g., another antibody or ligand for a receptor) to generate a bispecific molecule that binds to at least two different binding sites or target molecules. The antibody may in fact be derivatized or linked to more than one other functional molecule to generate biparatopic or multi-specific molecules that bind to more than two different binding sites and/or target molecules; such biparatopic or multi-specific molecules. To create a bispecific molecule of the disclosure, an antibody can be functionally linked (e.g., by chemical coupling, genetic fusion, non-covalent association or otherwise) to one or more other binding molecules, such as another antibody, antibody fragment, peptide or binding mimetic, such that a bispecific molecule results.

Further clinical benefits may be provided by the binding of two or more antigens within one antibody (Coloma et al., (1997); Merchant et al., (1998); Alt et al., (1999); Zuo et al., (2000); Lu et al., (2004); Lu et al., (2005); Marvin et al., (2005); Marvin et al., (2006); Shen et al., (2007); Wu et al., (2007); Dimasi et al., (2009); Michaelson et al., (2009)). (Morrison et al., (1997) Nature Biotech. 15:159-163; Alt et al. (1999) FEBS Letters 454:90-94; Zuo et al., (2000) Protein Engineering 13:361-367; Lu et al., (2004) JBC 279:2856-2865; Lu et al., (2005) JBC 280:19665-19672; Marvin et al., (2005) Acta Pharmacologica Sinica 26:649-658; Marvin et al., (2006) Curr Opin Drug Disc Develop 9:184-193; Shen et al., (2007) J Immun Methods 218:65-74; Wu et al., (2007) Nat Biotechnol. 11:1290-1297; Dimasi et al., (2009) J Mol Biol. 393:672-692; and Michaelson et al., (2009) mAbs 1:128-141.

The bispecific molecules of the present disclosure can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al., (1984) J. Exp. Med. 160:1686; Liu et al., (1985) Proc. Natl. Acad. Sci. USA 82:8648). Other methods include those described in Paulus (1985) Behring Ins. Mitt. No. 78:118-132; Brennan et al., (1985) Science 229:81-83), and Glennie et al., (1987) J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb x mAb, mAb x Fab, Fab x F(ab')$_2$ or ligand x Fab fusion protein. A bispecific molecule can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455, 030; 4,881,175; 5,132,405; 5,091,513; 5,476,786; 5,013, 653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present disclosure provides multivalent compounds comprising at least two identical or different fragments of the antibodies binding to Notch 3. The antibody fragments can be linked together via protein fusion or covalent or non-covalent linkage. Tetravalent compounds can be obtained for example by cross-linking antibodies of the antibodies with an antibody that binds to the constant regions of the antibodies of the disclosure, for example the Fc or hinge region. Trimerizing domain are described for example in Borean patent EP 1012280B1. Pentamerizing modules are described for example in PCT/EP97/05897.

In one embodiment, a biparatopic/bispecific binds to amino acid residues within the LNR and HD of Notch 3.

In another embodiment, the disclosure pertains to dual function antibodies in which a single monoclonal antibody has been modified such that the antigen binding site binds to more than one antigen, such as a dual function antibody which binds both Notch 3 and another antigen (e.g., Notch 1, EGFR). Thus, a dual function antibody may bind to both Notch 3 and Notch 1 or EGFR. The dual binding specificity of the dual function antibody may further translate into dual activity, or inhibition of activity. (See e.g., Jenny Bostrom et al., (2009) Science: 323; 1610-1614).

Antibodies with Extended Half Life

The present disclosure provides for antibodies that specifically bind to Notch 3 protein which have an extended half-life in vivo.

Many factors may affect a protein's half-life in vivo. For examples, kidney filtration, metabolism in the liver, degradation by proteolytic enzymes (proteases), and immunogenic responses (e.g., protein neutralization by antibodies and uptake by macrophages and dendritic cells). A variety of strategies can be used to extend the half-life of the antibodies of the present disclosure. For example, by chemical linkage to polyethylene glycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nanocarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the disclosure. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a nonnative amino acid any place an amber codon is positioned, converting the amber from a stop codon to one that signals incorporation of the chemically specified amino acid.

Recombinant pegylation technology (rPEG) can also be used for serum half-life extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum half-life of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology include the use of hydroxy ethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin in order to make the antibody or antibody fragment more stable in vivo or have a longer half-life in vivo. The techniques are well-known in the art, see, e.g., International Publication Nos. WO 93/15199, WO 93/15200, and WO 01/77137; and European Patent No. EP 413,622.

The Notch 3 antibody or a fragment thereof may also be fused to one or more human serum albumin (HSA) polypeptides, or a portion thereof. HSA, a protein of 585 amino acids in its mature form, is responsible for a significant proportion of the osmotic pressure of serum and also functions as a carrier of endogenous and exogenous ligands. The role of albumin as a carrier molecule and its inert nature are desirable properties for use as a carrier and transporter of polypeptides in vivo. The use of albumin as a component of an albumin fusion protein as a carrier for various proteins has been suggested in WO 93/15199, WO 93/15200, and EP 413 622. The use of N-terminal fragments of HSA for fusions to polypeptides has also been proposed (EP 399 666). Accordingly, by genetically or chemically fusing or conjugating the antibodies or fragments thereof to albumin, can stabilize or extend the shelf-life, and/or to retain the molecule's activity for extended periods of time in solution, in vitro and/or in vivo.

Fusion of albumin to another protein may be achieved by genetic manipulation, such that the DNA coding for HSA, or a fragment thereof, is joined to the DNA coding for the protein. A suitable host is then transformed or transfected with the fused nucleotide sequences, so arranged on a suitable plasmid as to express a fusion polypeptide. The expression may be effected in vitro from, for example, prokaryotic or eukaryotic cells, or in vivo e.g. from a transgenic organism. Additional methods pertaining to HSA fusions can be found, for example, in WO 2001077137 and WO 200306007, incorporated herein by reference. In a specific embodiment, the expression of the fusion protein is performed in mammalian cell lines, for example, CHO cell lines. Altered differential binding of an antibody to a receptor at low or high pHs is also contemplated to be within the scope of the disclosure. For example, the affinity of an antibody may be modified such that it remains bound to its receptor at a low pH, e.g., the low pH within a lyzozome, by modifying the antibody to include additional amino acids such as a histine in a CDR of the antibody (See e.g., Tomoyuki Igawa et al. (2010) Nature Biotechnology; 28, 1203-1207).

Antibody Conjugates

The present disclosure provides antibodies or fragments thereof that specifically bind to a Notch 3 protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the disclosure provides fusion proteins comprising an antibody fragment described herein (e.g., a Fab fragment, Fd fragment, Fv fragment, F(ab)2 fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., (1991) Proc. Natl. Acad. Sci. USA 88:10535-10539; Zheng et al., (1995) J. Immunol. 154:5590-5600; and Vil et al. (1992) Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al. (1997) Curr. Opinion Biotechnol. 8:724-33; Harayama (1998) Trends Biotechnol. 16(2):76-82; Hansson et al. (1999) J. Mol. Biol. 287:265-76; and Lorenzo and Blasco (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a Notch 3 protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., (1989) Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "flag" tag.

In other embodiments, antibodies of the present disclosure or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I,), carbon ($^{14}$C), sulfur ($^{35}$S), tritium ($^{3}$H), indium ($^{115}$In, $^{113}$In, $^{112}$In, and $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, 47Sc, $^{186}$Re, $^{188}$Re, $^{142}$PR, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; and positron emitting metals using various positron emission tomographies, and nonradioactive paramagnetic metal ions.

The present disclosure further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine. In one embodiment, the anti-Notch 3 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). (See e.g., Seattle Genetics US20090304721).

Other examples of therapeutic cytotoxins that can be conjugated to an antibody include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264.

Antibodies of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the disclosure. In certain embodiments, the macrocyclic chelator is 1,4,7,10-tetraazacyclododecane-N,N',N",N"'-tetraacetic acid (DOTA) which can be attached to the antibody via a linker molecule. Such linker molecules are commonly known in the art and described in Denardo et al., (1998) Clin Cancer Res. 4(10): 2483-90; Peterson et al., (1999) Bioconjug. Chem. 10(4): 553-7; and Zimmerman et al., (1999) Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., (1982) Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

An another aspect, the disclosure pertains to Notch 3 antibodies, or fragments thereof used in combination with other therapeutic agents such as another antibodies, small molecule inhibitors, and standard of care therapies such as EGFR, and platinum chemotherapy.

Methods of Producing Antibodies
(i) Nucleic Acids Encoding the Antibodies

The disclosure provides substantially purified nucleic acid molecules which encode polypeptides comprising segments or domains of the Notch 3 antibody chains described above. Some of the nucleic acids comprise the nucleotide sequence encoding the Notch 3 antibody heavy chain variable region, and/or the nucleotide sequence encoding the light chain variable region. In a specific embodiment, the nucleic acid molecules are those identified in Table 2. Some other nucleic acid molecules comprise nucleotide sequences that are substantially identical (e.g., at least 65, 80%, 95%, or 99%) to the nucleotide sequences of those identified in Table 2. When expressed from appropriate expression vectors, polypeptides encoded by these polynucleotides are capable of exhibiting Notch 3 antigen binding capacity.

Also provided in the disclosure are polynucleotides which encode at least one CDR region and usually all three CDR regions from the heavy or light chain of the Notch 3 antibody set forth above. Some other polynucleotides encode all or substantially all of the variable region sequence of the heavy chain and/or the light chain of the Notch 3 antibody set forth above. Because of the degeneracy of the code, a variety of nucleic acid sequences will encode each of the immunoglobulin amino acid sequences.

The nucleic acid molecules can encode both a variable region and a constant region of the antibody. Some of nucleic acid sequences comprise nucleotides encoding a mature heavy chain variable region sequence that is substantially identical (e.g., at least 80%, 90%, or 99%) to the mature heavy chain variable region sequence of a Notch 3 antibody set forth in Table 2. Some other nucleic acid sequences comprising nucleotide encoding a mature light chain variable region sequence that is substantially identical (e.g., at least 80%, 90%, or 99%) to the mature light chain variable region sequence of a Notch 3 antibody set forth in Table 2.

The polynucleotide sequences can be produced by de novo solid-phase DNA synthesis or by PCR mutagenesis of an existing sequence (e.g., sequences as described in the Examples below) encoding an Notch 3 antibody or its binding fragment. Direct chemical synthesis of nucleic acids can be accomplished by methods known in the art, such as the phosphotriester method of Narang et al., (1979) Meth. Enzymol. 68:90; the phosphodiester method of Brown et al., (1979) Meth. Enzymol. 68:109; the diethylphosphoramidite method of Beaucage et al., (1981) Tetra. Lett., 22:1859; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, Calif., 1990; Manila et al., (1991) Nucleic Acids Res. 19:967; and Eckert et al., (1991) PCR Methods and Applications 1:17.

Also provided in the disclosure are expression vectors and host cells for producing the Notch 3-binding antibodies described above. Various expression vectors can be employed to express the polynucleotides encoding the Notch 3 antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., (1997) Nat Genet 15:345). For example, nonviral vectors useful for expression of the Notch 3-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., (1995) supra; Smith, Annu. Rev. Microbiol. 49:807; and Rosenfeld et al., (1992) Cell 68:143.

The choice of expression vector depends on the intended host cells in which the vector is to be expressed. Typically, the expression vectors contain a promoter and other regulatory sequences (e.g., enhancers) that are operably linked to the polynucleotides encoding an Notch 3 antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an Notch 3 antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., (1994) Results Probl. Cell Differ. 20:125; and Bittner et al., (1987) Meth. Enzymol., 153:516). For example, the SV40 enhancer or CMV enhancer may be used to increase expression in mammalian host cells.

The expression vectors may also provide a secretion signal sequence position to form a fusion protein with polypeptides encoded by inserted Notch 3 antibody sequences. More often, the inserted Notch 3 antibody sequences are linked to a signal sequences before inclusion in the vector. Vectors to be used to receive sequences encoding Notch 3 antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the Notch 3 antibody chains can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express Notch 3-binding polypeptides of the disclosure. Insect cells in combination with baculovirus vectors can also be used.

In some embodiments, mammalian host cells are used to express and produce the Notch 3-binding polypeptides of the present disclosure. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen et al., (1986) Immunol. Rev. 89:49-68), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, (1997) Cell 88:223), agent-enhanced uptake of DNA, and ex vivo transduction. For long-term, high-yield production of recombinant proteins, stable expression will often be desired. For example, cell lines which stably express Notch 3 antibody chains or binding fragments can be prepared using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

(ii) Generation of Monoclonal Antibodies

Monoclonal antibodies (mAbs) can be produced by a variety of techniques, including conventional monoclonal antibody methodology e.g., the standard somatic cell hybridization technique of Kohler and Milstein, (1975) Nature 256:495. Many techniques for producing monoclonal antibody can be employed e.g., viral or oncogenic transformation of B lymphocytes.

An animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, the antibodies are human monoclonal antibodies. Such human monoclonal antibodies directed against Notch 3 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (µ and γ) and κ light chain immunoglobulin sequences, together with targeted mutations that inactivate the endogenous µ and κ chain loci (see e.g., Lonberg et al., (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg et al., (1994) supra; reviewed in Lonberg, (1994) Handbook of Experimental Pharmacology 113:49-101; Lonberg and Huszar, (1995) Intern. Rev. Immunol. 13:65-93, and Harding and Lonberg, (1995) Ann. N. Y. Acad. Sci. 764:536-546). The preparation and use of HuMAb mice, and the genomic modifications carried by such mice, is further described in Taylor et al., (1992) Nucleic Acids Research 20:6287-6295; Chen et al., (1993) International Immunology 5:647-656; Tuaillon et al., (1993) Proc. Natl. Acad. Sci. USA 94:3720-3724; Choi et al., (1993) Nature Genetics 4:117-123; Chen et al., (1993) EMBO J. 12:821-830; Tuaillon et al., (1994) J. Immunol. 152:2912-2920; Taylor et al., (1994) International Immunology 579-591; and Fishwild et al., (1996) Nature Biotechnology 14:845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise Notch 3-binding antibodies of the disclosure. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise Notch 3-binding antibodies of the disclosure. For example, mice carrying both a human heavy chain transchromosome and a human light chain tranchromosome, referred to as "TC mice" can be used; such mice are described in Tomizuka et al., (2000) Proc. Natl. Acad. Sci. USA 97:722-727. Furthermore, cows carrying human heavy and light chain transchromosomes have been described in the art (Kuroiwa et al., (2002) Nature Biotechnology 20:889-894) and can be used to raise Notch 3-binding antibodies of the disclosure.

Human monoclonal antibodies can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

(iii) Framework or Fc Engineering

Engineered antibodies include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the disclosure.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies may be engineered to include modifications within the Fc region, typically to alter one or more functional properties of the antibody, such as serum half-life, complement fixation, Fc receptor binding, and/or antigen-dependent cellular cytotoxicity. Furthermore, an antibody may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRl, FcγRII, FcγRIII and FcRn have been mapped and variants with improved binding have been described (see Shields et al., (2001) J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen'. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields et al., (2002) J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., (1999) Nat. Biotech. 17:176-180).

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

(iv) Methods of Engineering Altered Antibodies

As discussed above, the Notch 3-binding antibodies having VH and VL sequences or full length heavy and light chain sequences shown herein can be used to create new Notch 3-binding antibodies by modifying full length heavy chain and/or light chain sequences, VH and/or VL sequences, or the constant region(s) attached thereto. Thus, in another aspect of the disclosure, the structural features of a Notch 3 antibody are used to create structurally related Notch 3-binding antibodies that retain at least one functional property of the antibodies of the disclosure, such as binding to human Notch 3 and also inhibiting one or more functional properties of Notch 3. For example, one or more CDR regions of the antibodies of the present disclosure, or mutations thereof, can be combined recombinantly with known framework regions and/or other CDRs to create additional, recombinantly-engineered, Notch 3-binding antibodies of the disclosure, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the disclosure provides a method for preparing a Notch 3 antibody consisting of: a heavy chain variable region antibody sequence having a CDR1 sequence selected from the group consisting of SEQ ID NOs: 3, 23, 43, 63, 83, 103, 123, 143, 163, 183, and 203; a CDR2 sequence selected from the group consisting of SEQ ID NOs: 4, 24, 44, 64, 84, 104, 124, 144, 164, 184, and 204; and/or a CDR3 sequence selected from the group consisting of SEQ ID NOs: 5, 25, 45, 65, 85, 105, 125, 145, 165, 185, and 205; and a light chain variable region antibody sequence having a CDR1 sequence selected from the group consisting of SEQ ID NOs: 13, 33, 53, 73, 93, 113, 133, 153, 173, 193, and 213; a CDR2 sequence selected from the group consisting of SEQ ID NOs: 14, 34, 54, 74, 94, 114, 134, 154, 174, 194, and 214; and/or a CDR3 sequence selected from the group consisting of SEQ ID NOs:15, 35, 55, 75, 95, 115, 135, 155, 175, 195, and 215; altering at least one amino acid residue within the heavy chain variable region antibody sequence and/or the light chain variable region antibody sequence to create at least one altered antibody sequence; and expressing the altered antibody sequence as a protein. The altered antibody sequence can also be prepared by screening antibody libraries having fixed CDR3 sequences or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the Notch 3-binding antibodies described herein, which functional properties include, but are not limited to, specifically binding to human and/or cynomolgus Notch 3; the antibody binds to Notch 3 and neutralizes Notch 3 biological activity by inhibiting the Notch 3 signaling activity in a reporter assay described herein.

The functional properties of the altered antibodies can be assessed using standard assays available in the art and/or described herein, such as those set forth in the Examples (e.g., ELISAs).

In certain embodiments of the methods of engineering antibodies of the disclosure, mutations can be introduced randomly or selectively along all or part of an Notch 3 antibody coding sequence and the resulting modified Notch 3-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Characterization of the Antibodies

The antibodies can be characterized by various functional assays. For example, they can be characterized by their ability to neutralize biological activity by inhibiting Notch 3 signaling using gene reporter assays as described herein, their affinity to a Notch 3 protein (e.g., human and/or cynomolgus Notch 3), the epitope binning, their resistance to proteolysis, and their ability to block Notch 3 downstream signaling. Various methods can be used to measure Notch 3-mediated signaling. For example, the Notch 3 signaling pathway can be monitored by measurement of ICD3.

The ability of an antibody to bind to Notch 3 can be detected by labelling the antibody of interest directly, or the antibody may be unlabelled and binding detected indirectly using various sandwich assay formats known in the art.

In some embodiments, the Notch 3 antibodies block or compete with binding of a reference Notch 3 antibody to a Notch 3 polypeptide or protein. These can be fully human Notch 3 antibodies described above. They can also be other mouse, chimeric or humanized Notch 3 antibodies which bind to the same epitope as the reference antibody. The capacity to block or compete with the reference antibody binding indicates that a Notch 3 antibody under test binds to the same or similar epitope as that defined by the reference antibody, or to an epitope which is sufficiently proximal to the epitope bound by the reference Notch 3 antibody. Such antibodies are especially likely to share the advantageous properties identified for the reference antibody. The capacity to block or compete with the reference antibody may be determined by, e.g., a competition binding assay. With a competition binding assay, the antibody under test is examined for ability to inhibit specific binding of the reference antibody to a common antigen, such as a Notch 3 polypeptide or protein. A test antibody competes with the reference antibody for specific binding to the antigen if an excess of the test antibody substantially inhibits binding of the reference antibody. Substantial inhibition means that the test antibody reduces specific binding of the reference antibody usually by at least 10%, 25%, 50%, 75%, or 90%.

There are a number of known competition binding assays that can be used to assess competition of a Notch 3 antibody with the reference Notch 3 antibody for binding to a Notch 3 protein. These include, e.g., solid phase direct or indirect radioimmunoassay (RIA), solid phase direct or indirect enzyme immunoassay (EIA), sandwich competition assay (see Stahli et al., (1983) Methods in Enzymology 9:242-253); solid phase direct biotin-avidin EIA (see Kirkland et al., (1986) J. Immunol. 137:3614-3619); solid phase direct labeled assay, solid phase direct labeled sandwich assay (see Harlow & Lane, supra); solid phase direct label RIA using I-125 label (see Morel et al., (1988) Molec. Immunol. 25:7-15); solid phase direct biotin-avidin EIA (Cheung et al., (1990) Virology 176:546-552); and direct labeled RIA (Moldenhauer et al., (1990) Scand. J. Immunol. 32:77-82). Typically, such an assay involves the use of purified antigen bound to a solid surface or cells bearing either of these, an unlabelled test Notch 3 antibody and a labelled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

To determine if the selected Notch 3 monoclonal antibodies bind to unique epitopes, each antibody can be biotinylated using commercially available reagents (e.g., reagents from Pierce, Rockford, Ill.). Competition studies using unlabeled monoclonal antibodies and biotinylated monoclonal antibodies can be performed using a Notch 3 polypeptide coated-ELISA plates. Biotinylated mAb binding can be detected with a strep-avidin-alkaline phosphatase probe. To determine the isotype of a purified Notch 3 antibody, isotype ELISAs can be performed. For example, wells of microtiter plates can be coated with 1 µg/ml of anti-human IgG overnight at 4° C. After blocking with 1% BSA, the plates are reacted with 1 µg/ml or less of the monoclonal Notch 3 antibody or purified isotype controls, at ambient temperature for one to two hours. The wells can then be reacted with either human IgG1 or human IgM-specific alkaline phosphatase-conjugated probes. Plates are then developed and analyzed so that the isotype of the purified antibody can be determined.

To demonstrate binding of monoclonal Notch 3 antibodies to live cells expressing a Notch 3 polypeptide, flow cytometry can be used. Briefly, cell lines expressing Notch 3 (grown under standard growth conditions) can be mixed with various concentrations of a Notch 3 antibody in PBS containing 0.1% BSA and 10% fetal calf serum, and incubated at 4° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Notch 3 antibodies can be further tested for reactivity with a Notch 3 polypeptide or antigenic fragment by Western blotting. Briefly, purified Notch 3 polypeptides or fusion proteins, or cell extracts from cells expressing Notch 3 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

A number of readouts can be used to assess the efficacy, and specificity, of Notch 3 antibodies in cell-based assays such as those described herein (e.g., ICD3 assay). Examples of functional assays are also described in the Example section below.

The ability of antibodies or fragments thereof to block in vivo growth of tumor xenografts of human tumor cell lines whose tumorigenic phenotype as shown herein is at least partly dependent on Notch 3 cell signaling, and can be assessed in immunocompromised mice either alone or in combination with an appropriate cytotoxic agent for the cell line in question.

Prophylactic and Therapeutic Uses

The present disclosure provides methods of treating a disease or disorder associated with the Notch 3 signaling pathway by administering to a subject in need thereof an effective amount of the antibodies of the disclosure. In a specific embodiment, the present disclosure provides a method of treating or preventing cancers (e.g., breast cancer, colorectal cancer, lung cancer, multiple myeloma, ovarian cancer, liver cancer, gastric cancer, pancreatic cancer, prostate cancer, acute myeloid leukemia, chronic myeloid leukemia, t-cell acute lymphoblastic leukemia, mantle cell lymphoma, chronic lymphocytic leukemia, Ewing's sarcoma, osteosarcoma, squamous cell carcinoma, peripheral nerve sheath tumors, schwannoma, head and neck cancer, bladder cancer, esophageal cancer, glioblastoma, clear cell sarcoma of soft tissue, malignant mesothelioma, neurofibromatosis, renal cancer and melanoma) by administering to a subject in need thereof an effective amount of the antibodies of the disclosure. In some embodiments, the present disclosure provides methods of treating or preventing cancers associated with a Notch 3 signaling pathway by administering to a subject in need thereof an effective amount of the antibodies of the disclosure.

In a specific embodiment, the present disclosure provides methods of treating cancers associated with a Notch 3 signaling pathway that include, but are not limited to breast cancer, lung cancer, and T-cell acute lymphoblastic leukemia (TALL).

Notch 3 antibodies can also be used to treat or prevent other disorders associated with aberrant or defective Notch 3 signaling, including but are not limited to respiratory diseases, osteoporosis, osteoarthritis, polycystic kidney disease, diabetes, schizophrenia, vascular disease, cardiac disease, non-oncogenic proliferative diseases, fibrosis, and neurodegenerative diseases such as Alzheimer's disease.

Suitable agents for combination treatment with Notch 3 antibodies include standard of care agents known in the art that are able to modulate the Notch signaling pathway. Suitable examples of standard of care agents for Notch 3 include, but are not limited to EGFR inhibitors or platinum based chemotherapy. Other agents that may be suitable for combination treatment with Notch 3 antibodies include, but are not limited to those that modulate receptor tyrosine kinases, G-protein coupled receptors, growth/survival signal transduction pathways, nuclear hormone receptors, apoptotic pathways, cell cycle and angiogenesis.

Diagnostic Uses

In one aspect, the disclosure encompasses diagnostic assays for determining Notch 3 protein and/or nucleic acid expression as well as Notch 3 protein function, in the context of a biological sample (e.g., blood, serum, cells, tissue) or from individual afflicted with cancer, or is at risk of developing cancer.

The present disclosure provides methods for identifying a disease or disorder associated with the Notch 3 signaling pathway by administering to a subject in need thereof an effective amount of the antibodies of the disclosure. In a specific embodiment, the present disclosure provides a method of treating or preventing cancers (e.g., breast cancer, colorectal cancer, lung cancer, multiple myeloma, ovarian cancer, liver cancer, gastric cancer, pancreatic cancer, prostate cancer, acute myeloid leukemia, chronic myeloid leukemia, t-cell acute lymphoblastic leukemia, mantle cell lymphoma, chronic lymphocytic leukemia, Ewing's sarcoma, osteosarcoma, squamous cell carcinoma, peripheral nerve sheath tumors, schwannoma, head and neck cancer, bladder cancer, esophageal cancer, glioblastoma, clear cell sarcoma of soft tissue, malignant mesothelioma, neurofibromatosis, renal cancer and melanoma) by administering to a subject in need thereof an effective amount of the antibodies of the disclosure. In some embodiments, the present disclosure provides methods of treating or preventing cancers associated with a Notch 3 signaling pathway by administering to a subject in need thereof an effective amount of the antibodies of the disclosure.

In a specific embodiment, the present disclosure provides methods for identifying cancers associated with a Notch 3 signaling pathway that include, but are not limited to breast cancer, lung cancer, and T-cell acute lymphoblastic leukemia (TALL).

The detection of Notch 3 mutations can be done by any number of ways, for example: DNA sequencing, PCR based methods, including RT-PCR, microarray analysis, Southern blotting, and Northern blotting and dip stick analysis.

The polymerase chain reaction (PCR) can be used to amplify and identify Notch 4 mutations from either genomic DNA or RNA extracted from tumor tissue. PCR is well known in the art and is described in detail in Saiki et al., Science 1988, 239:487 and in U.S. Pat. Nos. 4,683,195 and 4,683,203.

Detection of gene expression can be by any appropriate method, including for example, detecting the quantity of mRNA transcribed from the gene or the quantity of cDNA produced from the reverse transcription of the mRNA transcribed from the gene or the quantity of the polypeptide or protein encoded by the gene. These methods can be performed on a sample by sample basis or modified for high throughput analysis. For example, using Affymetrix™ microarray chips.

In one aspect, gene expression is detected and quantitated by hybridization to a probe that specifically hybridizes to the appropriate probe for that biomarker. The probes also can be attached to a solid support for use in high throughput screening assays using methods known in the art. WO 97/10365 and U.S. Pat. Nos. 5,405,783, 5,412,087 and 5,445,934, for example, disclose the construction of high density oligonucleotide chips which can contain one or more of the sequences disclosed herein. Using the methods disclosed in U.S. Pat. Nos. 5,405,783, 5,412,087 and 5,445,934, the probes of this invention are synthesized on a derivatized glass surface. Photoprotected nucleoside phosporamidites are coupled to the glass surface, selectively deprotected by photolysis through a photolithographic mask, and reacted with a second protected nucleoside phosphoramidite. The coupling/deprotection process is repeated until the desired probe is complete.

Alternatively any one of gene copy number, transcription, or translation can be determined using known techniques. For example, an amplification method such as PCR may be useful. General procedures for PCR are taught in MacPherson et al., PCR: A Practical Approach, (IRL Press at Oxford University Press (1991)). However, PCR conditions used for each application reaction are empirically determined. A number of parameters influence the success of a reaction. Among them are annealing temperature and time, extension time, Mg 2+ and/or ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination.

In one embodiment, the hybridized nucleic acids are detected by detecting one or more labels attached to the sample nucleic acids. The labels can be incorporated by any of a number of means well known to those of skill in the art. However, in one aspect, the label is simultaneously incorporated during the amplification step in the preparation of the sample nucleic acid. Thus, for example, polymerase chain reaction (PCR) with labelled primers or labelled nucleotides will provide a labelled amplification product. In a separate embodiment, transcription amplification, as described above, using a labelled nucleotide (e.g. fluorescein-labelled UTP and/or CTP) incorporates a label in to the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g. with a labelled RNA) by kinasing of the nucleic acid and subsequent attachment (ligation) of a nucleic acid linker joining the sample nucleic acid to a label (e.g., a fluorophore).

Detectable labels suitable for use in the present disclosure include any composition detectable by spectroscopic, photochemical, biochemical, immunochemical, electrical, optical or chemical means. Useful labels in the present invention include biotin for staining with labelled streptavidin conjugate, magnetic beads (e.g., Dynabeads™), fluorescent dyes (e.g., fluorescein, texas red, rhodamine, green fluorescent protein, and the like), radiolabels (e.g., $3^H$, $125^I$, $35^S$, $14^C$, or $32^P$) enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Detection of labels is well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the coloured label.

The detectable label may be added to the target (sample) nucleic acid(s) prior to, or after the hybridization, such as described in WO 97/10365. These detectable labels are directly attached to or incorporated into the target (sample) nucleic acid prior to hybridization. In contrast, "indirect labels" are joined to the hybrid duplex after hybridization. Generally, the indirect label is attached to a binding moiety that has been attached to the target nucleic acid prior to the hybridization. For example, the target nucleic acid may be biotinylated before the hybridization. After hybridization, an avidin-conjugated fluorophore will bind the biotin bearing hybrid duplexes providing a label that is easily detected. For a detailed review of methods of labelling nucleic acids and detecting labelled hybridized nucleic acids see Laboratory Techniques in Biochemistry and Molecular Biology, Vol. 24: Hybridization with Nucleic Acid Probes, P. Tijssen, ed. Elsevier, N.Y. (1993).

Notch 3 mutations when translated into proteins can be detected by specific antibodies. Expression level of Notch 3 mutations can also be determined by examining protein expression or the protein product of Notch 3 mutants. Determining the protein level involves measuring the amount of any immunospecific binding that occurs between an antibody that selectively recognizes and binds to the polypeptide of the biomarker in a sample obtained from a patient and comparing this to the amount of immunospecific binding of at least one biomarker in a control sample. The amount of protein expression of the Notch 3 can be increased or reduced when compared with control expression.

Diagnostic assays, such as competitive assays rely on the ability of a labelled analogue (the "tracer") to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of analyte present in the test sample. These assays are called ELISA systems when enzymes are used as the detectable markers. In an assay of this form, competitive binding between antibodies and Notch 3 antibodies results in the bound Notch 3 protein, preferably the Notch 3 epitopes of the disclosure, being a measure of antibodies in the serum sample, most particularly, neutralizing antibodies in the serum sample.

A significant advantage of the assay is that measurement is made of neutralizing antibodies directly (i.e., those which interfere with binding of Notch 3 protein, specifically, epitopes). Such an assay, particularly in the form of an ELISA test has considerable applications in the clinical environment and in routine blood screening.

Assaying for Biomarkers

Another aspect of the disclosure provides methods for determining Notch 3 nucleic acid expression or Notch 3 protein activity in an individual to thereby select appropriate therapeutic or prophylactic agents for that individual (referred to herein as "pharmacogenomics"). Pharmacogenomics allows for the selection of agents (e.g., small molecule drugs or biologics such as antibodies or fragments thereof) for therapeutic or prophylactic treatment of an individual based on the genotype of the individual (e.g., the genotype of the individual examined to determine the ability of the individual to respond to a particular agent.)

Yet another aspect of the disclosure pertains to monitoring the influence of agents (e.g., small molecule drugs or biologics such as antibodies or fragments thereof) on the expression or activity of Notch 3 protein in clinical trials.

Once a patient has been assayed for Notch 3 mutation and predicted to be sensitive to a Notch 3 inhibitor (e.g., a small molecule inhibitor or a biologic such as a Notch 3 antibody or fragment thereof) administration of any Notch 3 inhibitor to a patient can be effected by dose, continuously or intermittently throughout the course of treatment. Suitable dosage formulations and methods of administering the agents may be empirically adjusted based on the presence and expression level of Notch 3 mutants.

Notch 3 mutations can be assayed for after Notch 3 inhibitor administration in order to determine if the patient remains sensitive to the Notch 3 treatment. In addition, Notch 3 mutations can be assayed for in multiple time points after a single Notch 3 inhibitor administration. For example, an initial bolus of a Notch 3 inhibitor is administered, a Notch 3 mutation can be assayed for at 1 hour, 2 hours, 3 hours, 4 hours, 8 hours, 16 hours, 24 hours, 48 hours, 3 days, 1 week or 1 month or several months after the first treatment.

The patient could undergo multiple Notch 3 inhibitor administrations and then assayed for Notch 3 mutations at different time points. For example, a course of treatment may require administration of an initial dose of Notch 3 inhibitor, a second dose a specified time period later, and still a third dose hours after the second dose. Notch 3 mutations can be assayed for at 1 hour, 2 hours, 3 hours, 4 hours, 8 hours, 16 hours, 24 hours, 48 hours, 3 days, 1 week or 1 month or several months after administration of each dose of the Notch 3 inhibitor.

Kits for assessing the activity of any Notch 3 inhibitor (e.g., antibody or fragment thereof) can be made. For example, a kit comprising nucleic acid primers for PCR or for microarray hybridization for a Notch 3 mutation can be used for assessing the presence of Notch 3 mutants. Alternatively, a kit supplied with antibodies or fragments thereof for the Notch 3 mutations listed in Table 2.

It is possible to use the Notch 3 mutations to screen for Notch 3 inhibitor. This method comprises providing for a cell containing a Notch 3 mutation from Table 2, contacting the cell with a candidate Notch 3 inhibitor (e.g., a small molecule or a biologic such as an antibody or fragment thereof, and comparing the $IC_{50}$ of the treated cell with a known Notch 3 inhibitor.

Pharmaceutical Compositions

To prepare pharmaceutical or sterile compositions including a Notch 3 antibodies or fragments thereof, the Notch 3 antibody or fragment thereof is mixed with a pharmaceutically acceptable carrier or excipient. The compositions can additionally contain one or more other therapeutic agents that are suitable for treating or preventing cancer (breast cancer, colorectal cancer, lung cancer, multiple myeloma, ovarian cancer, liver cancer, gastric cancer, pancreatic cancer, prostate cancer, acute myeloid leukemia, T-cell acute lymphoblastic leukemia, mantle cell lymphoma, chronic lymphocytic leukemia, Ewing's sarcoma, chronic myeloid leukemia, osteosarcoma, squamous cell carcinoma, peripheral nerve sheath tumors schwannoma, head and neck cancer, bladder cancer, esophageal cancer, glioblastoma, clear cell sarcoma of soft tissue, malignant mesothelioma, neurofibromatosis, renal cancer, and melanoma).

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al., (2003) New Engl. J. Med. 348:601-608; Milgrom et al., (1999) New Engl. J. Med. 341:1966-1973; Slamon et al., (2001) New Engl. J. Med. 344:783-792; Beniaminovitz et al., (2000) New Engl. J. Med. 342:613-619; Ghosh et al., (2003) New Engl. J. Med. 348:24-32; Lipsky et al., (2000) New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof can be provided by continuous infusion or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 25 mg/kg, or at least 50 mg/kg (see, e.g., Yang et al., (2003) New Engl. J. Med. 349:427-434; Herold et al., (2002) New Engl. J. Med. 346:1692-1698; Liu et al., (1999) J. Neurol. Neurosurg. Psych. 67:451-456; Portielji et al., (2003) Cancer Immunol. Immunother. 52:133-144). The desired dose of antibodies or fragments thereof is about the same as for an antibody or polypeptide, on a moles/kg body weight basis. The desired plasma concentration of the antibodies or fragments thereof is about, on a moles/kg body weight basis. The dose may be at least 15 µg at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more.

For antibodies or fragments thereof of the disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the antibodies or fragments thereof may be calculated using the patient's weight in kilograms (kg) multiplied by the dose to be administered in mg/kg. The dosage of the antibodies or fragments thereof may be 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of a patient's body weight.

Unit dose of the antibodies or fragments thereof may be 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the antibodies or fragments thereof may achieve a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in a subject. Alternatively, the dosage of the antibodies or fragments thereof may achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in the subject.

Doses of antibodies or fragments thereof may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side effects (see, e.g., Maynard et al., (1996) A Handbook of SOPs for Good Clinical Practice, Interpharm Press, Boca Raton, Fla.; Dent (2001) Good Laboratory and Good Clinical Practice, Urch Publ., London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., (1983) Biopolymers 22:547-556; Langer et al., (1981) J. Biomed. Mater. Res. 15:167-277; Langer (1982) Chem. Tech. 12:98-105; Epstein et al., (1985) Proc. Natl. Acad. Sci. USA 82:3688-3692; Hwang et al., (1980) Proc. Natl. Acad. Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985, 320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present disclosure may also be administered via one or more routes of administration using one or more of a variety of methods known in the art. As will be appreciated by the skilled artisan, the route and/or mode of administration will vary depending upon the desired results. Selected routes of administration for antibodies or fragments thereof include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition can be administered via a non-parenteral route, such as a topical, epidermal or mucosal route of administration, for example, intranasally, orally, vaginally, rectally, sublingually or topically. In one embodiment, the antibodies or fragments thereof is administered by infusion. In another embodiment, the multispecific epitope binding protein is administered subcutaneously.

If the antibodies or fragments thereof are administered in a controlled release or sustained release system, a pump may be used to achieve controlled or sustained release (see Langer, supra; Sefton, (1987) CRC Crit. Ref Biomed. Eng. 14:20; Buchwald et al., (1980), Surgery 88:507; Saudek et al., (1989) N. Engl. J. Med. 321:574). Polymeric materials can be used to achieve controlled or sustained release of the therapies (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, (1983) J. Macromol. Sci. Rev. Macromol. Chem. 23:61; see also Levy et al., (1985) Science 228:190; During et al., (1989) Ann. Neurol. 25:351; Howard et al., (1989) J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer, (1990), Science 249:1527-1533). Any technique known to one of skill in the art can be used to produce sustained release formulations comprising one or more antibodies or fragments thereof of the disclosure. See, e.g., U.S. Pat. No. 4,526,938, PCT publication WO 91/05548, PCT publication WO 96/20698, Ning et al., (1996), Radiotherapy & Oncology 39:179-189, Song et al., (1995) PDA Journal of Pharmaceutical Science & Technology 50:372-397, Cleek et al., (1997) Pro. Int'l. Symp. Control. Rel. Bioact. Mater. 24:853-854, and Lam et al., (1997) Proc. Int'l. Symp. Control Rel. Bioact. Mater. 24:759-760, each of which is incorporated herein by reference in their entirety.

If the antibodies or fragments thereof are administered topically, they can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as Freon) or in a squeeze bottle. Moisturizers or humectants can also be added to pharmaceutical compositions and dosage forms if desired. Examples of such additional ingredients are well-known in the art.

If the compositions comprising antibodies or fragments thereof are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the antibodies or fragments thereof may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies or fragments thereof of the disclosure. The two or more therapies may be administered within one same patient visit.

The antibodies or fragments thereof and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the antibodies or fragments thereof can be formulated to ensure proper distribution in vivo. For example, the blood-brain barrier (BBB) excludes many highly hydrophilic compounds. To ensure that the therapeutic compounds cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al); mannosides (Umezawa et al., (1988) Biochem. Biophys. Res. Commun. 153:1038); antibodies (Bloeman et al. (1995) FEBS Lett. 357:140; Owais et al., (1995) Antimicrob. Agents Chemother. 39:180); surfactant protein A receptor (Briscoe et al. (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The disclosure provides protocols for the administration of pharmaceutical composition comprising antibodies or fragments thereof alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof are administered to a subject in a sequence and within a time interval such that the antibodies can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

The disclosure having been fully described, it is further illustrated by the following examples and claims, which are illustrative and are not meant to be further limiting.

ICD3 Assay and Uses Thereof

In one aspect, the disclosure pertains to an assay for detecting Notch 3 signal transduction. Notch signaling is activated by a series of proteolytic cleavages. The gamma secretase complex mediates the final cleavage of the Notch receptor ultimately releasing the Notch intracellular domain (ICD) that translocates to the nucleus to activate Notch target gene transcription. A neoepitope antibody (detection antibody) was generated to detect the gamma secretase cleaved form of the Notch3 ICD (ICD3) only when cleaved between amino acids Gly 1661 and Val 1662 of human Notch 3.

The assay comprises using a detection antibody that detects a neoepitope VMVARRK (SEQ ID NO: 243) in the gamma secretase cleaved domain of Notch 3 (ICD3). The ICD3 can be produced by cleavage at positions Gly 1661-Val 1662 of either wild type Notch 3 or mutant Notch 3.

Detection of the ICD3 by the assay disclosed herein indicates Notch 3 signal activation and transduction. An antibody or fragment thereof that prevents Notch 3 signal activation and transduction prevents the production of ICD3, and thereby detection of the neoepitope contained therein by the detection antibody. In one embodiment, the antibody or fragment thereof holds the Notch 3 in an autoinhibited conformation, thereby precluding exposure of the S2, and S3 cleavage sites to proteases, thereby preventing the formation of ICD3 comprising the neoepitope recognized by the detection antibody.

In one aspect, the disclosure encompasses diagnostic assays for determining Notch 3 protein and/or nucleic acid expression as well as Notch 3 protein function, in the context of a biological sample (e.g., blood, serum, cells, tissue) or from individual afflicted with cancer, or is at risk of developing cancer.

The ICD3 assay can be used to detect the presence of activated Notch3 signaling. Activation of Notch3 signaling may be achieved by Notch 3 mutations or high Notch3 expression/gene amplification. A biological sample may be prepared and analyzed for the presence or absence of ICD3 protein. If the Notch 3 ICD is present, the NRR domain may contain a mutation that results in the autoinhibited conformation of the NRR being altered thereby exposing the HD domain to protease cleavage and the production of the ICD3, which can be detected by the detecting antibody of the disclosure. Results of these tests and interpretive information can be returned to the health care provider for communication to the tested individual. Such diagnoses may be performed by diagnostic laboratories, or, alternatively, diagnostic kits can manufactured and sold to health care providers or to private individuals for self-diagnosis.

Another aspect of the disclosure provides methods for determining Notch 3 nucleic acid expression or Notch 3 protein activity in an individual to thereby select appropriate therapeutic or prophylactic agents for that individual (referred to herein as "pharmacogenomics"). Pharmacogenomics allows for the selection of agents (e.g., small molecule drugs or biologics such as antibodies or fragments thereof) for therapeutic or prophylactic treatment of an individual based on the genotype of the individual (e.g., the genotype of the individual examined to determine the ability of the individual to respond to a particular agent.)

Yet another aspect of the disclosure pertains to monitoring the influence of agents (e.g., small molecule drugs or biologics such as antibodies or fragments thereof) on the expression or activity of Notch 3 protein in clinical trials.

EXAMPLES

Example 1: Cloning of Cynomolgus Monkey Notch3

As the sequence of cynomolgus monkey Notch3 was not available in public data bases, it was cloned as follows:
Cynomolgus Total RNA All total RNAs were purchased from Zyagen (http://zyagen.com/index.php), San Diego, Calif. 92121). Total RNAs were extracted from various tissues (brain, kidney, liver, lung, skeletal muscle, pancreas, spleen, skin, stomach, testis, thymus, thyroid, bone marrow) of cynomolgus monkeys. Origin and individual monkey's references were not specified by Zyagen. Total RNA was routinely extracted from tissues/cells using the guanidine isothiocyanate-phenol: chloroform extraction method which allows the rapid isolation of total RNA including microRNA. RNA was treated with RNase-free DNase to remove residual DNA, precisely quantified, and stored at −80° C. The integrity of each RNA sample, as indicated by intact ribosomal RNA, was verified by denatured agarose gel electrophoresis. The purity of RNA was assessed by spectrophotometer (A260/A280: 1.9-2.1). RNA was ideal for Northern blotting, ribonuclease protection assay, SI nuclease assay, RT-PCR/Q-PCR analysis, rapid amplification of cDNA ends (RACE) and purification of mRNA for library construction. Total RNA was provided in RNase-free water, 1 mM sodium citrate, or 0.1 mM EDTA at a concentration of 1 mg/ml and shipped on dry ice. After receipt all Total RNAs samples are stored at −80° C.

Reverse Transcription of RNA to cDNA and PCR Amplification

All Total RNAs were reverse transcribed using the Thermo Script RT-PCR System (Invitrogen, Cat. 11146-016) and oligodT. 2 µg of Total RNA was generally used for each cDNA pool and was eluted in 20 µl. 1 µl primer (50 µM Oligo (dT20), 2 µg (tissue). Total RNA and 2 µl 10 mM dNTPs mix were combined and the volume adjusted to 12 µl with DEPC-treated water. After incubation at 65° C. for 5 min, a master mix of 4 µl 5× cDNA Synthesis buffer, 1 µl of 0.1 M DTT, 1 µl RNaseOUT™ (40 U/µl), 1 µl DEPC-treated water and 1 µl ThermoScript™ RT (15 units/ul) was prepared and the 8 µl total volume was added to each previous reaction tube on ice. The reverse transcription phase of the total RNA sample was completed in 90 minutes at 55° C. This reaction was then stopped by incubating the whole reaction at 85° C. for five minutes. At last, 1 µl of RNase H was added and the samples were incubated at 37° C. for 20 minutes. The cDNA reactions were stored at −20° C. as base material for all polymerase chain reactions.

PCR amplifications were performed using 2 µl of cDNA. Primers were designed in the UTR regions and in the coding sequences. PCR products were directly gel extracted and analyzed by direct sequencing.

PCR Primers for Cynomolgus Notch3 Gene Fishing

The target sequences of non-human primates for example gorilla, orangutan, and rhesus were aligned to human sequence for primer design and specificity testing. Mouse and rat sequences of the target sequences may also be required. The target sequences for the alignment can be extracted from databases like NCBI, eEnsembl or UniProt.

| Primers | | Sequences |
|---|---|---|
| RS4242 | UTR Fw | 5'-CGGAGCCCAGGGAAGGAGGGAGGAGGGGAGG GTCGCGGCCGGCCGCC-3' (SEQ ID NO: 244) |
| RS4243 | UTR Rev | 5'-CAGGACGGGGGTCTCTTTAGGCCCCCAAGATC TAAGAACTGACGAGCGTCTCA-3' (SEQ ID NO: 245) |
| RS4244 FW | CDS1825bp | 5'-CCATGGCGGCAAATGCCTAGACCTGGTGG-3' (SEQ ID NO: 246) |
| RS4245 Rev | CDS 1999bp | 5'-CAAAGGGGCCCTGTGAAGCCAGGTTGGCAGA CACAGTCG-3' (SEQ ID NO: 247) |
| RS4246 Fw | CDS 4384bp | 5'-CTTCAACAACAGCCGCTGCGACCCCGCCTGCA GCTCG-3' (SEQ ID NO: 248) |
| RS4247 Rev | CDS 4560bp | 5'-CAGCCGCACTCCTCCGTGTTGCAGCCCTGGTC G-3' (SEQ ID NO: 249) |

| Primers | Sequences |
|---|---|
| RS4277 CDS 1137bp Rev | 5'-GTCACAGATAGCATCCTCGTGGCAGGGGTTGCTGACACAGG-3' (SEQ ID NO: 250) |
| RS4278 CDS 821bp Fw | 5'-GGGACATGCGTGGATGGCGTCAACACCTATAACTGCCAGTGCCC-3' (SEQ ID NO: 251) |
| RS4279 CDS 3136bp Rev | 5'-GGCCCCAGTCTGGACGCAGCGACCCCCGTTTTGACAAGGC-3' (SEQ ID NO: 252) |
| RS4280 CDS 2905bp Fw | 5'-GAACTCGTTCAGCTGCCTGTGCCGTCCCGGCTACACAGGAGCCCACTGC-3' (SEQ ID NO: 253) |
| RS4281 CDS 5692bp Rev | 5'-GCCTGAGTGGTCCTGGGCATTGGTGTCTGCCCCAGCATCC-3' (SEQ ID NO: 254) |
| RS4282 cds5501bp Fw | 5'-GAAGAGGATGAGGCAGATGACACATCAGCTAGCATCATCTCC-3' (SEQ ID NO: 255) |
| RS4302 CDS 3091bp Fw | 5'-TCACTGTGCCCAGCCGTTCT-3' (SEQ ID NO: 256) |
| RS4303 CDS 4147bp Fw | 5'-CTTCTTCCGCTGCGCTTGCGCGCAG-3' (SEQ ID NO: 257) |
| RS4304 CDS 5046bp Rev | 5'-ATGACCAGCAGCAAGACAGCGC-3' (SEQ ID NO: 258) |
| RS4305 CDS 5100bp Rev | 5'-CAGAGGGTGCTGTGCTCGCGCTTG-3' (SEQ ID NO: 259) |
| RS4306 CDS 3901bp Fw | 5'-ACAGTGCTGCTGCCGCCAGAGGAGCTAC-3' (SEQ ID NO: 260) |
| RS4361 CDS Seq. Fw | 5'-CAGTCCCAGGACATGGCGAGGAGTAC-3' (SEQ ID NO: 261) |
| RS4362 UTR Fw | 5'-AGCCCAGGGAAGGAGGGAGGAGGGGAGGGTCG-3' (SEQ ID NO: 262) |
| RS4363 CDS 861bp Rev | 5'-ACTGGCAGTTATAGGTGTTGACGCCATCCACGC-3' (SEQ ID NO: 263) |
| RS4364 CDS 1950bp Rev | 5'-GCACAGTCGTCAATGTTCACTTCGCAG-3' (SEQ ID NO: 264) |
| RS4365 CDS 2822bp Fw | 5'-TACGGAGGCTTCCACTGCGAACAG-3' (SEQ ID NO: 265) |
| RS4366 CDS 4067bp Rev | 5'-CGACCCCGAGAAACTGCGGCAGGAG-3' (SEQ ID NO: 266) |
| RS4367 UTR Rev | 5'-CCCCAAGATCTAAGAACTGACGAGC-3' (SEQ ID NO: 267) |

PCR and Gel Purification

PCR of the cDNA was achieved by the Corbett® Rotor-Gene 6000 (now QIAGEN® Rotor-Gene Q) RT-PCR using KAPA™ SYBR® FAST Master Mix (2X). The KAPA™ SYBR® FAST qPCR Master Mix (2X) Universal, a ready-to-use cocktail containing antibody-mediated hot start, SYBR® Green I fluorescent dye, MgCl2, dNTPs and stabilizers for the amplification and detection of DNA in qPCR (KAPABIOSYSTEMS). For PCR, a reaction mix with a volume of 20 μl, consisting of 10 μl SYBR® green, 0.4 μl forward-primer (10 μM), 0.4 μl reverse-primer (10 μM), 2 μl template and 7.2 μl H$_2$O RNase-free was prepared to each 0.1 ml PCR tube and the tubes closed by caps. The PCR cycling was preceded by a hold temperature of 95° C. for five minutes and the cycling steps were repeated 45 times. The denaturation consisted of heating the reaction to a temperature of 95° C. for ten seconds. After that step the temperature was reduced to 60° C. for 30 seconds, allowing annealing of the primers to the single-stranded DNA template. The elongation was obtained by increasing temperature to 72° C. for 30 seconds and the cycling steps were repeated. All PCR products were then loaded on a 1×TBE agarose gel, 1%, PCR fragment size and gel extracted and stained with Ethidium Bromide (3×10⁻³ mg/ml).

Then gel extractions of target DNA fragments were then performed. In this case, a procedure based on the QIAquick® Gel Extraction Kit protocol in combination with a NucleoSpin® 8/96 Extract II by MACHEREY-NAGEL® was used to purify the DNA fragment. For the extraction of the PCR DNA fragment, 400 µl QG solubilization buffer of QIAGEN® were added to each piece of gel band in a 96-well plate. To melt down the gel bands, the Deep well plate was placed into hot water bath (50 to 60° C.) for about 15 minutes. Before pipetting the solution onto the NucleoSpin® 8/96 Extract II filter plate, the solution was vortexed carefully. An additional 100 µl of Isopropanol was used if the DNA bands were lower than 400 bp. The solution was filtrated two times. After this step, the column was washed by 650 µl wash buffer NT3 two times and then dried by placing it under vacuum for 20 minutes before elution of DNA fragment with RNase-free water. For that the collection-reservoir below the NucleoSpin® 8/96 Extract II filter plate was replaced by an elution plate "U-bottom" and 100 µl of RNase-free water was added directly onto the middle of membrane without touching it. The extraction of DNA was achieved by the usage of vacuum filtration and the eluate could finally be used for sequencing.

Sequencing and Data Analysis

For sequencing purified DNA fragment, 8 µl of purified PCR sample was mixed with 4 µl H₂O RNase-free and 1 µl forward or 1 µl reversed primer (10 µM). The sequencing of the PCR fragments was completed with the Sanger method in combination with an Applied Biosystems® ABI 3730xl DNA Analyzer. The DNA sequence reads were imported to the program, trimmed and then assembled to a reference, in this case the sequence of the human gene. The sequence of the corresponding gene was directly copied from Ensembl or Swiss-Prot genome database browser into Vector NTI®. The use of the reference sequences allowed identification of full-length sequences.

Cynomolgus monkey Notch3 sequence. Three natural SNPs were identified at positions: 213S/N; 719E/D; and 2053V/A.

(SEQ ID NO: 268)
MGPGARGRRRRRPMSPPPPPVRALPLLLLLAGPGAAVPPCLDGSPCANG

GRCTQLPSREAACLCPPGWVGERCQLEDPCHSGPCAGRGVCQSSVVAGTA

RFSCRCPRGFRGPDCSLPDPCLSSPCAHSARCSVGPDGRFLCSCPPGYQG

RSCRSDVDECRVGEPCRHGGTCLNTPGSFRCQCPAGYTGPLCENPAVPCA

PSPCRNGGTCRQSSGDLTYDCACLPGFEGQNCEVNVDDCPGHRCLNGGTC

VDGVNTYNCQCPPEWTGQFCTEDVDECQLQPNACHNGGTCFNTLGGHSCV

CVNGWTGESCSQNIDDCATAVCFHGATCHDRVASFYCACPMGKTGLLCHL

DDACVSNPCHEDAICDTNPVNGRAICTCPPGFTGGACDQDVDECSIGANP

CEHLGRCVNTQGSFLCQCGRGYTGPRCETDVNECLSGPCRNQATCLDRIG

QFTCICMAGFTGTYCEVDIDECQSSPCVNGGICKDRVNGFSCTCPSGFSG

STCQLDVDECASTPCRNGAKCVDQPDGYECRCAEGFEGMLCERNVDDCSP

DPCHHGRCVDGIASFSCACAPGYTGTRCESQVDECRSQPCRHGGKCLDLV

DKYLCRCPSGTTGVNCEVNIDDCASNPCSFGVCRDGINRYDCVCQPGFTG

PLCNVEINECASSPCGEGGSCVDGENGFRCLCPPGSLPPLCLPPSHPCAH

EPCSHGICYDAPGGFRCVCEPGWSGPRCSQSLARDACESQPCRAGGTCSS

DGMGFHCTCPPGVQGRQCELLSPCTPNPCEHGGRCESAPGQLPVCSCPQG

WQGPRCQQDVDECAGPAPCGPHGICTNLAGSFSCTCHGGYTGPSCDQDIN

DCDPNPCLNGGSCQDGVGSFSCSCLLGFAGPRCARDVDECLSNPCGPGTC

TDHVASFTCTCPPGYGGFHCEQDLPDCSPSSCFNGGTCVDGVNSFSCLCR

PGYTGAHCQHEADPCLSRPCLHGGVCSAAHPGFRCTCPQSFTGPQCQTLV

DWCSRQPCQNGGRCVQTGAYCLCPPGWSGRLCDIRSLPCREAAAQIGVRL

EQLCQAGGQCVDEDSSHYCVCPEGRTGSHCEQEVDPCLAQPCQHGGTCRG

YMGGYMCECLPGYNGENCEDDVDECASQPCQHGGSCIDLVARYLCSCPPG

TLGVLCEINEDDCGPGPPLDSGPRCLHNGTCVDLVGGFRCTCPPGYTGLR

CEADINECRSGACHAAHTRDCLQDPGGGFRCLCHAGFSGPRCQTVLSPCE

SQPCQHGGQCRPSPGPGGGLTFTCHCAQPFWGPRCERVARSCRELQCPVG

VPCQQTPRGPRCACPPGLSGPSCRSFSGSPPGASNASCAAAPCLHGGSCR

PAPLAPFFRCACAQGWTGPRCEAPAAAPEVSEEPRCPRAACQAKRGDQRC

DRECNSPGCGWDGGDCSLSVGDPWRQCEALQCWRLFNNSRCDPACSSPAC

LYDNFDCHAGGRERTCNPVYEKYCADHFADGRCDQGCNTEECGWDGLDCA

SEVPALLARGVLVLTVLLPPEELLRSSADFLQRLSAILRTSLRFRLDAHG

QAMVFPYHRPSPGSEPRARRELAPEVIGSVVMLEIDNRLCLQSPENDHCF

PDAQSAADYLGALSAVERLDFPYPLRDVRGEPLEPPEPSVPLLPLLVAGA

VLLLVILVLGVMVARRKREHSTLWFPEGFSLHKDVAAGHKGRREPVGQDA

LGMKNMAKGESLMGEVATDWMDTECPEAKRLKVEELGMGAEEAVDCRQWT

QHHLVAADIRVAPAMALTPPQGDADADGMDVNVRGPDGFTPLMLASFCGG

ALEPMPTEEDEADDTSASIISDLICQGAQLGARTDRTGETALHLAARYAR

ADAAKRLLDAGADTNAQDHSGRTPLHTAVTADAQGVFQILIRNRSTDLDA

RMADGSTALILAARLAVEGMVEELIASHADVNAVDELGKSALHWAAAVNN

VEATLALLKNGANKDMQDSKEETPLFLAAREGSYEAAKLLLDHFANREIT

DHLDRLPRDVAQERLHQDIVRLLDQPSGPRSPPGTHGLGPLLCPPGAFLP

GLKVVTQSGSKKSRRPPGKAGLGPQGPRGRGKKLTLACPGPLADSSVTLS

PVDSLDSPRPFGGPPASPGGFPLEGPYAAATATAVSLAQLGGPGRAGLGR

QPPGGCVLSLGLLNPVAVPLDWARLPPPAPPGPSFLLPLAPGPQLLNPGT

PVSPQERPPPYLAVPGHGEEYPAAGAHSSPPKARFLRVPSEHPYLTPSPE

SPEHWASPSPPSLSDWSESTPSPATATGAMATATGALPAQPLPLSVPSSL

AQAQTQLGPQPEVTPKRQVLA.

Example 2: Screening for Notch3 Antibodies and Evaluation of Protein/Cell Binding For selection of antibodies recognizing human Notch 3, several recombinant proteins representing key regions of the Notch 3 receptor were used (see extracellular domain structure schematic in FIG. 1) in pannings with a phage display library. The NRR, EGF32-NRR and ligand binding (LBD) regions of Notch 3 were used in pannings. In addition, cell lines expressing either exogenous or endogenous Notch3 were used in either whole cell panning or differential whole cell panning as described below. Antibodies against human Notch3 proteins were generated by selection of clones having high affinity binding affinities, using as the source of antibody variant proteins a commercially available phage display library, the Morphosys HuCAL PLATINUM® library. The binding properties of Notch 3 antibodies to both recombinant proteins (human, mouse, cyno) as well as to cells expressing Notch 3 is shown in FIGS. 3-6.

Cell Lines

U2OS, MDA-MB-468, HCC1143 were purchased from ATCC and routinely maintained in growth media supplemented with 10% FBS and 1% Penicillin-Streptomycin. Cell line TALL-1 was purchased from DSMZ and routinely maintained in growth media supplemented with 10% FBS and 1% Penicillin-Streptomycin. HLR PathDetect cells were purchased from Stratagene, and maintained according to manufacturer's instructions.

Generation of Expression Vectors for Notch3-NRR Domain and Notch3-NRR-EGF Domain The coding sequence for the human Notch 3 NRR domain (amino acids 1378-1640) was gene synthesized and subcloned into a derivative of the expression vector pRS5a to include the mouse IgK signal peptide and C-terminal six histidine purification tag. Similarly, the human, cyno and mouse EGF32-NRR dual domains (amino acids 1246-1640, 1246-1640, 1247-1641, respectively) were gene synthesized and cloned into pRS5a to include the mouse IgK signal peptide and C-terminal six histidine purification tag. pRS5a contains the CMV promoter and was used for expression of the proteins by transient transfection of HEK293 Freestyle cells (Invitrogen).

Expression/Purification of Recombinant Notch3 Proteins

The vectors for expression of Notch3 proteins were transiently transfected into HEK293 Freestyle cells using a ratio of 1:3 DNA:PEI transfection reagent. Seven days after transfection, cell supernatant was applied to a Nickel-NTA column (Qiagen) for purification of the histidine-tagged proteins. Protein was eluted with imidazole, followed by further purification by size exclusion on Superdex 200 (GE) in PBS to remove any aggregated protein. Protein was analyzed by SDS-PAGE and HPLC-size exclusion to assess purity and aggregation state.

Notch3-LBD Proteins

Recombinant human Notch3-Fc Chimera (Accession # Q9UM47, aa 40-467) was purchased from R&D systems (#1559-NT-050). Recombinant mouse Notch3-Fc Chimera (Accession # Q61982, aa 40-468) was purchased from R&D systems (#1308-NT-050)

Generation of Notch3 Over-Expressing Cell Lines

To generate a cell line that overexpresses Notch3, and Notch3-GFP cDNA was purchased from Origene (cat#RG224711). U2OS cells were electroporated using the NEON electroporation machine (Invitrogen) following instruction from the manufacturer. Electroporation parameters were: 1230V pulse voltage, 10 ms pulse width, 4 pulses. One million U2OS cells were mixed with 2 μg Notch3-GFP cDNA using 100 μl NEON tips (Invitrogen, cat#MPK10096). Twenty four hours after electroporation, the cells were put under selection (G418 at 200 μg/mL) for 2 weeks. Notch3 GFP positive cells were FACS sorted into two populations—high GFP and medium GFP positive cells. Clonal lines from each sub population were selected and further tested for Notch3 cell surface expression by FACS.

HuCAL PLATINUM® Pannings

For selection of antibodies recognizing human Notch3 multiple panning strategies were employed. Therapeutic antibodies against human Notch3 proteins were generated by selection of clones having high affinity binding affinities, using as the source of antibody variant proteins a commercially available phage display library, the Morphosys HuCAL PLATINUM® library. The phagemid library is based on the HuCAL® concept (Knappik et al., (2000) J Mol Biol 296: 57-86) and employs the CysDisplay® technology for displaying the Fab on the phage surface (Lohning, WO 01/05950). For isolation of anti-Notch3 antibodies, standard panning strategies were performed using solid phase, solution, whole cell and differential whole cell panning approaches.

Solid Phase Panning

Prior to the antigen selection process a coating check ELISA was performed to determine the optimal coating concentration for the antigen. An appropriate number (dependent on the number of sub-library pools) of wells of a 96-well Maxisorp™ plate were coated with 300 μl of Notch3 antigen overnight (o/n) at 4° C. For each panning, about $4 \times 10^{13}$ HuCAL PLATINUM® phage-antibodies were blocked with PBS/0.05% Tween20/5% milk powder/5% BSA. After the blocking procedure, the pre-blocked phage mix was added to each antigen coated and blocked well and incubated for 2 h at room temperature (RT) on a microtiter plate shaker. Afterwards, unspecific bound phages were washed off by several washing steps and for elution of specifically bound phages, DTT in 10 mM Tris/HCl pH 8 was used. The DTT eluate was transferred into 14 ml of *E. coli* TG1, and afterwards the mix of *E. coli* TG1 and DTT eluate was incubated for 45 min in a water bath at 37° C. for phage infection. The bacterial pellets were resuspended in 2×YT medium, plated on LB/Cam agar plates and incubated o/n at 30° C. Colonies were scraped off the plates and were used for phage rescue, polyclonal amplification of selected clones, and phage production. With purified phages the next panning round was started.

The second and third round of solid phase panning was performed according to the protocol of the first round except for decreased amounts of antigen and more stringent washing conditions.

Solution Panning Protocol with Streptavidin-Coupled Magnetic Beads

Prerequisite for a solution panning was biotinylation of the antigen and confirmation of retained activity of biotinylated antigen. During solution panning, the Fab displaying phages and the biotinylated antigen were incubated in solution which facilitated the accessibility of the antigen by the phages.

Per phage pool, Streptavidin beads (Dynabeads® M-280 Streptavidin; Invitrogen) and for each panning, HuCAL PLATINUM® phage-antibodies were blocked with Chemiblocker. Then, 100 nM biotinylated Notch3 antigen was added to the phage particles and incubated for 1-2 h at RT on a rotator. The phage-antigen complexes were captured using 2 mg blocked Streptavidin beads and phage particles bound to the Streptavidin beads were collected with a magnetic separator. Unspecific bound phages were washed off by several washing steps using PBS/0.05% Tween20 and PBS. For elution of specifically bound phages from Streptavidin beads, DTT was used. The DTT eluate was then transferred into *E. coli* TG1, and the mix of TG1 and DTT eluate was incubated for 45 min in a water bath at 37° C. for phage infection. The bacterial pellets were resuspended in 2×YT medium, plated on LB/Cam agar plates and incubated o/n at 30° C. Colonies were scraped off the plates and were used for phage rescue, polyclonal amplification of selected clones, and phage production. With purified phages the next panning round was started.

The second and third round of the solution panning was performed according to the protocol of the first round except for decreased amounts of antigen and more stringent washing conditions.

Whole Cell Panning Against Notch3

For each panning, about $4 \times 10^{13}$ HuCAL PLATINUM® phage-antibodies were blocked in PBS/5% FCS. In parallel, $0.5$-$1.0 \times 10^7$ target cells expressing Notch3 antigen and (if applied) $0.5$-$1.0 \times 10^7$ adsorption cells without expression of Notch3 per phage pool were resuspended in 1 ml PBS/5% FCS for blocking on ice. The blocked target cells were spun down, resuspended in the pre-blocked phage particles and incubated for 2 h at 4° C. on a rotator. The phage-cell complexes were washed three times in PBS/5% FCS. Elution of specifically bound phages from target cells was performed by 10 min acidic elution with 0.1 M glycine-HCl/0.5 M NaCl, pH 2.2. After centrifugation, the supernatant (eluate) was neutralized by adding 2 M unbuffered Tris. The final supernatant was used for phage infection of E. coli TG1 culture. The bacterial pellets were resuspended in 2×YT medium, plated on LB/Cam agar plates and incubated o/n at 30° C. Colonies were scraped off the plates and were used for phage rescue and phage amplification. Amplified phages were used for the next panning round.

The second and third round of the whole cell panning was performed according to the protocol of the first round.

Differential Whole Cell Panning Against Notch3

In the differential whole cell panning, the selection was done alternating on cells and purified protein. The selection rounds on purified antigen were performed as described for solid phase pannings. For the selection rounds on cells please refer to the procedure for whole cell panning. In contrast to whole cell panning, post-adsorption could be omitted in DWCP.

Maturation Pannings

To increase affinity and biological activity of selected antibody fragments, L-CDR3 and H-CDR2 regions were optimized in parallel by cassette mutagenesis using trinucleotide directed mutagenesis (Virnekas et al., (1994) Nucleic Acids Res. 22:5600-5607), while the framework regions were kept constant. Prior to cloning for affinity maturation, parental Fab fragments were subcloned from the corresponding expression vector into the display vector.

For the selection of affinity improved binders phage derived from maturation libraries were subjected to three rounds of solid phase, solution or differential whole cell panning using Notch3 antigens (hN3_EGF4-11_Fc, hN3_EGF4-11_Fc_biot, hN3_EGF32_NRR_His and hN3_NRR_His_biot). Stringency was increased by lowering the antigen concentration in each panning round (Low et al., (1996) J Mol Biol 260: 359-368). In addition to antigen reduction off-rate selection (Hawkins et al., (1992) J Mol Biol 226: 889-896) was performed. This was combined with prolonged washing steps at 22° C.

Subcloning and Microexpression of Selected Fab Fragments

To facilitate rapid expression of soluble Fab, the Fab encoding inserts of the selected HuCAL PLATINUM® phage were subcloned from pMORPH®30 display vector into pMORPH® x11 expression vector pMORPH® x11_FH.

Subcloning was performed by triple digest via EcoRI/XbaI/BmtI. After transformation of E. coli TG1-F-single clone expression and preparation of periplasmic extracts containing HuCAL®-Fab fragments were performed as described previously (Rauchenberger et al., (2003) J Biol Chem. 278:38194-38205).

Preparation of Fab Containing Bacterial Lysates for ELISA Screening

5 µl of each o/n culture were transferred to a sterile 384-well microtiter plate pre-filled with 40 µl 2×YT medium (34 µg/ml chloramphenicol (Cam); 0.1% Glucose) per well. Plates were incubated at 37° C. until the cultures were slightly turbid. To these expression plates, 10 µl 2×YT medium (34 µg/ml Cam and 5 mM IPTG) was added per well. Plates were sealed with a gas-permeable tape, and incubated o/n at 22° C. To each well of the expression plates, 15 µl BEL buffer (2.5 mg/ml lysozyme, 4 mM EDTA, 10 U/µl Benzonase) was added and plates were incubated for 1 h at 22° C. For subsequent ELISA screening Fab containing E. coli lysates were blocked by adding 15 µl 12.5% MPBST to each well and shaking the plates for at least 30 min at 400 rpm and 22° C. Expression plates were used immediately or stored at −20° C.

Preparation of Fab Containing Bacterial Lysates for FACS Screening

5 µl of each o/n culture were transferred to a sterile 96-well microtiter plate pre-filled with 100 µl 2×YT medium (34 µg/ml Cam; 0.1% Glucose) per well. Plates were incubated at 22° C. until the cultures were slightly turbid. To these expression plates, 20 µl 2×YT medium (34 µg/ml Cam; 3 mM IPTG) was added per well. Plates were sealed with a gas-permeable tape, and incubated o/n at 22° C. To each well of the expression plates, 15 µl BEL buffer (2.5 mg/ml lysozyme, 4 mM EDTA, 10 U/µl Benzonase) was added and plates were incubated for 1 h at 22° C. For subsequent FACS screening Fab containing E. coli lysates were blocked by adding 15 µl 16% FBS to each well and shaking the plates for at least 30 min at 400 rpm and 22° C. After incubation, BEL-lysates were centrifuges to spin down bacterial cell debris. Fab containing supernatants were used for screening purposes immediately or store at −20° C.

ELISA Screening on Directly Coated Antigen

Maxisorp™ 384 well plates were coated with Notch3 antigens hN3_NRR_His, hN3_EGF32_NRR_His and hN3_EGF4-11_Fc at a concentration of 2.5 µg/ml, 5 µg/ml or 1.25 µg/ml respectively, in PBS. After blocking of plates with 5% skim milk powder in PBS, Fab-containing E. coli lysates were added. Binding of Fabs was detected by F(ab)2 specific goat anti-human IgG conjugated to alkaline phosphatase (Jackson Immuno Research#109-055-097; diluted 1:5000) using Attophos fluorescence substrate (Roche, #11681982001). Fluorescence emission at 535 nm was recorded with excitation at 430 nm.

ELISA Screening of Biotinylated Antigen

NeutrAvidin™-Coated plates were coated with either 2.5-5 µg/ml hN3_NRR_His, 5-10 µg/ml hN3_EGF32_NRR_His biotinylated Notch3 antigens or with 1.25 µg/ml hN3_EGF4-11_Fc antigen diluted in PBS. After blocking with 3% bovine serum albumin in PBS, Fab-containing E. coli lysates were added. Subsequently the captured HuCAL®-Fab fragments were detected by F(ab)2 specific goat anti-human IgG conjugated to alkaline phosphatase (Jackson Immuno Research#109-055-097; diluted 1:5000) using Attophos fluorescence substrate (Roche, #11681982001). Fluorescence emission at 535 nm was recorded with excitation at 430 nm.

FACS Screening

In FACS screening, single Fab clones binding to cell surface expressed antigen were identified from the panning output. Fabs were tested using Fab containing crude E. coli lysates. Cell lines used were U2OS cells (ATCC #HTB-96; either unmodified cells=U2OS_par or genetically modified to highly express human Notch3=U2OS_N3) and breast cancer cell line HCC1143 (ATCC #CRL-2321) harboring an amplification of the Notch3 gene.

100 µl of cell-suspension were transferred into a fresh 96-well plate (resulting in $1\times10^5$ cells/well). Target cell suspension containing plate was centrifuged and supernatant was discarded. Remaining cell pellet was resuspended and 50 µl of Fab containing FACS BEL extracts was added to the corresponding wells. Plate was incubated on ice for 1 hour. Following incubation, cells were spun down and washed three times with 200 µl FACS buffer (PBS, 3% FCS). After each washing step, cells were centrifuged and carefully resuspended.

The PE conjugated goat-anti-human IgG secondary detection antibody (Jackson, Cat#109-116-098) was added and samples were incubate on ice and subsequently washed according to Fab incubation.

Finally, cell pellets were resuspended in 150 µl FACS buffer per well and samples were analyzed in a BD FACS array.

Screening after Affinity Maturation

For ranking of the matured binders by Solution Equilibrium Titration based on the principles described by (Haenel et al., (2005) Anal Biochem. 339:182-184), a constant amount of diluted BEL extract was equilibrated over night with different concentrations of antigen.

Then the mixture was transferred to MSD Plates which were previously coated with antigen, and after incubation and washing, a suitable MSD-Sulfo-tag labeled detection antibody was added.

Subsequently, the concentration of unbound Fab was quantified via ECL detection using the Sector Imager 6000 (Meso Scale Discovery, Gaithersburg, Md., USA).

Results were processed using XLfit (IDBS) software, applying the corresponding fit model to estimate affinities and thus identify clones most improved by the maturation.

Expression and Purification of his-Tagged HuCAL® Fab Fragments in E. coli (mg Scale)

Expression of Fab fragments encoded by pMORPH® x11_Fab_FH in E. coli TG1 F-cells was carried out in shake flask cultures using 500 ml of 2×YT medium supplemented with 0.1% glucose and 34 µg/ml chloramphenicol. Cultures were shaken at 30° C. until the OD600 reached a value of 0.5. Fab expression was induced by addition IPTG (isopropyl-β-D-thiogalactopyranoside) at a final concentration of 0.75 mM and further cultivation for 20 h at 30° C. Cells were harvested and disrupted using lysozyme. His6-tagged Fab fragments were isolated via IMAC (Bio-Rad, Germany) and eluted using imidazole. Buffer exchange to 1× Dulbecco's PBS (pH 7.2) was performed using PD10 columns (GE Healthcare, Germany). Samples were sterile filtered (0.2 µm). Protein concentrations were determined by UV-spectrophotometry. The purity of the samples was analyzed in denaturing, reducing 15% SDS-PAGE. The homogeneity of Fab preparations was determined in native state by size exclusion chromatography (HP-SEC) with calibration standards.

Conversion to IgG

In order to express full length IgG, variable domain fragments of heavy (VH) and light chains (VL) were subcloned from Fab expression vectors into appropriate pMorph4®_hIgGlf vectors for human IgGlf.

Transient Expression of Human IgG in IgG Screening Scale

Eukaryotic HEK293 c18 cells (ATCC #CRL-10852) were used in a 96-well expression system for the generation of conditioned cell culture supernatants containing full-length IgG for the subsequent use in specificity and/or functional screening assays.

HuCAL® Fab fragments were subcloned from pMORPH® expression or display vectors into pMORPH®4 Ig expression vectors. The resulting ligations were used for transformation of E. coli XL1 Blue followed by plating the samples onto LB plates containing 100 µg/ml ampicillin and 1% glucose.

DNA preparations of single colonies were prepared by using an appropriate DNA preparation kit in combination with the BioRobot®8000 device. Individual DNA concentrations were determined by UV-spectrophotometry.

Eukaryotic HEK293 c18 cells were seeded in a 96-well flat-bottom plate to a density of $\sim4\times10^4$ cells/50 µl/well the day before and transfected with equal amounts of Ig expression vector DNA. After incubation for 40-50 h at 37° C. and 6% $CO_2$ the culture supernatants were transferred to a 96-well U-bottom plate and cleared by centrifugation. The resulting Ig supernatants were tested by an anti-Fd capture ELISA for calculation of Ig concentration in reference to known standards and stored at −20° C. for later use in specificity and/or functional screening assays.

ELISA with Purified IgGs on Directly Coated Antigen

Maxisorp™ 384 well plates were coated with Notch3 antigens hN3_NRR_His (2.5 µg/ml), N3_EGF32_NRR_His (5 µg/ml for human, cyno and mouse) and N3_EGF4-11_Fc (hu 1.25 µg/ml; cyno and mouse: 5 µg/ml) in PBS. After blocking of plates with 5% skim milk powder in PBS, IgGs from exploratory scale expression were added (For ELISA EC50-determinations, 12 point titration down from 50 µg/ml (333.3 nM), in 1:3 dilution steps were performed). Binding of IgGs was detected by F(ab)2 specific goat anti-human IgG conjugated to alkaline phosphatase (Jackson Immuno Research#109-055-097; diluted 1:5000) using Attophos fluorescence substrate (Roche, #11681982001). Fluorescence emission at 535 nm was recorded with excitation at 430 nm.

FACS Screening with Exploratory Scale IgGs

In FACS screening, IgGs from exploratory scale expression binding to cell surface expressed antigen were identified. Cell lines used were U2OS cells (ATCC #HTB-96; either unmodified cells=U2OS_par or genetically modified to highly express human Notch3=U2OS_N3) and breast cancer cell line HCC1143 (ATCC #CRL-2321) harboring an amplification of the Notch3 gene.

100 µl of cell-suspension were transferred into a fresh 96-well plate (resulting in $1\times10^5$ cells/well). Target cell suspension containing plate was centrifuged and supernatant was discarded. Remaining cell pellet was resuspended and 50 µl of IgG dilution was added to the corresponding wells. FACS $EC_{50}$ determination was performed down from 20 µg/ml in 1:5 dilution steps. Plate was incubated on ice for 1 hour. Following incubation, cells were spun down and washed three times with 200 µl FACS buffer (PBS, 3% FCS). After each washing step, cells were centrifuged and carefully resuspended. The PE conjugated goat-anti-human IgG secondary detection antibody (Jackson, Cat #109-116-098) was added and samples were incubate on ice and subsequently washed according to Fab incubation. Finally, cell pellets were resuspended in 150 µl FACS buffer per well and samples were analyzed in a BD FACS array.

Expression Vectors for Generation of Stable Cells Lines Expressing Notch3 Antibodies For larger scale expression of Notch3 antibodies, light and heavy chain coding sequences were cloned from phage vectors into a single dual CMV promoter plasmid containing mouse IgK signal peptides for generation of stable cell lines. Cells were screened by ELISA for high level expression of Notch3 antibodies.

Biacore Kd Determination

Affinity determination by determining kinetic parameters were performed via SPR using the Biacore 3000 instrument (Biacore, GE Healthcare) as described subsequently.

Biacore determination on directly coated antigen. Binding to immobilized antigen was analyzed as follows. The antigen was immobilized on a chip surface following the manufacturer's protocol. Kinetic measurements were done using six different Fab concentrations (2-fold serial dilution). After each cycle the sensor chip was regenerated. A blank injection of running buffer was used for double referencing. All sensorgrams were fitted using BIA evaluation software 4.1.1 (Biacore, GE Healthcare), to determine $k_{on}$ and $k_{off}$ rate constants, which were used to calculate KD.

Alternatively, for qualitative binding experiments, IgG samples were used as samples. The binding curves were fitted using the same model as for Fab fragments for relative comparison of the IgG samples.

Approximately 100 RU hN3_NRR_His (or 400RU hN3_EGF32_NRR_His) diluted in 10 mM acetate buffer, pH 4.5 to 10 µg/mL was immobilized on a CM5 chip (Biacore, GE Healthcare) using standard EDC-NHS amine coupling chemistry. The reference flow cell 1 was only activated and deactivated. The running buffer was PBS (GIBCO) pH7.2 with 0.005% (v/v) Tween 20 with a flow rate of 25 µl/min. Fab concentrations ranging from 15.6 to 500 nM were used with an injection time of 120 s and an appropriate dissociation time of e.g. 240 s. Regeneration of bound analyte was done with 1 injection of Glycine/HCl pH2.5 (20s) and 1 injection of Glycine/HCl pH2 (20s). Fitting was performed with parameters Rmax set to "global" and RI set to 0.

Biacore KD determination via antibody capture setup. Binding of monomeric antigen to captured antibody was analyzed as follows. On a CM5 chip (Biacore, GE Healthcare) an appropriate capture antibody (Biacore, GE Healthcare) was covalently immobilized using EDC/NHS chemistry. Kinetic measurements were done by capturing the antibody and subsequent injection of six different antigen concentrations (2-fold serial dilution). After each cycle the sensor chip was regenerated. A blank injection of running buffer was used for double referencing. All sensorgrams were fitted using BIA evaluation software 4.1.1 (Biacore, GE Healthcare), to determine kon and koff rate constants, which were used to calculate KD.

Running buffer was PBS (GIBCO) pH7.2 with 0.05% Tween 20. 100 RU IgG was captured using an anti-human Fc antibody (Biacore, GE Healthcare). Antigen concentrations (hN3_NRR_R His or hN3_EGF32_NRR_His), e.g. ranging from 15.6 to 500 nM were used with a flow rate of 30 µl/min, an injection time of 180 s and an appropriate dissociation time of e.g. 360 s. Regeneration of the antibody/antigen complex was done with 2 injections of 3M $MgCl_2$ at 30s. Fitting was performed with parameters Rmax set to "global" and RI set to 0.

For Biacore $K_D$ determination via antigen capture. Binding of Fab to captured antigen was analyzed as follows. On a CM5 chip (Biacore, GE Healthcare) an appropriate anti-antigen tag capture antibody was covalently immobilized using EDC/NHS chemistry. Kinetic measurements were done by capturing the antigen and subsequent injection of six different Fab concentrations (2n serial dilution). After each cycle the sensor chip was regenerated. A blank injection of running buffer was used for double referencing. All sensorgrams were fitted using BIA evaluation software 4.1.1 (Biacore, GE Healthcare), to determine kon and koff rate constants, which were used to calculate $K_D$.

Running buffer was PBS (GIBCO) pH7.2 with 0.05% Tween 20. Approximately 75 RU antigen (e.g. hN3_EGF4-11_Fc, 50 nM) was captured using an anti-human Fc antibody (Biacore, GE Healthcare). Antibody Fab fragment concentrations, e.g. ranging from 15.6 to 500 nM were used with a flow rate of 30 µl/min, an injection time of 180 s and an appropriate dissociation time (e.g. up to 1800 s). Regeneration of the antibody/antigen complex was done with 2 injections 3 M $MgCl_2$ at 35 s. Fitting was performed with parameters Rmax set to "global" and RI set to 0.

Solution Equilibrium Titration (SET) Method for KD Determination Using Sector Imager 6000 (MSD)

Affinity determination in solution was basically performed as described in the literature (Friquet et al., (1985) J Immunol Methods 77: 305-319). In order to improve the sensitivity and accuracy of the SET method, it was transferred from classical ELISA to ECL based technology (Haenel et al., (2005) Anal Biochem 339: 182-184).

1 mg/ml goat-anti-human (Fab)2 fragment specific antibodies (Dianova, or Bethyl) were labeled with MSD Sulfo-TAGTM NHS-Ester (Meso Scale Discovery, Gaithersburg, Md., USA) according to the manufacturer's instructions. For $K_D$ determination of mouse antibodies, a corresponding anti-mouse-IgG was labeled and used as detection reagent.

The experiments were carried out in polypropylene microtiter plates and PBS pH 7.4 containing 0.5% BSA and 0.02% Tween-20 as assay buffer. Unlabeled antigen was diluted in a 2-fold series, starting with a concentration at least 10 times higher than the expected KD. Wells without antigen were used to determine Bmax values; wells containing only assay buffer were used to determine background. After addition of appropriate amount of binder (antibody concentration similar to or below the expected $K_D$, 60 µl final volume), the mixture was incubated over night at RT.

MSD plates were coated with antigen (30 µl per well). After washing the plate with PBS with 0.02% Tween-20, the equilibrated samples were transferred to those plates (30 µl per well) and incubated for 20 min. After washing, 30 µl per well of the MSD-Sulfo-tag labeled detection antibody (anti-human (Fab)2, final dilution typically 1:2,000) was added to the MSD plate and incubated for 30 min at RT on an Eppendorf shaker (700 rpm).

After washing the MSD plate and adding 30 µl/well MSD Read Buffer T with surfactant, electrochemiluminescence signals were detected using a Sector Imager 6000 (Meso Scale Discovery, Gaithersburg, Md., USA).

The data was evaluated with XLfit (IDBS) software applying customized fitting models. For KD determination of Fab molecules the following fit model was used (according to (Haenel et al., (2005) Anal Biochem 339: 182-184), modified according to (Abraham et al., (1996) J Mol Recognit. 9, 456-461):

$$y = B_{max} - \left( \frac{B_{max}}{2[Fab]_t} \left( [Fab]_t + x + K_D - \sqrt{([Fab]_t + x + K_D)^2 - 4x[Fab]_t} \right) \right)$$

[Fab]t: applied total Fab concentration
x: applied total soluble antigen concentration (binding sites)
Bmax: maximal signal of Fab without antigen
KD: affinity For KD determination of IgG molecules the following fit model for IgG was used (modified according to (Piehler et al., (1997) J Immunol Methods 201: 189-206):

$$y = \frac{2B_{max}}{[IgG]} \left( \frac{[IgG]}{2} - \frac{\left(\frac{x+[IgG]+K_D}{2} - \sqrt{\frac{(x+[IgG]+K_D)^2}{4} - x[IgG]}\right)^2}{2[IgG]} \right)$$

[IgG]: applied total IgG concentration
x: applied total soluble antigen concentration (binding sites)
Bmax: maximal signal of IgG without antigen
$K_D$: affinity
Experimental Settings:

$K_D$ determination of HuCAL®_Fab (or IgG) was basically performed as follows: Antigen hN3_EGF4-11_Fc was coated at 0.2 µg/mL in PBS o/n at 4° C. on standard MSD plates (or hN3_NRR_His at 1 µg/mL, depending on the samples' specificities). Subsequently MSD plates were blocked with PBS containing 3% BSA for 1 h at RT. Monomeric antigen (hN3_NRR_His) had to be used for titration of IgG samples; for KD determination of Fab fragments both hN3_NRR_His and hN3_EGF4-11_Fc could be used.

Summary of Panning Strategies and Screening 11 initial panning strategies were performed using recombinant Notch3 antigens as well as Notch3 expressing cell lines, either alone or in combination. Panning output was screened for antigen binding and functional activity. 3771 primary hits showed binding to Notch3 recombinant antigen, 774 were positive on cells expressing Notch3 and resulted in 295 unique clones. Complete antibody characterization was performed with 55 IgGs, 12 candidates were selected for affinity maturation (including 5 clones binding to Notch3 NRR-domain and 7 clones binding to Notch3 LBD-domain). SET-screening after affinity maturation resulted in 315 improved unique clones (9 families) 111µ-scale expressed IgGs were screened for antigen binding and functionality. 31/111 IgGs (from 8 different HCDR3 families) were further characterized and resulted in 9 prioritized clones belonging to 4 different HCDR3 families.

Example 3: Characterization of Notch3 Antibodies in a Ligand-Driven Reporter Gene Assay Canonical Notch signaling is activated when a Notch receptor on one cell interacts with a ligand on a neighboring cell. In mammals there are five trans-membrane ligands, three Delta-like ligands (DLL1, DLL4, and DLL3) and two Jagged ligands (Jag1, Jag2). To determine the capacity of anti-Notch3 antibodies to inhibit Notch3 ligand-induced signaling, a reporter gene assay (RGA) using the double stable reporter cell line HLR-huNotch3-Gal4-NLS-VP16/Gal4-UA-Luciferase was developed. Using this assay the inhibition of Notch3 signaling activated by either Jag1 or DLL1 was examined. Similar assays were developed for human Notch1 and Notch2 receptors. Testing of Notch3 antibodies in this series of Notch receptor-specific RGA assay allowed specificity assessment of the antibodies for inhibition of Notch3.

To determine the capacity of anti-Notch3 antibodies to inhibit Notch3 ligand-induced signaling, a reporter gene assay (RGA) using the double stable reporter cell line HLR-huNotch3-Gal4-NLS-VP16/Gal4-UA-Luciferase was developed.

Generation of a Cell Line Expressing Human Notch3-Gal4-NLS-VP16/Gal4-UA-Luciferase Human Notch1, Notch2 and Notch3 as well as cyno Notch3 extracellular and trans-membrane portions followed by Gal4 DNA binding domain, VP16 and a nuclear localization sequence (NLS) were cloned into the retroviral vector pLNCX2 (Clontech, cat#631503). Generation of these chimeric Notch receptors and corresponding reporter gene assays allowed for examination of the effects of Notch3 antibodies of Notch receptor specific signaling.

Expression vectors for Notch1-, Notch2-, and Notch3-Gal4-VP16

The coding sequence for Gal4-VP16 was gene synthesized and cloned into the SalI-ClaI sites of the vector pLNXC2 (Clontech) to make pLNXC2-Gal4-VP16. The extracellular (ECD) and transmembrane domains of cyno Notch3 (amino acids 1-1669), human Notch1 (amino acids 1-1762) and human Notch 2 (1-1704) were gene synthesized and cloned into the HindIII-SalI sites of pLNXC2-Gal4-VP16 to produce fusions of the respective Notch proteins to Gal4-VP16.

Constructs for Notch-Gal4-VP16 Expression Vectors

Human Notch3-Gal4-VP16
(SEQ ID NO: 272)

MGPGARGRRRRRRPMSPPPPPPPVRALPLLLLLAGPGAAAPPCLDGSPCA

NGGRCTQLPSREAACLCPPGWVGERCQLEDPCHSGPCAGRGVCQSSVVAG

TARFSCRCPRGFRGPDCSLPDPCLSSPCAHGARCSVGPDGRFLCSCPPGY

QGRSCRSDVDECRVGEPCRHGGTCLNTPGSFRCQCPAGYTGPLCENPAVP

CAPSPCRNGGTCRQSGDLTYDCACLPGFEGQNCEVNVDDCPGHRCLNGGT

CVDGVNTYNCQCPPEWTGQFCTEDVDECQLQPNACHNGGTCFNTLGGHSC

VCVNGWTGESCSQNIDDCATAVCFHGATCHDRVASFYCACPMGKTGLLCH

LDDACVSNPCHEDAICDTNPVNGRAICTCPPGFTGGACDQDVDECSIGAN

PCEHLGRCVNTQGSFLCQCGRGYTGPRCETDVNECLSGPCRNQATCLDRI

GQFTCICMAGFTGTYCEVDIDECQSSPCVNGGVCKDRVNGFSCTCPSGFS

GSTCQLDVDECASTPCRNGAKCVDQPDGYECRCAEGFEGTLCDRNVDDCS

PDPCHHGRCVDGIASFSCACAPGYTGTRCESQVDECRSQPCRHGGKCLDL

VDKYLCRCPSGTTGVNCEVNIDDCASNPCTFGVCRDGINRYDCVCQPGFT

GPLCNVEINECASSPCGEGGSCVDGENGFRCLCPPGSLPPLCLPPSHPCA

HEPCSHGICYDAPGGFRCVCEPGWSGPRCSQSLARDACESQPCRAGGTCS

SDGMGFHCTCPPGVQGRQCELLSPCTPNPCEHGGRCESAPGQLPVCSCPQ

GWQGPRCQQDVDECAGPAPCGPHGICTNLAGSFSCTCHGGYTGPSCDQDI

NDCDPNPCLNGGSCQDGVGSFSCSCLPGFAGPRCARDVDECLSNPCGPGT

CTDHVASFTCTCPPGYGGFHCEQDLPDCSPSSCFNGGTCVDGVNSFSCLC

RPGYTGAHCQHEADPCLSRPCLHGGVCSAAHPGFRCTCLESFTGPQCQTL

VDWCSRQPCQNGGRCVQTGAYCLCPPGWSGRLCDIRSLPCREAAAQIGVR

LEQLCQAGGQCVDEDSSHYCVCPEGRTGSHCEQEVDPCLAQPCQHGGTCR

GYMGGYMCECLPGYNGDNCEDDVDECASQPCQHGGSCIDLVARYLCSCPP

GTLGVLCEINEDDCGPGPPLDSGPRCLHNGTCVDLVGGFRCTCPPGYTGL

RCEADINECRSGACHAAHTRDCLQDPGGGFRCLCHAGFSGPRCQTVLSPC

-continued
ESQPCQHGGQCRPSPGPGGGLTFTCHCAQPFWGPRCERVARSCRELQCPV

GVPCQQTPRGPRCACPPGLSGPSCRSFPGSPPGASNASCAAAPCLHGGSC

RPAPLAPFFRCACAQGWTGPRCEAPAAAPEVSEEPRCPRAACQAKRGDQR

CDRECNSPGCGWDGGDCSLSVGDPWRQCEALQCWRLFNNSRCDPACSSPA

CLYDNFDCHAGGRERTCNPVYEKYCADHFADGRCDQGCNTEECGWDGLDC

ASEVPALLARGVLVLTVLLPPEELLRSSADFLQRLSAILRTSLRFRLDAH

GQAMVFPYHRPSPGSEPRARRELAPEVIGSVVMLEIDNRLCLQSPENDHC

FPDAQSAADYLGALSAVERLDFPYPLRDVRGEPLEPPEPSVPLLPLLVAG

AVLLLVILVLGVMVARRKRVDKLLSSIEQACDICRLKKLKCSKEKPKCAK

CLKNNWECRYSPKTKRSPLTRAHLTEVESRLERLEQLFLLIFPREDLDMI

LKMDSLQDIKALLTGLFVQDNVNKDAVTDRLASVETDMPLTLRQHRISAT

SSSEESSNKGQRQLTVSKLKLLSSIEQACPKKKRKVDEFPGISTAPPTDV

SLGDELHLDGEDVAMAHADALDDFDLDMLGDGDSPGPG

Cyno Notch3-Gal4-VP16
(SEQ ID NO: 273)
MGPGARGRRRRRPMSPPPPPVRALPLLLLLAGPGAAVPPCLDGSPCANG

GRCTQLPSREAACLCPPGWVGERCQLEDPCHSGPCAGRGVCQSSVVAGTA

RFSCRCPRGFRGPDCSLPDPCLSSPCAHSARCSVGPDGRFLCSCPPGYQG

RSCRSDVDECRVGEPCRHGGTCLNTPGSFRCQCPAGYTGPLCENPAVPCA

PSPCRNGGTCRQSGDLTYDCACLPGFEGQNCEVNVDDCPGHRCLNGGTCV

DGVNTYNCQCPPEWTGQFCTEDVDECQLPNACHNGGTCFNTLGGHSCVC

VNGGWTGESCSQNIDDCATAVCFHGATCHDRVASFYCACPMGKTGLLCHLD

DACVSNPCHEDAICDTNPVNGRAICTCPPGFTGGACDQDVDECSIGANPC

EHLGRCVNTQGSFLCQCGRGYTGPRCETDVNECLSGPCRNQATCLDRIGQ

FTCICMAGFTGTYCEVDIDECQSSPCVNGGICKDRVNGFSCTCPSGFSGS

TCQLDVDECASTPCRNGAKCVDQPDGYECRCAEGFEGMLCERNVDDCSPD

PCHHGRCVDGIASFSCACAPGYTGTRCESQVDECRSQPCRHGGKCLDLVD

KYLCRCPSGTTGVNCEVNIDDCASNPCSFGVCRDGINRYDCVCQPGFTGP

LCNVEINECASSPCGEGGSCVDGENGFRCLCPPGSLPPLCLPPSHPCAHE

PCSHGICYDAPGGFRCVCEPGWSGPRCSQSLARDACESQPCRAGGTCSSD

GMGFHCTCPPGVQGRQCELLSPCTPNPCEHGGRCESAPGQLPVCSCPQGW

QGPRCQQDVDECAGPAPCGPHGICTNLAGSFSCTCHGGYTGPSCDQDIND

CDPNPCLNGGSCQDGVGSFSCSCLLGFAGPRCARDVDECLSNPCGPGTCT

DHVASFTCTCPPGYGGFHCEQDLPDCSPSSCFNGGTCVDGVNSFSCLCRP

GYTGAHCQHEADPCLSRPCLHGGVCSAAHPGFRCTCPQSFTGPQCQTLVD

WCSRQPCQNGGRCVQTGAYCLCPPGWSGRLCDIRSLPCREAAAQIGVRLE

QLCQAGGQCVDEDSSHYCVCPEGRTGSHCEQEVDPCLAQPCQHGGTCRGY

MGGYMCECLPGYNGENCEDDVDECASQPCQHGGSCIDLVARYLCSCPPGT

LGVLCEINEDDCGPGPPLDSGPRCLHNGTCVDLVGGFRCTCPPGYTGLRC

EADINECRSGACHAAHTRDCLQDPGGGFRCLCHAGFSGPRCQTVLSPCES

QPCQHGGQCRPSPGPGGGLTFTCHCAQPFWGPRCERVARSCRELQCPVG

PCQQTPRGPRCACPPGLSGPSCRSFSGSPPGASNASCAAAPCLHGGSCRP

-continued
APLAPFFRCACAQGWTGPRCEAPAAAPEVSEEPRCPRAACQAKRGDQRCD

RECNSPGCGWDGGDCSLSVGDPWRQCEALQCWRLFNNSRCDPACSSPACL

YDNFDCHAGGRERTCNPVYEKYCADHFADGRCDQGCNTEECGWDGLDCAS

EVPALLARGVLVLTVLLPPEELLRSSADFLQRLSAILRTSLRFRLDAHGQ

AMVFPYHRPSPGSEPRARRELAPEVIGSVVMLEIDNRLCLQSPENDHCFP

DAQSAADYLGALSAVERLDFPYPLRDVRGEPLEPPEPSVPLLPLLVAGAV

LLLVILVLGVMVARRKRVDKLLSSIEQACDICRLKKLKCSKEKPKCAKCL

KNNWECRYSPKTKRSPLTRAHLTEVESRLERLEQLFLLIFPREDLDMILK

MDSLQDIKALLTGLFVQDNVNKDAVTDRLASVETDMPLTLRQHRISATSS

SEESSNKGQRQLTVSQLKLLSSIEQACPKKKRKVDEFPGISTAPPTDVSL

GDELHLDGEDVAMAHADALDDFDLDMLGDGDSPGPG

Human Notch1-Gal4-VP16
(SEQ ID NO: 274)
MPPLLAPLLCLALLPALAARGPRCSQPGETCLNGGKCEAANGTEACVCGG

AFVGPRCQDPNPCLSTPCKNAGTCHVVDRRGVADYACSCALGFSGPLCLT

PLDNACLTNPCRNGGTCDLLTLTEYKCRCPPGWSGKSCQQADPCASNPCA

NGGQCLPFEASYICHCPPSFHGPTCRQDVNECGQKPGLCRHGGTCHNEVG

SYRCVCRATHTGPNCERPYVPCSPSPCQNGGTCRPTGDVTHECACLPGFT

GQNCEENIDDCPGNNCKNGGACVDGVNTYNCRCPPEWTGQYCTEDVDECQ

LMPNACQNGGTCHNTHGGYNCVCVNGWTGEDCSENIDDCASAACFHGATC

HDRVASFYCECPHGRTGLLCHLNDACISNPCNEGSNCDTNPVNGKAICTC

PSGYTGPACSQDVDECSLGANPCEHAGKCINTLGSFECQCLQGYTGPRCE

IDVNECVSNPCQNDATCLDQIGEFQCICMPGYEGVHCEVNTDECASSPCL

HNGRCLDKINEFQCECPTGFTGHLCQYDVDECASTPCKNGAKCLDGPNTY

TCVCTEGYTGTHCEVDIDECDPDPCHYGSCKDGVATFTCLCRPGYTGHHC

ETNINECSSQPCRHGGTCQDRDNAYLCFCLKGTTGPNCEINLDDCASSPC

DSGTCLDKIDGYECACEPGYTGSMCNINIDECAGNPCHNGGTCEDGINGF

TCRCPEGYHDPTCLSEVNECSNPCVHGACRDSLNGYKCDCDPGWSGTNC

DINNNECESNPCVNGGTCKDMTSGYVCTCREGFSGPNCQTNINECASNPC

LNQGTCIDDVAGYKCNCLLPYTGATCEVVLAPCAPSPCRNGGECRQSEDY

ESFSCVCPTGWQGQTCEVDINECVLSPCRHGASCQNTHGGYRCHCQAGYS

GRNCETDIDDCRPNPCHNGGSCTDGINTAFCDCLPGFRGTFCEEDINECA

SDPCRNGANCTDCVDSYTCTCPAGFSGIHCENNTPDCTESSCFNGGTCVD

GINSFTCLCPPGFTGSYCQHDVNECDSQPCLHGGTCQDGCGSYRCTCPQG

YTGPNCQNLVHWCDSSPCKNGGKCWQTHTQYRCECPSGWTGLYCDVPSVS

CEVAAQRQGVDVARLCQHGGLCVDAGNTHHCRCQAGYTGSYCEDLVDECS

PSPCQNGATCTDYLGGYSCKCVAGYHGVNCSEEIDECLSHPCQNGGTCLD

LPNTYKCSCPRGTQGVHCEINVDDCNPPVDPVSRSPKCFNNGTCVDQVGG

YSCTCPPGFVGERCEGDVNECLSNPCDARGTQNCVQRVNDFHCECRAGHT

GRRCESVINGCKGKPCKNGGTCAVASNTARGFICKCPAGFEGATCENDAR

TCGSLRCLNGGTCISGPRSPTCLCLGPFTGPECQFPASSPCLGGNPCYNQ

```
GTCEPTSESPFYRCLCPAKFNGLLCHILDYSFGGGAGRDIPPPLIEEACE

LPECQEDAGNKVCSLQCNNHACGWDGGDCSLNFNDPWKNCTQSLQCWKYF

SDGHCDSQCNSAGCLFDGFDCQRAEGQCNPLYDQYCKDHFSDGHCDQGCN

SAECEWDGLDCAEHVPERLAAGTLVVVVLMPPEQLRNSSFHFLRELSRVL

HTNVVFKRDAHGQQMIFPYYGREEELRKHPIKRAAEGWAAPDALLGQVKA

SLLPGGSEGGRRRRELDPMDVRGSIVYLEIDNRQCVQASSQCFQSATDVA

AFLGALASLGSLNIPYKIEAVQSETVEPPPPAQLHFMYVAAAAFVLLFFV

GCGVLLSRKRRRVDKLLSSIEQACDICRLKKLKCSKEKPKCAKCLKNNWE

CRYSPKTKRSPLTRAHLTEVESRLERLEQLFLLIFPREDLDMILKMDSLQ

DIKALLTGLFVQDNVNKDAVTDRLASVETDMPLTLRQHRISATSSSEESS

NKGQRQLTVSQLKLLSSIEQACPKKKRKVDEFPGISTAPPTDVSLGDELH

LDGEDVAMAHADALDDFDLDMLGDGDSPGPG
```

Human Notch2-Gal4-VP16
(SEQ ID NO: 275)
```
MPALRPALLWALLALWLCCAAPAHALQCRDGYEPCVNEGMCVTYHNGTGY

CKCPEGFLGEYCQHRDPCEKNRCQNGGTCVAQAMLGKATCRCASGFTGED

CQYSTSHPCFVSRPCLNGGTCHMLSRDTYECTCQVGFTGKECQWTDACLS

HPCANGSTCTTVANQFSCKCLTGFTGQKCETDVNECDIPGHCQHGGTCLN

LPGSYQCQCPQGFTGQYCDSLYVPCAPSPCVNGGTCRQTGDFTFECNCLP

GFEGSTCERNIDDCPNHRCQNGGVCVDGVNTYNCRCPPQWTGQFCTEDVD

ECLLQPNACQNGGTCANRNGGYGCVCVNGWSGDDCSENIDDCAFASCTPG

STCIDRVASFSCMCPEGKAGLLCHLDDACISNPCHKGALCDTNPLNGQYI

CTCPQGYKGADCTEDVDECAMANSNPCEHAGKCVNTDGAFHCECLKGYAG

PRCEMDINECHSDPCQNDATCLDKIGGFTCLCMPGFKGVHCELEINECQS

NPCVNNGQCVDKVNRFQCLCPPGFTGPVCQIDIDDCSSTPCLNGAKCIDH

PNGYECQCATGFTGVLCEENIDNCDPDPCHHGQCQDGIDSYTCICNPGYM

GAICSDQIDECYSSPCLNDGRCIDLVNGYQCNCQPGTSGVNCEINFDDCA

SNPCIHGICMDGINRYSCVCSPGFTGQRCNIDIDECASNPCRKGATCING

VNGFRCICPEGPHHPSCYSQVNECLSNPCIHGNCTGGLSGYKCLCDAGWV

GINCEVDKNECLSNPCQNGGTCDNLVNGYRCTCKKGFKGYNCQVNIDECA

SNPCLNQGTCFDDISGYTCHCVLPYTGKNCQTVLAPCSPNPCENAAVCKE

SPNFESYTCLCAPGWQGQRCTIDIDECISKPCMNHGLCHNTQGSYMCECP

PGFSGMDCEEDIDDCLANPCQNGGSCMDGVNTFSCLCLPGFTGDKCQTDM

NECLSEPCKNGGTCSDYVNSYTCKCQAGFDGVHCENNINECTESSCFNGG

TCVDGINSFSCLCPVGFTGSFCLHEINECSSHPCLNEGTCVDGLGTYRCS

CPLGYTGKNCQTLVNLCSRSPCKNKGTCVQKKAESQCLCPSGWAGAYCDV

PNVSCDIAASRRGVLVEHLCQHSGVCINAGNTHYCQCPLGYTGSYCEEQL

DECASNPCQHGATCSDFIGGYRCECVPGYQGVNCEYEVDECQNQPCQNGG

TCIDLVNHFKCSCPPGTRGLLCEENIDDCARGPHCLNGGQCMDRIGGYSC

RCLPGFAGERCEGDINECLSNPCSSEGSLDCIQLTNDYLCVCRSAFTGRH

CETFVDVCPQMPCLNGGTCAVASNMPDGFICRCPPGFSGARCQSSCGQVK

CRKGEQCVHTASGPRCFCPSPRDCESGCASSPCQHGGSCHPQRQPPYYSC

QCAPPFSGSRCELYTAPPSTPPATCLSQYCADKARDGVCDEACNSHACQW

DGGDCSLTMENPWANCSSPLPCWDYINNQCDELCNTVECLFDNFECQGNS

KTCKYDKYCADHFKDNHCDQGCNSEECGWDGLDCAADQPENLAEGTLVIV

VLMPPEQLLQDARSFLRALGTLLHTNLRIKRDSQGELMVYPYYGEKSAAM

KKQRMTRRSLPGEQEQEVAGSKVFLEIDNRQCVQDSDHCFKNTDAAAALL

ASHAIQGTLSYPLVSVVSESLTPERTQLLYLLAVAVVIILFIILLGVIMA

KRKRVDKLLSSIEQACDICRLKKLKCSKEKPKCAKCLKNNWECRYSPKTK

RSPLTRAHLTEVESRLERLEQLFLLIFPREDLDMILKMDSLQDIKALLTG

LFVQDNVNKDAVTDRLASVETDMPLTLRQHRISATSSSEESSNKGQRQLT

VSQLKLLSSIEQACPKKKRKVDEFPGISTAPPTDVSLGDELHLDGEDVAM

AHADALDDFDLDMLGDGDSPGPG
```

Generation of a Retrovirus to Expression Notch3-Gal4-VP16

Retrovirus was produced transfecting 293-GP2 Packaging Cell Line (Clontech, cat#631458) with the appropriate retroviral vector (pLNCX2_hNotch1_Gal4-VP16, pLNCX2_hNotch2_Gal4-VP16 pLNCX2_hNotch3_Gal4-VP16 pLNCX2_cNotch3_Gal4-VP16). Promega's Fugene6 was used as the lipid-based transfection reagent. Transfection was carried out according to manufacturer's instructions. Virus was collected at 48 h after transfection and immediately used to transduce HLR cells (HLR-PathDetect, Stratagene). Transduced cells were under selection for at least two weeks, before they were tested in a co-culture assay. Clonal populations for each cell line were selected.

Notch3-Gal4-NLS-VP16-UA-Luciferase Ligand-Induced Reporter Gene Assay

HLR-Notch3-Gal4-NLS-VP16/Gal4-UA-TATA-Luciferase (HLR-N3) cells are activated byco-culture with L cells stably expressing either cell surface expressed rrJagged1 (SN3T9) or rrDelta1 (DLL1-19) (Hicks C et al. (2000) Nature Cell Bio 2:515-520; Lindsell C et al. (1995) Cell 80:909-917). Co-culture with ligand expressing cells results in activation of Notch3 signaling and proteolytic cleavage of the Notch3 chimeric receptors to release the Gal4-NLS-VP16. This Gal4-NLS-VP16 translocates to the nuclease where it binds to the Gal4-luciferase reporter resulting in production of luciferase. At 90% confluency HLR-N3 cells were detached using Trypsin-EDTA and diluted in assay medium (DMEM, High glucose, L-Glu, Invitrogen, Cat#21063-029; supplemented with 10% FBS, 1% P/S) to a concentration of $2\times10^5$ cells/ml. 50 µl HLR-N3 cells per well (=$1\times10^4$ cells) were seeded into white flat-bottomed 96-well plates (Costar, Cat #:3917) and incubated at 37° C. and 5% $CO_2$ overnight.

The next day, the HuCAL® antibodies (IgGs) were diluted at the desired concentrations in PBS. Per well 10 µl of antibody dilution were added to the seeded cells and incubated for 2 h at 37° C. and 5% $CO_2$. Next Jagged1 and Delta1 ligand expressing mouse L-cells were detached using Trypsin-EDTA and diluted in assay media to a concentration of $8\times10^5$ cells/ml. Per well 50 µl mouse L-cells (=$4\times10^4$ cells/well) were added to the cultured HLR-N3 cells (50 µl HLR cells+10 µl antibody+50 µl mouse cells=110 µl final volume) and incubated over night at 37° C. and 5% $CO_2$. As a control 50 µl mouse parental L-cells were added instead for the ligand independent setting.

After overnight incubation, 50 μl of freshly prepared Bright-Glo reagent was adapted to room temperature (Promega, Cat #E2610) and added to each well. After 5 min incubation time, the luminescence was read in a luminometer (GeniosPro, Tecan). $IC_{50}$ values were calculated using Prism after full titration of the respective antibodies. Percentage inhibition relative to an IgG control is indicated. If increased signaling was detected upon antibody addition then a negative number is used.

Summary and Discussion

In addition to the huNotch3 RGA, cynoNotch3 RGAs as well as huNotch1 RGA (only DLL1 ligand setting) and huNotch2 RGA (Jagged1 and DLL1) were performed as described above. None of the Notch3 antibodies described, showed any activity in the huNotch1 or huNotch2 RGAs up to a maximal concentration of 10 μg/ml. Notch3 antibodies were identified that inhibit both Jagged1 and Delta1 induced Notch3 signaling. The percentage of inhibition and $IC_{50}$ varied depending on the antibody and the ligand used for activation. Antibodies that were identified from pannings directed against the LBD domain (12229, 20364, 20802) were most effective in inhibiting signaling from this ligand-driven RGA assay, as shown in FIGS. 7A-D.

Example 4: Effects of Notch3 Antibodies on Notch Target Gene mRNA Levels

In order to identify Notch target genes in a series of breast cancer cell lines the effect of gamma secretase inhibitor (GSI) treatment on the mRNA expression of genes was evaluated. Affymetrix human U133A Arrays were used to profile treatment of HCC70, MDA-MB468 or HCC1143 cells with either DMSO or 10 μM DAPT (Calbiochem 565770) for 72 h. There were three replicates per time point. The R/Bioconductor framework was used and the Limma package was employed to determine differentially expressed genes between the DMSO treatment and the DAPT treatment. An adjusted P-value of 0.05 was used as the threshold to determine the set of differentially expressed genes. Ultimately, two target genes were selected per cell line, and are summarized in the table below. Hes1, MMP7 and VSNL1 mRNA levels are decreased upon inhibition of Notch signaling while DKK1 mRNA levels are increased upon inhibition of Notch signaling.

| Gene | Cell Line |
| --- | --- |
| PP1A | All |
| Hes1 | HCC1143, MDA-MB-468 |
| MMP7 | HCC1143 |
| DKK1 | MDA-MB-468 |
| Hey2 | HCC70 |
| VSNL1 | HCC70 |

To quantitate mRNA levels of the above genes, cell lines HCC70, MDA-MB-468 or HCC1143 were plated in 100 μL in 96-well plates (Costar, cat#3610) at a cell density of $1 \times 10^5$ cells/mL. Plates were incubated overnight at 37° C. before treatment with antibodies at appropriate concentrations. Treated plates were returned to the incubator for an extra 72 h before being lysed for RNA extraction using Qiagen's RNeasy kit (cat#74181). cDNA was synthesized using Taqman Reverse Transcription Reagents (Applied Biosystems, cat# N808-0234). mRNA expression was determined by real-time PCR (Taqman Fast Advanced Master Mix, Applied Biosystems, cat#4444557). Real-time PCR was run in a ViiA 7 Real-Time PCR System or 7900HT Fast Real-Time PCR System (Applied Biosystems). To quantitate the levels of each target gene, 2-[delta][delta]Ct method was employed. Calculation of deltadelta Ct involves comparing the Ct values of the samples of interest with a control such as a non-treated sample or DMSO treated sample (Schmittgen and Livak 2008 Nature Protocols 3: 1101-1108)

Summary and Discussion

As shown in FIG. 8, Notch3 antibodies were identified that could inhibit endogenous Notch3 signaling in a series of breast cancer cell lines. Treatment of breast cancer cell lines with Notch3 antibodies resulted in decreased expression of HES1 or MMP7 mRNA and increased expression of DKK1 mRNA.

Example 5: Identification and Characterization of Mutations in Notch3 NRR and PEST Domains To date, the evidence for Notch receptors in cancer has focused primarily on alterations in Notch1 signaling. Although Notch3 is amplified in ovarian cancer there is no direct evidence that its amplification leads to dependence on Notch3 signaling. In addition, there is no evidence for activating mutations in Notch3. Notch 3 was sequenced in a panel of cells lines to identify mutations in the gene for further characterization.

The Cancer Cell Line encyclopedia (CCLE) was used to characterize 947 human cancer cell lines (Barretina J. et al. (2012) Nature 483:603-7). Mutation information was obtained for >1600 genes by massively parallel sequencing using a solution phase hybrid capture technology. Multiplexed libraries for exome capture sequencing were constructed as described using the SureSelect Target Enrichment system (Aligent Technologies). Notch3 was one of the genes sequenced and the data was analyzed to identify any mutations in the NRR (exon 25, 26, amino acid 1378-1640) and PEST (exon 33 amino acid 1972-2322) domains of the protein. Upon close examination of the sequence data from the 947 cancer cell lines, it was determined that there was insufficient sequence coverage in exons 25 and 33 to identify mutations. The table shows the average coverage of exons in Notch3. The numbers listed are the average number of reads per base pair in Table 3.

TABLE 3

Notch 3 Exon reads.

| Exon of Notch3 | Average coverage |
| --- | --- |
| e01 | 0.03 |
| e02 | — |
| e03 | — |
| e04 | 10.49 |
| e05 | 595.39 |
| e06 | 277.47 |
| e07 | 79.71 |
| e08 | 99.63 |
| e09 | 210.51 |
| e10 | 0.58 |
| e11 | 42.39 |
| e12 | 558.77 |
| e13 | 0.77 |
| e14 | 0.66 |
| e15 | 1.71 |
| e16 | 168.88 |
| e17 | 1.65 |
| e18 | 1.13 |
| e19 | 111.12 |
| e20 | 53.03 |
| e21 | 414.89 |
| e22 | 12.79 |

TABLE 3-continued

Notch 3 Exon reads.

| Exon of Notch3 | Average coverage |
| --- | --- |
| e23 | 6.72 |
| e24 | — |
| e25 | 0.44 |
| e26 | 171.70 |
| e27 | 52.77 |
| e28 | 3.44 |
| e29 | 36.78 |
| e30 | 280.90 |
| e31 | 404.35 |
| e32 | 223.13 |
| e33 | 1.27 |

In order to determine whether any of these cell lines or primary tumors contain mutations in these regions, three approaches were used including Sanger Sequencing (Genewiz), RainDance (Tewhey et al. (2009) Nature Biotechnology 27:1025-1031) and RNAseq (Wang et al. (2009) Nature Reviews Genetics 10:57-63). Mutations were identified in both the NRR and PEST domain in multiple cell lines and tumor samples as shown in FIG. 9. In FIG. 9a the upper panel shows cells lines with NRR mutations while the lower panel has PEST mutations. The NRR mutations identified in primary tumors are indicated in FIG. 9b.

Isolation of Primary Tumors and Generation of a Bank of Primary Tumor Xenografts Data obtained from primary human tumor xenografts was generated in the following manner: tumor specimens were collected in RPMI supplemented with 1% penicillin/streptomycin from patients during surgical resection with ischemic time less than one hour. Fragments of 15-30 mm$^3$ free of necrotic tissue were grafted subcutaneously into interscapular fat pad of 6- to 8-week-old female nude mice under isoflurane anesthesia. Mice were maintained in specific pathogen-free animal housing and handled in accordance with approved protocols and regulations. Xenografts appeared at the graft site 2 to 8 months after grafting. They were subsequently transplanted from mouse to mouse once tumors reached 700-800 mm$^3$ until a reasonably consistent growth rate is achieved. Frozen stocks in RPMI supplemented with 50% FBS and 10% DMSO were generated during serial passage in mice and were tested to ensure successful establishment of a xenograft model. Fragments of 30-50 mg from patients and xenografts at each passage were snap frozen for gene expression profiling, copy number as well as mutation analyses. Fragments of 150 mg of each successfully engrafted xenograft model were also collected and subject to histological analysis. An established tumor xenograft model was further used for in vivo studies after passage four. For gene expression profiling, total RNA was isolated using affinity resin (QIAGEN RNeasy Mini Kit; QIAGEN AG). RNA integrity and purity were assessed with the RNA 6000 Nano LabChip system on a Bioanalyzer 2100 (Agilent Technologies).

Example 6: Characterization of Notch3 NRR Mutations in a Reporter Gene Assay Generation of Notch3 Expression Vectors with Notch3 NRR Mutations Two mutations were selected for characterization. TALL-1 cells are a t-cell acute lymphoblastic cell line with a S1580L mutation. TALL-1 cells were purchased from DSMZ (#ACC 521). A breast tumor (X-1004) was also identified with a G1487D mutation. The RNA used for RNAseq analysis to detect mutations in the X-1004 sample was from a passage 5 mouse. These mutations were introduced into the vector pLNCX2 Notch3-GAL4-NLS-VP16.

Constructs

Notch3_S1580L_Gal4-VP16
(SEQ ID NO: 276)
MGPGARGRRRRRRPMSPPPPPPPVRALPLLLLLAGPGAAAPPCLDGSPCA

NGGRCTQLPSREAACLCPPGWVGERCQLEDPCHSGPCAGRGVCQSSVVAG

TARFSCRCPRGFRGPDCSLPDPCLSSPCAHGARCSVGPDGRFLCSCPPGY

QGRSCRSDVDECRVGEPCRHGGTCLNTPGSFRCQCPAGYTGPLCENPAVP

CAPSPCRNGGTCRQSGDLTYDCACLPGFEGQNCEVNVDDCPGHRCLNGGT

CVDGVNTYNCQCPPEWTGQFCTEDVDECQLQPNACHNGGTCFNTLGGHSC

VCVNGWTGESCSQNIDDCATAVCFHGATCHDRVASFYCACPMGKTGLLCH

LDDACVSNPCHEDAICDTNPVNGRAICTCPPGFTGGACDQDVDECSIGAN

PCEHLGRCVNTQGSFLCQCGRGYTGPRCETDVNECLSGPCRNQATCLDRI

GQFTCICMAGFTGTYCEVDIDECQSSPCVNGGVCKDRVNGFSCTCPSGFS

GSTCQLDVDECASTPCRNGAKCVDQPDGYECRCAEGFEGTLCDRNVDDCS

PDPCHHGRCVDGIASFSCACAPGYTGTRCESQVDECRSQPCRHGGKCLDL

VDKYLCRCPSGTTGVNCEVNIDDCASNPCTFGVCRDGINRYDCVCQPGFT

GPLCNVEINECASSPCGEGGSCVDGENGFRCLCPPGSLPPLCLPPSHPCA

HEPCSHGICYDAPGGFRCVCEPGWSGPRCSQSLARDACESQPCRAGGTCS

SDGMGFHCTCPPGVQGRQCELLSPCTPNPCEHGGRCESAPGQLPVCSCPQ

GWQGPRCQQDVDECAGPAPCGPHGICTNLAGSFSCTCHGGYTGPSCDQDI

NDCDPNPCLNGGSCQDGVGSFSCSCLPGFAGPRCARDVDECLSNPCGPGT

CTDHVASFTCTCPPGYGGFHCEQDLPDCSPSSCFNGGTCVDGVNSFSCLC

RPGYTGAHCQHEADPCLSRPCLHGGVCSAAHPGFRCTCLESFTGPQCQTL

VDWCSRQPCQNGGRCVQTGAYCLCPPGWSGRLCDIRSLPCREAAAQIGVR

LEQLCQAGGQCVDEDSSHYCVCPEGRTGSHCEQEVDPCLAQPCQHGGTCR

GYMGGYMCECLPGYNGDNCEDDVDECASQPCQHGGSCIDLVARYLCSCPP

GTLGVLCEINEDDCGPGPPLDSGPRCLHNGTCVDLVGGFRCTCPPGYTGL

RCEADINECRSGACHAAHTRDCLQDPGGGFRCLCHAGFSGPRCQTVLSPC

ESQPCQHGGQCRPSPGPGGGLTFTCHCAQPFWGPRCERVARSCRELQCPV

GVPCQQTPRGPRCACPPGLSGPSCRSFPGSPPGASNASCAAAPCLHGGSC

RPAPLAPFFRCACAQGWTGPRCEAPAAAPEVSEEPRCPRAACQAKRGDQR

CDRECNSPGCGWDGGDCSLSVGDPWRQCEALQCWRLFNNSRCDPACSSPA

CLYDNFDCHAGGRERTCNPVYEKYCADHFADGRCDQGCNTEECGWDGLDC

ASEVPALLARGVLVLTVLLPPEELLRSSADFLQRLSAILRTSLRFRLDAH

GQAMVFPYHRPSPGSEPRARRELAPEVIGLVVMLEIDNRLCLQSPENDHC

FPDAQSAADYLGALSAVERLDFPYPLRDVRGEPLEPPEPSVPLLPLLVAG

AVLLLVILVLGVMVARRKRVDKLLSSIEQACDICRLKKLKCSKEKPKCAK

CLKNNWECRYSPKTKRSPLTRAHLTEVESRLERLEQLFLLIFPREDLDMI

LKMDSLQDIKALLTGLFVQDNVNKDAVTDRLASVETDMPLTLRQHRISAT

-continued
SSSEESSNKGQRQLTVSKLKLLSSIEQACPKKKRKVDEFPGISTAPPTDV

SLGDELHLDGEDVAMAHADALDDFDLDMLGDGDSPGPG

Notch3_G1487D_Gal4-VP16
(SEQ ID NO: 277)
MGPGARGRRRRRPMSPPPPPPPVRALPLLLLLAGPGAAAPPCLDGSPCA

NGGRCTQLPSREAACLCPPGWVGERCQLEDPCHSGPCAGRGVCQSSVVAG

TARFSCRCPRGFRGPDCSLPDPCLSSPCAHGARCSVGPDGRFLCSCPPGY

QGRSCRSDVDECRVGEPCRHGGTCLNTPGSFRCQCPAGYTGPLCENPAVP

CAPSPCRNGGTCRQSGDLTYDCACLPGFEGQNCEVNVDDCPGHRCLNGGT

CVDGVNTYNCQCPPEWTGQFCTEDVDECQLQPNACHNGGTCFNTLGGHSC

VCVNGWTGESCSQNIDDCATAVCFHGATCHDRVASFYCACPMGKTGLLCH

LDDACVSNPCHEDAICDTNPVNGRAICTCPPGFTGGACDQDVDECSIGAN

PCEHLGRCVNTQGSFLCQCGRGYTGPRCETDVNECLSGPCRNQATCLDRI

GQFTCICMAGFTGTYCEVDIDECQSSPCVNGGVCKDRVNGFSCTCPSGFS

GSTCQLDVDECASTPCRNGAKCVDQPDGYECRCAEGFEGTLCDRNVDDCS

PDPCHHGRCVDGIASFSCACAPGYTGTRCESQVDECRSQPCRHGGKCLDL

VDKYLCRCPSGTTGVNCEVNIDDCASNPCTFGVCRDGINRYDCVCQPGFT

GPLCNVEINECASSPCGEGGSCVDGENGFRCLCPPGSLPPLCLPPSHPCA

HEPCSHGICYDAPGGFRCVCEPGWSGPRCSQSLARDACESQPCRAGGTCS

SDGMGFHCTCPPGVQGRQCELLSPCTPNPCEHGGRCESAPGQLPVCSCPQ

GWQGPRCQQDVDECAGPAPCGPHGICTNLAGSFSCTCHGGYTGPSCDQDI

NDCDPNPCLNGGSCQDGVGSFSCSCLPGFAGPRCARDVDECLSNPCGPGT

CTDHVASFTCTCPPGYGGFHCEQDLPDCSPSSCFNGGTCVDGVNSFSCLC

RPGYTGAHCQHEADPCLSRPCLHGGVCSAAHPGFRCTCLESFTGPQCQTL

VDWCSRQPCQNGGRCVQTGAYCLCPPGWSGRLCDIRSLPCREAAAQIGVR

LEQLCQAGGQCVDEDSSHYCVCPEGRTGSHCEQEVDPCLAQPCQHGGTCR

GYMGGYMCECLPGYNGDNCEDDVDECASQPCQHGGSCIDLVARYLCSCPP

GTLGVLCEINEDDCGPGPPLDSGPRCLHNGTCVDLVGGFRCTCPPGYTGL

RCEADINECRSGACHAAHTRDCLQDPGGGFRCLCHAGFSGPRCQTVLSPC

ESQPCQHGGQCRPSPGPGGGLTFTCHCAQPFWGPRCERVARSCRELQCPV

GVPCQQTPRGPRCACPPGLSGPSCRSFPGSPPGASNASCAAAPCLHGGSC

RPAPLAPFFRCACAQGWTGPRCEAPAAAPEVSEEPRCPRAACQAKRGDQR

CDRECNSPGCGWDGGDCSLSVGDPWRQCEALQCWRLFNNSRCDPACSSPA

CLYDNFDCHAGGRERTCNPVYEKYCADHFADGRCDQDCNTEECGWDGLDC

ASEVPALLARGVLVLTVLLPPEELLRSSADFLQRLSAILRTSLRFRLDAH

GQAMVFPYHRPSPGSEPRARRELAPEVIGSVVMLEIDNRLCLQSPENDHC

FPDAQSAADYLGALSAVERLDFPYPLRDVRGEPLEPPEPSVPLLPLLVAG

AVLLLVILVLGVMVARRKRVDKLLSSIEQACDICRLKKLKCSKEKPKCAK

CLKNNWECRYSPKTKRSPLTRAHLTEVESRLERLEQLFLLIFPPREDLDMI

LKMDSLQDIKALLTGLFVQDNVNKDAVTDRLASVETDMPLTLRQHRISAT

SSSEESSNKGQRQLTVSKLKLLSSIEQACPKKKRKVDEFPGISTAPPTDV

SLGDELHLDGEDVAMAHADALDDFDLDMLGDGDSPGPG

Retrovirus was produced by transfecting 293-GP2 Packaging Cell Line (Clontech, cat#631458) with the appropriate retroviral vector. Promega's Fugene6 was used as the lipid-based transfection reagent. Transfection was carried out according to manufacturer's instructions. Virus was collected at 48 hrs after transfection and immediately used to transduce HLR cells (HLR-PathDetect, Stratage). HLR cells (Stratagene) were transduced with either Notch3 wt-Gal4-VP16, Notch3_p.S1850L-Gal4-VP16 or Notch3_p.G1487D-Gal4-VP16 retroviral particles. Cells were selected with G418 for 2 weeks before testing.

Notch3 Reporter Gene Assay to Assess Basal Activity of Notch3 Wild-Type and Notch3 NRR Mutant Receptors Notch3 reporter gene assay: HLR-Notch3 wt-Gal4-VP16, HLR-Notch3_p.S1580L-Gal4-VP16 and HLR-Notch3_p.G1487D-Gal4-VP16 cells were maintained in DMEM no phenol red, 10% FBS (Hyclone, cat# SH30071), 1% penicillin-streptomycin (Gibco cat#15140-122), L-Glutamine (Gibco, cat#25030-081), 100 µg/mL hygromycin (Gibco, cat#10687-010) and 400 µg/mL G418 (Gibco, cat#10131-027). The HLR parental line was maintained in DMEM no phenol red, 10% FBS (Hyclone, cat# SH30071), 1% penicillin-streptomycin (Gibco cat#15140-122), L-Glutamine (Gibco, cat#25030-081) and 100 µg/mL hygromycin (Gibco, cat#10687-010). Sub-confluent cells grown in complete medium were washed with PBS (Gibco, cat#20012-027), trypsinized with TrypLE (Gibco, cat#12605010), and diluted into $4 \times 10^4$ cells/mL; 100 µL of cell suspension was plated in 96-well clear bottom white plates (Costar, cat#3610) at a density of 4000 cells/well. All plates were then incubated overnight at 37° C. prior to treatment with DAPT (10 µM, CalBiochem). Plates were returned to the incubator for 24 hrs before luciferase activity was determined using Bright-Glo (Promega). The Envision plate reader (PerkinElmer) was used to determine amount of luminescence.

FACS Assay to Assess Cell Surface Levels of Wild-Type and Mutant Notch3 Receptors To demonstrate expression of mutant Notch3 receptors in a cell line, flow cytometry was used. Cell lines expressing mutant Notch3 and wild-type Notch3 (grown under standard conditions) were mixed with an anti-Notch3 binding and detection antibody that contains an APC fluorescein label (R&D cat# FAB1559A) in PBS containing 0.1% BSA and 0.01% sodium azide, and incubated for 1 hr at 4° C. After washing, the cells were analyzed by BD FACSCanto instrument using light and side scatter properties to gate on single cells.

The level of Notch3 receptors on the cell surface was determined by binding of commercially available anti-Notch3 APC (R&D # FAB1559A) labeled antibody to cells expressing mutant and endogenous Notch3 and assessed by FACS. Cells were trypsinized (Invitrogen TrypLE cat#12605-010) and diluted to $2 \times 10^6$ cells/mL in FACS Buffer (PBS/3% FBS/0.01% NaN3). $2.5 \times 10^5$ cells/well were added to each well of a 96 well plate (Corning cat#3610) and centrifuged at 1500 rpm for 5 min at 4° C. before removing the supernatant. Anti-Notch3 APC antibody or Sheep IgG Isotype Control labeled with APC (R&D cat#IC016A) was added to the cell pellets at a final concentration of 0.1 µg in 100 µL of FACS buffer and incubated for 1 hour at 4° C. The cells were washed and pelleted 2 times with 100 µL FACS Buffer. Finally cells were resuspended in 200 µL FACS buffer and fluorescence values were measured with a BD FACSCanto (BD Biosciences). The amount of cell surface bound anti-Notch3 APC antibody was assessed by measuring the mean channel fluorescence.

Summary and Discussion

Introduction of either a S1580L mutation or a G1487D mutation into a Notch3 receptor resulted in an approximately 10 fold increase in the basal signaling from the receptor relative to a wild-type control. In this system the wild-type and mutant receptors were expressed at approximately equivalent levels as determined by FACS assay. This data suggests that these mutations activate Notch3 signaling in cell lines and tumors expressing these and other similar mutations (see further discussion in Examples 7, 9, 10, 11, 15).

Example 7: Effect of Notch3 Antibodies on Notch3 Signaling and In Vitro Proliferation in TALL-1 Cells The TALL-1 cell line has a mutation in the NRR domain of Notch3 at S1580L. Introduction of this mutation into a Notch3 expression construct resulted in activation of Notch3 signaling. To further characterize the effects of inhibition of Notch3 signaling in this cells line, the mRNA levels of Notch target genes were examined and the in vitro proliferation of the cells was monitored in the presence of Notch 3 antibodies.

TALL-1 In Vitro Proliferation Assay $1 \times 10^4$ TALL-1 cells/well were seeded into 96-well tissue culture plates (Corning, Catalog #3610) in 100 ul medium (RPMI-1640 supplemented with 10% fetal bovine serum and 1% penicillin/streptomycin). The same day, antibody dilutions were prepared in 1×PBS from which 5 µl of 20× antibody dilution was added per well. Cells were incubated with antibody at 37° C./5% $CO_2$. After incubation for 0 and 9 days at 37° C./5% $CO_2$, 100 µl of CellTiter-Glo reagent (Promega) was added and the plates were incubated for 10 min on plate shaker. The amount of luminescence was determined using a Perkin Elmer Envision plate reader. CellTiter-Glo luminescene values of cells treated with an IgG control were used to normalize the data and calculate percentage inhibition of proliferation due to treatment with Notch3 antibodies.

TALL-1 mRNA Quantitation Assay

Deltex1 is a well characterized target gene of Notch signaling in TALL lines (Weng et al., 2006, Genes Dev. 20:2096-2109). $1 \times 10^4$ TALL-1 cells/well were seeded into 96-well tissue culture plates (Corning, cat#3610) in 100 µl medium (RPMI-1640 supplemented with 10% fetal bovine serum and 1% penicillin streptomycin). The same day, antibody and compound dilutions were prepared in 1×PBS from which 5 µl of 20× antibody or compound dilution was added per well. DAPT (Calbiochem, cat#565770) and DMSO (ATCC, Catalog #4-X-5) were the compounds used for this assay. Cells were incubated with antibody or compound at 37° C./5% $CO_2$ for 72 hr. RNA was isolated using the Qiagen RNeasy 96 kit. cDNA was made using the TaqMan Reverse Transcription reagents (Life Technologies) and the MJ Research PTC-225 Thermal cycler. TaqMan gene expression assays were run using TaqMan Universal PCR Master Mix (Life Technologies) along with gene expression probes for Deltex1 (DTX1) (Hs00269995_m1, Life Technologies) and the housekeeping gene PP1A (Hs99999904_m1, Life Technologies). TaqMan gene expression assays were run on the Applied Biosystems ABI Prism 7900HT Fast Real-Time PCR system. To quantitate the levels of Deltex 1, 2-[delta][delta]Ct method was employed. Calculation of delta delta Ct involves comparing the Ct values of the samples of interest with a control such as a non-treated sample or DMSO treated sample (Schmittgen and Livak (2008) Nature Protocols 3: 1101-1108).

Summary and Discussion

Figure 11A:
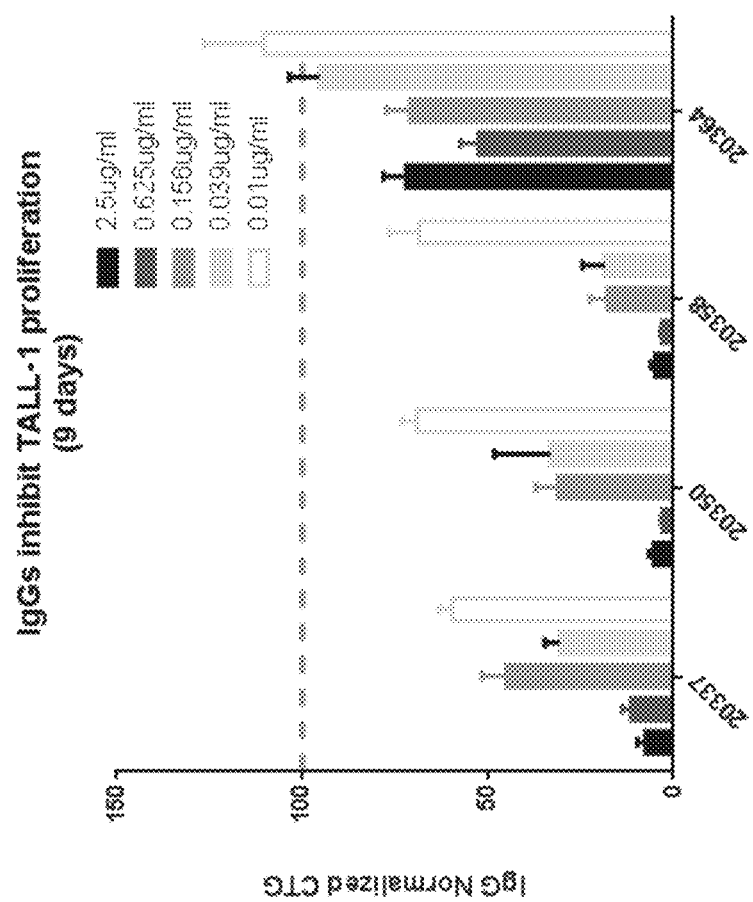
FIG. 11A-B: Graphs showing TALL-1 mRNA and inhibition of proliferation in the presence of Notch 3 antibodies.
Figure 11B:
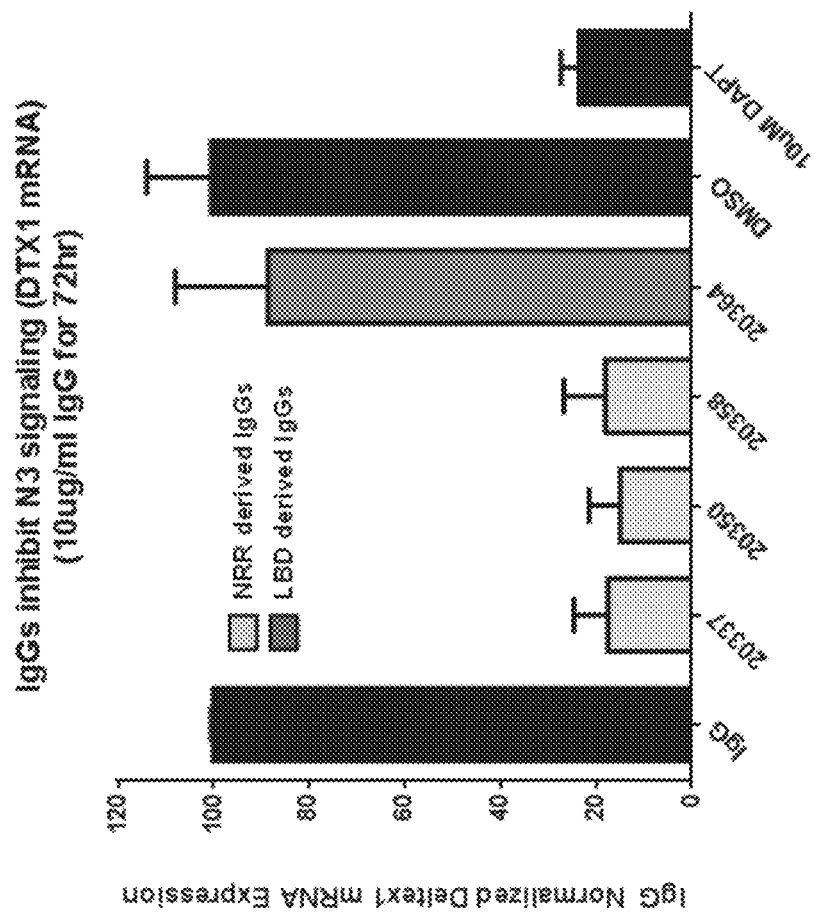

As shown in FIGS. 11A-B, Notch3 antibodies that were identified from pannings against NRR domain or EGF32-NRR domain (20350, 20358, 20337) potently inhibited Deltex1 mRNA expression in TALL-1 cells. In contrast antibodies directed to the LBD domain (20364) did not significantly inhibit Deltex1 mRNA. In addition, 20350, 20358, 20337 significantly inhibited TALL-1 proliferation in a dose-dependent manner. When Notch3 antibodies were tested in a panel of other TALL cell lines (DND41, P12-Ichikawa, SUPT1, SUPT11 and RPMI-8402), no effects on proliferation of were detected.

Example 8: Generation of a Neo-Epitope Antibody that Detects the Gamma Secretase Cleaved Form of the Notch3 Intracellular Domain Notch signaling is activated by a series of proteolytic cleavages. The gamma secretase complex mediates the final cleavage of the Notch receptor ultimately releasing the Notch intracellular domain (ICD) that translocates to the nucleus to activate Notch target gene transcription. A neo-epitope antibody was generated to detect the gamma secretase cleaved form of the Notch3 ICD (ICD3) only when cleaved between amino acids Gly 1661 and Val 1662 (human Notch3).

Generation of a ICD3 Rabbit Polyclonal Antibody

The peptides used for immunization and negative selection (depletion peptide) are indicated.

Immunization peptide: $H_2$N-VMVARRK(dPEG4)C-amide (SEQ ID NO: 278).

Depletion peptide: Ac-VILVLGVMVARRK(dPEG4)C-amide (SEQ ID NO: 279). A rabbit polyclonal antibody was generated at Covance using standard procedures. Briefly, a 77 day protocol was employed with a primary boost with 500 µg of immunizing peptide and Freund's adjuvant. Additional boosts with 500 µg of immunizing peptide were performed on day 21, 42 and 63. To deplete non-specific antibodies that recognize the VMVARRK (SEQ ID NO: 243) sequence of Notch3, but not the neo-epitope following gamma secretase cleavage, a depletion peptide was used for negative selection. The purified sample was depleted using the depletion peptide by "negative" affinity chromatography. Peptides were coupled to a column using terminal cysteine to properly orient the peptide. Cross reacting antibodies were removed from the sample and confirmed by ELISA. Serum from rabbit was tested by Western blot in TALL-1 cells to determine if a specific band was detected.

Conversion of the Rabbit Polyclonal ICD3 Antibody to a Rabbit Monoclonal Antibody To convert the rabbit polyclonal antibody to a rabbit monoclonal antibody, a final IV boost of immunizing peptide was performed on the selected rabbit. 4 days later a splenectomy was performed and rabbit hybridomas were generated by standard procedures at Epitomics. Briefly all the lymphocytes from 1 rabbit spleen were isolated. Fusion and standard ELISA screen of 40×96 well plates was performed. All ELISA positive hybridomas were expanded to 24 well plates and an ELISA was again performed with both the immunizing peptide and the depletion peptide. Supernatant from the 139 positive hybridomas were analyzed by Western blotting in TALL-1 cells. Based on Western screening of the ELISA positive hybridomas, 3 hybridomas (73, 128, 95) were chosen for subcloning. To subclone hybridomas, a limited dilution of the selected parental hybridomas (0.5 cells/well) was performed and these sub-clones were plated in 4×96 well plates. Subclones were again screened by ELISA using both the immunizing peptide and the depletion peptide. Clones were expanded to 24 well plates and supernatants from ELISA positive sub-clones were screened by Western blotting in TALL-1 cells. Exemplary Western data from 3 sub-clones are shown. (FIG. 12A). The sequence of the rabbit polyclonal antibody was determined using standard techniques and is shown in Table 2, "ICD3 Ab".

In Vitro Screening of Notch3 Signaling Inhibition Using an ICD3 Antibody

An antibody targeting the Notch3 ICD was used to assess pathway activity. Cell line TALL-1 was purchased from DSMZ and routinely maintained in growth media supplemented with 10% FBS and 1% Penicillin-Streptomycin. Experimental set up: 5 million TALL-1 cells were plated in 10 mL of medium in a 25 cm² tissue culture flask (Corning, cat#430639). Cells were treated with either 0.5% DMSO or 10 µM DAPT (Calbiochem, cat#565770) for 72 h. TALL-1 cells were spun down and then washed in PBS. Cells were lysed in 60 µL of 1× Cell Lysis Buffer (CST, cat#9803) with the addition of N-ethylmaleimide (Thermo Scientific, cat#23030) and protease and phosphatase inhibitors (Pierce, Cat#78444). Protein quantitation was performed using the BCA method and read in a Spectramax M5 microplate reader. 30 µL of protein samples were loaded per well in a 4-12% Bis-Tris gel (Invitrogen, cat# NP0006-1).

SDS-PAGE: Samples were run under standard conditions in 1× NuPage MOPS SDS running buffer (Invitrogen, cat# NP0001) for approximately 90 min at 180 V. Before transfer to a nitrocellulose membrane (iBlot, Invitrogen), gels were soaked in 2× Transfer Buffer (Invitrogen, cat#NP0006-1) with 20% methanol. Membranes were blocked in 4% milk-TBST for one hour; supernatants from hybidoma supernatants were diluted 1:4 in 2% milk-TBST and incubated ON at 4° C. with gentle shaking. Secondary antibodies were added in 2% milk-TBST for 45 minutes, after a series of membrane washes with TBST. Membrane was developed using ECL Plus Western Detection System (GE healthcare, cat# RPN2232).

Screening of a Panel of T-Cell Acute Lymphoblastic Leukemia Cells Lines with an ICD3 Antibody.

Cell lines TALL-1 (# ACC521), RPMI8402 (#ACC290), DND41 (#ACC525), SUPT11 (#ACC605), and P12-Ichikawa (#ACC34) were purchased from DSMZ and routinely maintained in growth media supplemented with 10% FBS and 1% Penicillin-Streptomycin. Cell lines HPB-ALL and Jurkat cells were obtained commercially from Andreas Strasser (Walter and Eliza Hall Institute of Medical Research, Australia. 5 million TALL-1 cells were plated in 10 mL of medium in a 25 cm² tissue culture flask (Corning, cat#430639). Cells were spun down and then washed in PBS. Cells were lysed and Western performed as described above. Purified antibody from hybridoma sub-clone 73-8 was used for further studies at a 1:5000 dilution. This antibody is hereafter referred to as "ICD3 Ab" and its sequence is detailed in Table2. ICD1 protein levels were assessed using an antibody from Cell Signaling (#2421) at a dilution of 1:1000.

Summary and Discussion

Figure 12B:
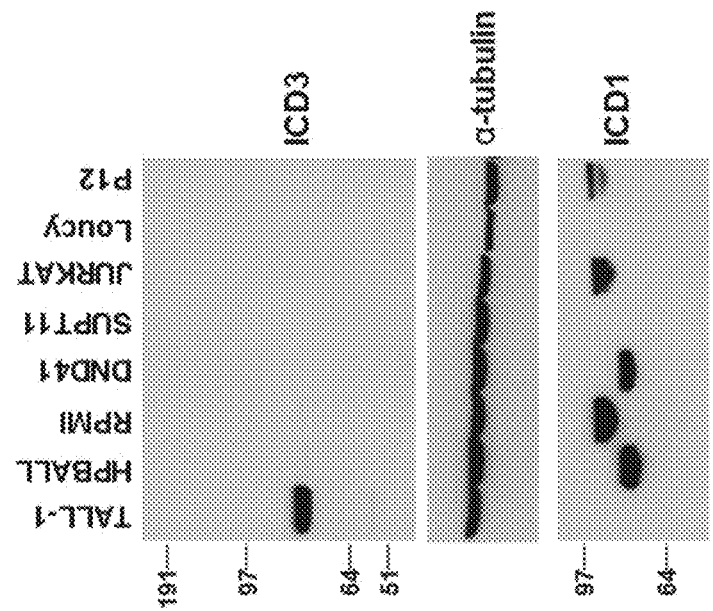
FIG. 12A-B: Photographs of Western blots showing the presence of a neo-epitope ICD3 antibody in TALL-1 cells only.
Figure 12A:
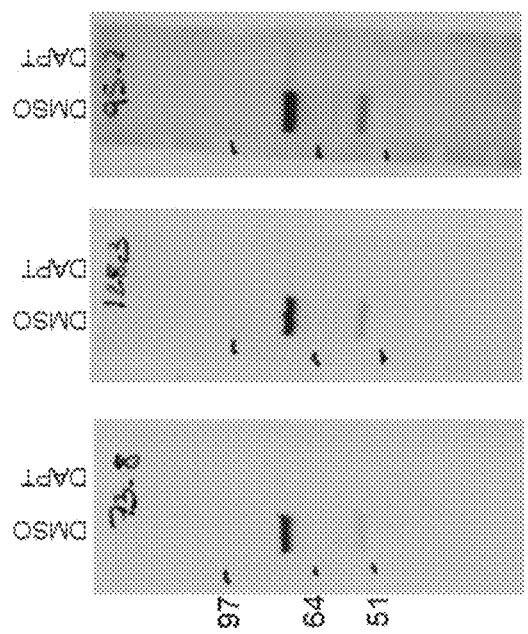

As shown in FIGS. 12A-B, high levels of ICD3 protein was only detected in TALL-1 cells but not in a panel of other T-cell acute lymphoblastic leukemia cell lines. High ICD1 levels can be detected in several TALL lines including HPBALL, RPMI-8402, DND41, P12 Ichikawa and Jurkat, which are known to have activating mutations in Notch1 (Weng et al. (2004) Science 306:269-71). The ICD3 antibody does not cross-react with ICD1 as evidenced by lack of signal in these other TALL lines with Notch1 mutations.

Example 9: In Vitro Assessment of Notch3 Signaling Inhibition Upon Antibody Treatment Evaluation of Notch3 mutation status in the panel of CCLE lines resulted in identification of TALL-1 with an NRR mutation and MDA-MB468 with a PEST domain mutation. MDA-MB468 cells have a frameshift mutation at amino acid 2034 which results in introduction of a premature stop codon. Therefore the ICD3 has an altered molecular weight which can be detected as a faster migrating band on a Western blot.

Sequences of Portions of WT and MDAMB468 PEST Domain:

WT Notch3 sequence (NP_000426) amino acid 2034-end
(SEQ ID NO: 280)
PSGPRSPPGPHGLGPLLCPPGAFLPGLKAAQSGSKKSRRPPGKAGLGPQG

PRGRGKKLTLACPGPLADSSVTLSPVDSLDSPRPFGGPPASPGGFPLEGP

YAAATATAVSLAQLGGPGRAGLGRQPPGGCVLSLGLLNPVAVPLDWARLP

PPAPPGPSFLLPLAPGPQLLNPGTPVSPQERPPPYLAVPGHGEEYPAAGA

HSSPPKARFLRVPSEHPYLTPSPESPEHWASPSPPSLSDWSESTPSPATA

TGAMATTTGALPAQPLPLSVPSSLAQAQTQLGPQPEVTPKRQVLA

MDA-MB468 sequence amino acid 2034-end
(SEQ ID NO: 281)
PSGPRSPPRSPRPGASALSSRGLPPWPQSGTVGVQEEQEAPREGGAGAAG

APGAGQEADAGLPGPPG

Initially these 2 cell line models were used to characterize the effects of Notch3 inhibitory antibodies on Notch3 signaling. Western blots with the ICD3 antibody were used to monitor signaling inhibition. Experimental set up: one million MDA-MB468 cells were plated in a 60 mm dish (Corning, cat#430196) in 3 mL of medium or 5 million TALL-1 cells in 10 mL of medium in a 25 cm² tissue culture flask (Corning, cat#430639). Plates were incubated overnight at 37° C. prior to treatment with 10 µg/mL final concentrations of Notch3 inhibitor antibodies 20337, 20350, 20358 and 20802 as well as an IgG control. Antibodies were added directly to the plate and they were further incubated for 72 hr at 37° C., 5% $CO_2$. In addition some cells were treated with either 0.5% DMSO or 10 µM DAPT (Calbiochem, cat#565770) for 72 h. Cells were harvested by aspirating the media and rinsing in 1 mL PBS (Gibco, cat#20012-027), scraping the cells off the plate, and spinning down on a bench top centrifuge. Suspension cells were spun down and then washed in PBS. Western blots were performed with the purified ICD3 antibody as described previously.

In addition, three other cells lines were characterized for ICD3 levels and signaling inhibition upon Notch3 antibody treatment:—(i) Ishikawaheraklio02_ER has a NRR mutation at N1597R, (ii) A549 has a PEST frameshift mutation at 2034, while (iii) TE-11 has a PEST frameshift mutation at 2260.

Summary and Discussion

Figure 13A:
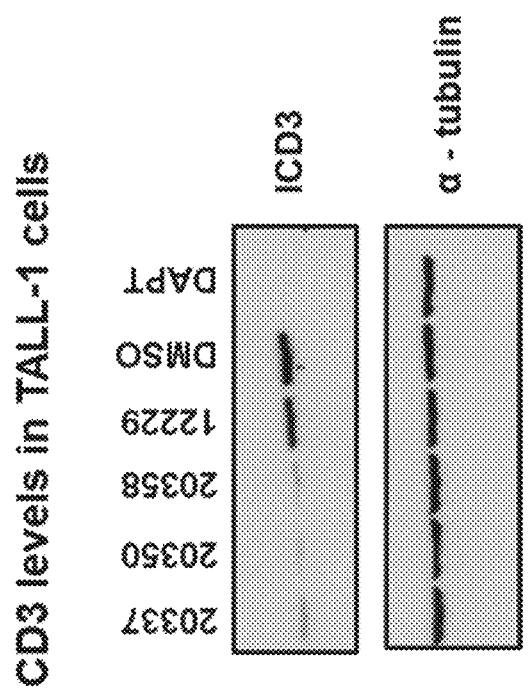
FIG. 13A-B: Photographs of Western blots showing decreased Notch 3 signaling with Notch 3 antibody treatment in TALL-1 cells and MDA-MB468 cells.
Figure 13B:
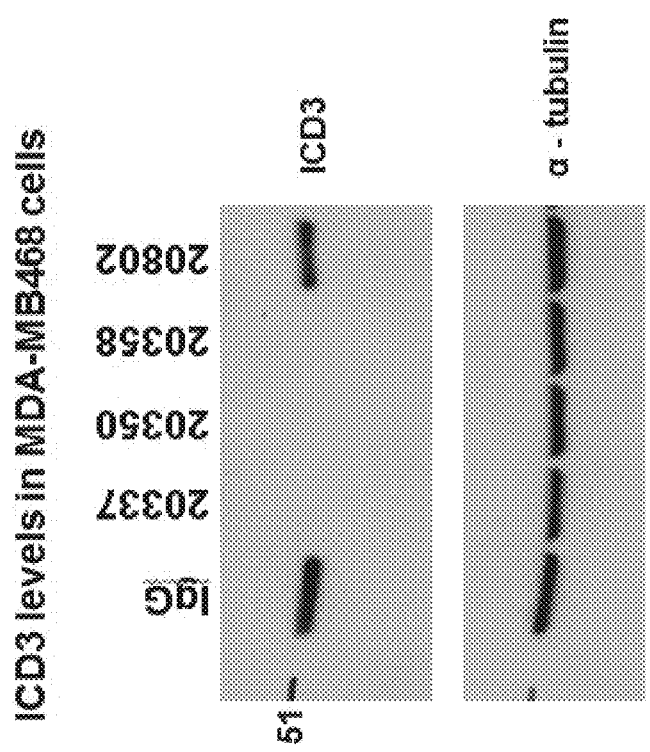
Figure 14B:
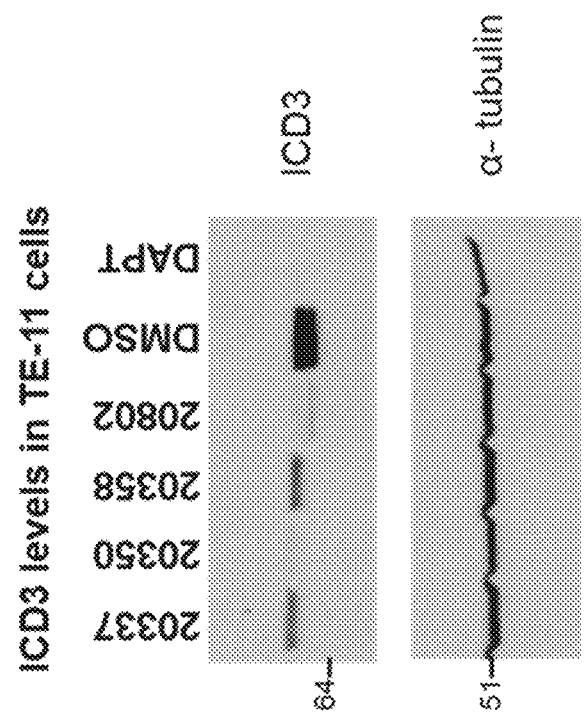
Figure 14C:
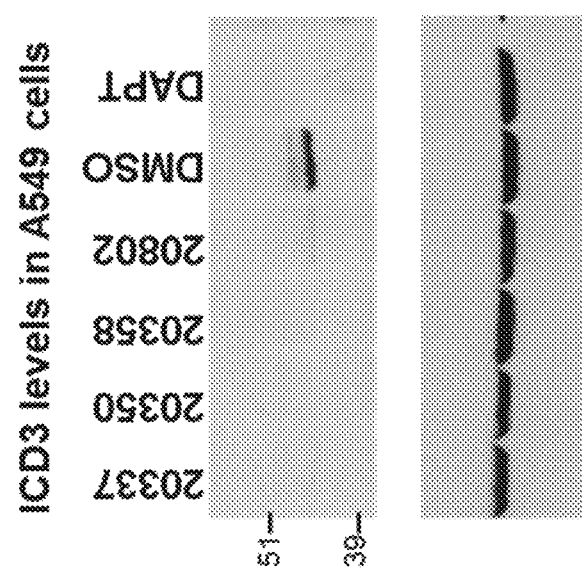

As shown in FIGS. 13A-B, in addition to the previously described ligand-driven RGA and Notch target gene mRNA quantitation, Notch3 signaling can also be monitored by measuring levels of ICD3. ICD3 levels are a membrane proximal readout of Notch3 signaling activity. Treatment of TALL-1 cells with Notch3 antibodies 20337, 20350, 20358 resulted in decreased levels of ICD3. Level of ICD3 was equivalent in the IgG control sample and the DMSO samples. This data is consistent with inhibition of Deltex1 mRNA and TALL-1 proliferation upon treatment with these antibodies. In contrast no effect on ICD3 levels was detected with 12229 treatment. As shown in FIG. 13 B, in MDA-MB468 cells, the frameshift mutation at amino acid 2034 results in a premature stop codon and smaller ICD3. This ICD3 can be detected as a faster migrating band on a Western blot. Upon treatment with Notch3 NRR antibodies 20337, 20350, 20358, decreased levels of ICD3 was detected. In contrast, treatment with 20802, a LBD antibody, did not alter ICD3 levels relative to a control IgG. As shown in FIG. 14 A-C, varying effects on ICD3 levels were detected upon Notch3 antibody treatment inIshikawaheraklio02_ER, TE-11, and A549 cells. However in all cell lines tested, 20350 treatment consistently resulted in significantly decreased ICD3 levels.

Example 10: In Vitro Assessment of Notch3 Signaling Inhibition Upon Antibody Treatment in a Notch3 Amplified Cell Line HCC1143 cells were described to have an amplification of Notch3 (Yamaguchi et al. (2008) Cancer Res. 68:1881-1888). The levels of active Notch3 signaling were examined in this cell line using the ICD3 antibody. Western blots with the ICD3 antibody were used to monitor signaling inhibition.

Figure 15:
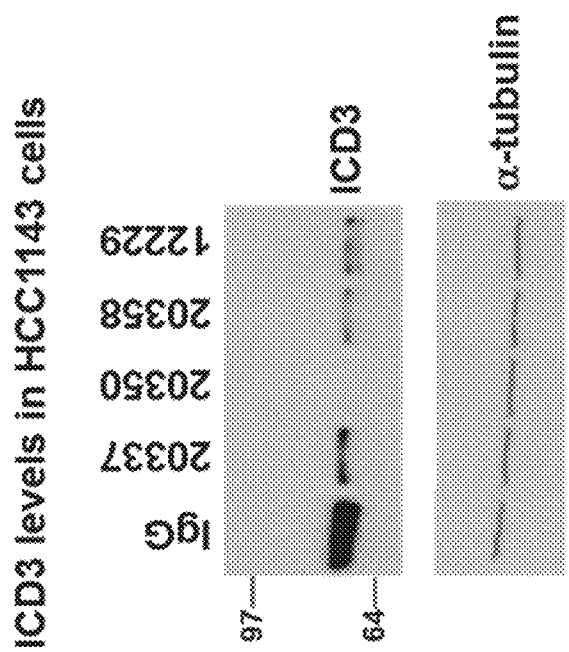
FIG. 15: Photographs of Western blots showing decreased Notch 3 signaling with Notch 3 antibody treatment in a Notch 3 amplified cell-line, HCC1143.

Experimental set up: one million HCC1143 cells were plated in a 60 mm dish (Corning, cat#430196) in 3 mL of medium in a 25 cm$^2$ tissue culture flask (Corning, cat#430639). Plates were incubated overnight at 37° C. prior to treatment with 10 µg/mL final concentrations of Notch3 inhibitor antibodies 20337, 20350, 20358 and 20802 as well as an IgG control. Antibodies were added directly to the plate and they were further incubated for 72 hr at 37° C., 5% CO$_2$. Cells were harvested and Western blots performed as described previously.
Summary and Discussion As shown in FIG. 15, HCC1143 cells are amplified for Notch3 and exhibit high levels of ICD3. All Notch3 antibody treatments resulted in decreased ICD3 levels. At 10 µg/ml, 20350 treatment resulted in the largest reduction of ICD3 levels.

Example 11: In Vivo PD Assessment

PD modulation was interrogated in three xenograft models harboring genetic aberrations in Notch3: the NRR mutant TALL-1 human leukemia model, the PEST mutant MDA-MB-468 human breast model, and the Notch3-amplified HLUX1823 patient-derived lung model.
In Vivo PD in the TALL-1 Human Leukemia Xenograft Model Female SCID-beige mice harboring TALL-1 xenografts were treated with a single dose of Notch3 antibodies. Mice were inoculated with 10×10$^6$ cells injected subcutaneously in a suspension of Hank's balanced salt solution. Once tumors reached between 300 and 500 mm$^3$ (n=3/group), mice were randomly assigned to receive a single intravenous 20 mg/kg dose of 3207 (IgG control), 20350, 20358 or 20802. Following treatment, tumors were harvested at selected time points and ICD3 was evaluated by Western blot and IHC, as described below.

In Vivo PD in the MDA-MB-468 Human Breast Cancer Xenograft Model

Female SCID-beige mice harboring MDA-MB-468 xenografts were treated with a single dose of Notch3 antibodies. A 3×3×3 mm$^3$ tumor fragment was passaged from a MDA-MB-468 tumor bearing mouse (donor) and implanted subcutaneously into SCID-beige recipient mice on both the left and right flank. Once tumors reached between 300 and 500 mm$^3$ (n=3/group), mice were randomly assigned to an untreated control group or received a single intravenous 20 mg/kg dose of 20350. In additional studies, the effects of a single intravenous 20 mg/kg dose of 20350, 20358, 20337 and 20802 relative to PBS or 3207 non-targeting IgG controls was assessed. Following the various treatments, tumors were harvested and ICD3 was evaluated by Western blot, as described below.
In Vivo PD in the HLUX1823 Patient Derived Lung Cancer Xenograft Model The activity of anti-Notch3 antibodies was also evaluated in a Notch3-amplified patient-derived primary lung cancer tumor xenograft model, HLUX-1823. In these studies, nu/nu mice were implanted subcutaneously with 3×3×3 mm$^3$ tumor fragments containing 50% phenol-red free matrigel (BD Biosciences) in DMEM and reached approximately 250 mm$^3$ at 30 days post-implantation. Once tumors reached between 300 and 500 mm$^3$ (n=3/group), mice were randomly assigned to receive either PBS or a single 20 mg/kg intravenous dose of either the 3207 non-targeting IgG control antibody, or 20358 or 12229 (the parental antibody from which 20364 and 20802 were derived). Following the various treatments, tumors were harvested and ICD3 was evaluated by Western blot, as described below.
Preparation of Tumor Cell Lysates and ICD3 Western Tumor samples were lysed in 200-400 µL of T-PER Tissue Protein Extraction Reagent (Pierce, cat#78510) with Complete mini EDTA free protease inhibitor cocktail tablets (Roche, Cat#04693159001), using a Tissue Lyser II (Qiagen) for 1 min at 30 Hz. One 5 mm stainless steel bead (Qiagen, cat#69965) was placed per tube to help with tissue lysis. After bead removal, samples were then centrifuged on a bench-top centrifuge at top speed for 15 min at 4° C. Supernatants were collected and either stored at −80° C. for studies at a later time or protein concentration as assessed using the BCA method (Pierce, cat#232550) and a Western blot for ICD3 was run as described previously. Where applicable, Western was also performed with a full-length Notch3 antibody to detect total levels of Notch3 (Cell Signaling #2889, 1:1000 dilution).
Detection of ICD3 Levels by IHC Xenograft tumors were fixed in 10% formalin and embedded in paraffin. 5 µm sections were placed on charged polylysine-coated slides. Immunohistochemistry protocol was optimized on an automated system Discovery ULTRA (Ventana Medical System).

Figure 16A:
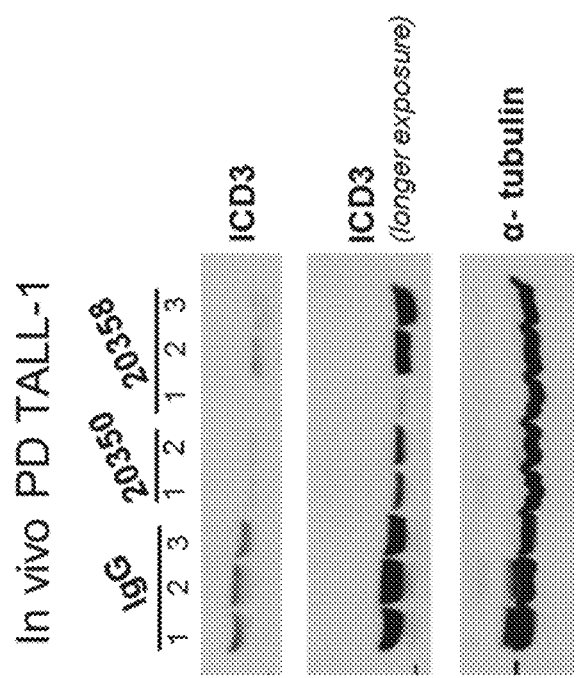
FIG. 16A-B: Photographs of Western blots and IHC photographs of in vivo PD studies in TALL-1 xenograft.
Figure 16B:
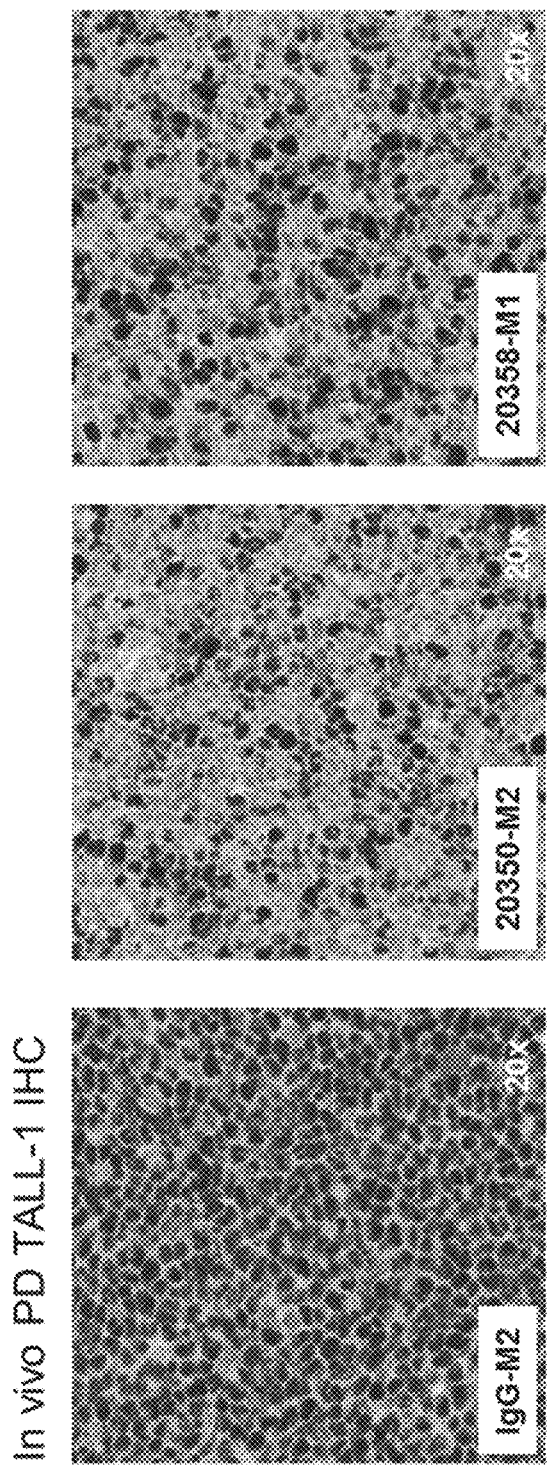
Figure 17A:
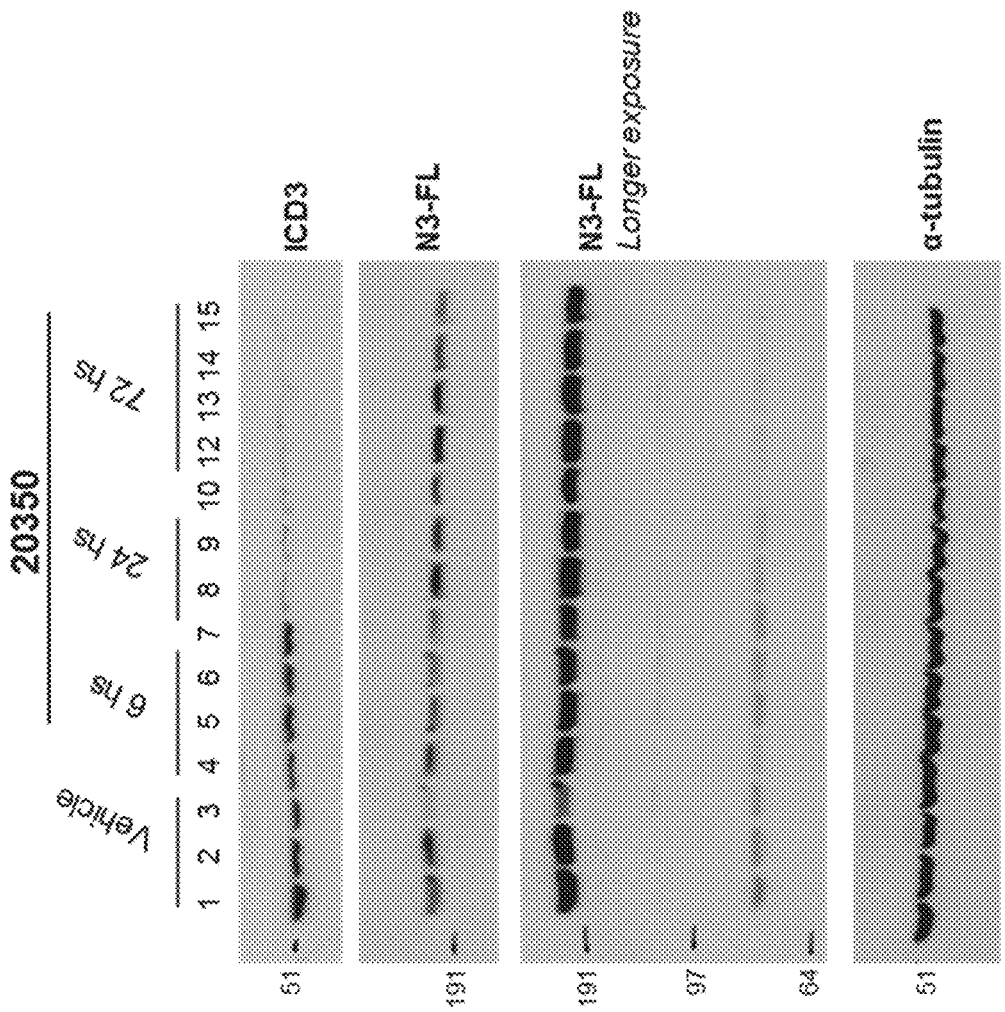
FIG. 17A-B: Photographs of Western blots of in vivo PD studies in MDA-MB468 xenograft.
Figure 17B:
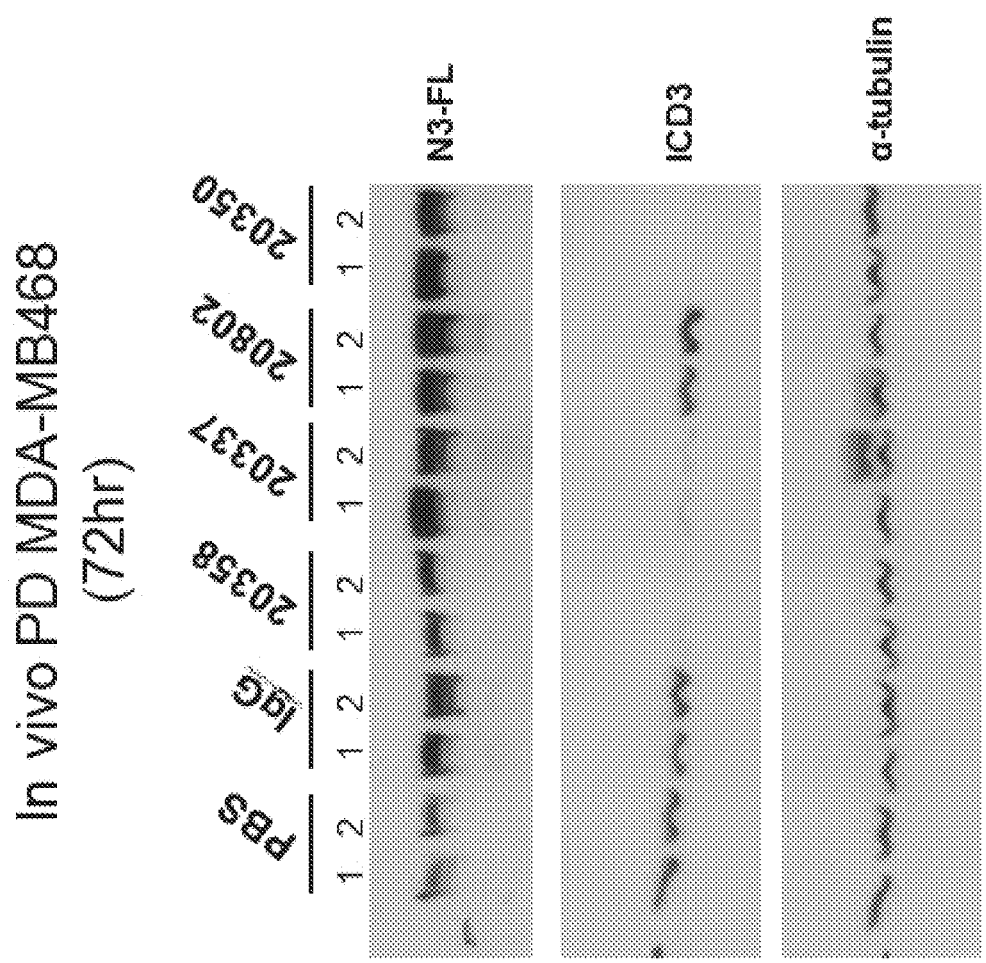
Figure 18:
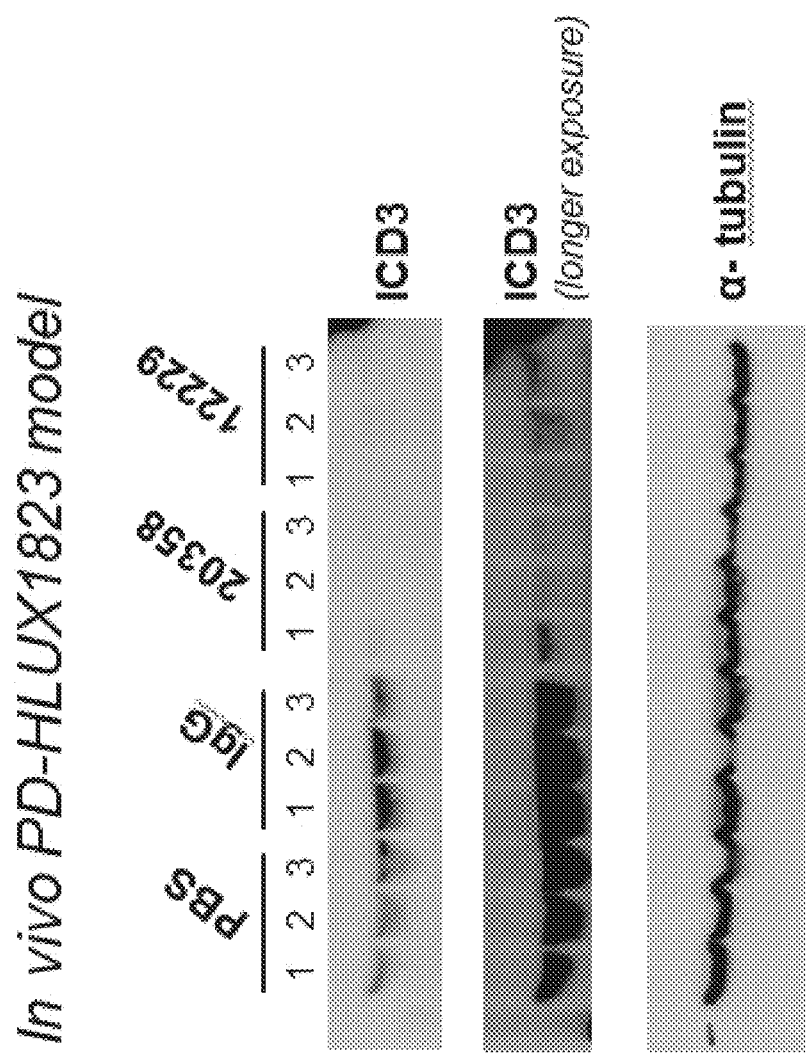
FIG. 18: Photographs of Western blots in an in vivo PD HLUX1823 model xenograft.

Sections were baked at 60° C. for 8 minutes, followed by deparaffination. Antigen retrieval was achieved in Cell Conditioning 1 (CC1, a TRIS based buffer with a slightly basic pH) at high temperature for 76 minutes. Blocking of non-specific binding of antibody was carried on using a specific Antibody Blocking (cat#760-4204). Primary antibody Notch3 ICD (20 µg/ml) was incubated at 37° C. for 60 minutes followed by incubation in secondary antibody for 32 minutes. Amplification step was performed using a specific Discovery Amplification HQ kit #760-052 (Ventana Medical Systems) as per manufacture specifications. Detection was achieved with diaminobenzidine (DAB) and counterstain with Hematoxylin. All these steps were run on Ventana Discovery ULTRA (Ventana Medical Systems).
Summary and Discussion
FIGS. 16-18 show in vivo PD studies in several xenograft models. As described earlier in this application, in vitro treatment of TALL-1 cells with Notch3 antibodies resulted in inhibition of signaling as assessed by both Deltex1 mRNA levels and ICD3 protein levels. TALL-1 cells were grown as a xenograft and mice were treated with Notch3 antibodies. Changes in Notch3 signaling in TALL-1 tumors was monitored by assessing ICD3 levels by Western blotting or IHC. Treatment with antibodies 20350 or 20358 resulted in decreased levels of ICD3 as shown in FIGS. 16A-B. ICD3 staining by IHC is indicated by the black/dark grey cells in the tumor section as shown in FIG. 16B. ICD3 levels in tumors were assessed 72 h following the last Notch3 antibody administration, and there were still some cells within the tumor that showed strong ICD3 expression. In the MDA-MB468 model, as assessed by Western blotting, animals treated with 20350 yielded a marked decrease in ICD3 24 hr and 72 hr post dose relative to untreated control mice (FIG. 17A). It was found that, at the 72 hr time point, 20350, 20358 and 20337, all of which target the Notch3 NRR, induced decreases in ICD3 levels relative to the PBS and 3207 (IgG) controls. In contrast, following treatment with 20802, which targets a region of Notch3 outside of the NRR, ICD3 levels appeared similar to control levels (FIG. 17B). In the HLUX1823 Notch3-gene amplified model, as assessed by Western blotting, animals treated with either 20358 or 12229 yielded a marked decrease in ICD3 at 72 hr post dose relative to control mice (FIG. 18). Taken together, these data demonstrate that the Notch3 NRR antibodies can inhibit Notch3 signaling in the presence of Notch3 gene-amplification or mutations in either the NRR or PEST domains, whereas Notch3 antibodies raised outside of this region can only inhibit Notch3 signaling in the presence of the gene-amplification and have more limited activity in the presence of mutations.

Example 12: In Vivo Efficacy in TALL-1 Xenografts

Generation of a TALL-1 Cell Line with Constitutive Expression of Luciferase
The TALL-1 cell line was transduced with pMMP-Luc-Neo retrovirus (see U.S. Pat. No. 7,399,851) and selected in 1 mg/mL of Geneticin (G418) for several weeks. TALL-1_Luc cells express high levels of luciferase compared to TALL-1 cells, where it was absent. Wild-type and luciferased cells were subjected to a proliferation experiment with Notch3 antibody inhibitors, showing identical results; suggesting that the infection did not interfere with TALL-1 sensitivity to Notch3 inhibition.
Assessment of In Vivo Activity of Notch3 Antibodies in a TALL-1 Cell-Line Xenograft Model
Mice were inoculated with $10 \times 10^6$ T-ALL1_Luc cells injected subcutaneously in a suspension of Hank's balanced salt solution and the presence of tumors was monitored using the Xenogen in vivo imaging system (Caliper Life Sciences). The presence of tumors was detectable by day 7. On day 11, tumor-bearing animals were randomly assigned to receive intravenous doses of either PBS or 20 mg/kg of 3207 negative control IgG antibody or the Notch3 antibodies 20337, 20350, 20358 or 20802 as single agents twice per week. Tumor size was monitored using the Xenogen in vivo imaging system.

Figure 19A:
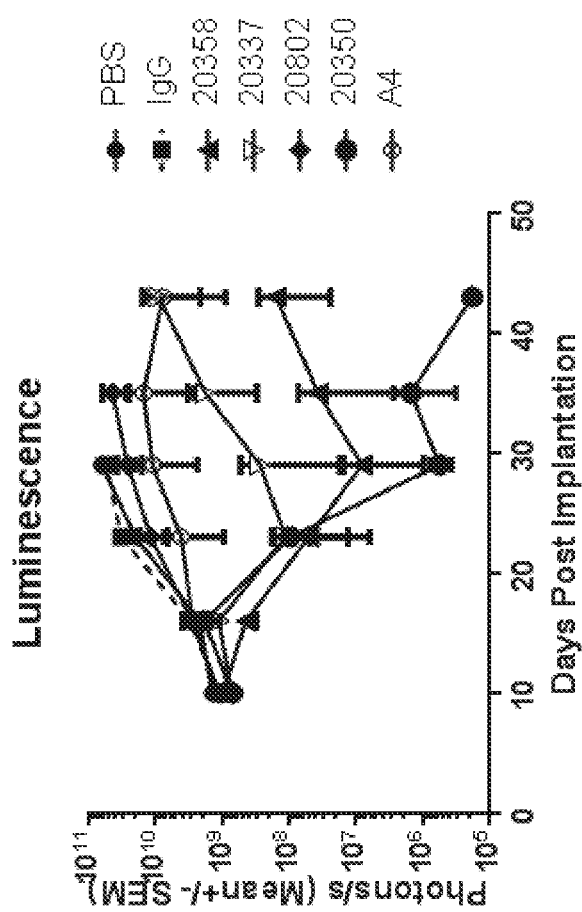
FIG. 19A-B: Photographs of mice showing TALL-1 in vivo efficacy.
Figure 19B:
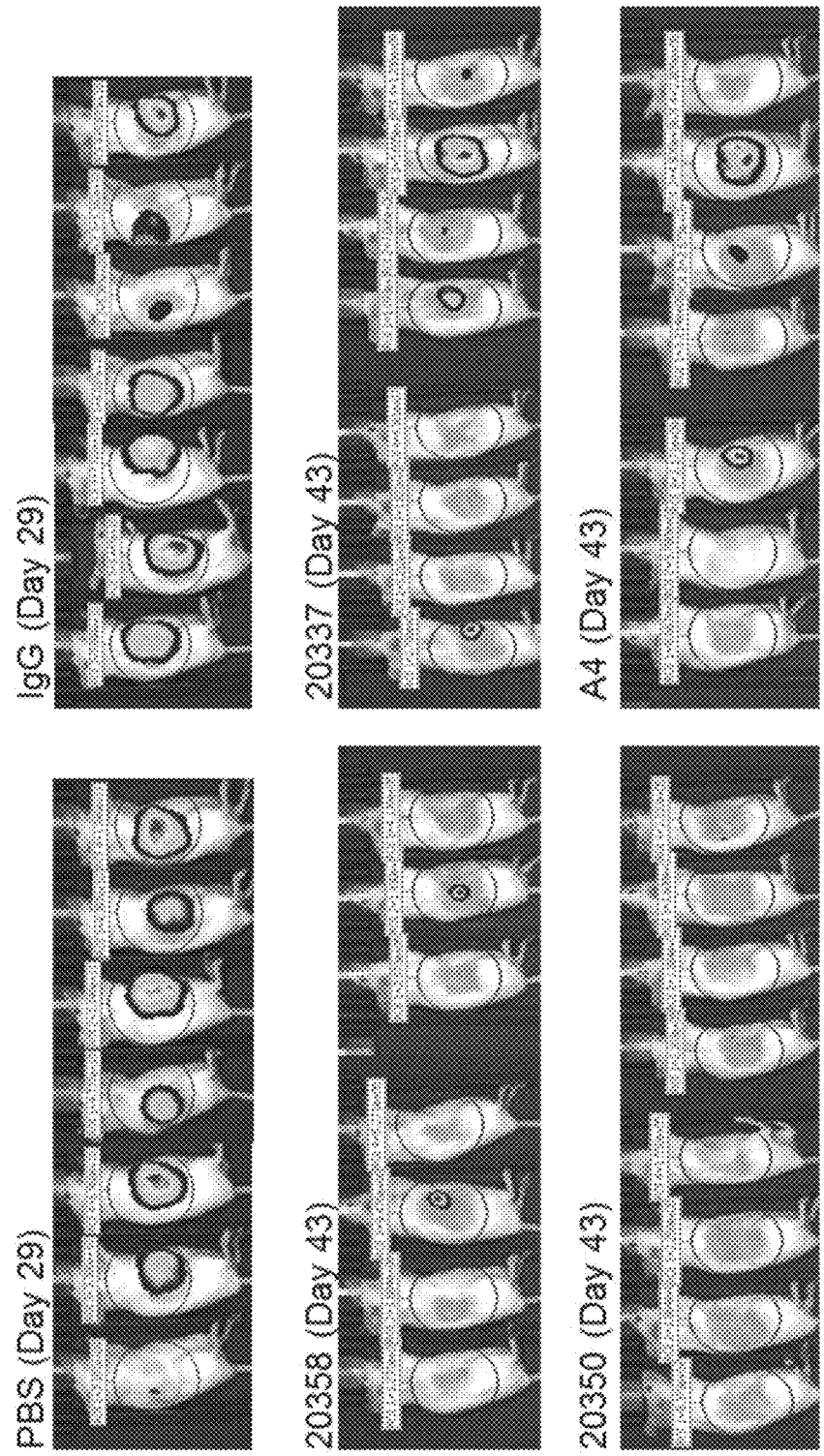

Summary and Discussion
As shown in FIG. 19, 20358 and 20350 showed the most anti-tumor activity of the antibodies evaluated in this study. FIG. 19A shows a graphical representation of the luminescent signal obtained following the various treatments over the time-course of the study and FIG. 19B shows the luminescent signal of the control groups at day 29 (the last time point that it was possible to image due to tumor size) and of the anti-Notch3 antibody treatment groups at day 43.

Example 13: Epitope Binning of NRR Notch 3 Antibodies with Biacore

Epitope binning via Biacore was performed to classify Notch 3 antibodies (IgG or Fab fragments) into groups of identical, or significantly overlapping epitopes, i.e. antibodies which were able to inhibit each other's binding.
Experimental Set-Up Epitope Binning with Biacore
For epitope binning in Biacore, a sensor chip with a low density of immobilized or captured antigen was used (comparable to a kinetic experiment). The same sample prerequisites as for KD determination applied (i.e. monomer content). Experimental conditions, concerning preparation of chip (antigen immobilization/capture), as well as regeneration conditions were identical to KD determination in Biacore. To achieve saturation of an epitope, only one (high) concentration per antibody was used (e.g. 250 nM for 90 s).
Antibody samples were injected pair wise in a full factorial assay design, e.g. for two antibody samples, A and B, the following pair wise injections were required: A-A, A-B, B-A, B-B.
The sensor chip had to be saturated with antibody by the first injection, so that the second antibody was only able to bind in case of a different epitope. Complete regeneration of bound antibodies had to be performed after each double injection.
For evaluation of the controls, i.e. double injections of the identical antibodies (A-A, B-B), their binding levels at the end of each injection were evaluated: The second injection was expected to give no additional binding. Double injections of different antibody sample pairs were compared for consistency, e.g. if the injection A-B resulted in additional binding of B (different epitopes) the injection of B-A was expected to result in additional binding of A, too. Possible causes for creating such inconsistencies were, e.g., partially overlapping epitopes, or large differences in KD.
Summary and Discussion:
FIG. 20 summarizing the evaluation of all pair wise antibody injections was compiled, indicating their mutual inhibition status from which epitope groups or bins could be concluded. Based on these studies, it was determined that the NRR antibodies identified from phage display screening have different conformational epitopes. As shown in FIG. 20 no additional binding was detected when 20345 was added first followed by either 20350 or 20351. Similar information was obtained independent of which antibody was added first in the experiment. Therefore 20345, 20350 and 20351 have overlapping epitopes, which is designated in the table with dark grey shading. This epitope is defined as NRR B. When 20337 was added first, additional binding to the Biacore could be detected with any of the following antibodies added second: 20345, 20350, 20351, 20358 and A4. The same conclusion was reached if the order of addition of the two antibodies was reversed. Therefore, 20337 has a distinct epitope to any of the other antibodies tested and was designated as epitope NRR_A. When 20358 was added first, additional binding was detected with 20337, 20345, 20350 and 20351. The same conclusion was reached if the order of addition of the two antibodies was reversed. Therefore, 20358 has a distinct epitope to these other antibodies tested and was designated as epitope NRR_C. In contrast when 20358 was added first and A4 was added second, there was minimal additional binding (see cells with light grey shading in summary table). This result was further confirmed in additional Biacore studies. In these experiments, either A4 or 20358 was immobilized to an appropriate sensor chip, Notch3 NRR (SEQ ID: 282) was flowed over the surface and the ability of the other antibody not immobilized to the sensor surface to bind to Notch3 NRR was evaluated. Under these assay conditions, it was found that 20358 could bind to Notch3 bound to immobilized A4 and that A4 could also bind to Notch3 bound to immobilized 20358 on the sensor surface. This data is entirely consistent with the other studies performed and with the conclusion that A4 and 20358 bind to distinct epitopes within the Notch3 NRR. Furthermore, when A4 was added first, additional binding was detected when the following antibodies were added second: 20337, 20345, 20350, 20351. The same conclusion was reached if the order of addition of the two antibodies was reversed. Therefore A4 has a distinct epitope to 20337, 20345, 20350, 20351 and was designated as epitope NRR_D.

Example 14: Co-Crystal Structure Studies with 20350 and NRR as Well as 20358 and NRR Two crystal structures of human Notch3 Negative Regulatory Region (NRR, SEQ ID NO: 282) bound to Fab fragment of 20350 or 20358 were determined. As detailed below, Notch3 NRR was expressed, purified and mixed with 20350 or 20358 Fab to form complex. Protein crystallography was employed to generate atomic resolution data for Notch3 NRR bound to 20350 or 20358 Fab, respectively, to define their epitopes (as Notch3 NRR residues within 5 Å distance to the antibody residues).
Protein Production The sequences of Notch3 NRR, 20350 Fab, and 20358 Fab produced for crystallography are shown below. Construct of Notch3 NRR comprises residues 1378 to 1640 (underlined) of human Notch3 (UniProt identifier Q9UM47, SEQ ID NO: 1), along with N- and C-terminal residues from recombinant expression vector (shown in lower case letters, SEQ ID NO: 282). The N-terminal signal sequence from mouse IgG kappa light chain was used for secreted expression and was cleaved during expression, leaving intact N-terminus of Notch3 NRR. For 20350 and 20358 Fab, the sequences of heavy and light chains are shown (SEQ ID NOs: —6 283, 284, 285, and 286).
Proteins Used for Crystal Structure Determination
Construct:

```
Human Notch3 NRR (Q9UM47)
                                           (SEQ ID NO: 1)
MGPGARGRRRRRRPMSPPPPPPPVRALPLLLLLAGPGAAAPPCLDGSPCA

NGGRCTQLPSREAACLCPPGWVGERCQLEDPCHSGPCAGRGVCQSSVVAG

TARFSCRCPRGFRGPDCSLPDPCLSSPCAHGARCSVGPDGRFLCSCPPGY

QGRSCRSDVDECRVGEPCRHGGTCLNTPGSFRCQCPAGYTGPLCENPAVP

CAPSPCRNGGTCRQSGDLTYDCACLPGFEGQNCEVNVDDCPGHRCLNGGT

CVDGVNTYNCQCPPEWTGQFCTEDVDECQLQPNACHNGGTCFNTLGGHSC

VCVNGWTGESCSQNIDDCATAVCFHGATCHDRVASFYCACPMGKTGLLCH

LDDACVSNPCHEDAICDTNPVNGRAICTCPPGFTGGACDQDVDECSIGAN

PCEHLGRCVNTQGSFLCQCGRGYTGPRCETDVNECLSGPCRNQATCLDRI

GQFTCICMAGFTGTYCEVDIDECQSSPCVNGGVCKDRVNGFSCTCPSGFS

GSTCQLDVDECASTPCRNGAKCVDQPDGYECRCAEGFEGTLCDRNVDDCS

PDPCHHGRCVDGIASFSCACAPGYTGTRCESQVDECRSQPCRHGGKCLDL

VDKYLCRCPSGTTGVNCEVNIDDCASNPCTFGVCRDGINRYDCVCQPGFT

GPLCNVEINECASSPCGEGGSCVDGENGFRCLCPPGSLPPLCLPPSHPCA

HEPCSHGICYDAPGGFRCVCEPGWSGPRCSQSLARDACESQPCRAGGTCS

SDGMGFHCTCPPGVQGRQCELLSPCTPNPCEHGGRCESAPGQLPVCSCPQ

GWQGPRCQQDVDECAGPAPCGPHGICTNLAGSFSCTCHGGYTGPSCDQDI

NDCDPNPCLNGGSCQDGVGSFSCSCLPGFAGPRCARDVDECLSNPCGPGT

CTDHVASFTCTCPPGYGGFHCEQDLPDCSPSSCFNGGTCVDGVNSFSCLC

RPGYTGAHCQHEADPCLSRPCLHGGVCSAAHPGFRCTCLESFTGPQCQTL

VDWCSRQPCQNGGRCVQTGAYCLCPPGWSGRLCDIRSLPCREAAAQIGVR

LEQLCQAGGQCVDEDSSHYCVCPEGRTGSHCEQEVDPCLAQPCQHGGTCR

GYMGGYMCECLPGYNGDNCEDDVDECASQPCQHGGSCIDLVARYLCSCPP

GTLGVLCEINEDDCGPGPPLDSGPRCLHNGTCVDLVGGFRCTCPPGYTGL

RCEADINECRSGACHAAHTRDCLQDPGGGFRCLCHAGFSGPRCQTVLSPC

ESQPCQHGGQCRPSPGPGGGLTFTCHCAQPFWGPRCERVARSCRELQCPV

GVPCQQTPRGPRCACPPGLSGPSCRSFPGSPPGASNASCAAAPCLHGGSC

RPAPLAPFFRCACAQGWTGPRCEAPAAAPEVSEEPRCPRAACQAKRGDQR

CDRECNSPGCGWDGGDCSLSVGDPWRQCEALQCWRLFNNSRCDPACSSPA

CLYDNFDCHAGGRERTCNPVYEKYCADHFADGRCDQGCNTEECGWDGLDC

ASEVPALLARGVLVLTVLLPPEELLRSSADFLQRLSAILRTSLRFRLDAH

GQAMVFPYHRPSPGSEPRARRELAPEVIGSVVMLEIDNRLCLQSPENDHC

FPDAQSAADYLGALSAVERLDFPYPLRDVRGEPLEPPEPSVPLLPLLVAG

AVLLLVILVLGVMVARRKREHSTLWFPEGFSLHKDVASGHKGRREPVGQD

ALGMKNMAKGESLMGEVATDWMDTECPEAKRLKVEEPGMGAEEEAVDCRQW

TQHHLVAADIRVAPAMALTPPQGDADADGMDVNVRGPDGFTPLMLASFCG

GALEPMPTEEDEADDTSASIISDLICQGAQLGARTDRTGETALHLAARYA

RADAAKRLLDAGADTNAQDHSGRTPLHTAVTADAQGVFQILIRNRSTDLD

ARMADGSTALILAARLAVEGMVEELIASHADVNAVDELGKSALHWAAAVN

NVEATLALLKNGANKDMQDSKEETPLFLAAREGSYEAAKLLLDHFANREI

TDHLDRLPRDVAQERLHQDIVRLLDQPSGPRSPPGPHGLGPLLCPPGAFL

PGLKAAQSGSKKSRRPPGKAGLGPQGPRGRGKKLTLACPGPLADSSVTLS

PVDSLDSPRPFGGPPASPGGFPLEGPYAAATATAVSLAQLGGPGRAGLGR

QPPGGCVLSLGLLNPVAVPLDWARLPPPAPPGPSFLLPLAPGPQLLNPGT

PVSPQERPPPYLAVPGHGEEYPAAGAHSSPPKARFLRVPSEHPYLTPSPE

SPEHWASPSPPSLSDWSESTPSPATATGAMATTTGALPAQPLPLSVPSSL

AQAQTQLGPQPEVTPKRQVLA
```

```
Notch3 NRR
                                          (SEQ ID NO: 282)
metdtlllwvlllwvpgstgAPEVSEEPRCPRAACQAKRGDQRCDRECNS

PGCGWDGGDCSLSVGDPWRQCEALQCWRLFNNSRCDPACSSPACLYDNFD

CHAGGRERTCNPVYEKYCADHFADGRCDQGCNTEECGWDGLDCASEVPAL

LARGVLVLTVLLPPEELLRSSADFLQRLSAILRTSLRFRLDAHGQAMVFP

YHRPSPGSEPRARRELAPEVIGSVVMLEIDNRLCLQSPENDHCFPDAQSA

ADYLGALSAVERLDFPYPLRDVRGEPLEPPEPSghhhhhh

20350 Fab heavy chain
                                          (SEQ ID NO: 283)
QVQLVQSGAEVKKPGSSVKVSCKASGGTFSSYTISWVRQAPGQGLEWMGW

IKPRWGAAHYAQKFQGRVTITADESTSTAYMELSSLRSEDTAVYYCARGS

FWFGYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKRVEPKSCDKTH

20350 Fab light chain
                                          (SEQ ID NO: 284)
DIQMTQSPSSLSASVGDRVTITCRASQGINNYLNWYQQKPGKAPKLLIYD

ASKLQSGVPSRFSGSGSGTDFTLTISSLQPEDFATYYCQQYLQYPMTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

20358 Fab heavy chain
                                          (SEQ ID NO: 285)
QVQLVQSGAEVKKPGSSVKVSCKASGGTFRTYAMHWVRQAPGQGLEWMGG

IVPYHGITDYAQKFQGRVTITADESTSTAYMELSSLRSEDTAVYYCARDD

YSTYAFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTH

20358 Fab light chain
                                          (SEQ ID NO: 286)
DIQMTQSPSSLSASVGDRVTITCRASQSIASYLAWYQQKPGKAPKLLIYD

ASNLQSGVPSRFSGSGSGTDFTLTISSLQPEDFATYYCQQAYKTPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Production of Notch 3 NRR

Notch3 NRR was expressed as a secreted protein in HEK293S GnTI-cells (ATCC). 1 mg of Notch3 NRR construct DNA was diluted into 50 ml of OptiMEM I medium (Life Technologies), and incubated with 2.5 mg of PEI (Polysciences) in 50 ml of the same medium for 30 min. The mixture was then added into 1 L of HEK293S GnTI-cells growing in suspension in FreeStyle™ 293 Expression medium (Life Technologies) at 1 million cells/ml at 37° C. with 8% of $CO_2$ for transfection. After 72 hours, the medium which contains Notch3 NRR was harvested by centrifugation. 3 ml of Ni-NTA Superflow resin (Qiagen) was added into the medium and continuously stirred at 4° C. overnight. The next day the resin was packed into a gravity column and washed with 50 mM Hepes pH 7.4, 500 mM NaCl, 20 mM imidazole. The target protein was eluted with the same buffer plus 300 mM imidazole and dialyzed in 20 mM Hepes pH 7.4, 150 mM NaCl, 10 mM $CaCl_2$ at 4° C. overnight. The protein was then concentrated to 1 mg/ml and diluted by 3 fold in 50 mM Tris pH 8.0, 10 mM $CaCl_2$ (buffer A). The diluted protein was loaded onto HiTrap Q HP column (GE Healthcare) equilibrated in buffer A plus 4% of 50 mM Tris pH 8.0, 1M $CaCl_2$ and 10 mM $CaCl_2$ (buffer B). The Q column was eluted by a gradient of buffer A plus 2%-100% of buffer B. The major peak containing Notch3 NRR was collected and treated with furin (NEB) at 30 units/mg of target protein at 4° C. overnight. The furin treated protein was then concentrated and loaded onto Superdex 75 10/300 GL (GE Healthcare) equilibrated in 20 mM Hepes pH 7.4, 150 mM NaCl. Peak fractions were analyzed by SDS-PAGE and LCMS, and pooled to complex with Fabs.

Production of 20350 and 20358 Fabs

1 L of HEK293F cells (Life Technologies) growing at 1 million cells/ml were transfected with 1 mg of DNA construct containing full-length IgG of 20350 (or 20358) for three days. The full-length IgG was purified from the medium by ProSep-vA High Capacity Chromatography Media resin (Millipore) according to manufacturer's protocol. The purified IgG was then digested by immobilized papain (Pierce) to generate Fab fragments. Specifically, IgG at 20 mg/ml in 20 mM sodium phosphate pH 7.0 and 10 mM EDTA was mixed with immobilized papain at a weight ratio of 80:1. The mixture was rotated in a 15 ml tube at 37° C. overnight. The next day the immobilized papain was removed by gravity flow column; the flow-through, which contains both Fab and Fc segments, was collected and loaded onto HiTrap MabSelect SURE column (GE Healthcare) to remove Fc segment. The flow-through from this step, which contains only Fab fragment, was concentrated and loaded onto HiLoad 16/60 Superdex 75 (GE Healthcare) equilibrated in 20 mM Hepes pH 7.4, 150 mM NaCl. Peak fractions were analyzed by SDS-PAGE and LCMS, then pooled to form complex with Notch3 NRR.

Crystallization and Structure Determination

The Notch3 NRR/20350 complex or the Notch3 NRR/20358 complex was prepared in the same way. Purified Notch3 NRR was mixed with the Fab at a 2:1 molar ratio (concentration measured via LCUV). The Notch3 NRR/Fab complex was incubated on ice for 30 min, and loaded onto a HiLoad 16/60 Superdex 75 (GE Healthcare) equilibrated in 20 mM Hepes pH 7.5, 150 mM NaCl. Peak fractions were analyzed by SDS-PAGE and LCMS. Fractions containing Notch3 NRR/Fab complex were concentrated to about 25 mg/ml for the Notch 3 NRR/20350 complex, or 18 mg/ml for the Notch 3 NRR/20358 complex. The Notch3 NRR/Fab complex was immediately centrifuged and screened for crystallization.

Crystals were grown by sitting drop vapor diffusion technique. Specifically for the NRR/20350 complex, 0.1 µl of the complex was mixed with 0.1 µl of reservoir solution which contains 0.1M NaAc pH 5.6, 17.5% PEG3000; and the drop was equilibrated against 45 µl of the reservoir solution at 20° C.

For the NRR/20358 complex, 0.1M Hepes pH 7.5, 10% PEG8000, 10% ethylene glycol was used; and the drop was equilibrated against 45 µl of the reservoir solution at 20° C.

Before data collection, the Notch3 NRR/Fab crystals were transferred to reservoir solution containing additional 22.5% glycerol for Notch3 NRR/20350 complex; or 20% ethylene glycol for Notch3 NRR/20358 complex prior to being flash cooled in liquid nitrogen.

Diffraction data was collected at beamline 17-ID at the Advanced Photon Source (Argonne National Laboratory, USA). Data was processed and scaled using HKL2000 (HKL Research). The data of Notch3 NRR/20350 complex was processed to 3.2 Å in space group C2 with cell dimensions a=91.92 Å, b=104.35 Å, c=92.85 Å, alpha=90°, beta=113.17°, gamma=90°. The data of the Notch3 NRR/20358 complex was processed to 2.1 Å in space group P2₁2₁2₁ with cell dimensions a=88.34 Å, b=123.86 Å, c=150.57 Å, alpha=90°, beta=90°, gamma=90°. The structures of Notch3 NRR/Fab complexes were solved by molecular replacement using Phaser (McCoy et al., (2007) J. Appl. Cryst. 40:658-674) with Notch1 NRR structure (PDB ID: 3ETO) and in-house Fab structures with highest sequence identity with 20350 or 20358 Fab as search models. The final models were built in COOT (Emsley & Cowtan (2004) Acta Cryst. 60:2126-2132) and refined with Buster (Global Phasing, LTD). For the Notch3 NRR/20350 complex, the $R_{work}$ and $R_{free}$ values were 23.0% and 26.9%, respectively; and rmsd values of bond lengths and bond angles are 0.008 Å and 1.17°, respectively. For the Notch3 NRR/20358 complex, the $R_{work}$ and $R_{free}$ values were 19.2% and 22.6%, respectively; and rmsd values of bond lengths and bond angles were 0.010 Å and 1.13°, respectively.

Residues of Notch3 NRR that contain atoms within 5 Å of any atom in 20350 or 20358 Fab are identified by PyMOL (Schrödinger, LLC) and listed in Tables 4 and 5. The buried surface area between Notch3 NRR and Fabs are calculated by AREAIMOL from CCP4 program suite (Winn et al., (2011) Acta. Cryst. D67:235-242).

Structure of Notch 3 NRR

The structures of Notch3 NRR are very similar between Notch3 NRR/20350 complex and Notch3 NRR/20358 complex. The root-mean-square distance (RMSD) of superposing Notch3 NRR from the two complexes is 0.42 Å, indicating almost identical structures of NRR. Therefore, Notch3 NRR/20358 complex is used as a representative to analyze the structure further.

Notch3 NRR has a similar overall folding as that of Notch1 (Gordan et al., (2009) Blood 113:4381-4390; Gordon et al., (2009) 4:e6613; Wu et al., (2010) Nature 464:1052-1057) and Notch2 (Gordon et al., (2007) Nat Struct Mol Biol 14:295-300). It is composed of three Lin12/Notch repeats (LNR), namely LNR-A, LNR-B and LNR-C; and a heterodimerization (HD) domain divided into N-terminal part (HD-N) and C-terminal part (HD-C) by furin cleavage at S1 site (between R1571 and E1572).

NRR domains regulate the activation of Notch receptors, which involves three proteolysis steps. Furin-like convertase cleaves at S1 site within NRR during maturation of Notch precursor, to prime the activation. ADAM proteases cleave at S2 site, also within NRR, to create the substrate for intramembrane proteolysis at S3 site by gamma secretase. Following S3 cleavage, the intracellular part of Notch enters nucleus to activate transcription. S2 cleavage is the key step of this activation series and is negatively regulated by NRR domains. The mechanism of this so called autoinhibition can be explained by NRR structures.

Figure 21:
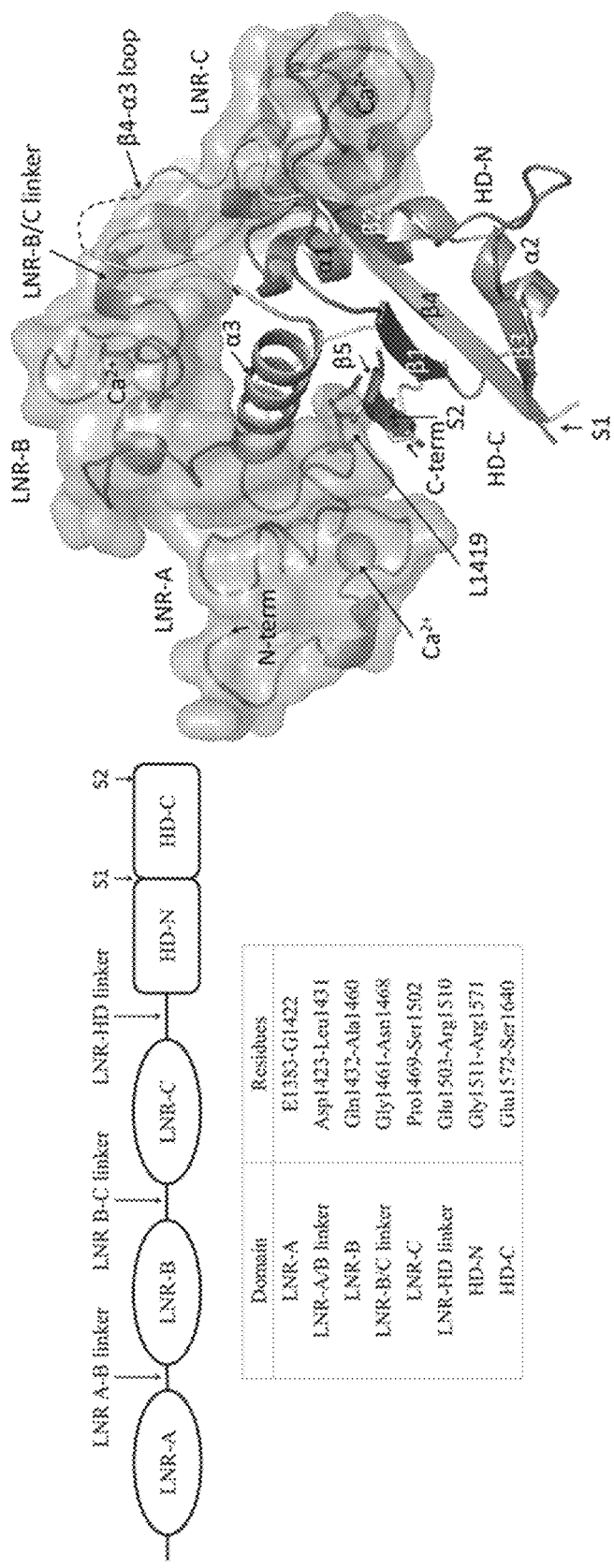
FIG. 21: Surface and ribbon representation of the Notch 3 NRR X-ray crystal structure; labelled are 1) N- and C-terminus of the proteins; 2) the three LNR repeats and the coordinated $Ca^{2+}$ ions; 3) L1419, the autoinhibitory plug; 4) S1 and S2 sites; 5) secondary structures within HD domain; and 6) the two regions in Notch3 with significantly different conformation than Notch1 and Notch2 (LNR-B/C linker plus first half of LNR-C, and β4-α3 loop in HD domain)

FIG. 21 shows the overall X-ray structure of Notch3 NRR. Labeled are 1) N- and C-terminus of the proteins; 2) the three LNR repeats and the coordinated $Ca^{2+}$ ions; 3) L1419, the autoinhibitory plug; 4) S1 and S2 sites; 5) secondary structures within HD domain; and 6) the two regions in Notch3 with significantly different conformation than Notch1 and Notch2 (LNR-B/C linker plus first half of LNR-C, and β4-α3 loop in HD domain).

As in the Notch3 NRR structure, three LNRs, each coordinating a $Ca^{2+}$ ion, wrap around HD to protect S2 site from access by ADAM proteases. Notably the conserved L1419 from LNR-A/B linker directly plugs into S2 site and sterically occludes it from protease access. The stability of the interactions between LNRs and HD, as well as those within the domains, is critical to maintain the autoinhibited conformation of NRR. Therefore, mutations destabilizing NRR, like those found in relevant cancers, could enhance activation of Notch3. On the other hand, reagents like antibodies that can stabilize LNR-HD interaction can potentially inhibit Notch3 signaling.

Figure 22:
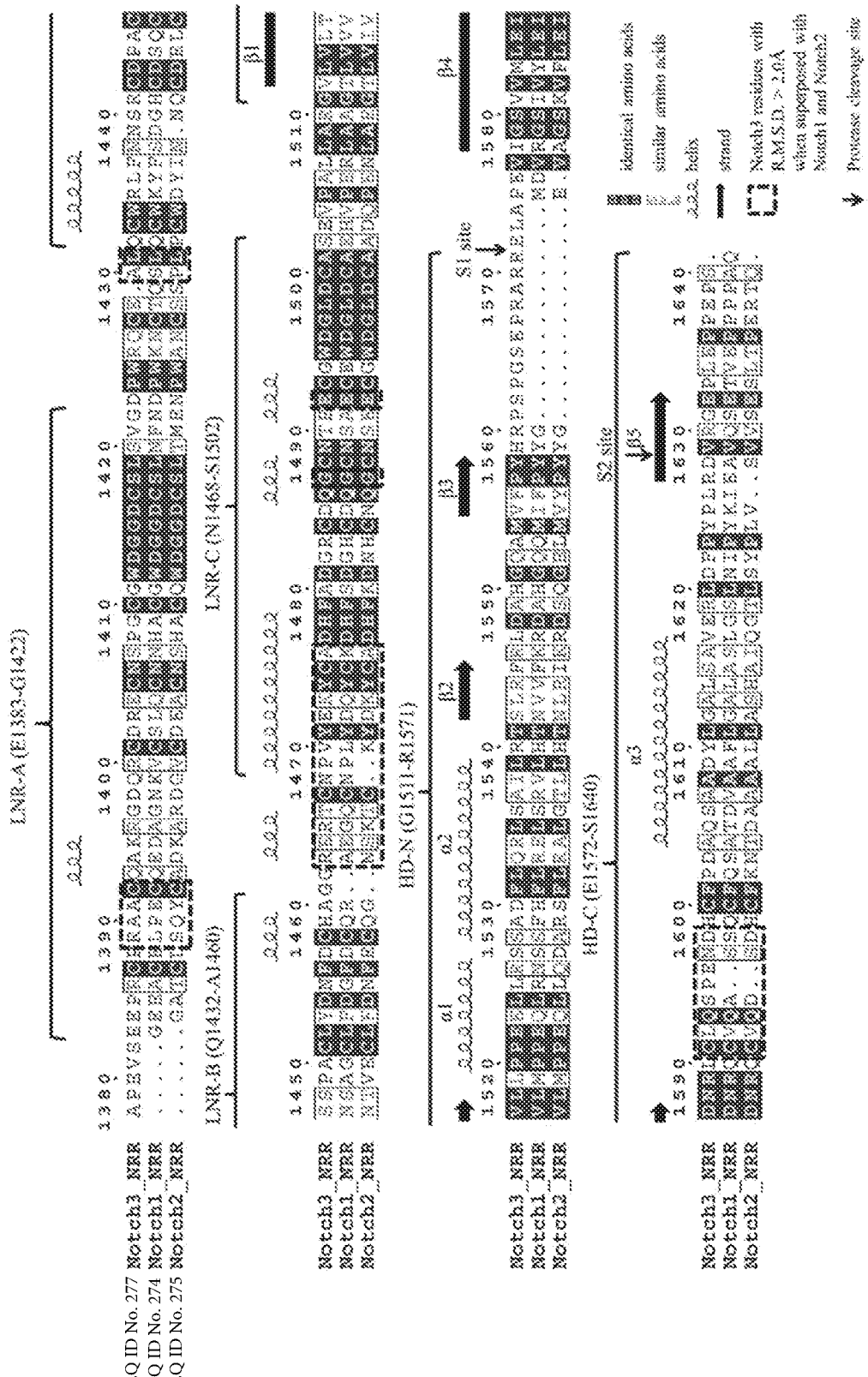
FIG. 22: A sequence alignment of human Notch 1, 2, and 3. Shown in the dashed boxes show are regions of Notch 3 with significantly different structures than Notch 1 or Notch 2.

FIG. 22 shows the sequence alignment of Notch1, Notch2 and Notch3 NRR. Labeled are 1) domain names and boundaries; 2) secondary structures; 3) uniquely structured regions of Notch3 vs. Notch1 and Notch2; and 4) S1 and S2 sites. Structural superposition of Notch3 NRR with Notch1 NRR (PDB ID: 3I08) and Notch2 NRR (PDB ID: 2OO4) result in RMSD values of 1.68 Å and 1.45 Å, indicating similar overall foldings. However, some parts of Notch3 NRR have significantly different conformations (RMSD values >2 Å), mainly in two regions, LNR-B/C linker plus first half of LNR-C(R1463-A1476) and β4-α3 loop (C1591-D1598) in HD domain. Interestingly, majority of these two unique regions are captured by 20350 and 20358 antibodies. The detailed interactions are described in the next section.

Notch3 Epitope for 20350 and 20358

20350 Epitope

Figure 23:
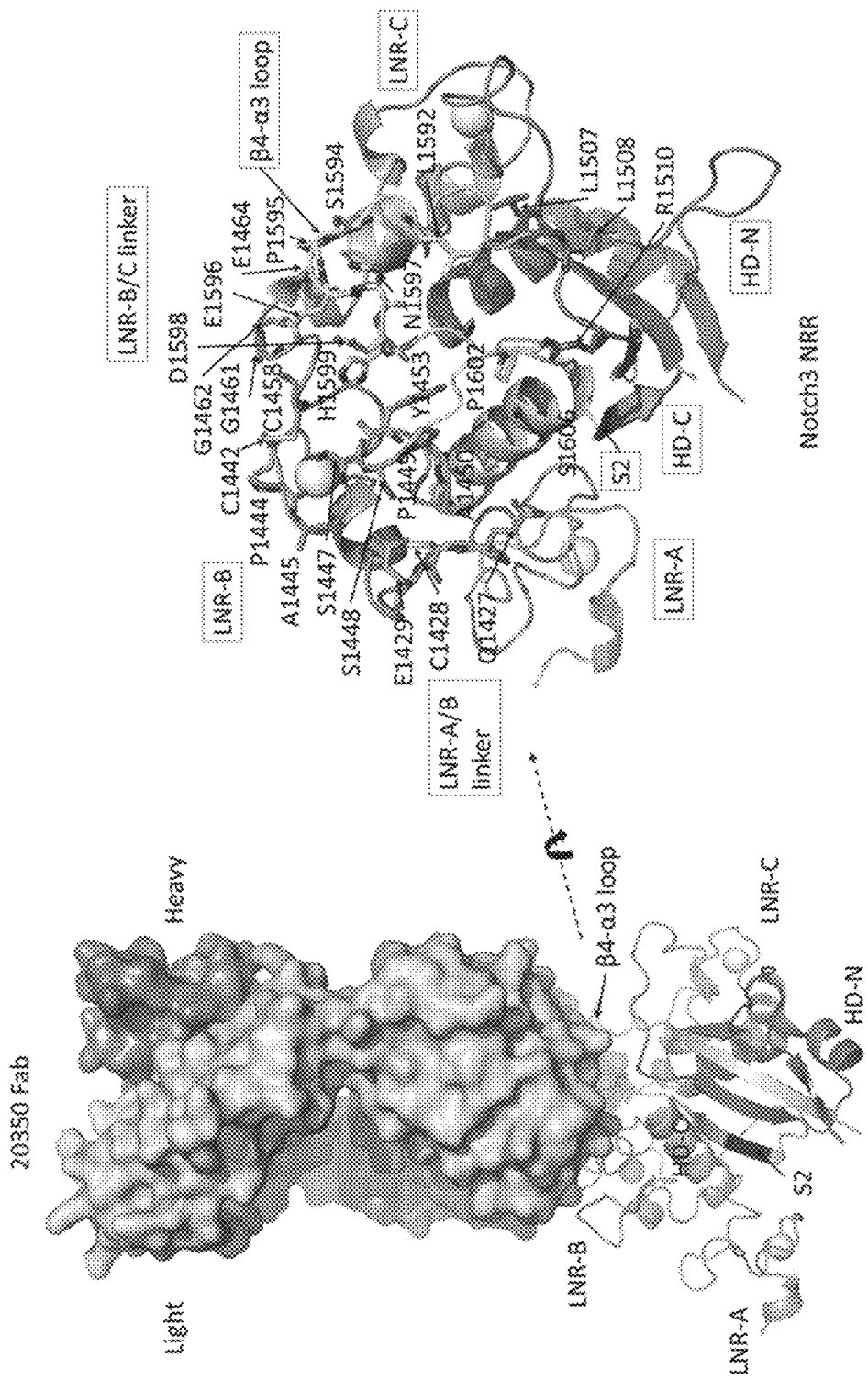
FIG. 23: X-ray crystal structure of the Notch3/20350 Fab complex determined at 3.2 Å, with the overall structure of 20350 Fab binding to Notch3 NRR (left panel) and detailed interactions on Notch3 NRR with epitope residues labelled (right panel)

The crystal structure of the Notch3 NRR/20350 Fab complex was used to identify the Notch3 epitope for 20350. The interaction surface on Notch3 NRR by 20350 Fab was formed by several discontinuous (i.e. noncontiguous) sequences: namely residues 1427-1429, 1442, 1444, 1445, 1447-1450, 1453, 1458, 1461, 1462, 1464, 1507, 1508, 1510, 1592, 1594-1599, 1602, and 1606, as detailed in Table 4. These residues form the three-dimensional surface that is recognized by 20350 Fab, as shown in FIG. 23. Interestingly, the β4-α3 loop in HD domain has a unique structure compared with Notch1 and Notch2, and a majority of this segment is within the 20350 epitope. Furthermore, this loop is mostly unstructured (no electron density due to flexibility) in Notch3 NRR/20358 complex, but is stabilized and structured in this 20350 complex by direct binding to the Fab.

TABLE 4

Interactions between human Notch3 NRR and 20350. Notch3 residues are numbered based on UniProt ID Q9UM47 (SEQ ID NO: 1), and grouped into domains. Fab heavy and light chain residues are numbered based upon their linear amino acid sequences SEQ ID NO: 283 and SEQ ID NO: 284, respectively. Notch3 residues shown have at least one atom within 5 Å of an atom in the 20350 Fab, to account for potential water mediated interactions.

| Notch3 NRR | | | 20350 Fab | | |
|---|---|---|---|---|---|
| Domain | Residue | Number | Residue | Number | Chain |
| LNR-A/B linker | GLN | 1427 | ASN | 30 | L |
|  |  |  | LEU | 92 | L |
|  |  |  | GLN | 93 | L |
|  | CYS | 1428 | GLN | 93 | L |
|  | GLU | 1429 | LEU | 92 | L |
|  |  |  | GLN | 93 | L |
|  |  |  | TYR | 94 | L |
| LNR-B | CYS | 1442 | TRP | 50 | H |
|  |  |  | ALA | 57 | H |
|  | PRO | 1444 | TRP | 50 | H |
|  |  |  | ALA | 57 | H |
|  |  |  | ALA | 58 | H |
|  |  |  | HIS | 59 | H |
|  |  |  | TYR | 94 | L |
|  | ALA | 1445 | HIS | 59 | H |
|  |  |  | TYR | 94 | L |
|  |  |  | GLN | 93 | L |
|  |  |  | TYR | 94 | L |

TABLE 4-continued

Interactions between human Notch3 NRR and 20350. Notch3 residues are numbered based on UniProt ID Q9UM47 (SEQ ID NO: 1), and grouped into domains. Fab heavy and light chain residues are numbered based upon their linear amino acid sequences SEQ ID NO: 283 and SEQ ID NO: 284, respectively. Notch3 residues shown have at least one atom within 5 Å of an atom in the 20350 Fab, to account for potential water mediated interactions.

| Notch3 NRR | | | 20350 Fab | | |
|---|---|---|---|---|---|
| Domain | Residue | Number | Residue | Number | Chain |
| | SER | 1447 | TRP | 50 | H |
| | | | HIS | 59 | H |
| | | | PHE | 101 | H |
| | | | TYR | 94 | L |
| | SER | 1448 | PHE | 101 | H |
| | | | LEU | 92 | L |
| | PRO | 1449 | PHE | 101 | H |
| | | | TYR | 32 | L |
| | | | TYR | 91 | L |
| | | | LEU | 92 | L |
| | ALA | 1450 | LEU | 92 | L |
| | | | GLN | 93 | L |
| | TYR | 1453 | PHE | 101 | H |
| | | | TYR | 32 | L |
| | CYS | 1458 | TRP | 50 | H |
| | | | LYS | 52 | H |
| LNR-B/C linker | GLY | 1461 | TRP | 55 | H |
| | GLY | 1462 | ARG | 54 | H |
| | | | TRP | 55 | H |
| | GLU | 1464 | ARG | 54 | H |
| LNR-HD linker | LEU | 1507 | TYR | 49 | L |
| | LEU | 1508 | LYS | 53 | L |
| | ARG | 1510 | ASN | 31 | L |
| | | | ASP | 50 | L |
| | | | ALA | 51 | L |
| | | | SER | 52 | L |
| | | | LYS | 53 | L |
| HD β4-α3 linker | LEU | 1592 | TRP | 102 | H |
| | | | TRP | 102 | H |
| | | | TYR | 49 | L |
| | SER | 1594 | TYR | 32 | H |
| | PRO | 1595 | SER | 31 | H |
| | | | TYR | 32 | H |
| | GLU | 1596 | SER | 31 | H |
| | | | TYR | 32 | H |
| | | | THR | 33 | H |
| | | | LYS | 52 | H |
| | | | SER | 100 | H |
| | ASN | 1597 | TRP | 102 | H |
| | ASP | 1598 | THR | 33 | H |
| | | | GLY | 99 | H |
| | | | SER | 100 | H |
| | | | PHE | 101 | H |
| | | | TRP | 102 | H |
| | ASP | 1598 | TYR | 91 | L |
| | HIS | 1599 | SER | 100 | H |
| | | | PHE | 101 | H |
| | PRO | 1602 | TYR | 32 | L |
| | | | ASP | 50 | L |
| | | | TYR | 91 | L |
| HD α3 helix | SER | 1606 | TYR | 32 | L |

20350 Fab binds across both LNR (mainly around LNR-B) and HD domains (mainly around β4-α3 loop) of Notch3 NRR. The buried surface area between 20350 Fab and LNR is 554.9 Å$^2$, and 535.2 Å$^2$ between 20350 Fab and HD domain. This positioning of the Fab indicates 20350 can clamp LNR and HD domain together, stabilize the autoinhibitory conformation of Notch3 NRR, and inhibit Notch 3 activation.

20358 Epitope

The crystal structure of the Notch3 NRR/20358 Fab complex was used to identify the Notch3 epitope for 20358. The interaction surface on Notch3 NRR by 20358 Fab was formed by several discontinuous (i.e. noncontiguous) sequences: namely residues 1440, 1463, 1465-1472, 1474, 1486, 1487, 1534, 1618, 1619, and 1621, as detailed in Table 5. These residues form the three-dimensional surface that is recognized by 20350 Fab, as shown in FIG. 24. Interestingly, the LNR-B/C linker in the first half LNR-C has a unique structure compared with Notch1 and Notch2, and a majority of this segment is within 20358 epitope.

TABLE 5

Interactions between human Notch3 NRR and 20358. Notch3 residues are numbered based on UniProt ID Q9UM47 (SEQ ID NO: 1), and grouped into domains. Fab heavy and light chain residues are numbered based upon their linear amino acid sequences SEQ ID NO: 4285 and SEQ ID NO: 5286, respectively. Notch3 residues shown have at least one atom within 5 Å of an atom in the 20358 Fab, to account for potential water mediated interactions.

| Notch3 NRR | | | 20358 Fab | | |
|---|---|---|---|---|---|
| Domain | Residue | Number | Residue | Number | Chain |
| LNR-B | SER | 1440 | SER | 31 | L |
| LNR-B/C linker | ARG | 1463 | PHE | 29 | H |
| | | | THR | 31 | H |
| | | | ASP | 99 | H |
| | | | ASP | 100 | H |
| | | | TYR | 101 | H |
| | | | SER | 102 | H |
| | | | THR | 103 | H |
| | | | TYR | 104 | H |
| | ARG | 1465 | TYR | 32 | L |
| | THR | 1466 | TYR | 104 | H |
| | | | TYR | 32 | L |
| | CYS | 1467 | TYR | 104 | H |
| | ASN | 1468 | THR | 31 | H |
| | | | ALA | 33 | H |
| | | | VAL | 52 | H |
| | | | ASP | 99 | H |
| | | | TYR | 104 | H |
| | | | TYR | 96 | L |
| LNR-C | PRO | 1469 | ASP | 59 | H |
| | | | TYR | 104 | H |
| | | | ALA | 91 | L |
| | | | TYR | 92 | L |
| | | | LYS | 93 | L |
| | | | THR | 94 | L |
| | | | TYR | 96 | L |
| | VAL | 1470 | ILE | 57 | H |
| | | | THR | 58 | H |
| | | | ASP | 59 | H |
| | | | GLY | 50 | H |
| | | | VAL | 52 | H |
| | | | HIS | 35 | H |
| | | | TRP | 47 | H |
| | | | GLY | 50 | H |
| | | | ASP | 59 | H |
| | | | THR | 94 | L |
| | | | TYR | 96 | L |
| | TYR | 1471 | VAL | 52 | H |
| | | | HIS | 55 | H |
| | | | ILE | 57 | H |
| | GLU | 1472 | LYS | 93 | L |
| | | | THR | 94 | L |
| | TYR | 1474 | ILE | 57 | H |
| | GLN | 1486 | HIS | 55 | H |
| | GLY | 1487 | HIS | 55 | H |
| | | | ILE | 57 | H |
| HD α2 helix | ARG | 1534 | LYS | 93 | L |
| HD α3-β5 linker | GLU | 1618 | SER | 28 | L |
| | ARG | 1619 | ALA | 30 | L |
| | | | SER | 31 | L |
| | | | TYR | 32 | L |
| | | | SER | 67 | L |
| | ASP | 1621 | GLN | 27 | L |
| | | | SER | 28 | L |
| | | | TYR | 92 | L |

20358 Fab binds across both LNR (mainly around LNR-B/C linker and LNR-C) and HD domains (mainly around α3-β5 loop) of Notch3 NRR. The buried surface area between 20358 Fab and LNR is 729.6 Å$^2$, and 152.2 Å$^2$ between 20358 Fab and HD domain. This positioning of the Fab indicates 20358 can clamp LNR and HD domain together, stabilize the autoinhibitory conformation of Notch3 NRR, and inhibit Notch 3 activation.

20350 and 20358 Epitopes do not Overlap

To determine whether the epitopes of 20350 and 20358 overlap, the crystal structures of Notch3 NRR/20350 complex and Notch3 NRR/20358 complex was superposed on Notch3 NRR, as shown in FIG. 25. This Figure clearly demonstrates that 20350 and 20358 bind to distinct separate conformational epitopes within the Notch 3 NRR that do not overlap. In fact, they are well separated in even the closest region (E1464-R54 hydrogen bond with 20350 and R1463-D100 salt bridge with 20358). This indicates that the two antibodies can bind Notch3 NRR at the same time, which is in agreement with the binning experiment showing that they are in different bins and do not compete with each other in binding Notch3 (see FIG. 20).

Epitope Comparison Among 20350, 20358, 256A-13, 256A-4 and 256A-8

Epitopes of 20350 and 20358 were compared with the epitope of 256A-13 (hereafter referred to as "A13") (US 2008/0118520 A1); and with the epitopes of 256A-4 (hereafter referred to as "A4") and 256A-8 (hereafter referred to as "A8") (U.S. Pat. No. 7,935,791 B2). For A13, its epitope comprises D1402, R1403 and E1404 in LNR-A domain, which is completely outside the epitopes of 20350 and 20358.

For A4 and A8, since they have been mapped to the same epitope on Notch3 (U.S. Pat. No. 7,935,791 B2), only A4 epitope will be used for comparison.

As shown in FIG. 26, the epitope of 20350 is completely outside that of A4; and the epitope of 20358 has three residues (Glu1618, Arg1619 and Asp1621) that may overlap, although highly unlikely to, for the following reasons: 1) The epitope of 20358 was determined by X-ray crystallography to a resolution of single atoms, and hence single residues, whereas the epitope of A4, was determined by mutagenesis to a limited resolution of three-to-eight-amino acid residue stretches. Fine epitope mapping was not conducted to further define the actual epitope for A4, or whether it was a linear or conformational epitope. This means that as long as there is one residue in contact with A4 within that 3-8 amino acid stretch, the rest of the stretch will be defined as epitope even though it is not. Thus, there remains a high degree of uncertainty on whether the three amino acids actually constitute an epitope for A4. 2) The epitope binning and binding experiments detailed in Example 13 shows that 20358 and A4 do not compete with each other in binding Notch3 NRR, and that both can bind simultaneously to Notch3 NRR This can only be achieved when the two antibodies do not have overlapped epitopes. Accordingly, the epitopes of 20358 and A4 are deemed not to overlap.

Cancer Mutations Mapped on Structure of Notch3 NRR

In order to gain additional mechanistic insight into the NRR of Notch 3, cancer mutations were mapped onto Notch3 NRR structure. Structural analysis suggested that some of these mutations disrupted intra- or inter-domain interactions, destabilize the autoinhibitory conformation of Notch3 NRR and cause Notch3 activation and signal transduction.

Meanwhile, comparison of these mutations with 20350 and 20358 epitopes shows that most of them are not within the epitopes, indicating that 20350 and 20358 can bind to both wild type and mutant Notch3 NRRs in an autoinhibited conformation to inhibit Notch 3 signal transduction.

TABLE 7

Shows the structure-based interpretation of Notch3 mutations

| Mutation | Cellular data | Structure-based interpretation |
|---|---|---|
| Group 1 | | |
| S1580L R1510H D1587N R1589Q Y1624H | Activating | Lose intra-domain hydrogen bonds and thus destabilize HD domain |
| Group 2 | | |
| G1487D A1476T A1609T L1518M A1537T | Activating | Affect structural integrity, cause clash |
| Group 3 | | |
| N1597K L1547V R1526C | Activating | On the surface of NRR, no obvious interpretation, but might interfere with protein-protein interaction |

Group 1 (S1580L, R1510H, D1587N, Y1624H, R1589Q)

Mutations in this group lose hydrogen bonds within HD domain and thus cause destabilization.

A representative from this group is S1580L. It activates Notch3 signaling in cellular assays (FIG. 13a) and is a driving force of TALL-1. In the structure, the side-chain oxygen of S1580 (in HD-N) forms a hydrogen bond with the backbone nitrogen of P1521 (in HD-C). S1580L mutation can lose this hydrogen bond and destabilize HD domain. Considering S1580 is close to S2 site (~10 Å), this destabilization can make S2 site more accessible to ADAM proteases and thus enhance activation of Notch3.

Similarly, R1510H mutation in HD-N can lose hydrogen bond with D1603 in HD-C, D1587N R1589Q mutation can lose salt bridge originally existing between the two residues t, and Y1624H mutation in HD-N can lose hydrogen bonds with S1527 and D1530 in HD-C. All these mutations can destabilize the HD domain and potentially activate Notch3 signaling.

Group 2 (G1487D, A1476T, A1608T, L1518M, A1537T)

Mutations in this group can affect structural integrity within domains or cause clash with surrounding residues, thus destabilize Notch3 NRR.

A representative from this group is G1487D. It activates Notch3 signaling in cellular assays. G1487 is adjacent to the C1475-C1488 disulfide bond of LNR-C, which is critical for the structural integrity and Ca$^{2+}$ coordination within this domain. G1487D mutation can interfere with the correction positioning of this disulfide bond and destabilize LNR-C domain.

L1518 is in a hydrophobic pocket adjacent to S2 site, formed by side-chains of R1627, Y1558, and I1578. L1518M mutation can clash with this hydrophobic pocket and thus destabilize S2 site.

A1537 in HD-N is only 3.3 Å away from E1492 in LNR-C. A1537T mutation can clash with E1492 and destabilize LNR-HD interaction.

Group 3 (N1597K, L1547V, R1526C)

Mutations in this group are on the surface of Notch3 NRR. N1597K activates Notch3 signaling in cellular assays (FIG. 14a), indicating these surface mutations might function through mechanisms other than destabilization of NRR, e.g. interference with protein-protein interaction events.

Cancer Mutations Vs. Epitopes

Cancer Mutations Vs. 20350 Epitope

The cancer mutations fall within or outside the majority of 20350 epitope, indicating 20350 can still bind to both wild-type and mutant Notch3 NRRs.

Two cancer mutations within the epitope are R1510H and N1597K. For example, R1510H might weaken the binding of 20350 to Notch3 NRR, because this mutation can lose several interactions with the light chain, including salt bridge with D50 and hydrogen bond with N31.

Cancer Mutations Vs. 20358 Epitope

All cancer mutations except G1487D are outside of 20358 epitope, indicating 20358 can still bind to both wild-type and mutant Notch3 NRRs.

G1487D might weaken the binding of 20358 to Notch3 NRR because this mutation can clash with and break the hydrogen bond between Y1471 (Notch3) and H55 (20358 heavy chain).

Example 15: HDx-MS Epitope Mapping of Human Notch3 NRR/20350, Human Notch3 NRR/20358 and Human Notch3 NRR/20337 Complexes Deuterium exchange mass spectrometry (HDx-MS) measures the deuterium uptake on the amide backbone of a protein; these measurements are sensitive to the amide's solvent accessibility and to changes in the hydrogen bonding network of the backbone amides. HDx-MS is often used to compare a protein in two different states, such as apo and ligand-bound, and coupled with rapid pepsin digestion. In such experiments one can locate regions, typically of 10 to 15 amino acids, that show differential deuterium uptake between two different states. Regions that are protected in complexes are either directly involved in ligand binding or allosterically affected by binding of the ligand.

In these experiments, the deuterium uptake of Notch 3 NRR protein (SEQ ID NO: 282) was measured with calcium in the absence and presence of three IgG antibodies: 20350 (SEQ ID NO: 287), 20358 (SEQ ID NO: 288) and 20337 (SEQ ID No: 289). Regions in Notch 3 NRR that show a decrease in deuterium uptake upon binding of the antibody are likely involved in the epitope; however, due to the nature of the measurement it is also possible to detect changes remote from the direct binding site (allosteric effects). In order to delineate direct binding events from allosteric effects orthogonal measurements (e. g. X-ray crystallography, shown in the previous example) were also conducted Proteins Used in HDx-MS Experiments:

Notch3 NRR
(SEQ ID NO: 282)
metdtlllwvlllwvpgstgAPEVSEEPRCPRAACQAKRGDQRCDRECNS

PGCGWDGGDCSLSVGDPWRQCEALQCWRLFNNSRCDPACSSPACLYDNFD

CHAGGRERTCNPVYEKYCADHFADGRCDQGCNTEECGWDGLDCASEVPAL

LARGVLVLTVLLPPEELLRSSADFLQRLSAILRTSLRFRLDAHGQAMVFP

YHRPSPGSEPRARRELAPEVIGSVVMLEIDNRLCLQSPENDHCFPDAQSA

ADYLGALSAVERLDFPYPLRDVRGEPLEPPEPSgshhhhhh

-continued

20350 IgG
(SEQ ID NO: 287)
MGLGARGRRRRRRLMALPPPPPPMRALPLLLLLAGLGAAAPPCLDGSPCA

NGGRCTHQQPSLEAACLCLPGWVGERCQLEDPCHSGPCAGRGVCQSSVVA

GTARFSCRCLRGFQGPDCSQPDPCVSRPCVHGAPCSVGPDGRFACACPPG

YQGQSCQSDIDECRSGTTCRHGGTCLNTPGSFRCQCPLGYTGLLCENPVV

PCAPSPCRNGGTCRQSSDVTYDCACLPGFEGQNCEVNVDDCPGHRCLNGG

TCVDGVNTYNCQCPPEWTGQFCTEDVDECQLQPNACHNGGTCFNLLGGHS

CVCVNGWTGESCSQNIDDCATAVCFHGATCHDRVASFYCACPMGKTGLLC

HLDDACVSNPCHEDAICDTNPVSGRAICTCPPGFTGGACDQDVDECSIGA

NPCEHLGRCVNTQGSFLCQCGRGYTGPRCETDVNECLSGPCRNQATCLDR

IGQFTCICMAGFTGTYCEVDIDECQSSPCVNGGVCKDRVNGFSCTCPSGF

SGSMCQLDVDECASTPCRNGAKCVDQPDGYECRCAEGFEGTLCERNVDDC

SPDPCHHGRCVDGIASFSCACAPGYTGIRCESQVDECRSQPCRYGGKCLD

LVDKYLCRCPPGTTGVNCEVNIDDCASNPCTFGVCRDGINRYDCVCQPGF

TGPLCNVEINECASSPCGEGGSCVDGENGFHCLCPPGSLPPLCLPANHPC

AHKPCSHGVCHDAPGGFRCVCEPGWSGPRCSQSLAPDACESQPCQAGGTC

TSDGIGFRCTCAPGFQGHQCEVLSPCTPSLCEHGGHCESDPDRLTVCSCP

PGWQGPRCQQDVDECAGASPCGPHGTCTNLPGNFRCICHRGYTGPFCDQD

IDDCDPNPCLHGGSCQDGVGSFSCSCLDGFAGPRCARDVDECLSSPCGPG

TCTDHVASFTCACPPGYGGFHCEIDLPDCSPSSCFNGGTCVDGVSSFSCL

CRPGYTGTHCQYEADPCFSRPCLHGGICNPTHPGFECTCREGFTGSQCQN

PVDWCSQAPCQNGGRCVQTGAYCICPPGWSGRLCDIQSLPCTEAAAQMGV

RLEQLCQEGGKCIDKGRSHYCVCPEGRTGSHCEHEVDPCTAQPCQHGGTC

RGYMGGYVCECPAGYAGDSCEDNIDECASQPCQNGGSCIDLVARYLCSCP

PGTLGVLCEINEDDCDLGPSLDSGVQCLHNGTCVDLVGGFRCNCPPGYTG

LHCEADINECRPGACHAAHTRDCLQDPGGHFRCVCHPGFTGPRCQIALSP

CESQPCQHGGQCRHSLGRGGGLTFTCHCVPPFWGLRCERVARSCRELQCP

VGIPCQQTARGPRCACPPGLSGPSCRVSRASPSGATNASCASAPCLHGGS

CLPVQSVPFFRCVCAPGWGGPRCETPSAAPEVPEEPRCPRAACQAKRGDQ

NCDRECNTPGCWDGGDCSLNVDDPWRQCEALQCWRLFNNSRCDPACSSP

ACLYDNFDCYSGGRDRTCNPVYEKYCADHFADGRCDQGCNTEECGWDGLD

CASEVPALLARGVLVLTVLLPPEELLRSSADFLQRLSAILRTSLRFRLDA

RGQAMVFPYHRPSPGSESRVRRELGPEVIGSVVMLEIDNRLCLQSAENDH

CFPDAQSAADYLGALSAVERLDFPYPLRDVRGEPLEAPEQSVPLLPLLVA

GAVFLLIIFILGVMVARRKREHSTLWFPEGFALHKDIAAGHKGRREPVGQ

DALGMKNMAKGESLMGEVVTDLNDSECPEAKRLKVEEPGMGAEEPEDCRQ

WTQHHLVAADIRVAPATALTPPQGDADADGVDVNVRGPDGFTPLMLASFC

GGALEPMPAEEDEADDTSASIISDLICQGAQLGARTDRTGETALHLAARY

ARADAAKRLLDAGADTNAQDHSGRTPLHTAVTADAQGVFQILIRNRSTDL

DARMADGSTALILAARLAVEGMVEELIASHADVNAVDELGKSALHWAAAV

-continued

NNVEATLALLKNGANKDMQDSKEETPLFLAAREGSYEAAKLLLDHLANRE
ITDHLDRLPRDVAQERLHQDIVRLLDQPSGPRSPSGPHGLGPLLCPPGAF
LPGLKAVQSGTKKSRRPPGKTGLGPQGTRGRGKKLTLACPGPLADSSVTL
SPVDSLDSPRPFSGPPASPGGFPLEGPYATTATAVSLAQLGASRAGPLGR
QPPGGCVLSFGLLNPVAVPLDWARLPPPAPPGPSFLLPLAPGPQLLNPGA
PVSPQERPPPYLAAPGHGEEYPAAGTRSSPTKARFLRVPSEHPYLTPSPE
SPEHWASPSPPSLSDWSDSTPSPATATNATASGALPAQPHPISVPSLPQS
QTQLGPQPEVTPKRQVMA

20358 IgG
(SEQ ID NO: 288)
MGLGARGRRRRRLMALPPPPPPMRALPLLLLLAGLGAAAPPCLDGSPCA
NGGRCTHQQPSLEAACLCLPGWVGERCQLEDPCHSGPCAGRGVCQSSVVA
GTARFSCRCLRGFQGPDCSQPDPCVSRPCVHGAPCSVGPDGRFACACPPG
YQGQSCQSDIDECRSGTTCRHGGTCLNTPGSFRCQCPLGYTGLLCENPVV
PCAPSPCRNGGTCRQSSDVTYDCACLPGFEGQNCEVNVDDCPGHRCLNGG
TCVDGVNTYNCQCPPEWTGQFCTEDVDECQLQPNACHNGGTCFNLLGGHS
CVCVNGWTGESCSQNIDDCATAVCFHGATCHDRVASFYCACPMGKTGLLC
HLDDACVSNPCHEDAICDTNPVSGRAICTCPPGFTGGACDQDVDECSIGA
NPCEHLGRCVNTQGSFLCQCGRGYTGPRCETDVNECLSGPCRNQATCLDR
IGQFTCICMAGFTGTYCEVDIDECQSSPCVNGGVCKDRVNGFSCTCPSGF
SGSMCQLDVDECASTPCRNGAKCVDQPDGYECRCAEGFEGTLCERNVDDC
SPDPCHHGRCVDGIASFSCACAPGYTGIRCESQVDECRSQPCRYGGKCLD
LVDKYLCRCPPGTTGVNCEVNIDDCASNPCTFGVCRDGINRYDCVCQPGF
TGPLCNVEINECASSPCGEGGSCVDGENGFHCLCPPGSLPPLCLPANHPC
AHKPCSHGVCHDAPGGFRCVCEPGWSGPRCSQSLAPDACESQPCQAGGTC
TSDGIGFRCTCAPGFQGHQCEVLSPCTPSLCEHGGHCESDPDRLTVCSCP
PGWQGPRCQQDVDECAGASPCGPHGTCTNLPGNFRCICHRGYTGPFCDQD
IDDCDPNPCLHGGSCQDGVGSFSCSCLDGFAGPRCARDVDECLSSPCGPG
TCTDHVASFTCACPPGYGGFHCEIDLPDCSPSSCFNGGTCVDGVSSFSCL
CRPGYTGTHCQYEADPCFSRPCLHGGICNPTHPGFECTCREGFTGSQCQN
PVDWCSQAPCQNGGRCVQTGAYCICPPGWSGRLCDIQSLPCTEAAAQMGV
RLEQLCQEGGKCIDKGRSHYCVCPEGRTGSHCEHEVDPCTAQPCQHGGTC
RGYMGGYVCECPAGYAGDSCEDNIDECASQPCQNGGSCIDLVARYLCSCP
PGTLGVLCEINEDDCDLGPSLDSGVQCLHNGTCVDLVGGFRCNCPPGYTG
LHCEADINECRPGACHAAHTRDCLQDPGGHFRCVCHPGFTGPRCQIALSP
CESQPCQHGGQCRHSLGRGGGLTFTCHCVPPFWGLRCERVARSCRELQCP
VGIPCQQTARGPRCACPPGLSGPSCRVSRASPSGATNASCASAPCLHGGS
CLPVQSVPFFRCVCAPGWGGPRCETPSAAPEVPEEPRCPRAACQAKRGDQ
NCDRECNTPGCGWDGGDCSLNVDDPWRQCEALQCWRLFNNSRCDPACSSP
ACLYDNFDCYSGGRDRTCNPVYEKYCADHFADGRCDQGCNTEECGWDGLD
CASEVPALLARGVLVLTVLLPPEELLRSSADFLQRLSAILRTSLRFRLDA
RGQAMVFPYHRPSPGSESRVRRELGPEVIGSVVMLEIDNRLCLQSAENDH

-continued

CFPDAQSAADYLGALSAVERLDFPYPLRDVRGEPLEAPEQSVPLLPLLVA
GAVFLLIIFILGVMVARRKREHSTLWFPEGFALHKDIAAGHKGRREPVGQ
DALGMKNMAKGESLMGEVVTDLNDSECPEAKRLKVEEPGMGAEEEPEDCRQ
WTQHHLVAADIRVAPATALTPPQGDADADGVDVNVRGPDGFTPLMLASFC
GGALEPMPAEEDEADDTSASIISDLICQGAQLGARTDRTGETALHLAARY
ARADAAKRLLDAGADTNAQDHSGRTPLHTAVTADAQGVFQILIRNRSTDL
DARMADGSTALILAARLAVEGMVEELIASHADVNAVDELGKSALHWAAAV
NNVEATLALLKNGANKDMQDSKEETPLFLAAREGSYEAAKLLLDHLANRE
ITDHLDRLPRDVAQERLHQDIVRLLDQPSGPRSPSGPHGLGPLLCPPGAF
LPGLKAVQSGTKKSRRPPGKTGLGPQGTRGRGKKLTLACPGPLADSSVTL
SPVDSLDSPRPFSGPPASPGGFPLEGPYATTATAVSLAQLGASRAGPLGR
QPPGGCVLSFGLLNPVAVPLDWARLPPPAPPGPSFLLPLAPGPQLLNPGA
PVSPQERPPPYLAAPGHGEEYPAAGTRSSPTKARFLRVPSEHPYLTPSPE
SPEHWASPSPPSLSDWSDSTPSPATATNATASGALPAQPHPISVPSLPQS
QTQLGPQPEVTPKRQVMA

20337 IgG
(SEQ ID NO: 289)
MGLGARGRRRRRLMALPPPPPPMRALPLLLLLAGLGAAAPPCLDGSPCA
NGGRCTHQQPSLEAACLCLPGWVGERCQLEDPCHSGPCAGRGVCQSSVVA
GTARFSCRCLRGFQGPDCSQPDPCVSRPCVHGAPCSVGPDGRFACACPPG
YQGQSCQSDIDECRSGTTCRHGGTCLNTPGSFRCQCPLGYTGLLCENPVV
PCAPSPCRNGGTCRQSSDVTYDCACLPGFEGQNCEVNVDDCPGHRCLNGG
TCVDGVNTYNCQCPPEWTGQFCTEDVDECQLQPNACHNGGTCFNLLGGHS
CVCVNGWTGESCSQNIDDCATAVCFHGATCHDRVASFYCACPMGKTGLLC
HLDDACVSNPCHEDAICDTNPVSGRAICTCPPGFTGGACDQDVDECSIGA
NPCEHLGRCVNTQGSFLCQCGRGYTGPRCETDVNECLSGPCRNQATCLDR
IGQFTCICMAGFTGTYCEVDIDECQSSPCVNGGVCKDRVNGFSCTCPSGF
SGSMCQLDVDECASTPCRNGAKCVDQPDGYECRCAEGFEGTLCERNVDDC
SPDPCHHGRCVDGIASFSCACAPGYTGIRCESQVDECRSQPCRYGGKCLD
LVDKYLCRCPPGTTGVNCEVNIDDCASNPCTFGVCRDGINRYDCVCQPGF
TGPLCNVEINECASSPCGEGGSCVDGENGFHCLCPPGSLPPLCLPANHPC
AHKPCSHGVCHDAPGGFRCVCEPGWSGPRCSQSLAPDACESQPCQAGGTC
TSDGIGFRCTCAPGFQGHQCEVLSPCTPSLCEHGGHCESDPDRLTVCSCP
PGWQGPRCQQDVDECAGASPCGPHGTCTNLPGNFRCICHRGYTGPFCDQD
IDDCDPNPCLHGGSCQDGVGSFSCSCLDGFAGPRCARDVDECLSSPCGPG
TCTDHVASFTCACPPGYGGFHCEIDLPDCSPSSCFNGGTCVDGVSSFSCL
CRPGYTGTHCQYEADPCFSRPCLHGGICNPTHPGFECTCREGFTGSQCQN
PVDWCSQAPCQNGGRCVQTGAYCICPPGWSGRLCDIQSLPCTEAAAQMGV
RLEQLCQEGGKCIDKGRSHYCVCPEGRTGSHCEHEVDPCTAQPCQHGGTC
RGYMGGYVCECPAGYAGDSCEDNIDECASQPCQNGGSCIDLVARYLCSCP
PGTLGVLCEINEDDCDLGPSLDSGVQCLHNGTCVDLVGGFRCNCPPGYTG

-continued

LHCEADINECRPGACHAAHTRDCLQDPGGHFRCVCHPGFTGPRCQIALSP

CESQPCQHGGQCRHSLGRGGGLTFTCHCVPPFWGLRCERVARSCRELQCP

VGIPCQQTARGPRCACPPGLSGPSCRVSRASPSGATNASCASAPCLHGGS

CLPVQSVPFFRCVCAPGWGGPRCETPSAAPEVPEEPRCPRAACQAKRGDQ

NCDRECNTPGCGWDGGDCSLNVDDPWRQCEALQCWRLFNNSRCDPACSSP

ACLYDNFDCYSGGRDRTCNPVYEKYCADHFADGRCDQGCNTEECGWDGLD

CASEVPALLARGVLVLTVLLPPEELLRSSADFLQRLSAILRTSLRFRLDA

RGQAMVFPYHRPSPGSESRVRRELGPEVIGSVVMLEIDNRLCLQSAENDH

CFPDAQSAADYLGALSAVERLDFPYPLRDVRGEPLEAPEQSVPLLPLLVA

GAVFLLIIFILGVMVARRKREHSTLWFPEGFALHKDIAAGHKGRREPVGQ

DALGMKNMAKGESLMGEVVTDLNDSECPEAKRLKVEEPGMGAEEPEDCRQ

WTQHHLVAADIRVAPATALTPPQGDADADGVDVNVRGPDGFTPLMLASFC

GGALEPMPAEEDEADDTSASIISDLICQGAQLGARTDRTGETALHLAARY

ARADAAKRLLDAGADTNAQDHSGRTPLHTAVTADAQGVFQILIRNRSTDL

DARMADGSTALILAARLAVEGMVEELIASHADVNAVDELGKSALHWAAAV

NNVEATLALLKNGANKDMQDSKEETPLFLAAREGSYEAAKLLLDHLANRE

ITDHLDRLPRDVAQERLHQDIVRLLDQPSGPRSPSGPHGLGPLLCPPGAF

LPGLKAVQSGTKKSRRPPGKTGLGPQGTRGRGKKLTLACPGPLADSSVTL

SPVDSLDSPRPFSGPPASPGGFPLEGPYATTATAVSLAQLGASRAGPLGR

QPPGGCVLSFGLLNPVAVPLDWARLPPPAPPGPSFLLPLAPGPQLLNPGA

PVSPQERPPPYLAAPGHGEEYPAAGTRSSPTKARFLRVPSEHPYLTPSPE

SPEHWASPSPPSLSDWSDSTPSPATATNATASGALPAQPHPISVPSLPQS

QTQLGPQPEVTPKRQVMA

HDx-MS Experimental Section

HDx-MS experiments were performed on a Waters Synapt G2 HDX platform, which includes LEAP robot system, nanoACQUITY UPLC System, and Synapt G2 mass spectrometer. Two experiment methods were used to perform HDx-MS measurements. In the first method all experiments α were carried out in solution, and in the second method the antibodies were immobilized onto beads to improve the peptide coverage of the Notch 3 NRR antigen.

In the first method, the experiments were automated by a LEAP robot operated by the LeapShell software, which performed initiation of the deuterium exchange reaction, reaction time control, quench reaction, injection onto the UPLC system and digestion time control. The Leap robot is equipped with two temperature controlled stacks maintained at 37° C. for HDx reaction and maintained at 2° C. for storage of protein and quench solution. Triplicate control experiments were carried out using 250 pmol of Notch 3 NNR antigen. Antigen was exchanged into deuterated Tris buffer (15 mM Tris HCl, 10 mM calcium chloride, 10 mM sodium chloride in D20, pH=7.6) at a final deuterium concentration of 90.0% D for 40 minutes at 37° C. Deuterium exchange was quenched by diluting the exchanged solution 1:1 with (6M Urea and 1M TCEP pH=2.5) for 5 minutes at 2° C. After quenching, the sample was injected onto the Waters UPLC system where it was digested using an immobilized pepsin column that was maintained at 12° C. After digestion, peptides were retained on a Waters UPLC HSS T3 2.1×5 mm pre-column. Peptides were then eluted from the pre-column and separated on a Waters UPLC CSH C18 1.0×100 mm column using an 8-minute 2 to 35% acetonitrile gradient. Next, triplicate experiments were carried out on antigen-mAb complex. In these experiments, the 250 pmol of Notch 3 NRR antigen was preincubated with 375 pmols of antibody at room temperature for 15 minutes in Tris buffer (15 mM TrisHCl, 10 mM calcium chloride, 10 mM sodium chloride in water, pH=7.6). All other experimental parameters were identical to the control experiments.

In order to improve the peptide coverage of Notch 3 NRR in the LNR-B domain, a second HDx-MS method that incorporates immobilization of the mAb to beads to minimize the antibody signal in the LC-MS experiments was used. In this method, triplicate control experiments were carried out as follows. 400 pmol of Notch3 NRR antigen was diluted into pre-warmed 37° C., 99% deuterated TRIS buffer (pH 7.6) and incubates at 37° C. in Thermo-mixer (700 rpm) for 40 minutes (% D=96.1%). Deuterium exchange was quenched by 1:1 dilution with cold quench buffer (6 M Urea and 1 M TCEP pH=2.5) on ice for 5 min. After quenching the tube was transferred onto a LEAP system and the quenched sample was injected by the LEAP system onto the UPLC system for analysis. The UPLC system incorporates an on-line pepsin digestion (maintained at 12° C.). An 8-minute 2 to 35% acetonitrile gradient and Waters UPLC CSH C18 1.0×100 mm column was used for separation. Next, triplicate experiments were carried out using the antibodies. 20350 and 20358 antibodies were immobilized on Protein G agarose beads (Thermo cat#22851) using standard techniques. Briefly, the antibody was centrifuged to remove a storage buffer. Then 200 µl of TRIS buffer (pH 7.6) and 400 pmol of Notch3 NRR were added to the immobilized Ab and incubated for 15 min at 25° C. After incubation, the complex was centrifuged and washed with 200 µl TRIS buffer and centrifuged again. For deuterium exchange, 200 µL of deuterated TRIS was added to the antigen-antibody complex for incubation at 37° C. for 40 minutes (% D=96.1%). Deuterium buffer was then removed, and immediately, 125 µL ice cold quench buffer was added. After quenching, the column was centrifuged and the flow-through was transferred into pre-chilled HPLC vial and analyzed using the same on-line pepsin digestion/LC-MS setup.

HDx-MS Results 20350 and 20358

Figure 27:
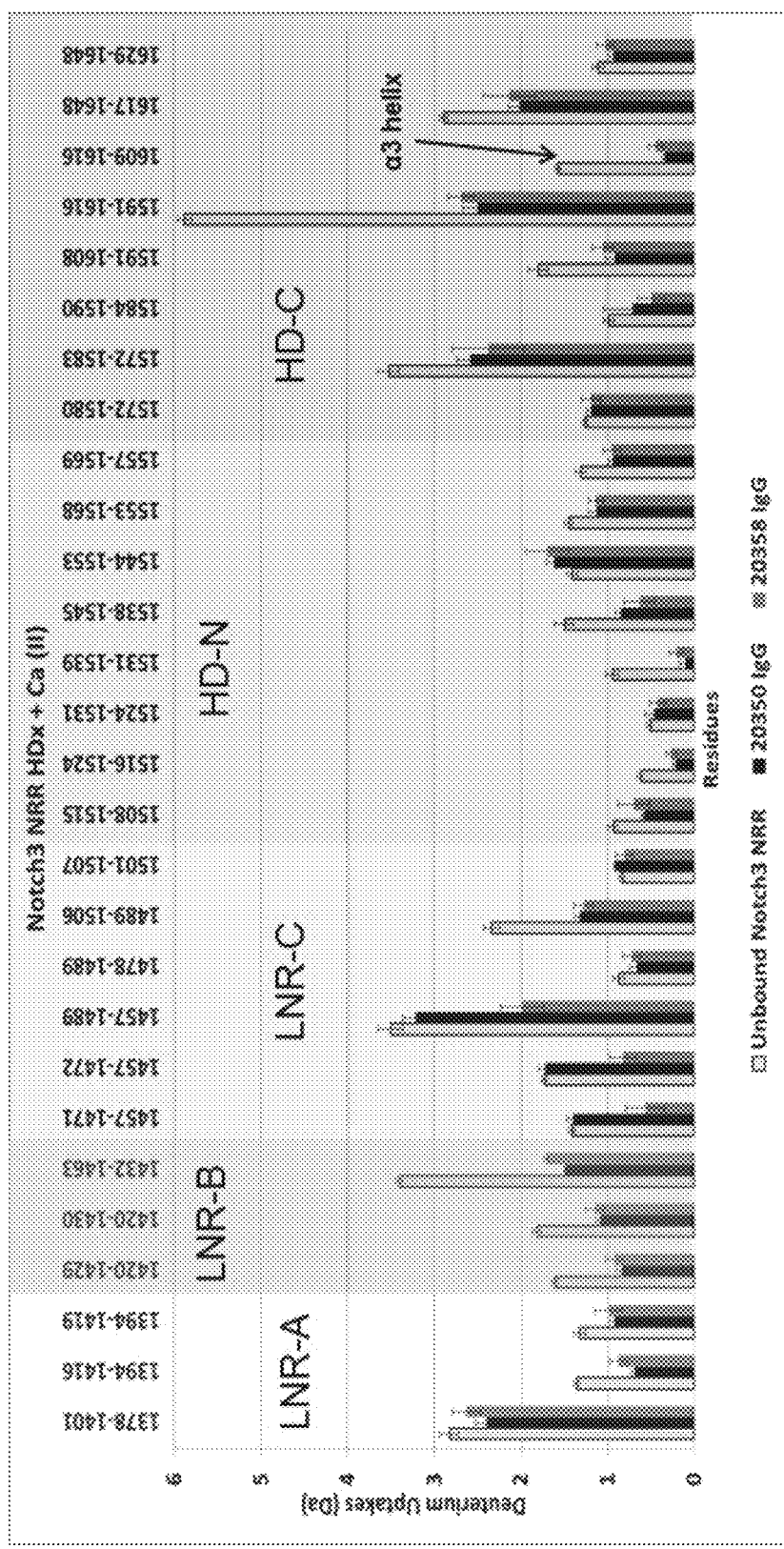
FIG. 27: HDx-MS epitope mapping of Notch 3 NRR+ $Ca^{2+}$ showing average deuterium uptake of Notch 3 NRR in an unbound state.
Figure 28:
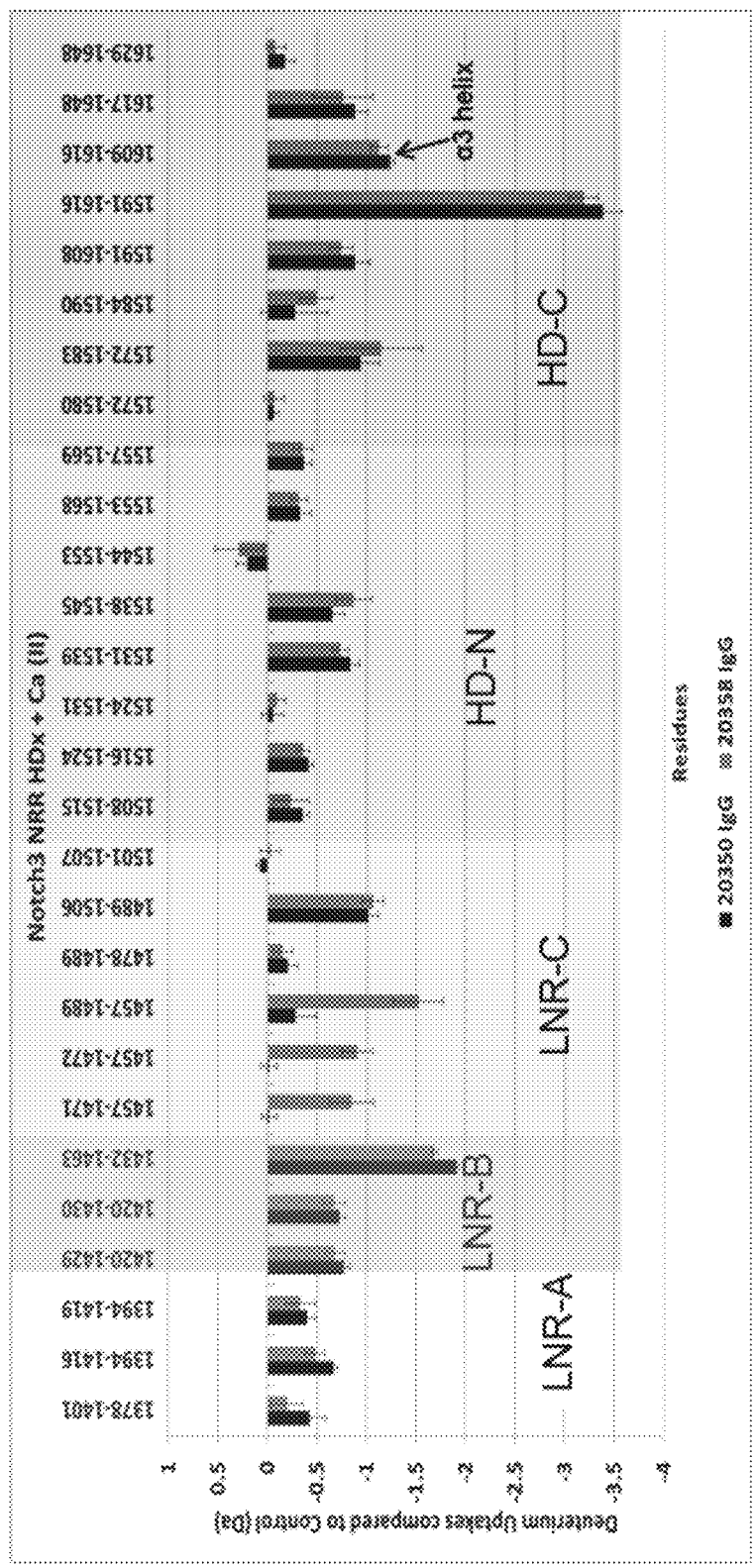
FIG. 28: Differential plot of Notch 3 NRR+$Ca^{2+}$ showing absolute protection amounts with 20350, 20358 antibody binding to Notch 3 NRR.

HDx-MS results are summarized in FIG. 27 and FIG. 28. FIG. 27 shows the average deuterium uptake for Notch 3 NRR peptides in the absence (control) and presence of 20350 and 20358. In FIG. 27 it is useful to examine two differences: differences between control and mAbs and differences between mAbs. FIG. 28 shows the difference between apo and bound states for 20350 and 20358 antibodies. Differences less than 0.5 Da are considered insignificant (e.g. no change relative to unbound Notch 3 NRR control). Examination of the differences allows one to determine the regions of Notch3 NRR that are protected upon IgG binding.

From FIGS. 27 and 28, in the LNR-A region there was an overall insignificant amount of protection. This observation suggests that neither the 20350 nor 20358 antibodies interact significantly with this region of the Notch 3 NRR. In the LNR-B domain there was an increase in protection especially in the peptide 1432-1463. This peptide spans the vast majority of LNR-B and part of the LNR-B/C linker and was only detected in the immobilized antibody experiments. In the LNR-B/C linker and LNR-C region a few peptides (1457-1471, 1457-1472, and 1457-1489) are protected in 20358, but these peptides are not protected in 20350. A shorter region 1478-1489 that was not protected by binding either antibody to Notch 3 NRR was also detected. With this information, one can deduce that the region that is differentially protected by 20358 is the region spanning 1457-1477. Lastly, one other region in LNR-C (1490-1500) was protected by both antibodies. In the HD-N domain, no protection by either of the antibodies studied was observed except for a region spanning 1532-1545. In the HD-C domain regions 1580-1583, 1592-1616, and 1617-1628 were both protected from deuterium exchange upon binding of either 20350 or 20358 to Notch 3 NRR.

Figure 29:
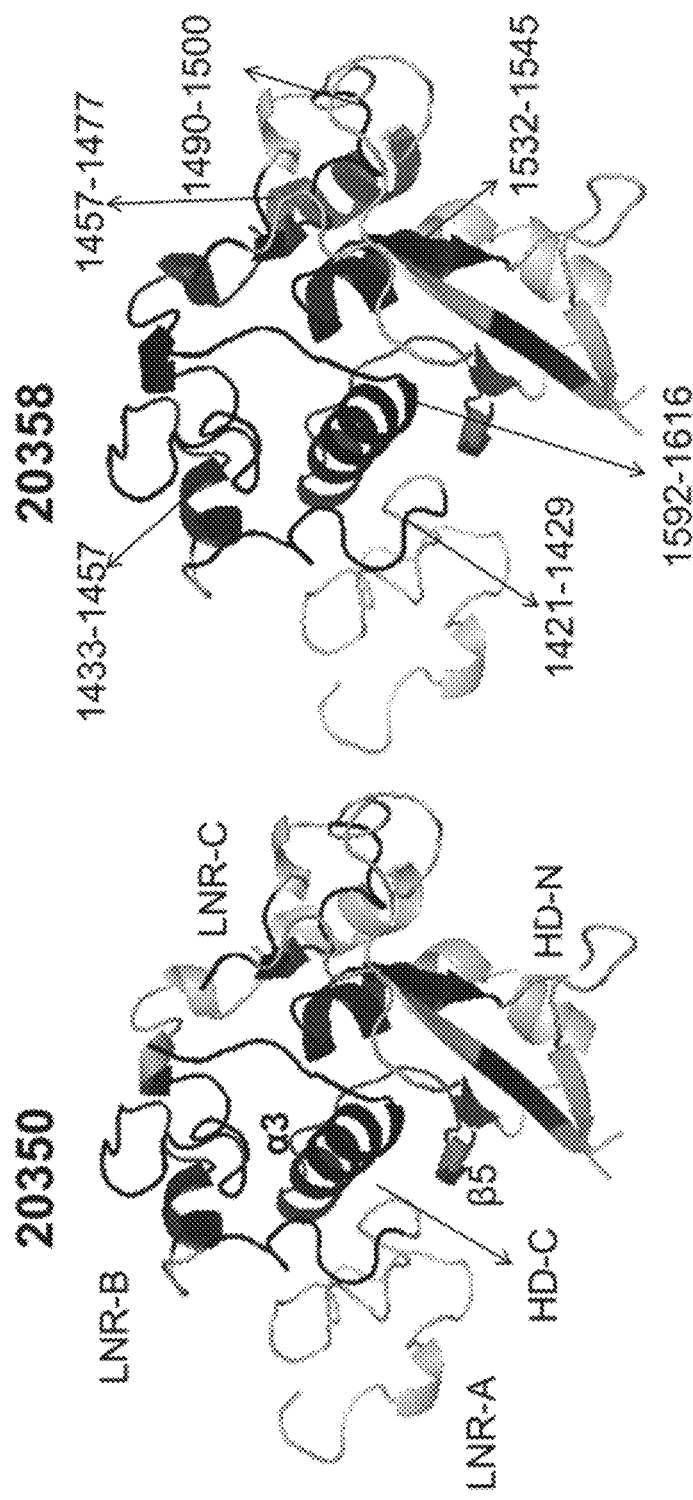
FIG. 29: Structures showing regions that are protected (black) upon 20350 and 20358 binding to Notch 3 NRR.

FIG. 29 shows a map of the protected regions in HDx-MS experiments using the Notch 3 NNR crystal structure shown in Example 14. Mapping the protected regions onto a structure allows one to delineate regions of protection that are more buried in the structure (likely allosteric effects) from those that are on the surface of the protein (potentially involved in forming the epitope). For example, in FIGS. 27 and 28 the region 1609-1616, which corresponds to the center section of the α3 helix, is protected substantially by both antibodies even though it does not directly interact with either 20350 or 20358. The protection is allosteric in nature and may be due to a stabilization of the LNR domains, which surround the α3 helix, upon antibody binding. Stabilization of the LNR domains surrounding the α3 helix can subsequently limit the deuterium accessibility to the center of the α3 helix. The α3 helix protection can also be due to an increase in the stabilization of the α3 helix hydrogen bonding network upon antibody binding.

Examining the protection on the surface, it was immediately observed that the region 1457-1477 was located on the surface. This region, which spans the entire LNR-B/C linker and the N-terminus of the LNR-C, was only protected upon binding of 20358 to Notch 3 NRR and not with 20350. The differential protection in this region can be used to differentiate the 20350 and 20358 antibodies and is in agreement with the X-ray crystallography studies (Example 14). From Table 5, the region 1457-1477 contains 11 residues that are buried in 20358 complex. In contrast, Table 4 indicates that this region contains only 4 residues that are buried in the 20350 complex. From FIG. 29 it is possible to interpret that both antibodies also interact substantially with the LNR-B domain. From X-ray crystallography (Example 14) only 20350 interacts substantially with this region (9 versus 1 buried residue on Notch 3 NRR). Limited resolution in the HDx-MS experiments and sensitivity to allosteric effects are likely responsible for the misleading interpretation. As mentioned earlier, in the LNR-B domain, the peptide that was most protected spans 31 amino acids ranging from 1432-1463. This peptide contains residues that are buried in both crystal structures (11 buried residues in 20350 vs. 2 buried residues in 20358). Because both complexes have similar protection from 1432-1457, binding of 20358 in the nearby LNR-C domain appears to also induce some allosteric protection in this region. Lastly, smaller peptides (e.g. 1420-1430) containing the C-terminus of LNR-A and AB linker also show some (and equal) protection by both antibodies. X-ray crystallography (Example 14) indicates that this region was only buried in the 20350 complex. The HDx-MS data suggest that this region was also allosterically protected upon 20358 binding and cannot be differentiated from the 20358 direct binding events.

Lastly, FIG. 30 provides a summary of the protected regions determined by HDx-MS and compares them to the buried residues from the X-ray crystallography studies (Example 14). Overall, the HDx-MS experiments detect protected regions containing almost all of the buried residues via X-ray crystallography. As mentioned previously, some additional regions of protection were also detected, that are likely allosteric in nature, such as the center of the α3 helix.

HDx-MS Experimental and Results for IgG Antibody 20337

Preliminary experiments with Notch 3 NRR in the absence of calcium were also performed using unbound Notch 3 NRR and Notch 3 in the presence of the two previously described IgG antibodies and one additional IgG antibody: 20337 (SEQ ID NO: 289) using the automated HDx-MS system. In these experiments 200 pmol Notch 3 NRR (control) or 200 pmol of Notch 3 NRR+300 pmol IgG antibody are exchanged into D-PBS (final % D=88.3%) for 40 minutes at 37 C. Deuterium exchange was quenched by diluting the exchanged solution 1:1 with (6 M Urea and 1 M TCEP pH=2.5) for 5 minutes at 2° C. After quenching, the sample was injected onto the Waters UPLC system where it was digested using an immobilized pepsin column that was maintained at 12° C. After digestion, peptides were retained on a Waters UPLC HSS T3 2.1×5 mm pre-column. Peptides were then eluted from the pre-column and separated on a Waters UPLC CSH C18 1.0×100 mm column using an 8-minute 2 to 35% acetonitrile gradient.

Figure 31:
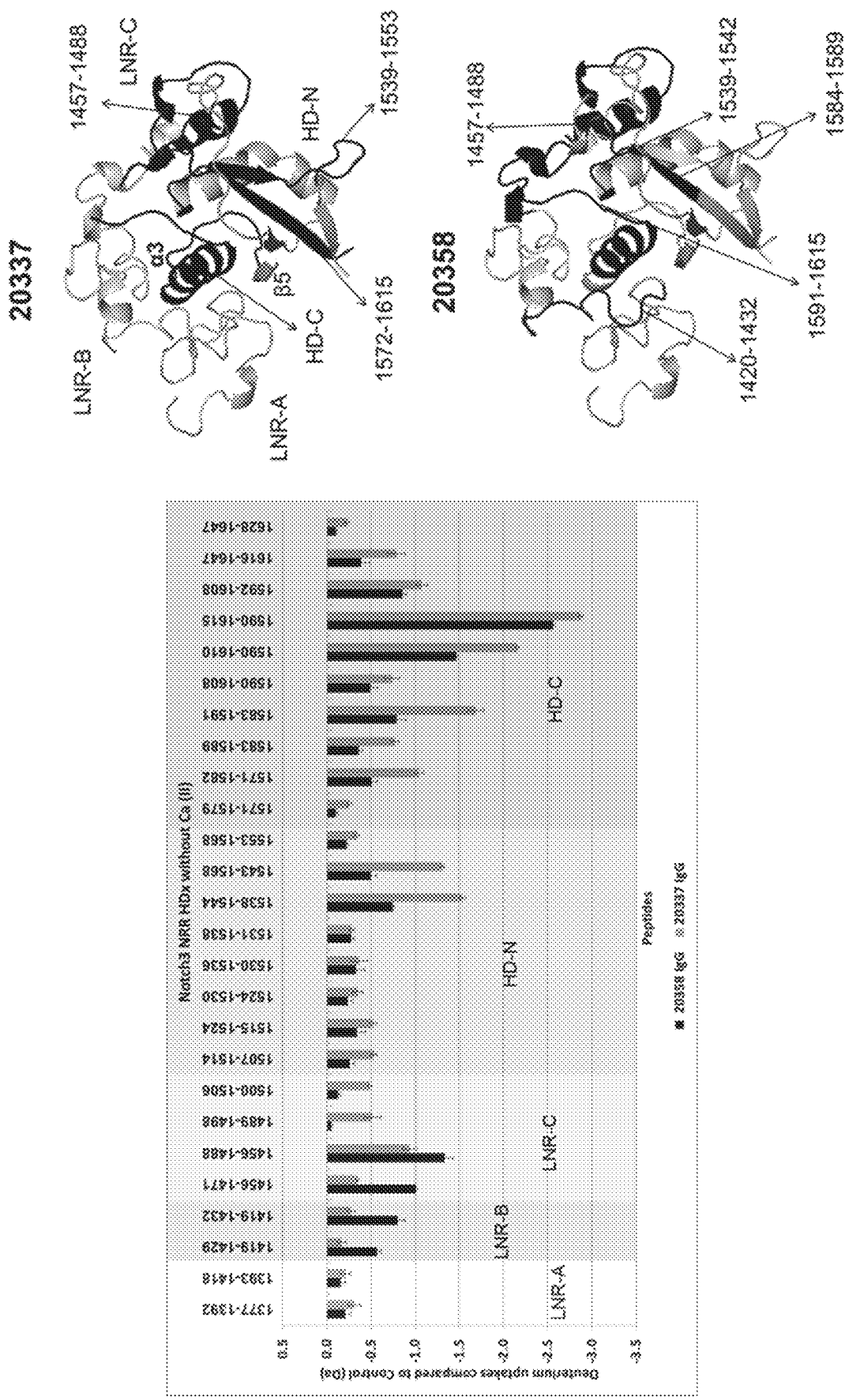
FIG. 31: Difference Plot for Notch 3 NRR without $Ca^{2+}$ for 20037 and 20358 and protected regions (black) mapped onto Notch 3 NRR structure.

The left side of FIG. 31 shows the HDX-MS difference plot for Notch 3 NRR complexed with either 20358 or 20337 in the absence of $Ca^{2+}$. Examination of this plot allows one to see regions that differentially protected between these two antibodies. For example, the regions 1419-1432 and 1456-1488 were more protected in the presence of 20358 relative to 20337. In contrast, the regions 1489-1498, 1500-1506, 1538-1568, 1571-1582, and 1583-1591 are more protected following 20337 binding to Notch 3 NRR relative to that of 20358. The protected regions for 20337 and 20358 are highlighted in black in the two figures on the right side of FIG. 31. The observation of differential HDx-MS indicates that 20337 antibody interact differently with Notch 3 NRR antigen relative to 20358 (data shown) and 20350 (data not shown) antibody. Overall, the HDx-MS data are consistent with the epitope binning data (Example 13) and X-ray crystallography (Example 14) that indicate that 20337, 20358, and 20350 have distinct interactions (and epitopes) on Notch 3 NRR.

The same experiment can be repeated in to acquire HDx-MS data corresponding to Notch3 NRR—20337 complex in the presence of $Ca^{2+}$, with an expectation that similar data to that seen in the absence $Ca^{2+}$ is likely, i.e., regions of Notch 3 NRR that are differentially protected by all three antibodies will be seen.

Example 16: Identification of Additional Conformational Epitopes of Notch 3 NRR

Figure 32:
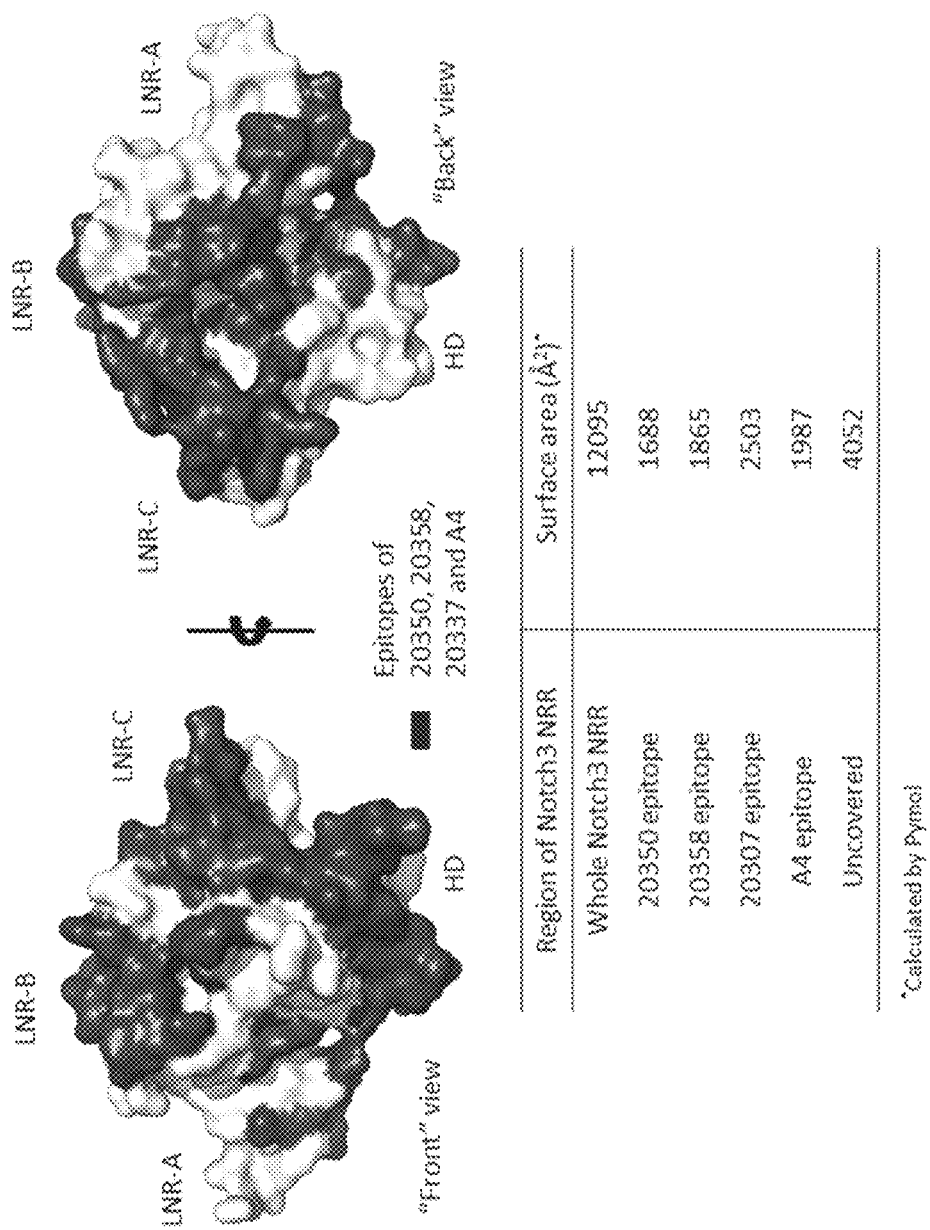
FIG. 32: Conformational epitopes of antibodies 20337, 20350, 20358 and A4 mapped onto Notch 3 NRR surface.
Figure 33:
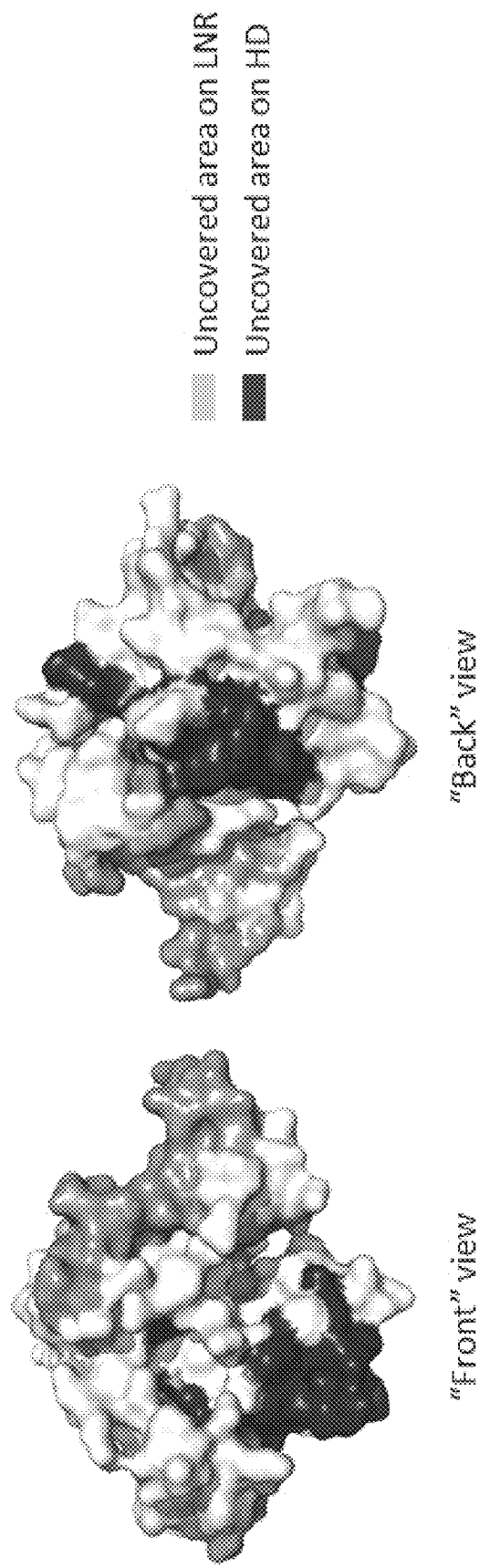
FIG. 33: Surface on Notch3 NRR left uncovered by antibodies 20337, 20350, 20358 and A4.

Additional conformational epitopes of Notch 3 NRR can be found by pre-blocking Notch3 NRR with the antibodies disclosed herein (e.g., 20337, 20350, 20358 and A4). Based on the structure of Notch 3 NRR disclosed herein, the epitopes of antibodies 20337, 20350, 20358 and A4 can be mapped onto the surface of Notch 3 NRR. As shown in FIG. 32, the epitopes of the four antibodies cover ~67% of the surface of Notch 3 NRR, leaving ~33% of the surface uncovered, across both LNR and HD domains (FIG. 32).

Figure 34:
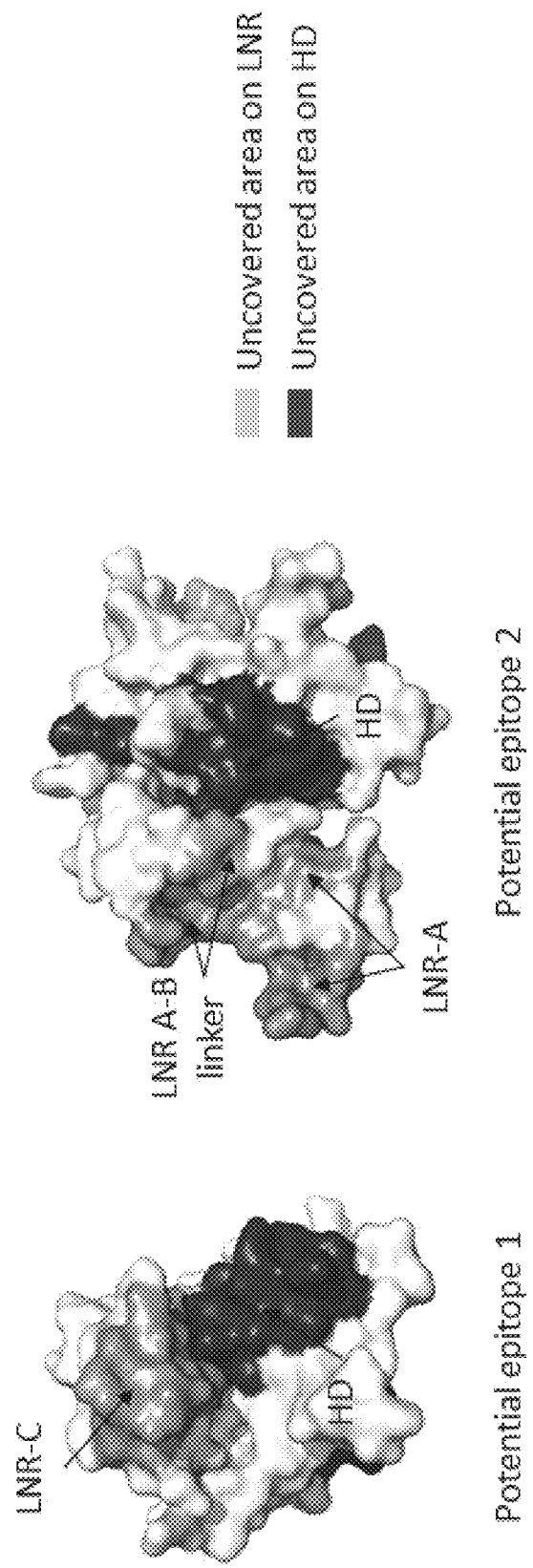
FIG. 34: Potential conformational epitopes on the surface of Notch3 NRR left uncovered by antibodies 20337, 20350, 20358 and A4.

As exemplified by the four antibodies disclosed herein, antibodies that bind conformational epitopes bridging LNR and HD is a potential mechanism for antibodies to inhibit Notch3 signaling. The antibodies function by clamping LNR and HD together and stabilizing the autoinhibitory state of Notch 3 NRR. At least two additional potential epitopes on the surface of Notch 3 NRR were identified that were left uncovered by 20337, 20350, 20358 and A4. As shown in FIG. 34, the first potential epitope comprises the LNR-C and HD domains and the second the LNR-A/B linker, LNR-A and HD domains. Regarding the favorable geometry of these two potential epitopes (directly bridging LNR and HD), it is likely that additional inhibitory antibodies of Notch 3 can be found against them.

To screen for antibodies that target these two potential epitopes as well as other conformational epitopes the following experimental strategy can be employed. In general, a previously identified Notch3 antibody (for example, either 20337, 20350 or 20358) can be pre-incubated with recombinant NRR protein prior to panning with a commercially available phage display library, such as the Morphosys HuCAL PLATINUM® library. In addition, these Notch3 antibodies (20337, 20350, 20358) could be pre-bound to cells expressing Notch 3 prior to panning. Pre-incubation with the Notch3 antibodies, either alone or in combination, would block the epitope of these antibodies and enrich for clones/antibodies that bind to a distinct and unique epitope. As described, comprehensive panning strategies using either solid phase or solution phase panning with recombinant NRR proteins and whole cell and differential whole cell panning would be used. Clones/antibodies would then be selected that show selective binding to Notch3 both as a recombinant protein as well as to cells expressing Notch3 as described in FIGS. 3-6. In addition, antibodies identified from the above approach would be screened for inhibition of Notch 3 signaling in cell-based functional assays (ligand driven reporter gene assay, Notch target gene mRNA quantitation, ICD3 protein levels, TALL-1 proliferation) as described in FIGS. 7, 8, 11, 13, 14, 15. In order to determine whether the newly identified Notch3 antibodies bind to the same epitope as 20337, 20350, 20358 or to a distinct non-overlapping epitope, three general approaches can be used: epitope binning with Biacore (FIG. 20); co-crystal structures with NRR protein (FIG. 21, 23, 24, 25); and HDx-MS epitope mapping of antibody/Notch 3 NRR complexes (FIGS. 27-31). Ultimately, co-crystal structures of these new antibodies with the NRR protein would allow one to identify the epitope of the antibodies and determine if the epitopes are distinct from 20337, 20358 and 20350.

EQUIVALENTS

The foregoing written specification is considered to be sufficient to enable one skilled in the art to practice the disclosure. The foregoing description and examples detail certain preferred embodiments of the disclosure and describe the best mode contemplated by the inventors. It will be appreciated, however, that no matter how detailed the foregoing may appear in text, the disclosure may be practiced in many ways and the disclosure should be construed in accordance with the appended claims and any equivalents thereof.

INCORPORATION BY REFERENCE

All references cited herein, including patents, patent applications, papers, textbooks, and the like, and the references cited therein, to the extent that they are not already, are hereby incorporated herein by reference in their entirety.

We claim:

1. An isolated antibody that binds to Notch 3 or a Notch3 binding fragment thereof, wherein the antibody or fragment comprises:
a heavy chain variable region comprising the CDR1 amino acid sequence of SEQ ID NO: 23; the CDR2 amino acid sequence of SEQ ID NO: 24; the CDR3 amino acid sequence of SEQ ID NO: 25; and a light chain variable region comprising the CDR1 amino acid sequence of SEQ ID NO: 33; the CDR2 amino acid sequence of SEQ ID NO: 34; and the CDR3 amino acid sequence of SEQ ID NO: 35.

2. The isolated antibody or fragment thereof of claim 1, comprising a variable heavy chain sequence and a variable light chain sequence selected from the group consisting of:
a variable heavy chain sequence having the amino acid sequence of SEQ ID NO:29 and a variable light chain sequence having the amino acid sequence of SEQ ID NO: 39.

3. A pharmaceutical composition comprising the antibody or fragment thereof of claim 1 and a pharmaceutically acceptable carrier.

4. The isolated antibody or fragment thereof of claim 1, wherein the antibody is selected from the group consisting of a monoclonal antibody, a polyclonal antibody, a chimeric antibody, a humanized antibody, and a synthetic antibody.

5. A single chain antibody that binds to Notch3 or a Notch 3 binding fragment thereof, wherein the antibody or fragment comprises:
a heavy chain variable region comprising the CDR1 amino acid sequence of SEQ ID NO:23; the CDR2 amino acid sequence of SEQ ID NO: 24; the CDR3 amino acid sequence of SEQ ID NO: 25; a light chain variable region comprising the CDR1 amino acid sequence of SEQ ID NO: 33; the CDR2 amino acid sequence of SEQ ID NO: 34; and the CDR3 amino acid sequence of SEQ ID NO: 35.

6. The single chain antibody or fragment thereof of claim 5, comprising a variable heavy chain sequence having the amino acid sequence of SEQ ID NO: 29 and a variable light chain sequence having the amino acid sequence of SEQ ID NO: 39.

* * * * *

SEQUENCE LISTING

```
<160> NUMBER OF SEQ ID NOS: 294

<210> SEQ ID NO 1
<211> LENGTH: 2321
<212> TYPE: PRT
<213> ORGANISM: Homo sapiens

<400> SEQUENCE: 1

Met Gly Pro Gly Ala Arg Gly Arg Arg Arg Arg Arg Pro Met Ser
1               5                   10                  15

Pro Pro Pro Pro Pro Pro Val Arg Ala Leu Pro Leu Leu Leu Leu
                20                  25                  30

Leu Ala Gly Pro Gly Ala Ala Ala Pro Pro Cys Leu Asp Gly Ser Pro
                35                  40                  45

Cys Ala Asn Gly Gly Arg Cys Thr Gln Leu Pro Ser Arg Glu Ala Ala
        50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
                100                 105                 110

Arg Gly Pro Asp Cys Ser Leu Pro Asp Pro Cys Leu Ser Ser Pro Cys
                115                 120                 125

Ala His Gly Ala Arg Cys Ser Val Gly Pro Asp Gly Arg Phe Leu Cys
        130                 135                 140

Ser Cys Pro Pro Gly Tyr Gln Gly Arg Ser Cys Arg Ser Asp Val Asp
145                 150                 155                 160
```

-continued

```
Glu Cys Arg Val Gly Glu Pro Cys Arg His Gly Thr Cys Leu Asn
            165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
            195                 200                 205

Gly Gly Thr Cys Arg Gln Ser Gly Asp Leu Thr Tyr Asp Cys Ala Cys
            210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
            275                 280                 285

Gly Thr Cys Phe Asn Thr Leu Gly Gly His Ser Cys Val Cys Val Asn
            290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
            355                 360                 365

Asn Pro Val Asn Gly Arg Ala Ile Cys Thr Cys Pro Pro Gly Phe Thr
            370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
            435                 440                 445

Arg Ile Gly Gln Phe Thr Cys Ile Cys Met Ala Gly Phe Thr Gly Thr
450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
            515                 520                 525

Tyr Glu Cys Arg Cys Ala Glu Gly Phe Glu Gly Thr Leu Cys Asp Arg
            530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575
```

```
Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
            595                 600                 605

Pro Ser Gly Thr Thr Gly Val Asn Cys Glu Val Asn Ile Asp Asp Cys
            610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
            675                 680                 685

Pro Pro Leu Cys Leu Pro Pro Ser His Pro Cys Ala His Glu Pro Cys
            690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
            755                 760                 765

Cys Glu Leu Leu Ser Pro Cys Thr Pro Asn Pro Cys Glu His Gly Gly
            770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
            835                 840                 845

Asp Ile Asn Asp Cys Asp Pro Asn Pro Cys Leu Asn Gly Gly Ser Cys
850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
            915                 920                 925

Ser Pro Ser Ser Cys Phe Asn Gly Gly Thr Cys Val Asp Gly Val Asn
930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                965                 970                 975

Cys Ser Ala Ala His Pro Gly Phe Arg Cys Thr Cys Leu Glu Ser Phe
            980                 985                 990

Thr Gly Pro Gln Cys Gln Thr Leu  Val Asp Trp Cys Ser  Arg Gln Pro
```

|     |     |     |     |     | 995 |     |     |     | 1000 |     |     |     |     | 1005 |     |     |
|-----|-----|-----|-----|-----|-----|-----|-----|-----|------|-----|-----|-----|-----|------|-----|-----|

Cys Gln Asn Gly Gly Arg Cys Val Gln Thr Gly Ala Tyr Cys Leu
          1010              1015              1020

Cys Pro Pro Gly Trp Ser Gly Arg Leu Cys Asp Ile Arg Ser Leu
          1025              1030              1035

Pro Cys Arg Glu Ala Ala Gln Ile Gly Val Arg Leu Glu Gln
          1040              1045              1050

Leu Cys Gln Ala Gly Gly Gln Cys Val Asp Glu Asp Ser Ser His
          1055              1060              1065

Tyr Cys Val Cys Pro Glu Gly Arg Thr Gly Ser His Cys Glu Gln
          1070              1075              1080

Glu Val Asp Pro Cys Leu Ala Gln Pro Cys Gln His Gly Gly Thr
          1085              1090              1095

Cys Arg Gly Tyr Met Gly Gly Tyr Met Cys Glu Cys Leu Pro Gly
          1100              1105              1110

Tyr Asn Gly Asp Asn Cys Glu Asp Asp Val Asp Glu Cys Ala Ser
          1115              1120              1125

Gln Pro Cys Gln His Gly Gly Ser Cys Ile Asp Leu Val Ala Arg
          1130              1135              1140

Tyr Leu Cys Ser Cys Pro Pro Gly Thr Leu Gly Val Leu Cys Glu
          1145              1150              1155

Ile Asn Glu Asp Asp Cys Gly Pro Gly Pro Pro Leu Asp Ser Gly
          1160              1165              1170

Pro Arg Cys Leu His Asn Gly Thr Cys Val Asp Leu Val Gly Gly
          1175              1180              1185

Phe Arg Cys Thr Cys Pro Pro Gly Tyr Thr Gly Leu Arg Cys Glu
          1190              1195              1200

Ala Asp Ile Asn Glu Cys Arg Ser Gly Ala Cys His Ala Ala His
          1205              1210              1215

Thr Arg Asp Cys Leu Gln Asp Pro Gly Gly Gly Phe Arg Cys Leu
          1220              1225              1230

Cys His Ala Gly Phe Ser Gly Pro Arg Cys Gln Thr Val Leu Ser
          1235              1240              1245

Pro Cys Glu Ser Gln Pro Cys Gln His Gly Gly Gln Cys Arg Pro
          1250              1255              1260

Ser Pro Gly Pro Gly Gly Leu Thr Phe Thr Cys His Cys Ala
          1265              1270              1275

Gln Pro Phe Trp Gly Pro Arg Cys Glu Arg Val Ala Arg Ser Cys
          1280              1285              1290

Arg Glu Leu Gln Cys Pro Val Gly Val Pro Cys Gln Gln Thr Pro
          1295              1300              1305

Arg Gly Pro Arg Cys Ala Cys Pro Pro Gly Leu Ser Gly Pro Ser
          1310              1315              1320

Cys Arg Ser Phe Pro Gly Ser Pro Pro Gly Ala Ser Asn Ala Ser
          1325              1330              1335

Cys Ala Ala Ala Pro Cys Leu His Gly Gly Ser Cys Arg Pro Ala
          1340              1345              1350

Pro Leu Ala Pro Phe Phe Arg Cys Ala Cys Ala Gln Gly Trp Thr
          1355              1360              1365

Gly Pro Arg Cys Glu Ala Pro Ala Ala Ala Pro Glu Val Ser Glu
          1370              1375              1380

Glu Pro Arg Cys Pro Arg Ala Ala Cys Gln Ala Lys Arg Gly Asp
          1385              1390              1395

```
Gln Arg Cys Asp Arg Glu Cys Asn Ser Pro Gly Cys Gly Trp Asp
1400              1405              1410

Gly Gly Asp Cys Ser Leu Ser Val Gly Asp Pro Trp Arg Gln Cys
1415              1420              1425

Glu Ala Leu Gln Cys Trp Arg Leu Phe Asn Asn Ser Arg Cys Asp
1430              1435              1440

Pro Ala Cys Ser Ser Pro Ala Cys Leu Tyr Asp Asn Phe Asp Cys
1445              1450              1455

His Ala Gly Gly Arg Glu Arg Thr Cys Asn Pro Val Tyr Glu Lys
1460              1465              1470

Tyr Cys Ala Asp His Phe Ala Asp Gly Arg Cys Asp Gln Gly Cys
1475              1480              1485

Asn Thr Glu Glu Cys Gly Trp Asp Gly Leu Asp Cys Ala Ser Glu
1490              1495              1500

Val Pro Ala Leu Leu Ala Arg Gly Val Leu Val Leu Thr Val Leu
1505              1510              1515

Leu Pro Pro Glu Glu Leu Leu Arg Ser Ser Ala Asp Phe Leu Gln
1520              1525              1530

Arg Leu Ser Ala Ile Leu Arg Thr Ser Leu Arg Phe Arg Leu Asp
1535              1540              1545

Ala His Gly Gln Ala Met Val Phe Pro Tyr His Arg Pro Ser Pro
1550              1555              1560

Gly Ser Glu Pro Arg Ala Arg Arg Glu Leu Ala Pro Glu Val Ile
1565              1570              1575

Gly Ser Val Val Met Leu Glu Ile Asp Asn Arg Leu Cys Leu Gln
1580              1585              1590

Ser Pro Glu Asn Asp His Cys Phe Pro Asp Ala Gln Ser Ala Ala
1595              1600              1605

Asp Tyr Leu Gly Ala Leu Ser Ala Val Glu Arg Leu Asp Phe Pro
1610              1615              1620

Tyr Pro Leu Arg Asp Val Arg Gly Glu Pro Leu Glu Pro Pro Glu
1625              1630              1635

Pro Ser Val Pro Leu Leu Pro Leu Leu Val Ala Gly Ala Val Leu
1640              1645              1650

Leu Leu Val Ile Leu Val Leu Gly Val Met Val Ala Arg Arg Lys
1655              1660              1665

Arg Glu His Ser Thr Leu Trp Phe Pro Glu Gly Phe Ser Leu His
1670              1675              1680

Lys Asp Val Ala Ser Gly His Lys Gly Arg Arg Glu Pro Val Gly
1685              1690              1695

Gln Asp Ala Leu Gly Met Lys Asn Met Ala Lys Gly Glu Ser Leu
1700              1705              1710

Met Gly Glu Val Ala Thr Asp Trp Met Asp Thr Glu Cys Pro Glu
1715              1720              1725

Ala Lys Arg Leu Lys Val Glu Glu Pro Gly Met Gly Ala Glu Glu
1730              1735              1740

Ala Val Asp Cys Arg Gln Trp Thr Gln His His Leu Val Ala Ala
1745              1750              1755

Asp Ile Arg Val Ala Pro Ala Met Ala Leu Thr Pro Pro Gln Gly
1760              1765              1770

Asp Ala Asp Ala Asp Gly Met Asp Val Asn Val Arg Gly Pro Asp
1775              1780              1785
```

```
Gly Phe Thr Pro Leu Met Leu Ala Ser Phe Cys Gly Gly Ala Leu
    1790            1795            1800

Glu Pro Met Pro Thr Glu Glu Asp Glu Ala Asp Thr Ser Ala
    1805            1810            1815

Ser Ile Ile Ser Asp Leu Ile Cys Gln Gly Ala Gln Leu Gly Ala
    1820            1825            1830

Arg Thr Asp Arg Thr Gly Glu Thr Ala Leu His Leu Ala Ala Arg
    1835            1840            1845

Tyr Ala Arg Ala Asp Ala Ala Lys Arg Leu Leu Asp Ala Gly Ala
    1850            1855            1860

Asp Thr Asn Ala Gln Asp His Ser Gly Arg Thr Pro Leu His Thr
    1865            1870            1875

Ala Val Thr Ala Asp Ala Gln Gly Val Phe Gln Ile Leu Ile Arg
    1880            1885            1890

Asn Arg Ser Thr Asp Leu Asp Ala Arg Met Ala Asp Gly Ser Thr
    1895            1900            1905

Ala Leu Ile Leu Ala Ala Arg Leu Ala Val Glu Gly Met Val Glu
    1910            1915            1920

Glu Leu Ile Ala Ser His Ala Asp Val Asn Ala Val Asp Glu Leu
    1925            1930            1935

Gly Lys Ser Ala Leu His Trp Ala Ala Ala Val Asn Asn Val Glu
    1940            1945            1950

Ala Thr Leu Ala Leu Leu Lys Asn Gly Ala Asn Lys Asp Met Gln
    1955            1960            1965

Asp Ser Lys Glu Glu Thr Pro Leu Phe Leu Ala Ala Arg Glu Gly
    1970            1975            1980

Ser Tyr Glu Ala Ala Lys Leu Leu Leu Asp His Phe Ala Asn Arg
    1985            1990            1995

Glu Ile Thr Asp His Leu Asp Arg Leu Pro Arg Asp Val Ala Gln
    2000            2005            2010

Glu Arg Leu His Gln Asp Ile Val Arg Leu Leu Asp Gln Pro Ser
    2015            2020            2025

Gly Pro Arg Ser Pro Pro Gly Pro His Gly Leu Gly Pro Leu Leu
    2030            2035            2040

Cys Pro Pro Gly Ala Phe Leu Pro Gly Leu Lys Ala Ala Gln Ser
    2045            2050            2055

Gly Ser Lys Lys Ser Arg Arg Pro Pro Gly Lys Ala Gly Leu Gly
    2060            2065            2070

Pro Gln Gly Pro Arg Gly Arg Gly Lys Lys Leu Thr Leu Ala Cys
    2075            2080            2085

Pro Gly Pro Leu Ala Asp Ser Ser Val Thr Leu Ser Pro Val Asp
    2090            2095            2100

Ser Leu Asp Ser Pro Arg Pro Phe Gly Gly Pro Pro Ala Ser Pro
    2105            2110            2115

Gly Gly Phe Pro Leu Glu Gly Pro Tyr Ala Ala Ala Thr Ala Thr
    2120            2125            2130

Ala Val Ser Leu Ala Gln Leu Gly Gly Pro Gly Arg Ala Gly Leu
    2135            2140            2145

Gly Arg Gln Pro Pro Gly Gly Cys Val Leu Ser Leu Gly Leu Leu
    2150            2155            2160

Asn Pro Val Ala Val Pro Leu Asp Trp Ala Arg Leu Pro Pro Pro
    2165            2170            2175

Ala Pro Pro Gly Pro Ser Phe Leu Leu Pro Leu Ala Pro Gly Pro
```

```
                2180                2185                2190

Gln Leu Leu Asn Pro Gly Thr Pro Val Ser Pro Gln Glu Arg Pro
        2195                2200                2205

Pro Pro Tyr Leu Ala Val Pro Gly His Gly Glu Glu Tyr Pro Ala
    2210                2215                2220

Ala Gly Ala His Ser Ser Pro Pro Lys Ala Arg Phe Leu Arg Val
    2225                2230                2235

Pro Ser Glu His Pro Tyr Leu Thr Pro Ser Pro Glu Ser Pro Glu
    2240                2245                2250

His Trp Ala Ser Pro Ser Pro Ser Leu Ser Asp Trp Ser Glu
    2255                2260                2265

Ser Thr Pro Ser Pro Ala Thr Ala Thr Gly Ala Met Ala Thr Thr
    2270                2275                2280

Thr Gly Ala Leu Pro Ala Gln Pro Leu Pro Leu Ser Val Pro Ser
    2285                2290                2295

Ser Leu Ala Gln Ala Gln Thr Gln Leu Gly Pro Gln Pro Glu Val
    2300                2305                2310

Thr Pro Lys Arg Gln Val Leu Ala
    2315                2320

<210> SEQ ID NO 2
<211> LENGTH: 2319
<212> TYPE: PRT
<213> ORGANISM: Macaca fascicularis

<400> SEQUENCE: 2

Met Gly Pro Gly Ala Arg Gly Arg Arg Arg Arg Arg Pro Met Ser
1               5                   10                  15

Pro Pro Pro Pro Pro Val Arg Ala Leu Pro Leu Leu Leu Leu Ala
                20                  25                  30

Gly Pro Gly Ala Ala Val Pro Pro Cys Leu Asp Gly Ser Pro Cys Ala
            35                  40                  45

Asn Gly Gly Arg Cys Thr Gln Leu Pro Ser Arg Glu Ala Ala Cys Leu
        50                  55                  60

Cys Pro Pro Gly Trp Val Gly Glu Arg Cys Gln Leu Glu Asp Pro Cys
65                  70                  75                  80

His Ser Gly Pro Cys Ala Gly Arg Gly Val Cys Gln Ser Ser Val Val
                85                  90                  95

Ala Gly Thr Ala Arg Phe Ser Cys Arg Cys Pro Arg Gly Phe Arg Gly
                100                 105                 110

Pro Asp Cys Ser Leu Pro Asp Pro Cys Leu Ser Ser Pro Cys Ala His
            115                 120                 125

Ser Ala Arg Cys Ser Val Gly Pro Asp Gly Arg Phe Leu Cys Ser Cys
        130                 135                 140

Pro Pro Gly Tyr Gln Gly Arg Ser Cys Arg Ser Asp Val Asp Glu Cys
145                 150                 155                 160

Arg Val Gly Glu Pro Cys Arg His Gly Gly Thr Cys Leu Asn Thr Pro
                165                 170                 175

Gly Ser Phe Arg Cys Gln Cys Pro Ala Gly Tyr Thr Gly Pro Leu Cys
            180                 185                 190

Glu Asn Pro Ala Val Pro Cys Ala Pro Ser Pro Cys Arg Asn Gly Gly
        195                 200                 205

Thr Cys Arg Gln Ser Gly Asp Leu Thr Tyr Asp Cys Ala Cys Leu Pro
    210                 215                 220
```

```
Gly Phe Glu Gly Gln Asn Cys Glu Val Asn Val Asp Asp Cys Pro Gly
225                 230                 235                 240

His Arg Cys Leu Asn Gly Gly Thr Cys Val Asp Gly Val Asn Thr Tyr
            245                 250                 255

Asn Cys Gln Cys Pro Pro Glu Trp Thr Gly Gln Phe Cys Thr Glu Asp
        260                 265                 270

Val Asp Glu Cys Gln Leu Gln Pro Asn Ala Cys His Asn Gly Gly Thr
    275                 280                 285

Cys Phe Asn Thr Leu Gly His Ser Cys Val Cys Val Asn Gly Trp
290                 295                 300

Thr Gly Glu Ser Cys Ser Gln Asn Ile Asp Asp Cys Ala Thr Ala Val
305                 310                 315                 320

Cys Phe His Gly Ala Thr Cys His Asp Arg Val Ala Ser Phe Tyr Cys
            325                 330                 335

Ala Cys Pro Met Gly Lys Thr Gly Leu Leu Cys His Leu Asp Asp Ala
        340                 345                 350

Cys Val Ser Asn Pro Cys His Glu Asp Ala Ile Cys Asp Thr Asn Pro
    355                 360                 365

Val Asn Gly Arg Ala Ile Cys Thr Cys Pro Pro Gly Phe Thr Gly Gly
370                 375                 380

Ala Cys Asp Gln Asp Val Asp Glu Cys Ser Ile Gly Ala Asn Pro Cys
385                 390                 395                 400

Glu His Leu Gly Arg Cys Val Asn Thr Gln Gly Ser Phe Leu Cys Gln
            405                 410                 415

Cys Gly Arg Gly Tyr Thr Gly Pro Arg Cys Glu Thr Asp Val Asn Glu
        420                 425                 430

Cys Leu Ser Gly Pro Cys Arg Asn Gln Ala Thr Cys Leu Asp Arg Ile
    435                 440                 445

Gly Gln Phe Thr Cys Ile Cys Met Ala Gly Phe Thr Gly Thr Tyr Cys
        450                 455                 460

Glu Val Asp Ile Asp Glu Cys Gln Ser Ser Pro Cys Val Asn Gly Gly
465                 470                 475                 480

Ile Cys Lys Asp Arg Val Asn Gly Phe Ser Cys Thr Cys Pro Ser Gly
            485                 490                 495

Phe Ser Gly Ser Thr Cys Gln Leu Asp Val Asp Glu Cys Ala Ser Thr
        500                 505                 510

Pro Cys Arg Asn Gly Ala Lys Cys Val Asp Gln Pro Asp Gly Tyr Glu
    515                 520                 525

Cys Arg Cys Ala Glu Gly Phe Glu Gly Met Leu Cys Glu Arg Asn Val
530                 535                 540

Asp Asp Cys Ser Pro Asp Pro Cys His His Gly Arg Cys Val Asp Gly
545                 550                 555                 560

Ile Ala Ser Phe Ser Cys Ala Cys Ala Pro Gly Tyr Thr Gly Thr Arg
            565                 570                 575

Cys Glu Ser Gln Val Asp Glu Cys Arg Ser Pro Cys Arg His Gly
        580                 585                 590

Gly Lys Cys Leu Asp Leu Val Asp Lys Tyr Leu Cys Arg Cys Pro Ser
    595                 600                 605

Gly Thr Thr Gly Val Asn Cys Glu Val Asn Ile Asp Asp Cys Ala Ser
610                 615                 620

Asn Pro Cys Ser Phe Gly Val Cys Arg Asp Gly Ile Asn Arg Tyr Asp
625                 630                 635                 640

Cys Val Cys Gln Pro Gly Phe Thr Gly Pro Leu Cys Asn Val Glu Ile
```

-continued

```
               645                 650                 655
Asn Glu Cys Ala Ser Ser Pro Cys Gly Glu Gly Gly Ser Cys Val Asp
               660                 665                 670
Gly Glu Asn Gly Phe Arg Cys Leu Cys Pro Pro Gly Ser Leu Pro Pro
               675                 680                 685
Leu Cys Leu Pro Pro Ser His Pro Cys Ala His Glu Pro Cys Ser His
               690                 695                 700
Gly Ile Cys Tyr Asp Ala Pro Gly Gly Phe Arg Cys Val Cys Glu Pro
705                 710                 715                 720
Gly Trp Ser Gly Pro Arg Cys Ser Gln Ser Leu Ala Arg Asp Ala Cys
                    725                 730                 735
Glu Ser Gln Pro Cys Arg Ala Gly Gly Thr Cys Ser Ser Asp Gly Met
               740                 745                 750
Gly Phe His Cys Thr Cys Pro Pro Gly Val Gln Gly Arg Gln Cys Glu
               755                 760                 765
Leu Leu Ser Pro Cys Thr Pro Asn Pro Cys Glu His Gly Gly Arg Cys
770                 775                 780
Glu Ser Ala Pro Gly Gln Leu Pro Val Cys Ser Cys Pro Gln Gly Trp
785                 790                 795                 800
Gln Gly Pro Arg Cys Gln Gln Asp Val Asp Glu Cys Ala Gly Pro Ala
                    805                 810                 815
Pro Cys Gly Pro His Gly Ile Cys Thr Asn Leu Ala Gly Ser Phe Ser
               820                 825                 830
Cys Thr Cys His Gly Gly Tyr Thr Gly Pro Ser Cys Asp Gln Asp Ile
               835                 840                 845
Asn Asp Cys Asp Pro Asn Pro Cys Leu Asn Gly Gly Ser Cys Gln Asp
850                 855                 860
Gly Val Gly Ser Phe Ser Cys Ser Cys Leu Leu Gly Phe Ala Gly Pro
865                 870                 875                 880
Arg Cys Ala Arg Asp Val Asp Glu Cys Leu Ser Asn Pro Cys Gly Pro
                    885                 890                 895
Gly Thr Cys Thr Asp His Val Ala Ser Phe Thr Cys Thr Cys Pro Pro
               900                 905                 910
Gly Tyr Gly Gly Phe His Cys Glu Gln Asp Leu Pro Asp Cys Ser Pro
               915                 920                 925
Ser Ser Cys Phe Asn Gly Gly Thr Cys Val Asp Gly Val Asn Ser Phe
930                 935                 940
Ser Cys Leu Cys Arg Pro Gly Tyr Thr Gly Ala His Cys Gln His Glu
945                 950                 955                 960
Ala Asp Pro Cys Leu Ser Arg Pro Cys Leu His Gly Gly Val Cys Ser
               965                 970                 975
Ala Ala His Pro Gly Phe Arg Cys Thr Cys Pro Gln Ser Phe Thr Gly
               980                 985                 990
Pro Gln Cys Gln Thr Leu Val Asp Trp Cys Ser Arg Gln Pro Cys Gln
               995                 1000                1005
Asn Gly Gly Arg Cys Val Gln Thr Gly Ala Tyr Cys Leu Cys Pro
    1010                1015                1020
Pro Gly Trp Ser Gly Arg Leu Cys Asp Ile Arg Ser Leu Pro Cys
    1025                1030                1035
Arg Glu Ala Ala Ala Gln Ile Gly Val Arg Leu Glu Gln Leu Cys
    1040                1045                1050
Gln Ala Gly Gly Gln Cys Val Asp Glu Asp Ser Ser His Tyr Cys
    1055                1060                1065
```

```
Val Cys Pro Glu Gly Arg Thr Gly Ser His Cys Glu Gln Glu Val
    1070                1075                1080

Asp Pro Cys Leu Ala Gln Pro Cys Gln His Gly Gly Thr Cys Arg
    1085                1090                1095

Gly Tyr Met Gly Gly Tyr Met Cys Glu Cys Leu Pro Gly Tyr Asn
    1100                1105                1110

Gly Glu Asn Cys Glu Asp Val Asp Glu Cys Ala Ser Gln Pro
    1115                1120                1125

Cys Gln His Gly Gly Ser Cys Ile Asp Leu Val Ala Arg Tyr Leu
    1130                1135                1140

Cys Ser Cys Pro Pro Gly Thr Leu Gly Val Leu Cys Glu Ile Asn
    1145                1150                1155

Glu Asp Asp Cys Gly Pro Gly Pro Pro Leu Asp Ser Gly Pro Arg
    1160                1165                1170

Cys Leu His Asn Gly Thr Cys Val Asp Leu Val Gly Gly Phe Arg
    1175                1180                1185

Cys Thr Cys Pro Pro Gly Tyr Thr Gly Leu Arg Cys Glu Ala Asp
    1190                1195                1200

Ile Asn Glu Cys Arg Ser Gly Ala Cys His Ala Ala His Thr Arg
    1205                1210                1215

Asp Cys Leu Gln Asp Pro Gly Gly Gly Phe Arg Cys Leu Cys His
    1220                1225                1230

Ala Gly Phe Ser Gly Pro Arg Cys Gln Thr Val Leu Ser Pro Cys
    1235                1240                1245

Glu Ser Gln Pro Cys Gln His Gly Gly Gln Cys Arg Pro Ser Pro
    1250                1255                1260

Gly Pro Gly Gly Gly Leu Thr Phe Thr Cys His Cys Ala Gln Pro
    1265                1270                1275

Phe Trp Gly Pro Arg Cys Glu Arg Val Ala Arg Ser Cys Arg Glu
    1280                1285                1290

Leu Gln Cys Pro Val Gly Val Pro Cys Gln Gln Thr Pro Arg Gly
    1295                1300                1305

Pro Arg Cys Ala Cys Pro Pro Gly Leu Ser Gly Pro Ser Cys Arg
    1310                1315                1320

Ser Phe Ser Gly Ser Pro Pro Gly Ala Ser Asn Ala Ser Cys Ala
    1325                1330                1335

Ala Ala Pro Cys Leu His Gly Gly Ser Cys Arg Pro Ala Pro Leu
    1340                1345                1350

Ala Pro Phe Phe Arg Cys Ala Cys Ala Gln Gly Trp Thr Gly Pro
    1355                1360                1365

Arg Cys Glu Ala Pro Ala Ala Pro Glu Val Ser Glu Glu Pro
    1370                1375                1380

Arg Cys Pro Arg Ala Ala Cys Gln Ala Lys Arg Gly Asp Gln Arg
    1385                1390                1395

Cys Asp Arg Glu Cys Asn Ser Pro Gly Cys Gly Trp Asp Gly Gly
    1400                1405                1410

Asp Cys Ser Leu Ser Val Gly Asp Pro Trp Arg Gln Cys Glu Ala
    1415                1420                1425

Leu Gln Cys Trp Arg Leu Phe Asn Asn Ser Arg Cys Asp Pro Ala
    1430                1435                1440

Cys Ser Ser Pro Ala Cys Leu Tyr Asp Asn Phe Asp Cys His Ala
    1445                1450                1455
```

```
Gly Gly Arg Glu Arg Thr Cys Asn Pro Val Tyr Glu Lys Tyr Cys
    1460                1465                1470

Ala Asp His Phe Ala Asp Gly Arg Cys Asp Gln Gly Cys Asn Thr
    1475                1480                1485

Glu Glu Cys Gly Trp Asp Gly Leu Asp Cys Ala Ser Glu Val Pro
    1490                1495                1500

Ala Leu Leu Ala Arg Gly Val Leu Val Leu Thr Val Leu Leu Pro
    1505                1510                1515

Pro Glu Leu Leu Arg Ser Ser Ala Asp Phe Leu Gln Arg Leu
    1520                1525                1530

Ser Ala Ile Leu Arg Thr Ser Leu Arg Phe Arg Leu Asp Ala His
    1535                1540                1545

Gly Gln Ala Met Val Phe Pro Tyr His Arg Pro Ser Pro Gly Ser
    1550                1555                1560

Glu Pro Arg Ala Arg Arg Glu Leu Ala Pro Glu Val Ile Gly Ser
    1565                1570                1575

Val Val Met Leu Glu Ile Asp Asn Arg Leu Cys Leu Gln Ser Pro
    1580                1585                1590

Glu Asn Asp His Cys Phe Pro Asp Ala Gln Ser Ala Ala Asp Tyr
    1595                1600                1605

Leu Gly Ala Leu Ser Ala Val Glu Arg Leu Asp Phe Pro Tyr Pro
    1610                1615                1620

Leu Arg Asp Val Arg Gly Glu Pro Leu Glu Pro Pro Glu Pro Ser
    1625                1630                1635

Val Pro Leu Leu Pro Leu Leu Val Ala Gly Ala Val Leu Leu Leu
    1640                1645                1650

Val Ile Leu Val Leu Gly Val Met Val Ala Arg Arg Lys Arg Glu
    1655                1660                1665

His Ser Thr Leu Trp Phe Pro Glu Gly Phe Ser Leu His Lys Asp
    1670                1675                1680

Val Ala Ala Gly His Lys Gly Arg Arg Glu Pro Val Gly Gln Asp
    1685                1690                1695

Ala Leu Gly Met Lys Asn Met Ala Lys Gly Glu Ser Leu Met Gly
    1700                1705                1710

Glu Val Ala Thr Asp Trp Met Asp Thr Glu Cys Pro Glu Ala Lys
    1715                1720                1725

Arg Leu Lys Val Glu Glu Leu Gly Met Gly Ala Glu Glu Ala Val
    1730                1735                1740

Asp Cys Arg Gln Trp Thr Gln His His Leu Val Ala Ala Asp Ile
    1745                1750                1755

Arg Val Ala Pro Ala Met Ala Leu Thr Pro Pro Gln Gly Asp Ala
    1760                1765                1770

Asp Ala Asp Gly Met Asp Val Asn Val Arg Gly Pro Asp Gly Phe
    1775                1780                1785

Thr Pro Leu Met Leu Ala Ser Phe Cys Gly Gly Ala Leu Glu Pro
    1790                1795                1800

Met Pro Thr Glu Glu Asp Glu Ala Asp Asp Thr Ser Ala Ser Ile
    1805                1810                1815

Ile Ser Asp Leu Ile Cys Gln Gly Ala Gln Leu Gly Ala Arg Thr
    1820                1825                1830

Asp Arg Thr Gly Glu Thr Ala Leu His Leu Ala Ala Arg Tyr Ala
    1835                1840                1845

Arg Ala Asp Ala Ala Lys Arg Leu Leu Asp Ala Gly Ala Asp Thr
```

```
                1850                1855                1860

Asn Ala Gln Asp His Ser Gly Arg Thr Pro Leu His Thr Ala Val
        1865                1870                1875

Thr Ala Asp Ala Gln Gly Val Phe Gln Ile Leu Ile Arg Asn Arg
        1880                1885                1890

Ser Thr Asp Leu Asp Ala Arg Met Ala Asp Gly Ser Thr Ala Leu
        1895                1900                1905

Ile Leu Ala Ala Arg Leu Ala Val Glu Gly Met Val Glu Glu Leu
        1910                1915                1920

Ile Ala Ser His Ala Asp Val Asn Ala Val Asp Glu Leu Gly Lys
        1925                1930                1935

Ser Ala Leu His Trp Ala Ala Val Asn Asn Val Glu Ala Thr
        1940                1945                1950

Leu Ala Leu Leu Lys Asn Gly Ala Asn Lys Asp Met Gln Asp Ser
        1955                1960                1965

Lys Glu Glu Thr Pro Leu Phe Leu Ala Ala Arg Glu Gly Ser Tyr
        1970                1975                1980

Glu Ala Ala Lys Leu Leu Leu Asp His Phe Ala Asn Arg Glu Ile
        1985                1990                1995

Thr Asp His Leu Asp Arg Leu Pro Arg Asp Val Ala Gln Glu Arg
        2000                2005                2010

Leu His Gln Asp Ile Val Arg Leu Leu Asp Gln Pro Ser Gly Pro
        2015                2020                2025

Arg Ser Pro Pro Gly Thr His Gly Leu Gly Pro Leu Leu Cys Pro
        2030                2035                2040

Pro Gly Ala Phe Leu Pro Gly Leu Lys Val Thr Gln Ser Gly Ser
        2045                2050                2055

Lys Lys Ser Arg Arg Pro Pro Gly Lys Ala Gly Leu Gly Pro Gln
        2060                2065                2070

Gly Pro Arg Gly Arg Gly Lys Lys Leu Thr Leu Ala Cys Pro Gly
        2075                2080                2085

Pro Leu Ala Asp Ser Ser Val Thr Leu Ser Pro Val Asp Ser Leu
        2090                2095                2100

Asp Ser Pro Arg Pro Phe Gly Gly Pro Pro Ala Ser Pro Gly Gly
        2105                2110                2115

Phe Pro Leu Glu Gly Pro Tyr Ala Ala Ala Thr Ala Thr Ala Val
        2120                2125                2130

Ser Leu Ala Gln Leu Gly Gly Pro Gly Arg Ala Gly Leu Gly Arg
        2135                2140                2145

Gln Pro Pro Gly Gly Cys Val Leu Ser Leu Gly Leu Leu Asn Pro
        2150                2155                2160

Val Ala Val Pro Leu Asp Trp Ala Arg Leu Pro Pro Pro Ala Pro
        2165                2170                2175

Pro Gly Pro Ser Phe Leu Leu Pro Leu Ala Pro Gly Pro Gln Leu
        2180                2185                2190

Leu Asn Pro Gly Thr Pro Val Ser Pro Gln Glu Arg Pro Pro Pro
        2195                2200                2205

Tyr Leu Ala Val Pro Gly His Gly Glu Glu Tyr Pro Ala Ala Gly
        2210                2215                2220

Ala His Ser Ser Pro Pro Lys Ala Arg Phe Leu Arg Val Pro Ser
        2225                2230                2235

Glu His Pro Tyr Leu Thr Pro Ser Pro Glu Ser Pro Glu His Trp
        2240                2245                2250
```

```
Ala Ser Pro Ser Pro Pro Ser Leu Ser Asp Trp Ser Glu Ser Thr
    2255                2260                2265

Pro Ser Pro Ala Thr Ala Thr Gly Ala Met Ala Thr Ala Thr Gly
    2270                2275                2280

Ala Leu Pro Ala Gln Pro Leu Pro Leu Ser Val Pro Ser Ser Leu
    2285                2290                2295

Ala Gln Ala Gln Thr Gln Leu Gly Pro Gln Pro Glu Val Thr Pro
    2300                2305                2310

Lys Arg Gln Val Leu Ala
    2315

<210> SEQ ID NO 3
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ser Tyr Thr Ile Ser
1               5

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Trp Ile Lys Pro Arg Trp Gly Ala Ala His Tyr Ala Gln Lys Phe Gln
1               5                   10                  15

Gly

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Ser Phe Trp Phe Gly Tyr
1               5

<210> SEQ ID NO 6
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Thr Phe Ser Ser Tyr
1               5
```

<210> SEQ ID NO 7
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 7

Lys Pro Arg Trp Gly Ala
1               5

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 8

Gly Ser Phe Trp Phe Gly Tyr
1               5

<210> SEQ ID NO 9
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Trp Ile Lys Pro Arg Trp Gly Ala Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Phe Trp Phe Gly Tyr Trp Gly Gln Gly Thr Leu Val
            100                 105                 110

Thr Val Ser Ser
        115

<210> SEQ ID NO 10
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10
caggtgcagc tggtgcagtc aggcgccgaa gtgaagaaac ccggctctag cgtgaaagtc    60

```
agctgtaaag ctagtggcgg aaccttctct agctacacta ttagctgggt cagacaggcc    120
ccaggtcaag gcctggagtg gatgggctgg attaagcctc gctggggcgc tgctcactac    180
gctcagaaat tcagggtag agtgactatc accgccgacg agtctactag caccgcctat    240
atggaactga gttccctgag gtcagaggac accgccgtct actactgcgc tagaggctcc    300
ttttggttcg gctactgggg tcagggcacc ctggtcaccg tgtctagc                 348
```

<210> SEQ ID NO 11
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Trp Ile Lys Pro Arg Trp Gly Ala Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Phe Trp Phe Gly Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
        435                 440                 445

<210> SEQ ID NO 12
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
caggtgcagc tggtgcagtc aggcgccgaa gtgaagaaac ccggctctag cgtgaaagtc      60
agctgtaaag ctagtggcgg aaccttctct agctacacta ttagctgggt cagacaggcc     120
ccaggtcaag gcctggagtg gatgggctgg attaagcctc gctggggcgc tgctcactac     180
gctcagaaat tcagggtag agtgactatc accgccgacg agtctactag caccgcctat      240
atggaactga gttccctgag gtcagaggac accgccgtct actactgcgc tagaggctcc     300
ttttggttcg gctactgggg tcagggcacc ctggtcaccg tgtctagcgc tagcactaag     360
ggcccaagtg tgtttcccct ggcccccagc agcaagtcta cttccggcgg aactgctgcc     420
ctgggttgcc tggtgaagga ctacttcccc gagcccgtga cagtgtcctg aactctgggg     480
gctctgactt ccggcgtgca caccttcccc gccgtgctgc agagcagcgg cctgtacagc     540
ctgagcagcg tggtgacagt gccctccagc tctctgggaa cccagaccta tatctgcaac     600
gtgaaccaca gcccagcaa caccaaggtg gacaagagag tggagcccaa gagctgcgac     660
aagacccaca cctgcccccc ctgcccagct ccagaactgc tgggagggcc ttccgtgttc     720
ctgttccccc ccaagcccaa ggacaccctg atgatcagca ggacccccga ggtgacctgc     780
gtggtggtgg acgtgtccca cgaggaccca gaggtgaagt tcaactggta cgtggacggc     840
gtggaggtgc acaacgccaa gaccaagccc agagaggagc agtacaacag cacctacagg     900
gtggtgtccg tgctgaccgt gctgcaccag gactggctga acggcaaaga atacaagtgc     960
aaagtctcca acaaggccct gccagcccca tcgaaaaga caatcagcaa ggccaagggc    1020
cagccacggg agccccaggt gtacaccctg ccccccagcc gggaggagat gaccaagaac    1080
caggtgtccc tgacctgtct ggtgaagggc ttctacccca gcgatatcgc cgtggagtgg    1140
gagagcaacg gccagcccga gaacaactac aagaccaccc cccagtgct ggacagcgac    1200

```
ggcagcttct tcctgtacag caagctgacc gtggacaagt ccaggtggca gcagggcaac    1260
gtgttcagct gcagcgtgat gcacgaggcc ctgcacaacc actacaccca gaagtccctg    1320
agcctgagcc ccggcaag                                                  1338
```

<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Arg Ala Ser Gln Gly Ile Asn Asn Tyr Leu Asn
1               5                   10

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Asp Ala Ser Lys Leu Gln Ser
1               5

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gln Gln Tyr Leu Gln Tyr Pro Met Thr
1               5

<210> SEQ ID NO 16
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ser Gln Gly Ile Asn Asn Tyr
1               5

<210> SEQ ID NO 17
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Asp Ala Ser
1

<210> SEQ ID NO 18
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Tyr Leu Gln Tyr Pro Met
1               5

<210> SEQ ID NO 19
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gln Tyr Pro Met
                85                  90                  95

Thr Phe Gly Gln Gly Thr Lys Val Glu Ile Lys
            100                 105

<210> SEQ ID NO 20
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
gatattcaga tgactcagtc acctagtagc ctgagcgcta gtgtgggcga tagagtgact    60
atcacctgta gagcctctca ggggattaac aactacctga actggtatca gcagaagccc   120
ggtaaagccc ctaagctgct gatctacgac gcctctaagc tgcagtcagg cgtgccctct   180
aggtttagcg gtagcggtag tggcaccgac ttcaccctga ctatctctag cctgcagccc   240
gaggacttcg ctacctacta ctgtcagcag tacctgcagt acctatgac cttcggtcaa   300 ggcactaagg tcgagattaa g                                             321

<210> SEQ ID NO 21
<211> LENGTH: 214
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Lys Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gln Tyr Pro Met
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
gatattcaga tgactcagtc acctagtagc ctgagcgcta gtgtgggcga tagagtgact      60
atcacctgta gagcctctca ggggattaac aactacctga actggtatca gcagaagccc     120
ggtaaagccc ctaagctgct gatctacgac gcctctaagc tgcagtcagg cgtgccctct     180
aggtttagcg gtagcggtag tggcaccgac ttcaccctga ctatctctag cctgcagccc     240
gaggacttcg ctacctacta ctgtcagcag tacctgcagt acccTatgac cttcggtcaa     300
ggcactaagg tcgagattaa gcgtacggtg gccgctccca gcgtgttcat cttcccccc     360 agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag caccctgacc     540
```

```
ctgagcaagg ccgactacga gaagcataag gtgtacgcct gcgaggtgac ccaccagggc    600
ctgtccagcc ccgtgaccaa gagcttcaac aggggcgagt gc                       642
```

<210> SEQ ID NO 23
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Thr Tyr Ala Met His
1               5

<210> SEQ ID NO 24
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Ile Val Pro Tyr His Gly Ile Thr Asp Tyr Ala Gln Lys Phe Gln
1               5                   10                  15

Gly

<210> SEQ ID NO 25
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Asp Asp Tyr Ser Thr Tyr Ala Phe Ala Tyr
1               5                   10

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gly Gly Thr Phe Arg Thr Tyr
1               5

<210> SEQ ID NO 27
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Val Pro Tyr His Gly Ile

<210> SEQ ID NO 28
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 28

Asp Asp Tyr Ser Thr Tyr Ala Phe Ala Tyr
1               5                   10

<210> SEQ ID NO 29
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Thr Tyr
            20                  25                  30

Ala Met His Trp Val Arg Gln Ala Pro Gly Gln Gly Leu Glu Trp Met
        35                  40                  45

Gly Gly Ile Val Pro Tyr His Gly Ile Thr Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Ser Thr Tyr Ala Phe Ala Tyr Trp Gly Gln Gly
            100                 105                 110

Thr Leu Val Thr Val Ser Ser
        115

<210> SEQ ID NO 30
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30
caggtgcagc tggtgcagtc aggcgccgaa gtgaagaaac ccggctctag cgtgaaagtc      60
agctgtaaag ctagtggcgg aacctttaga acctacgcta tgcactgggt cagacaggcc     120
ccaggtcaag gcctggagtg gatgggcgga atcgtgccct atcacggaat caccgactac     180
gctcagaaat tcagggtag agtgactatc accgccacg agtctactag caccgccat      240 atggaactga gttccctgag gtcagaggac accgccgtct actactgcgc tagggacgac     300
tactctacct acgccttcgc ctactggggt caaggcaccc tggtcaccgt gtctagc        357

<210> SEQ ID NO 31

```
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Thr Tyr
            20                  25                  30

Ala Met His Trp Val Arg Gln Ala Pro Gly Gln Gly Leu Glu Trp Met
        35                  40                  45

Gly Gly Ile Val Pro Tyr His Gly Ile Thr Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Ser Thr Tyr Ala Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys
```

<210> SEQ ID NO 32
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32

```
caggtgcagc tggtgcagtc aggcgccgaa gtgaagaaac ccggctctag cgtgaaagtc      60
agctgtaaag ctagtggcgg aacctttaga acctacgcta tgcactgggt cagacaggcc     120
ccaggtcaag gcctggagtg gatgggcgga atcgtgccct atcacggaat caccgactac     180
gctcagaaat ttcagggtag agtgactatc accgccgacg agtctactag caccgcctat     240
atggaactga gttccctgag gtcagaggac accgccgtct actactgcgc tagggacgac     300
tactctacct acgccttcgc ctactggggt caaggcaccc tggtcaccgt gtctagcgct     360
agcactaagg gcccaagtgt gtttcccctg gcccccagca gcaagtctac ttccggcgga     420
actgctgccc tgggttgcct ggtgaaggac tacttccccg agcccgtgac agtgtcctgg     480
aactctgggg ctctgacttc cggcgtgcac accttccccg ccgtgctgca gagcagcggc     540
ctgtacagcc tgagcagcgt ggtgacagtg ccctccagct ctctgggaac ccagacctat     600
atctgcaacg tgaaccacaa gcccagcaac accaaggtgg acaagagagt ggagcccaag     660
agctgcgaca gacccacac tgcccccccc tgcccagctc cagaactgct gggagggcct     720
tccgtgttcc tgttcccccc caagcccaag gacaccctga tgatcagcag gacccccgag     780
gtgacctgcg tggtggtgga cgtgtcccac gaggacccag aggtgaagtt caactggtac     840
gtggacggcg tggaggtgca caacgccaag accaagccca gagaggagca gtacaacagc     900
acctacaggg tggtgtccgt gctgaccgtg ctgcaccagg actggctgaa cggcaaagaa     960
tacaagtgca aagtctccaa caaggccctg ccagccccaa tcgaaaagac aatcagcaag    1020
gccaagggcc agccacggga gccccaggtg tacaccctgc cccccagccg ggaggagatg    1080
accaagaacc aggtgtccct gacctgtctg gtgaagggct tctacccag cgatatcgcc    1140
gtggagtggg agagcaacgg ccagcccgag aacaactaca gaccaccccc cccagtgctg    1200
gacagcgacg gcagcttctt cctgtacagc aagctgaccg tggacaagtc caggtggcag    1260
cagggcaacg tgttcagctg cagcgtgatg cacgaggccc tgcacaacca ctacacccag    1320
aagtccctga gcctgagccc cggcaag                                        1347
```

<210> SEQ ID NO 33
<211> LENGTH: 11
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Arg Ala Ser Gln Ser Ile Ala Ser Tyr Leu Ala
1               5                   10

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Asp Ala Ser Asn Leu Gln Ser
1               5

<210> SEQ ID NO 35
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gln Gln Ala Tyr Lys Thr Pro Tyr Thr
1               5

<210> SEQ ID NO 36
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ser Gln Ser Ile Ala Ser Tyr
1               5

<210> SEQ ID NO 37
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Asp Ala Ser
1

<210> SEQ ID NO 38
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 38

Ala Tyr Lys Thr Pro Tyr
1               5

<210> SEQ ID NO 39
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Lys Thr Pro Tyr
                85                  90                  95

Thr Phe Gly Gln Gly Thr Lys Val Glu Ile Lys
            100                 105

<210> SEQ ID NO 40
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40
gatattcaga tgactcagtc acctagtagc ctgagcgcta gtgtgggcga tagagtgact      60
atcacctgta gagcctctca gtctatcgct agttacctgg cctggtatca gcagaagccc     120
ggtaaagccc ctaagctgct gatctacgac gcctctaacc tgcagtcagg cgtgccctct     180
aggtttagcg gtagcggtag tggcaccgac ttcaccctga ctatctctag cctgcagccc     240
gaggacttcg ctacctacta ctgtcagcag gcctataaga ccccctacac cttcggtcaa     300
ggcactaagg tcgagattaa g                                                321

<210> SEQ ID NO 41
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Lys Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 42
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42
gatattcaga tgactcagtc acctagtagc ctgagcgcta gtgtgggcga tagagtgact      60
atcacctgta gagcctctca gtctatcgct agttacctgg cctggtatca gcagaagccc     120
ggtaaagccc ctaagctgct gatctacgac gcctctaacc tgcagtcagg cgtgccctct     180
aggtttagcg gtagcggtag tggcaccgac ttcaccctga ctatctctag cctgcagccc     240
gaggacttcg ctacctacta ctgtcagcag gcctataaga ccccctacac cttcggtcaa     300
ggcactaagg tcgagattaa gcgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag caccctgacc     540
ctgagcaagg ccgactacga gaagcataag gtgtacgcct gcgaggtgac ccaccagggc     600
ctgtccagcc ccgtgaccaa gagcttcaac agggcgagt gc                         642

<210> SEQ ID NO 43
<211> LENGTH: 5
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 43

Ser Tyr Thr Met Asn
1               5

<210> SEQ ID NO 44
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Arg Val Lys Gly Glu Gln Phe Gly Gly Ser Ile His Tyr Ala Ala Ser
1               5                   10                  15

Val Lys Gly

<210> SEQ ID NO 45
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Glu Arg Ser Arg Ala Gly Ser Ile Phe Asp Pro
1               5                   10

<210> SEQ ID NO 46
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gly Phe Thr Phe Ser Ser Tyr
1               5

<210> SEQ ID NO 47
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Lys Gly Glu Gln Phe Gly Gly Ser
1               5

<210> SEQ ID NO 48
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 48

Glu Arg Ser Arg Ala Gly Ser Ile Phe Asp Pro
1               5                   10

<210> SEQ ID NO 49
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Gly Arg Val Lys Gly Glu Gln Phe Gly Gly Ser Ile His Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Glu Arg Ser Arg Ala Gly Ser Ile Phe Asp Pro Trp
            100                 105                 110

Gly Gln Gly Thr Leu Val Thr Val Ser Ser
        115                 120

<210> SEQ ID NO 50
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50
caggtgcagc tggtggaatc aggcggcgga ctggtcaagc ctggcggtag cctgagactg      60
agctgcgctg ctagtggctt caccttctct agctacacta tgaactgggt cagacaggcc    120
cctggtaaag gcctggagtg ggtcggaaga gtgaagggcg agcagttcgg cggctctatt    180
cactacgccg ctagtgtgaa gggccggttc actatctcta gggacgactc taagaacacc    240
ctgtacctgc agatgaatag cctgaaaacc gaggacaccg ccgtctacta ctgcgctaga    300
gagcggtcta gggccggctc tatcttcgac ccttggggtc aaggcaccct ggtcaccgtg    360
tctagc                                                                366

<210> SEQ ID NO 51
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 51

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
             20                  25                  30

Thr Met Asn Trp Val Arg Gln Ala Pro Gly Lys Gly Leu Glu Trp Val
         35                  40                  45

Gly Arg Val Lys Gly Glu Gln Phe Gly Gly Ser Ile His Tyr Ala Ala
     50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Arg Glu Arg Ser Arg Ala Gly Ser Ile Phe Asp Pro Trp
            100                 105                 110

Gly Gln Gly Thr Leu Val Thr Val Ser Ala Ser Thr Lys Gly Pro
        115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 52
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 52

```
caggtgcagc tggtggaatc aggcggcgga ctggtcaagc ctggcggtag cctgagactg      60
agctgcgctg ctagtggctt caccttctct agctacacta tgaactgggt cagacaggcc     120
cctggtaaag gcctggagtg ggtcggaaga gtgaagggcg agcagttcgg cggctctatt     180
cactacgccg ctagtgtgaa gggccggttc actatctcta gggacgactc taagaacacc     240
ctgtacctgc agatgaatag cctgaaaacc gaggacaccg ccgtctacta ctgcgctaga     300
gagcggtcta gggccggctc tatcttcgac ccttggggtc aaggcacccc tggtcaccgtg    360
tctagcgcta gcactaaggg cccaagtgtg tttcccctgg cccccagcag caagtctact     420
tccggcggaa ctgctgccct gggttgcctg gtgaaggact acttcccgga gcccgtgaca     480
gtgtcctgga actctggggc tctgacttcc ggcgtgcaca ccttcccgc cgtgctgcag      540
agcagcggcc tgtacagcct gagcagcgtg gtgacagtgc cctccagctc tctgggaacc     600
cagacctata tctgcaacgt gaaccacaag cccagcaaca ccaaggtgga caagagagtg     660
gagcccaaga gctgcgacaa gacccacacc tgccccccct gcccagctcc agaactgctg     720
ggagggcctt ccgtgttcct gttccccccc aagcccaagg acaccctgat gatcagcagg     780
accccccgagg tgacctgcgt ggtggtggac gtgtcccacg aggacccaga ggtgaagttc     840
aactggtacg tggacggcgt ggaggtgcac aacgccaaga ccaagcccag agaggagcag     900
tacaacagca cctacagggt ggtgtccgtg ctgaccgtgc tgcaccagga ctggctgaac     960
ggcaaagaat acaagtgcaa agtctccaac aaggccctgc cagccccaat cgaaaagaca    1020
atcagcaagg ccaagggcca gccacgggag cccaggtgt acaccctgcc ccccagccgg     1080
gaggagatga ccaagaacca ggtgtccctg acctgtctgg tgaagggctt ctaccccagc    1140
gatatcgccg tggagtggga gagcaacggc cagcccgaga caactacaa gaccacccc     1200
ccagtgctgg acagcgacgg cagcttcttc ctgtacagca agctgaccgt ggacaagtcc    1260
aggtggcagc agggcaacgt gttcagctgc agcgtgatgc acgaggccct gcacaaccac    1320
tacacccaga gtccctgag cctgagcccc ggcaag                              1356
```

<210> SEQ ID NO 53
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 53

```
Ser Gly Ser Ser Ser Asn Ile Gly Phe Asn Tyr Val Ser
1               5                   10
```

```
<210> SEQ ID NO 54
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Tyr Asn Asn Gln Arg Pro Ser
1               5
```

```
<210> SEQ ID NO 55
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ser Thr Trp Thr Gly Thr Ser Glu Ser His Val
1               5                   10
```

```
<210> SEQ ID NO 56
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ser Ser Ser Asn Ile Gly Phe Asn Tyr
1               5
```

```
<210> SEQ ID NO 57
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Tyr Asn Asn
1
```

```
<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Trp Thr Gly Thr Ser Glu Ser His
1               5
```

<210> SEQ ID NO 59
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 59

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Phe Asn
            20                  25                  30

Tyr Val Ser Trp Tyr Gln Gln Leu Pro Gly Thr Ala Pro Lys Leu Leu
        35                  40                  45

Ile Tyr Tyr Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Thr Trp Thr Gly Thr Ser
                85                  90                  95

Glu Ser His Val Phe Gly Gly Gly Thr Lys Leu Thr Val Leu
            100                 105                 110
```

<210> SEQ ID NO 60
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 60

```
cagtcagtcc tgactcagcc ccctagcgtc agcggcgctc ccggtcaaag agtgactatt       60
agctgtagcg gctctagctc taatatcggc tttaactacg tcagctggta tcagcagctg      120
cccggcaccg cccctaagct gctgatctac tataacaatc agcggcctag cggcgtgccc      180
gataggttta gcggatctaa gtcaggcact tctgctagtc tggctatcac cggactgcag      240
gctgaggacg aggccgacta ctactgctct acctggaccg gaactagcga gtctcacgtg      300
ttcggcggag gcactaagct gaccgtgctg                                       330
```

<210> SEQ ID NO 61
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Phe Asn
            20                  25                  30

Tyr Val Ser Trp Tyr Gln Gln Leu Pro Gly Thr Ala Pro Lys Leu Leu
        35                  40                  45

Ile Tyr Tyr Asn Asn Gln Arg Pro Ser Gly Val Pro Asp Arg Phe Ser
```

50                  55                  60
Gly Ser Lys Ser Gly Thr Ser Ala Ser Leu Ala Ile Thr Gly Leu Gln
 65                  70                  75                  80

Ala Glu Asp Glu Ala Asp Tyr Tyr Cys Ser Thr Trp Thr Gly Thr Ser
                 85                  90                  95

Glu Ser His Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 62
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
cagtcagtcc tgactcagcc ccctagcgtc agcggcgctc ccggtcaaag agtgactatt      60
agctgtagcg gctctagctc taatatcggc tttaactacg tcagctggta tcagcagctg     120
cccggcaccg cccctaagct gctgatctac tataacaatc agcggcctag cggcgtgccc     180
gataggttta gcggatctaa gtcaggcact tctgctagtc tggctatcac cggactgcag     240
gctgaggacg aggccgacta ctactgctct acctggaccg gaactagcga gtctcacgtg     300
ttcggcggag gcactaagct gaccgtgctg ggtcaaccta aggctgcccc cagcgtgacc     360
ctgttccccc ccagcagcga ggagctgcag gccaacaagg ccaccctggt gtgcctgatc     420
agcgacttct acccaggcgc cgtgaccgtg gcctggaagg ccgacagcag ccccgtgaag     480
gccggcgtgg agaccaccac ccccagcaag cagagcaaca acaagtacgc cgccagcagc     540
tacctgagcc tgacccccga gcagtggaag agccacaggt cctacagctg ccaggtgacc     600
cacgagggca gcaccgtgga aaagaccgtg gccccaaccg agtgcagc                 648

<210> SEQ ID NO 63
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Thr Tyr Val Met His

```
1               5

<210> SEQ ID NO 64
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Arg Ile Arg Ala Asn Ala Tyr Gly Gly Ala Ala Asp Tyr Ala Ala Pro
1               5                   10                  15

Val Lys Gly

<210> SEQ ID NO 65
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ala Glu Ala Arg Tyr Arg Asp Val
1               5

<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Gly Phe Thr Phe Ser Thr Tyr
1               5

<210> SEQ ID NO 67
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Arg Ala Asn Ala Tyr Gly Gly Ala
1               5

<210> SEQ ID NO 68
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ala Glu Ala Arg Tyr Arg Asp Val
1               5
```

<210> SEQ ID NO 69
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 69

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Val Met His Trp Val Arg Gln Ala Pro Gly Lys Gly Leu Glu Trp Val
        35                  40                  45

Gly Arg Ile Arg Ala Asn Ala Tyr Gly Gly Ala Ala Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Glu Ala Arg Tyr Arg Asp Val Trp Gly Gln Gly
            100                 105                 110

Thr Leu Val Thr Val Ser Ser
        115

<210> SEQ ID NO 70
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 70
caggtgcagc tggtggaatc aggcggcgga ctggtcaagc ctggcggctc cctgaggctg      60
agctgcgctg ctagtggctt cacctttagc acctacgtga tgcactgggt ccgccaggcc     120
cctggtaaag gcctggagtg ggtcggacgg attagagcta acgcctacgg cggagccgcc     180
gactacgctg cccctgtgaa gggccggttc actatctcta gggacgactc taagaacacc     240
ctgtacctgc agatgaatag cctgaaaacc gaggacaccg ccgtctacta ctgcgctaga     300
gccgaggcta gatataggga cgtgtggggt caaggcaccc tggtcaccgt gtctagc        357

<210> SEQ ID NO 71
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Val Met His Trp Val Arg Gln Ala Pro Gly Lys Gly Leu Glu Trp Val

```
                35                  40                  45
Gly Arg Ile Arg Ala Asn Ala Tyr Gly Gly Ala Ala Asp Tyr Ala Ala
 50                  55                  60
Pro Val Lys Gly Arg Phe Thr Ile Ser Arg Asp Asp Ser Lys Asn Thr
 65                  70                  75                  80
Leu Tyr Leu Gln Met Asn Ser Leu Lys Thr Glu Asp Thr Ala Val Tyr
                 85                  90                  95
Tyr Cys Ala Arg Ala Glu Ala Arg Tyr Arg Asp Val Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys
```

<210> SEQ ID NO 72
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72

```
caggtgcagc tggtggaatc aggcggcgga ctggtcaagc ctggcggctc cctgaggctg      60
agctgcgctg ctagtggctt cacctttagc acctacgtga tgcactgggt ccgccaggcc     120
cctggtaaag gcctggagtg ggtcggacgg attagagcta acgcctacgg cggagccgcc     180
gactacgctg cccctgtgaa gggccggttc actatctcta gggacgactc taagaacacc     240
ctgtacctgc agatgaatag cctgaaaacc gaggacaccg ccgtctacta ctgcgctaga     300
gccgaggcta gatataggga cgtgtggggt caaggcaccc tggtcaccgt gtctagcgct     360
agcactaagg gcccaagtgt gtttcccctg gcccccagca gcaagtctac ttccggcgga     420
actgctgccc tgggttgcct ggtgaaggac tacttccccg agcccgtgac agtgtcctgg     480
aactctgggg ctctgacttc cggcgtgcac accttccccg ccgtgctgca gagcagcggc     540
ctgtacagcc tgagcagcgt ggtgacagtg ccctccagct ctctgggaac ccagacctat     600
atctgcaacg tgaaccacaa gcccagcaac accaaggtgg acaagagagt ggagcccaag     660
agctgcgaca gacccacac ctgccccccc tgcccagctc cagaactgct gggagggcct     720
tccgtgttcc tgttcccccc caagcccaag gacaccctga tgatcagcag gacccccgag     780
gtgacctgcg tggtggtgga cgtgtcccac gaggacccag aggtgaagtt caactggtac     840
gtggacggcg tggaggtgca caacgccaag accaagccca gaggagca gtacaacagc     900
acctacaggg tggtgtccgt gctgaccgtg ctgcaccagg actggctgaa cggcaaagaa     960
tacaagtgca aagtctccaa caaggccctg ccagccccaa tcgaaaagac aatcagcaag    1020
gccaagggcc agccacggga gccccaggtg tacaccctgc cccccagccg ggaggagatg    1080
accaagaacc aggtgtccct gacctgtctg gtgaagggct tctacccag cgatatcgcc    1140
gtggagtggg agagcaacgg ccagcccgag aacaactaca gaccaccc cccagtgctg    1200
gacagcgacg gcagcttctt cctgtacagc aagctgaccg tggacaagtc caggtggcag    1260
cagggcaacg tgttcagctg cagcgtgatg cacgaggccc tgcacaacca ctacacccag    1320
aagtccctga gcctgagccc cggcaag                                        1347
```

<210> SEQ ID NO 73
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Arg Ala Ser Gln Ser Ile Ser Ser His Leu Asn
1               5                   10

<210> SEQ ID NO 74
<211> LENGTH: 7
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 74

Ala Ala Ser Asn Leu Gln Ser
1               5

<210> SEQ ID NO 75
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Gln Gln Asp Tyr His Thr Pro Phe Thr
1               5

<210> SEQ ID NO 76
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Ser Gln Ser Ile Ser Ser His
1               5

<210> SEQ ID NO 77
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Ala Ala Ser
1

<210> SEQ ID NO 78
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Asp Tyr His Thr Pro Phe
1               5

<210> SEQ ID NO 79
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr His Thr Pro Phe
                85                  90                  95

Thr Phe Gly Gln Gly Thr Lys Val Glu Ile Lys
            100                 105

<210> SEQ ID NO 80
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 80
gatattcaga tgactcagtc acctagtagc ctgagcgcta gtgtgggcga tagagtgact      60
atcacctgta gagcctctca gtctattagc tctcacctga actggtatca gcagaagccc     120
ggtaaagccc ctaagctgct gatctacgcc gcctctaacc tgcagtcagg cgtgccctct     180
aggtttagcg gtagcggtag tggcaccgac ttcaccctga ctatctctag cctgcagccc     240
gaggacttcg ctacctacta ctgtcagcag gactatcaca ccccctttac cttcggtcaa     300
ggcactaagg tcgagattaa g                                                321

<210> SEQ ID NO 81
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr His Thr Pro Phe
                85                  90                  95

Thr Phe Gly Gln Gly Thr Lys Val Glu Ile Lys Arg Thr Val Ala Ala
            100                 105                 110

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 82
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 82

| | | |
|---|---|---|
| gatattcaga tgactcagtc acctagtagc ctgagcgcta gtgtgggcga tagagtgact | 60 |
| atcacctgta gagcctctca gtctattagc tctcacctga actggtatca gcagaagccc | 120 |
| ggtaaagccc ctaagctgct gatctacgcc gcctctaacc tgcagtcagg cgtgccctct | 180 |
| aggtttagcg gtagcggtag tggcaccgac ttcaccctga ctatctctag cctgcagccc | 240 |
| gaggacttcg ctacctacta ctgtcagcag gactatcaca ccccccttcac cttcggtcaa | 300 |
| ggcactaagg tcgagattaa gcgtacggtg gccgctccca gcgtgttcat cttcccccc | 360 |
| agcgacgagc agctgaagag cggcaccgcc agcgtggtgt gcctgctgaa caacttctac | 420 |
| ccccgggagg ccaaggtgca gtggaaggtg gacaacgccc tgcagagcgg caacagccag | 480 |
| gagagcgtca ccgagcagga cagcaaggac tccacctaca gcctgagcag caccctgacc | 540 |
| ctgagcaagg ccgactacga aagcataag gtgtacgcct gcgaggtgac ccaccagggc | 600 |
| ctgtccagcc ccgtgaccaa gagcttcaac aggggcgagt gc | 642 |

<210> SEQ ID NO 83
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 83

```
Ser Tyr Thr Ile Ser
1               5
```

<210> SEQ ID NO 84
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic peptide"

<400> SEQUENCE: 84

Trp Ile Lys Pro Lys Leu Gly Met Ala His Tyr Ala Gln Lys Phe Gln
1               5                   10                  15
Gly

<210> SEQ ID NO 85
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Gly Ser Phe Trp Phe Gly Tyr
1               5

<210> SEQ ID NO 86
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Gly Gly Thr Phe Ser Ser Tyr
1               5

<210> SEQ ID NO 87
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Lys Pro Lys Leu Gly Met
1               5

<210> SEQ ID NO 88
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Gly Ser Phe Trp Phe Gly Tyr
1               5

<210> SEQ ID NO 89
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Trp Ile Lys Pro Lys Leu Gly Met Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Phe Trp Phe Gly Tyr Trp Gly Gln Gly Thr Leu Val
            100                 105                 110

Thr Val Ser Ser
        115

<210> SEQ ID NO 90
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90
caggtgcaat tggtgcagag cggtgccgaa gtgaaaaaac cgggcagcag cgtgaaagtt      60
agctgcaaag catccggagg gacgttttct tcttacacta tctcttgggt gcgccaggcc     120
ccgggccagg gcctcgagtg gatgggctgg atcaaaccga aactgggcat ggctcattac     180
gcccagaaat tcagggccgg ggtgaccatt accgccgatg aaagcaccag caccgcctat     240
atggaactga gcagcctgcg cagcgaagat acggccgtgt attattgcgc gcgtggttct     300
ttctggttcg gttactgggg ccaaggcacc ctggtgactg ttagctca                 348

<210> SEQ ID NO 91
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Trp Ile Lys Pro Lys Leu Gly Met Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Phe Trp Phe Gly Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 92
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 92

```
caggtgcaat tggtgcagag cggtgccgaa gtgaaaaaac cgggcagcag cgtgaaagtt      60
agctgcaaag catccggagg gacgttttct tcttacacta tctcttgggt gcgccaggcc     120
ccgggccagg gcctcgagtg gatgggctgg atcaaaccga aactgggcat ggctcattac     180
gcccagaaat ttcagggccg ggtgaccatt accgccgatg aaagcaccag caccgcctat     240
atggaactga gcagcctgcg cagcgaagat acggccgtgt attattgcgc gcgtggttct     300
ttctggttcg gttactgggg ccaaggcacc ctggtgactg ttagctcagc ctccaccaag     360
ggtccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagagag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgg     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccatccc gggaggagat gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaa                                                  1338
```

<210> SEQ ID NO 93
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Arg Ala Ser Gln Gly Ile Asn Asn Tyr Leu Asn
1               5                   10

<210> SEQ ID NO 94
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Asp Ala Ser Lys Leu Gln Ser
1               5

<210> SEQ ID NO 95
<211> LENGTH: 9

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Gln Gln Tyr Leu Gln Tyr Pro Met Thr
1               5

<210> SEQ ID NO 96
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Ser Gln Gly Ile Asn Asn Tyr
1               5

<210> SEQ ID NO 97
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Asp Ala Ser
1

<210> SEQ ID NO 98
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Tyr Leu Gln Tyr Pro Met
1               5

<210> SEQ ID NO 99
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Lys Leu Gln Ser Gly Val Pro Ser Arg Phe Ser Gly
```

```
                50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Gln Tyr Pro Met
                 85                  90                  95

Thr Phe Gly Gln Gly Thr Lys Val Glu Ile Lys
            100                 105

<210> SEQ ID NO 100
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100
gatatccaga tgacccagag cccgagcagc ctgagcgcca gcgtgggcga tcgcgtgacc        60
attacctgca gagccagcca gggtattaac aactacctga actggtacca gcagaaaccg       120
ggcaaagcgc cgaaactatt aatctacgac gcttctaaac tgcaaagcgg cgtgccgagc       180
cgctttagcg gcagcggatc cggcaccgat ttcaccctga ccattagctc tctgcaaccg       240
gaagactttg cgacctatta ttgccagcag tacctgcagt acccgatgac ctttggccag       300
ggcacgaaag ttgaaattaa a                                                 321

<210> SEQ ID NO 101
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Asn Asn Tyr
                20                  25                  30

Leu Asn Trp Tyr Gln Gln Lys Pro Gly Lys Ala Pro Lys Leu Leu Ile
             35                  40                  45

Tyr Asp Ala Ser Lys Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Gln Tyr Pro Met
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 102
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 102
gatatccaga tgacccagag cccgagcagc ctgagcgcca gcgtgggcga tcgcgtgacc      60
attacctgca gagccagcca gggtattaac aactacctga actggtacca gcagaaaccg     120
ggcaaagcgc cgaaactatt aatctacgac gcttctaaac tgcaaagcgg cgtgccgagc     180
cgctttagcg gcagcggatc cggcaccgat ttcaccctga ccattagctc tctgcaaccg     240
gaagactttg cgacctatta ttgccagcag tacctgcagt acccgatgac ctttggccag     300
ggcacgaaag ttgaaattaa acgtacggtg gccgctccca gcgtgttcat cttcccccc      360 agcgacgagc agctgaagag cggcaccgcc agcgtggtgt gcctgctgaa caacttctac     420 cccgggagg ccaaggtgca gtggaaggtg acaacgccc tgcagagcgg caacagccag       480
gaaagcgtca ccgagcagga cagcaaggac tccacctaca gcctgagcag caccctgacc     540
ctgagcaagg ccgactacga gaagcacaag gtgtacgcct gcgaggtgac ccaccagggc     600
ctgtccagcc ccgtgaccaa gagcttcaac cggggcgagt gt                        642

<210> SEQ ID NO 103
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Ser Tyr Thr Ile Ser
1               5

<210> SEQ ID NO 104
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Trp Ile Lys Pro Arg Tyr Gly Ala Ala Met Tyr Ala Gln Lys Phe Gln
1               5                   10                  15

Gly

<210> SEQ ID NO 105
<211> LENGTH: 7

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Gly Ser Phe Trp Phe Gly Tyr
1               5

<210> SEQ ID NO 106
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Gly Gly Thr Phe Ser Ser Tyr
1               5

<210> SEQ ID NO 107
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Lys Pro Arg Tyr Gly Ala
1               5

<210> SEQ ID NO 108
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Gly Ser Phe Trp Phe Gly Tyr
1               5

<210> SEQ ID NO 109
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Trp Ile Lys Pro Arg Tyr Gly Ala Ala Met Tyr Ala Gln Lys Phe
```

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Phe Trp Phe Gly Tyr Trp Gly Gln Gly Thr Leu Val
            100                 105                 110

Thr Val Ser Ser
        115

<210> SEQ ID NO 110
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 110
caggtgcaat tggtgcagag cggtgccgaa gtgaaaaaac cgggcagcag cgtgaaagtt      60
agctgcaaag catccggagg gacgtttfct tcttacacta tctcttgggt gcgccaggcc     120
ccgggccagg gcctcgagtg gatgggctgg atcaaaccgc gttacggcgc tgctatgtac     180
gcccagaaat tcagggccg gtgaccatt accgccgatg aaagcaccag caccgcctat      240
atggaactga gcagcctgcg cagcgaagat acggccgtgt attattgcgc gcgtggttct     300
ttctggttcg gttactgggg ccaaggcacc ctggtgactg ttagctca                 348

<210> SEQ ID NO 111
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Trp Ile Lys Pro Arg Tyr Gly Ala Ala Met Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Phe Trp Phe Gly Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 112
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 112
caggtgcaat tggtgcagag cggtgccgaa gtgaaaaaac cgggcagcag cgtgaaagtt      60
agctgcaaag catccggagg gacgtttttct tcttacacta tctcttgggt gcgccaggcc    120
ccgggccagg gcctcgagtg gatgggctgg atcaaaccgc gttacggcgc tgctatgtac    180
gcccagaaat tcagggccg gtgaccatt accgccgatg aaagcaccag caccgcctat      240
atggaactga gcagcctgcg cagcgaagat acggccgtgt attattgcgc gcgtggttct    300
ttctggttcg gttactgggg ccaaggcacc ctggtgactg ttagctcagc ctccaccaag    360

-continued

```
ggtccatcgg tcttcccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca ccttcccg gctgtcctac agtcctcagg actctactcc      540
ctcagcagcg tggtgaccgt gccctccagc agcttgggca cccagaccta catctgcaac    600
gtgaatcaca agcccagcaa caccaaggtg gacaagagag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggaccctga ggtcacatgc     780 gtggtggtgg acgtgagcca cgaagaccct gaggtcaagt tcaactggta cgtggacggc    840
gtggaggtgc ataatgccaa gacaaagccg cgggaggagc agtacaacag cacgtaccgg    900
gtggtcagcg tcctcaccgt cctgcaccag gactggctga atggcaagga gtacaagtgc    960
aaggtctcca acaaagccct cccagccccc atcgagaaaa ccatctccaa agccaaaggg    1020
cagccccgag aaccacaggt gtacaccctg cccccatccc gggaggagat gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaa                                                  1338
```

<210> SEQ ID NO 113
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 113

Arg Ala Ser Gln Gly Ile Asn Asn Tyr Leu Asn
1               5                   10

<210> SEQ ID NO 114
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 114

Asp Ala Ser Lys Leu Gln Ser
1               5

<210> SEQ ID NO 115
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 115

Gln Gln Tyr Leu Gln Tyr Pro Met Thr
1               5

<210> SEQ ID NO 116
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 116

Ser Gln Gly Ile Asn Asn Tyr
1               5

<210> SEQ ID NO 117
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 117

Asp Ala Ser
1

<210> SEQ ID NO 118
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 118

Tyr Leu Gln Tyr Pro Met
1               5

<210> SEQ ID NO 119
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gln Tyr Pro Met
                85                  90                  95

Thr Phe Gly Gln Gly Thr Lys Val Glu Ile Lys
            100                 105

<210> SEQ ID NO 120
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 120

```
gatatccaga tgacccagag cccgagcagc ctgagcgcca gcgtgggcga tcgcgtgacc      60
attacctgca gagccagcca gggtattaac aactacctga actggtacca gcagaaaccg     120
ggcaaagcgc cgaaactatt aatctacgac gcttctaaac tgcaaagcgg cgtgccgagc     180
cgctttagcg gcagcggatc cggcaccgat ttcaccctga ccattagctc tctgcaaccg     240
gaagactttg cgacctatta ttgccagcag tacctgcagt acccgatgac ctttggccag     300
ggcacgaaag ttgaaattaa a                                               321
```

<210> SEQ ID NO 121
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 121

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gln Tyr Pro Met
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 122

```
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 122
gatatccaga tgacccagag cccgagcagc ctgagcgcca gcgtgggcga tcgcgtgacc      60
attacctgca gagccagcca gggtattaac aactacctga actggtacca gcagaaaccg     120
ggcaaagcgc cgaaactatt aatctacgac gcttctaaac tgcaaagcgg cgtgccgagc     180
cgctttagcg gcagcggatc cggcaccgat ttcaccctga ccattagctc tctgcaaccg     240
gaagactttg cgacctatta ttgccagcag tacctgcagt acccgatgac ctttggccag     300
ggcacgaaag ttgaaattaa acgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg acaacgccc tgcagagcgg caacagccag      480
gaaagcgtca ccgagcagga cagcaaggac tccacctaca gcctgagcag caccctgacc     540
ctgagcaagg ccgactacga aagcacaag gtgtacgcct gcgaggtgac ccaccagggc      600
ctgtccagcc ccgtgaccaa gagcttcaac cggggcgagt gt                       642

<210> SEQ ID NO 123
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Thr Tyr Val Met His
1               5

<210> SEQ ID NO 124
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Arg Ile Arg Ser Asn Thr Tyr Gly Gly Ile Thr Asp Tyr Ala Ala Pro
1               5                   10                  15
Val Lys Gly

<210> SEQ ID NO 125
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Ala Glu Ala Arg Tyr Arg Asp Val
1               5
```

<210> SEQ ID NO 126
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 126

Gly Phe Thr Phe Ser Thr Tyr
1               5

<210> SEQ ID NO 127
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 127

Arg Ser Asn Thr Tyr Gly Gly Ile
1               5

<210> SEQ ID NO 128
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 128

Ala Glu Ala Arg Tyr Arg Asp Val
1               5

<210> SEQ ID NO 129
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 129

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Val Met His Trp Val Arg Gln Ala Pro Gly Lys Gly Leu Glu Trp Val
        35                  40                  45

Gly Arg Ile Arg Ser Asn Thr Tyr Gly Gly Ile Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Glu Ala Arg Tyr Arg Asp Val Trp Gly Gln Gly
            100                 105                 110

Thr Leu Val Thr Val Ser Ser

-continued

115

<210> SEQ ID NO 130
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 130

```
caggtgcaat tggtggaaag cggcggtggc ctggtgaaac caggcggcag cctgcgcctg      60
agctgcgccg cctccggatt cacctttct acttacgtta tgcattgggt gcgccaggcc     120
ccgggcaaag gtctcgagtg ggtgggccgt atccgttcta acacttacgg tggtatcact     180
gactatgccg ccccagtgaa aggccgcttt accattagcc gcgatgattc gaaaaacacc     240
ctgtatctgc aaatgaacag cctgaaaacc gaagatacgg ccgtgtatta ttgcgcgcgt     300
gctgaagctc gttaccgtga tgtttggggc caaggcaccc tggtgactgt tagctca       357
```

<210> SEQ ID NO 131
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 131

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Val Met His Trp Val Arg Gln Ala Pro Gly Lys Gly Leu Glu Trp Val
        35                  40                  45

Gly Arg Ile Arg Ser Asn Thr Tyr Gly Gly Ile Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Glu Ala Arg Tyr Arg Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys
```

<210> SEQ ID NO 132
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 132

```
caggtgcaat tggtggaaag cggcggtggc ctggtgaaac caggcggcag cctgcgcctg      60
agctgcgccg cctccggatt caccttttct acttacgtta tgcattgggt gcgccaggcc     120
ccgggcaaag gtctcgagtg ggtgggccgt atccgttcta acacttacgg tggtatcact     180
gactatgccg ccccagtgaa aggccgcttt accattagcc gcgatgattc gaaaaacacc     240
ctgtatctgc aaatgaacag cctgaaaacc gaagatacgg ccgtgtatta ttgcgcgcgt     300
gctgaagctc gttaccgtga tgtttggggc caaggcaccc tggtgactgt agctcagcc     360 tccaccaagg gtccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
```

```
tcttgtgaca aaactcacac atgcccaccg tgcccagcac ctgaactcct ggggggaccg    720
tcagtcttcc tcttccccccc aaacccaag dacaccctca tgatctcccg gaccccctgag    780 gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccggg tggtcagcgt cctcaccgtc ctgcaccagg actggctgaa tggcaaggag    960
tacaagtgca aggtctccaa caaagccctc ccagcccca tcgagaaaac catctccaaa    1020
gccaaagggc agccccgaga accacaggtg tacaccctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 133
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 133

Arg Ala Ser Gln Ser Ile Ser Ser His Leu Asn
1               5                   10

<210> SEQ ID NO 134
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 134

Ala Ala Ser Asn Leu Gln Ser
1               5

<210> SEQ ID NO 135
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 135

Gln Gln Asp Tyr His Thr Pro Phe Thr
1               5

<210> SEQ ID NO 136
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 136

Ser Gln Ser Ile Ser Ser His
1               5

<210> SEQ ID NO 137
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Ala Ala Ser
1

<210> SEQ ID NO 138
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Asp Tyr His Thr Pro Phe
1               5

<210> SEQ ID NO 139
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr His Thr Pro Phe
                85                  90                  95

Thr Phe Gly Gln Gly Thr Lys Val Glu Ile Lys
            100                 105

<210> SEQ ID NO 140
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 140
```

```
gatatccaga tgacccagag cccgagcagc ctgagcgcca gcgtgggcga tcgcgtgacc      60
attacctgca gagccagcca gtctatttct tctcatctga actggtacca gcagaaaccg     120
ggcaaagcgc cgaaactatt aatctacgct gcttctaacc tgcaaagcgg cgtgccgagc     180
cgctttagcg gcagcggatc cggcaccgat ttcaccctga ccattagctc tctgcaaccg     240
gaagactttg cgacctatta ttgccagcag gactaccata ctccgttcac ctttggccag     300
ggcacgaaag ttgaaattaa a                                               321
```

<210> SEQ ID NO 141
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 141

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr His Thr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 142
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 142

```
gatatccaga tgacccagag cccgagcagc ctgagcgcca gcgtgggcga tcgcgtgacc    60
attacctgca gagccagcca gtctatttct tctcatctga actggtacca gcagaaaccg   120
ggcaaagcgc cgaaactatt aatctacgct gcttctaacc tgcaaagcgg cgtgccgagc   180
cgctttagcg gcagcggatc cggcaccgat tcaccctga ccattagctc tctgcaaccg    240
gaagactttg cgacctatta ttgccagcag gactaccata ctccgttcac ctttggccag   300
ggcacgaaag ttgaaattaa acgtacggtg gccgctccca gcgtgttcat cttcccccc    360 agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gaaagcgtca ccgagcagga cagcaaggac tccacctaca gcctgagcag caccctgacc   540
ctgagcaagg ccgactacga aagcacaag gtgtacgcct gcgaggtgac ccaccagggc    600
ctgtccagcc ccgtgaccaa gagcttcaac cggggcgagt gt                      642
```

<210> SEQ ID NO 143
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Ser Tyr Thr Ile Ser
1               5

<210> SEQ ID NO 144
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Trp Ile Lys Pro Ala Phe Gly Thr Ala Asn Tyr Ala Gln Lys Phe Gln
1               5                   10                  15
Gly

<210> SEQ ID NO 145
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Gly Ser Phe Trp Phe Gly Tyr
1               5

<210> SEQ ID NO 146
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Gly Gly Thr Phe Ser Ser Tyr
1               5

<210> SEQ ID NO 147
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Lys Pro Ala Phe Gly Thr
1               5

<210> SEQ ID NO 148
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Gly Ser Phe Trp Phe Gly Tyr
1               5

<210> SEQ ID NO 149
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Trp Ile Lys Pro Ala Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Phe Trp Phe Gly Tyr Trp Gly Gln Gly Thr Leu Val
            100                 105                 110

Thr Val Ser Ser
        115

<210> SEQ ID NO 150
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 150

```
caggtgcaat tggtgcagag cggtgccgaa gtgaaaaaac cgggcagcag cgtgaaagtt      60
agctgcaaag catccggagg gacgttttct tcttacacta tctcttgggt gcgccaggcc     120
ccgggccagg gcctcgagtg gatgggctgg atcaaaccgg ctttcggcac tgcgaactac     180
gcccagaaat tcagggccg ggtgaccatt accgccgatg aaagcaccag caccgcctat      240
atggaactga gcagcctgcg cagcgaagat acggccgtgt attattgcgc gcgtggttct     300
ttctggttcg gttactgggg ccaaggcacc ctggtgactg ttagctca                  348
```

<210> SEQ ID NO 151
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 151

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Trp Ile Lys Pro Ala Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Phe Trp Phe Gly Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 152
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 152
caggtgcaat tggtgcagag cggtgccgaa gtgaaaaaac cgggcagcag cgtgaaagtt      60
agctgcaaag catccggagg gacgttttct tcttacacta tctcttgggt gcgccaggcc     120
ccgggccagg gcctcgagtg gatgggctgg atcaaaccgg ctttcggcac tgcgaactac     180
gcccagaaat ttcagggccg ggtgaccatt accgccgatg aaagcaccag caccgcctat     240
atggaactga gcagcctgcg cagcgaagat acggccgtgt attattgcgc gcgtggttct     300
ttctggttcg gttactgggg ccaaggcacc ctggtgactg ttagctcagc ctccaccaag     360
ggtccatcgg tcttcccect ggcaccctcc tccaagagca cctctggggg cacagcggcc     420
ctgggctgcc tggtcaagga ctacttcccc gaaccggtga cggtgtcgtg aactcaggc     480 gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagagag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgg     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
```

```
cagccccgag aaccacaggt gtacaccctg cccccatccc gggaggagat gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaa                                                  1338
```

```
<210> SEQ ID NO 153
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Arg Ala Ser Gln Gly Ile Asn Asn Tyr Leu Asn
1               5                   10

<210> SEQ ID NO 154
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Asp Ala Ser Lys Leu Gln Ser
1               5

<210> SEQ ID NO 155
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Gln Gln Tyr Leu Gln Tyr Pro Met Thr
1               5

<210> SEQ ID NO 156
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Ser Gln Gly Ile Asn Asn Tyr
1               5

<210> SEQ ID NO 157
<211> LENGTH: 3
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 157

Asp Ala Ser
1

<210> SEQ ID NO 158
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Tyr Leu Gln Tyr Pro Met
1               5

<210> SEQ ID NO 159
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gln Tyr Pro Met
                85                  90                  95

Thr Phe Gly Gln Gly Thr Lys Val Glu Ile Lys
            100                 105

<210> SEQ ID NO 160
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 160
gatatccaga tgacccagag cccgagcagc ctgagcgcca gcgtgggcga tcgcgtgacc      60
attacctgca gagccagcca gggtattaac aactacctga actggtacca gcagaaaccg     120
ggcaaagcgc cgaaactatt aatctacgac gcttctaaac tgcaaagcgg cgtgccgagc     180
cgctttagcg gcagcggatc cggcaccgat tcacccctga ccattagctc tctgcaaccg     240
gaagactttg cgacctatta ttgccagcag tacctgcagt acccgatgac ctttggccag     300
ggcacgaaag ttgaaattaa a                                                321

<210> SEQ ID NO 161
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 161

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gln Tyr Pro Met
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 162
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 162

```
gatatccaga tgacccagag cccgagcagc ctgagcgcca gcgtgggcga tcgcgtgacc      60
attacctgca gagccagcca gggtattaac aactacctga actggtacca gcagaaaccg     120
ggcaaagcgc cgaaactatt aatctacgac gcttctaaac tgcaaagcgg cgtgccgagc     180
cgctttagcg gcagcggatc cggcaccgat ttcaccctga ccattagctc tctgcaaccg     240
gaagactttg cgacctatta ttgccagcag tacctgcagt acccgatgac ctttggccag     300
ggcacgaaag ttgaaattaa acgtacggtg gccgctccca gcgtgttcat cttccccccc     360
```

```
agcgacgagc agctgaagag cggcaccgcc agcgtggtgt gcctgctgaa caacttctac      420
ccccgggagg ccaaggtgca gtggaaggtg gacaacgccc tgcagagcgg caacagccag      480
gaaagcgtca ccgagcagga cagcaaggac tccacctaca gcctgagcag caccctgacc      540
ctgagcaagg ccgactacga gaagcacaag gtgtacgcct gcgaggtgac ccaccagggc      600
ctgtccagcc ccgtgaccaa gagcttcaac cggggcgagt gt                        642
```

<210> SEQ ID NO 163
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 163

```
Thr Tyr Ala Met His
1               5
```

<210> SEQ ID NO 164
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 164

```
Gly Ile Ile Pro Ile Phe Gly Ile Ala Asn Tyr Ala Gln Lys Phe Gln
1               5                   10                  15

Gly
```

<210> SEQ ID NO 165
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 165

```
Asp Asp Tyr Ser Thr Tyr Ala Phe Ala Tyr
1               5                   10
```

<210> SEQ ID NO 166
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 166

```
Gly Gly Thr Phe Arg Thr Tyr
1               5
```

<210> SEQ ID NO 167
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 167

Ile Pro Ile Phe Gly Ile
1               5

<210> SEQ ID NO 168
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 168

Asp Asp Tyr Ser Thr Tyr Ala Phe Ala Tyr
1               5                   10

<210> SEQ ID NO 169
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 169

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Thr Tyr
            20                  25                  30

Ala Met His Trp Val Arg Gln Ala Pro Gly Gln Gly Leu Glu Trp Met
        35                  40                  45

Gly Gly Ile Ile Pro Ile Phe Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Ser Thr Tyr Ala Phe Ala Tyr Trp Gly Gln Gly
            100                 105                 110

Thr Leu Val Thr Val Ser Ser
        115

<210> SEQ ID NO 170
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 170
caggtgcaat tggtgcagag cggtgccgaa gtgaaaaaac cgggcagcag cgtgaaagtt     60
agctgcaaag catccggagg acgtttcgt acttacgcta tgcattgggt gcgccaggcc    120
ccgggccagg gcctcgagtg gatgggcggt atcatcccga tcttcggcat cgcgaactac    180
gcccagaaat ttcagggccg ggtgaccatt accgccgatg aaagcaccag caccgcctat    240

```
atggaactga gcagcctgcg cagcgaagat acggccgtgt attattgcgc gcgtgacgac    300
tactctactt acgctttcgc ttactggggc caaggcaccc tggtgactgt tagctca      357
```

<210> SEQ ID NO 171
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 171

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Thr Tyr
            20                  25                  30

Ala Met His Trp Val Arg Gln Ala Pro Gly Gln Gly Leu Glu Trp Met
        35                  40                  45

Gly Gly Ile Ile Pro Ile Phe Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Ser Thr Tyr Ala Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys
```

<210> SEQ ID NO 172
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 172

| | | |
|---|---|---|
| caggtgcaat tggtgcagag cggtgccgaa gtgaaaaaac cgggcagcag cgtgaaagtt | 60 |
| agctgcaaag catccggagg gacgtttcgt acttacgcta tgcattgggt gcgccaggcc | 120 |
| ccgggccagg gcctcgagtg gatgggcggt atcatcccga tcttcggcat cgcgaactac | 180 |
| gcccagaaat tcagggccg gtgaccatt accgccgatg aaagcaccag caccgcctat | 240 |
| atggaactga gcagcctgcg cagcgaagat acggccgtgt attattgcgc gcgtgacgac | 300 |
| tactctactt acgctttcgc ttactggggc caaggcaccc tggtgactgt tagctcagcc | 360 |
| tccaccaagg gtccatcggt cttccccctg gcaccctcct ccaagagcac ctctgggggc | 420 |
| acagcggccc tgggctgcct ggtcaaggac tacttccccg aaccggtgac ggtgtcgtgg | 480 |
| aactcaggcg ccctgaccag cggcgtgcac accttcccgg ctgtcctaca gtcctcagga | 540 |
| ctctactccc tcagcagcgt ggtgaccgtg ccctccagca gcttgggcac ccagacctac | 600 |
| atctgcaacg tgaatcacaa gcccagcaac accaaggtgg acaagagagt tgagcccaaa | 660 |
| tcttgtgaca aaactcacac atgcccaccg tgcccagcac ctgaactcct ggggggaccg | 720 |
| tcagtcttcc tcttcccccc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacaacagc | 900 |
| acgtaccggg tggtcagcgt cctcaccgtc ctgcaccagg actggctgaa tggcaaggag | 960 |
| tacaagtgca aggtctccaa caaagccctc ccagccccca tcgagaaaac catctccaaa | 1020 |
| gccaaagggc agccccgaga accacaggtg tacaccctgc ccccatcccg ggaggagatg | 1080 |
| accaagaacc aggtcagcct gacctgcctg gtcaaaggct tctatcccag cgacatcgcc | 1140 |
| gtggagtggg agagcaatgg gcagccggag aacaactaca agaccacgcc tcccgtgctg | 1200 |
| gactccgacg gctccttctt cctctacagc aagctcaccg tggacaagag caggtggcag | 1260 |
| caggggaacg tcttctcatg ctccgtgatg catgaggctc tgcacaacca ctacacgcag | 1320 |

-continued aagagcctct ccctgtctcc gggtaaa                                          1347

<210> SEQ ID NO 173
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Arg Ala Ser Gln Ser Ile Ala Ser Tyr Leu Ala
1               5                   10

<210> SEQ ID NO 174
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Asp Ala Ser Asn Leu Gln Ser
1               5

<210> SEQ ID NO 175
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Gln Gln Ala Tyr Lys Thr Pro Tyr Thr
1               5

<210> SEQ ID NO 176
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Ser Gln Ser Ile Ala Ser Tyr
1               5

<210> SEQ ID NO 177
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Asp Ala Ser
1

<210> SEQ ID NO 178

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Ala Tyr Lys Thr Pro Tyr
1               5

<210> SEQ ID NO 179
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Lys Thr Pro Tyr
                85                  90                  95

Thr Phe Gly Gln Gly Thr Lys Val Glu Ile Lys
            100                 105

<210> SEQ ID NO 180
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 180
gatatccaga tgacccagag cccgagcagc ctgagcgcca gcgtgggcga tcgcgtgacc     60
attacctgca gagccagcca gtctattgct tcttacctgg cttggtacca gcagaaaccg    120
ggcaaagcgc cgaaactatt aatctacgac gcttctaacc tgcaaagcgg cgtgccgagc    180
cgctttagcg gcagcggatc cggcaccgat tcacccctga ccattagctc tctgcaaccg    240
gaagactttg cgacctatta ttgccagcag gcttacaaaa ctccgtacac ctttggccag    300
ggcacgaaag ttgaaattaa a                                              321

<210> SEQ ID NO 181
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 181

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Lys Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 182
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 182

```
gatatccaga tgacccagag cccgagcagc ctgagcgcca gcgtgggcga tcgcgtgacc    60
attacctgca gagccagcca gtctattgct tcttacctgg cttggtacca gcagaaaccg   120
ggcaaagcgc cgaaactatt aatctacgac gcttctaacc tgcaaagcgg cgtgccgagc   180
cgctttagcg gcagcggatc cggcaccgat tcaccctga ccattagctc tctgcaaccg   240
gaagactttg cgacctatta ttgccagcag gcttacaaaa ctccgtacac ctttggccag   300
ggcacgaaag ttgaaattaa acgtacggtg gccgctccca gcgtgttcat cttcccccccc   360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gaaagcgtca ccgagcagga cagcaaggac tccacctaca gcctgagcag caccctgacc   540
ctgagcaagg ccgactacga gaagcacaag gtgtacgcct gcgaggtgac ccaccagggc   600
ctgtccagcc ccgtgaccaa gagcttcaac cggggcgagt gt                      642
```

<210> SEQ ID NO 183
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Ser Tyr Thr Met Asn
1               5

<210> SEQ ID NO 184
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Arg Val Lys Gly Glu Gln Phe Gly Gly Ser Ile His Tyr Ala Ala Ser
1               5                   10                  15

Val Lys Gly

<210> SEQ ID NO 185
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Glu Arg Ser Arg Ala Gly Ser Ile Phe Asp Pro
1               5                   10

<210> SEQ ID NO 186
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Gly Phe Thr Phe Ser Ser Tyr
1               5

<210> SEQ ID NO 187
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Lys Gly Glu Gln Phe Gly Gly Ser
1               5

<210> SEQ ID NO 188

<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 188

Glu Arg Ser Arg Ala Gly Ser Ile Phe Asp Pro
1               5                   10

<210> SEQ ID NO 189
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 189

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Gly Arg Val Lys Gly Glu Gln Phe Gly Gly Ser Ile His Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Glu Arg Ser Arg Ala Gly Ser Ile Phe Asp Pro Trp
            100                 105                 110

Gly Gln Gly Thr Leu Val Thr Val Ser Ser
        115                 120

<210> SEQ ID NO 190
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 190
caggtgcaat tggtggaaag cggcggtggc ctggtgaaac caggcggcag cctgcgcctg      60
agctgcgccg cctccggatt cacctttctc tcttacacta tgaactgggt gcgccaggcc     120
ccgggcaaag gtctcgagtg gtgggccgt gttaaaggtg aacagttcgg cggttctatc      180
cattatgccg cctctgtgaa aggccgcttt accattagcc gcgatgattc gaaaaacacc     240
ctgtatctgc aaatgaacag cctgaaaacc gaagatacgg ccgtgtatta ttgcgcgcgt     300
gaacgttctc gtgctggttc tatcttcgat ccgtggggcc aaggcaccct ggtgactgtt     360
agctca                                                                366

<210> SEQ ID NO 191
<211> LENGTH: 452
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 191

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Gly Arg Val Lys Gly Glu Gln Phe Gly Gly Ser Ile His Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Glu Arg Ser Arg Ala Gly Ser Ile Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
        435                 440                 445

Ser Pro Gly Lys
    450

<210> SEQ ID NO 192
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 192
caggtgcaat tggtggaaag cggcggtggc ctggtgaaac aggcggcag cctgcgcctg      60 agctgcgccg cctccggatt caccttttct tcttacacta tgaactgggt gcgccaggcc    120
ccgggcaaag gtctcgagtg gtgggccgt gttaaaggtg aacagttcgg cggttctatc     180
cattatgccg cctctgtgaa aggccgcttt accattagcc gcgatgattc gaaaaacacc    240
ctgtatctgc aaatgaacag cctgaaaacc gaagatacgg ccgtgtatta ttgcgcgcgt    300
gaacgttctc gtgctggttc tatcttcgat ccgtggggcc aaggcaccct ggtgactgtt    360
agctcagcct ccaccaaggg tccatcggtc ttccccctgg caccctcctc aagagcacc    420 tctggggca gcggccct gggctgcctg gtcaaggact acttccccga accggtgacg      480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
gagcccaaat cttgtgacaa aactcacaca tgcccaccgt gcccagcacc tgaactcctg    720
gggggaccgt cagtcttcct cttcccccca aaacccaagg acaccctcat gatctcccgg    780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgggt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaaagggca gccccgagaa ccacaggtgt acaccctgcc cccatcccgg   1080
gaggagatga ccaagaacca ggtcagcctg acctgcctgg tcaaaggctt ctatcccagc   1140
gacatcgccg tggagtggga gagcaatggg cagccggaga caactacaa gaccacgcct   1200 cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaa                             1356

<210> SEQ ID NO 193
<211> LENGTH: 13
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 193

Ser Gly Ser Ser Ser Asn Ile Gly Phe Asn Tyr Val Ser
1               5                   10

<210> SEQ ID NO 194
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Tyr Asn Asn Gln Arg Pro Ser
1               5

<210> SEQ ID NO 195
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Ser Thr Trp Thr Gly Thr Ser Glu Ser His Val
1               5                   10

<210> SEQ ID NO 196
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Ser Ser Ser Asn Ile Gly Phe Asn Tyr
1               5

<210> SEQ ID NO 197
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Tyr Asn Asn
1

<210> SEQ ID NO 198
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 198

Trp Thr Gly Thr Ser Glu Ser His
1               5

<210> SEQ ID NO 199
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Phe Asn
            20                  25                  30

Tyr Val Ser Trp Tyr Gln Gln Leu Pro Gly Thr Ala Pro Lys Leu Leu
        35                  40                  45

Ile Tyr Tyr Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Thr Trp Thr Gly Thr Ser
                85                  90                  95

Glu Ser His Val Phe Gly Gly Gly Thr Lys Leu Thr Val Leu
            100                 105                 110

<210> SEQ ID NO 200
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 200
gatatcgtgc tgacccagcc gccgagcgtg agcggtgcac cgggccagcg cgtgaccatt        60
agctgtagcg gcagcagcag caacattggt ttcaactacg tgtcttggta ccagcagctg       120
ccgggcacgg cgccgaaact gctgatctac tacaacaacc agcgcccgag cggcgtgccg       180
gatcgcttta gcggatccaa aagcggcacc agcgccagcc tggcgattac cggcctgcaa       240
gcagaagacg aagcggatta ttactgctct acttggactg gtacttctga atctcatgtg       300
tttggcggcg gcacgaagtt aaccgtccta                                         330

<210> SEQ ID NO 201
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 201

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Phe Asn

```
                  20                  25                  30
Tyr Val Ser Trp Tyr Gln Gln Leu Pro Gly Thr Ala Pro Lys Leu Leu
             35                  40                  45
Ile Tyr Tyr Asn Asn Gln Arg Pro Ser Gly Val Pro Asp Arg Phe Ser
         50                  55                  60
Gly Ser Lys Ser Gly Thr Ser Ala Ser Leu Ala Ile Thr Gly Leu Gln
 65                  70                  75                  80
Ala Glu Asp Glu Ala Asp Tyr Tyr Cys Ser Thr Trp Thr Gly Thr Ser
                 85                  90                  95
Glu Ser His Val Phe Gly Gly Gly Thr Lys Leu Thr Val Leu Gly Gln
            100                 105                 110
Pro Lys Ala Ala Pro Ser Val Thr Leu Phe Pro Pro Ser Ser Glu Glu
        115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Cys Ser
    210                 215
```

<210> SEQ ID NO 202
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 202

```
gatatcgtgc tgacccagcc gccgagcgtg agcggtgcac cgggccagcg cgtgaccatt      60
agctgtagcg gcagcagcag caacattggt ttcaactacg tgtcttggta ccagcagctg     120
ccgggcacgg cgccgaaact gctgatctac tacaacaacc agcgcccgag cggcgtgccg     180
gatcgcttta gcggatccaa aagcggcacc agcgccagcc tggcgattac cggcctgcaa     240
gcagaagacg aagcggatta ttactgctct acttggactg gtacttctga atctcatgtg     300
tttggcggcg gcacgaagtt aaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca acaagtacgc ggccagcagc     540
tatctgagcc tgacgcctga gcagtggaag tcccacagaa gctacagctg ccaggtcacg     600
catgaaggga gcaccgtgga agacagtg gcccctacag aatgttca                    648
```

<210> SEQ ID NO 203
<211> LENGTH: 5
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 203

Ser Tyr Thr Met Asn
1               5

<210> SEQ ID NO 204
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Arg Ile Lys Thr Lys Thr Asn Gly Gly Thr Thr Asp Tyr Ala Ala Pro
1               5                   10                  15

Val Lys Gly

<210> SEQ ID NO 205
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Glu Arg Ser Arg Ala Gly Ser Ile Phe Asp Pro
1               5                   10

<210> SEQ ID NO 206
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Gly Phe Thr Phe Ser Ser Tyr
1               5

<210> SEQ ID NO 207
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Lys Thr Lys Thr Asn Gly Gly Thr
1               5

<210> SEQ ID NO 208
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 208

Glu Arg Ser Arg Ala Gly Ser Ile Phe Asp Pro
1               5                   10

<210> SEQ ID NO 209
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 209

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Gly Arg Ile Lys Thr Lys Thr Asn Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Glu Arg Ser Arg Ala Gly Ser Ile Phe Asp Pro Trp
            100                 105                 110

Gly Gln Gly Thr Leu Val Thr Val Ser Ser
        115                 120

<210> SEQ ID NO 210
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 210
caggtgcaat tggtggaaag cggcggtggc ctggtgaaac aggcggcag cctgcgcctg      60 agctgcgccg cctccggatt cacctttct tcttacacta tgaactgggt gcgccaggcc    120
ccgggcaaag gtctcgagtg ggtgggccgt atcaaaacta aaactaacgg tggtactact    180
gactatgccg ccccagtgaa aggccgcttt accattagcc gcgatgattc gaaaaacacc    240
ctgtatctgc aaatgaacag cctgaaaacc gaagatacgg ccgtgtatta ttgcgcgcgt    300
gaacgttctc gtgctggttc tatcttcgat ccgtggggcc aaggcaccct ggtgactgtt    360
agctca                                                              366

<210> SEQ ID NO 211
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 211

-continued

```
Gln Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Gly Arg Ile Lys Thr Lys Thr Asn Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Glu Arg Ser Arg Ala Gly Ser Ile Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 212
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 212

```
caggtgcaat tggtggaaag cggcggtggc ctggtgaaac caggcggcag cctgcgcctg      60
agctgcgccg cctccggatt cacctttctt tcttacacta tgaactgggt gcgccaggcc     120
ccgggcaaag gtctcgagtg ggtgggccgt atcaaaacta aaactaacgg tggtactact     180
gactatgccg ccccagtgaa aggccgcttt accattagcc gcgatgattc gaaaacacc      240 ctgtatctgc aaatgaacag cctgaaaacc gaagatacgg ccgtgtatta ttgcgcgcgt     300
gaacgttctc gtgctggttc tatcttcgat ccgtggggcc aaggcaccct ggtgactgtt     360
agctcagcct ccaccaaggg tccatcggtc ttccccctgg caccctcctc caagagcacc     420
tctgggggca gcggccct gggctgcctg gtcaaggact acttcccga accggtgacg     480 gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactcacaca tgcccaccgt gcccagcacc tgaactcctg     720
gggggaccgt cagtcttcct cttccccccca aaacccaagg acaccctcat gatctcccgg     780
acccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgggt ggtcagcgtc ctcaccgtcc tgcaccagga ctggctgaat     960
ggcaaggagt acaagtgcaa ggtctccaac aaagccctcc cagcccccat cgagaaaacc    1020
atctccaaag ccaaagggca gccccgagaa ccacaggtgt acaccctgcc cccatcccgg    1080
gaggagatga ccaagaacca ggtcagcctg acctgcctgg tcaaaggctt ctatcccagc    1140
gacatcgccg tggagtggga gagcaatggg cagccggaga caactacaa gaccacgcct    1200 cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga gagcctctc cctgtctccg ggtaaa                              1356
```

<210> SEQ ID NO 213
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Ser Gly Ser Ser Ser Asn Ile Gly Phe Asn Tyr Val Ser
1               5                   10

<210> SEQ ID NO 214
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Tyr Asn Asn Gln Arg Pro Ser
1               5

<210> SEQ ID NO 215
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Ser Thr Trp Thr Gly Thr Ser Glu Ser His Val
1               5                   10

<210> SEQ ID NO 216
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Ser Ser Ser Asn Ile Gly Phe Asn Tyr
1               5

<210> SEQ ID NO 217
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Tyr Asn Asn
1

<210> SEQ ID NO 218
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Trp Thr Gly Thr Ser Glu Ser His
1               5

```
<210> SEQ ID NO 219
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 219

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Phe Asn
            20                  25                  30

Tyr Val Ser Trp Tyr Gln Gln Leu Pro Gly Thr Ala Pro Lys Leu Leu
        35                  40                  45

Ile Tyr Tyr Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Thr Trp Thr Gly Thr Ser
                85                  90                  95

Glu Ser His Val Phe Gly Gly Gly Thr Lys Leu Thr Val Leu
            100                 105                 110

<210> SEQ ID NO 220
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 220
gatatcgtgc tgacccagcc gccgagcgtg agcggtgcac cgggccagcg cgtgaccatt      60
agctgtagcg gcagcagcag caacattggt ttcaactacg tgtcttggta ccagcagctg     120
ccgggcacgg cgccgaaact gctgatctac tacaacaacc agcgcccgag cggcgtgccg     180
gatcgcttta gcggatccaa aagcggcacc agcgccagcc tggcgattac cggcctgcaa     240
gcagaagacg aagcggatta ttactgctct acttggactg gtacttctga atctcatgtg     300
tttggcggcg gcacgaagtt aaccgtccta                                      330

<210> SEQ ID NO 221
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 221

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Phe Asn
            20                  25                  30

Tyr Val Ser Trp Tyr Gln Gln Leu Pro Gly Thr Ala Pro Lys Leu Leu
        35                  40                  45

Ile Tyr Tyr Asn Asn Gln Arg Pro Ser Gly Val Pro Asp Arg Phe Ser
    50                  55                  60
```

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Thr Trp Thr Gly Thr Ser
                85                  90                  95

Glu Ser His Val Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 222
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 222
gatatcgtgc tgacccagcc gccgagcgtg agcggtgcac cgggccagcg cgtgaccatt      60
agctgtagcg gcagcagcag caacattggt ttcaactacg tgtcttggta ccagcagctg     120
ccgggcacgg cgccgaaact gctgatctac tacaacaacc agcgcccgag cggcgtgccg     180
gatcgcttta gcggatccaa aagcggcacc agcgccagcc tggcgattac cggcctgcaa     240
gcagaagacg aagcggatta ttactgctct acttggactg gtacttctga atctcatgtg     300
tttggcggcg gcacgaagtt aaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca acaagtacgc ggccagcagc     540
tatctgagcc tgacgcctga gcagtggaag tcccacagaa gctacagctg ccaggtcacg     600
catgaaggga gcaccgtgga agacagtg gcccctacag aatgttca                   648

<210> SEQ ID NO 223
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Lys Asn Ala Tyr Met Cys
1               5

<210> SEQ ID NO 224
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Cys Ile Glu Thr Gly Asp Gly Thr Thr Tyr Tyr Ala Ser Trp Ala Lys
1               5                   10                  15

Gly

<210> SEQ ID NO 225
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Glu Leu Tyr Asp Asp Tyr Gly Asp Tyr Phe Asn Leu
1               5                   10

<210> SEQ ID NO 226
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Gly Phe Ser Phe Thr Lys Asn Ala
1               5

<210> SEQ ID NO 227
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Glu Thr Gly Asp Gly Thr
1               5

<210> SEQ ID NO 228
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Glu Leu Tyr Asp Asp Tyr Gly Asp Tyr Phe Asn Leu
1               5                   10

```
<210> SEQ ID NO 229
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 229

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Thr Lys Asn Ala
            20                  25                  30

Tyr Met Cys Trp Asp Arg Gln Ala Pro Gly Lys Arg Pro Glu Trp Ile
        35                  40                  45

Ala Cys Ile Glu Thr Gly Asp Gly Thr Thr Tyr Tyr Ala Ser Trp Ala
    50                  55                  60

Lys Gly Arg Phe Thr Val Ser Lys Thr Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Glu Leu Tyr Asp Asp Tyr Gly Asp Tyr Phe Asn Leu Trp Gly Pro
            100                 105                 110

Gly Thr Leu Val Thr Val Ser Ser
        115                 120

<210> SEQ ID NO 230
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 230
cagtcgttgg aggagtctgg gggagacctg gtcaagcctg ggcatccct gacactcacc        60 tgcacagcct ctggattctc cttcactaag aacgcctaca tgtgctggga ccgccaggct       120
ccagggaaga ggcctgagtg gatcgcatgc attgagactg gtgacggcac cacatattat       180
gcgagctggg cgaaaggccg attcaccgtc tccaaaacct cgtcgaccac ggtgactctg       240
caaatgacca gtctgacagc cgcggacacg gccacctatt tctgtgcgag ggaattatac       300
gatgactatg gtgattactt caatttgtgg ggcccaggca ccctggtcac cgtctcctca       360

<210> SEQ ID NO 231
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 231

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Thr Lys Asn Ala
            20                  25                  30

Tyr Met Cys Trp Asp Arg Gln Ala Pro Gly Lys Arg Pro Glu Trp Ile
        35                  40                  45
```

Ala Cys Ile Glu Thr Gly Asp Gly Thr Thr Tyr Tyr Ala Ser Trp Ala
 50                  55                  60

Lys Gly Arg Phe Thr Val Ser Lys Thr Ser Ser Thr Thr Val Thr Leu
 65                  70                  75                  80

Gln Met Thr Ser Leu Thr Ala Ala Asp Thr Ala Thr Tyr Phe Cys Ala
                 85                  90                  95

Arg Glu Leu Tyr Asp Asp Tyr Gly Asp Tyr Phe Asn Leu Trp Gly Pro
                100                 105                 110

Gly Thr Leu Val Thr Val Ser Ser Gly Gln Pro Lys Ala Pro Ser Val
            115                 120                 125

Phe Pro Leu Ala Pro Cys Cys Gly Asp Thr Pro Ser Ser Thr Val Thr
        130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                165                 170                 175

Arg Gln Ser Ser Gly Leu Tyr Ser Leu Ser Ser Val Val Ser Val Thr
                180                 185                 190

Ser Ser Ser Gln Pro Val Thr Cys Asn Val Ala His Pro Ala Thr Asn
            195                 200                 205

Thr Lys Val Asp Lys Thr Val Ala Pro Ser Thr Cys Ser Lys Pro Thr
        210                 215                 220

Cys Pro Pro Pro Glu Leu Leu Gly Gly Pro Ser Val Phe Ile Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Asp Asp Pro Glu Val Gln Phe Thr
                260                 265                 270

Trp Tyr Ile Asn Asn Glu Gln Val Arg Thr Ala Arg Pro Pro Leu Arg
            275                 280                 285

Glu Gln Gln Phe Asn Ser Thr Ile Arg Val Val Ser Thr Leu Pro Ile
        290                 295                 300

Ala His Gln Asp Trp Leu Arg Gly Lys Glu Phe Lys Cys Lys Val His
305                 310                 315                 320

Asn Lys Ala Leu Pro Ala Pro Ile Glu Lys Thr Ile Ser Lys Ala Arg
                325                 330                 335

Gly Gln Pro Leu Glu Pro Lys Val Tyr Thr Met Gly Pro Pro Arg Glu
            340                 345                 350

Glu Leu Ser Ser Arg Ser Val Ser Leu Thr Cys Met Ile Asn Gly Phe
        355                 360                 365

Tyr Pro Ser Asp Ile Ser Val Glu Trp Glu Lys Asn Gly Lys Ala Glu
370                 375                 380

Asp Asn Tyr Lys Thr Thr Pro Ala Val Leu Asp Ser Asp Gly Ser Tyr
385                 390                 395                 400

Phe Leu Tyr Ser Lys Leu Ser Val Pro Thr Ser Glu Trp Gln Arg Gly
                405                 410                 415

Asp Val Phe Thr Cys Ser Val Met His Glu Ala Leu His Asn His Tyr
            420                 425                 430

Thr Gln Lys Ser Ile Ser Arg Ser Pro Gly Lys
        435                 440

<210> SEQ ID NO 232
<211> LENGTH: 1329

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 232

```
cagtcgttgg aggagtctgg gggagacctg gtcaagcctg ggcatccct gacactcacc    60
tgcacagcct ctggattctc cttcactaag aacgcctaca tgtgctggga ccgccaggct   120
ccagggaaga ggcctgagtg gatcgcatgc attgagactg gtgacggcac acatattat   180
gcgagctggg cgaaaggccg attcaccgtc tccaaaacct cgtcgaccac ggtgactctg   240
caaatgacca gtctgacagc cgcggacacg gccacctatt tctgtgcgag ggaattatac   300
gatgactatg gtgattactt caatttgtgg ggcccaggca ccctggtcac cgtctcctca   360
gggcaaccta aggctccatc agtcttccca ctggcccct gctgcgggga cacccagc    420
tccacggtga ccctgggctg cctggtcaaa gggtacctcc cggagccagt gaccgtgacc   480
tggaactcgg gcaccctcac caatggggta cgcaccttcc cgtccgtccg gcagtcctca   540
ggcctctact cgctgagcag cgtggtgagc gtgacctcaa gcagccagcc cgtcacctgc   600
aacgtggccc acccagccac caacaccaaa gtggacaaga ccgttgcgcc ctcgacatgc   660
agcaagccca gtgcccaccc cctgaactc ctggggggac cgtctgtctt catcttcccc   720
ccaaaaccca aggacaccct catgatctca cgcaccccg aggtcacatg cgtggtggtg   780
gacgtgagcc aggatgaccc cgaggtgcag ttcacatggt acataaacaa cgagcaggtg   840
cgcaccgccc ggccgccgct acgggagcag cagttcaaca gcacgatccg cgtggtcagc   900
accctcccca tcgcgcacca ggactggctg aggggcaagg agttcaagtg caaagtccac   960
aacaaggcac tcccggcccc catcgagaaa accatctcca agccagagg gcagcccctg  1020
gagccgaagg tctacaccat gggccctccc cgggaggagc tgagcagcag gtcggtcagc  1080
ctgacctgca tgatcaacgg cttctaccct tccgacatct cggtggagtg ggagaagaac  1140
gggaaggcag aggacaacta caagaccacg ccggccgtgc tggacagcga cggctcctac  1200
ttcctctaca gcaagctctc agtgcccacg agtgagtggc agcggggcga cgtcttcacc  1260
tgctccgtga tgcacgaggc cttgcacaac cactacacgc agaagtccat ctcccgctct  1320
ccgggtaaa                                                         1329
```

<210> SEQ ID NO 233
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 233

Gln Thr Ser Glu Asn Phe Tyr Ser Asn Asp Ile Leu Ser
1               5                   10

<210> SEQ ID NO 234
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 234

Glu Ala Ser Thr Leu Ala Ser
1               5

<210> SEQ ID NO 235
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Gln Gly Ser Val Leu Asp Ser Gly Trp Tyr Asp Ile Ser
1               5                   10

<210> SEQ ID NO 236
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Ser Glu Asn Phe Tyr Ser Asn Asp Ile
1               5

<210> SEQ ID NO 237
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Glu Ala Ser
1

<210> SEQ ID NO 238
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Ser Val Leu Asp Ser Gly Trp Tyr Asp Ile
1               5                   10

<210> SEQ ID NO 239
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 239

Ala Leu Val Met Thr Gln Thr Pro Ser Ser Val Ser Ala Ala Val Gly
```

```
            1               5                  10                 15
Gly Thr Val Thr Ile Asn Cys Gln Thr Ser Glu Asn Phe Tyr Ser Asn
                20                  25                  30

Asp Ile Leu Ser Trp Tyr Gln Gln Lys Pro Gly Gln Pro Pro Lys Leu
            35                  40                  45

Leu Ile Tyr Glu Ala Ser Thr Leu Ala Ser Gly Val Pro Ser Arg Phe
        50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Gln Gly Ser Val Leu Asp
                85                  90                  95

Ser Gly Trp Tyr Asp Ile Ser Phe Gly Gly Gly Thr Glu Val Val Val
            100                 105                 110

Lys
```

<210> SEQ ID NO 240
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 240

```
gcccttgtga tgacccagac tccatcgtcc gtgtctgcag ctgtgggagg cacagtcacc        60
atcaattgcc agaccagtga aatttttat agtaacgaca tcttatcctg gtatcagcag       120
aagccaggc agcctcccaa gctcctgatc tatgaagcat ccactctggc atctggggtc       180
ccctcgcgat tcaaaggcag tggatctggg acacagttca ctctcaccat cagcgacgtg       240
cagtgtgacg atgctgccac ttactattgt caaggcagtg ttcttgatag tggttggtac       300
gatatttctt tcggcggagg gaccgaggtg gtggtcaaa                              339
```

<210> SEQ ID NO 241
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 241

```
Ala Leu Val Met Thr Gln Thr Pro Ser Ser Val Ser Ala Ala Val Gly
1               5                   10                  15

Gly Thr Val Thr Ile Asn Cys Gln Thr Ser Glu Asn Phe Tyr Ser Asn
            20                  25                  30

Asp Ile Leu Ser Trp Tyr Gln Gln Lys Pro Gly Gln Pro Pro Lys Leu
            35                  40                  45

Leu Ile Tyr Glu Ala Ser Thr Leu Ala Ser Gly Val Pro Ser Arg Phe
        50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Gln Gly Ser Val Leu Asp
                85                  90                  95

Ser Gly Trp Tyr Asp Ile Ser Phe Gly Gly Gly Thr Glu Val Val Val
            100                 105                 110
```

```
Lys Gly Asp Pro Val Ala Pro Thr Val Leu Ile Phe Pro Pro Ala Ala
            115                 120                 125

Asp Gln Val Ala Thr Gly Thr Val Thr Ile Val Cys Val Ala Asn Lys
        130                 135                 140

Tyr Phe Pro Asp Val Thr Val Thr Trp Glu Val Asp Gly Thr Thr Gln
145                 150                 155                 160

Thr Thr Gly Ile Glu Asn Ser Lys Thr Pro Gln Asn Ser Ala Asp Cys
                165                 170                 175

Thr Tyr Asn Leu Ser Ser Thr Leu Thr Leu Thr Ser Thr Gln Tyr Asn
                180                 185                 190

Ser His Lys Glu Tyr Thr Cys Lys Val Thr Gln Gly Thr Thr Ser Val
                195                 200                 205

Val Gln Ser Phe Asn Arg Gly Asp Cys
        210                 215

<210> SEQ ID NO 242
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 242
gcccttgtga tgacccagac tccatcgtcc gtgtctgcag ctgtgggagg cacagtcacc      60
atcaattgcc agaccagtga gattttttat agtaacgaca tcttatcctg gtatcagcag     120
aagccagggc agcctcccaa gctcctgatc tatgaagcat ccactctggc atctggggtc     180
ccctcgcgat tcaaaggcag tggatctggg acacagttca ctctcaccat cagcgacgtg     240
cagtgtgacg atgctgccac ttactattgt caaggcagtg ttcttgatag tggttggtac     300
gatatttctt tcggcggagg gaccgaggtg gtggtcaaag gtgatccagt tgcacctact     360
gtcctcatct tcccaccagc tgctgatcag gtggcaactg gaacagtcac catcgtgtgt     420
gtggcgaata atactttttcc cgatgtcact gtcacctggg aggtggatgg caccacccaa     480
acaactggca tcgagaacag taaaacaccg cagaattctg cagattgtac ctacaacctc     540
agcagcactc tgacactgac cagcacacag tacaacagcc acaaagagta cacctgcaag     600
gtgacccagg gcacgacctc agtcgtccag agcttcaata ggggtgactg t               651

<210> SEQ ID NO 243
<211> LENGTH: 7
<212> TYPE: PRT
<213> ORGANISM: Homo sapiens

<400> SEQUENCE: 243

Val Met Val Ala Arg Arg Lys
1               5

<210> SEQ ID NO 244
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 244
cggagcccag ggaaggaggg aggaggggag ggtcgcggcc ggccgcc                    47
```

<210> SEQ ID NO 245
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 245
caggacgggg gtctctttag gcccccaaga tctaagaact gacgagcgtc tca        53

<210> SEQ ID NO 246
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 246
ccatggcggc aaatgcctag acctggtgg                                    29

<210> SEQ ID NO 247
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 247
caaaggggcc ctgtgaagcc aggttggcag acacagtcg                         39

<210> SEQ ID NO 248
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 248
cttcaacaac agccgctgcg accccgcctg cagctcg                           37

<210> SEQ ID NO 249
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 249
cagccgcact cctccgtgtt gcagccctgg tcg                               33

<210> SEQ ID NO 250
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 250
gtcacagata gcatcctcgt ggcaggggtt gctgacacag g           41

<210> SEQ ID NO 251
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 251
gggacatgcg tggatggcgt caacacctat aactgccagt gccc          44

<210> SEQ ID NO 252
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 252
ggccccagtc tggacgcagc gaccccgtt ttgacaaggc              40

<210> SEQ ID NO 253
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 253
gaactcgttc agctgcctgt gccgtcccgg ctacacagga gcccactgc        49

<210> SEQ ID NO 254
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 254
gcctgagtgg tcctgggcat tggtgtctgc cccagcatcc              40

<210> SEQ ID NO 255
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 255
gaagaggatg aggcagatga cacatcagct agcatcatct cc            42

<210> SEQ ID NO 256
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 256
tcactgtgcc cagccgttct                                                     20

<210> SEQ ID NO 257
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 257
cttcttccgc tgcgcttgcg cgcag                                               25

<210> SEQ ID NO 258
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 258
atgaccagca gcaagacagc gc                                                  22

<210> SEQ ID NO 259
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 259
cagagggtgc tgtgctcgcg cttg                                                24

<210> SEQ ID NO 260
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 260
acagtgctgc tgccgccaga ggagctac                                            28

<210> SEQ ID NO 261
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 261
```
cagtcccagg acatggcgag gagtac                                          26

<210> SEQ ID NO 262
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 262
agcccaggga aggagggagg aggggagggt cg                                   32

<210> SEQ ID NO 263
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 263
actggcagtt ataggtgttg acgccatcca cgc                                  33

<210> SEQ ID NO 264
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 264
gcacagtcgt caatgttcac ttcgcag                                         27

<210> SEQ ID NO 265
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 265
tacggaggct tccactgcga acag                                            24

<210> SEQ ID NO 266
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 266
cgaccccgag aaactgcggc aggag                                           25

<210> SEQ ID NO 267
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 267
ccccaagatc taagaactga cgagc 25

<210> SEQ ID NO 268
<211> LENGTH: 2321
<212> TYPE: PRT
<213> ORGANISM: Macaca fascicularis

<400> SEQUENCE: 268

```
Met Gly Pro Gly Ala Arg Gly Arg Arg Arg Arg Pro Met Ser
1               5                   10                  15

Pro Pro Pro Pro Val Arg Ala Leu Pro Leu Leu Leu Leu Ala
                20                  25                  30

Gly Pro Gly Ala Ala Val Pro Pro Cys Leu Asp Gly Ser Pro Cys Ala
                35                  40                  45

Asn Gly Gly Arg Cys Thr Gln Leu Pro Ser Arg Glu Ala Ala Cys Leu
    50                  55                  60

Cys Pro Pro Gly Trp Val Gly Glu Arg Cys Gln Leu Glu Asp Pro Cys
65                  70                  75                  80

His Ser Gly Pro Cys Ala Gly Arg Gly Val Cys Gln Ser Ser Val Val
                85                  90                  95

Ala Gly Thr Ala Arg Phe Ser Cys Arg Cys Pro Arg Gly Phe Arg Gly
                100                 105                 110

Pro Asp Cys Ser Leu Pro Asp Pro Cys Leu Ser Ser Pro Cys Ala His
            115                 120                 125

Ser Ala Arg Cys Ser Val Gly Pro Asp Gly Arg Phe Leu Cys Ser Cys
    130                 135                 140

Pro Pro Gly Tyr Gln Gly Arg Ser Cys Arg Ser Asp Val Asp Glu Cys
145                 150                 155                 160

Arg Val Gly Glu Pro Cys Arg His Gly Gly Thr Cys Leu Asn Thr Pro
                165                 170                 175

Gly Ser Phe Arg Cys Gln Cys Pro Ala Gly Tyr Thr Gly Pro Leu Cys
            180                 185                 190

Glu Asn Pro Ala Val Pro Cys Ala Pro Ser Pro Cys Arg Asn Gly Gly
        195                 200                 205

Thr Cys Arg Gln Ser Ser Gly Asp Leu Thr Tyr Asp Cys Ala Cys Leu
    210                 215                 220

Pro Gly Phe Glu Gly Gln Asn Cys Glu Val Asn Val Asp Asp Cys Pro
225                 230                 235                 240

Gly His Arg Cys Leu Asn Gly Gly Thr Cys Val Asp Gly Val Asn Thr
                245                 250                 255

Tyr Asn Cys Gln Cys Pro Pro Glu Trp Thr Gly Gln Phe Cys Thr Glu
            260                 265                 270

Asp Val Asp Glu Cys Gln Leu Gln Pro Asn Ala Cys His Asn Gly Gly
        275                 280                 285

Thr Cys Phe Asn Thr Leu Gly Gly His Ser Cys Val Cys Val Asn Gly
    290                 295                 300

Trp Thr Gly Glu Ser Cys Ser Gln Asn Ile Asp Asp Cys Ala Thr Ala
305                 310                 315                 320

Val Cys Phe His Gly Ala Thr Cys His Asp Arg Val Ala Ser Phe Tyr
                325                 330                 335

Cys Ala Cys Pro Met Gly Lys Thr Gly Leu Leu Cys His Leu Asp Asp
```

-continued

```
              340                 345                 350
Ala Cys Val Ser Asn Pro Cys His Glu Asp Ala Ile Cys Asp Thr Asn
                355                 360                 365
Pro Val Asn Gly Arg Ala Ile Cys Thr Cys Pro Pro Gly Phe Thr Gly
    370                 375                 380
Gly Ala Cys Asp Gln Asp Val Asp Glu Cys Ser Ile Gly Ala Asn Pro
385                 390                 395                 400
Cys Glu His Leu Gly Arg Cys Val Asn Thr Gln Gly Ser Phe Leu Cys
                405                 410                 415
Gln Cys Gly Arg Gly Tyr Thr Gly Pro Arg Cys Glu Thr Asp Val Asn
            420                 425                 430
Glu Cys Leu Ser Gly Pro Cys Arg Asn Gln Ala Thr Cys Leu Asp Arg
        435                 440                 445
Ile Gly Gln Phe Thr Cys Ile Cys Met Ala Gly Phe Thr Gly Thr Tyr
    450                 455                 460
Cys Glu Val Asp Ile Asp Glu Cys Gln Ser Pro Cys Val Asn Gly
465                 470                 475                 480
Gly Ile Cys Lys Asp Arg Val Asn Gly Phe Ser Cys Thr Cys Pro Ser
                485                 490                 495
Gly Phe Ser Gly Ser Thr Cys Gln Leu Asp Val Asp Glu Cys Ala Ser
            500                 505                 510
Thr Pro Cys Arg Asn Gly Ala Lys Cys Val Asp Gln Pro Asp Gly Tyr
        515                 520                 525
Glu Cys Arg Cys Ala Glu Gly Phe Glu Gly Met Leu Cys Glu Arg Asn
    530                 535                 540
Val Asp Asp Cys Ser Pro Asp Pro Cys His His Gly Arg Cys Val Asp
545                 550                 555                 560
Gly Ile Ala Ser Phe Ser Cys Ala Cys Ala Pro Gly Tyr Thr Gly Thr
                565                 570                 575
Arg Cys Glu Ser Gln Val Asp Glu Cys Arg Ser Gln Pro Cys Arg His
            580                 585                 590
Gly Gly Lys Cys Leu Asp Leu Val Asp Lys Tyr Leu Cys Arg Cys Pro
        595                 600                 605
Ser Gly Thr Thr Gly Val Asn Cys Glu Val Asn Ile Asp Asp Cys Ala
    610                 615                 620
Ser Asn Pro Cys Ser Phe Gly Val Cys Arg Asp Gly Ile Asn Arg Tyr
625                 630                 635                 640
Asp Cys Val Cys Gln Pro Gly Phe Thr Gly Pro Leu Cys Asn Val Glu
                645                 650                 655
Ile Asn Glu Cys Ala Ser Ser Pro Cys Gly Glu Gly Ser Cys Val
            660                 665                 670
Asp Gly Glu Asn Gly Phe Arg Cys Leu Cys Pro Pro Gly Ser Leu Pro
        675                 680                 685
Pro Leu Cys Leu Pro Pro Ser His Pro Cys Ala His Glu Pro Cys Ser
    690                 695                 700
His Gly Ile Cys Tyr Asp Ala Pro Gly Gly Phe Arg Cys Val Cys Glu
705                 710                 715                 720
Pro Gly Trp Ser Gly Pro Arg Cys Ser Gln Ser Leu Ala Arg Asp Ala
                725                 730                 735
Cys Glu Ser Gln Pro Cys Arg Ala Gly Gly Thr Cys Ser Ser Asp Gly
            740                 745                 750
Met Gly Phe His Cys Thr Cys Pro Pro Gly Val Gln Gly Arg Gln Cys
        755                 760                 765
```

-continued

```
Glu Leu Leu Ser Pro Cys Thr Pro Asn Pro Cys Glu His Gly Gly Arg
770                 775                 780
Cys Glu Ser Ala Pro Gly Gln Leu Pro Val Cys Ser Cys Pro Gln Gly
785                 790                 795                 800
Trp Gln Gly Pro Arg Cys Gln Gln Asp Val Asp Glu Cys Ala Gly Pro
                805                 810                 815
Ala Pro Cys Gly Pro His Gly Ile Cys Thr Asn Leu Ala Gly Ser Phe
                820                 825                 830
Ser Cys Thr Cys His Gly Gly Tyr Thr Gly Pro Ser Cys Asp Gln Asp
                835                 840                 845
Ile Asn Asp Cys Asp Pro Asn Pro Cys Leu Asn Gly Gly Ser Cys Gln
850                 855                 860
Asp Gly Val Gly Ser Phe Ser Cys Ser Cys Leu Leu Gly Phe Ala Gly
865                 870                 875                 880
Pro Arg Cys Ala Arg Asp Val Asp Glu Cys Leu Ser Asn Pro Cys Gly
                885                 890                 895
Pro Gly Thr Cys Thr Asp His Val Ala Ser Phe Thr Cys Thr Cys Pro
                900                 905                 910
Pro Gly Tyr Gly Gly Phe His Cys Glu Gln Asp Leu Pro Asp Cys Ser
                915                 920                 925
Pro Ser Ser Cys Phe Asn Gly Gly Thr Cys Val Asp Gly Val Asn Ser
                930                 935                 940
Phe Ser Cys Leu Cys Arg Pro Gly Tyr Thr Gly Ala His Cys Gln His
945                 950                 955                 960
Glu Ala Asp Pro Cys Leu Ser Arg Pro Cys Leu His Gly Gly Val Cys
                965                 970                 975
Ser Ala Ala His Pro Gly Phe Arg Cys Thr Cys Pro Gln Ser Phe Thr
                980                 985                 990
Gly Pro Gln Cys Gln Thr Leu Val Asp Trp Cys Ser Arg Gln Pro Cys
                995                 1000                1005
Gln Asn Gly Gly Arg Cys Val Gln Thr Gly Ala Tyr Cys Leu Cys
        1010                1015                1020
Pro Pro Gly Trp Ser Gly Arg Leu Cys Asp Ile Arg Ser Leu Pro
        1025                1030                1035
Cys Arg Glu Ala Ala Ala Gln Ile Gly Val Arg Leu Glu Gln Leu
        1040                1045                1050
Cys Gln Ala Gly Gly Gln Cys Val Asp Glu Asp Ser Ser His Tyr
        1055                1060                1065
Cys Val Cys Pro Glu Gly Arg Thr Gly Ser His Cys Glu Gln Glu
        1070                1075                1080
Val Asp Pro Cys Leu Ala Gln Pro Cys Gln His Gly Gly Thr Cys
        1085                1090                1095
Arg Gly Tyr Met Gly Gly Tyr Met Cys Glu Cys Leu Pro Gly Tyr
        1100                1105                1110
Asn Gly Glu Asn Cys Glu Asp Asp Val Asp Glu Cys Ala Ser Gln
        1115                1120                1125
Pro Cys Gln His Gly Gly Ser Cys Ile Asp Leu Val Ala Arg Tyr
        1130                1135                1140
Leu Cys Ser Cys Pro Pro Gly Thr Leu Gly Val Leu Cys Glu Ile
        1145                1150                1155
Asn Glu Asp Asp Cys Gly Pro Gly Pro Pro Leu Asp Ser Gly Pro
        1160                1165                1170
```

-continued

Arg Cys Leu His Asn Gly Thr Cys Val Asp Leu Val Gly Gly Phe
1175                1180                1185

Arg Cys Thr Cys Pro Pro Gly Tyr Thr Gly Leu Arg Cys Glu Ala
1190                1195                1200

Asp Ile Asn Glu Cys Arg Ser Gly Ala Cys His Ala Ala His Thr
1205                1210                1215

Arg Asp Cys Leu Gln Asp Pro Gly Gly Phe Arg Cys Leu Cys
1220                1225                1230

His Ala Gly Phe Ser Gly Pro Arg Cys Gln Thr Val Leu Ser Pro
1235                1240                1245

Cys Glu Ser Gln Pro Cys Gln His Gly Gly Gln Cys Arg Pro Ser
1250                1255                1260

Pro Gly Pro Gly Gly Gly Leu Thr Phe Thr Cys His Cys Ala Gln
1265                1270                1275

Pro Phe Trp Gly Pro Arg Cys Glu Arg Val Ala Arg Ser Cys Arg
1280                1285                1290

Glu Leu Gln Cys Pro Val Gly Val Pro Cys Gln Gln Thr Pro Arg
1295                1300                1305

Gly Pro Arg Cys Ala Cys Pro Pro Gly Leu Ser Gly Pro Ser Cys
1310                1315                1320

Arg Ser Phe Ser Gly Ser Pro Pro Gly Ala Ser Asn Ala Ser Cys
1325                1330                1335

Ala Ala Ala Pro Cys Leu His Gly Gly Ser Cys Arg Pro Ala Pro
1340                1345                1350

Leu Ala Pro Phe Phe Arg Cys Ala Cys Ala Gln Gly Trp Thr Gly
1355                1360                1365

Pro Arg Cys Glu Ala Pro Ala Ala Ala Pro Glu Val Ser Glu Glu
1370                1375                1380

Pro Arg Cys Pro Arg Ala Ala Cys Gln Ala Lys Arg Gly Asp Gln
1385                1390                1395

Arg Cys Asp Arg Glu Cys Asn Ser Pro Gly Cys Gly Trp Asp Gly
1400                1405                1410

Gly Asp Cys Ser Leu Ser Val Gly Asp Pro Trp Arg Gln Cys Glu
1415                1420                1425

Ala Leu Gln Cys Trp Arg Leu Phe Asn Asn Ser Arg Cys Asp Pro
1430                1435                1440

Ala Cys Ser Ser Pro Ala Cys Leu Tyr Asp Asn Phe Asp Cys His
1445                1450                1455

Ala Gly Gly Arg Glu Arg Thr Cys Asn Pro Val Tyr Glu Lys Tyr
1460                1465                1470

Cys Ala Asp His Phe Ala Asp Gly Arg Cys Asp Gln Gly Cys Asn
1475                1480                1485

Thr Glu Glu Cys Gly Trp Asp Gly Leu Asp Cys Ala Ser Glu Val
1490                1495                1500

Pro Ala Leu Leu Ala Arg Gly Val Leu Val Leu Thr Val Leu Leu
1505                1510                1515

Pro Pro Glu Glu Leu Leu Arg Ser Ser Ala Asp Phe Leu Gln Arg
1520                1525                1530

Leu Ser Ala Ile Leu Arg Thr Ser Leu Arg Phe Arg Leu Asp Ala
1535                1540                1545

His Gly Gln Ala Met Val Phe Pro Tyr His Arg Pro Ser Pro Gly
1550                1555                1560

Ser Glu Pro Arg Ala Arg Arg Glu Leu Ala Pro Glu Val Ile Gly

-continued

```
            1565                1570                1575

Ser Val Val Met Leu Glu Ile Asp Asn Arg Leu Cys Leu Gln Ser
            1580                1585                1590

Pro Glu Asn Asp His Cys Phe Pro Asp Ala Gln Ser Ala Ala Asp
            1595                1600                1605

Tyr Leu Gly Ala Leu Ser Ala Val Glu Arg Leu Asp Phe Pro Tyr
            1610                1615                1620

Pro Leu Arg Asp Val Arg Gly Glu Pro Leu Glu Pro Pro Glu Pro
            1625                1630                1635

Ser Val Pro Leu Leu Pro Leu Leu Val Ala Gly Ala Val Leu Leu
            1640                1645                1650

Leu Val Ile Leu Val Leu Gly Val Met Val Ala Arg Arg Lys Arg
            1655                1660                1665

Glu His Ser Thr Leu Trp Phe Pro Glu Gly Phe Ser Leu His Lys
            1670                1675                1680

Asp Val Ala Ala Gly His Lys Gly Arg Arg Glu Pro Val Gly Gln
            1685                1690                1695

Asp Ala Leu Gly Met Lys Asn Met Ala Lys Gly Glu Ser Leu Met
            1700                1705                1710

Gly Glu Val Ala Thr Asp Trp Met Asp Thr Glu Cys Pro Glu Ala
            1715                1720                1725

Lys Arg Leu Lys Val Glu Glu Leu Gly Met Gly Ala Glu Glu Ala
            1730                1735                1740

Val Asp Cys Arg Gln Trp Thr Gln His His Leu Val Ala Ala Asp
            1745                1750                1755

Ile Arg Val Ala Pro Ala Met Ala Leu Thr Pro Pro Gln Gly Asp
            1760                1765                1770

Ala Asp Ala Asp Gly Met Asp Val Asn Val Arg Gly Pro Asp Gly
            1775                1780                1785

Phe Thr Pro Leu Met Leu Ala Ser Phe Cys Gly Gly Ala Leu Glu
            1790                1795                1800

Pro Met Pro Thr Glu Glu Asp Glu Ala Asp Asp Thr Ser Ala Ser
            1805                1810                1815

Ile Ile Ser Asp Leu Ile Cys Gln Gly Ala Gln Leu Gly Ala Arg
            1820                1825                1830

Thr Asp Arg Thr Gly Glu Thr Ala Leu His Leu Ala Ala Arg Tyr
            1835                1840                1845

Ala Arg Ala Asp Ala Ala Lys Arg Leu Leu Asp Ala Gly Ala Asp
            1850                1855                1860

Thr Asn Ala Gln Asp His Ser Gly Arg Thr Pro Leu His Thr Ala
            1865                1870                1875

Val Thr Ala Asp Ala Gln Gly Val Phe Gln Ile Leu Ile Arg Asn
            1880                1885                1890

Arg Ser Thr Asp Leu Asp Ala Arg Met Ala Asp Gly Ser Thr Ala
            1895                1900                1905

Leu Ile Leu Ala Ala Arg Leu Ala Val Glu Gly Met Val Glu Glu
            1910                1915                1920

Leu Ile Ala Ser His Ala Asp Val Asn Ala Val Asp Glu Leu Gly
            1925                1930                1935

Lys Ser Ala Leu His Trp Ala Ala Ala Val Asn Asn Val Glu Ala
            1940                1945                1950

Thr Leu Ala Leu Leu Lys Asn Gly Ala Asn Lys Asp Met Gln Asp
            1955                1960                1965
```

| | | | | | | | | | | |
|---|---|---|---|---|---|---|---|---|---|---|
| Ser | Lys | Glu | Glu | Thr | Pro | Leu | Phe | Leu | Ala | Ala | Arg | Glu | Gly | Ser |
| | 1970 | | | | 1975 | | | | 1980 | |

Tyr Glu Ala Ala Lys Leu Leu Leu Asp His Phe Ala Asn Arg Glu
    1985            1990            1995

Ile Thr Asp His Leu Asp Arg Leu Pro Arg Asp Val Ala Gln Glu
    2000            2005            2010

Arg Leu His Gln Asp Ile Val Arg Leu Leu Asp Gln Pro Ser Gly
    2015            2020            2025

Pro Arg Ser Pro Pro Gly Thr His Gly Leu Gly Pro Leu Leu Cys
    2030            2035            2040

Pro Pro Gly Ala Phe Leu Pro Gly Leu Lys Val Val Thr Gln Ser
    2045            2050            2055

Gly Ser Lys Lys Ser Arg Arg Pro Pro Gly Lys Ala Gly Leu Gly
    2060            2065            2070

Pro Gln Gly Pro Arg Gly Arg Gly Lys Lys Leu Thr Leu Ala Cys
    2075            2080            2085

Pro Gly Pro Leu Ala Asp Ser Ser Val Thr Leu Ser Pro Val Asp
    2090            2095            2100

Ser Leu Asp Ser Pro Arg Pro Phe Gly Gly Pro Pro Ala Ser Pro
    2105            2110            2115

Gly Gly Phe Pro Leu Glu Gly Pro Tyr Ala Ala Ala Thr Ala Thr
    2120            2125            2130

Ala Val Ser Leu Ala Gln Leu Gly Gly Pro Gly Arg Ala Gly Leu
    2135            2140            2145

Gly Arg Gln Pro Pro Gly Gly Cys Val Leu Ser Leu Gly Leu Leu
    2150            2155            2160

Asn Pro Val Ala Val Pro Leu Asp Trp Ala Arg Leu Pro Pro Pro
    2165            2170            2175

Ala Pro Pro Gly Pro Ser Phe Leu Leu Pro Leu Ala Pro Gly Pro
    2180            2185            2190

Gln Leu Leu Asn Pro Gly Thr Pro Val Ser Pro Gln Glu Arg Pro
    2195            2200            2205

Pro Pro Tyr Leu Ala Val Pro Gly His Gly Glu Glu Tyr Pro Ala
    2210            2215            2220

Ala Gly Ala His Ser Ser Pro Pro Lys Ala Arg Phe Leu Arg Val
    2225            2230            2235

Pro Ser Glu His Pro Tyr Leu Thr Pro Ser Pro Glu Ser Pro Glu
    2240            2245            2250

His Trp Ala Ser Pro Ser Pro Pro Ser Leu Ser Asp Trp Ser Glu
    2255            2260            2265

Ser Thr Pro Ser Pro Ala Thr Ala Thr Gly Ala Met Ala Thr Ala
    2270            2275            2280

Thr Gly Ala Leu Pro Ala Gln Pro Leu Pro Leu Ser Val Pro Ser
    2285            2290            2295

Ser Leu Ala Gln Ala Gln Thr Gln Leu Gly Pro Gln Pro Glu Val
    2300            2305            2310

Thr Pro Lys Arg Gln Val Leu Ala
    2315            2320

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272
<211> LENGTH: 1888
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 272

```
Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
            20                  25                  30

Leu Ala Gly Pro Gly Ala Ala Pro Pro Cys Leu Asp Gly Ser Pro
        35                  40                  45

Cys Ala Asn Gly Gly Arg Cys Thr Gln Leu Pro Ser Arg Glu Ala Ala
50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
        115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
        195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
```

```
                275                 280                 285
Gly Thr Cys Phe Asn Thr Leu Gly Gly His Ser Cys Val Cys Asn
290                 295                 300
Gly Trp Thr Gly Glu Ser Cys Ser Gln Asn Ile Asp Asp Cys Ala Thr
305                 310                 315                 320
Ala Val Cys Phe His Gly Ala Thr Cys His Asp Arg Val Ala Ser Phe
                325                 330                 335
Tyr Cys Ala Cys Pro Met Gly Lys Thr Gly Leu Leu Cys His Leu Asp
                340                 345                 350
Asp Ala Cys Val Ser Asn Pro Cys His Glu Asp Ala Ile Cys Asp Thr
                355                 360                 365
Asn Pro Val Asn Gly Arg Ala Ile Cys Thr Cys Pro Pro Gly Phe Thr
370                 375                 380
Gly Gly Ala Cys Asp Gln Asp Val Asp Glu Cys Ser Ile Gly Ala Asn
385                 390                 395                 400
Pro Cys Glu His Leu Gly Arg Cys Val Asn Thr Gln Gly Ser Phe Leu
                405                 410                 415
Cys Gln Cys Gly Arg Gly Tyr Thr Gly Pro Arg Cys Glu Thr Asp Val
                420                 425                 430
Asn Glu Cys Leu Ser Gly Pro Cys Arg Asn Gln Ala Thr Cys Leu Asp
                435                 440                 445
Arg Ile Gly Gln Phe Thr Cys Ile Cys Met Ala Gly Phe Thr Gly Thr
450                 455                 460
Tyr Cys Glu Val Asp Ile Asp Glu Cys Gln Ser Ser Pro Cys Val Asn
465                 470                 475                 480
Gly Gly Val Cys Lys Asp Arg Val Asn Gly Phe Ser Cys Thr Cys Pro
                485                 490                 495
Ser Gly Phe Ser Gly Ser Thr Cys Gln Leu Asp Val Asp Glu Cys Ala
                500                 505                 510
Ser Thr Pro Cys Arg Asn Gly Ala Lys Cys Val Asp Gln Pro Asp Gly
                515                 520                 525
Tyr Glu Cys Arg Cys Ala Glu Gly Phe Glu Gly Thr Leu Cys Asp Arg
                530                 535                 540
Asn Val Asp Asp Cys Ser Pro Asp Pro Cys His His Gly Arg Cys Val
545                 550                 555                 560
Asp Gly Ile Ala Ser Phe Ser Cys Ala Cys Ala Pro Gly Tyr Thr Gly
                565                 570                 575
Thr Arg Cys Glu Ser Gln Val Asp Glu Cys Arg Ser Gln Pro Cys Arg
                580                 585                 590
His Gly Gly Lys Cys Leu Asp Leu Val Asp Lys Tyr Leu Cys Arg Cys
                595                 600                 605
Pro Ser Gly Thr Thr Gly Val Asn Cys Glu Val Asn Ile Asp Asp Cys
610                 615                 620
Ala Ser Asn Pro Cys Thr Phe Gly Val Cys Arg Asp Gly Ile Asn Arg
625                 630                 635                 640
Tyr Asp Cys Val Cys Gln Pro Gly Phe Thr Gly Pro Leu Cys Asn Val
                645                 650                 655
Glu Ile Asn Glu Cys Ala Ser Ser Pro Cys Gly Glu Gly Gly Ser Cys
                660                 665                 670
Val Asp Gly Glu Asn Gly Phe Arg Cys Leu Cys Pro Pro Gly Ser Leu
                675                 680                 685
Pro Pro Leu Cys Leu Pro Pro Ser His Pro Cys Ala His Glu Pro Cys
690                 695                 700
```

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
        755                 760                 765

Cys Glu Leu Leu Ser Pro Cys Thr Pro Asn Pro Cys Glu His Gly Gly
    770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
        835                 840                 845

Asp Ile Asn Asp Cys Asp Pro Asn Pro Cys Leu Asn Gly Gly Ser Cys
    850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
        915                 920                 925

Ser Pro Ser Ser Cys Phe Asn Gly Gly Thr Cys Val Asp Gly Val Asn
    930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                965                 970                 975

Cys Ser Ala Ala His Pro Gly Phe Arg Cys Thr Cys Leu Glu Ser Phe
            980                 985                 990

Thr Gly Pro Gln Cys Gln Thr Leu Val Asp Trp Cys Ser Arg Gln Pro
        995                 1000                1005

Cys Gln Asn Gly Gly Arg Cys Val Gln Thr Gly Ala Tyr Cys Leu
    1010                1015                1020

Cys Pro Pro Gly Trp Ser Gly Arg Leu Cys Asp Ile Arg Ser Leu
    1025                1030                1035

Pro Cys Arg Glu Ala Ala Ala Gln Ile Gly Val Arg Leu Glu Gln
    1040                1045                1050

Leu Cys Gln Ala Gly Gly Gln Cys Val Asp Glu Asp Ser Ser His
    1055                1060                1065

Tyr Cys Val Cys Pro Glu Gly Arg Thr Gly Ser His Cys Glu Gln
    1070                1075                1080

Glu Val Asp Pro Cys Leu Ala Gln Pro Cys Gln His Gly Gly Thr
    1085                1090                1095

Cys Arg Gly Tyr Met Gly Gly Tyr Met Cys Glu Cys Leu Pro Gly
    1100                1105                1110

Tyr Asn Gly Asp Asn Cys Glu Asp Val Asp Glu Cys Ala Ser
1115                1120                1125

Gln Pro Cys Gln His Gly Gly Ser Cys Ile Asp Leu Val Ala Arg
1130                1135                1140

Tyr Leu Cys Ser Cys Pro Pro Gly Thr Leu Gly Val Leu Cys Glu
1145                1150                1155

Ile Asn Glu Asp Asp Cys Gly Pro Gly Pro Pro Leu Asp Ser Gly
1160                1165                1170

Pro Arg Cys Leu His Asn Gly Thr Cys Val Asp Leu Val Gly Gly
1175                1180                1185

Phe Arg Cys Thr Cys Pro Pro Gly Tyr Thr Gly Leu Arg Cys Glu
1190                1195                1200

Ala Asp Ile Asn Glu Cys Arg Ser Gly Ala Cys His Ala Ala His
1205                1210                1215

Thr Arg Asp Cys Leu Gln Asp Pro Gly Gly Gly Phe Arg Cys Leu
1220                1225                1230

Cys His Ala Gly Phe Ser Gly Pro Arg Cys Gln Thr Val Leu Ser
1235                1240                1245

Pro Cys Glu Ser Gln Pro Cys Gln His Gly Gly Gln Cys Arg Pro
1250                1255                1260

Ser Pro Gly Pro Gly Gly Gly Leu Thr Phe Thr Cys His Cys Ala
1265                1270                1275

Gln Pro Phe Trp Gly Pro Arg Cys Glu Arg Val Ala Arg Ser Cys
1280                1285                1290

Arg Glu Leu Gln Cys Pro Val Gly Val Pro Cys Gln Gln Thr Pro
1295                1300                1305

Arg Gly Pro Arg Cys Ala Cys Pro Pro Gly Leu Ser Gly Pro Ser
1310                1315                1320

Cys Arg Ser Phe Pro Gly Ser Pro Pro Gly Ala Ser Asn Ala Ser
1325                1330                1335

Cys Ala Ala Ala Pro Cys Leu His Gly Gly Ser Cys Arg Pro Ala
1340                1345                1350

Pro Leu Ala Pro Phe Phe Arg Cys Ala Cys Ala Gln Gly Trp Thr
1355                1360                1365

Gly Pro Arg Cys Glu Ala Pro Ala Ala Ala Pro Glu Val Ser Glu
1370                1375                1380

Glu Pro Arg Cys Pro Arg Ala Ala Cys Gln Ala Lys Arg Gly Asp
1385                1390                1395

Gln Arg Cys Asp Arg Glu Cys Asn Ser Pro Gly Cys Gly Trp Asp
1400                1405                1410

Gly Gly Asp Cys Ser Leu Ser Val Gly Asp Pro Trp Arg Gln Cys
1415                1420                1425

Glu Ala Leu Gln Cys Trp Arg Leu Phe Asn Asn Ser Arg Cys Asp
1430                1435                1440

Pro Ala Cys Ser Ser Pro Ala Cys Leu Tyr Asp Asn Phe Asp Cys
1445                1450                1455

His Ala Gly Gly Arg Glu Arg Thr Cys Asn Pro Val Tyr Glu Lys
1460                1465                1470

Tyr Cys Ala Asp His Phe Ala Asp Gly Arg Cys Asp Gln Gly Cys
1475                1480                1485

Asn Thr Glu Glu Cys Gly Trp Asp Gly Leu Asp Cys Ala Ser Glu
1490                1495                1500

Val Pro Ala Leu Leu Ala Arg Gly Val Leu Val Leu Thr Val Leu

```
            1505                1510                1515

Leu Pro Pro Glu Glu Leu Leu Arg Ser Ser Ala Asp Phe Leu Gln
        1520                1525                1530

Arg Leu Ser Ala Ile Leu Arg Thr Ser Leu Arg Phe Arg Leu Asp
        1535                1540                1545

Ala His Gly Gln Ala Met Val Phe Pro Tyr His Arg Pro Ser Pro
        1550                1555                1560

Gly Ser Glu Pro Arg Ala Arg Arg Glu Leu Ala Pro Glu Val Ile
        1565                1570                1575

Gly Ser Val Val Met Leu Glu Ile Asp Asn Arg Leu Cys Leu Gln
        1580                1585                1590

Ser Pro Glu Asn Asp His Cys Phe Pro Asp Ala Gln Ser Ala Ala
        1595                1600                1605

Asp Tyr Leu Gly Ala Leu Ser Ala Val Glu Arg Leu Asp Phe Pro
        1610                1615                1620

Tyr Pro Leu Arg Asp Val Arg Gly Glu Pro Leu Glu Pro Pro Glu
        1625                1630                1635

Pro Ser Val Pro Leu Leu Pro Leu Leu Val Ala Gly Ala Val Leu
        1640                1645                1650

Leu Leu Val Ile Leu Val Leu Gly Val Met Val Ala Arg Arg Lys
        1655                1660                1665

Arg Val Asp Lys Leu Leu Ser Ser Ile Glu Gln Ala Cys Asp Ile
        1670                1675                1680

Cys Arg Leu Lys Lys Leu Lys Cys Ser Lys Glu Lys Pro Lys Cys
        1685                1690                1695

Ala Lys Cys Leu Lys Asn Asn Trp Glu Cys Arg Tyr Ser Pro Lys
        1700                1705                1710

Thr Lys Arg Ser Pro Leu Thr Arg Ala His Leu Thr Glu Val Glu
        1715                1720                1725

Ser Arg Leu Glu Arg Leu Glu Gln Leu Phe Leu Leu Ile Phe Pro
        1730                1735                1740

Arg Glu Asp Leu Asp Met Ile Leu Lys Met Asp Ser Leu Gln Asp
        1745                1750                1755

Ile Lys Ala Leu Leu Thr Gly Leu Phe Val Gln Asp Asn Val Asn
        1760                1765                1770

Lys Asp Ala Val Thr Asp Arg Leu Ala Ser Val Glu Thr Asp Met
        1775                1780                1785

Pro Leu Thr Leu Arg Gln His Arg Ile Ser Ala Thr Ser Ser Ser
        1790                1795                1800

Glu Glu Ser Ser Asn Lys Gly Gln Arg Gln Leu Thr Val Ser Lys
        1805                1810                1815

Leu Lys Leu Leu Ser Ser Ile Glu Gln Ala Cys Pro Lys Lys Lys
        1820                1825                1830

Arg Lys Val Asp Glu Phe Pro Gly Ile Ser Thr Ala Pro Pro Thr
        1835                1840                1845

Asp Val Ser Leu Gly Asp Glu Leu His Leu Asp Gly Glu Asp Val
        1850                1855                1860

Ala Met Ala His Ala Asp Ala Leu Asp Asp Phe Asp Leu Asp Met
        1865                1870                1875

Leu Gly Asp Gly Asp Ser Pro Gly Pro Gly
        1880                1885

<210> SEQ ID NO 273
```

```
<211> LENGTH: 1886
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 273
```

| | | | | | | | | | | | | | | | |
|---|---|---|---|---|---|---|---|---|---|---|---|---|---|---|---|
| Met | Gly | Pro | Gly | Ala | Arg | Gly | Arg | Arg | Arg | Arg | Arg | Pro | Met | Ser | |
| 1 | | | | 5 | | | | | 10 | | | | | 15 | |
| Pro | Pro | Pro | Pro | Pro | Val | Arg | Ala | Leu | Pro | Leu | Leu | Leu | Leu | Leu | Ala |
| | | | 20 | | | | | 25 | | | | | 30 | | |
| Gly | Pro | Gly | Ala | Ala | Val | Pro | Pro | Cys | Leu | Asp | Gly | Ser | Pro | Cys | Ala |
| | | 35 | | | | | 40 | | | | | 45 | | | |
| Asn | Gly | Gly | Arg | Cys | Thr | Gln | Leu | Pro | Ser | Arg | Glu | Ala | Ala | Cys | Leu |
| | 50 | | | | | 55 | | | | | 60 | | | | |
| Cys | Pro | Pro | Gly | Trp | Val | Gly | Glu | Arg | Cys | Gln | Leu | Glu | Asp | Pro | Cys |
| 65 | | | | | 70 | | | | | 75 | | | | | 80 |
| His | Ser | Gly | Pro | Cys | Ala | Gly | Arg | Gly | Val | Cys | Gln | Ser | Ser | Val | Val |
| | | | | 85 | | | | | 90 | | | | | 95 | |
| Ala | Gly | Thr | Ala | Arg | Phe | Ser | Cys | Arg | Cys | Pro | Arg | Gly | Phe | Arg | Gly |
| | | | | 100 | | | | | 105 | | | | | 110 | |
| Pro | Asp | Cys | Ser | Leu | Pro | Asp | Pro | Cys | Leu | Ser | Ser | Pro | Cys | Ala | His |
| | | | 115 | | | | | 120 | | | | | 125 | | |
| Ser | Ala | Arg | Cys | Ser | Val | Gly | Pro | Asp | Gly | Arg | Phe | Leu | Cys | Ser | Cys |
| | 130 | | | | | 135 | | | | | 140 | | | | |
| Pro | Pro | Gly | Tyr | Gln | Gly | Arg | Ser | Cys | Arg | Ser | Asp | Val | Asp | Glu | Cys |
| 145 | | | | | 150 | | | | | 155 | | | | | 160 |
| Arg | Val | Gly | Glu | Pro | Cys | Arg | His | Gly | Gly | Thr | Cys | Leu | Asn | Thr | Pro |
| | | | | 165 | | | | | 170 | | | | | 175 | |
| Gly | Ser | Phe | Arg | Cys | Gln | Cys | Pro | Ala | Gly | Tyr | Thr | Gly | Pro | Leu | Cys |
| | | | | 180 | | | | | 185 | | | | | 190 | |
| Glu | Asn | Pro | Ala | Val | Pro | Cys | Ala | Pro | Ser | Pro | Cys | Arg | Asn | Gly | Gly |
| | | | 195 | | | | | 200 | | | | | 205 | | |
| Thr | Cys | Arg | Gln | Ser | Gly | Asp | Leu | Thr | Tyr | Asp | Cys | Ala | Cys | Leu | Pro |
| | 210 | | | | | 215 | | | | | 220 | | | | |
| Gly | Phe | Glu | Gly | Gln | Asn | Cys | Glu | Val | Asn | Val | Asp | Asp | Cys | Pro | Gly |
| 225 | | | | | 230 | | | | | 235 | | | | | 240 |
| His | Arg | Cys | Leu | Asn | Gly | Gly | Thr | Cys | Val | Asp | Gly | Val | Asn | Thr | Tyr |
| | | | | 245 | | | | | 250 | | | | | 255 | |
| Asn | Cys | Gln | Cys | Pro | Pro | Glu | Trp | Thr | Gly | Gln | Phe | Cys | Thr | Glu | Asp |
| | | | | 260 | | | | | 265 | | | | | 270 | |
| Val | Asp | Glu | Cys | Gln | Leu | Gln | Pro | Asn | Ala | Cys | His | Asn | Gly | Gly | Thr |
| | | | 275 | | | | | 280 | | | | | 285 | | |
| Cys | Phe | Asn | Thr | Leu | Gly | Gly | His | Ser | Cys | Val | Cys | Val | Asn | Gly | Trp |
| | 290 | | | | | 295 | | | | | 300 | | | | |
| Thr | Gly | Glu | Ser | Cys | Ser | Gln | Asn | Ile | Asp | Asp | Cys | Ala | Thr | Ala | Val |
| 305 | | | | | 310 | | | | | 315 | | | | | 320 |
| Cys | Phe | His | Gly | Ala | Thr | Cys | His | Asp | Arg | Val | Ala | Ser | Phe | Tyr | Cys |
| | | | | 325 | | | | | 330 | | | | | 335 | |
| Ala | Cys | Pro | Met | Gly | Lys | Thr | Gly | Leu | Leu | Cys | His | Leu | Asp | Asp | Ala |
| | | | | 340 | | | | | 345 | | | | | 350 | |
| Cys | Val | Ser | Asn | Pro | Cys | His | Glu | Asp | Ala | Ile | Cys | Asp | Thr | Asn | Pro |
| | | | 355 | | | | | 360 | | | | | 365 | | |

Val Asn Gly Arg Ala Ile Cys Thr Cys Pro Gly Phe Thr Gly
370                 375                 380

Ala Cys Asp Gln Asp Val Asp Glu Cys Ser Ile Gly Ala Asn Pro Cys
385                 390                 395                 400

Glu His Leu Gly Arg Cys Val Asn Thr Gln Gly Ser Phe Leu Cys Gln
                405                 410                 415

Cys Gly Arg Gly Tyr Thr Gly Pro Arg Cys Glu Thr Asp Val Asn Glu
                420                 425                 430

Cys Leu Ser Gly Pro Cys Arg Asn Gln Ala Thr Cys Leu Asp Arg Ile
                435                 440                 445

Gly Gln Phe Thr Cys Ile Cys Met Ala Gly Phe Thr Gly Thr Tyr Cys
450                 455                 460

Glu Val Asp Ile Asp Glu Cys Gln Ser Ser Pro Cys Val Asn Gly Gly
465                 470                 475                 480

Ile Cys Lys Asp Arg Val Asn Gly Phe Ser Cys Thr Cys Pro Ser Gly
                485                 490                 495

Phe Ser Gly Ser Thr Cys Gln Leu Asp Val Asp Glu Cys Ala Ser Thr
                500                 505                 510

Pro Cys Arg Asn Gly Ala Lys Cys Val Asp Gln Pro Asp Gly Tyr Glu
                515                 520                 525

Cys Arg Cys Ala Glu Gly Phe Glu Gly Met Leu Cys Glu Arg Asn Val
530                 535                 540

Asp Asp Cys Ser Pro Asp Pro Cys His His Gly Arg Cys Val Asp Gly
545                 550                 555                 560

Ile Ala Ser Phe Ser Cys Ala Cys Ala Pro Gly Tyr Thr Gly Thr Arg
                565                 570                 575

Cys Glu Ser Gln Val Asp Glu Cys Arg Ser Gln Pro Cys Arg His Gly
                580                 585                 590

Gly Lys Cys Leu Asp Leu Val Asp Lys Tyr Leu Cys Arg Cys Pro Ser
                595                 600                 605

Gly Thr Thr Gly Val Asn Cys Glu Val Asn Ile Asp Asp Cys Ala Ser
                610                 615                 620

Asn Pro Cys Ser Phe Gly Val Cys Arg Asp Gly Ile Asn Arg Tyr Asp
625                 630                 635                 640

Cys Val Cys Gln Pro Gly Phe Thr Gly Pro Leu Cys Asn Val Glu Ile
                645                 650                 655

Asn Glu Cys Ala Ser Ser Pro Cys Gly Glu Gly Gly Ser Cys Val Asp
                660                 665                 670

Gly Glu Asn Gly Phe Arg Cys Leu Cys Pro Pro Gly Ser Leu Pro Pro
                675                 680                 685

Leu Cys Leu Pro Pro Ser His Pro Cys Ala His Glu Pro Cys Ser His
690                 695                 700

Gly Ile Cys Tyr Asp Ala Pro Gly Gly Phe Arg Cys Val Cys Glu Pro
705                 710                 715                 720

Gly Trp Ser Gly Pro Arg Cys Ser Gln Ser Leu Ala Arg Asp Ala Cys
                725                 730                 735

Glu Ser Gln Pro Cys Arg Ala Gly Gly Thr Cys Ser Ser Asp Gly Met
                740                 745                 750

Gly Phe His Cys Thr Cys Pro Pro Gly Val Gln Gly Arg Gln Cys Glu
                755                 760                 765

Leu Leu Ser Pro Cys Thr Pro Asn Pro Cys Glu His Gly Gly Arg Cys
770                 775                 780

Glu Ser Ala Pro Gly Gln Leu Pro Val Cys Ser Cys Pro Gln Gly Trp

```
                785              790              795              800
         Gln Gly Pro Arg Cys Gln Gln Asp Val Asp Glu Cys Ala Gly Pro Ala
                     805              810              815
         Pro Cys Gly Pro His Gly Ile Cys Thr Asn Leu Ala Gly Ser Phe Ser
                     820              825              830
         Cys Thr Cys His Gly Gly Tyr Thr Gly Pro Ser Cys Asp Gln Asp Ile
                     835              840              845
         Asn Asp Cys Asp Pro Asn Pro Cys Leu Asn Gly Gly Ser Cys Gln Asp
                 850              855              860
         Gly Val Gly Ser Phe Ser Cys Ser Cys Leu Leu Gly Phe Ala Gly Pro
         865              870              875              880
         Arg Cys Ala Arg Asp Val Asp Glu Cys Leu Ser Asn Pro Cys Gly Pro
                     885              890              895
         Gly Thr Cys Thr Asp His Val Ala Ser Phe Thr Cys Thr Cys Pro Pro
                     900              905              910
         Gly Tyr Gly Gly Phe His Cys Glu Gln Asp Leu Pro Asp Cys Ser Pro
                     915              920              925
         Ser Ser Cys Phe Asn Gly Gly Thr Cys Val Asp Gly Val Asn Ser Phe
                 930              935              940
         Ser Cys Leu Cys Arg Pro Gly Tyr Thr Gly Ala His Cys Gln His Glu
         945              950              955              960
         Ala Asp Pro Cys Leu Ser Arg Pro Cys Leu His Gly Gly Val Cys Ser
                     965              970              975
         Ala Ala His Pro Gly Phe Arg Cys Thr Cys Pro Gln Ser Phe Thr Gly
                     980              985              990
         Pro Gln Cys Gln Thr Leu Val Asp  Trp Cys Ser Arg Gln  Pro Cys Gln
                 995             1000                          1005
         Asn Gly  Gly Arg Cys Val Gln  Thr Gly Ala Tyr Cys  Leu Cys Pro
                 1010             1015             1020
         Pro Gly  Trp Ser Gly Arg Leu  Cys Asp Ile Arg Ser  Leu Pro Cys
                 1025             1030             1035
         Arg Glu  Ala Ala Ala Gln Ile  Gly Val Arg Leu Glu  Gln Leu Cys
                 1040             1045             1050
         Gln Ala  Gly Gly Gln Cys Val  Asp Glu Asp Ser Ser  His Tyr Cys
                 1055             1060             1065
         Val Cys  Pro Glu Gly Arg Thr  Gly Ser His Cys Glu  Gln Glu Val
                 1070             1075             1080
         Asp Pro  Cys Leu Ala Gln Pro  Cys Gln His Gly Gly  Thr Cys Arg
                 1085             1090             1095
         Gly Tyr  Met Gly Gly Tyr Met  Cys Glu Cys Leu Pro  Gly Tyr Asn
                 1100             1105             1110
         Gly Glu  Asn Cys Glu Asp Asp  Val Asp Glu Cys Ala  Ser Gln Pro
                 1115             1120             1125
         Cys Gln  His Gly Gly Ser Cys  Ile Asp Leu Val Ala  Arg Tyr Leu
                 1130             1135             1140
         Cys Ser  Cys Pro Pro Gly Thr  Leu Gly Val Leu Cys  Glu Ile Asn
                 1145             1150             1155
         Glu Asp  Asp Cys Gly Pro Gly  Pro Pro Leu Asp Ser  Gly Pro Arg
                 1160             1165             1170
         Cys Leu  His Asn Gly Thr Cys  Val Asp Leu Val Gly  Gly Phe Arg
                 1175             1180             1185
         Cys Thr  Cys Pro Pro Gly Tyr  Thr Gly Leu Arg Cys  Glu Ala Asp
                 1190             1195             1200
```

-continued

Ile Asn Glu Cys Arg Ser Gly Ala Cys His Ala Ala His Thr Arg
1205            1210              1215

Asp Cys Leu Gln Asp Pro Gly Gly Phe Arg Cys Leu Cys His
1220            1225              1230

Ala Gly Phe Ser Gly Pro Arg Cys Gln Thr Val Leu Ser Pro Cys
1235            1240              1245

Glu Ser Gln Pro Cys Gln His Gly Gly Gln Cys Arg Pro Ser Pro
1250            1255              1260

Gly Pro Gly Gly Gly Leu Thr Phe Thr Cys His Cys Ala Gln Pro
1265            1270              1275

Phe Trp Gly Pro Arg Cys Glu Arg Val Ala Arg Ser Cys Arg Glu
1280            1285              1290

Leu Gln Cys Pro Val Gly Val Pro Cys Gln Gln Thr Pro Arg Gly
1295            1300              1305

Pro Arg Cys Ala Cys Pro Pro Gly Leu Ser Gly Pro Ser Cys Arg
1310            1315              1320

Ser Phe Ser Gly Ser Pro Pro Gly Ala Ser Asn Ala Ser Cys Ala
1325            1330              1335

Ala Ala Pro Cys Leu His Gly Gly Ser Cys Arg Pro Ala Pro Leu
1340            1345              1350

Ala Pro Phe Phe Arg Cys Ala Cys Ala Gln Gly Trp Thr Gly Pro
1355            1360              1365

Arg Cys Glu Ala Pro Ala Ala Ala Pro Glu Val Ser Glu Glu Pro
1370            1375              1380

Arg Cys Pro Arg Ala Ala Cys Gln Ala Lys Arg Gly Asp Gln Arg
1385            1390              1395

Cys Asp Arg Glu Cys Asn Ser Pro Gly Cys Gly Trp Asp Gly Gly
1400            1405              1410

Asp Cys Ser Leu Ser Val Gly Asp Pro Trp Arg Gln Cys Glu Ala
1415            1420              1425

Leu Gln Cys Trp Arg Leu Phe Asn Asn Ser Arg Cys Asp Pro Ala
1430            1435              1440

Cys Ser Ser Pro Ala Cys Leu Tyr Asp Asn Phe Asp Cys His Ala
1445            1450              1455

Gly Gly Arg Glu Arg Thr Cys Asn Pro Val Tyr Glu Lys Tyr Cys
1460            1465              1470

Ala Asp His Phe Ala Asp Gly Arg Cys Asp Gln Gly Cys Asn Thr
1475            1480              1485

Glu Glu Cys Gly Trp Asp Gly Leu Asp Cys Ala Ser Glu Val Pro
1490            1495              1500

Ala Leu Leu Ala Arg Gly Val Leu Val Leu Thr Val Leu Leu Pro
1505            1510              1515

Pro Glu Glu Leu Leu Arg Ser Ser Ala Asp Phe Leu Gln Arg Leu
1520            1525              1530

Ser Ala Ile Leu Arg Thr Ser Leu Arg Phe Arg Leu Asp Ala His
1535            1540              1545

Gly Gln Ala Met Val Phe Pro Tyr His Arg Pro Ser Pro Gly Ser
1550            1555              1560

Glu Pro Arg Ala Arg Arg Glu Leu Ala Pro Glu Val Ile Gly Ser
1565            1570              1575

Val Val Met Leu Glu Ile Asp Asn Arg Leu Cys Leu Gln Ser Pro
1580            1585              1590

```
Glu Asn Asp His Cys Phe Pro Asp Ala Gln Ser Ala Ala Asp Tyr
    1595                1600                1605

Leu Gly Ala Leu Ser Ala Val Glu Arg Leu Asp Phe Pro Tyr Pro
    1610                1615                1620

Leu Arg Asp Val Arg Gly Glu Pro Leu Glu Pro Pro Glu Pro Ser
    1625                1630                1635

Val Pro Leu Leu Pro Leu Leu Val Ala Gly Ala Val Leu Leu Leu
    1640                1645                1650

Val Ile Leu Val Leu Gly Val Met Val Ala Arg Arg Lys Arg Val
    1655                1660                1665

Asp Lys Leu Leu Ser Ser Ile Glu Gln Ala Cys Asp Ile Cys Arg
    1670                1675                1680

Leu Lys Lys Leu Lys Cys Ser Lys Glu Lys Pro Lys Cys Ala Lys
    1685                1690                1695

Cys Leu Lys Asn Asn Trp Glu Cys Arg Tyr Ser Pro Lys Thr Lys
    1700                1705                1710

Arg Ser Pro Leu Thr Arg Ala His Leu Thr Glu Val Glu Ser Arg
    1715                1720                1725

Leu Glu Arg Leu Glu Gln Leu Phe Leu Leu Ile Phe Pro Arg Glu
    1730                1735                1740

Asp Leu Asp Met Ile Leu Lys Met Asp Ser Leu Gln Asp Ile Lys
    1745                1750                1755

Ala Leu Leu Thr Gly Leu Phe Val Gln Asp Asn Val Asn Lys Asp
    1760                1765                1770

Ala Val Thr Asp Arg Leu Ala Ser Val Glu Thr Asp Met Pro Leu
    1775                1780                1785

Thr Leu Arg Gln His Arg Ile Ser Ala Thr Ser Ser Ser Glu Glu
    1790                1795                1800

Ser Ser Asn Lys Gly Gln Arg Gln Leu Thr Val Ser Gln Leu Lys
    1805                1810                1815

Leu Leu Ser Ser Ile Glu Gln Ala Cys Pro Lys Lys Lys Arg Lys
    1820                1825                1830

Val Asp Glu Phe Pro Gly Ile Ser Thr Ala Pro Pro Thr Asp Val
    1835                1840                1845

Ser Leu Gly Asp Glu Leu His Leu Asp Gly Glu Asp Val Ala Met
    1850                1855                1860

Ala His Ala Asp Ala Leu Asp Asp Phe Asp Leu Asp Met Leu Gly
    1865                1870                1875

Asp Gly Asp Ser Pro Gly Pro Gly
    1880                1885

<210> SEQ ID NO 274
<211> LENGTH: 1981
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 274

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
                20                  25                  30

Asn Gly Gly Lys Cys Glu Ala Ala Asn Gly Thr Glu Ala Cys Val Cys
```

-continued

```
                35                  40                  45
Gly Gly Ala Phe Val Gly Pro Arg Cys Gln Asp Pro Asn Pro Cys Leu
 50                  55                  60
Ser Thr Pro Cys Lys Asn Ala Gly Thr Cys His Val Val Asp Arg Arg
 65                  70                  75                  80
Gly Val Ala Asp Tyr Ala Cys Ser Cys Ala Leu Gly Phe Ser Gly Pro
                 85                  90                  95
Leu Cys Leu Thr Pro Leu Asp Asn Ala Cys Leu Thr Asn Pro Cys Arg
            100                 105                 110
Asn Gly Gly Thr Cys Asp Leu Leu Thr Leu Thr Glu Tyr Lys Cys Arg
            115                 120                 125
Cys Pro Pro Gly Trp Ser Gly Lys Ser Cys Gln Gln Ala Asp Pro Cys
    130                 135                 140
Ala Ser Asn Pro Cys Ala Asn Gly Gly Gln Cys Leu Pro Phe Glu Ala
145                 150                 155                 160
Ser Tyr Ile Cys His Cys Pro Pro Ser Phe His Gly Pro Thr Cys Arg
                165                 170                 175
Gln Asp Val Asn Glu Cys Gly Gln Lys Pro Gly Leu Cys Arg His Gly
            180                 185                 190
Gly Thr Cys His Asn Glu Val Gly Ser Tyr Arg Cys Val Cys Arg Ala
            195                 200                 205
Thr His Thr Gly Pro Asn Cys Glu Arg Pro Tyr Val Pro Cys Ser Pro
    210                 215                 220
Ser Pro Cys Gln Asn Gly Gly Thr Cys Arg Pro Thr Gly Asp Val Thr
225                 230                 235                 240
His Glu Cys Ala Cys Leu Pro Gly Phe Thr Gly Gln Asn Cys Glu Glu
                245                 250                 255
Asn Ile Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Trp Thr
        275                 280                 285
Gly Gln Tyr Cys Thr Glu Asp Val Asp Glu Cys Gln Leu Met Pro Asn
    290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe His Gly Ala Thr Cys His Asp
            340                 345                 350
Arg Val Ala Ser Phe Tyr Cys Glu Cys Pro His Gly Arg Thr Gly Leu
            355                 360                 365
Leu Cys His Leu Asn Asp Ala Cys Ile Ser Asn Pro Cys Asn Glu Gly
        370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
                405                 410                 415
Ser Leu Gly Ala Asn Pro Cys Glu His Ala Gly Lys Cys Ile Asn Thr
            420                 425                 430
Leu Gly Ser Phe Glu Cys Gln Cys Leu Gln Gly Tyr Thr Gly Pro Arg
            435                 440                 445
Cys Glu Ile Asp Val Asn Glu Cys Val Ser Asn Pro Cys Gln Asn Asp
    450                 455                 460
```

```
Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
            485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
            515                 520                 525

Val Asp Glu Cys Ala Ser Thr Pro Cys Lys Asn Gly Ala Lys Cys Leu
530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
            595                 600                 605

Ser Gln Pro Cys Arg His Gly Gly Thr Cys Gln Asp Arg Asp Asn Ala
610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
                660                 665                 670

Ser Met Cys Asn Ile Asn Ile Asp Glu Cys Ala Gly Asn Pro Cys His
            675                 680                 685

Asn Gly Gly Thr Cys Glu Asp Gly Ile Asn Gly Phe Thr Cys Arg Cys
            690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
            725                 730                 735

Tyr Lys Cys Asp Cys Asp Pro Gly Trp Ser Gly Thr Asn Cys Asp Ile
                740                 745                 750

Asn Asn Asn Glu Cys Glu Ser Asn Pro Cys Val Asn Gly Gly Thr Cys
            755                 760                 765

Lys Asp Met Thr Ser Gly Tyr Val Cys Thr Cys Arg Glu Gly Phe Ser
            770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
            835                 840                 845

Asp Tyr Glu Ser Phe Ser Cys Val Cys Pro Thr Gly Trp Gln Gly Gln
            850                 855                 860

Thr Cys Glu Val Asp Ile Asn Glu Cys Val Leu Ser Pro Cys Arg His
865                 870                 875                 880
```

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
        900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
        965                 970                 975

Gly Ile His Cys Glu Asn Asn Thr Pro Asp Cys Thr Glu Ser Ser Cys
        980                 985                 990

Phe Asn Gly Gly Thr Cys Val Asp Gly Ile Asn Ser Phe Thr Cys Leu
        995                 1000                1005

Cys Pro Pro Gly Phe Thr Gly Ser Tyr Cys Gln His Asp Val Asn
    1010                1015                1020

Glu Cys Asp Ser Gln Pro Cys Leu His Gly Gly Thr Cys Gln Asp
    1025                1030                1035

Gly Cys Gly Ser Tyr Arg Cys Thr Cys Pro Gln Gly Tyr Thr Gly
    1040                1045                1050

Pro Asn Cys Gln Asn Leu Val His Trp Cys Asp Ser Ser Pro Cys
    1055                1060                1065

Lys Asn Gly Gly Lys Cys Trp Gln Thr His Thr Gln Tyr Arg Cys
    1070                1075                1080

Glu Cys Pro Ser Gly Trp Thr Gly Leu Tyr Cys Asp Val Pro Ser
    1085                1090                1095

Val Ser Cys Glu Val Ala Ala Gln Arg Gln Gly Val Asp Val Ala
    1100                1105                1110

Arg Leu Cys Gln His Gly Gly Leu Cys Val Asp Ala Gly Asn Thr
    1115                1120                1125

His His Cys Arg Cys Gln Ala Gly Tyr Thr Gly Ser Tyr Cys Glu
    1130                1135                1140

Asp Leu Val Asp Glu Cys Ser Pro Ser Pro Cys Gln Asn Gly Ala
    1145                1150                1155

Thr Cys Thr Asp Tyr Leu Gly Gly Tyr Ser Cys Lys Cys Val Ala
    1160                1165                1170

Gly Tyr His Gly Val Asn Cys Ser Glu Glu Ile Asp Glu Cys Leu
    1175                1180                1185

Ser His Pro Cys Gln Asn Gly Gly Thr Cys Leu Asp Leu Pro Asn
    1190                1195                1200

Thr Tyr Lys Cys Ser Cys Pro Arg Gly Thr Gln Gly Val His Cys
    1205                1210                1215

Glu Ile Asn Val Asp Asp Cys Asn Pro Pro Val Asp Pro Val Ser
    1220                1225                1230

Arg Ser Pro Lys Cys Phe Asn Asn Gly Thr Cys Val Asp Gln Val
    1235                1240                1245

Gly Gly Tyr Ser Cys Thr Cys Pro Pro Gly Phe Val Gly Glu Arg
    1250                1255                1260

Cys Glu Gly Asp Val Asn Glu Cys Leu Ser Asn Pro Cys Asp Ala
    1265                1270                1275

Arg Gly Thr Gln Asn Cys Val Gln Arg Val Asn Asp Phe His Cys

```
            1280                1285                1290

Glu Cys Arg Ala Gly His Thr Gly Arg Arg Cys Glu Ser Val Ile
    1295                1300                1305

Asn Gly Cys Lys Gly Lys Pro Cys Lys Asn Gly Gly Thr Cys Ala
    1310                1315                1320

Val Ala Ser Asn Thr Ala Arg Gly Phe Ile Cys Lys Cys Pro Ala
    1325                1330                1335

Gly Phe Glu Gly Ala Thr Cys Glu Asn Asp Ala Arg Thr Cys Gly
    1340                1345                1350

Ser Leu Arg Cys Leu Asn Gly Gly Thr Cys Ile Ser Gly Pro Arg
    1355                1360                1365

Ser Pro Thr Cys Leu Cys Leu Gly Pro Phe Thr Gly Pro Glu Cys
    1370                1375                1380

Gln Phe Pro Ala Ser Ser Pro Cys Leu Gly Gly Asn Pro Cys Tyr
    1385                1390                1395

Asn Gln Gly Thr Cys Glu Pro Thr Ser Glu Ser Pro Phe Tyr Arg
    1400                1405                1410

Cys Leu Cys Pro Ala Lys Phe Asn Gly Leu Leu Cys His Ile Leu
    1415                1420                1425

Asp Tyr Ser Phe Gly Gly Gly Ala Gly Arg Asp Ile Pro Pro Pro
    1430                1435                1440

Leu Ile Glu Glu Ala Cys Glu Leu Pro Glu Cys Gln Glu Asp Ala
    1445                1450                1455

Gly Asn Lys Val Cys Ser Leu Gln Cys Asn Asn His Ala Cys Gly
    1460                1465                1470

Trp Asp Gly Gly Asp Cys Ser Leu Asn Phe Asn Asp Pro Trp Lys
    1475                1480                1485

Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
    1505                1510                1515

Phe Asp Cys Gln Arg Ala Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Val Val Val
    1565                1570                1575

Leu Met Pro Pro Glu Gln Leu Arg Asn Ser Ser Phe His Phe Leu
    1580                1585                1590

Arg Glu Leu Ser Arg Val Leu His Thr Asn Val Val Phe Lys Arg
    1595                1600                1605

Asp Ala His Gly Gln Gln Met Ile Phe Pro Tyr Tyr Gly Arg Glu
    1610                1615                1620

Glu Glu Leu Arg Lys His Pro Ile Lys Arg Ala Ala Glu Gly Trp
    1625                1630                1635

Ala Ala Pro Asp Ala Leu Leu Gly Gln Val Lys Ala Ser Leu Leu
    1640                1645                1650

Pro Gly Gly Ser Glu Gly Gly Arg Arg Arg Arg Glu Leu Asp Pro
    1655                1660                1665

Met Asp Val Arg Gly Ser Ile Val Tyr Leu Glu Ile Asp Asn Arg
    1670                1675                1680
```

```
Gln Cys Val Gln Ala Ser Ser Gln Cys Phe Gln Ser Ala Thr Asp
    1685                1690                1695

Val Ala Ala Phe Leu Gly Ala Leu Ala Ser Leu Gly Ser Leu Asn
    1700                1705                1710

Ile Pro Tyr Lys Ile Glu Ala Val Gln Ser Glu Thr Val Glu Pro
    1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg
    1745                1750                1755

Lys Arg Arg Arg Val Asp Lys Leu Leu Ser Ser Ile Glu Gln Ala
    1760                1765                1770

Cys Asp Ile Cys Arg Leu Lys Lys Leu Lys Cys Ser Lys Glu Lys
    1775                1780                1785

Pro Lys Cys Ala Lys Cys Leu Lys Asn Asn Trp Glu Cys Arg Tyr
    1790                1795                1800

Ser Pro Lys Thr Lys Arg Ser Pro Leu Thr Arg Ala His Leu Thr
    1805                1810                1815

Glu Val Glu Ser Arg Leu Glu Arg Leu Glu Gln Leu Phe Leu Leu
    1820                1825                1830

Ile Phe Pro Arg Glu Asp Leu Asp Met Ile Leu Lys Met Asp Ser
    1835                1840                1845

Leu Gln Asp Ile Lys Ala Leu Leu Thr Gly Leu Phe Val Gln Asp
    1850                1855                1860

Asn Val Asn Lys Asp Ala Val Thr Asp Arg Leu Ala Ser Val Glu
    1865                1870                1875

Thr Asp Met Pro Leu Thr Leu Arg Gln His Arg Ile Ser Ala Thr
    1880                1885                1890

Ser Ser Ser Glu Glu Ser Ser Asn Lys Gly Gln Arg Gln Leu Thr
    1895                1900                1905

Val Ser Gln Leu Lys Leu Leu Ser Ser Ile Glu Gln Ala Cys Pro
    1910                1915                1920

Lys Lys Lys Arg Lys Val Asp Glu Phe Pro Gly Ile Ser Thr Ala
    1925                1930                1935

Pro Pro Thr Asp Val Ser Leu Gly Asp Glu Leu His Leu Asp Gly
    1940                1945                1950

Glu Asp Val Ala Met Ala His Ala Asp Ala Leu Asp Asp Phe Asp
    1955                1960                1965

Leu Asp Met Leu Gly Asp Gly Asp Ser Pro Gly Pro Gly
    1970                1975                1980

<210> SEQ ID NO 275
<211> LENGTH: 1923
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 275

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30
```

-continued

```
Glu Pro Cys Val Asn Glu Gly Met Cys Val Thr Tyr His Asn Gly Thr
         35                  40                  45
Gly Tyr Cys Lys Cys Pro Glu Gly Phe Leu Gly Glu Tyr Cys Gln His
 50                  55                  60
Arg Asp Pro Cys Glu Lys Asn Arg Cys Gln Asn Gly Gly Thr Cys Val
65                   70                  75                  80
Ala Gln Ala Met Leu Gly Lys Ala Thr Cys Arg Cys Ala Ser Gly Phe
                 85                  90                  95
Thr Gly Glu Asp Cys Gln Tyr Ser Thr Ser His Pro Cys Phe Val Ser
            100                 105                 110
Arg Pro Cys Leu Asn Gly Gly Thr Cys His Met Leu Ser Arg Asp Thr
        115                 120                 125
Tyr Glu Cys Thr Cys Gln Val Gly Phe Thr Gly Lys Glu Cys Gln Trp
130                 135                 140
Thr Asp Ala Cys Leu Ser His Pro Cys Ala Asn Gly Ser Thr Cys Thr
145                 150                 155                 160
Thr Val Ala Asn Gln Phe Ser Cys Lys Cys Leu Thr Gly Phe Thr Gly
                165                 170                 175
Gln Lys Cys Glu Thr Asp Val Asn Glu Cys Asp Ile Pro Gly His Cys
            180                 185                 190
Gln His Gly Gly Thr Cys Leu Asn Leu Pro Gly Ser Tyr Gln Cys Gln
        195                 200                 205
Cys Pro Gln Gly Phe Thr Gly Gln Tyr Cys Asp Ser Leu Tyr Val Pro
    210                 215                 220
Cys Ala Pro Ser Pro Cys Val Asn Gly Gly Thr Cys Arg Gln Thr Gly
225                 230                 235                 240
Asp Phe Thr Phe Glu Cys Asn Cys Leu Pro Gly Phe Glu Gly Ser Thr
                245                 250                 255
Cys Glu Arg Asn Ile Asp Asp Cys Pro Asn His Arg Cys Gln Asn Gly
            260                 265                 270
Gly Val Cys Val Asp Gly Val Asn Thr Tyr Asn Cys Arg Cys Pro Pro
        275                 280                 285
Gln Trp Thr Gly Gln Phe Cys Thr Glu Asp Val Asp Glu Cys Leu Leu
    290                 295                 300
Gln Pro Asn Ala Cys Gln Asn Gly Gly Thr Cys Ala Asn Arg Asn Gly
305                 310                 315                 320
Gly Tyr Gly Cys Val Cys Val Asn Gly Trp Ser Gly Asp Asp Cys Ser
                325                 330                 335
Glu Asn Ile Asp Asp Cys Ala Phe Ala Ser Cys Thr Pro Gly Ser Thr
            340                 345                 350
Cys Ile Asp Arg Val Ala Ser Phe Ser Cys Met Cys Pro Glu Gly Lys
        355                 360                 365
Ala Gly Leu Leu Cys His Leu Asp Asp Ala Cys Ile Ser Asn Pro Cys
    370                 375                 380
His Lys Gly Ala Leu Cys Asp Thr Asn Pro Leu Asn Gly Gln Tyr Ile
385                 390                 395                 400
Cys Thr Cys Pro Gln Gly Tyr Lys Gly Ala Asp Cys Thr Glu Asp Val
                405                 410                 415
Asp Glu Cys Ala Met Ala Asn Ser Asn Pro Cys Glu His Ala Gly Lys
            420                 425                 430
Cys Val Asn Thr Asp Gly Ala Phe His Cys Glu Cys Leu Lys Gly Tyr
        435                 440                 445
Ala Gly Pro Arg Cys Glu Met Asp Ile Asn Glu Cys His Ser Asp Pro
```

-continued

```
            450                 455                 460
Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
            515                 520                 525

Cys Gln Ile Asp Ile Asp Asp Cys Ser Ser Thr Pro Cys Leu Asn Gly
            530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
                580                 585                 590

Cys Ile Cys Asn Pro Gly Tyr Met Gly Ala Ile Cys Ser Asp Gln Ile
                595                 600                 605

Asp Glu Cys Tyr Ser Ser Pro Cys Leu Asn Asp Gly Arg Cys Ile Asp
            610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
                660                 665                 670

Gly Phe Thr Gly Gln Arg Cys Asn Ile Asp Ile Asp Glu Cys Ala Ser
                675                 680                 685

Asn Pro Cys Arg Lys Gly Ala Thr Cys Ile Asn Gly Val Asn Gly Phe
            690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
                740                 745                 750

Asn Cys Glu Val Asp Lys Asn Glu Cys Leu Ser Asn Pro Cys Gln Asn
                755                 760                 765

Gly Gly Thr Cys Asp Asn Leu Val Asn Gly Tyr Arg Cys Thr Cys Lys
            770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
                805                 810                 815

Tyr Thr Cys His Cys Val Leu Pro Tyr Thr Gly Lys Asn Cys Gln Thr
                820                 825                 830

Val Leu Ala Pro Cys Ser Pro Asn Pro Cys Glu Asn Ala Ala Val Cys
            835                 840                 845

Lys Glu Ser Pro Asn Phe Glu Ser Tyr Thr Cys Leu Cys Ala Pro Gly
850                 855                 860

Trp Gln Gly Gln Arg Cys Thr Ile Asp Ile Asp Glu Cys Ile Ser Lys
865                 870                 875                 880
```

-continued

Pro Cys Met Asn His Gly Leu Cys His Asn Thr Gln Gly Ser Tyr Met
            885                 890                 895

Cys Glu Cys Pro Pro Gly Phe Ser Gly Met Asp Cys Glu Glu Asp Ile
        900                 905                 910

Asp Asp Cys Leu Ala Asn Pro Cys Gln Asn Gly Gly Ser Cys Met Asp
    915                 920                 925

Gly Val Asn Thr Phe Ser Cys Leu Cys Leu Pro Gly Phe Thr Gly Asp
930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
            965                 970                 975

Ala Gly Phe Asp Gly Val His Cys Glu Asn Asn Ile Asn Glu Cys Thr
            980                 985                 990

Glu Ser Ser Cys Phe Asn Gly Gly Thr Cys Val Asp Gly Ile Asn Ser
        995                 1000                1005

Phe Ser Cys Leu Cys Pro Val Gly Phe Thr Gly Ser Phe Cys Leu
    1010                1015                1020

His Glu Ile Asn Glu Cys Ser Ser His Pro Cys Leu Asn Glu Gly
    1025                1030                1035

Thr Cys Val Asp Gly Leu Gly Thr Tyr Arg Cys Ser Cys Pro Leu
    1040                1045                1050

Gly Tyr Thr Gly Lys Asn Cys Gln Thr Leu Val Asn Leu Cys Ser
    1055                1060                1065

Arg Ser Pro Cys Lys Asn Lys Gly Thr Cys Val Gln Lys Lys Ala
    1070                1075                1080

Glu Ser Gln Cys Leu Cys Pro Ser Gly Trp Ala Gly Ala Tyr Cys
    1085                1090                1095

Asp Val Pro Asn Val Ser Cys Asp Ile Ala Ala Ser Arg Arg Gly
    1100                1105                1110

Val Leu Val Glu His Leu Cys Gln His Ser Gly Val Cys Ile Asn
    1115                1120                1125

Ala Gly Asn Thr His Tyr Cys Gln Cys Pro Leu Gly Tyr Thr Gly
    1130                1135                1140

Ser Tyr Cys Glu Glu Gln Leu Asp Glu Cys Ala Ser Asn Pro Cys
    1145                1150                1155

Gln His Gly Ala Thr Cys Ser Asp Phe Ile Gly Gly Tyr Arg Cys
    1160                1165                1170

Glu Cys Val Pro Gly Tyr Gln Gly Val Asn Cys Glu Tyr Glu Val
    1175                1180                1185

Asp Glu Cys Gln Asn Gln Pro Cys Gln Asn Gly Gly Thr Cys Ile
    1190                1195                1200

Asp Leu Val Asn His Phe Lys Cys Ser Cys Pro Pro Gly Thr Arg
    1205                1210                1215

Gly Leu Leu Cys Glu Glu Asn Ile Asp Asp Cys Ala Arg Gly Pro
    1220                1225                1230

His Cys Leu Asn Gly Gly Gln Cys Met Asp Arg Ile Gly Gly Tyr
    1235                1240                1245

Ser Cys Arg Cys Leu Pro Gly Phe Ala Gly Glu Arg Cys Glu Gly
    1250                1255                1260

Asp Ile Asn Glu Cys Leu Ser Asn Pro Cys Ser Ser Glu Gly Ser
    1265                1270                1275

```
Leu Asp Cys Ile Gln Leu Thr Asn Asp Tyr Leu Cys Val Cys Arg
    1280                1285                1290

Ser Ala Phe Thr Gly Arg His Cys Glu Thr Phe Val Asp Val Cys
    1295                1300                1305

Pro Gln Met Pro Cys Leu Asn Gly Gly Thr Cys Ala Val Ala Ser
    1310                1315                1320

Asn Met Pro Asp Gly Phe Ile Cys Arg Cys Pro Pro Gly Phe Ser
    1325                1330                1335

Gly Ala Arg Cys Gln Ser Ser Cys Gly Gln Val Lys Cys Arg Lys
    1340                1345                1350

Gly Glu Gln Cys Val His Thr Ala Ser Gly Pro Arg Cys Phe Cys
    1355                1360                1365

Pro Ser Pro Arg Asp Cys Glu Ser Gly Cys Ala Ser Ser Pro Cys
    1370                1375                1380

Gln His Gly Gly Ser Cys His Pro Gln Arg Gln Pro Pro Tyr Tyr
    1385                1390                1395

Ser Cys Gln Cys Ala Pro Pro Phe Ser Gly Ser Arg Cys Glu Leu
    1400                1405                1410

Tyr Thr Ala Pro Pro Ser Thr Pro Pro Ala Thr Cys Leu Ser Gln
    1415                1420                1425

Tyr Cys Ala Asp Lys Ala Arg Asp Gly Val Cys Asp Glu Ala Cys
    1430                1435                1440

Asn Ser His Ala Cys Gln Trp Asp Gly Gly Asp Cys Ser Leu Thr
    1445                1450                1455

Met Glu Asn Pro Trp Ala Asn Cys Ser Ser Pro Leu Pro Cys Trp
    1460                1465                1470

Asp Tyr Ile Asn Asn Gln Cys Asp Glu Leu Cys Asn Thr Val Glu
    1475                1480                1485

Cys Leu Phe Asp Asn Phe Glu Cys Gln Gly Asn Ser Lys Thr Cys
    1490                1495                1500

Lys Tyr Asp Lys Tyr Cys Ala Asp His Phe Lys Asp Asn His Cys
    1505                1510                1515

Asp Gln Gly Cys Asn Ser Glu Glu Cys Gly Trp Asp Gly Leu Asp
    1520                1525                1530

Cys Ala Ala Asp Gln Pro Glu Asn Leu Ala Glu Gly Thr Leu Val
    1535                1540                1545

Ile Val Val Leu Met Pro Pro Glu Gln Leu Leu Gln Asp Ala Arg
    1550                1555                1560

Ser Phe Leu Arg Ala Leu Gly Thr Leu Leu His Thr Asn Leu Arg
    1565                1570                1575

Ile Lys Arg Asp Ser Gln Gly Glu Leu Met Val Tyr Pro Tyr Tyr
    1580                1585                1590

Gly Glu Lys Ser Ala Ala Met Lys Lys Gln Arg Met Thr Arg Arg
    1595                1600                1605

Ser Leu Pro Gly Glu Gln Glu Gln Glu Val Ala Gly Ser Lys Val
    1610                1615                1620

Phe Leu Glu Ile Asp Asn Arg Gln Cys Val Gln Asp Ser Asp His
    1625                1630                1635

Cys Phe Lys Asn Thr Asp Ala Ala Ala Ala Leu Leu Ala Ser His
    1640                1645                1650

Ala Ile Gln Gly Thr Leu Ser Tyr Pro Leu Val Ser Val Val Ser
    1655                1660                1665

Glu Ser Leu Thr Pro Glu Arg Thr Gln Leu Leu Tyr Leu Leu Ala
```

```
                1670                1675                1680

Val Ala Val Val Ile Ile Leu Phe Ile Ile Leu Leu Gly Val Ile
        1685                1690                1695

Met Ala Lys Arg Lys Arg Val Asp Lys Leu Leu Ser Ser Ile Glu
        1700                1705                1710

Gln Ala Cys Asp Ile Cys Arg Leu Lys Lys Leu Lys Cys Ser Lys
        1715                1720                1725

Glu Lys Pro Lys Cys Ala Lys Cys Leu Lys Asn Asn Trp Glu Cys
        1730                1735                1740

Arg Tyr Ser Pro Lys Thr Lys Arg Ser Pro Leu Thr Arg Ala His
        1745                1750                1755

Leu Thr Glu Val Glu Ser Arg Leu Glu Arg Leu Glu Gln Leu Phe
        1760                1765                1770

Leu Leu Ile Phe Pro Arg Glu Asp Leu Asp Met Ile Leu Lys Met
        1775                1780                1785

Asp Ser Leu Gln Asp Ile Lys Ala Leu Leu Thr Gly Leu Phe Val
        1790                1795                1800

Gln Asp Asn Val Asn Lys Asp Ala Val Thr Asp Arg Leu Ala Ser
        1805                1810                1815

Val Glu Thr Asp Met Pro Leu Thr Leu Arg Gln His Arg Ile Ser
        1820                1825                1830

Ala Thr Ser Ser Ser Glu Glu Ser Ser Asn Lys Gly Gln Arg Gln
        1835                1840                1845

Leu Thr Val Ser Gln Leu Lys Leu Leu Ser Ser Ile Glu Gln Ala
        1850                1855                1860

Cys Pro Lys Lys Lys Arg Lys Val Asp Glu Phe Pro Gly Ile Ser
        1865                1870                1875

Thr Ala Pro Pro Thr Asp Val Ser Leu Gly Asp Glu Leu His Leu
        1880                1885                1890

Asp Gly Glu Asp Val Ala Met Ala His Ala Asp Ala Leu Asp Asp
        1895                1900                1905

Phe Asp Leu Asp Met Leu Gly Asp Gly Asp Ser Pro Gly Pro Gly
        1910                1915                1920

<210> SEQ ID NO 276
<211> LENGTH: 1888
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 276

Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
            20                  25                  30

Leu Ala Gly Pro Gly Ala Ala Ala Pro Pro Cys Leu Asp Gly Ser Pro
        35                  40                  45

Cys Ala Asn Gly Gly Arg Cys Thr Gln Leu Pro Ser Arg Glu Ala Ala
        50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95
```

```
Val Val Ala Gly Thr Ala Arg Phe Ser Cys Arg Cys Pro Arg Gly Phe
            100                 105                 110
Arg Gly Pro Asp Cys Ser Leu Pro Asp Pro Cys Leu Ser Pro Cys
            115                 120                 125
Ala His Gly Ala Arg Cys Ser Val Gly Pro Asp Gly Arg Phe Leu Cys
            130                 135                 140
Ser Cys Pro Pro Gly Tyr Gln Gly Arg Ser Cys Arg Ser Asp Val Asp
145                 150                 155                 160
Glu Cys Arg Val Gly Glu Pro Cys Arg His Gly Gly Thr Cys Leu Asn
                165                 170                 175
Thr Pro Gly Ser Phe Arg Cys Gln Cys Pro Ala Gly Tyr Thr Gly Pro
            180                 185                 190
Leu Cys Glu Asn Pro Ala Val Pro Cys Ala Pro Ser Pro Cys Arg Asn
            195                 200                 205
Gly Gly Thr Cys Arg Gln Ser Gly Asp Leu Thr Tyr Asp Cys Ala Cys
            210                 215                 220
Leu Pro Gly Phe Glu Gly Gln Asn Cys Glu Val Asn Val Asp Asp Cys
225                 230                 235                 240
Pro Gly His Arg Cys Leu Asn Gly Gly Thr Cys Val Asp Gly Val Asn
                245                 250                 255
Thr Tyr Asn Cys Gln Cys Pro Pro Glu Trp Thr Gly Gln Phe Cys Thr
            260                 265                 270
Glu Asp Val Asp Glu Cys Gln Leu Gln Pro Asn Ala Cys His Asn Gly
            275                 280                 285
Gly Thr Cys Phe Asn Thr Leu Gly Gly His Ser Cys Val Cys Val Asn
            290                 295                 300
Gly Trp Thr Gly Glu Ser Cys Ser Gln Asn Ile Asp Asp Cys Ala Thr
305                 310                 315                 320
Ala Val Cys Phe His Gly Ala Thr Cys His Asp Arg Val Ala Ser Phe
                325                 330                 335
Tyr Cys Ala Cys Pro Met Gly Lys Thr Gly Leu Leu Cys His Leu Asp
            340                 345                 350
Asp Ala Cys Val Ser Asn Pro Cys His Glu Asp Ala Ile Cys Asp Thr
            355                 360                 365
Asn Pro Val Asn Gly Arg Ala Ile Cys Thr Cys Pro Pro Gly Phe Thr
            370                 375                 380
Gly Gly Ala Cys Asp Gln Asp Val Asp Glu Cys Ser Ile Gly Ala Asn
385                 390                 395                 400
Pro Cys Glu His Leu Gly Arg Cys Val Asn Thr Gln Gly Ser Phe Leu
                405                 410                 415
Cys Gln Cys Gly Arg Gly Tyr Thr Gly Pro Arg Cys Glu Thr Asp Val
            420                 425                 430
Asn Glu Cys Leu Ser Gly Pro Cys Arg Asn Gln Ala Thr Cys Leu Asp
            435                 440                 445
Arg Ile Gly Gln Phe Thr Cys Ile Cys Met Ala Gly Phe Thr Gly Thr
            450                 455                 460
Tyr Cys Glu Val Asp Ile Asp Glu Cys Gln Ser Ser Pro Cys Val Asn
465                 470                 475                 480
Gly Gly Val Cys Lys Asp Arg Val Asn Gly Phe Ser Cys Thr Cys Pro
                485                 490                 495
Ser Gly Phe Ser Gly Ser Thr Cys Gln Leu Asp Val Asp Glu Cys Ala
            500                 505                 510
```

```
Ser Thr Pro Cys Arg Asn Gly Ala Lys Cys Val Asp Gln Pro Asp Gly
        515                 520                 525

Tyr Glu Cys Arg Cys Ala Glu Gly Phe Glu Gly Thr Leu Cys Asp Arg
    530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
        595                 600                 605

Pro Ser Gly Thr Thr Gly Val Asn Cys Glu Val Asn Ile Asp Asp Cys
    610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
        675                 680                 685

Pro Pro Leu Cys Leu Pro Ser His Pro Cys Ala His Glu Pro Cys
    690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
        755                 760                 765

Cys Glu Leu Leu Ser Pro Cys Thr Pro Asn Pro Cys Glu His Gly Gly
    770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
        835                 840                 845

Asp Ile Asn Asp Cys Asp Pro Asn Pro Cys Leu Asn Gly Gly Ser Cys
    850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
        915                 920                 925

Ser Pro Ser Ser Cys Phe Asn Gly Gly Thr Cys Val Asp Gly Val Asn
```

```
                  930            935              940
Ser Phe Ser Cys Leu Cys Arg Pro Gly Tyr Thr Gly Ala His Cys Gln
945                 950              955                 960

His Glu Ala Asp Pro Cys Leu Ser Arg Pro Cys Leu His Gly Gly Val
                965              970              975

Cys Ser Ala Ala His Pro Gly Phe Arg Cys Thr Cys Leu Glu Ser Phe
                980              985              990

Thr Gly Pro Gln Cys Gln Thr Leu Val Asp Trp Cys Ser Arg Gln Pro
                995             1000             1005

Cys Gln Asn Gly Gly Arg Cys Val Gln Thr Gly Ala Tyr Cys Leu
    1010             1015             1020

Cys Pro Pro Gly Trp Ser Gly Arg Leu Cys Asp Ile Arg Ser Leu
    1025             1030             1035

Pro Cys Arg Glu Ala Ala Ala Gln Ile Gly Val Arg Leu Glu Gln
    1040             1045             1050

Leu Cys Gln Ala Gly Gly Gln Cys Val Asp Glu Asp Ser Ser His
    1055             1060             1065

Tyr Cys Val Cys Pro Glu Gly Arg Thr Gly Ser His Cys Glu Gln
    1070             1075             1080

Glu Val Asp Pro Cys Leu Ala Gln Pro Cys Gln His Gly Gly Thr
    1085             1090             1095

Cys Arg Gly Tyr Met Gly Gly Tyr Met Cys Glu Cys Leu Pro Gly
    1100             1105             1110

Tyr Asn Gly Asp Asn Cys Glu Asp Val Asp Glu Cys Ala Ser
    1115             1120             1125

Gln Pro Cys Gln His Gly Gly Ser Cys Ile Asp Leu Val Ala Arg
    1130             1135             1140

Tyr Leu Cys Ser Cys Pro Pro Gly Thr Leu Gly Val Leu Cys Glu
    1145             1150             1155

Ile Asn Glu Asp Asp Cys Gly Pro Gly Pro Pro Leu Asp Ser Gly
    1160             1165             1170

Pro Arg Cys Leu His Asn Gly Thr Cys Val Asp Leu Val Gly Gly
    1175             1180             1185

Phe Arg Cys Thr Cys Pro Pro Gly Tyr Thr Gly Leu Arg Cys Glu
    1190             1195             1200

Ala Asp Ile Asn Glu Cys Arg Ser Gly Ala Cys His Ala Ala His
    1205             1210             1215

Thr Arg Asp Cys Leu Gln Asp Pro Gly Gly Gly Phe Arg Cys Leu
    1220             1225             1230

Cys His Ala Gly Phe Ser Gly Pro Arg Cys Gln Thr Val Leu Ser
    1235             1240             1245

Pro Cys Glu Ser Gln Pro Cys Gln His Gly Gly Gln Cys Arg Pro
    1250             1255             1260

Ser Pro Gly Pro Gly Gly Leu Thr Phe Thr Cys His Cys Ala
    1265             1270             1275

Gln Pro Phe Trp Gly Pro Arg Cys Glu Arg Val Ala Arg Ser Cys
    1280             1285             1290

Arg Glu Leu Gln Cys Pro Val Gly Val Pro Cys Gln Gln Thr Pro
    1295             1300             1305

Arg Gly Pro Arg Cys Ala Cys Pro Pro Gly Leu Ser Gly Pro Ser
    1310             1315             1320

Cys Arg Ser Phe Pro Gly Ser Pro Pro Gly Ala Ser Asn Ala Ser
    1325             1330             1335
```

```
Cys Ala Ala Ala Pro Cys Leu His Gly Gly Ser Cys Arg Pro Ala
        1340            1345                1350

Pro Leu Ala Pro Phe Phe Arg Cys Ala Cys Ala Gln Gly Trp Thr
        1355            1360                1365

Gly Pro Arg Cys Glu Ala Pro Ala Ala Ala Pro Glu Val Ser Glu
        1370            1375                1380

Glu Pro Arg Cys Pro Arg Ala Ala Cys Gln Ala Lys Arg Gly Asp
        1385            1390                1395

Gln Arg Cys Asp Arg Glu Cys Asn Ser Pro Gly Cys Gly Trp Asp
        1400            1405                1410

Gly Gly Asp Cys Ser Leu Ser Val Gly Asp Pro Trp Arg Gln Cys
        1415            1420                1425

Glu Ala Leu Gln Cys Trp Arg Leu Phe Asn Asn Ser Arg Cys Asp
        1430            1435                1440

Pro Ala Cys Ser Ser Pro Ala Cys Leu Tyr Asp Asn Phe Asp Cys
        1445            1450                1455

His Ala Gly Gly Arg Glu Arg Thr Cys Asn Pro Val Tyr Glu Lys
        1460            1465                1470

Tyr Cys Ala Asp His Phe Ala Asp Gly Arg Cys Asp Gln Gly Cys
        1475            1480                1485

Asn Thr Glu Glu Cys Gly Trp Asp Gly Leu Asp Cys Ala Ser Glu
        1490            1495                1500

Val Pro Ala Leu Leu Ala Arg Gly Val Leu Val Leu Thr Val Leu
        1505            1510                1515

Leu Pro Pro Glu Glu Leu Leu Arg Ser Ser Ala Asp Phe Leu Gln
        1520            1525                1530

Arg Leu Ser Ala Ile Leu Arg Thr Ser Leu Arg Phe Arg Leu Asp
        1535            1540                1545

Ala His Gly Gln Ala Met Val Phe Pro Tyr His Arg Pro Ser Pro
        1550            1555                1560

Gly Ser Glu Pro Arg Ala Arg Arg Glu Leu Ala Pro Glu Val Ile
        1565            1570                1575

Gly Leu Val Val Met Leu Glu Ile Asp Asn Arg Leu Cys Leu Gln
        1580            1585                1590

Ser Pro Glu Asn Asp His Cys Phe Pro Asp Ala Gln Ser Ala Ala
        1595            1600                1605

Asp Tyr Leu Gly Ala Leu Ser Ala Val Glu Arg Leu Asp Phe Pro
        1610            1615                1620

Tyr Pro Leu Arg Asp Val Arg Gly Glu Pro Leu Glu Pro Pro Glu
        1625            1630                1635

Pro Ser Val Pro Leu Leu Pro Leu Leu Val Ala Gly Ala Val Leu
        1640            1645                1650

Leu Leu Val Ile Leu Val Leu Gly Val Met Val Ala Arg Arg Lys
        1655            1660                1665

Arg Val Asp Lys Leu Leu Ser Ser Ile Glu Gln Ala Cys Asp Ile
        1670            1675                1680

Cys Arg Leu Lys Lys Leu Lys Cys Ser Lys Glu Lys Pro Lys Cys
        1685            1690                1695

Ala Lys Cys Leu Lys Asn Asn Trp Glu Cys Arg Tyr Ser Pro Lys
        1700            1705                1710

Thr Lys Arg Ser Pro Leu Thr Arg Ala His Leu Thr Glu Val Glu
        1715            1720                1725
```

```
Ser Arg Leu Glu Arg Leu Glu Gln Leu Phe Leu Leu Ile Phe Pro
    1730                1735                1740

Arg Glu Asp Leu Asp Met Ile Leu Lys Met Asp Ser Leu Gln Asp
    1745                1750                1755

Ile Lys Ala Leu Leu Thr Gly Leu Phe Val Gln Asp Asn Val Asn
    1760                1765                1770

Lys Asp Ala Val Thr Asp Arg Leu Ala Ser Val Glu Thr Asp Met
    1775                1780                1785

Pro Leu Thr Leu Arg Gln His Arg Ile Ser Ala Thr Ser Ser Ser
    1790                1795                1800

Glu Glu Ser Ser Asn Lys Gly Gln Arg Gln Leu Thr Val Ser Lys
    1805                1810                1815

Leu Lys Leu Leu Ser Ser Ile Glu Gln Ala Cys Pro Lys Lys Lys
    1820                1825                1830

Arg Lys Val Asp Glu Phe Pro Gly Ile Ser Thr Ala Pro Pro Thr
    1835                1840                1845

Asp Val Ser Leu Gly Asp Glu Leu His Leu Asp Gly Glu Asp Val
    1850                1855                1860

Ala Met Ala His Ala Asp Ala Leu Asp Asp Phe Asp Leu Asp Met
    1865                1870                1875

Leu Gly Asp Gly Asp Ser Pro Gly Pro Gly
    1880                1885
```

<210> SEQ ID NO 277
<211> LENGTH: 1888
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 277

```
Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
                20                  25                  30

Leu Ala Gly Pro Gly Ala Ala Ala Pro Pro Cys Leu Asp Gly Ser Pro
            35                  40                  45

Cys Ala Asn Gly Gly Arg Cys Thr Gln Leu Pro Ser Arg Glu Ala Ala
    50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
                100                 105                 110

Arg Gly Pro Asp Cys Ser Leu Pro Asp Pro Cys Leu Ser Ser Pro Cys
            115                 120                 125

Ala His Gly Ala Arg Cys Ser Val Gly Pro Asp Gly Arg Phe Leu Cys
130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
```

-continued

```
                180                 185                 190
Leu Cys Glu Asn Pro Ala Val Pro Cys Ala Pro Ser Pro Cys Arg Asn
        195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
        275                 280                 285

Gly Thr Cys Phe Asn Thr Leu Gly Gly His Ser Cys Val Cys Val Asn
    290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
        355                 360                 365

Asn Pro Val Asn Gly Arg Ala Ile Cys Thr Cys Pro Pro Gly Phe Thr
    370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
        435                 440                 445

Arg Ile Gly Gln Phe Thr Cys Ile Cys Met Ala Gly Phe Thr Gly Thr
    450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
        515                 520                 525

Tyr Glu Cys Arg Cys Ala Glu Gly Phe Glu Gly Thr Leu Cys Asp Arg
    530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
        595                 600                 605
```

```
Pro Ser Gly Thr Thr Gly Val Asn Cys Glu Val Asn Ile Asp Asp Cys
    610                 615                 620
Ala Ser Asn Pro Cys Thr Phe Gly Val Cys Arg Asp Gly Ile Asn Arg
625                 630                 635                 640
Tyr Asp Cys Val Cys Gln Pro Gly Phe Thr Gly Pro Leu Cys Asn Val
                645                 650                 655
Glu Ile Asn Glu Cys Ala Ser Ser Pro Cys Gly Glu Gly Ser Cys
            660                 665                 670
Val Asp Gly Glu Asn Gly Phe Arg Cys Leu Cys Pro Pro Gly Ser Leu
        675                 680                 685
Pro Pro Leu Cys Leu Pro Ser His Pro Cys Ala His Glu Pro Cys
690                 695                 700
Ser His Gly Ile Cys Tyr Asp Ala Pro Gly Gly Phe Arg Cys Val Cys
705                 710                 715                 720
Glu Pro Gly Trp Ser Gly Pro Arg Cys Ser Gln Ser Leu Ala Arg Asp
                725                 730                 735
Ala Cys Glu Ser Gln Pro Cys Arg Ala Gly Gly Thr Cys Ser Ser Asp
            740                 745                 750
Gly Met Gly Phe His Cys Thr Cys Pro Pro Gly Val Gln Gly Arg Gln
        755                 760                 765
Cys Glu Leu Leu Ser Pro Cys Thr Pro Asn Pro Cys Glu His Gly Gly
770                 775                 780
Arg Cys Glu Ser Ala Pro Gly Gln Leu Pro Val Cys Ser Cys Pro Gln
785                 790                 795                 800
Gly Trp Gln Gly Pro Arg Cys Gln Asp Val Asp Glu Cys Ala Gly
                805                 810                 815
Pro Ala Pro Cys Gly Pro His Gly Ile Cys Thr Asn Leu Ala Gly Ser
            820                 825                 830
Phe Ser Cys Thr Cys His Gly Gly Tyr Thr Gly Pro Ser Cys Asp Gln
        835                 840                 845
Asp Ile Asn Asp Cys Asp Pro Asn Pro Cys Leu Asn Gly Gly Ser Cys
850                 855                 860
Gln Asp Gly Val Gly Ser Phe Ser Cys Ser Cys Leu Pro Gly Phe Ala
865                 870                 875                 880
Gly Pro Arg Cys Ala Arg Asp Val Asp Glu Cys Leu Ser Asn Pro Cys
                885                 890                 895
Gly Pro Gly Thr Cys Thr Asp His Val Ala Ser Phe Thr Cys Thr Cys
            900                 905                 910
Pro Pro Gly Tyr Gly Gly Phe His Cys Glu Gln Asp Leu Pro Asp Cys
        915                 920                 925
Ser Pro Ser Ser Cys Phe Asn Gly Gly Thr Cys Val Asp Gly Val Asn
930                 935                 940
Ser Phe Ser Cys Leu Cys Arg Pro Gly Tyr Thr Gly Ala His Cys Gln
945                 950                 955                 960
His Glu Ala Asp Pro Cys Leu Ser Arg Pro Cys Leu His Gly Gly Val
                965                 970                 975
Cys Ser Ala Ala His Pro Gly Phe Arg Cys Thr Cys Leu Glu Ser Phe
            980                 985                 990
Thr Gly Pro Gln Cys Gln Thr Leu Val Asp Trp Cys Ser Arg Gln Pro
        995                 1000                1005
Cys Gln Asn Gly Gly Arg Cys Val Gln Thr Gly Ala Tyr Cys Leu
    1010                1015                1020
```

-continued

```
Cys Pro Pro Gly Trp Ser Gly Arg Leu Cys Asp Ile Arg Ser Leu
    1025                1030                1035

Pro Cys Arg Glu Ala Ala Ala Gln Ile Gly Val Arg Leu Glu Gln
    1040                1045                1050

Leu Cys Gln Ala Gly Gly Gln Cys Val Asp Glu Asp Ser Ser His
    1055                1060                1065

Tyr Cys Val Cys Pro Glu Gly Arg Thr Gly Ser His Cys Glu Gln
    1070                1075                1080

Glu Val Asp Pro Cys Leu Ala Gln Pro Cys Gln His Gly Gly Thr
    1085                1090                1095

Cys Arg Gly Tyr Met Gly Gly Tyr Met Cys Glu Cys Leu Pro Gly
    1100                1105                1110

Tyr Asn Gly Asp Asn Cys Glu Asp Val Asp Glu Cys Ala Ser
    1115                1120                1125

Gln Pro Cys Gln His Gly Gly Ser Cys Ile Asp Leu Val Ala Arg
    1130                1135                1140

Tyr Leu Cys Ser Cys Pro Pro Gly Thr Leu Gly Val Leu Cys Glu
    1145                1150                1155

Ile Asn Glu Asp Asp Cys Gly Pro Gly Pro Pro Leu Asp Ser Gly
    1160                1165                1170

Pro Arg Cys Leu His Asn Gly Thr Cys Val Asp Leu Val Gly Gly
    1175                1180                1185

Phe Arg Cys Thr Cys Pro Pro Gly Tyr Thr Gly Leu Arg Cys Glu
    1190                1195                1200

Ala Asp Ile Asn Glu Cys Arg Ser Gly Ala Cys His Ala Ala His
    1205                1210                1215

Thr Arg Asp Cys Leu Gln Asp Pro Gly Gly Gly Phe Arg Cys Leu
    1220                1225                1230

Cys His Ala Gly Phe Ser Gly Pro Arg Cys Gln Thr Val Leu Ser
    1235                1240                1245

Pro Cys Glu Ser Gln Pro Cys Gln His Gly Gly Gln Cys Arg Pro
    1250                1255                1260

Ser Pro Gly Pro Gly Gly Leu Thr Phe Thr Cys His Cys Ala
    1265                1270                1275

Gln Pro Phe Trp Gly Pro Arg Cys Glu Arg Val Ala Arg Ser Cys
    1280                1285                1290

Arg Glu Leu Gln Cys Pro Val Gly Val Pro Cys Gln Gln Thr Pro
    1295                1300                1305

Arg Gly Pro Arg Cys Ala Cys Pro Pro Gly Leu Ser Gly Pro Ser
    1310                1315                1320

Cys Arg Ser Phe Pro Gly Ser Pro Pro Gly Ala Ser Asn Ala Ser
    1325                1330                1335

Cys Ala Ala Ala Pro Cys Leu His Gly Gly Ser Cys Arg Pro Ala
    1340                1345                1350

Pro Leu Ala Pro Phe Phe Arg Cys Ala Cys Ala Gln Gly Trp Thr
    1355                1360                1365

Gly Pro Arg Cys Glu Ala Pro Ala Ala Ala Pro Glu Val Ser Glu
    1370                1375                1380

Glu Pro Arg Cys Pro Arg Ala Ala Cys Gln Ala Lys Arg Gly Asp
    1385                1390                1395

Gln Arg Cys Asp Arg Glu Cys Asn Ser Pro Gly Cys Gly Trp Asp
    1400                1405                1410

Gly Gly Asp Cys Ser Leu Ser Val Gly Asp Pro Trp Arg Gln Cys
```

-continued

```
              1415                1420                1425

Glu  Ala  Leu  Gln  Cys  Trp  Arg  Leu  Phe  Asn  Asn  Ser  Arg  Cys  Asp
              1430                1435                1440

Pro  Ala  Cys  Ser  Ser  Pro  Ala  Cys  Leu  Tyr  Asp  Asn  Phe  Asp  Cys
              1445                1450                1455

His  Ala  Gly  Gly  Arg  Glu  Arg  Thr  Cys  Asn  Pro  Val  Tyr  Glu  Lys
              1460                1465                1470

Tyr  Cys  Ala  Asp  His  Phe  Ala  Asp  Gly  Arg  Cys  Asp  Gln  Asp  Cys
              1475                1480                1485

Asn  Thr  Glu  Glu  Cys  Gly  Trp  Asp  Gly  Leu  Asp  Cys  Ala  Ser  Glu
              1490                1495                1500

Val  Pro  Ala  Leu  Leu  Ala  Arg  Gly  Val  Leu  Val  Leu  Thr  Val  Leu
              1505                1510                1515

Leu  Pro  Pro  Glu  Glu  Leu  Leu  Arg  Ser  Ser  Ala  Asp  Phe  Leu  Gln
              1520                1525                1530

Arg  Leu  Ser  Ala  Ile  Leu  Arg  Thr  Ser  Leu  Arg  Phe  Arg  Leu  Asp
              1535                1540                1545

Ala  His  Gly  Gln  Ala  Met  Val  Phe  Pro  Tyr  His  Arg  Pro  Ser  Pro
              1550                1555                1560

Gly  Ser  Glu  Pro  Arg  Ala  Arg  Arg  Glu  Leu  Ala  Pro  Glu  Val  Ile
              1565                1570                1575

Gly  Ser  Val  Val  Met  Leu  Glu  Ile  Asp  Asn  Arg  Leu  Cys  Leu  Gln
              1580                1585                1590

Ser  Pro  Glu  Asn  Asp  His  Cys  Phe  Pro  Asp  Ala  Gln  Ser  Ala  Ala
              1595                1600                1605

Asp  Tyr  Leu  Gly  Ala  Leu  Ser  Ala  Val  Glu  Arg  Leu  Asp  Phe  Pro
              1610                1615                1620

Tyr  Pro  Leu  Arg  Asp  Val  Arg  Gly  Glu  Pro  Leu  Glu  Pro  Pro  Glu
              1625                1630                1635

Pro  Ser  Val  Pro  Leu  Leu  Pro  Leu  Leu  Val  Ala  Gly  Ala  Val  Leu
              1640                1645                1650

Leu  Leu  Val  Ile  Leu  Val  Leu  Gly  Val  Met  Val  Ala  Arg  Arg  Lys
              1655                1660                1665

Arg  Val  Asp  Lys  Leu  Leu  Ser  Ser  Ile  Glu  Gln  Ala  Cys  Asp  Ile
              1670                1675                1680

Cys  Arg  Leu  Lys  Lys  Leu  Lys  Cys  Ser  Lys  Glu  Lys  Pro  Lys  Cys
              1685                1690                1695

Ala  Lys  Cys  Leu  Lys  Asn  Asn  Trp  Glu  Cys  Arg  Tyr  Ser  Pro  Lys
              1700                1705                1710

Thr  Lys  Arg  Ser  Pro  Leu  Thr  Arg  Ala  His  Leu  Thr  Glu  Val  Glu
              1715                1720                1725

Ser  Arg  Leu  Glu  Arg  Leu  Glu  Gln  Leu  Phe  Leu  Leu  Ile  Phe  Pro
              1730                1735                1740

Arg  Glu  Asp  Leu  Asp  Met  Ile  Leu  Lys  Met  Asp  Ser  Leu  Gln  Asp
              1745                1750                1755

Ile  Lys  Ala  Leu  Leu  Thr  Gly  Leu  Phe  Val  Gln  Asp  Asn  Val  Asn
              1760                1765                1770

Lys  Asp  Ala  Val  Thr  Asp  Arg  Leu  Ala  Ser  Val  Glu  Thr  Asp  Met
              1775                1780                1785

Pro  Leu  Thr  Leu  Arg  Gln  His  Arg  Ile  Ser  Ala  Thr  Ser  Ser  Ser
              1790                1795                1800

Glu  Glu  Ser  Ser  Asn  Lys  Gly  Gln  Arg  Gln  Leu  Thr  Val  Ser  Lys
              1805                1810                1815
```

```
Leu Lys Leu Leu Ser Ser Ile Glu Gln Ala Cys Pro Lys Lys Lys
    1820                1825                1830

Arg Lys Val Asp Glu Phe Pro Gly Ile Ser Thr Ala Pro Pro Thr
    1835                1840                1845

Asp Val Ser Leu Gly Asp Glu Leu His Leu Asp Gly Glu Asp Val
    1850                1855                1860

Ala Met Ala His Ala Asp Ala Leu Asp Asp Phe Asp Leu Asp Met
    1865                1870                1875

Leu Gly Asp Gly Asp Ser Pro Gly Pro Gly
    1880                1885

<210> SEQ ID NO 278
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Val Met Val Ala Arg Arg Lys Cys
1               5

<210> SEQ ID NO 279
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Val Ile Leu Val Leu Gly Val Met Val Ala Arg Arg Lys Cys
1               5                   10

<210> SEQ ID NO 280
<211> LENGTH: 295
<212> TYPE: PRT
<213> ORGANISM: Homo sapiens

<400> SEQUENCE: 280

Pro Ser Gly Pro Arg Ser Pro Pro Gly Pro His Gly Leu Gly Pro Leu
1               5                   10                  15

Leu Cys Pro Pro Gly Ala Phe Leu Pro Gly Leu Lys Ala Ala Gln Ser
                20                  25                  30

Gly Ser Lys Lys Ser Arg Arg Pro Pro Gly Lys Ala Gly Leu Gly Pro
            35                  40                  45

Gln Gly Pro Arg Gly Arg Gly Lys Lys Leu Thr Leu Ala Cys Pro Gly
        50                  55                  60

Pro Leu Ala Asp Ser Ser Val Thr Leu Ser Pro Val Asp Ser Leu Asp
65                  70                  75                  80

Ser Pro Arg Pro Phe Gly Gly Pro Pro Ala Ser Pro Gly Phe Pro
                85                  90                  95

Leu Glu Gly Pro Tyr Ala Ala Ala Thr Ala Thr Ala Val Ser Leu Ala
                100                 105                 110

Gln Leu Gly Gly Pro Gly Arg Ala Gly Leu Gly Arg Gln Pro Pro Gly
            115                 120                 125

Gly Cys Val Leu Ser Leu Gly Leu Leu Asn Pro Val Ala Val Pro Leu
```

```
                130                 135                 140
Asp Trp Ala Arg Leu Pro Pro Ala Pro Gly Pro Ser Phe Leu
145                 150                 155                 160

Leu Pro Leu Ala Pro Gly Pro Gln Leu Leu Asn Pro Gly Thr Pro Val
                165                 170                 175

Ser Pro Gln Glu Arg Pro Pro Tyr Leu Ala Val Pro Gly His Gly
            180                 185                 190

Glu Glu Tyr Pro Ala Ala Gly Ala His Ser Ser Pro Lys Ala Arg
            195                 200                 205

Phe Leu Arg Val Pro Ser Glu His Pro Tyr Leu Thr Pro Ser Pro Glu
                210                 215                 220

Ser Pro Glu His Trp Ala Ser Pro Ser Pro Ser Leu Ser Asp Trp
225                 230                 235                 240

Ser Glu Ser Thr Pro Ser Pro Ala Thr Ala Thr Gly Ala Met Ala Thr
                245                 250                 255

Thr Thr Gly Ala Leu Pro Ala Gln Pro Leu Pro Leu Ser Val Pro Ser
                260                 265                 270

Ser Leu Ala Gln Ala Gln Thr Gln Leu Gly Pro Gln Pro Glu Val Thr
                275                 280                 285

Pro Lys Arg Gln Val Leu Ala
    290                 295

<210> SEQ ID NO 281
<211> LENGTH: 67
<212> TYPE: PRT
<213> ORGANISM: Homo sapiens

<400> SEQUENCE: 281

Pro Ser Gly Pro Arg Ser Pro Arg Ser Pro Arg Pro Gly Ala Ser
1               5                   10                  15

Ala Leu Ser Ser Arg Gly Leu Pro Pro Trp Pro Gln Ser Gly Thr Val
                20                  25                  30

Gly Val Gln Glu Gln Glu Ala Pro Arg Glu Gly Ala Gly Ala
            35                  40                  45

Ala Gly Ala Pro Gly Ala Gly Gln Glu Ala Asp Ala Gly Leu Pro Gly
        50                  55                  60

Pro Pro Gly
65

<210> SEQ ID NO 282
<211> LENGTH: 291
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 282

Met Glu Thr Asp Thr Leu Leu Leu Trp Val Leu Leu Trp Val Pro
1               5                   10                  15

Gly Ser Thr Gly Ala Pro Glu Val Ser Glu Glu Pro Arg Cys Pro Arg
                20                  25                  30

Ala Ala Cys Gln Ala Lys Arg Gly Asp Gln Arg Cys Asp Arg Glu Cys
            35                  40                  45

Asn Ser Pro Gly Cys Gly Trp Asp Gly Gly Asp Cys Ser Leu Ser Val
        50                  55                  60
```

Gly Asp Pro Trp Arg Gln Cys Glu Ala Leu Gln Cys Trp Arg Leu Phe
65                  70                  75                  80

Asn Asn Ser Arg Cys Asp Pro Ala Cys Ser Pro Ala Cys Leu Tyr
            85                  90                  95

Asp Asn Phe Asp Cys His Ala Gly Arg Glu Arg Thr Cys Asn Pro
            100                 105                 110

Val Tyr Glu Lys Tyr Cys Ala Asp His Phe Ala Asp Gly Arg Cys Asp
            115                 120                 125

Gln Gly Cys Asn Thr Glu Glu Cys Gly Trp Asp Gly Leu Asp Cys Ala
            130                 135                 140

Ser Glu Val Pro Ala Leu Leu Ala Arg Gly Val Leu Val Leu Thr Val
145                 150                 155                 160

Leu Leu Pro Pro Glu Glu Leu Leu Arg Ser Ser Ala Asp Phe Leu Gln
                165                 170                 175

Arg Leu Ser Ala Ile Leu Arg Thr Ser Leu Arg Phe Arg Leu Asp Ala
            180                 185                 190

His Gly Gln Ala Met Val Phe Pro Tyr His Arg Pro Ser Pro Gly Ser
            195                 200                 205

Glu Pro Arg Ala Arg Arg Glu Leu Ala Pro Glu Val Ile Gly Ser Val
            210                 215                 220

Val Met Leu Glu Ile Asp Asn Arg Leu Cys Leu Gln Ser Pro Glu Asn
225                 230                 235                 240

Asp His Cys Phe Pro Asp Ala Gln Ser Ala Ala Asp Tyr Leu Gly Ala
                245                 250                 255

Leu Ser Ala Val Glu Arg Leu Asp Phe Pro Tyr Pro Leu Arg Asp Val
            260                 265                 270

Arg Gly Glu Pro Leu Glu Pro Pro Glu Pro Ser Gly Ser His His His
            275                 280                 285

His His His
      290

<210> SEQ ID NO 283
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 283

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
            35                  40                  45

Gly Trp Ile Lys Pro Arg Trp Gly Ala Ala His Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Ser Phe Trp Phe Gly Tyr Trp Gly Gln Gly Thr Leu Val
            100                 105                 110

Thr Val Ser Ser Ala Ser Thr Lys Gly Pro Ser Val Phe Pro Leu Ala

```
                    115                 120                 125
Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His
210                 215                 220
```

<210> SEQ ID NO 284
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 284

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gln Tyr Pro Met
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 285
<211> LENGTH: 226
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 285

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Thr Tyr
            20                  25                  30

Ala Met His Trp Val Arg Gln Ala Pro Gly Gln Gly Leu Glu Trp Met
        35                  40                  45

Gly Gly Ile Val Pro Tyr His Gly Ile Thr Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Ser Thr Tyr Ala Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His
225

<210> SEQ ID NO 286
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 286

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ala Tyr Lys Thr Pro Tyr
             85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130             135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 287
<211> LENGTH: 2318
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 287

```
Met Gly Leu Gly Ala Arg Gly Arg Arg Arg Arg Arg Leu Met Ala
1                5                  10                  15

Leu Pro Pro Pro Pro Pro Met Arg Ala Leu Pro Leu Leu Leu Leu
                 20                  25                  30

Leu Ala Gly Leu Gly Ala Ala Ala Pro Pro Cys Leu Asp Gly Ser Pro
            35                  40                  45

Cys Ala Asn Gly Gly Arg Cys Thr His Gln Gln Pro Ser Leu Glu Ala
50                  55                  60

Ala Cys Leu Cys Leu Pro Gly Trp Val Gly Glu Arg Cys Gln Leu Glu
65                  70                  75                  80

Asp Pro Cys His Ser Gly Pro Cys Ala Gly Arg Gly Val Cys Gln Ser
                85                  90                  95

Ser Val Val Ala Gly Thr Ala Arg Phe Ser Cys Arg Cys Leu Arg Gly
            100                 105                 110

Phe Gln Gly Pro Asp Cys Ser Gln Pro Asp Pro Cys Val Ser Arg Pro
            115                 120                 125

Cys Val His Gly Ala Pro Cys Ser Val Gly Pro Asp Gly Arg Phe Ala
130                 135                 140

Cys Ala Cys Pro Pro Gly Tyr Gln Gly Gln Ser Cys Gln Ser Asp Ile
145                 150                 155                 160

Asp Glu Cys Arg Ser Gly Thr Thr Cys Arg His Gly Gly Thr Cys Leu
                165                 170                 175

Asn Thr Pro Gly Ser Phe Arg Cys Gln Cys Pro Leu Gly Tyr Thr Gly
            180                 185                 190

Leu Leu Cys Glu Asn Pro Val Val Pro Cys Ala Pro Ser Pro Cys Arg
            195                 200                 205

Asn Gly Gly Thr Cys Arg Gln Ser Ser Asp Val Thr Tyr Asp Cys Ala
```

```
            210                 215                 220
Cys Leu Pro Gly Phe Glu Gly Gln Asn Cys Glu Val Asn Val Asp Asp
225                 230                 235                 240

Cys Pro Gly His Arg Cys Leu Asn Gly Gly Thr Cys Val Asp Gly Val
                    245                 250                 255

Asn Thr Tyr Asn Cys Gln Cys Pro Pro Glu Trp Thr Gly Gln Phe Cys
                260                 265                 270

Thr Glu Asp Val Asp Glu Cys Gln Leu Gln Pro Asn Ala Cys His Asn
            275                 280                 285

Gly Gly Thr Cys Phe Asn Leu Leu Gly Gly His Ser Cys Val Cys Val
        290                 295                 300

Asn Gly Trp Thr Gly Glu Ser Cys Ser Gln Asn Ile Asp Asp Cys Ala
305                 310                 315                 320

Thr Ala Val Cys Phe His Gly Ala Thr Cys His Asp Arg Val Ala Ser
                325                 330                 335

Phe Tyr Cys Ala Cys Pro Met Gly Lys Thr Gly Leu Leu Cys His Leu
                340                 345                 350

Asp Asp Ala Cys Val Ser Asn Pro Cys His Glu Asp Ala Ile Cys Asp
            355                 360                 365

Thr Asn Pro Val Ser Gly Arg Ala Ile Cys Thr Cys Pro Pro Gly Phe
        370                 375                 380

Thr Gly Gly Ala Cys Asp Gln Asp Val Asp Glu Cys Ser Ile Gly Ala
385                 390                 395                 400

Asn Pro Cys Glu His Leu Gly Arg Cys Val Asn Thr Gln Gly Ser Phe
                    405                 410                 415

Leu Cys Gln Cys Gly Arg Gly Tyr Thr Gly Pro Arg Cys Glu Thr Asp
                420                 425                 430

Val Asn Glu Cys Leu Ser Gly Pro Cys Arg Asn Gln Ala Thr Cys Leu
            435                 440                 445

Asp Arg Ile Gly Gln Phe Thr Cys Ile Cys Met Ala Gly Phe Thr Gly
450                 455                 460

Thr Tyr Cys Glu Val Asp Ile Asp Glu Cys Gln Ser Ser Pro Cys Val
465                 470                 475                 480

Asn Gly Gly Val Cys Lys Asp Arg Val Asn Gly Phe Ser Cys Thr Cys
                    485                 490                 495

Pro Ser Gly Phe Ser Gly Ser Met Cys Gln Leu Asp Val Asp Glu Cys
                500                 505                 510

Ala Ser Thr Pro Cys Arg Asn Gly Ala Lys Cys Val Asp Gln Pro Asp
            515                 520                 525

Gly Tyr Glu Cys Arg Cys Ala Glu Gly Phe Glu Gly Thr Leu Cys Glu
        530                 535                 540

Arg Asn Val Asp Asp Cys Ser Pro Asp Pro Cys His His Gly Arg Cys
545                 550                 555                 560

Val Asp Gly Ile Ala Ser Phe Ser Cys Ala Cys Ala Pro Gly Tyr Thr
                565                 570                 575

Gly Ile Arg Cys Glu Ser Gln Val Asp Glu Cys Arg Ser Gln Pro Cys
                580                 585                 590

Arg Tyr Gly Gly Lys Cys Leu Asp Leu Val Asp Lys Tyr Leu Cys Arg
                595                 600                 605

Cys Pro Pro Gly Thr Thr Gly Val Asn Cys Glu Val Asn Ile Asp Asp
610                 615                 620

Cys Ala Ser Asn Pro Cys Thr Phe Gly Val Cys Arg Asp Gly Ile Asn
625                 630                 635                 640
```

-continued

```
Arg Tyr Asp Cys Val Cys Gln Pro Gly Phe Thr Gly Pro Leu Cys Asn
                645                 650                 655

Val Glu Ile Asn Glu Cys Ala Ser Ser Pro Cys Gly Glu Gly Gly Ser
            660                 665                 670

Cys Val Asp Gly Glu Asn Gly Phe His Cys Leu Cys Pro Pro Gly Ser
        675                 680                 685

Leu Pro Pro Leu Cys Leu Pro Ala Asn His Pro Cys Ala His Lys Pro
    690                 695                 700

Cys Ser His Gly Val Cys His Asp Ala Pro Gly Gly Phe Arg Cys Val
705                 710                 715                 720

Cys Glu Pro Gly Trp Ser Gly Pro Arg Cys Ser Gln Ser Leu Ala Pro
                725                 730                 735

Asp Ala Cys Glu Ser Gln Pro Cys Gln Ala Gly Gly Thr Cys Thr Ser
            740                 745                 750

Asp Gly Ile Gly Phe Arg Cys Thr Cys Ala Pro Gly Phe Gln Gly His
        755                 760                 765

Gln Cys Glu Val Leu Ser Pro Cys Thr Pro Ser Leu Cys Glu His Gly
    770                 775                 780

Gly His Cys Glu Ser Asp Pro Asp Arg Leu Thr Val Cys Ser Cys Pro
785                 790                 795                 800

Pro Gly Trp Gln Gly Pro Arg Cys Gln Gln Asp Val Asp Glu Cys Ala
                805                 810                 815

Gly Ala Ser Pro Cys Gly Pro His Gly Thr Cys Thr Asn Leu Pro Gly
            820                 825                 830

Asn Phe Arg Cys Ile Cys His Arg Gly Tyr Thr Gly Pro Phe Cys Asp
        835                 840                 845

Gln Asp Ile Asp Asp Cys Asp Pro Asn Pro Cys Leu His Gly Gly Ser
    850                 855                 860

Cys Gln Asp Gly Val Gly Ser Phe Ser Cys Ser Cys Leu Asp Gly Phe
865                 870                 875                 880

Ala Gly Pro Arg Cys Ala Arg Asp Val Asp Glu Cys Leu Ser Ser Pro
                885                 890                 895

Cys Gly Pro Gly Thr Cys Thr Asp His Val Ala Ser Phe Thr Cys Ala
            900                 905                 910

Cys Pro Pro Gly Tyr Gly Gly Phe His Cys Glu Ile Asp Leu Pro Asp
        915                 920                 925

Cys Ser Pro Ser Ser Cys Phe Asn Gly Gly Thr Cys Val Asp Gly Val
    930                 935                 940

Ser Ser Phe Ser Cys Leu Cys Arg Pro Gly Tyr Thr Gly Thr His Cys
945                 950                 955                 960

Gln Tyr Glu Ala Asp Pro Cys Phe Ser Arg Pro Cys Leu His Gly Gly
                965                 970                 975

Ile Cys Asn Pro Thr His Pro Gly Phe Glu Cys Thr Cys Arg Glu Gly
            980                 985                 990

Phe Thr Gly Ser Gln Cys Gln Asn  Pro Val Asp Trp Cys  Ser Gln Ala
        995                 1000                1005

Pro Cys  Gln Asn Gly Gly Arg  Cys Val Gln Thr Gly  Ala Tyr Cys
    1010                1015                1020

Ile Cys  Pro Pro Gly Trp Ser  Gly Arg Leu Cys Asp  Ile Gln Ser
    1025                1030                1035

Leu Pro  Cys Thr Glu Ala Ala  Ala Gln Met Gly Val  Arg Leu Glu
    1040                1045                1050
```

-continued

```
Gln Leu Cys Gln Glu Gly Gly Lys Cys Ile Asp Lys Gly Arg Ser
    1055                1060                1065

His Tyr Cys Val Cys Pro Glu Gly Arg Thr Gly Ser His Cys Glu
    1070                1075                1080

His Glu Val Asp Pro Cys Thr Ala Gln Pro Cys Gln His Gly Gly
    1085                1090                1095

Thr Cys Arg Gly Tyr Met Gly Gly Tyr Val Cys Glu Cys Pro Ala
    1100                1105                1110

Gly Tyr Ala Gly Asp Ser Cys Glu Asp Asn Ile Asp Glu Cys Ala
    1115                1120                1125

Ser Gln Pro Cys Gln Asn Gly Gly Ser Cys Ile Asp Leu Val Ala
    1130                1135                1140

Arg Tyr Leu Cys Ser Cys Pro Pro Gly Thr Leu Gly Val Leu Cys
    1145                1150                1155

Glu Ile Asn Glu Asp Asp Cys Asp Leu Gly Pro Ser Leu Asp Ser
    1160                1165                1170

Gly Val Gln Cys Leu His Asn Gly Thr Cys Val Asp Leu Val Gly
    1175                1180                1185

Gly Phe Arg Cys Asn Cys Pro Pro Gly Tyr Thr Gly Leu His Cys
    1190                1195                1200

Glu Ala Asp Ile Asn Glu Cys Arg Pro Gly Ala Cys His Ala Ala
    1205                1210                1215

His Thr Arg Asp Cys Leu Gln Asp Pro Gly Gly His Phe Arg Cys
    1220                1225                1230

Val Cys His Pro Gly Phe Thr Gly Pro Arg Cys Gln Ile Ala Leu
    1235                1240                1245

Ser Pro Cys Glu Ser Gln Pro Cys Gln His Gly Gly Gln Cys Arg
    1250                1255                1260

His Ser Leu Gly Arg Gly Gly Leu Thr Phe Thr Cys His Cys
    1265                1270                1275

Val Pro Pro Phe Trp Gly Leu Arg Cys Glu Arg Val Ala Arg Ser
    1280                1285                1290

Cys Arg Glu Leu Gln Cys Pro Val Gly Ile Pro Cys Gln Gln Thr
    1295                1300                1305

Ala Arg Gly Pro Arg Cys Ala Cys Pro Pro Gly Leu Ser Gly Pro
    1310                1315                1320

Ser Cys Arg Val Ser Arg Ala Ser Pro Ser Gly Ala Thr Asn Ala
    1325                1330                1335

Ser Cys Ala Ser Ala Pro Cys Leu His Gly Gly Ser Cys Leu Pro
    1340                1345                1350

Val Gln Ser Val Pro Phe Arg Cys Val Cys Ala Pro Gly Trp
    1355                1360                1365

Gly Gly Pro Arg Cys Glu Thr Pro Ser Ala Ala Pro Glu Val Pro
    1370                1375                1380

Glu Glu Pro Arg Cys Pro Arg Ala Ala Cys Gln Ala Lys Arg Gly
    1385                1390                1395

Asp Gln Asn Cys Asp Arg Glu Cys Asn Thr Pro Gly Cys Gly Trp
    1400                1405                1410

Asp Gly Gly Asp Cys Ser Leu Asn Val Asp Asp Pro Trp Arg Gln
    1415                1420                1425

Cys Glu Ala Leu Gln Cys Trp Arg Leu Phe Asn Asn Ser Arg Cys
    1430                1435                1440

Asp Pro Ala Cys Ser Ser Pro Ala Cys Leu Tyr Asp Asn Phe Asp
```

```
                1445                1450                1455
Cys Tyr Ser Gly Gly Arg Asp Arg Thr Cys Asn Pro Val Tyr Glu
    1460                1465                1470

Lys Tyr Cys Ala Asp His Phe Ala Asp Gly Arg Cys Asp Gln Gly
    1475                1480                1485

Cys Asn Thr Glu Glu Cys Gly Trp Asp Gly Leu Asp Cys Ala Ser
    1490                1495                1500

Glu Val Pro Ala Leu Ala Arg Gly Val Leu Leu Thr Val
    1505                1510                1515

Leu Leu Pro Pro Glu Glu Leu Leu Arg Ser Ser Ala Asp Phe Leu
    1520                1525                1530

Gln Arg Leu Ser Ala Ile Leu Arg Thr Ser Leu Arg Phe Arg Leu
    1535                1540                1545

Asp Ala Arg Gly Gln Ala Met Val Phe Pro Tyr His Arg Pro Ser
    1550                1555                1560

Pro Gly Ser Glu Ser Arg Val Arg Arg Glu Leu Gly Pro Glu Val
    1565                1570                1575

Ile Gly Ser Val Val Met Leu Glu Ile Asp Asn Arg Leu Cys Leu
    1580                1585                1590

Gln Ser Ala Glu Asn Asp His Cys Phe Pro Asp Ala Gln Ser Ala
    1595                1600                1605

Ala Asp Tyr Leu Gly Ala Leu Ser Ala Val Glu Arg Leu Asp Phe
    1610                1615                1620

Pro Tyr Pro Leu Arg Asp Val Arg Gly Glu Pro Leu Glu Ala Pro
    1625                1630                1635

Glu Gln Ser Val Pro Leu Leu Pro Leu Leu Val Ala Gly Ala Val
    1640                1645                1650

Phe Leu Leu Ile Ile Phe Ile Leu Gly Val Met Val Ala Arg Arg
    1655                1660                1665

Lys Arg Glu His Ser Thr Leu Trp Phe Pro Glu Gly Phe Ala Leu
    1670                1675                1680

His Lys Asp Ile Ala Ala Gly His Lys Gly Arg Arg Glu Pro Val
    1685                1690                1695

Gly Gln Asp Ala Leu Gly Met Lys Asn Met Ala Lys Gly Glu Ser
    1700                1705                1710

Leu Met Gly Glu Val Val Thr Asp Leu Asn Asp Ser Glu Cys Pro
    1715                1720                1725

Glu Ala Lys Arg Leu Lys Val Glu Glu Pro Gly Met Gly Ala Glu
    1730                1735                1740

Glu Pro Glu Asp Cys Arg Gln Trp Thr Gln His His Leu Val Ala
    1745                1750                1755

Ala Asp Ile Arg Val Ala Pro Ala Thr Ala Leu Thr Pro Pro Gln
    1760                1765                1770

Gly Asp Ala Asp Ala Asp Gly Val Asp Val Asn Val Arg Gly Pro
    1775                1780                1785

Asp Gly Phe Thr Pro Leu Met Leu Ala Ser Phe Cys Gly Gly Ala
    1790                1795                1800

Leu Glu Pro Met Pro Ala Glu Glu Asp Glu Ala Asp Asp Thr Ser
    1805                1810                1815

Ala Ser Ile Ile Ser Asp Leu Ile Cys Gln Gly Ala Gln Leu Gly
    1820                1825                1830

Ala Arg Thr Asp Arg Thr Gly Glu Thr Ala Leu His Leu Ala Ala
    1835                1840                1845
```

```
Arg Tyr Ala Arg Ala Asp Ala Ala Lys Arg Leu Leu Asp Ala Gly
1850            1855                1860

Ala Asp Thr Asn Ala Gln Asp His Ser Gly Arg Thr Pro Leu His
1865            1870                1875

Thr Ala Val Thr Ala Asp Ala Gln Gly Val Phe Gln Ile Leu Ile
1880            1885                1890

Arg Asn Arg Ser Thr Asp Leu Asp Ala Arg Met Ala Asp Gly Ser
1895            1900                1905

Thr Ala Leu Ile Leu Ala Ala Arg Leu Ala Val Glu Gly Met Val
1910            1915                1920

Glu Glu Leu Ile Ala Ser His Ala Asp Val Asn Ala Val Asp Glu
1925            1930                1935

Leu Gly Lys Ser Ala Leu His Trp Ala Ala Val Asn Asn Val
1940            1945                1950

Glu Ala Thr Leu Ala Leu Leu Lys Asn Gly Ala Asn Lys Asp Met
1955            1960                1965

Gln Asp Ser Lys Glu Glu Thr Pro Leu Phe Leu Ala Ala Arg Glu
1970            1975                1980

Gly Ser Tyr Glu Ala Ala Lys Leu Leu Leu Asp His Leu Ala Asn
1985            1990                1995

Arg Glu Ile Thr Asp His Leu Asp Arg Leu Pro Arg Asp Val Ala
2000            2005                2010

Gln Glu Arg Leu His Gln Asp Ile Val Arg Leu Leu Asp Gln Pro
2015            2020                2025

Ser Gly Pro Arg Ser Pro Ser Gly Pro His Gly Leu Gly Pro Leu
2030            2035                2040

Leu Cys Pro Pro Gly Ala Phe Leu Pro Gly Leu Lys Ala Val Gln
2045            2050                2055

Ser Gly Thr Lys Lys Ser Arg Arg Pro Pro Gly Lys Thr Gly Leu
2060            2065                2070

Gly Pro Gln Gly Thr Arg Gly Arg Gly Lys Lys Leu Thr Leu Ala
2075            2080                2085

Cys Pro Gly Pro Leu Ala Asp Ser Ser Val Thr Leu Ser Pro Val
2090            2095                2100

Asp Ser Leu Asp Ser Pro Arg Pro Phe Ser Gly Pro Pro Ala Ser
2105            2110                2115

Pro Gly Gly Phe Pro Leu Glu Gly Pro Tyr Ala Thr Thr Ala Thr
2120            2125                2130

Ala Val Ser Leu Ala Gln Leu Gly Ala Ser Arg Ala Gly Pro Leu
2135            2140                2145

Gly Arg Gln Pro Pro Gly Gly Cys Val Leu Ser Phe Gly Leu Leu
2150            2155                2160

Asn Pro Val Ala Val Pro Leu Asp Trp Ala Arg Leu Pro Pro Pro
2165            2170                2175

Ala Pro Pro Gly Pro Ser Phe Leu Leu Pro Leu Ala Pro Gly Pro
2180            2185                2190

Gln Leu Leu Asn Pro Gly Ala Pro Val Ser Pro Gln Glu Arg Pro
2195            2200                2205

Pro Pro Tyr Leu Ala Ala Pro Gly His Gly Glu Glu Tyr Pro Ala
2210            2215                2220

Ala Gly Thr Arg Ser Ser Pro Thr Lys Ala Arg Phe Leu Arg Val
2225            2230                2235
```

```
Pro Ser Glu His Pro Tyr Leu Thr Ser Pro Glu Ser Pro Glu
    2240            2245            2250

His Trp Ala Ser Pro Ser Pro Pro Ser Leu Ser Asp Trp Ser Asp
    2255            2260            2265

Ser Thr Pro Ser Pro Ala Thr Ala Thr Asn Ala Thr Ala Ser Gly
    2270            2275            2280

Ala Leu Pro Ala Gln Pro His Pro Ile Ser Val Pro Ser Leu Pro
    2285            2290            2295

Gln Ser Gln Thr Gln Leu Gly Pro Gln Pro Glu Val Thr Pro Lys
    2300            2305            2310

Arg Gln Val Met Ala
    2315

<210> SEQ ID NO 288
<211> LENGTH: 2318
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 288

Met Gly Leu Gly Ala Arg Gly Arg Arg Arg Arg Leu Met Ala
1               5                   10                  15

Leu Pro Pro Pro Pro Pro Met Arg Ala Leu Pro Leu Leu Leu
                20                  25                  30

Leu Ala Gly Leu Gly Ala Ala Pro Pro Cys Leu Asp Gly Ser Pro
                35                  40                  45

Cys Ala Asn Gly Gly Arg Cys Thr His Gln Gln Pro Ser Leu Glu Ala
    50                  55                  60

Ala Cys Leu Cys Leu Pro Gly Trp Val Gly Glu Arg Cys Gln Leu Glu
65                  70                  75                  80

Asp Pro Cys His Ser Gly Pro Cys Ala Gly Arg Gly Val Cys Gln Ser
                85                  90                  95

Ser Val Val Ala Gly Thr Ala Arg Phe Ser Cys Arg Cys Leu Arg Gly
                100                 105                 110

Phe Gln Gly Pro Asp Cys Ser Gln Pro Asp Pro Cys Val Ser Arg Pro
                115                 120                 125

Cys Val His Gly Ala Pro Cys Ser Val Gly Pro Asp Gly Arg Phe Ala
    130                 135                 140

Cys Ala Cys Pro Pro Gly Tyr Gln Gly Gln Ser Cys Gln Ser Asp Ile
145                 150                 155                 160

Asp Glu Cys Arg Ser Gly Thr Thr Cys Arg His Gly Gly Thr Cys Leu
                165                 170                 175

Asn Thr Pro Gly Ser Phe Arg Cys Gln Cys Pro Leu Gly Tyr Thr Gly
                180                 185                 190

Leu Leu Cys Glu Asn Pro Val Val Pro Cys Ala Pro Ser Pro Cys Arg
                195                 200                 205

Asn Gly Gly Thr Cys Arg Gln Ser Ser Asp Val Thr Tyr Asp Cys Ala
    210                 215                 220

Cys Leu Pro Gly Phe Glu Gly Gln Asn Cys Glu Val Asn Val Asp Asp
225                 230                 235                 240

Cys Pro Gly His Arg Cys Leu Asn Gly Gly Thr Cys Val Asp Gly Val
                245                 250                 255

Asn Thr Tyr Asn Cys Gln Cys Pro Pro Glu Trp Thr Gly Gln Phe Cys
```

```
            260                 265                 270
Thr Glu Asp Val Asp Glu Cys Gln Leu Gln Pro Asn Ala Cys His Asn
            275                 280                 285
Gly Gly Thr Cys Phe Asn Leu Leu Gly Gly His Ser Cys Val Cys Val
            290                 295                 300
Asn Gly Trp Thr Gly Glu Ser Cys Ser Gln Asn Ile Asp Asp Cys Ala
305                 310                 315                 320
Thr Ala Val Cys Phe His Gly Ala Thr Cys His Asp Arg Val Ala Ser
                    325                 330                 335
Phe Tyr Cys Ala Cys Pro Met Gly Lys Thr Gly Leu Leu Cys His Leu
                340                 345                 350
Asp Asp Ala Cys Val Ser Asn Pro Cys His Glu Asp Ala Ile Cys Asp
            355                 360                 365
Thr Asn Pro Val Ser Gly Arg Ala Ile Cys Thr Cys Pro Pro Gly Phe
            370                 375                 380
Thr Gly Gly Ala Cys Asp Gln Asp Val Asp Glu Cys Ser Ile Gly Ala
385                 390                 395                 400
Asn Pro Cys Glu His Leu Gly Arg Cys Val Asn Thr Gln Gly Ser Phe
                    405                 410                 415
Leu Cys Gln Cys Gly Arg Gly Tyr Thr Gly Pro Arg Cys Glu Thr Asp
                420                 425                 430
Val Asn Glu Cys Leu Ser Gly Pro Cys Arg Asn Gln Ala Thr Cys Leu
            435                 440                 445
Asp Arg Ile Gly Gln Phe Thr Cys Ile Cys Met Ala Gly Phe Thr Gly
            450                 455                 460
Thr Tyr Cys Glu Val Asp Ile Asp Glu Cys Gln Ser Ser Pro Cys Val
465                 470                 475                 480
Asn Gly Gly Val Cys Lys Asp Arg Val Asn Gly Phe Ser Cys Thr Cys
                    485                 490                 495
Pro Ser Gly Phe Ser Gly Ser Met Cys Gln Leu Asp Val Asp Glu Cys
                500                 505                 510
Ala Ser Thr Pro Cys Arg Asn Gly Ala Lys Cys Val Asp Gln Pro Asp
            515                 520                 525
Gly Tyr Glu Cys Arg Cys Ala Glu Gly Phe Glu Gly Thr Leu Cys Glu
            530                 535                 540
Arg Asn Val Asp Asp Cys Ser Pro Asp Pro Cys His His Gly Arg Cys
545                 550                 555                 560
Val Asp Gly Ile Ala Ser Phe Ser Cys Ala Cys Ala Pro Gly Tyr Thr
                    565                 570                 575
Gly Ile Arg Cys Glu Ser Gln Val Asp Glu Cys Arg Ser Gln Pro Cys
                580                 585                 590
Arg Tyr Gly Gly Lys Cys Leu Asp Leu Val Asp Lys Tyr Leu Cys Arg
            595                 600                 605
Cys Pro Pro Gly Thr Thr Gly Val Asn Cys Glu Val Asn Ile Asp Asp
            610                 615                 620
Cys Ala Ser Asn Pro Cys Thr Phe Gly Val Cys Arg Asp Gly Ile Asn
625                 630                 635                 640
Arg Tyr Asp Cys Val Cys Gln Pro Gly Phe Thr Gly Pro Leu Cys Asn
                    645                 650                 655
Val Glu Ile Asn Glu Cys Ala Ser Ser Pro Cys Gly Glu Gly Gly Ser
                660                 665                 670
Cys Val Asp Gly Glu Asn Gly Phe His Cys Leu Cys Pro Pro Gly Ser
            675                 680                 685
```

```
Leu Pro Pro Leu Cys Leu Pro Ala Asn His Pro Cys Ala His Lys Pro
    690             695                 700

Cys Ser His Gly Val Cys His Asp Ala Pro Gly Gly Phe Arg Cys Val
705                 710                 715                 720

Cys Glu Pro Gly Trp Ser Gly Pro Arg Cys Ser Gln Ser Leu Ala Pro
                725                 730                 735

Asp Ala Cys Glu Ser Gln Pro Cys Gln Ala Gly Gly Thr Cys Thr Ser
            740                 745                 750

Asp Gly Ile Gly Phe Arg Cys Thr Cys Ala Pro Gly Phe Gln Gly His
        755                 760                 765

Gln Cys Glu Val Leu Ser Pro Cys Thr Pro Ser Leu Cys Glu His Gly
    770                 775                 780

Gly His Cys Glu Ser Asp Pro Asp Arg Leu Thr Val Cys Ser Cys Pro
785                 790                 795                 800

Pro Gly Trp Gln Gly Pro Arg Cys Gln Gln Asp Val Asp Glu Cys Ala
                805                 810                 815

Gly Ala Ser Pro Cys Gly Pro His Gly Thr Cys Thr Asn Leu Pro Gly
            820                 825                 830

Asn Phe Arg Cys Ile Cys His Arg Gly Tyr Thr Gly Pro Phe Cys Asp
        835                 840                 845

Gln Asp Ile Asp Asp Cys Asp Pro Asn Pro Cys Leu His Gly Gly Ser
    850                 855                 860

Cys Gln Asp Gly Val Gly Ser Phe Ser Cys Ser Cys Leu Asp Gly Phe
865                 870                 875                 880

Ala Gly Pro Arg Cys Ala Arg Asp Val Asp Glu Cys Leu Ser Ser Pro
                885                 890                 895

Cys Gly Pro Gly Thr Cys Thr Asp His Val Ala Ser Phe Thr Cys Ala
            900                 905                 910

Cys Pro Pro Gly Tyr Gly Gly Phe His Cys Glu Ile Asp Leu Pro Asp
        915                 920                 925

Cys Ser Pro Ser Ser Cys Phe Asn Gly Gly Thr Cys Val Asp Gly Val
    930                 935                 940

Ser Ser Phe Ser Cys Leu Cys Arg Pro Gly Tyr Thr Gly Thr His Cys
945                 950                 955                 960

Gln Tyr Glu Ala Asp Pro Cys Phe Ser Arg Pro Cys Leu His Gly Gly
                965                 970                 975

Ile Cys Asn Pro Thr His Pro Gly Phe Glu Cys Thr Cys Arg Glu Gly
            980                 985                 990

Phe Thr Gly Ser Gln Cys Gln Asn Pro Val Asp Trp Cys Ser Gln Ala
        995                 1000                1005

Pro Cys Gln Asn Gly Gly Arg Cys Val Gln Thr Gly Ala Tyr Cys
    1010                1015                1020

Ile Cys Pro Pro Gly Trp Ser Gly Arg Leu Cys Asp Ile Gln Ser
    1025                1030                1035

Leu Pro Cys Thr Glu Ala Ala Ala Gln Met Gly Val Arg Leu Glu
    1040                1045                1050

Gln Leu Cys Gln Glu Gly Gly Lys Cys Ile Asp Lys Gly Arg Ser
    1055                1060                1065

His Tyr Cys Val Cys Pro Glu Gly Arg Thr Gly Ser His Cys Glu
    1070                1075                1080

His Glu Val Asp Pro Cys Thr Ala Gln Pro Cys Gln His Gly Gly
    1085                1090                1095
```

-continued

```
Thr Cys Arg Gly Tyr Met Gly Gly Tyr Val Cys Glu Cys Pro Ala
    1100            1105                1110

Gly Tyr Ala Gly Asp Ser Cys Glu Asp Asn Ile Asp Glu Cys Ala
    1115            1120                1125

Ser Gln Pro Cys Gln Asn Gly Gly Ser Cys Ile Asp Leu Val Ala
    1130            1135                1140

Arg Tyr Leu Cys Ser Cys Pro Pro Gly Thr Leu Gly Val Leu Cys
    1145            1150                1155

Glu Ile Asn Glu Asp Asp Cys Asp Leu Gly Pro Ser Leu Asp Ser
    1160            1165                1170

Gly Val Gln Cys Leu His Asn Gly Thr Cys Val Asp Leu Val Gly
    1175            1180                1185

Gly Phe Arg Cys Asn Cys Pro Pro Gly Tyr Thr Gly Leu His Cys
    1190            1195                1200

Glu Ala Asp Ile Asn Glu Cys Arg Pro Gly Ala Cys His Ala Ala
    1205            1210                1215

His Thr Arg Asp Cys Leu Gln Asp Pro Gly Gly His Phe Arg Cys
    1220            1225                1230

Val Cys His Pro Gly Phe Thr Gly Pro Arg Cys Gln Ile Ala Leu
    1235            1240                1245

Ser Pro Cys Glu Ser Gln Pro Cys Gln His Gly Gly Gln Cys Arg
    1250            1255                1260

His Ser Leu Gly Arg Gly Gly Gly Leu Thr Phe Thr Cys His Cys
    1265            1270                1275

Val Pro Pro Phe Trp Gly Leu Arg Cys Glu Arg Val Ala Arg Ser
    1280            1285                1290

Cys Arg Glu Leu Gln Cys Pro Val Gly Ile Pro Cys Gln Gln Thr
    1295            1300                1305

Ala Arg Gly Pro Arg Cys Ala Cys Pro Pro Gly Leu Ser Gly Pro
    1310            1315                1320

Ser Cys Arg Val Ser Arg Ala Ser Pro Ser Gly Ala Thr Asn Ala
    1325            1330                1335

Ser Cys Ala Ser Ala Pro Cys Leu His Gly Gly Ser Cys Leu Pro
    1340            1345                1350

Val Gln Ser Val Pro Phe Phe Arg Cys Val Cys Ala Pro Gly Trp
    1355            1360                1365

Gly Gly Pro Arg Cys Glu Thr Pro Ser Ala Ala Pro Glu Val Pro
    1370            1375                1380

Glu Glu Pro Arg Cys Pro Arg Ala Ala Cys Gln Ala Lys Arg Gly
    1385            1390                1395

Asp Gln Asn Cys Asp Arg Glu Cys Asn Thr Pro Gly Cys Gly Trp
    1400            1405                1410

Asp Gly Gly Asp Cys Ser Leu Asn Val Asp Asp Pro Trp Arg Gln
    1415            1420                1425

Cys Glu Ala Leu Gln Cys Trp Arg Leu Phe Asn Asn Ser Arg Cys
    1430            1435                1440

Asp Pro Ala Cys Ser Ser Pro Ala Cys Leu Tyr Asp Asn Phe Asp
    1445            1450                1455

Cys Tyr Ser Gly Gly Arg Asp Arg Thr Cys Asn Pro Val Tyr Glu
    1460            1465                1470

Lys Tyr Cys Ala Asp His Phe Ala Asp Gly Arg Cys Asp Gln Gly
    1475            1480                1485

Cys Asn Thr Glu Glu Cys Gly Trp Asp Gly Leu Asp Cys Ala Ser
```

```
            1490                1495                1500

Glu Val Pro Ala Leu Leu Ala Arg Gly Val Leu Val Leu Thr Val
    1505                1510                1515

Leu Leu Pro Pro Glu Glu Leu Leu Arg Ser Ser Ala Asp Phe Leu
    1520                1525                1530

Gln Arg Leu Ser Ala Ile Leu Arg Thr Ser Leu Arg Phe Arg Leu
    1535                1540                1545

Asp Ala Arg Gly Gln Ala Met Val Phe Pro Tyr His Arg Pro Ser
    1550                1555                1560

Pro Gly Ser Glu Ser Arg Val Arg Arg Glu Leu Gly Pro Glu Val
    1565                1570                1575

Ile Gly Ser Val Val Met Leu Glu Ile Asp Asn Arg Leu Cys Leu
    1580                1585                1590

Gln Ser Ala Glu Asn Asp His Cys Phe Pro Asp Ala Gln Ser Ala
    1595                1600                1605

Ala Asp Tyr Leu Gly Ala Leu Ser Ala Val Glu Arg Leu Asp Phe
    1610                1615                1620

Pro Tyr Pro Leu Arg Asp Val Arg Gly Glu Pro Leu Glu Ala Pro
    1625                1630                1635

Glu Gln Ser Val Pro Leu Leu Pro Leu Leu Val Ala Gly Ala Val
    1640                1645                1650

Phe Leu Leu Ile Ile Phe Ile Leu Gly Val Met Val Ala Arg Arg
    1655                1660                1665

Lys Arg Glu His Ser Thr Leu Trp Phe Pro Glu Gly Phe Ala Leu
    1670                1675                1680

His Lys Asp Ile Ala Ala Gly His Lys Gly Arg Arg Glu Pro Val
    1685                1690                1695

Gly Gln Asp Ala Leu Gly Met Lys Asn Met Ala Lys Gly Glu Ser
    1700                1705                1710

Leu Met Gly Glu Val Val Thr Asp Leu Asn Asp Ser Glu Cys Pro
    1715                1720                1725

Glu Ala Lys Arg Leu Lys Val Glu Glu Pro Gly Met Gly Ala Glu
    1730                1735                1740

Glu Pro Glu Asp Cys Arg Gln Trp Thr Gln His His Leu Val Ala
    1745                1750                1755

Ala Asp Ile Arg Val Ala Pro Ala Thr Ala Leu Thr Pro Pro Gln
    1760                1765                1770

Gly Asp Ala Asp Ala Asp Gly Val Asp Val Asn Val Arg Gly Pro
    1775                1780                1785

Asp Gly Phe Thr Pro Leu Met Leu Ala Ser Phe Cys Gly Gly Ala
    1790                1795                1800

Leu Glu Pro Met Pro Ala Glu Asp Glu Ala Asp Asp Thr Ser
    1805                1810                1815

Ala Ser Ile Ile Ser Asp Leu Ile Cys Gln Gly Ala Gln Leu Gly
    1820                1825                1830

Ala Arg Thr Asp Arg Thr Gly Glu Thr Ala Leu His Leu Ala Ala
    1835                1840                1845

Arg Tyr Ala Arg Ala Asp Ala Ala Lys Arg Leu Leu Asp Ala Gly
    1850                1855                1860

Ala Asp Thr Asn Ala Gln Asp His Ser Gly Arg Thr Pro Leu His
    1865                1870                1875

Thr Ala Val Thr Ala Asp Ala Gln Gly Val Phe Gln Ile Leu Ile
    1880                1885                1890
```

```
Arg Asn Arg Ser Thr Asp Leu Asp Ala Arg Met Ala Asp Gly Ser
    1895            1900                1905

Thr Ala Leu Ile Leu Ala Ala Arg Leu Ala Val Glu Gly Met Val
    1910            1915                1920

Glu Glu Leu Ile Ala Ser His Ala Asp Val Asn Ala Val Asp Glu
    1925            1930                1935

Leu Gly Lys Ser Ala Leu His Trp Ala Ala Val Asn Asn Val
    1940            1945                1950

Glu Ala Thr Leu Ala Leu Leu Lys Asn Gly Ala Asn Lys Asp Met
    1955            1960                1965

Gln Asp Ser Lys Glu Glu Thr Pro Leu Phe Leu Ala Ala Arg Glu
    1970            1975                1980

Gly Ser Tyr Glu Ala Ala Lys Leu Leu Leu Asp His Leu Ala Asn
    1985            1990                1995

Arg Glu Ile Thr Asp His Leu Asp Arg Leu Pro Arg Asp Val Ala
    2000            2005                2010

Gln Glu Arg Leu His Gln Asp Ile Val Arg Leu Leu Asp Gln Pro
    2015            2020                2025

Ser Gly Pro Arg Ser Pro Ser Gly Pro His Gly Leu Gly Pro Leu
    2030            2035                2040

Leu Cys Pro Pro Gly Ala Phe Leu Pro Gly Leu Lys Ala Val Gln
    2045            2050                2055

Ser Gly Thr Lys Lys Ser Arg Arg Pro Pro Gly Lys Thr Gly Leu
    2060            2065                2070

Gly Pro Gln Gly Thr Arg Gly Arg Gly Lys Lys Leu Thr Leu Ala
    2075            2080                2085

Cys Pro Gly Pro Leu Ala Asp Ser Ser Val Thr Leu Ser Pro Val
    2090            2095                2100

Asp Ser Leu Asp Ser Pro Arg Pro Phe Ser Gly Pro Pro Ala Ser
    2105            2110                2115

Pro Gly Gly Phe Pro Leu Glu Gly Pro Tyr Ala Thr Thr Ala Thr
    2120            2125                2130

Ala Val Ser Leu Ala Gln Leu Gly Ala Ser Arg Ala Gly Pro Leu
    2135            2140                2145

Gly Arg Gln Pro Pro Gly Gly Cys Val Leu Ser Phe Gly Leu Leu
    2150            2155                2160

Asn Pro Val Ala Val Pro Leu Asp Trp Ala Arg Leu Pro Pro Pro
    2165            2170                2175

Ala Pro Pro Gly Pro Ser Phe Leu Leu Pro Leu Ala Pro Gly Pro
    2180            2185                2190

Gln Leu Leu Asn Pro Gly Ala Pro Val Ser Pro Gln Glu Arg Pro
    2195            2200                2205

Pro Pro Tyr Leu Ala Ala Pro Gly His Gly Glu Glu Tyr Pro Ala
    2210            2215                2220

Ala Gly Thr Arg Ser Ser Pro Thr Lys Ala Arg Phe Leu Arg Val
    2225            2230                2235

Pro Ser Glu His Pro Tyr Leu Thr Pro Ser Pro Glu Ser Pro Glu
    2240            2245                2250

His Trp Ala Ser Pro Ser Pro Pro Ser Leu Ser Asp Trp Ser Asp
    2255            2260                2265

Ser Thr Pro Ser Pro Ala Thr Ala Thr Asn Ala Thr Ala Ser Gly
    2270            2275                2280
```

-continued

```
Ala Leu Pro Ala Gln Pro His Pro Ile Ser Val Pro Ser Leu Pro
    2285                2290                2295

Gln Ser Gln Thr Gln Leu Gly Pro Gln Pro Glu Val Thr Pro Lys
    2300                2305                2310

Arg Gln Val Met Ala
    2315

<210> SEQ ID NO 289
<211> LENGTH: 2318
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 289

Met Gly Leu Gly Ala Arg Gly Arg Arg Arg Arg Leu Met Ala
1               5                   10                  15

Leu Pro Pro Pro Pro Pro Met Arg Ala Leu Pro Leu Leu Leu
            20                  25                  30

Leu Ala Gly Leu Gly Ala Ala Ala Pro Pro Cys Leu Asp Gly Ser Pro
            35                  40                  45

Cys Ala Asn Gly Gly Arg Cys Thr His Gln Pro Ser Leu Glu Ala
50                  55                  60

Ala Cys Leu Cys Leu Pro Gly Trp Val Gly Glu Arg Cys Gln Leu Glu
65                  70                  75                  80

Asp Pro Cys His Ser Gly Pro Cys Ala Gly Arg Gly Val Cys Gln Ser
                    85                  90                  95

Ser Val Val Ala Gly Thr Ala Arg Phe Ser Cys Arg Cys Leu Arg Gly
                100                 105                 110

Phe Gln Gly Pro Asp Cys Ser Gln Pro Asp Pro Cys Val Ser Arg Pro
            115                 120                 125

Cys Val His Gly Ala Pro Cys Ser Val Gly Pro Asp Gly Arg Phe Ala
    130                 135                 140

Cys Ala Cys Pro Pro Gly Tyr Gln Gly Gln Ser Cys Gln Ser Asp Ile
145                 150                 155                 160

Asp Glu Cys Arg Ser Gly Thr Thr Cys Arg His Gly Gly Thr Cys Leu
                165                 170                 175

Asn Thr Pro Gly Ser Phe Arg Cys Gln Cys Pro Leu Gly Tyr Thr Gly
            180                 185                 190

Leu Leu Cys Glu Asn Pro Val Val Pro Cys Ala Pro Ser Pro Cys Arg
            195                 200                 205

Asn Gly Gly Thr Cys Arg Gln Ser Ser Asp Val Thr Tyr Asp Cys Ala
    210                 215                 220

Cys Leu Pro Gly Phe Glu Gly Gln Asn Cys Glu Val Asn Val Asp Asp
225                 230                 235                 240

Cys Pro Gly His Arg Cys Leu Asn Gly Gly Thr Cys Val Asp Gly Val
                245                 250                 255

Asn Thr Tyr Asn Cys Gln Cys Pro Pro Glu Trp Thr Gly Gln Phe Cys
            260                 265                 270

Thr Glu Asp Val Asp Glu Cys Gln Leu Gln Pro Asn Ala Cys His Asn
            275                 280                 285

Gly Gly Thr Cys Phe Asn Leu Leu Gly Gly His Ser Cys Val Cys Val
    290                 295                 300

Asn Gly Trp Thr Gly Glu Ser Cys Ser Gln Asn Ile Asp Asp Cys Ala
```

```
              305                 310                 315                 320
          Thr Ala Val Cys Phe His Gly Ala Thr Cys His Asp Arg Val Ala Ser
                          325                 330                 335
          Phe Tyr Cys Ala Cys Pro Met Gly Lys Thr Gly Leu Leu Cys His Leu
                          340                 345                 350
          Asp Asp Ala Cys Val Ser Asn Pro Cys His Glu Asp Ala Ile Cys Asp
                          355                 360                 365
          Thr Asn Pro Val Ser Gly Arg Ala Ile Cys Thr Cys Pro Pro Gly Phe
              370                 375                 380
          Thr Gly Gly Ala Cys Asp Gln Asp Val Asp Glu Cys Ser Ile Gly Ala
          385                 390                 395                 400
          Asn Pro Cys Glu His Leu Gly Arg Cys Val Asn Thr Gln Gly Ser Phe
                          405                 410                 415
          Leu Cys Gln Cys Gly Arg Gly Tyr Thr Gly Pro Arg Cys Glu Thr Asp
                          420                 425                 430
          Val Asn Glu Cys Leu Ser Gly Pro Cys Arg Asn Gln Ala Thr Cys Leu
                          435                 440                 445
          Asp Arg Ile Gly Gln Phe Thr Cys Ile Cys Met Ala Gly Phe Thr Gly
              450                 455                 460
          Thr Tyr Cys Glu Val Asp Ile Asp Glu Cys Gln Ser Ser Pro Cys Val
          465                 470                 475                 480
          Asn Gly Gly Val Cys Lys Asp Arg Val Asn Gly Phe Ser Cys Thr Cys
                          485                 490                 495
          Pro Ser Gly Phe Ser Gly Ser Met Cys Gln Leu Asp Val Asp Glu Cys
                          500                 505                 510
          Ala Ser Thr Pro Cys Arg Asn Gly Ala Lys Cys Val Asp Gln Pro Asp
                          515                 520                 525
          Gly Tyr Glu Cys Arg Cys Ala Glu Gly Phe Glu Gly Thr Leu Cys Glu
                          530                 535                 540
          Arg Asn Val Asp Asp Cys Ser Pro Asp Pro Cys His His Gly Arg Cys
          545                 550                 555                 560
          Val Asp Gly Ile Ala Ser Phe Ser Cys Ala Cys Ala Pro Gly Tyr Thr
                          565                 570                 575
          Gly Ile Arg Cys Glu Ser Gln Val Asp Glu Cys Arg Ser Gln Pro Cys
                          580                 585                 590
          Arg Tyr Gly Gly Lys Cys Leu Asp Leu Val Asp Lys Tyr Leu Cys Arg
                          595                 600                 605
          Cys Pro Pro Gly Thr Thr Gly Val Asn Cys Glu Val Asn Ile Asp Asp
              610                 615                 620
          Cys Ala Ser Asn Pro Cys Thr Phe Gly Val Cys Arg Asp Gly Ile Asn
          625                 630                 635                 640
          Arg Tyr Asp Cys Val Cys Gln Pro Gly Phe Thr Gly Pro Leu Cys Asn
                          645                 650                 655
          Val Glu Ile Asn Glu Cys Ala Ser Ser Pro Cys Gly Glu Gly Gly Ser
                          660                 665                 670
          Cys Val Asp Gly Glu Asn Gly Phe His Cys Leu Cys Pro Pro Gly Ser
                          675                 680                 685
          Leu Pro Pro Leu Cys Leu Pro Ala Asn His Pro Cys Ala His Lys Pro
                          690                 695                 700
          Cys Ser His Gly Val Cys His Asp Ala Pro Gly Gly Phe Arg Cys Val
          705                 710                 715                 720
          Cys Glu Pro Gly Trp Ser Gly Pro Arg Cys Ser Gln Ser Leu Ala Pro
                          725                 730                 735
```

```
Asp Ala Cys Glu Ser Gln Pro Cys Gln Ala Gly Gly Thr Cys Thr Ser
            740                 745                 750

Asp Gly Ile Gly Phe Arg Cys Thr Cys Ala Pro Gly Phe Gln Gly His
            755                 760                 765

Gln Cys Glu Val Leu Ser Pro Cys Thr Pro Ser Leu Cys Glu His Gly
            770                 775                 780

Gly His Cys Glu Ser Asp Pro Asp Arg Leu Thr Val Cys Ser Cys Pro
785                 790                 795                 800

Pro Gly Trp Gln Gly Pro Arg Cys Gln Gln Asp Val Asp Glu Cys Ala
                805                 810                 815

Gly Ala Ser Pro Cys Gly Pro His Gly Thr Cys Thr Asn Leu Pro Gly
            820                 825                 830

Asn Phe Arg Cys Ile Cys His Arg Gly Tyr Thr Gly Pro Phe Cys Asp
            835                 840                 845

Gln Asp Ile Asp Asp Cys Asp Pro Asn Pro Cys Leu His Gly Gly Ser
            850                 855                 860

Cys Gln Asp Gly Val Gly Ser Phe Ser Cys Ser Cys Leu Asp Gly Phe
865                 870                 875                 880

Ala Gly Pro Arg Cys Ala Arg Asp Val Asp Glu Cys Leu Ser Ser Pro
                885                 890                 895

Cys Gly Pro Gly Thr Cys Thr Asp His Val Ala Ser Phe Thr Cys Ala
            900                 905                 910

Cys Pro Pro Gly Tyr Gly Gly Phe His Cys Glu Ile Asp Leu Pro Asp
            915                 920                 925

Cys Ser Pro Ser Ser Cys Phe Asn Gly Gly Thr Cys Val Asp Gly Val
            930                 935                 940

Ser Ser Phe Ser Cys Leu Cys Arg Pro Gly Tyr Thr Gly Thr His Cys
945                 950                 955                 960

Gln Tyr Glu Ala Asp Pro Cys Phe Ser Arg Pro Cys Leu His Gly Gly
            965                 970                 975

Ile Cys Asn Pro Thr His Pro Gly Phe Glu Cys Thr Cys Arg Glu Gly
            980                 985                 990

Phe Thr Gly Ser Gln Cys Gln Asn Pro Val Asp Trp Cys Ser Gln Ala
            995                 1000                1005

Pro Cys Gln Asn Gly Gly Arg Cys Val Gln Thr Gly Ala Tyr Cys
    1010                1015                1020

Ile Cys Pro Pro Gly Trp Ser Gly Arg Leu Cys Asp Ile Gln Ser
    1025                1030                1035

Leu Pro Cys Thr Glu Ala Ala Ala Gln Met Gly Val Arg Leu Glu
    1040                1045                1050

Gln Leu Cys Gln Glu Gly Gly Lys Cys Ile Asp Lys Gly Arg Ser
    1055                1060                1065

His Tyr Cys Val Cys Pro Glu Gly Arg Thr Gly Ser His Cys Glu
    1070                1075                1080

His Glu Val Asp Pro Cys Thr Ala Gln Pro Cys Gln His Gly Gly
    1085                1090                1095

Thr Cys Arg Gly Tyr Met Gly Gly Tyr Val Cys Glu Cys Pro Ala
    1100                1105                1110

Gly Tyr Ala Gly Asp Ser Cys Glu Asp Asn Ile Asp Glu Cys Ala
    1115                1120                1125

Ser Gln Pro Cys Gln Asn Gly Gly Ser Cys Ile Asp Leu Val Ala
    1130                1135                1140
```

-continued

```
Arg Tyr Leu Cys Ser Cys Pro Pro Gly Thr Leu Gly Val Leu Cys
1145                1150                1155

Glu Ile Asn Glu Asp Asp Cys Asp Leu Gly Pro Ser Leu Asp Ser
1160                1165                1170

Gly Val Gln Cys Leu His Asn Gly Thr Cys Val Asp Leu Val Gly
1175                1180                1185

Gly Phe Arg Cys Asn Cys Pro Pro Gly Tyr Thr Gly Leu His Cys
1190                1195                1200

Glu Ala Asp Ile Asn Glu Cys Arg Pro Gly Ala Cys His Ala Ala
1205                1210                1215

His Thr Arg Asp Cys Leu Gln Asp Pro Gly Gly His Phe Arg Cys
1220                1225                1230

Val Cys His Pro Gly Phe Thr Gly Pro Arg Cys Gln Ile Ala Leu
1235                1240                1245

Ser Pro Cys Glu Ser Gln Pro Cys Gln His Gly Gly Gln Cys Arg
1250                1255                1260

His Ser Leu Gly Arg Gly Gly Leu Thr Phe Thr Cys His Cys
1265                1270                1275

Val Pro Pro Phe Trp Gly Leu Arg Cys Glu Arg Val Ala Arg Ser
1280                1285                1290

Cys Arg Glu Leu Gln Cys Pro Val Gly Ile Pro Cys Gln Gln Thr
1295                1300                1305

Ala Arg Gly Pro Arg Cys Ala Cys Pro Pro Gly Leu Ser Gly Pro
1310                1315                1320

Ser Cys Arg Val Ser Arg Ala Ser Pro Ser Gly Ala Thr Asn Ala
1325                1330                1335

Ser Cys Ala Ser Ala Pro Cys Leu His Gly Gly Ser Cys Leu Pro
1340                1345                1350

Val Gln Ser Val Pro Phe Phe Arg Cys Val Cys Ala Pro Gly Trp
1355                1360                1365

Gly Gly Pro Arg Cys Glu Thr Pro Ser Ala Ala Pro Glu Val Pro
1370                1375                1380

Glu Glu Pro Arg Cys Pro Arg Ala Ala Cys Gln Ala Lys Arg Gly
1385                1390                1395

Asp Gln Asn Cys Asp Arg Glu Cys Asn Thr Pro Gly Cys Gly Trp
1400                1405                1410

Asp Gly Gly Asp Cys Ser Leu Asn Val Asp Asp Pro Trp Arg Gln
1415                1420                1425

Cys Glu Ala Leu Gln Cys Trp Arg Leu Phe Asn Asn Ser Arg Cys
1430                1435                1440

Asp Pro Ala Cys Ser Ser Pro Ala Cys Leu Tyr Asp Asn Phe Asp
1445                1450                1455

Cys Tyr Ser Gly Gly Arg Asp Arg Thr Cys Asn Pro Val Tyr Glu
1460                1465                1470

Lys Tyr Cys Ala Asp His Phe Ala Asp Gly Arg Cys Asp Gln Gly
1475                1480                1485

Cys Asn Thr Glu Glu Cys Gly Trp Asp Gly Leu Asp Cys Ala Ser
1490                1495                1500

Glu Val Pro Ala Leu Leu Ala Arg Gly Val Leu Val Leu Thr Val
1505                1510                1515

Leu Leu Pro Pro Glu Glu Leu Leu Arg Ser Ser Ala Asp Phe Leu
1520                1525                1530

Gln Arg Leu Ser Ala Ile Leu Arg Thr Ser Leu Arg Phe Arg Leu
```

```
            1535                1540                1545

Asp Ala Arg Gly Gln Ala Met Val Phe Pro Tyr His Arg Pro Ser
            1550                1555                1560

Pro Gly Ser Glu Ser Arg Val Arg Arg Glu Leu Gly Pro Glu Val
            1565                1570                1575

Ile Gly Ser Val Val Met Leu Glu Ile Asp Asn Arg Leu Cys Leu
            1580                1585                1590

Gln Ser Ala Glu Asn Asp His Cys Phe Pro Asp Ala Gln Ser Ala
            1595                1600                1605

Ala Asp Tyr Leu Gly Ala Leu Ser Ala Val Glu Arg Leu Asp Phe
            1610                1615                1620

Pro Tyr Pro Leu Arg Asp Val Arg Gly Glu Pro Leu Glu Ala Pro
            1625                1630                1635

Glu Gln Ser Val Pro Leu Leu Pro Leu Leu Val Ala Gly Ala Val
            1640                1645                1650

Phe Leu Leu Ile Ile Phe Ile Leu Gly Val Met Val Ala Arg Arg
            1655                1660                1665

Lys Arg Glu His Ser Thr Leu Trp Phe Pro Glu Gly Phe Ala Leu
            1670                1675                1680

His Lys Asp Ile Ala Ala Gly His Lys Gly Arg Arg Glu Pro Val
            1685                1690                1695

Gly Gln Asp Ala Leu Gly Met Lys Asn Met Ala Lys Gly Glu Ser
            1700                1705                1710

Leu Met Gly Glu Val Val Thr Asp Leu Asn Asp Ser Glu Cys Pro
            1715                1720                1725

Glu Ala Lys Arg Leu Lys Val Glu Glu Pro Gly Met Gly Ala Glu
            1730                1735                1740

Glu Pro Glu Asp Cys Arg Gln Trp Thr Gln His His Leu Val Ala
            1745                1750                1755

Ala Asp Ile Arg Val Ala Pro Ala Thr Ala Leu Thr Pro Pro Gln
            1760                1765                1770

Gly Asp Ala Asp Ala Asp Gly Val Asp Val Asn Val Arg Gly Pro
            1775                1780                1785

Asp Gly Phe Thr Pro Leu Met Leu Ala Ser Phe Cys Gly Gly Ala
            1790                1795                1800

Leu Glu Pro Met Pro Ala Glu Glu Asp Glu Ala Asp Asp Thr Ser
            1805                1810                1815

Ala Ser Ile Ile Ser Asp Leu Ile Cys Gln Gly Ala Gln Leu Gly
            1820                1825                1830

Ala Arg Thr Asp Arg Thr Gly Glu Thr Ala Leu His Leu Ala Ala
            1835                1840                1845

Arg Tyr Ala Arg Ala Asp Ala Ala Lys Arg Leu Leu Asp Ala Gly
            1850                1855                1860

Ala Asp Thr Asn Ala Gln Asp His Ser Gly Arg Thr Pro Leu His
            1865                1870                1875

Thr Ala Val Thr Ala Asp Ala Gln Gly Val Phe Gln Ile Leu Ile
            1880                1885                1890

Arg Asn Arg Ser Thr Asp Leu Asp Ala Arg Met Ala Asp Gly Ser
            1895                1900                1905

Thr Ala Leu Ile Leu Ala Ala Arg Leu Ala Val Glu Gly Met Val
            1910                1915                1920

Glu Glu Leu Ile Ala Ser His Ala Asp Val Asn Ala Val Asp Glu
            1925                1930                1935
```

-continued

Leu Gly Lys Ser Ala Leu His Trp Ala Ala Val Asn Asn Val
1940            1945            1950

Glu Ala Thr Leu Ala Leu Leu Lys Asn Gly Ala Asn Lys Asp Met
1955            1960            1965

Gln Asp Ser Lys Glu Glu Thr Pro Leu Phe Leu Ala Ala Arg Glu
1970            1975            1980

Gly Ser Tyr Glu Ala Ala Lys Leu Leu Leu Asp His Leu Ala Asn
1985            1990            1995

Arg Glu Ile Thr Asp His Leu Asp Arg Leu Pro Arg Asp Val Ala
2000            2005            2010

Gln Glu Arg Leu His Gln Asp Ile Val Arg Leu Leu Asp Gln Pro
2015            2020            2025

Ser Gly Pro Arg Ser Pro Ser Gly Pro His Gly Leu Gly Pro Leu
2030            2035            2040

Leu Cys Pro Pro Gly Ala Phe Leu Pro Gly Leu Lys Ala Val Gln
2045            2050            2055

Ser Gly Thr Lys Lys Ser Arg Arg Pro Pro Gly Lys Thr Gly Leu
2060            2065            2070

Gly Pro Gln Gly Thr Arg Gly Arg Gly Lys Lys Leu Thr Leu Ala
2075            2080            2085

Cys Pro Gly Pro Leu Ala Asp Ser Ser Val Thr Leu Ser Pro Val
2090            2095            2100

Asp Ser Leu Asp Ser Pro Arg Pro Phe Ser Gly Pro Pro Ala Ser
2105            2110            2115

Pro Gly Gly Phe Pro Leu Glu Gly Pro Tyr Ala Thr Thr Ala Thr
2120            2125            2130

Ala Val Ser Leu Ala Gln Leu Gly Ala Ser Arg Ala Gly Pro Leu
2135            2140            2145

Gly Arg Gln Pro Pro Gly Gly Cys Val Leu Ser Phe Gly Leu Leu
2150            2155            2160

Asn Pro Val Ala Val Pro Leu Asp Trp Ala Arg Leu Pro Pro Pro
2165            2170            2175

Ala Pro Pro Gly Pro Ser Phe Leu Leu Pro Leu Ala Pro Gly Pro
2180            2185            2190

Gln Leu Leu Asn Pro Gly Ala Pro Val Ser Pro Gln Glu Arg Pro
2195            2200            2205

Pro Pro Tyr Leu Ala Ala Pro Gly His Gly Glu Glu Tyr Pro Ala
2210            2215            2220

Ala Gly Thr Arg Ser Ser Pro Thr Lys Ala Arg Phe Leu Arg Val
2225            2230            2235

Pro Ser Glu His Pro Tyr Leu Thr Pro Ser Pro Glu Ser Pro Glu
2240            2245            2250

His Trp Ala Ser Pro Ser Pro Pro Ser Leu Ser Asp Trp Ser Asp
2255            2260            2265

Ser Thr Pro Ser Pro Ala Thr Ala Thr Asn Ala Thr Ala Ser Gly
2270            2275            2280

Ala Leu Pro Ala Gln Pro His Pro Ile Ser Val Pro Ser Leu Pro
2285            2290            2295

Gln Ser Gln Thr Gln Leu Gly Pro Gln Pro Glu Val Thr Pro Lys
2300            2305            2310

Arg Gln Val Met Ala
2315

<210> SEQ ID NO 290
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 6xHis tag"

<400> SEQUENCE: 290

His His His His His His
1               5

<210> SEQ ID NO 291
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 291
tttttttttt tttttttttt                                         20

<210> SEQ ID NO 292
<211> LENGTH: 263
<212> TYPE: PRT
<213> ORGANISM: Homo sapiens

<400> SEQUENCE: 292

Ala Pro Glu Val Ser Glu Glu Pro Arg Cys Pro Arg Ala Ala Cys Gln
1               5                   10                  15

Ala Lys Arg Gly Asp Gln Arg Cys Asp Arg Glu Cys Asn Ser Pro Gly
            20                  25                  30

Cys Gly Trp Asp Gly Gly Asp Cys Ser Leu Ser Val Gly Asp Pro Trp
        35                  40                  45

Arg Gln Cys Glu Ala Leu Gln Cys Trp Arg Leu Phe Asn Asn Ser Arg
    50                  55                  60

Cys Asp Pro Ala Cys Ser Ser Pro Ala Cys Leu Tyr Asp Asn Phe Asp
65                  70                  75                  80

Cys His Ala Gly Gly Arg Glu Arg Thr Cys Asn Pro Val Tyr Glu Lys
                85                  90                  95

Tyr Cys Ala Asp His Phe Ala Asp Gly Arg Cys Asp Gln Gly Cys Asn
            100                 105                 110

Thr Glu Glu Cys Gly Trp Asp Gly Leu Asp Cys Ala Ser Glu Val Pro
        115                 120                 125

Ala Leu Leu Ala Arg Gly Val Leu Val Leu Thr Val Leu Leu Pro Pro
    130                 135                 140

Glu Glu Leu Leu Arg Ser Ser Ala Asp Phe Leu Gln Arg Leu Ser Ala
145                 150                 155                 160

Ile Leu Arg Thr Ser Leu Arg Phe Arg Leu Asp Ala His Gly Gln Ala
                165                 170                 175

Met Val Phe Pro Tyr His Arg Pro Ser Pro Gly Ser Glu Pro Arg Ala
            180                 185                 190

Arg Arg Glu Leu Ala Pro Glu Val Ile Gly Ser Val Val Met Leu Glu
        195                 200                 205

Ile Asp Asn Arg Leu Cys Leu Gln Ser Pro Glu Asn Asp His Cys Phe
    210                 215                 220

```
Pro Asp Ala Gln Ser Ala Ala Asp Tyr Leu Gly Leu Ser Ala Val
225                 230                 235                 240

Glu Arg Leu Asp Phe Pro Tyr Pro Leu Arg Asp Val Arg Gly Glu Pro
                245                 250                 255

Leu Glu Pro Pro Glu Pro Ser
            260
```

<210> SEQ ID NO 293
<211> LENGTH: 242
<212> TYPE: PRT
<213> ORGANISM: Homo sapiens

<400> SEQUENCE: 293

```
Gly Glu Glu Ala Cys Glu Leu Pro Glu Cys Gln Glu Asp Ala Gly Asn
1               5                   10                  15

Lys Val Cys Ser Leu Gln Cys Asn Asn His Ala Cys Gly Trp Asp Gly
                20                  25                  30

Gly Asp Cys Ser Leu Asn Phe Asn Asp Pro Trp Lys Asn Cys Thr Gln
                35                  40                  45

Ser Leu Gln Cys Trp Lys Tyr Phe Ser Asp Gly His Cys Asp Ser Gln
50                  55                  60

Cys Asn Ser Ala Gly Cys Leu Phe Asp Gly Phe Asp Cys Gln Arg Ala
65                  70                  75                  80

Glu Gly Gln Cys Asn Pro Leu Tyr Asp Gln Tyr Cys Lys Asp His Phe
                85                  90                  95

Ser Asp Gly His Cys Asp Gln Gly Cys Asn Ser Ala Glu Cys Glu Trp
                100                 105                 110

Asp Gly Leu Asp Cys Ala Glu His Val Pro Glu Arg Leu Ala Ala Gly
                115                 120                 125

Thr Leu Val Val Val Leu Met Pro Pro Glu Gln Leu Arg Asn Ser
130                 135                 140

Ser Phe His Phe Leu Arg Glu Leu Ser Arg Val Leu His Thr Asn Val
145                 150                 155                 160

Val Phe Lys Arg Asp Ala His Gly Gln Gln Met Ile Phe Pro Tyr Tyr
                165                 170                 175

Gly Met Asp Val Arg Gly Ser Ile Val Tyr Leu Glu Ile Asp Asn Arg
                180                 185                 190

Gln Cys Val Gln Ala Ser Ser Gln Cys Phe Gln Ser Ala Thr Asp Val
                195                 200                 205

Ala Ala Phe Leu Gly Ala Leu Ala Ser Leu Gly Ser Leu Asn Ile Pro
210                 215                 220

Tyr Lys Ile Glu Ala Val Gln Ser Glu Thr Val Glu Pro Pro Pro Pro
225                 230                 235                 240

Ala Gln
```

<210> SEQ ID NO 294
<211> LENGTH: 234
<212> TYPE: PRT
<213> ORGANISM: Homo sapiens

<400> SEQUENCE: 294

```
Gly Ala Thr Cys Leu Ser Gln Tyr Cys Ala Asp Lys Ala Arg Asp Gly
1               5                   10                  15

Val Cys Asp Glu Ala Cys Asn Ser His Ala Cys Gln Trp Asp Gly Gly
                20                  25                  30

Asp Cys Ser Leu Thr Met Glu Asn Pro Trp Ala Asn Cys Ser Ser Pro
```

-continued

```
            35                      40                      45
Leu Pro Cys Trp Asp Tyr Ile Asn Asn Gln Cys Asp Glu Leu Cys Asn
        50                      55                      60

Thr Val Glu Cys Leu Phe Asp Asn Phe Glu Cys Gln Gly Asn Ser Lys
65                      70                      75                      80

Thr Cys Lys Tyr Asp Lys Tyr Cys Ala Asp His Phe Lys Asp Asn His
                85                      90                      95

Cys Asn Gln Gly Cys Asn Ser Glu Glu Cys Gly Trp Asp Gly Leu Asp
                100                     105                     110

Cys Ala Ala Asp Gln Pro Glu Asn Leu Ala Glu Gly Thr Leu Val Ile
        115                     120                     125

Val Val Leu Met Pro Pro Glu Gln Leu Leu Gln Asp Ala Arg Ser Phe
        130                     135                     140

Leu Arg Ala Leu Gly Thr Leu Leu His Thr Asn Leu Arg Ile Lys Arg
145                     150                     155                     160

Asp Ser Gln Gly Glu Leu Met Val Tyr Pro Tyr Tyr Gly Glu Val Ala
                165                     170                     175

Gly Ser Lys Val Phe Leu Glu Ile Asp Asn Arg Gln Cys Val Gln Asp
                180                     185                     190

Ser Asp His Cys Phe Lys Asn Thr Asp Ala Ala Ala Leu Leu Ala
        195                     200                     205

Ser His Ala Ile Gln Gly Thr Leu Ser Tyr Pro Leu Val Ser Val Val
        210                     215                     220

Ser Glu Ser Leu Thr Pro Glu Arg Thr Gln
225                     230
```